United States Patent
Singh et al.

(10) Patent No.: US 11,547,301 B2
(45) Date of Patent: Jan. 10, 2023

(54) METHODS FOR COLLECTING AND TESTING BACTERIA CONTAINING SAMPLES FROM WITHIN THE GASTROINTESTINAL TRACT

(71) Applicant: Progenity, Inc., San Diego, CA (US)

(72) Inventors: Sharat Singh, Rancho Santa Fe, CA (US); Mitchell Lawrence Jones, La Jolla, CA (US); Christopher Loren Wahl, La Jolla, CA (US)

(73) Assignee: Biora Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/197,125

(22) Filed: Mar. 10, 2021

(65) Prior Publication Data

US 2021/0196127 A1    Jul. 1, 2021

Related U.S. Application Data

(63) Continuation of application No. 15/835,237, filed on Dec. 7, 2017.

(Continued)

(51) Int. Cl.
| | | |
|---|---|---|
| *A61B 10/00* | (2006.01) | |
| *A61B 5/00* | (2006.01) | |
| *G01N 21/76* | (2006.01) | |
| *C12Q 1/06* | (2006.01) | |
| *G01N 1/10* | (2006.01) | |
| *G01N 33/58* | (2006.01) | |
| *C12Q 1/04* | (2006.01) | |
| *A61K 45/06* | (2006.01) | |
| *C12Q 1/10* | (2006.01) | |
| *A61B 5/07* | (2006.01) | |
| *C12M 1/00* | (2006.01) | |
| *C12N 1/20* | (2006.01) | |
| *G01N 1/20* | (2006.01) | |
| *G01N 1/38* | (2006.01) | |
| *A61K 49/00* | (2006.01) | |
| *G01N 33/483* | (2006.01) | |
| *G01N 33/487* | (2006.01) | |
| *A61B 5/01* | (2006.01) | |

(Continued)

(52) U.S. Cl.
CPC ............ *A61B 5/0071* (2013.01); *A61B 5/073* (2013.01); *A61B 5/4238* (2013.01); *A61B 5/4255* (2013.01); *A61B 5/6861* (2013.01); *A61B 10/0045* (2013.01); *A61K 45/06* (2013.01); *A61K 49/0019* (2013.01); *A61K 49/0058* (2013.01); *C12M 29/26* (2013.01); *C12N 1/20* (2013.01); *C12Q 1/045* (2013.01); *C12Q 1/06* (2013.01); *C12Q 1/10* (2013.01); *G01N 1/10* (2013.01); *G01N 1/20* (2013.01); *G01N 1/38* (2013.01); *G01N 21/76* (2013.01); *G01N 33/487* (2013.01); *G01N 33/4833* (2013.01); *G01N 33/582* (2013.01); *A61B 5/0084* (2013.01); *A61B 5/01* (2013.01); *A61B 5/036* (2013.01); *A61B 5/14503* (2013.01); *A61B 5/14539* (2013.01); *A61B 5/14546* (2013.01); *A61B 5/14552* (2013.01); *A61B 5/42* (2013.01); *A61B 10/0038* (2013.01); *A61B 2010/0061* (2013.01); *A61B 2010/0074* (2013.01); *A61B 2562/0233* (2013.01); *G01N 2001/1031* (2013.01)

(58) Field of Classification Search
CPC ....... A61B 5/0071; A61B 5/42; A61B 5/6861; A61B 5/6873; A61B 5/4255; A61B 10/0045; A61B 5/4238; C12Q 1/06
See application file for complete search history.

(56) References Cited

U.S. PATENT DOCUMENTS 3,057,344 A    10/1962  Alberto
3,118,439 A     1/1964  Perrenoud
(Continued)

FOREIGN PATENT DOCUMENTS

CN       1856290      11/2006
CN     101495164       7/2009
(Continued)

OTHER PUBLICATIONS

Bures et al. Small Intestinal Bacterial Overgrowth Syndrome; World Journal of Gastroenterology, vol. 16, No. 24, pp. 2978-2990. (Year: 2010).*

Gross et al. The Effective Use of Both Positive and Negative Controls in Screening Experiments; Biometrics, vol. 23, No. 2, pp. 285-295. (Year: 1967).*

(Continued)

*Primary Examiner* — Neil P Hammell
*Assistant Examiner* — Paul C Martin
(74) *Attorney, Agent, or Firm* — Procopio Cory Hargreaves and Savitch LLP

(57) ABSTRACT

The present disclosure relates to methods of collecting and testing bacteria containing samples from within the gastrointestinal (GI) tract of a subject. The methods may include disposing an ingestible device in the GI tract, collecting a bacteria-containing sample from the GI tract, selectively lysing eukaryotic cells in the sample by combining the sample with a dried reagent, exposing bacteria in the sample to resazurin in the ingestible device to produce resorufin, emitting light from the ingestible device, the emitted light being filtered through an optical filter to control for scatter so that the light interacts with the resorufin to produce fluorescence, and measuring a total fluorescence from the resorufin; or a rate of change of fluorescence from the resorufin as a function of time within the GI tract of the subject; and correlating the measured parameter to a number of viable bacterial cells in the sample.

39 Claims, 151 Drawing Sheets

Related U.S. Application Data

(60) Provisional application No. 62/583,768, filed on Nov. 9, 2017, provisional application No. 62/560,618, filed on Sep. 19, 2017, provisional application No. 62/545,157, filed on Aug. 14, 2017, provisional application No. 62/502,383, filed on May 5, 2017, provisional application No. 62/478,753, filed on Mar. 30, 2017, provisional application No. 62/434,320, filed on Dec. 14, 2016, provisional application No. 62/431,297, filed on Dec. 7, 2016.

(51) Int. Cl.
*A61B 5/03* (2006.01)
*A61B 5/145* (2006.01)
*A61B 5/1455* (2006.01)

(56) References Cited

U.S. PATENT DOCUMENTS

| | | |
|---|---|---|
| 3,315,660 A | 4/1967 | Abella |
| 3,485,235 A | 12/1969 | Felson |
| 4,223,680 A | 9/1980 | Jobsis |
| 4,239,040 A | 12/1980 | Hosoya |
| 4,292,961 A | 10/1981 | Kawashima |
| 4,425,117 A | 1/1984 | Hugeman |
| 4,507,115 A | 3/1985 | Kambara |
| 4,522,625 A | 6/1985 | Edgren |
| 4,573,447 A | 3/1986 | Thrash et al. |
| 4,844,076 A | 7/1989 | Lesho |
| 5,164,301 A | 11/1992 | Thompson et al. |
| 5,170,801 A | 12/1992 | Casper |
| 5,247,941 A | 9/1993 | Andresen |
| 5,279,607 A | 1/1994 | Schentag |
| 5,395,366 A | 3/1995 | Andrea |
| 5,604,531 A | 2/1997 | Iddan et al. |
| 5,858,001 A | 1/1999 | Tsals et al. |
| 5,951,538 A | 9/1999 | Joshi |
| 5,984,860 A | 11/1999 | Shan |
| 6,082,366 A | 7/2000 | Andra et al. |
| 6,344,027 B1 | 2/2002 | Goll |
| 6,355,449 B1 | 3/2002 | Chen |
| 6,428,469 B1 | 8/2002 | Iddan et al. |
| 6,576,429 B1 | 6/2003 | Hallgren |
| 6,632,216 B2 | 10/2003 | Houzego |
| 7,056,673 B2 | 6/2006 | Kamme et al. |
| 7,347,817 B2* | 3/2008 | Glukhovsky ...... A61B 1/00186 600/160 |
| 7,553,276 B2 | 6/2009 | Iddan |
| 7,611,480 B2 | 11/2009 | Levy |
| 7,684,840 B2 | 3/2010 | Palti |
| 7,797,033 B2 | 9/2010 | D'Andrea et al. |
| 8,185,185 B2 | 5/2012 | Gilreath |
| 8,206,285 B2 | 6/2012 | Blijevsky |
| 8,394,034 B2 | 3/2013 | Iddan |
| 8,515,507 B2 | 8/2013 | Rabinovitz |
| 8,540,623 B2 | 9/2013 | Blijevsky |
| 8,626,268 B2 | 1/2014 | Adler |
| 8,696,602 B2 | 4/2014 | Semler et al. |
| 8,911,368 B2 | 12/2014 | Rabinovitz et al. |
| 9,026,192 B2 | 5/2015 | Blit et al. |
| 9,131,842 B2 | 9/2015 | Old |
| 9,324,145 B1 | 4/2016 | Cherevatsky |
| 10,588,608 B2 | 3/2020 | Jones et al. |
| 10,610,104 B2 | 4/2020 | Pak |
| 10,835,152 B2* | 11/2020 | Jones ............ A61B 5/0086 |
| 2001/0035902 A1 | 11/2001 | Iddan et al. |
| 2002/0025534 A1 | 2/2002 | Goh |
| 2002/0039599 A1 | 4/2002 | Lin |
| 2002/0099310 A1 | 7/2002 | Kimchy et al. |
| 2002/0168295 A1 | 11/2002 | Cunningham |
| 2002/0198470 A1 | 12/2002 | Imran et al. |
| 2003/0117491 A1 | 6/2003 | Avni |
| 2003/0139661 A1 | 7/2003 | Kimchy |
| 2003/0191430 A1 | 10/2003 | Andrea et al. |
| 2004/0181344 A1 | 9/2004 | Stephanopoulos |
| 2004/0253304 A1 | 12/2004 | Gross et al. |
| 2004/0254455 A1 | 12/2004 | Iddan |
| 2005/0010168 A1 | 1/2005 | Kendall |
| 2005/0049462 A1 | 3/2005 | Kanazawa |
| 2005/0065441 A1 | 3/2005 | Glukhovsky |
| 2005/0148842 A1 | 7/2005 | Wang et al. |
| 2005/0158246 A1 | 7/2005 | Takizawa |
| 2005/0266074 A1 | 12/2005 | Zilberstein et al. |
| 2006/0057738 A1* | 3/2006 | Hall, Jr. ............ G01N 1/38 436/177 |
| 2006/0069317 A1 | 3/2006 | Horn et al. |
| 2006/0178557 A1 | 8/2006 | Mintchev |
| 2007/0027362 A1 | 2/2007 | Handa |
| 2007/0043320 A1 | 2/2007 | Kenany |
| 2007/0092401 A1 | 4/2007 | Liao et al. |
| 2007/0111276 A1 | 5/2007 | Lefevre |
| 2007/0161928 A1 | 7/2007 | Sprenkels |
| 2007/0276211 A1 | 11/2007 | Mir |
| 2007/0293736 A1 | 12/2007 | Casset |
| 2008/0027329 A1 | 1/2008 | Glukhovsky |
| 2008/0051633 A1 | 2/2008 | Blijevsky |
| 2008/0064923 A1 | 3/2008 | Rabinovitz |
| 2008/0146896 A1 | 6/2008 | Rabinowitz |
| 2008/0194912 A1 | 8/2008 | Trovato |
| 2008/0208077 A1 | 8/2008 | Iddan et al. |
| 2008/0234548 A1 | 9/2008 | Amit |
| 2008/0294023 A1 | 11/2008 | Rabinovitz et al. |
| 2009/0131784 A1 | 5/2009 | Betesh |
| 2009/0196854 A1* | 8/2009 | Clark ............ A61P 25/00 424/93.2 |
| 2010/0045786 A1 | 2/2010 | Kitamura |
| 2010/0111763 A1 | 5/2010 | Kahn et al. |
| 2010/0249645 A1 | 9/2010 | Semler et al. |
| 2010/0285475 A1 | 11/2010 | Palanisanny |
| 2011/0046458 A1 | 2/2011 | Pinedo |
| 2011/0092787 A1 | 4/2011 | Bulitta |
| 2011/0125007 A1 | 5/2011 | Steinberg |
| 2011/0125031 A1 | 5/2011 | Blit et al. |
| 2011/0236998 A1 | 9/2011 | Liscidini |
| 2011/0306055 A1 | 12/2011 | Haince |
| 2011/0313348 A1 | 12/2011 | Potter et al. |
| 2011/0319738 A1 | 12/2011 | Woodruff |
| 2012/0041465 A1 | 2/2012 | Shalon |
| 2012/0136209 A1 | 5/2012 | Kostenich et al. |
| 2012/0258473 A1 | 10/2012 | Moriya et al. |
| 2013/0013031 A1 | 1/2013 | Ben-Yehuda et al. |
| 2013/0018279 A1 | 1/2013 | Plante et al. |
| 2013/0022983 A1 | 1/2013 | Grifantini |
| 2013/0085414 A1 | 4/2013 | Yamatani |
| 2013/0158344 A1 | 6/2013 | Taniguchi |
| 2014/0087361 A1 | 3/2014 | Dobbelaer et al. |
| 2014/0113313 A1 | 4/2014 | Moreau |
| 2014/0128833 A1 | 5/2014 | Vogt |
| 2014/0186832 A1 | 7/2014 | Fuchs et al. |
| 2014/0206956 A1 | 7/2014 | Rabinovitz et al. |
| 2014/0271363 A1 | 9/2014 | Izmailov |
| 2014/0296666 A1 | 10/2014 | Rabinovitz et al. |
| 2014/0343451 A1 | 11/2014 | Pannell |
| 2015/0011874 A1 | 1/2015 | Amoako-Tuffour |
| 2015/0057548 A1 | 2/2015 | Kaufman |
| 2016/0033373 A1 | 2/2016 | Hill et al. |
| 2016/0038086 A1 | 2/2016 | Wrigglesworth |
| 2016/0066855 A1 | 3/2016 | Hyde |
| 2016/0114142 A1 | 4/2016 | Ziaie et al. |
| 2016/0213234 A1 | 7/2016 | Poon |
| 2016/0249793 A1* | 9/2016 | Wang ............ A61B 1/31 600/109 |
| 2017/0006202 A1 | 1/2017 | Otani |
| 2017/0106099 A1 | 4/2017 | Bellinger et al. |
| 2017/0246438 A1 | 8/2017 | Aran et al. |
| 2017/0258583 A1 | 9/2017 | McCawley |
| 2017/0296092 A1 | 10/2017 | Jones et al. |
| 2018/0049725 A1 | 2/2018 | Jones et al. |
| 2018/0052084 A1 | 2/2018 | Jones et al. |
| 2018/0070857 A1 | 3/2018 | Jones et al. |
| 2018/0160950 A1 | 6/2018 | Rabinovitz |
| 2018/0164221 A1 | 6/2018 | Singh |
| 2018/0206769 A1 | 7/2018 | Pak |

(56) References Cited

U.S. PATENT DOCUMENTS

| | | |
|---|---|---|
| 2018/0279908 A1 | 10/2018 | Jones et al. |
| 2020/0221954 A1 | 7/2020 | Singh et al. |
| 2020/0245897 A1 | 8/2020 | Jones et al. |

FOREIGN PATENT DOCUMENTS

| | | | |
|---|---|---|---|
| CN | | 102006823 A | 4/2011 |
| CN | | 103209632 | 7/2013 |
| EP | | 0108607 | 2/1983 |
| EP | | 0113103 | 7/1984 |
| EP | | 0113103 A1 | 7/1984 |
| EP | | 0149165 | 7/1985 |
| EP | | 0167335 | 1/1986 |
| EP | | 0167355 | 1/1986 |
| EP | | 1243524 | 9/2002 |
| EP | | 1530950 | 5/2005 |
| EP | | 1932462 | 6/2008 |
| EP | | 2057934 | 5/2009 |
| EP | | 2198885 | 6/2010 |
| EP | | 2999408 | 3/2016 |
| EP | | 3108810 | 12/2016 |
| JP | | 2005073888 | 3/2005 |
| JP | | 2013500815 | 1/2013 |
| JP | | 2015509744 | 4/2015 |
| JP | | 2012516186 A | 8/2016 |
| JP | | 2014516554 A | 6/2017 |
| KR | | 100931946 | 12/2009 |
| RU | | 2269343 | 2/2006 |
| WO | | 7900811 A1 | 10/1979 |
| WO | WO 2001045552 | | 6/2001 |
| WO | WO 2010016911 | | 2/2010 |
| WO | | 2010086859 A1 | 8/2010 |
| WO | WO 2010091926 | | 8/2010 |
| WO | WO 2010146588 | | 12/2010 |
| WO | WO 2011016002 | | 2/2011 |
| WO | WO 2012024034 | | 2/2012 |
| WO | | 2012168003 A1 | 12/2012 |
| WO | WO 2013088444 | | 6/2013 |
| WO | WO 2013120184 | | 8/2013 |
| WO | WO 2013180811 | | 12/2013 |
| WO | WO 2014102791 | | 7/2014 |
| WO | WO 2014182927 | | 11/2014 |
| WO | WO 2015059569 | | 4/2015 |
| WO | WO 2015099749 | | 7/2015 |
| WO | WO 2015147305 | | 10/2015 |
| WO | WO 2016054015 | | 4/2016 |
| WO | WO 2017004000 | | 1/2017 |
| WO | WO 2016049602 | | 3/2018 |
| WO | WO 2018050647 | | 3/2018 |
| WO | WO 2018183711 | | 10/2018 |

OTHER PUBLICATIONS

Bueno et al. The Excited-State Interaction of Resazurin and Resorufin With Amines in Aqueous Solutions. Photophysics and Photochemical Reaction; Photochemistry and Photobiology, vol. 76. No. 4, pp. 385-390. (Year: 2002).*

Anselmo et al., "Non-invasive delivery strategies for biologies", Nature Reviews, Drug Discovery, Jan. 2019, 18:19-40.

Aran et al., "An oral microjet vaccination system elicits antibody production in rabbits," Sci. Transl. Med., Mar. 2017, 9:eaaf6413, 10 pages.

Bao et al., "Motion estimation of the endoscopy capsule using region-based kernel SVM classifier," IEEE International Conference on Electro-Information Technology , EIT 2013, May 2013, 5 pages.

Barolet et al., "Current trends in needle-free jet injection: an update," Clinical, Cosmetic and Investigational Dermatology, May 2018, 11:231-238.

Battula et al., "A Miniature Shock Wave Driven Micro-Jet Injector for Needle-Free Vaccine/Drug Deliveiy," Biotechnology and Bioengineering, Nov. 2016, 113(11):2507-2512.

Chen et al., "Developing assessment system for wireless capsule endoscopy videos based on event detection," Proceedings of SPIE, Mar. 2009, 7260:72601G-1-72601G-11.

Dingle et al., "Stable and Noncompetitive RNA Internal Control for Routine Clinical Diagnostic Reverse Transcription—PCR," Journal of Clinical Microbiology, Mar. 2004, 42(3):1003-1011.

EP Office Action in European Appln. No. 17825673.1, dated Jun. 23, 2020, 11 pages.

Hunter et al., "Aerosol delivery of Virus-like Particles to the genital tract induces local and systemic antibody responses," Vaccine, Jun. 2011, 29(28):4584-4592.

Iversen et al., "An innate antiviral pathway acting before interferons at epithelial surfaces," Nature Immunology, Feb. 2016, 17(2):150-158, 12 pages.

Jacques, "Optical properties of biological tissues: a review," Phys., Med. Biol., IPEM, May 2013, 58(11):R37-R61, 28 pages.

Kale et al., "Needle free injection technology—An overview," Innovations in Pharmacy, Jan. 2014, 5(1):448, 10 pages.

Kane et al., "Fecal Lactoferrin Is a Sensitive and Specific Marker in Identifying Intestinal Inflammation," The American Journal of Gastroenterology, Jun. 2003, 98(6):1309-1314.

Kostic et al., "The Gut Microbiome and Disease," Gastroenterology, May 2014, 146(6):1489-1499.

Lambert et al., "Autonomous telemetric capsule to explore the small bowel," Med Biol Eng Comput, Mar. 1991, 29(2):191-196.

Lee et al., "Automatic Classification of Digestive Organs in Wireless Capsule Endoscopy Videos," Proceedings of the 2007 ACM Symposium on Applied Computing, Mar. 2007, 1041-1045.

Lehmann et al.,"The role and utility of faecal markers in inflammatory bowel disease," Therapeutic Advances in Gastroenterology, 2015, 8(1):23-36.

Li et al., "Outlier detection and removal improves accuracy of machine learning approach to multispectral burn diagnostic imaging," J. Biomed. Opt., Dec. 2015, 20(12):121305, 10 pages.

Lin et al., "Scintigraphy Demonstrates High Rate of False-positive Results From Glucose Breath Tests for Small Bowel Bacterial Overgrowth," Clinical Gastroenterol Hepatol, Feb. 2016, 14(2):203-208.

Lo et al., "The use of carbon dioxide in gastrointestinal endoscopy," Gastrointestinal Endoscopy, Mar. 2016, 83(5):857-865.

Pan et al., "A comparison of conventional methods for the quantification of bacterial cells after exposure to metal oxide nanoparticles," BMC Microbiology, Aug. 2014, 14(222):1-11.

PCT International Search Report and Written Opinion in International Application No. PCT/US2017/065139, dated May 2, 2018, 20 pages.

PCT International Search Report and Written Opinion in International Application No. PCT/US2017/065178, dated Apr. 10, 2018, 17 pages.

PCT Invitation to Pay Additional Fees in International Application No. PCT/US2017/065139, dated Mar. 9, 2018.

Rao et al., "Small Intestinal Bacterial Overgrowth: Clinical Features and Therapeutic Management," Clin Transl Gastroenterol., Oct. 2019, 10(10): e00078, 1-14.

Reuter, "Culture media for enterococci and group D-streptococci," Int. J. Food Microbiol., 1992, 17(2):101-111.

Rezaie et al., "Hydrogen and Methane-Based Breath Testing in Gastrointestinal Disorders: The North American Consensus," Am J Gastroenterol, May 2017, 112(5):775-784, 10 pages.

Saad et al., "Breath testing for small intestinal bacterial overgrowth: maximizing test accuracy," Clinical Gastroenterology and Hepatology, Dec. 2014, 12(12):1964-1972, 9 pages.

Sandberg et al., "Pros and cons of using resazurin staining for quantification of viable *Staphylococcus aureus* biofilms in a screening assay," J. Microbiol. Med., Jul. 2009, 78(1):104-106.

Sanschagrin et al., "Next-generation Sequencing of 16S Ribosomal RNA Gene Amplicons," Journal of Visualized Experiments, Aug. 2014, 90:51709, 6 pages.

Sartor et al., "Intestinal Microbes in Inflammatory Bowel Diseases," The American Journal of Gastroenterology Supplements, 2012, 1(1):15-21.

(56) References Cited

OTHER PUBLICATIONS

Singh et al., "Sa1717—Development of a Swallowable Diganostic Capsule to Monitor Gastrointestinal Health," AGA Abstracts, May 2019, 156(6): S-376.
Wright et al., "Recent Advances in Characterizing the Gastrointestinal Microbiome in Crohn's Disease: A Systematic Review," Inflammatory Bowel Disease Journal, Jun. 2015, 21(6):1219-1228.
Yu et al., "Combined oro-caecal scintigraphy and lactulose hydrogen breath testing demonstrate that breath testing detects oro-caecal transit, not small intestinal bacterial overgrowth in patients with IBS," Gut, Mar. 2011, 60(3):334-340, 8 pages.
Office Action in Application No. 2019-530427, dated Dec. 7, 2021, Japan Patent Office.
Office Action in Application No. 201780076327.9, dated Apr. 25, 2022, National Intellectual Property Administration of the People's Republic of China.
Office Action in Application No. 201780076327.9, dated Oct. 27, 2021, National Intellectual Property Administration of the People's Republic of China.

\* cited by examiner

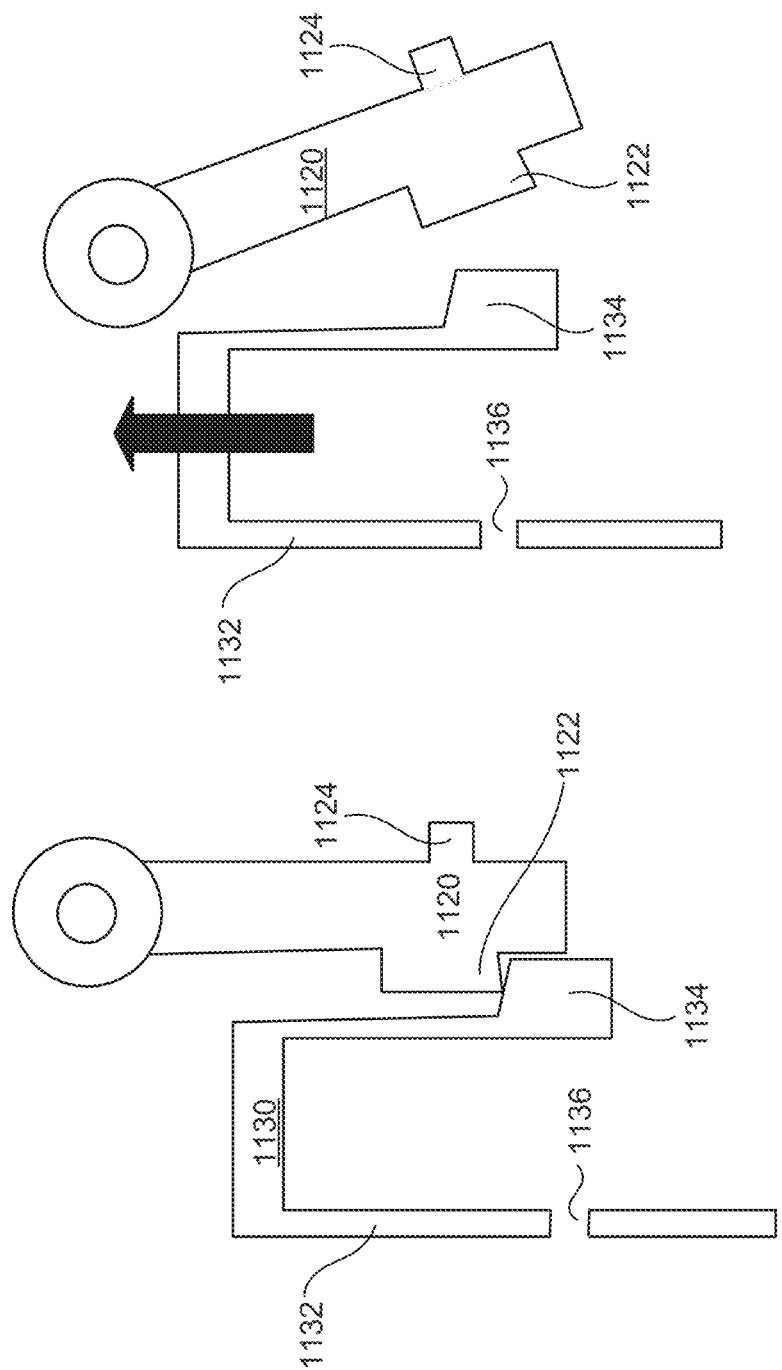

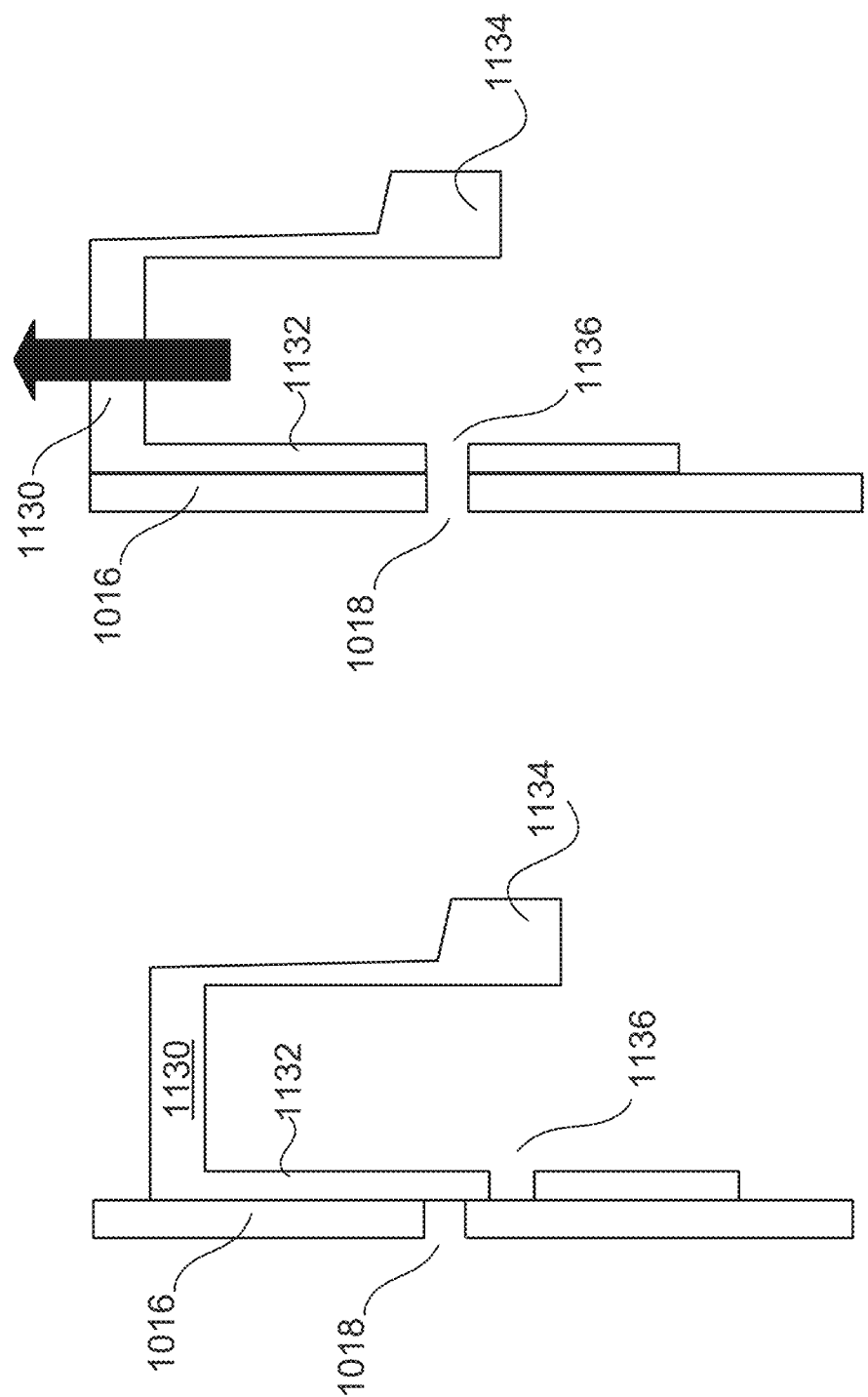

|   | 1 | 2 | 3 | 4 | 5 | 6 | 7 | 8 | 9 | 10 | 11 | 12 |
|---|---|---|---|---|---|---|---|---|---|----|----|----|
| A | 10^7 | | | | | | | | | | | |
| B | 10^6 | | | | | | | | | | | |
| C | 10^5 | | | | | | | | | | | |
| D | 10^4 | | | | | | | | | | | |
| E | 10^7 | | | | | | | | | | | |
| F | 10^6 | | | | | | | | | | | |
| G | 10^5 | | | | | | | | | | | |
| H | 10^4 | | | | | | | | | | | |
|   | 1.4mM | 3.0mM | 5.5mM | 0.5% | 1.00% | 1.5% | 6.5 | 7 | 810^2 | 10^3 | PBS | Cont |
|   | Bile Acid | | | Mucin | | | pH | | C. albicans | | | |

Rows A–D: E. coli; Rows E–H: S. aureus

FIG. 75C

| | 1 | 2 | 3 | 4 | 5 | 6 | 7 | 8 | 9 | 10 | 11 | 12 | |
|---|---|---|---|---|---|---|---|---|---|---|---|---|---|
| A | | | | | | | | | | | | | |
| B | | 10^7 | 10^7 | 10^7 | 10^7 | 10^7 | | | | | | | 90 ul jejunal/FaSSif plus 10 ul spike O/N |
| C | | 10^6 | 10^6 | 10^6 | 10^6 | 10^6 | | | | | | | 90 ul jejunal/FaSSif plus 10 ul spike 10^7 |
| D | 10^5 | 10^5 | 10^5 | 10^5 | 10^5 | 10^5 | | | | | | | 90 ul jejunal/FaSSif plus 10 ul spike 10^6 |
| E | | 10^4 | 10^4 | 10^4 | 10^4 | 10^4 | | | | | | | 90 ul jejunal/FaSSif plus 10 ul spike 10^5 |
| F | | 0 | 0 | 0 | 0 | 0 | | | | | | | 100 ul jejunal/FaSSif |
| G | | | | | | | | | | | | | |
| H | | | | | | | | | | | | | | jejunal sample   FaSSIF jejunal Sample MDB 115-01-050.1

FIG. 79A

| Simulated Matrix | | | |
|---|---|---|---|
| Failure modes | 6 | | |
| SIBO+ | 46 | | |
| SIBO- | 34 | | |
| Variable (SIBO-) | 10 | | |
| Total samples | 96 | | |
| | | Truth | |
| | | SIBO+ | SIBO- |
| Test | SIBO+ | 40 | 6 |
| | SIBO- | 0 | 34 |
| | *without variables as SIBO- | | |
| | **without failure modes | | |
| | N | 80 | 80 |
| | PPV | 86.96% | |
| | NPV | 100.00% | |
| | P Test | 92.50% | |
| | Total Agreement | 100.00% | |
| | Sensitivity | 100.00% | |
| | Specificity | 85.00% | |
| | Pe | 0.50000 | |
| | Kappa | 0.850 | |
| | | Truth | |
| | | SIBO+ | SIBO- |
| Test | SIBO+ | 40 | 6 |
| | SIBO- | 6 | 38 |
| | *includes variable as SIBO- | | |
| | **without failure modes | | |
| | N | 90 | 90 |
| | PPV | 86.96% | |
| | NPV | 86.36% | |
| | P Test | 86.67% | |

FIG. 80A

| | | Truth | |
|---|---|---|---|
| | Total Agreement | 93.33% | |
| | Sensitivity | 86.96% | |
| | Specificity | 86.36% | |
| | Pe | 0.50025 | |
| | Kappa | 0.733 | |
| | | | |
| | | Truth | |
| | | SIBO+ | SIBO- |
| Test | SIBO+ | 41 | 7 |
| | SIBO- | 6 | 38 |
| | *includes variable as SIBO- | | |
| | **includes failure modes | | |
| | N | 96 | 92 |
| | PPV | 85.42% | |
| | NPV | 86.36% | |
| | P Test | 85.87% | |
| | Total Agreement | 93.48% | |
| | Sensitivity | 87.23% | |
| | Specificity | 84.44% | |
| | Pe | 0.50047 | |
| | Kappa | 0.717 | |

| Jejunal Matrix | | | |
|---|---|---|---|
| Failure modes | | 6 | |
| SIBO+ | | 41 | |
| SIBO- | | 34 | |
| Variable (SIBO-) | | 10 | |
| Total samples | | 91 | |
| | | | |
| | | Truth | |
| | | SIBO+ | SIBO- |
| Test | SIBO+ | 41 | 6 |
| | SIBO- | 3 | 31 |
| | *without variables as SIBO- | | |
| | **without failure modes | | |
| | N | 75 | 81 |
| | PPV | 87.23% | |
| | NPV | 91.18% | |
| P Test | | 88.89% | |
| Total Agreement | | 96.30% | |
| Sensitivity | | 93.18% | |
| Specificity | | 83.78% | |
| Pe | | 0.50693 | |
| Kappa | | 0.775 | |
| | | | |
| | | Truth | |
| | | SIBO+ | SIBO- |
| Test | SIBO+ | 41 | 6 |
| | SIBO- | 9 | 35 |
| | *includes variable as SIBO- | | |
| | **without failure modes | | |
| | N | 85 | 91 |
| | PPV | 87.23% | |
| | NPV | 79.55% | |
| P Test | | 83.52% | |

FIG. 80B

Staphylococcus aureus titration
Buffer B
March 15th, 2016 CF

|  | S.Aureus HC2-Ab2 | | S.Aureus HC2-Ab6 | | S.Aureus HC10-Ab10 | | S.Aureus AB10-Ab10 | |
|---|---|---|---|---|---|---|---|---|
|  | Mean | SEM | Mean | SEM | Mean | SEM | Mean | SEM |
| 9.6e1 | 1.053 | 0.020 | 1.064 | 0.023 | 1.029 | 0.033 | 0.901 | 0.031 |
| 9.6e2 | 1.057 | 0.015 | 1.083 | 0.022 | 1.129 | 0.043 | 0.903 | 0.016 |
| 9.6e3 | 1.091 | 0.013 | 1.101 | 0.025 | 1.133 | 0.070 | 1.029 | 0.051 |
| 9.6e4 | 1.143 | 0.018 | 1.130 | 0.029 | 1.245 | 0.021 | 1.128 | 0.028 |
| 9.6e5 | 1.493 | 0.025 | 1.558 | 0.037 | 1.521 | 0.024 | 1.179 | 0.038 |
| 9.6e6 | 5.916 | 0.119 | 9.360 | 0.207 | 2.284 | 0.094 | 1.416 | 0.067 |

Assay : 10 µL S.Aureus dilutions
  20 µL of 0.3nM Biotin-Ab/40 µg/mL AlphaLISA Ab mix
  60 min at 37°C
  20 µL of 10µg/mLSA-Donor beads
  30 min at 37°C

|  | E. Coli HC2-Ab2 | | E. Coli HC2-Ab6 | | E. Coli HC10-Ab10 | | E. Coli AB10-Ab10 | |
|---|---|---|---|---|---|---|---|---|
|  | Mean | SEM | Mean | SEM | Mean | SEM | Mean | SEM |
| No Bacteria | 1.000 | 0.017 | 1.000 | 0.019 | 1.000 | 0.024 | 1.000 | 0.072 |
| 5e2 | 0.997 | 0.048 | 1.013 | 0.019 | 1.042 | 0.023 | 1.039 | 0.073 |
| 5e3 | 1.009 | 0.014 | 1.015 | 0.019 | 0.960 | 0.040 | 0.968 | 0.081 |
| 5e4 | 1.022 | 0.027 | 1.049 | 0.015 | 0.996 | 0.023 | 1.064 | 0.057 |
| 5e5 | 1.048 | 0.018 | 1.051 | 0.019 | 1.246 | 0.042 | 1.153 | 0.065 |
| 5e6 | 1.085 | 0.021 | 1.095 | 0.015 | 3.152 | 0.054 | 2.007 | 0.126 |
| 5e7 | 3.035 | 0.060 | 5.110 | 0.101 | 2.358 | 0.040 | 1.332 | 0.083 |
| 5e8 | 1.044 | 0.064 | 2.032 | 0.157 | 0.250 | 0.033 | 0.325 | 0.019 |

Assay: 10 μL E. coli Dilutions
20 μL of 3 nM Biotin-Ab/40 μg/mL AlphaLISA Ab mix
60 min at 37° C
20 μL of 10 μg/mL SA-Donor Beads
30 min at 37° C Assay: 10 μL of E.Coli or S.Aureus
10 μL of LBP mix (Bio-LBP and His-LBP)
30-min Incubation at 37C
10 μL of Ni2+Acceptors (20μ g/mL Final)
30-min Incubation at 37C
20 μL of SA-Donor (20 μg/mL Final)
30-min Incubation at 37C Assay: 10 μL of E.Coli or S.Aureus
10 μL of His-LBP
30-min Incubation at 37C
10 μL of Ni2+Acceptors (20μ g/mL Final)
30-min Incubation at 37C
20 μL of Ni2+ Donor (20μ g/mL Final)
30-min Incubation at 37C 1.4x10$^7$ beads.mL    1.4x10$^6$ beads.mL

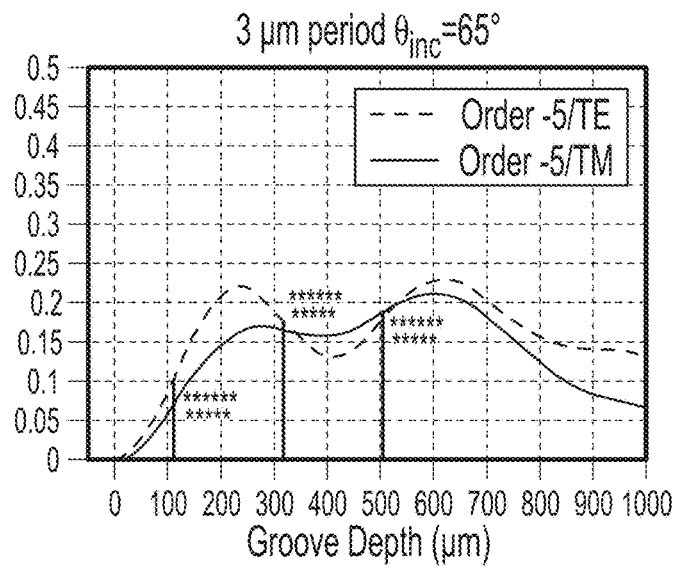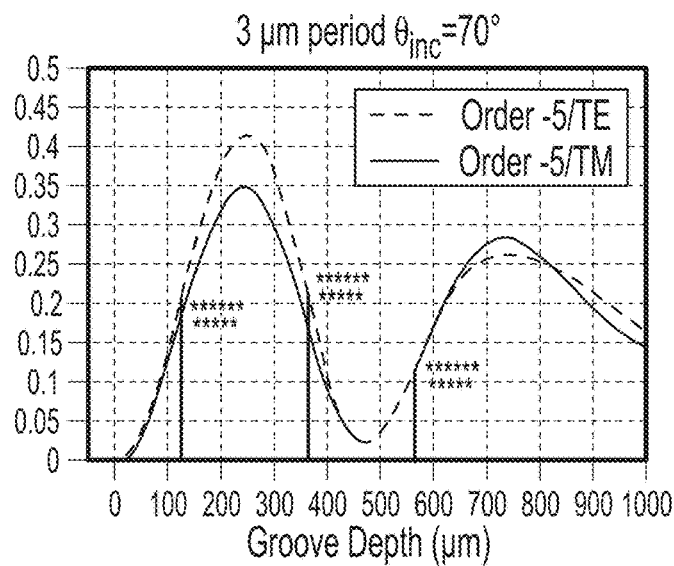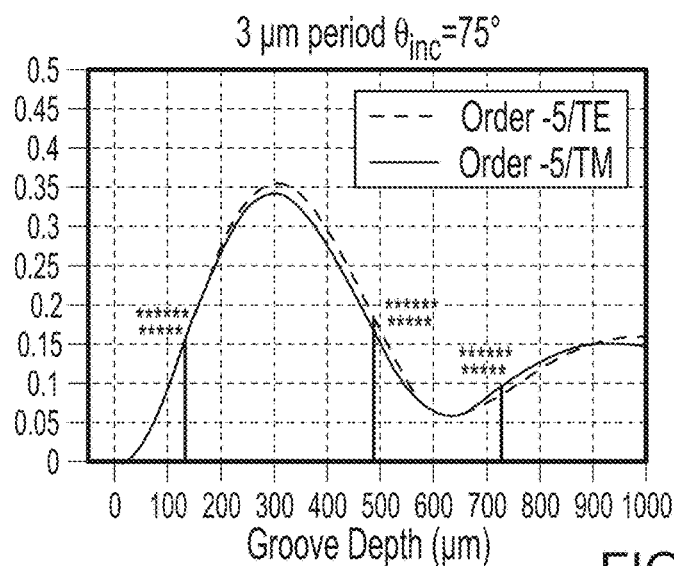
FIG. 129 (Cont.)

| | B. vulgatus 8482 | | | B. vulgatus 29327 | | | C. butyricum 19398 | | |
|---|---|---|---|---|---|---|---|---|---|
| | CFU/mL | Mean Max Signal | SD | CFU/mL | Mean Max Signal | SD | CFU/mL | Mean Max Signal | SD |
| 24 hrs | 7.54 | 6.82 | 0.11 | 7.30 | 10.14 | 2.80 | 3.55 | 5.58 | 0.06 |
| 1:10 | 6.40 | 3.57 | 0.30 | 5.19 | 4.28 | 0.81 | 2.18 | 3.84 | 0.83 |
| 6 hrs | 6.78 | 3.96 | 0.75 | 6.60 | 4.76 | 0.35 | 3.85 | 4.33 | 0.19 |
| 1:10 | 5.79 | 3.46 | 1.05 | 5.60 | 3.65 | 0.74 | 3.08 | 4.01 | 0.35 |
| 4 hrs | 6.90 | 3.99 | 1.02 | 6.54 | 4.46 | 0.07 | 4.65 | 4.20 | 0.14 |
| 1:10 | 6.31 | 3.55 | 0.94 | 5.78 | 3.60 | 0.83 | 3.28 | 4.26 | 0.16 |
| 2 hrs | 6.78 | 3.99 | 1.33 | 5.78 | 3.75 | 1.01 | 6.30 | 3.75 | 0.67 |

FIG. 131A

| | C. perfringens 13124 | | | C. sporogenes 7955 | | | Clinical | | |
|---|---|---|---|---|---|---|---|---|---|
| | CFU/mL | Mean Max Signal | SD | CFU/mL | Mean Max Signal | SD | CFU/mL | Mean Max Signal | SD |
| 24 hrs | 7.15 | 8.29 | 0.52 | 7.60 | 10.67 | 1.72 | 6.48 | 41.04 | 10.47 |
| 1:10 | 6.30 | 5.05 | 0.00 | 6.45 | 6.26 | 0.22 | 5.53 | 9.84 | 0.33 |
| 6 hrs | 5.60 | 886.76 | 8.19 | 5.70 | 4.00 | 0.76 | 5.18 | 6.14 | 1.59 |
| 1:10 | 7.40 | 6.26 | 0.21 | 5.00 | 4.02 | 0.38 | 3.54 | 3.46 | 1.23 |
| 4 hrs | 8.93 | 137.77 | 3.54 | 6.11 | 4.30 | 0.33 | 5.41 | 6.27 | 1.57 |
| 1:10 | 7.18 | 6.60 | 0.50 | 5.18 | 3.76 | 0.71 | 4.40 | 3.39 | 0.84 |
| 2 hrs | 7.95 | 1269.85 | 28.17 | 6.10 | 3.73 | 0.88 | 5.04 | 5.35 | 1.20 |

FIG. 131B

FIG. 132A 330 min

| CFU/mL | C. butyricum 19398 (8 hr) 2 | CFU/mL | B. vulgatus 8482 3 | CFU/mL | C. sporogenes 7955 5 | CFU/mL | RNA 6 Clinical Anaerobe 9 | CFU/mL | RNA 5 Clinical Anaerobe 10 | CFU/mL | F1:100 O/N 11 |
|---|---|---|---|---|---|---|---|---|---|---|---|
| 10^5 | 16.14 | 10^8 | 1332.38 | 10^8 | 917.61 | 10^8 | 98.72 | 10^8 | 408.09 | 10^8 | 117.67 |
| 10^4 | 8.07 | 10^7 | 21.03 | 10^7 | 102.09 | 10^7 | 300.64 | 10^7 | 116.03 | 10^7 | 968.50 |
| 10^3 | 4.23 | 10^6 | 6.94 | 10^6 | 8.32 | 10^6 | 56.87 | 10^6 | 13.67 | 10^6 | 121.69 |
| 0 | 5.60 | 10^5 | 5.71 | 10^5 | 5.67 | 10^5 | 14.03 | 10^5 | 6.27 | 10^5 | 46.49 |
| 0 | 5.57 | 10^3 | 3.85 | 10^4 | 5.26 | 10^4 | 6.06 | 10^4 | 5.69 | 10^4 | 30.02 |
| 0 | 3.50 | 0 | 5.40 | 10^3 | 5.56 | 10^3 | 6.04 | 10^3 | 5.65 | 10^3 | 15.80 |
| 0 | 5.76 | 0 | 5.46 | 10^2 | 5.77 | 10^2 | 5.78 | 10^2 | 5.81 | 10^2 | 6.37 |
| CONT | 3.87 | CONT | 4.32 | CONT | 5.59 | CONT | 5.62 | CONT | 6.29 | CONT | 6.41 |

FIG. 132B 20 hours

| CFU/mL | C. butyricum 19398 (8 hr) 2 | CFU/mL | B. vulgatus 8482 3 | CFU/mL | C. sporogenes 7955 5 | CFU/mL | RNA 6 Clinical Anaerobe 9 | CFU/mL | RNA 5 Clinical Anaerobe 10 | CFU/mL | F1:100 O/N 11 |
|---|---|---|---|---|---|---|---|---|---|---|---|
| 10^5 | 10.39 | 10^8 | 1332.38 | 10^8 | 917.61 | 10^8 | 98.72 | 10^8 | 408.09 | 10^8 | 117.67 |
| 10^4 | 4.39 | 10^7 | 7.50 | 10^7 | 102.09 | 10^7 | 300.64 | 10^7 | 116.03 | 10^7 | 968.50 |
| 10^3 | 2.13 | 10^6 | 3.50 | 10^6 | 3.72 | 10^6 | 56.87 | 10^6 | 5.57 | 10^6 | 121.69 |
| 0 | 3.04 | 10^5 | 3.15 | 10^5 | 3.12 | 10^5 | 5.23 | 10^5 | 3.36 | 10^5 | 46.49 |
| 0 | 3.05 | 10^3 | 2.05 | 10^4 | 3.04 | 10^4 | 3.28 | 10^4 | 3.16 | 10^4 | 30.02 |
| 0 | 1.92 | 0 | 3.01 | 10^3 | 3.07 | 10^3 | 3.28 | 10^3 | 3.02 | 10^3 | 22.86 |
| 0 | 3.04 | 0 | 3.04 | 10^2 | 3.10 | 10^2 | 3.07 | 10^2 | 3.10 | 10^2 | 17.45 |
| CONT | 2.12 | CONT | 2.39 | CONT | 2.61 | CONT | 3.04 | CONT | 3.12 | CONT | 3.17 |

FIG. 132C

END point

| CFU/mL | C. butyricum 19398 (8 hr) 2 | CFU/mL | B. vulgatus 8482 3 | CFU/mL | C. sporogenes 7955 5 | CFU/mL | RNA 6 Clinical Anaerobe 9 | CFU/mL | RNA 5 Clinical Anaerobe 10 | CFU/mL | F1:100 O/N 11 |
|---|---|---|---|---|---|---|---|---|---|---|---|
| 10^5 | 31.04 | 10^8 | 71.48 | 10^8 | 140.33 | 10^8 | 14.87 | 10^8 | 91.32 | 10^8 | 24.43 |
| 10^4 | 6.13 | 10^7 | 3.73 | 10^7 | 45.45 | 10^7 | 96.29 | 10^7 | 49.40 | 10^7 | 8.63 |
| 10^3 | 4.63 | 10^6 | 6.06 | 10^6 | 5.78 | 10^6 | 33.86 | 10^6 | 5.63 | 10^6 | 133.04 |
| 0 | 4.32 | 10^5 | 5.26 | 10^5 | 4.43 | 10^5 | 6.47 | 10^5 | 5.10 | 10^5 | 20.95 |
| 0 | 4.16 | 10^3 | 4.37 | 10^4 | 5.52 | 10^4 | 5.23 | 10^4 | 5.67 | 10^4 | 41.11 |
| 0 | 3.99 | 0 | 4.13 | 10^3 | 5.56 | 10^3 | 5.43 | 10^3 | 5.45 | 10^3 | 11.91 |
| 0 | 4.39 | 0 | 4.36 | 10^2 | 4.37 | 10^2 | 5.32 | 10^2 | 4.52 | 10^2 | 1.56 |
| CONT | 6.05 | CONT | 5.81 | CONT | 6.03 | CONT | 5.71 | CONT | 5.69 | CONT | 4.51 |

METHODS FOR COLLECTING AND TESTING BACTERIA CONTAINING SAMPLES FROM WITHIN THE GASTROINTESTINAL TRACT

CROSS-REFERENCE TO RELATED APPLICATIONS

This application is a continuation of U.S. patent application Ser. No. 15/835,237, entitled "Gastrointestinal Tract Detection Methods, Devices and Systems," filed on Dec. 7, 2017, which claims priority to the following U.S. Patent Applications: U.S. Ser. No. 62/431,297, entitled "Compositions, Methods, and Devices for Bacteria Detection and Quantitation," filed on Dec. 7, 2016; U.S. Ser. No. 62/434,320, entitled "An Ingestible Device for Sampling, Diluting and Culturing a Biological Sample," filed on Dec. 14, 2016; U.S. Ser. No. 62/502,383, entitled "Devices for Analyte Detection" filed on May 5, 2017; U.S. Ser. No. 62/560,618, entitled "Ingestible Devices and Related Systems and Methods," filed on Sep. 19, 2017; U.S. Ser. No. 62/478,753, entitled "Treatment of a Disease of the Gastrointestinal Tract with an IL-6R Inhibitor," filed on Mar. 30, 2017; U.S. Ser. No. 62/545,157, entitled "Treatment of a Disease of the Gastrointestinal Tract with an Immunosuppressant," filed on Aug. 14, 2017; and U.S. Ser. No. 62/583,768, entitled "Treatment of a Disease of the Gastrointestinal Tract with a TNF Inhibitor," filed on Nov. 9, 2017.

INCORPORATION BY REFERENCE

The application incorporates by reference the following U.S. patent applications: U.S. Ser. No. 62/431,297, entitled "Compositions, Methods, and Devices for Bacteria Detection and Quantitation," filed on Dec. 7, 2016; U.S. Ser. No. 62/434,320, entitled "An Ingestible Device for Sampling, Diluting and Culturing a Biological Sample," filed on Dec. 14, 2016; U.S. Ser. No. 62/502,383, entitled "Devices for Analyte Detection" filed on May 5, 2017; U.S. Ser. No. 62/560,618, entitled "Ingestible Devices and Related Systems and Methods," filed on Sep. 19, 2017; U.S. Ser. No. 62/478,753, entitled "Treatment of a Disease of the Gastrointestinal Tract with an IL-6R Inhibitor," filed on Mar. 30, 2017; U.S. Ser. No. 62/545,157, entitled "Treatment of a Disease of the Gastrointestinal Tract with an Immunosuppressant," filed on Aug. 14, 2017; U.S. Ser. No. 62/583,768, entitled "Treatment of a Disease of the Gastrointestinal Tract with a TNF Inhibitor," filed on Nov. 9, 2017; U.S. Ser. No. 14/460,893, entitled "Ingestible Medical Device," and filed Aug. 15, 2014; U.S. Ser. No. 15/514,413, entitled "Electromechanical Pill Device with Localization Capabilities," and filed Mar. 24, 2017; U.S. Ser. No. 15/680,400, entitled "Systems and Methods for Obtaining Samples using Ingestible Devices," filed on Aug. 18, 2017; U.S. Ser. No. 15/680,430, entitled "Sampling Systems and Related Materials and Methods," filed on Aug. 18, 2017; U.S. Ser. No. 15/699,848, entitled "Electromechanical Ingestible Delivery of a Dispensable Substance," filed on Sep. 8, 2017; U.S. Ser. No. 62/480,187, entitled "Localization Systems and Methods for an Optoelectromechanical Pill Device," filed on Mar. 31, 2017; and U.S. Ser. No. 62/540,873, entitled "Localization Systems and Methods for an Ingestible Device," filed on Aug. 3, 2017.

FIELD

The disclosure relates to gastrointestinal (GI) tract detection methods, devices and systems.

BACKGROUND

The GI tract can contain information regarding an individual's body.

SUMMARY

The disclosure relates to gastrointestinal (GI) tract detection methods, devices and systems.

The technology disclosed herein allows for rapid, real time assessment of information relating to a subject (e.g., information relating to the subject's GI tract). In some embodiments, the information can relate to the presence and/or quantity of an analyte of interest (e.g., an analyte of interest in the GI tract of a subject). In certain embodiments, the technology can be implemented using an ingestible device that may be used to take one or more samples of a subject (e.g., one or more samples in one or more locations of the GI tract of the subject). Such a device can be implemented in an autonomous fashion. For example, information can be exchanged between the ingestible device when present in the subject (in vivo) and outside the subject (ex vivo). In some embodiments, the information can be exchanged in real time. In certain embodiments, the technology can be used to help determine whether a subject has a given GI disorder. In some embodiments, the technology can be used to help determine a treatment protocol and/or to monitor or assess efficacy of a treatment protocol for a subject (e.g., a GI disorder treatment protocol for the subject). The detection techniques disclosed herein can be used individually or in any combination, as desired. In some embodiments, an ingestible device is configured such that different detection techniques are performed in different chambers (e.g., sample chambers) of an ingestible device. Optionally, multiple different detection methods may be used to provide complementary information regarding a subject (e.g., provide information relating to the subject's GI tract) and/or supplementary information regarding a subject e.g., provide information relating to the subject's GI.

In one aspect, provided herein a method, comprising transferring a fluid sample from the gastrointestinal (GI) tract or from the reproductive tract of a subject into a first dilution chamber of a device in vivo; and combining the fluid sample and a first dilution fluid in the first dilution chamber to produce a first diluted sample. In some embodiments, the device comprises a plurality of dilution chambers; and for each at least some of the plurality of dilution chambers, the method comprises: transferring a fluid sample into the dilution chamber; and combining the fluid sample and the first dilution fluid in the first dilution chamber to produce a diluted sample. In some embodiments, the method further comprises combining diluted samples from at least two different dilution chambers to provide a further diluted sample.

In some embodiments, the device is an ingestible device. In some embodiments, the method further comprises orally administering the device to the subject. In some embodiments, the method further comprises introducing the device into the reproductive tract of the subject.

In some embodiments, the first dilution fluid comprises a sterile medium.

In some embodiments, the method further comprises culturing the diluted sample to produce a cultured sample. In some embodiments, the culturing is performed in vivo. In some embodiments, the culturing is performed ex vivo.

In some embodiments, the method further comprises recovering the device ex vivo. In some embodiments, the method further comprises removing the sample from the device.

In some embodiments, the method further comprises detecting an analyte in the sample. In some embodiments, the detecting occurs in vivo. In some embodiments, the analyte comprises a cell. In some embodiments, the cell comprises a bacteria. In some embodiments, the cell comprises a eukaryotic cell. In some embodiments, the eukaryotic cell is selected from the group consisting of an epithelial cell and a peripheral blood mononuclear cell (PBMC).

In some embodiments, the device comprises a port, a valve and/or a pump; and transferring the fluid sample to the dilution first chamber comprises controlling the port, valve and/or pump.

In some embodiments, the device comprises a port having an open position and a first position; in the open position, the port is in fluid communication with the GI tract or with the reproductive tract of the subject, and the fluid sample enters the port; and in the first position, the port is in fluid communication with the first dilution chamber and the fluid sample combines with the first dilution fluid. In some embodiments, when the port is in its open position, the fluid sample enters the port; and when the port is in its first position, the fluid sample combines with the first dilution fluid to provide a first dilution. In some embodiments, the port has a second position in which the port is in fluid communication with a second dilution chamber comprising a fluid; and the method further comprises moving the port from its first position to its second position so that the first dilution combines with the fluid in the second chamber to provide a second dilution. In some embodiments, before the port moves from its first position to its second position, the fluid in the second dilution chamber comprises a sterile medium; and the second dilution comprises the sterile medium. In some embodiments, the method comprises moving in the port sequentially from its open position to its first and then second positions, to sequentially provide the first and then second dilutions. In some embodiments, the port has a third position in which the port is in fluid communication with a third dilution chamber which comprises a fluid; and the method further comprises moving the port from its second position to its third position so that the second dilution combines with the fluid in the third chamber to provide a third dilution. In some embodiments, the method comprises moving in the port sequentially from its open position to its first, second and then third positions, to sequentially provide the first, second and then third dilutions. In some embodiments, the port has a fourth position in which the port is in fluid communication with a fourth dilution chamber which comprises a fluid; and the method further comprises moving the port from its third position to its fourth position so that the third dilution combines with the fluid in the fourth chamber to provide a fourth dilution. In some embodiments, the method comprises moving in the port sequentially from its open position to its first, second, third and then fourth positions, to sequentially provide the first, second, third and fourth dilutions.

In some embodiments, the device further comprises a microcontroller configured to control an actuator configured to rotate the port. In some embodiments, the microcontroller is configured to control a rotatable element which is configured to move the port.

In some embodiments, a ratio of a volume of the fluid sample to a volume of the dilution fluid is from about 1:1 and about 1:1000. In some embodiments, the ratio is from about 1:1 and to about 1:100. In some embodiments, the ratio is from about 1:1 to about 1:20. In some embodiments, the ratio is from about 1:1 to about 1:10.

In some embodiments, the first dilution fluid comprises an anti-fungal agent. In some embodiments, the anti-fungal agent comprises amphotericin B.

In some embodiments, the first dilution fluid comprises a sterile medium. In some embodiments, the first dilution medium comprises a preservative. In some embodiments, the sterile medium comprise an agent that inhibits growth of a cell and/or an agent that promotes the growth of a cell. In some embodiments, the cell comprises a bacterium. In some embodiments, the sterile medium is selective for one or more types of bacteria. In some embodiments, the medium is selective for Gram-negative bacteria.

In some embodiments, the first dilution fluid comprises sterile media, and the sterile media comprise an antibiotic.

In some embodiments, the method further comprises culturing the first diluted sample to produce a cultured sample. In some embodiments, the method further comprises detecting the presence or absence of bacterial growth within the cultured sample. In some embodiments, the presence of bacterial growth indicates the presence of bacteria that are resistant to the antibiotic in the fluid sample.

In some embodiments, the first dilution fluid comprises an indicator media. In some embodiments, the method further comprises detecting an analyte in the first dilution at a plurality of time points. In some embodiments, the analyte comprises a cell.

In some embodiments, the method further comprises detecting an analyte in one or more of the first dilution, the second dilution, the third dilution and/or the fourth dilution at a first time point and at a second time point. In some embodiments, the analyte comprises a cell. In some embodiments, the first time point represents a control. In some embodiments, the second time point is between about 1 hour and about 6 hours after the first time point. In some embodiments, the second point in time is between about 1 hour and 4 hours after the first time point.

In some embodiments, the method further comprises culturing the one or more diluted samples to produce one or more cultured samples, and detecting the presence or absence of an analyte in the one or more cultured samples. In some embodiments, the analyte comprises a cell. In some embodiments, the cell is a bacterium, and the method comprises detecting the presence or absence of bacterial growth in the one or more cultured samples.

In some embodiments, the volume of the fluid sample is about 5 μL, the dilution of the fluid sample is a dilution of about 1:10000 and detecting the presence of bacterial growth in the dilution is indicative of a bacterial concentration of $10^5$ or greater colony forming units (CFU)/mL in the fluid sample. In some embodiments, the fluid sample is jejunal fluid and a bacterial concentration of $10^5$ CFU/mL or greater in the jejunal fluid is indicative that the subject has Small Intestinal Bacterial Overgrowth (SIBO).

In some embodiments, the method further comprises detecting a level of bacteria in the one or more diluted or cultured samples, wherein the fluid sample is jejunal fluid and a bacterial concentration of $10^5$ CFU/mL or greater in the jejunal fluid is indicative that the subject has SIBO. In some embodiments, the method comprises detecting the level of bacteria at three or more time points to generate one or more growth curves for the one or more cultured samples. In some embodiments, the method further comprises comparing the one or more growth curves to one or more standard growth curves. In some embodiments, the standard growth curves are representative of fluid samples with a known total bacterial count. In some embodiments, the standard growth curves are representative of samples from subjects with SIBO.

In some embodiments, the method comprises detecting the level of an analyte in the one or more diluted samples or cultured samples in the one or more dilution chambers.

In some embodiments, the method further comprises transferring the diluted sample or cultured sample to a detection chamber, and detecting the level of an analyte in the diluted sample or cultured sample in the detection chamber. In some embodiments, the analyte comprises a cell.

In some embodiments, detecting comprises using a Coulter counter.

In some embodiments, detecting comprises using a light source and a photodetector. In some embodiments, detecting comprises measuring an absorbance of the one or more diluted samples or cultured samples at a wavelength. In some embodiments, the wavelength is between about 400 and 1000 nm. In some embodiments, the wavelength is between about 500 and 700 nm. In some embodiments, the wavelength is about 600 nm.

In some embodiments, the device comprises an environmental sensor. In some embodiments, the method further comprises measuring environmental data of the GI tract or reproductive tract external to the device in the subject. In some embodiments, the method further comprises measuring environmental data of the GI tract external to the device in the subject at a plurality of time points as the device passes through the GI tract of the subject. In some embodiments, the method comprises measuring at least one parameter selected from the group consisting of capacitance, temperature, impedance, pH, and reflectance. In some embodiments, the method further comprises using the environmental data to determine a location of the device within the GI tract of the subject.

In some embodiments, the transferring the fluid sample into the first dilution chamber happens when the device is in the small intestine of the subject.

In some embodiments, transferring the fluid sample into the first dilution chamber happens when the device is in the jejunum of the subject.

In some embodiments, the method further comprises determining the total bacterial count (TBC) of the fluid sample based on the level of bacteria within the one or more diluted samples or cultured samples. In some embodiments, the fluid sample is jejunal fluid, and the method comprises diagnosing the subject as having SIBO if the TBC of the fluid sample is greater than $10^5$ CFU/mL.

In some embodiments, the method further comprises identifying one or more characteristics of a cell within the one or more diluted samples or cultured samples. In some embodiments, the cell is a bacterium and the method comprises identifying the bacterium as Gram-positive or Gram-negative. In some embodiments, the dilution fluid comprises conjugated bile acids, and the method comprises measuring bile salt hydrolase activity in the one or more diluted samples or cultured samples. In some embodiments, the cell is a eukaryotic cell and the method comprises detecting one or more biomarkers associated with cancer or inflammation.

In some embodiments, the method further comprises transmitting data from the device to an external base station and/or receiving operating parameters from an external base station. In some embodiments, the data comprises a measure of the concentration of an analyte in the fluid sample. In some embodiments, the analyte comprises a cell. In some embodiments, the operating parameters comprise timing instructions for transferring all or part of the fluid sample from the GI tract or from the reproductive tract into the one or more dilution chambers.

In one aspect, provided herein is a device, comprising a chamber configured to dilute a fluid sample from the GI tract or the reproductive tract of a subject; and a dilution chamber configured to house dilution fluid to dilute the fluid sample in the dilution chamber, wherein the device is an ingestible device.

In some embodiments, the device comprises one or more ports, valves and/or pumps configured to control transfer of fluid from the GI tract or from the reproductive tract into the dilution chamber. In some embodiments, the device comprises a plurality of dilution chambers and one or more ports, valves and/or pumps configured to control transfer of fluid between the dilution chambers. In some embodiments, the device further comprises a microcontroller configured to control the one or more ports, valves and/or pumps. In some embodiments, the device is configured to combine fluid sample with dilution fluid in the plurality of dilution chambers to produce a dilution series. In some embodiments, the device comprises a port configured to receive the fluid sample from the GI tract or reproductive tract. In some embodiments, the port is movable between an open position and a first position; in the open position, the port is exposed on an external surface of the device; and in the first position, the port is in fluid communication with a first dilution chamber of the device. In some embodiments, the port is movable between its first position and a second position; in its second position, the port is in fluid communication with a second dilution chamber of the device. In some embodiments, the port is movable between its second position and a third position; and in its third position, the port is in fluid communication with a dilution incubation chamber of the device. In some embodiments, the port is movable between its third position and a fourth position; and in its fourth position, the port is in fluid communication with a fourth dilution chamber of the device. In some embodiments, the device further comprises an actuator configured to move the port. In some embodiments, the actuator is coupled to a rotatable element, and the rotatable element is configured to rotate the port. In some embodiments, the port has a fluid volume of about 1 µL to about 50 µL. In some embodiments, the port is a depression on a surface of the rotatable element. In some embodiments, the one or more dilution chambers are positioned circumferentially around an axis of rotation of the rotatable element.

In some embodiments, the device further comprises the dilution fluid. In some embodiments, the dilution fluid comprises an anti-fungal agent. In some embodiments, the anti-fungal agent comprises amphotericin B. In some embodiments, the dilution fluid comprises sterile media. In some embodiments, the sterile media comprises at least one member selected from the group consisting of an agent that promotes growth of a cell, and an agent that inhibits growth of a cell. In some embodiments, the sterile media comprises an antibiotic. In some embodiments, the sterile media is selective for the growth of one or more types of cells. In some embodiments, the sterile media is selective for the growth of a eukaryotic cell.

In some embodiments, the device further comprises a detection system configured to detect an analyte in the fluid sample or dilution thereof. In some embodiments, the analyte comprises a cell. In some embodiments, the device further comprises a detection chamber in fluid communication with the one or more dilution incubation chambers. In some embodiments, fluid communication between the detection chamber and the one or more dilution chambers is controlled by one or more ports, valves and/or pumps. In some embodiments, the detection system is configured to detect the analyte in the fluid sample or dilution thereof at a plurality of time points. In some embodiments, the detection system is configured to detect the analyte at a first time point and at a second time point. In some embodiments, the first time point represents a control. In some embodiments, the second time point is between 1 hour and 6 hours after the first time point.

In some embodiments, the detection system is configured to detect the presence or absence of bacterial growth in the one or more dilution chambers or in the one or more detection chambers.

In some embodiments, the volume of the fluid sample is about 5 µL.

In some embodiments, the device further comprises a detection system configured to detect a level of bacteria in the one or more dilution chambers or in the one or more detection chambers. In some embodiments, the detection system is configured to detect the level of bacteria at three or more time points to produce a growth curve.

In some embodiments, the device comprises a Coulter counter.

In some embodiments, the device comprises a light source and a photodetector. In some embodiments, the light source and photodetector are operable to define a light path through the one or more dilution chambers or through the one or more detection chambers.

In some embodiments, the device comprises a detection system configured to detect an analyte in the fluid sample or dilution thereof. In some embodiments, the analyte is a byproduct from a bacterium.

In some embodiments, the device further comprises an environmental sensor configured to measure environmental data of the GI tract or of the reproductive tract external to the device in the subject. In some embodiments, the environmental sensor comprises at least one member selected from the group consisting of a capacitance sensor, a temperature sensor, an impedance sensor, a pH level sensor, and a light sensor. In some embodiments, the environmental data is usable to determine a location of the device within the GI tract of the subject.

In some embodiments, the device further comprises a microcontroller configured to control operation of the device. In some embodiments, the microcontroller is configured to control transfer of the fluid sample from the GI tract to the one or more dilution chambers based on the location of the device within the GI tract. In some embodiments, the microcontroller controls one or more ports, valves and/or pumps.

In some embodiments, the device further comprises a sensor configured to identify the types of cells or the characteristics of the cells within the one or more dilution chambers.

In some embodiments, the device further comprises a communication sub-unit that is configured to receive operating parameters from an external base station and/or transmit data to an external base station. In some embodiments, the operating parameters comprise timing instructions for obtaining a fluid sample from the GI tract or from the reproductive tract and transferring the fluid sample into one or more dilution chambers. In some embodiments, the data is indicative of the presence and/or absence of bacterial growth in the one or more dilution chambers.

In one aspect, provided herein is a device, comprising an element having a port on a wall of the element; and a shell surrounding the element to define a first dilution chamber between the element and the shell, wherein the device is configured to allow relative movement between the element and the shell; the shell has an aperture configured to expose a portion of the wall of the element to an exterior of the device; and the device is an ingestible device. In some embodiments, the device is configured to allow relative rotational movement between the element and the shell. In some embodiments, the element is rotatable. In some embodiments, the element is cylindrical. In some embodiments, the shell is cylindrical.

In some embodiments, the device is configured so that relative movement between the element and the shell aligns the port with the aperture so that an exterior of the device is in fluid communication with the port via the aperture.

In some embodiments, the element and the shell define a first dilution chamber; and the device is configured so that relative movement between the element results in fluid communication between the port and the first dilution chamber. In some embodiments, the shell and the element define a second dilution chamber that is separate from the first dilution chamber; and the device is configured so that relative movement between the element results in fluid communication between the port and a second dilution chamber. In some embodiments, the first dilution chamber contains a first dilution fluid, and the second dilution chamber contains a second dilution fluid. In some embodiments, the device is configured so that, during use of the device, the first dilution fluid is pumped into the first dilution chamber from a reservoir of the ingestible device when the ingestible device arrives at a target location of the GI tract.

In some embodiments, the wall of the element comprises any of one or more ports, valves and pumps configured to transfer fluid from an exterior of the device to the first dilution chamber.

In some embodiments, the shell and the element define a plurality of dilution chambers, and one or more ports, valves and/or pumps are configured to control transfer of fluid between the dilution chambers.

In some embodiments, the device comprises an actuator coupled to the element to move the port.

In some embodiments, the port is a depression on the wall of the rotatable element. In some embodiments, the first dilution chamber and the second dilution chamber are positioned circumferentially about the element.

In some embodiments, the first dilution fluid comprises a media to culture a GI fluid sample. In some embodiments, the device is configured so that the dilution and culturing of the GI fluid sample are performed in vivo. In some embodiments, the device is configured so that culturing of the GI fluid sample is performed ex vivo after the ingestible device has been evacuated and recovered from the subject.

In some embodiments, the device further comprises a microcontroller configured to control a movement of the element.

In some embodiments, the device further comprises a sensor configured to identify types of cells and/or characteristics of the cells.

In some embodiments, the device further comprises a communication sub-unit that is configured to receive operating parameters from an external base station and/or transmit data to an external base station. In some embodiments, the operating parameters include timing instructions for obtaining a fluid sample from the GI tract or from the reproductive tract and transferring the fluid sample into one or more dilution chambers. In some embodiments, the data is indicative of the presence and/or absence of bacterial growth in the one or more dilution chambers.

In one aspect, provided herein is a method comprising using the device to obtain a fluid sample in the GI tract of a subject. In some embodiments, the method further comprises serially rotating the element to sequentially align the port with a series of dilution chambers.

In one aspect, provided herein is a composition, comprising a dye; and a reagent capable of selectively lysing eukaryotic cells. In some embodiments, the dye is capable of binding to or reacting with a target component of a viable cell. In some embodiments, the dye exhibits fluorescence that is measurably altered when the dye is bound to or reacted with the target component of the viable cell. In some embodiments, the dye is internalizable by the viable cell.

In some embodiments, the target component of the viable cell comprises a member selected from the group consisting of a nucleic acid, actin, tubulin, an enzyme, a nucleotide-binding protein, an ion-transport protein, mitochondria, a cytoplasmic component, and a membrane component.

In some embodiments, the dye exhibits fluorescence when bound to a nucleic acid. In some embodiments, the dye comprises a member selected from the group consisting of acridine orange, calcein-AM, DAPI, Hoechst 33342, Hoechst 33258, PicoGreen, SYTO 16, SYBR Green I, Texas Red, Redmond Red, a Bodipy dye, Oregon Green, ethidium bromide, and propidium iodide.

In some embodiments, the dye is a fluorogenic dye that exhibits fluorescence when metabolized by the viable cell.

In some embodiments, the dye is a lipophilic dye that exhibits fluorescence when metabolized by a cell.

In some embodiments, the dye exhibits fluorescence when reduced by a cell or a cell component.

In some embodiments, the dye comprises a member selected from the group consisting of resazurin, $C^{12}$-resazurin, 7-hydroxy-9H-(1,3 dichloro-9,9-dimethylacridin-2-ol) N-oxide, 6-chloro-9-nitro-5-oxo-5H-benzo[a]phenoxazine, and a tetrazolium salt.

In some embodiments, the dye exhibits fluorescence when oxidized by a cell or a cell component. In some embodiments, the dye comprises a member selected from the group consisting of dihydrocalcein AM, dihydrorhodamine 123, dihydroethidium; 2,3,4,5,6-pentafluorotetramethyldihydrorosamine, and 3'-(p-aminophenyl) fluorescein.

In some embodiments, the dye exhibits fluorescence when de-acetylated and/or oxidized by a cell or a cell component.

In some embodiments, the dye comprises a member selected from the group consisting of dihydrorhodamines, dihydrofluoresceins, 2', 7'-dichlorodihydrofluorescein diacetate; 5-(and 6-)carboxy-2', 7'-dichlorodihydrofluorescein diacetate, and chloromethyl-2', 7'-dichlorodihydrofluorescein diacetate acetyl ester.

In some embodiments, the dye exhibits fluorescence when reacted with a peptidase. In some embodiments, the dye comprises a member selected from the group consisting of: (CBZ-Ala-Ala-Ala-Ala)2-R110 elastase 2; (CBZ-Ala-Ala-Asp)2-R110 granzyme B; and 7-amino-4-methylcoumarin; and N-CBZ-L-aspartyl-L-glutamyl-L-valyl-L-aspartic acid amide.

In some embodiments, the dye comprises a chemiluminescent dye that exhibits chemiluminescence when metabolized by a viable cell.

In some embodiments, the dye comprises luminol.

In some embodiments, the reagent comprises a detergent. In some embodiments, the reagent comprises a non-ionic detergent. In some embodiments, the reagent comprises a member selected from the group consisting of Nonidet P40, deoxycholate, Igepal Calif. 630, Triton-X 100, Zwittergent, SDS, and Tween 20.

In some embodiments, the reagent comprises deoxycholate. In some embodiments, the composition comprises deoxycholate at a concentration of from 0.0001 wt % to 1 wt %. In some embodiments, the composition comprises deoxycholate at a concentration of 0.005 wt %.

In some embodiments, the composition further comprises a second reagent capable of selectively lysing eukaryotic cells. In some embodiments, the second reagent comprises a detergent. In some embodiments, the second reagent comprises a member selected the group consisting of Nonidet P40, deoxycholate, Igepal Calif. 630, Triton-X 100, Zwittergent, sodium dodecyl sulfate (SDS), and Tween 20. In some embodiments, the second reagent is Triton X-100. In some embodiments, the composition comprises Triton X-100 at a concentration of from 0.1 wt % to 0.05 wt %.

In some embodiments, the composition further comprises an electrolyte. In some embodiments, the electrolyte is a divalent electrolyte. In some embodiments, the electrolyte is $MgCl_2$. In some embodiments, the composition comprises $MgCl_2$ at a concentration of from 0.1 mM to 100 mM. In some embodiments, the composition comprises $MgCl_2$ at a concentration of from 0.5 mM to 50 mM.

In some embodiments, the composition further comprises water.

In some embodiments, the composition is an aqueous solution.

In some embodiments, the composition has a pH of from 5 to 8. In some embodiments, the composition has a pH of from 6 to 7.8.

In some embodiments, the composition is a solid or semi-solid.

In some embodiments, the viable cell is a bacterial cell.

In one aspect, provided herein is an article comprising a member comprising an absorptive material; and a composition described herein, wherein the composition is at least partially absorbed in the absorptive material. In some embodiments, the absorptive material comprises a sponge. In some embodiments, the sponge comprises a hydrophilic sponge. In some embodiments, the absorptive material comprises a material selected from the group consisting of cotton, rayon, glass, polyester, polyethylene, polyurethane, and nitrocellulose.

In one aspect, provided herein is a device comprising a member comprising an absorptive material; and a composition provided herein, wherein the composition is at least partially absorbed in the absorptive material, and the device is an ingestible device. In some embodiments, the device further comprises a housing with an opening configured, wherein the absorptive material is disposed within the housing such that the absorptive material is in fluid communication with an exterior of the device via the opening in the housing.

In some embodiments, the ingestible device, comprises a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states; the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system comprises: an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises: a chamber; and a sampling system in the interior of the ingestible device, wherein: the sampling system comprises: a first member comprising absorptive material; and a second member comprising a second absorptive material different from the first absorptive material; and the sampling system is configured so that fluid that flows from the exterior of the ingestible device to the interior of the ingestible device enters the first absorptive material; and the sampling system is configured to allow fluid to flow from the first absorptive material to the second absorptive material.

In some embodiments, the ingestible device has an opening between an interior of the ingestible device and an exterior of the ingestible device, and the ingestible device comprises: a chamber; and a sampling system in the interior of the ingestible device configured to absorb a fluid that enters the interior of the ingestible device via the opening, the sampling system comprising the absorptive material and at least one preservative at least partially absorbed in the absorptive material.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the device further comprises: one or more processing devices; and one or more machine readable hardware storage devices storing instructions that are executable by the one or more processing devices to determine a location of the ingestible device in a portion of a gastrointestinal (GI) tract of a subject to an accuracy of at least 85%.

In some embodiments, the device further comprises: one or more processing devices; and one or more machine readable hardware storage devices storing instructions that are executable by the one or more processing devices to determine that the ingestible device is in the cecum of a subject to an accuracy of at least 70%.

In some embodiments, the device further comprises: one or more processing devices; and one or more machine readable hardware storage devices storing instructions that are executable by the one or more processing devices to transmit data to a device capable of implementing the data to determine a location of the ingestible device in a portion of a GI tract of a subject to an accuracy of at least 85%.

In some embodiments, the device further comprises: one or more processing devices; and one or more machine readable hardware storage devices storing instructions that are executable by the one or more processing devices to transmit data to an external device capable of implementing the data to determine that the ingestible device is in the cecum of subject to an accuracy of at least 70%.

In some embodiments, the device further comprises first and second light sources, wherein the first light source is configured to emit light at a first wavelength, and the second light source is configured to emit light at a second wavelength different from the first wavelength. In some embodiments, the device further comprises first and second detectors, wherein the first detector is configured to detect light at the first wavelength, and the second detector is configured to detect light at the second wavelength.

In one aspect, provided herein is a kit, comprising: a member comprising an absorptive material; and a composition described herein, wherein the composition is at least partially absorbed in the absorptive material.

In one aspect, provided herein is a kit, comprising an article described herein or a device described herein.

In one aspect, provided herein is a method, comprising: contacting a sample with either a composition described herein, an article described herein, or a device described herein, to yield a product; and measuring fluorescence of the product to detect viable bacterial cells in the sample.

In some embodiments, the method comprises measuring the total fluorescence of the product to detect viable bacterial cells in the sample. In some embodiments, the method further comprises comparing the measured total fluorescence of the product to a total fluorescence produced by a control, to detect viable bacterial cells in the sample. In some embodiments, the method further comprises correlating the comparative total fluorescence to the number of viable bacterial cells in the sample.

In some embodiments, the method comprises measuring a change in fluorescence of the product as a function of time to detect viable bacterial cells in the sample. In some embodiments, the method further comprises comparing a measured rate of change of fluorescence of the product as a function of time to a rate of change of fluorescence as a function of time produced by a control, to detect viable bacterial cells in the sample. In some embodiments, the method further comprises correlating the comparative rate of change of fluorescence as a function of time to the number of viable bacterial cells in the sample.

In some embodiments, the control comprises a composition identical to the sample but that does not comprise viable bacterial cells.

In some embodiments, the control comprises a composition identical to the sample but comprises a known number of viable bacterial cells.

In some embodiments, the sample comprises a biological sample. In some embodiments, the sample comprises an environmental sample. In some embodiments, the sample comprises a human sample. In some embodiments, the sample comprises a human GI tract sample.

In some embodiments, the viable bacterial cells comprise bacterial cells selected from the group consisting of *Escherichia coli, Bacillus anthracis, Bacillus cereus, Clostridium botulinum, Yersinia pestis, Yersinia enterocolitica, Brucella species, Clostridium perfringens, Burkholderia mallei, Burkholderia pseudomallei, Staphylococcus species, Mycobacterium species*, Group A *Streptococcus*, Group B *Streptococcus, Streptococcus pneumoniae, Helicobacter pylori, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella burnetti, Faecalibacterium prausnitzii, Roseburia hominis, Eubacterium rectale, Dialister invisus, Ruminococcus albus, Ruminococcus callidus*, and *Ruminococcus bromii*.

In one aspect, provided herein is a method of assessing or monitoring the need to treat a subject suffering from or at risk of overgrowth of bacterial cells in the GI tract, the method comprising: contacting a sample from the GI tract of the subject with a composition described herein to provide a product; measuring a parameter selected from: i) total fluorescence of the product; or ii) rate of change of fluorescence of the product as a function of time; and correlating the parameter to a number of viable bacterial cells in the sample. In some embodiments, the method further comprises using the correlation to determine whether the subject is suffering from or at risk of overgrowth of bacterial cells in the GI tract. In some embodiments, the method further comprises determining that when the number of the viable bacterial cells in the sample is greater than about $10^5$ colony forming units (CFU)/mL, the subject needs treatment for overgrowth of bacterial cells in the GI tract. In some embodiments, the parameter comprises the total fluorescence of the product. In some embodiments, the parameter comprises the rate of change of fluorescence of the product as a function of time.

In some embodiments, the method comprises obtaining the sample from the GI tract of the subject; measuring the total fluorescence of the product; comparing the measured total fluorescence to a total fluorescence produced by a control; and correlating the comparative fluorescence to the number of viable bacterial cells present in the sample. In some embodiments, the method further comprises determining that when the number of the viable bacterial cells in the sample is greater than about $10^5$ CFU/mL, the subject needs treatment for overgrowth of bacterial cells in the GI tract.

In some embodiments, the method comprises obtaining the sample from the GI tract of the subject; measuring the total fluorescence of the product; comparing a rate of change of fluorescence of the product as a function of time to a rate of change of fluorescence as a function of time produced by a control; and correlating the comparative rate of change of fluorescence as a function of time to the number of viable bacterial cells in the sample. In some embodiments, the control comprises a composition identical to the sample that does not comprise viable bacterial cells. In some embodiments, the control comprises a composition identical to the sample but that comprises a known number of viable bacterial cells.

In one aspect, provided herein is a method, comprising: disposing a sample in an article described herein, thereby producing a product; and measuring a parameter selected from total fluorescence of the product in the article, and a rate of change of fluorescence as a function of time of the product in the article.

In some embodiments, the sample comprises an aqueous solution. In some embodiments, the method further comprises removing water from the product.

In some embodiments, the method further comprises heating the product. In some embodiments, the product is heated to a temperature above 0° C. In some embodiments, the product is heated to a temperature of at most 100° C.

In some embodiments, the method comprises reducing a total water content of the product by at least 50%.

In some embodiments, the parameter is total fluorescence of the product in the article.

In some embodiments, the method further comprises comparing the measured total fluorescence detected in the product to a total fluorescence produced by a control, and correlating the comparative fluorescence to detect viable bacterial cells in the sample. In some embodiments, the method further comprises correlating the comparative total fluorescence detected in the product to the number of viable bacterial cells in the sample.

In some embodiments, the parameter is the rate of change of fluorescence as a function of time of the product in the article, and the method further comprises comparing the rate of change of fluorescence as a function of time to a rate of change of fluorescence as a function of time produced by a control to detect the viable bacterial cells in the sample. In some embodiments, the method further comprises correlating the comparative rate of change of fluorescence as a function of time to the number of viable bacterial cells in the sample.

In some embodiments, the control comprises a product identical to the product but that is devoid of viable bacterial cells. In some embodiments, the control comprises a product identical to the product but comprises a known number of viable bacterial cells.

In some embodiments, the method comprises continuously measuring for up to 330 minutes.

In some embodiments, the sample comprises a biological sample. In some embodiments, the sample comprises an environmental sample. In some embodiments, the sample comprises a human sample. In some embodiments, the sample comprises a human GI tract sample.

In some embodiments, the viable bacterial cells comprise bacterial cells selected from the group consisting of *Escherichia coli, Bacillus anthracis, Bacillus cereus, Clostridium botulinum, Yersinia pestis, Yersinia enterocolitica, Francisella tularensis, Brucella species, Clostridium perfringens, Burkholderia mallei, Burkholderia pseudomallei, Staphylococcus* species, *Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella burnetti, Faecalibacterium prausnitzii, Roseburia hominis, Eubacterium rectale, Dialister invisus, Ruminococcus albus, Ruminococcus callidus*, and *Ruminococcus bromii*.

In one aspect, provided herein is a method of assessing or monitoring the need to treat a subject suffering from or at risk of overgrowth of bacterial cells in the GI tract, the method comprising: obtaining a sample from the gastrointestinal tract of the subject; disposing the sample in an article described herein to provide a product; measuring a parameter selected from a total fluorescence of the product; and a rate of change of fluorescence of the product as a function of time; correlating the measured parameter to a number of viable bacterial cells in the sample; and determining that the subject is in need of treatment for or at risk of overgrowth of bacterial cells in the gastrointestinal tract, when the number of viable bacterial cells is greater than about $10^5$ CFU/mL.

In some embodiments, the parameter comprises the total fluorescence of the product, and the method further comprises: comparing the measured total fluorescence to a total fluorescence produced by a control; and correlating the comparative total fluorescence to the number of viable bacterial cells in the sample.

In some embodiments, the parameter comprises the rate of change of fluorescence of the product as a function of time, and the method further comprises: comparing the measured rate of change of fluorescence of the product as a function of time to a rate of change of fluorescence as a function of time produced by a control; correlating the comparative rate of change of fluorescence as a function of time to the number of viable bacterial cells in the sample. In some embodiments, the control comprises a composition identical to the sample but does not comprise viable bacterial cells. In some embodiments, the control comprises a composition identical to the sample but comprises a known number of viable bacterial cells.

In some embodiments, the method comprises collecting the sample from the GI tract of a subject. In some embodiments, the method comprises disposing the sample into an ingestible device while the ingestible device is in the GI tract of the subject.

In some embodiments, the method is performed within the body of the subject.

In some embodiments, the method is partially performed outside the body of the subject.

In some embodiments, the ingestible device, comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states; the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system comprises: an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises: a chamber; and a sampling system in the interior of the ingestible device, wherein: the sampling system comprises: a first member comprising a first absorptive material; and a second member comprising a second absorbent member different from the first absorptive material; and the sampling system is configured so that fluid that flows from the exterior of the ingestible device to the interior of the ingestible device enters the first absorptive material; and the sampling system is configured to allow fluid to flow from the first absorptive material to the second absorptive material.

In some embodiments, the ingestible device has an opening between an interior of the ingestible device and an exterior of the ingestible device, and the ingestible device comprises: a chamber; and a sampling system in the interior of the ingestible device configured to absorb a fluid that enters the interior of the ingestible device via the opening, the sampling system comprising a member which comprises an absorptive material and at least one preservative at least partially absorbed in the absorptive material.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the ingestible device further comprises: one or more processing devices; and one or more machine readable hardware storage devices storing instructions that are executable by the one or more processing devices to determine a location of the ingestible device in a portion of a GI tract of a subject to an accuracy of at least 85%.

In some embodiments, the ingestible device further comprises: one or more processing devices; and one or more machine readable hardware storage devices storing instructions that are executable by the one or more processing devices to determine that the ingestible device is in the cecum of a subject to an accuracy of at least 70%.

In some embodiments, the ingestible device further comprises: one or more processing devices; and one or more machine readable hardware storage devices storing instructions that are executable by the one or more processing devices to transmit data to a device capable of implementing the data to determine a location of the ingestible device in a portion of a GI tract of a subject to an accuracy of at least 85%.

In some embodiments, the ingestible device further comprises: one or more processing devices; and one or more machine readable hardware storage devices storing instructions that are executable by the one or more processing devices to transmit data to an external device capable of implementing the data to determine that the ingestible device is in the cecum of subject to an accuracy of at least 70%.

In some embodiments, the ingestible device further comprises first and second light sources, wherein the first light source is configured to emit light at a first wavelength, and the second light source is configured to emit light at a second wavelength different from the first wavelength. In some embodiments, the ingestible device further comprises first and second detectors, wherein the first detector is configured to detect light at the first wavelength, and the second detector is configured to detect light at the second wavelength.

In one aspect, provided herein is a device, comprising: a sampling chamber; and a composition in the sampling chamber, wherein: the composition comprises a plurality of donor particles and a plurality of acceptor particles, each donor particle comprises a photosensitizer coupled to a first analyte-binding agent that binds to an analyte, in an excited state, the photosensitizer generates singlet oxygen; each acceptor particle comprises a chemiluminescent compound coupled to a second analyte-binding agent that binds to the analyte; the chemiluminescent compound reacts with singlet oxygen to emit luminescence; and the device is an ingestible device.

In some embodiments, the composition further comprises an aqueous medium comprising the donor and acceptor particles. In some embodiments, the donor and acceptor particles are suspended in the aqueous medium.

In some embodiments, the acceptor particles comprise particles selected from the group consisting of latex particles, lipid bilayers, oil droplets, silica particles, and metal sols.

In some embodiments, the acceptor particles comprise latex particles.

In some embodiments, the chemiluminescent compound comprises a compound selected from the group consisting of Chemiluminescer, Thioxene+Diphenyl anthracence, Thioxene+Umbelliferone derivative, Thioxene+Europium chelate, Thioxene+Samarium Chelate, Thioxene+terbium Chelate, N-Phenyl Oxazine+Umbelliferone derivative, N-Phenyl Oxazine+Europium chelate, N-phenyl Oxazine+Samarium Chelate, N-phenyl Oxazine+terbium Chelate, Dioxene+Umbelliferone derivative, Dioxene+Europium chelate, Dioxene+Samarium Chelate, and N-phenyl Oxazine+terbium Chelate.

In some embodiments, the donor particles comprise particles selected from the group consisting of latex particles, lipid bilayers, oil droplets, silica particles, and metal sols.

In some embodiments, the donor particles comprise latex particles. In some embodiments, the donor particles further comprise streptavidin. In some embodiments, the streptavidin is coated on the latex particles.

In some embodiments, the photosensitizer comprises a material selected from the group consisting of a dye, an aromatic compound, an enzyme, and a metal salt.

In some embodiments, a ratio of a number of the donor particles to a number of the acceptor particles in the composition is between 10:1 to 10:1.

In one aspect, provided herein is a device, comprising: a sampling chamber; and a composition in the sampling chamber, wherein the composition comprises: a first analyte-binding agent comprising a first fluorescent dye, wherein the first analyte-binding agent is capable of binding to an analyte; and a second analyte-binding agent comprising a second fluorescent dye, wherein the second analyte-binding agent is capable of binding to the analyte, and wherein the second fluorescent dye exhibits increased fluorescence when spatially proximal to the first fluorescent dye; and wherein the device is an ingestible device. In some embodiments, the spatial proximity between the first fluorescent dye and the second fluorescent dye results in energy transfer from the first fluorescent dye to the second fluorescent dye.

In one aspect, provided herein is a device, comprising: a sampling chamber; and a composition in the sampling chamber, wherein the composition comprises: a first analyte-binding agent comprising a photosensitizer, wherein the first analyte-binding agent is capable of binding to an analyte, and wherein the photosensitizer generates singlet oxygen in an excited state; and a second analyte-binding agent comprising a fluorogenic dye, wherein the fluorogenic dye emits fluorescence upon reacting with singlet oxygen; and wherein the device is an ingestible device.

In some embodiments, the composition comprises an aqueous medium. In some embodiments, the aqueous medium comprises a preservative.

In some embodiments, the first analyte-binding agent and/or the second analyte-binding agent is an antigen-binding agent.

In some embodiments, the first analyte-binding agent and/or the second analyte-binding agent is an antibody.

In some embodiments, the device is configured detect the analyte in vivo.

In some embodiments, the sampling chamber is configured to house an absorptive material. In some embodiments, the absorptive material is configured to at least partially absorb the composition. In some embodiments, the absorptive material comprises a sponge.

In some embodiments, the analyte comprises a biomolecule, a microorganism, a therapeutic agent, a drug, a biomarker, a pesticide, a pollutant, a fragment thereof, or a metabolite thereof.

In some embodiments, the analyte comprises a protein, an aptamer, a nucleic acid, a steroid, a polysaccharide, or a metabolite.

In some embodiments, the protein is selected from the group consisting of an antibody, an affimer, a cytokine, a chemokine, an enzyme, a hormone, a cancer antigen, a tissue-specific antigen, a histone, an albumin, a globulin, a scleroprotein, a phosphoprotein, a mucoprotein, a chromoprotein, a lipoprotein, a nucleoprotein, a glycoprotein, a receptor, a membrane-anchored protein, a transmembrane protein, a secreted protein, a human leukocyte antigen (HLA), a blood clotting factor, a microbial protein, and fragments thereof.

In some embodiments, the metabolite is selected from the group consisting of serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, the microorganism is a bacterium, a virus, a prion, a protozoan, a fungus, or a parasite.

In some embodiments, the bacterium is selected from the group consisting of *Escherichia coli, Bacillus anthracis, Bacillus cereus, Clostridium botulinum, Clostridium difficile, Yersinia pestis, Yersinia enterocolitica, Francisella tularensis, Brucella species, Clostridium perfringens, Burkholderia mallei, Burkholderia pseudomallei, Staphylococcus* species, *Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella burnetti, Faecalibacterium prausnitzii, Roseburia hominis, Eubacterium rectale, Dialister invisus, Ruminococcus albus, Ruminococcus callidus*, and *Ruminococcus bromii*.

In some embodiments, the therapeutic agent is selected from the group consisting of a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor.

In some embodiments, the analyte is a bile acid or a bile acid salt. In some embodiments, the analyte is an antibiotic. In some embodiments, the analyte is associated with a disease, a disorder, or a pathogen.

In some embodiments, the analyte comprises TNFα, lipoteichoic acid (LTA), lipopolysaccharide (LPS), lipopolysaccharide binding protein (LBP), a cytokine, a chemokine, IL12/23, IL-6, IL-10, MADCAM, α4β7 integrin, hepatocyte growth factor (HGF), epidermal growth factor (EGF), heparin-binding epidermal growth factor (HB-EGF), TGFβ, adalimumab, infliximab, certolizumab pegol, vedolizumab, natalizumab, golimumab, bevacizumab, or cetuximab.

In some embodiments, the first analyte-binding agent comprises an agent selected from the group consisting of an antibody, an affimer, an antigen, a small molecule, a nucleic acid, a receptor, an aptamer, a receptor ligand, biotin, streptavidin, avidin, protein A, protein G, protein L, and derivatives thereof.

In some embodiments, the second analyte-binding agent are comprises an agent selected from the group consisting of an antibody, an affimer, an antigen, a small molecule, a nucleic acid, a receptor, an aptamer, a receptor ligand, biotin, streptavidin, avidin, protein A, protein G, protein L, and derivatives thereof.

In some embodiments, the first analyte-binding agent is different from the second analyte-binding agent. In some embodiments, the first analyte-binding agent is the same as the second analyte-binding agent.

In some embodiments, the first analyte-binding agent comprises an antibody. In some embodiments, the second analyte-binding agent comprises an antibody. In some embodiments, the first analyte-binding agent comprises a biotinylated antibody. In some embodiments, the antibody comprises an anti-bacterial antibody. In some embodiments, the antibody comprises an antibody selected from the group consisting of an anti-Gram-positive bacteria antibody, an anti-Gram-negative bacteria antibody, an anti-lipoteichoic acid (LTA) antibody, an anti-*E. coli* antibody, an anti-lipid A antibody, an anti-TNFα antibody, and derivatives thereof. In some embodiments, the antibody comprises an antibody selected from the group consisting of MA1-7401 antibody, MA1-40134 antibody, ab127996 antibody, ab35654 antibody, ab35654 antibody, ab137967 antibody, ab8467 antibody, and derivatives or fragments thereof.

In some embodiments, the first analyte-binding agent comprises a biotinylated antibody, and the donor particles comprise a coating which comprises streptavidin. In some embodiments, the second analyte-binding agent comprises an antibody covalently conjugated to the acceptor particles.

In some embodiments, the composition further comprises cyclodextrin having a concentration range of 25-50 nM.

In some embodiments, the device further comprises an internal calibrator.

In some embodiments, the device further comprises a light source. In some embodiments, the light source is configured to provide light having at least one wavelength selected from the group consisting of 678 nm, 633 nm, and 780 nm. In some embodiments, the light source is configured to irradiate the composition with light.

In some embodiments, the device further comprises a detector configured to detect luminescence emitted by the chemiluminescent compound. In some embodiments, the detector comprises a photodiode configured to detect luminescence emitted by the chemiluminescent compound. In some embodiments, the detector comprises a photodiode configured to detect luminescence emitted by the chemiluminescent compound at at least one wavelength selected from the group consisting of 613 nm and 660 nm.

In one aspect, provided herein is a kit comprising a device described herein.

In one aspect, provided herein is a method comprising using a device described herein to detect the analyte.

In some embodiments, the method further comprises disposing a sample from a subject into the sampling chamber. In some embodiments, the sample is disposed in the sampling chamber in vivo. In some embodiments, the method further comprises irradiating the sample, and detecting luminescence emitted from the sample.

In some embodiments, detecting luminescence comprises measuring an amount of luminescence. In some embodiments, detecting luminescence comprises measuring a total amount of luminescence. In some embodiments, detecting luminescence comprises measuring a rate of change of luminescence as a function of time.

In some embodiments, the fluid sample is taken from the gastrointestinal (GI) tract of the subject.

In some embodiments, the method further comprises quantifying an amount of the analyte based on measured total luminescence. In some embodiments, the method further comprises quantifying an amount of the analyte based a rate of change of luminescence.

In some embodiments, the analyte comprises a biomolecule, a microorganism, a therapeutic agent, a drug, a biomarker, a pesticide, a pollutant, a fragment thereof, or a metabolite thereof.

In some embodiments, the analyte comprises a protein, an aptamer, nucleic acid, a steroid, a polysaccharide, or a metabolite.

In some embodiments, the protein is selected from the group consisting of an antibody, an affimer, a cytokine, a chemokine, an enzyme, a hormone, a cancer antigen, a tissue-specific antigen, a histone, an albumin, a globulin, a scleroprotein, a phosphoprotein, a mucoprotein, a chromoprotein, a lipoprotein, a nucleoprotein, a glycoprotein, a receptor, a membrane-anchored protein, a transmembrane protein, a secreted protein, a human leukocyte antigen (HLA), a blood clotting factor, a microbial protein, and fragments thereof.

In some embodiments, the metabolite is selected from the group consisting of serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, the microorganism is a bacterium, a virus, a prion, a protozoan, a fungus, or a parasite.

In some embodiments, the bacterium is selected from the group consisting of *Escherichia coli, Bacillus anthracis, Bacillus cereus, Clostridium botulinum, Clostridium difficile, Yersinia pestis, Yersinia enterocolitica, Francisella tularensis, Brucella* species, *Clostridium perfringens, Burkholderia mallei, Burkholderia pseudomallei, Staphylococcus* species, *Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella burnetti, Faecalibacterium prausnitzii, Roseburia hominis, Eubacterium rectale, Dialister invisus, Ruminococcus albus, Ruminococcus callidus*, and *Ruminococcus bromii*.

In some embodiments, the therapeutic agent is selected from the group consisting of a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor.

In some embodiments, the analyte is a bile acid or a bile acid salt. In some embodiments, the analyte is an antibiotic. In some embodiments, the analyte is associated with a disease, a disorder, or a pathogen.

In some embodiments, the analyte comprises TNFα, lipoteichoic acid (LTA), lipopolysaccharide (LPS), lipopolysaccharide binding protein (LBP), a cytokine, a chemokine, IL12/23, IL-6, IL-10, MADCAM, α4β7 integrin, hepatocyte growth factor (HGF), epidermal growth factor (EGF), heparin-binding epidermal growth factor (HB-EGF), TGFβ, adalimumab, infliximab, certolizumab pegol, vedolizumab, natalizumab, golimumab, bevacizumab, or cetuximab.

In some embodiments, the method further comprises determining, based on the detected luminescence, that the subject is suffering from or at risk of overgrowth of bacterial cells in the GI tract. In some embodiments, the method further comprises correlating a total luminescence and/or a rate of change of luminescence as a function of time measured in the sample to the amount of the analyte in the sample. In some embodiments, the method further comprises correlating the amount of the analyte in the sample to the number of viable bacterial cells in the sample. In some embodiments, determining that the determined number of the viable bacterial cells is greater than about $10^5$ CFU/mL indicates a need for treatment.

In some embodiments, the method further comprises determining, based on the detected luminescence, that the subject is suffering from or at risk of overgrowth of bacterial cells in the gastrointestinal tract.

In some embodiments, the subject is suffering from or at risk of overgrowth of bacterial cells in the gastrointestinal tract.

In some embodiments, the device comprises a plurality of sampling chambers, and the method further comprises disposing different samples in different sampling chambers. In some embodiments, the method comprises taking different samples at different times. In some embodiments, the method comprises taking different samples at different locations within the gastrointestinal tract. In some embodiments, the different locations comprise locations selected from the group consisting of the mouth, the throat, the esophagus, the stomach, the small intestine, the large intestine, the duodenum, the jejunum, the ileum, the ascending colon, the transverse colon, and the descending colon. In some embodiments, the method further comprises creating a molecular map that maps each location from the number of different locations within the GI tract to a respective measurement of the analyte.

In one aspect, provided herein is a device, comprising a diffractive optics sensor, wherein the device is an ingestible device. In some embodiments, the diffractive optics sensor is configured to detect an analyte present in the device. In some embodiments, the diffractive optics sensor comprises: a diffraction grating; an analyte-binding agent linked to the diffraction grating, wherein the analyte-binding agent is capable of binding to the analyte; and a detector configured to detect light diffracted by the diffraction grating, wherein the device is configured so that, when the analyte is bound to the analyte-binding agent, a diffraction pattern of light diffracted by the diffraction grating changes. In some embodiments, the change in the diffraction pattern comprises a change in an intensity of light diffracted by the diffraction grating. In some embodiments, a magnitude of the change in the intensity of light diffracted by the diffraction grating is indicative of the concentration of the analyte in the sample.

In some embodiments, the device further comprises a light source configured so that light emitted by the light source impinges on the diffraction grating with an angle of incidence 60° measured from surface. In some embodiments, the light source is configured to generate light having a wavelength of 670 nm.

In some embodiments, the diffraction grating has a period of 15 μm. In some embodiments, the diffraction grating comprises a series of grooves comprising adjacent recessed portions and wherein raised portions of the grooves have a depth from about 1 nm to about 1000 nm.

In some embodiments, the diffraction pattern comprises light in a plurality of diffraction orders, and the detector detects an intensity of light in one or more of the diffraction orders.

In some embodiments, the diffraction optics are configured for total internal reflection.

In some embodiments, the analyte comprises a member selected from the group consisting of a biomolecule, a microorganism, a therapeutic agent, a drug, a biomarker, a pesticide, a pollutant, fragments thereof, and metabolites thereof.

In some embodiments, the analyte comprises a member selected from the group consisting of a protein, a nucleic acid, a steroid, a polysaccharide, and a metabolite. In some embodiments, the analyte comprises a protein selected from the group consisting of an antibody, an aptamer, an affimer, a cytokine, a chemokine, an enzyme, a hormone, a cancer antigen, a tissue-specific antigen, a histone, an albumin, a globulin, a scleroprotein, a phosphoprotein, a mucoprotein, a chromoprotein, a lipoprotein, a nucleoprotein, a glycoprotein, a receptor, a membrane-anchored protein, a transmembrane protein, a secreted protein, a human leukocyte antigen (HLA), a blood clotting factor, a microbial protein, and fragments thereof.

In some embodiments, the analyte comprises a metabolite selected from the group consisting of serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, the analyte comprises a bile acid or a bile acid salt.

In some embodiments, the analyte comprises an antibiotic.

In some embodiments, the analyte comprises a microorganism selected from the group consisting of a bacterium, a virus, a prion, a protozoan, a fungus, and a parasite.

In some embodiments, the bacterium comprises a member selected from the group *consisting of Escherichia coli, Bacillus anthracis, Bacillus cereus, Clostridium botulinum, Clostridium difficile, Yersinia pestis, Yersinia enterocolitica, Francisella tularensis, Brucella* species, *Clostridium perfringens, Burkholderia mallei, Burkholderia pseudomallei, Staphylococcus* species, *Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis, Coxiella burnetti, Faecalibacterium prausnitzii, Roseburia hominis, Eubacterium rectale, Dialister invisus, Ruminococcus albus, Ruminococcus callidus,* and *Ruminococcus bromii.*

In some embodiments, the therapeutic agent comprises a member selected from the group consisting of a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor.

In some embodiments, the analyte is associated with a disease, a disorder, or a pathogen. In some embodiments, the analyte-binding agent comprises an antibody, an affimer, an antigen, a small molecule, a nucleic acid, a receptor, or an aptamer.

In some embodiments, the analyte-binding agent specifically binds to an analyte present in a particular genus, species or strain of microorganism.

In some embodiments, the analyte-binding agent is covalently linked to the substrate. In some embodiments, the analyte-binding agent is non-covalently linked to the substrate. In some embodiments, the analyte-binding agent is directly linked to the substrate. In some embodiments, the analyte-binding agent is indirectly linked to the substrate. In some embodiments, the analyte-binding agent is indirectly linked to the substrate through a spacer.

In some embodiments, the analyte-binding agent comprises an antibody which comprises an Fc region, and the analyte-binding agent is directly or indirectly linked to the substrate through the Fc region.

In some embodiments, the diffraction grating comprises a series of grooves comprising adjacent recessed portions and raised portions, and the analyte-binding agent is linked to the raised portions. In some embodiments, the diffraction grating comprises a series of grooves comprising adjacent recessed portions and raised portions, and the analyte-binding agent is linked to the recessed portions.

In some embodiments, the device further comprises a first chamber configured to contain a sample. In some embodiments, the first chamber has a volume of at most 1000 µL. In some embodiments, the diffractive optics sensor is configured to analyze the sample when the sample is contained in the first chamber.

In some embodiments, the device further comprises an opening and a cover, wherein: the cover has a first position and a second position; in the first position, the cover prevents fluid from entering the first chamber from an exterior of the device and also prevents fluid from exiting the first chamber to the exterior of the device; and in the second position, the cover allows fluid to enter the first chamber from the exterior of the device.

In some embodiments, the device further comprises a second chamber configured so that the sample can move from the first chamber to the second chamber, wherein the second chamber is configured to incubate the sample when the sample is in the second chamber. In some embodiments, the second chamber has a volume of at most 1000 µL. In some embodiments, the diffractive optics sensor is configured to analyze the sample when the sample is contained in the second chamber.

In some embodiments, the device further comprises at least one member selected from the group consisting of a port, a valve and a pump, wherein the at least one member is configured to move the sample when the sample is in the device. In some embodiments, the device is configured so that the sample movement in the device does not substantially disrupt binding of the analyte to the analyte-binding agent.

In some embodiments, the device is configured so that flow of the sample through the incubation chamber is less than 500 µL/min. In some embodiments, the diffractive optics sensor comprises a plurality of diffraction gratings, wherein each diffraction grating comprises an analyte-binding agent capable of binding to a different analyte.

In some embodiments, the device is configured to detect the analyte at a location within the gastrointestinal (GI) tract of a subject. In some embodiments, the location within the GI tract of the subject comprises a member selected from the group consisting of the mouth, the throat, the esophagus, the stomach, the small intestine, the large intestine, the rectum, the anus, the sphincter, the duodenum, the jejunum, the ileum, and the colon.

In some embodiments, the device further comprises a system configured to determine a location of the device within the GI tract of a subject.

In some embodiments, the system comprises at least one member selected from the group consisting of a spectrometer, a capacitance sensor, a temperature sensor, an impedance sensor, a pH sensor, a heart rate sensor, an acoustic sensor, a reflected light sensor, an image sensor, and a movement sensor.

In some embodiments, the device further comprises a unit configured to: a) transmit data to a base station; and/or b) receive data from the base station. In some embodiments, the base station is ex vivo.

In some embodiments, the device further comprises a processing unit configured to determine a presence and/or an amount of an analyte in a sample contained in the device based on a signal generated by the diffractive optics sensor. In some embodiments, the processing unit is configured to determine the presence and/or the level of the analyte by comparing a signal generated by the diffractive optics sensor to one or more control levels.

In some embodiments, the device further comprises a secondary detection agent that binds to the analyte and increases a refractive index of a complex comprising the analyte bound to the analyte-binding agent when bound to the complex. In some embodiments, the secondary detection agent comprises a nanoparticle.

In some embodiments, the ingestible device, comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states; the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system comprises: an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises: a chamber; and a sampling system in the interior of the ingestible device, wherein: the sampling system comprises: a first member comprising a first absorptive material; and a second member comprising a second absorptive material different from the first absorptive material; and the sampling system is configured so that fluid that flows from the exterior of the ingestible device to the interior of the ingestible device enters the first absorptive material; and the sampling system is configured to allow fluid to flow from the first absorptive material to the second absorptive material.

In some embodiments, the ingestible device has an opening between an interior of the ingestible device and an exterior of the ingestible device, and the ingestible device comprises: a chamber; and a sampling system in the interior of the ingestible device configured to absorb a fluid that enters the interior of the ingestible device via the opening, the sampling system comprising a member which comprises an absorptive material and at least one preservative at least partially absorbed in the absorptive material.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains a member comprising an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the device further comprises: one or more processing devices; and one or more machine readable hardware storage devices storing instructions that are executable by the one or more processing devices to determine a location of the ingestible device in a portion of a GI tract of a subject to an accuracy of at least 85%.

In some embodiments, the device further comprises: one or more processing devices; and one or more machine readable hardware storage devices storing instructions that are executable by the one or more processing devices to determine that the ingestible device is in the cecum of a subject to an accuracy of at least 70%.

In some embodiments, the device further comprises: one or more processing devices; and one or more machine readable hardware storage devices storing instructions that are executable by the one or more processing devices to transmit data to a device capable of implementing the data to determine a location of the medical device in a portion of a GI tract of a subject to an accuracy of at least 85%.

In some embodiments, the device further comprises one or more processing devices; and one or more machine readable hardware storage devices storing instructions that are executable by the one or more processing devices to transmit data to an external device capable of implementing the data to determine that the ingestible device is in the cecum of subject to an accuracy of at least 70%.

In some embodiments, the device further comprises first and second light sources, wherein the first light source is configured to emit light at a first wavelength, and the second light source is configured to emit light at a second wavelength different from the first wavelength.

In some embodiments, the device further comprises first and second detectors, wherein the first detector is configured to detect light at the first wavelength, and the second detector is configured to detect light at the second wavelength.

In one aspect, provided herein is a system, comprising an ingestible device described herein; and a processing unit configured to determine a presence and/or a level of an analyte in a sample based on a signal generated by the diffractive optics sensor, wherein the processing unit is external to the ingestible device.

In some embodiments, the processing unit is configured to determine the presence and/or the level of the analyte by comparing a signal generated by the diffractive optics sensor to one or more control levels. In some embodiments, the processing unit is located ex vivo, and the ingestible device comprises a communications unit for transmitting the signal to the processing unit.

In one aspect, provided herein is a method comprising operating an ingestible device within the GI tract of a subject to detect an analyte, wherein the ingestible device is a device described herein.

In some embodiments, the method further comprises: collecting a sample from the GI tract of the subject; after collecting the sample, using the diffractive optics sensor to measure a diffraction pattern; and using the diffraction pattern to detect a presence and/or a level of the analyte in the sample. In some embodiments, the method further comprises measuring the diffraction pattern at more than one point in time.

In some embodiments, the method further comprises using a secondary detection agent to bind to the analyte, thereby increasing a refractive index of a complex comprising the analyte bound to the analyte-binding agent. In some embodiments, the secondary detection agent comprises a nanoparticle.

In some embodiments, the method further comprises incubating the sample. In some embodiments, the method further comprises, before administering the device to the subject, determining the location within the GI tract of the subject.

In some embodiments, the method further comprises transmitting data from the device to a base station and/or transmitting data from the base station to the device, wherein the base station is external to the subject. In some embodiments, the data is representative of a signal generated by the diffractive optics biosensor.

In one aspect, provided herein is a method, comprising: using an ingestible device to obtain a sample within a GI tract of a subject; and using diffractive optics to analyze the sample. In some embodiments, the ingestible device comprises the diffractive optics. In some embodiments, the sample is analyzed in vivo.

In some embodiments, the ingestible device, comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states; the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system comprises: an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises: a chamber; and a sampling system in the interior of the ingestible device, wherein: the sampling system comprises: a first member comprising a first absorptive material; and a second member comprising a second absorptive material different from the first absorptive material; and the sampling system is configured so that fluid that flows from the exterior of the ingestible device to the interior of the ingestible device enters the first absorptive material; and the sampling system is configured to allow fluid to flow from the first absorptive material to the second absorptive material.

In some embodiments, the ingestible device has an opening between an interior of the ingestible device and an exterior of the ingestible device, and the ingestible device comprises: a chamber; and a sampling system in the interior of the ingestible device configured to absorb a fluid that enters the interior of the ingestible device via the opening, the sampling system comprising a member which comprises an absorptive material and at least one preservative at least partially absorbed in the absorptive material.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the ingestible device further comprises: one or more processing devices; and one or more machine readable hardware storage devices storing instructions that are executable by the one or more processing devices to determine a location of the ingestible device in a portion of a GI tract of a subject to an accuracy of at least 85%.

In some embodiments, the ingestible device further comprises: one or more processing devices; and one or more machine readable hardware storage devices storing instructions that are executable by the one or more processing devices to determine that the ingestible device is in the cecum of a subject to an accuracy of at least 70%.

In some embodiments, the ingestible device further comprises: one or more processing devices; and one or more machine readable hardware storage devices storing instructions that are executable by the one or more processing devices to transmit data to a device capable of implementing the data to determine a location of the medical device in a portion of a GI tract of a subject to an accuracy of at least 85%.

In some embodiments, the ingestible device further comprises: one or more processing devices; and one or more machine readable hardware storage devices storing instructions that are executable by the one or more processing devices to transmit data to an external device capable of implementing the data to determine that the ingestible device is in the cecum of subject to an accuracy of at least 70%.

In some embodiments, the ingestible device further comprises first and second light sources, wherein the first light source is configured to emit light at a first wavelength, and the second light source is configured to emit light at a second wavelength different from the first wavelength.

In some embodiments, the ingestible device further comprises first and second detectors, wherein the first detector is configured to detect light at the first wavelength, and the second detector is configured to detect light at the second wavelength.

BRIEF DESCRIPTION OF THE DRAWINGS

Exemplary embodiments of the disclosure are provided below with reference to the drawings.

FIGS. 14A and 14B illustrate a portion of a two-stage valve system in its first and second stages, respectively.
FIGS. 15A and 15B illustrate a portion of a two-stage valve system in its first and second stages, respectively.

FIG. 75C shows a sample challenge plate lay out. Each plate represents 1 replicate (4 replicates performed).

FIG. 79A shows an exemplary sample challenge plate in triplicate by using a Sterilin 96 well round bottom microtitre plate (P/N H511A), where the plate was loaded with 100 μL of a diluted dynamic range of bacteria or failure modes.

FIGS. 131A and 131B show the quantitation of anaerobic bacterial strains using a resazurin-based assay in liquid format. S/D=standard deviation; Mean max signal shown as relative fluorescence units (RFU); diagonal from upper right to lower left=<6 CFU; diagonal from upper left to lower right=<5 CFU; cross-hatch=regression slope>3 standard deviations of blank control (3.10+(3×0.438))=4.41); 1:10=dilution of exponential phase culture in cell above in SJFA.

FIG. 132A shows the quantitation of anaerobic bacterial strains using a resazurin-based assay in liquid format performed under microaerophilic conditions and read over 330 minutes. Mean max signal shown as relative fluorescence units (RFU); diagonal from upper left to lower right=regression slope>20; diagonal from upper right to lower left=regression slope<10; F 1:100 O/N=overnight control read; CONT=PBS control.

FIG. 132B shows the quantitation of anaerobic bacterial strains using a resazurin-based assay in liquid format performed under microaerophilic conditions and read over 20 hours. Mean max signal shown as relative fluorescence units (RFU); diagonal from upper left to lower right=regression slope>20; diagonal from upper right to lower left=regression slope<10; F 1:100 O/N=overnight control read; CONT=PBS control.

FIG. 132C shows the quantitation of anaerobic bacterial strains using a resazurin-based assay in liquid format performed under strict aerobic conditions and read over 24 hours. Mean max signal shown as relative fluorescence units (RFU); diagonal from upper left to lower right=regression slope>20; diagonal from upper right to lower left=regression slope<10; F 1:100 O/N=overnight control read; CONT=PBS control.

FIG. 135A corresponds to $10^3$ CFU/mL; FIG. 135B corresponds to $10^4$ CFU/mL; FIG. 135C corresponds to $10^5$ CFU/mL; and FIG. 135D corresponds to $10^6$ CFU/mL.

FIG. 136A corresponds to $10^3$ CFU/mL; FIG. 136B corresponds to $10^4$ CFU/mL; FIG. 136C corresponds to $10^5$ CFU/mL; and FIG. 136D corresponds to $10^6$ CFU/mL.

DESCRIPTION OF EXEMPLARY EMBODIMENTS

Figure 1:
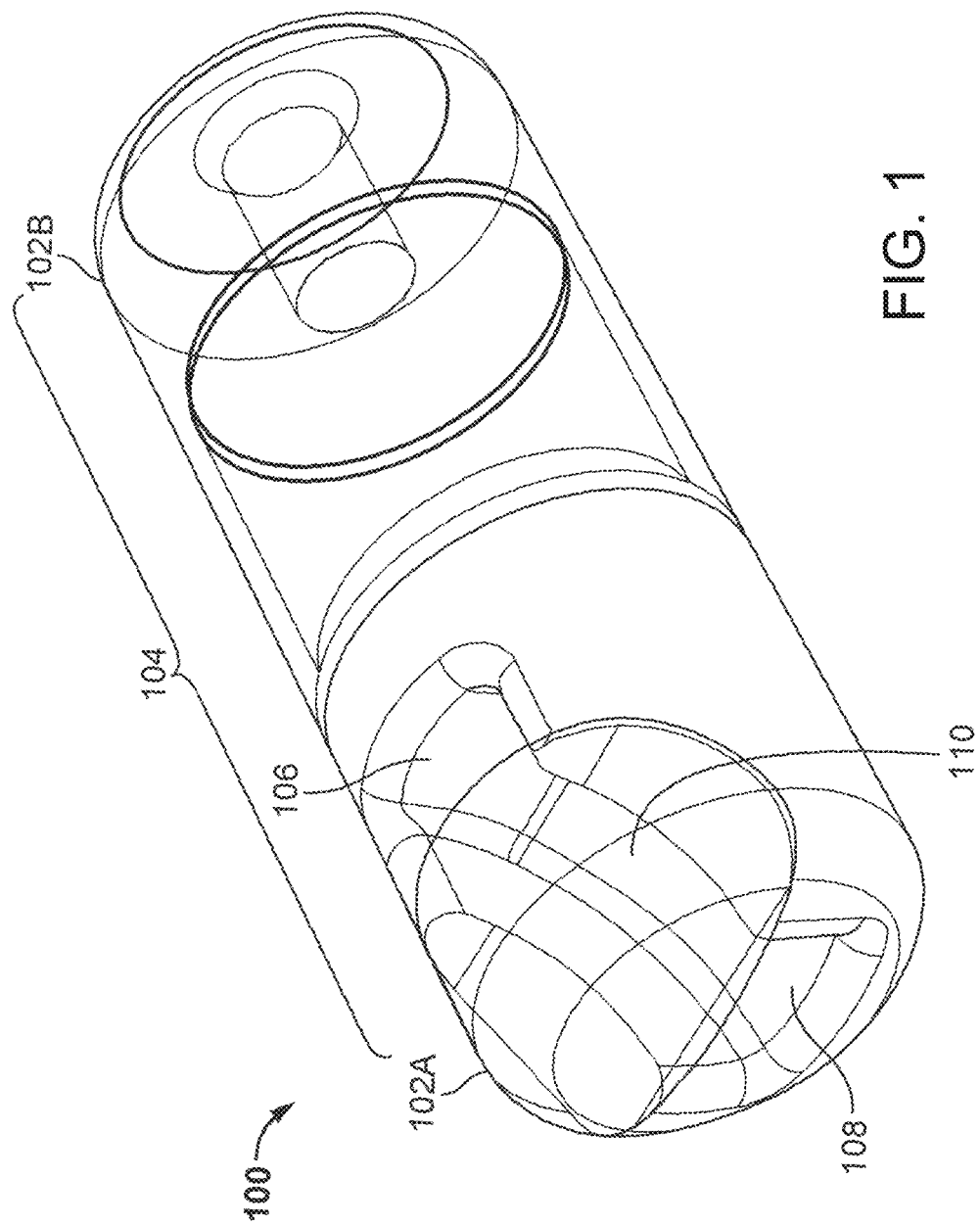
FIG. 1 shows an ingestible device.

Various apparatuses, systems, devices, components and/or processes will be described below to provide illustrative and non-limiting examples. No embodiment described below limits the subject matter covered by any claim, and any claim may cover processes or apparatuses that differ from those described below. As an example, the subject matter covered by the claims is not limited to apparatuses, systems, devices, components and/or processes having all of the features of any one apparatus, system, device, component and/or process described below or to features common to multiple or all of the apparatuses or processes described below. It is possible that a given apparatus, system, device, component and/or or process described below is not covered by a given claim. Any embodiment disclosed herein that is not covered by one or more claims in this document may be coveed by one or more claims in one or more other protective instruments, such as, for example, one or more continuing patent applications and/or one or more divisional patent applications. The Applicants, inventors and/or owners do not necessarily intend to abandon, disclaim or dedicate to the public any subject matter disclosed herein but not covered by a claim herein.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it is to be understood that the embodiments described herein may be practiced without these specific details. In other instances, well-known methods, procedures and components may have not been described in detail so as not to obscure the embodiments described herein. Also, the description is not to be considered as limiting the scope of the embodiments described herein.

Definitions

Unless otherwise defined herein, scientific and technical terms used in this disclosure shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification.

Chemistry terms used herein are used according to conventional usage in the art, as exemplified by "The McGraw-Hill Dictionary of Chemical Terms," Parker S., Ed., McGraw-Hill, San Francisco, Calif. (1985).

All of the publications, patents and published patent disclosures referred to in this disclosure are specifically incorporated by reference herein. In case of conflict, the present specification, including its specific definitions, will control.

The term "reproductive tract" as used herein refers to all portions of an organ system responsible for sexual reproduction in a woman, including but not limited to, the ovaries, Fallopian tube, uterus, cervix and vagina.

A "patient," "subject," or "individual" are used interchangeably and refer to either a human or a non-human animal. These terms include mammals, such as humans, primates, livestock animals (including bovine, porcine, etc.), companion animals (e.g., canine, feline, etc.) and rodents (e.g., mice and rats). The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The terms "treating," "treat," or "treatment" embrace both preventative, i.e., prophylactic, and palliative treatment. In some embodiments, the methods described herein include the use of an ingestible device for detecting a GI disorder in a subject who has or is at risk of developing a GI disorder. In some embodiments, the subject has been previously identified as having a GI disorder. Some embodiments of any of the methods provided herein further include, prior to the providing an ingestible device step, determining that the subject has a GI disorder. Some embodiments of any of the methods can further include identifying or diagnosing a subject as having a GI disorder.

"Eukaryotic" as recited herein relates to any type of eukaryotic organism excluding fungi, such as animals, in particular animals containing blood, and includes invertebrate animals such as crustaceans and vertebrates. Vertebrates include both cold-blooded (fish, reptiles, amphibians) and warm blooded animal (birds and mammals). Mammals include in particular primates and more particularly humans.

"Selective lysis" as used in the present disclosure is obtained in a sample when a certain type of cell (e.g., a bacterial cell (e.g., a Gram-positive or a Gram-negative bacterial cell) or a eukaryotic cell) is preferentially lysed over a different type of cell in the sample (e.g., eukaryotic cell or a bacterial cell). In some embodiments cells of a particular genera, species or strain are preferentially lysed over cells of a different genera, species or strain. In some embodiments, the percentage of cells of a first genera, species, or strain in the sample that remain intact is significantly higher (e.g. 2, 5, 10, 20, 50, 100, 250, 500, or 1,000 times more) than the percentage of cells of a second genera, species, or strain in the sample that remain intact, upon treatment of or contact with a composition or device as described herein. In some embodiments, the percentage of the bacterial cell in the sample is significantly lower (e.g., 2, 5, 10, 20, 50, 100, 250, 500, or 1,000 times less) than the percentage of the eukaryotic cells in the sample that remain intact, upon treatment of or contact with a composition or device described herein. In some embodiments, the percentage of bacterial cells in the sample that remain intact is significantly higher (e.g. 2, 5, 10, 20, 50, 100, 250, 500, or 1,000 times more) than the percentage of the eukaryotic cells in the sample that remain intact, upon treatment of or contact with a composition or device as described herein. In some embodiments, the percentage of Gram-positive bacterial cell in the sample that remain intact is significantly higher (e.g. 2, 5, 10, 20, 50, 100, 250, 500, or 1,000 times more) than the percentage of the Gram-negative bacterial cells in the sample that remain intact, upon treatment of or contact with a composition or device as described herein. In some embodiments, the percentage of Gram-negative bacterial cell in the sample that remain intact is significantly higher (e.g. 2, 5, 10, 20, 50, 100, 250, 500, or 1,000 times more) than the percentage of the Gram-positive bacterial cells in the sample that remain intact, upon treatment of or contact with a composition or device as described herein.

A "sample" as used in the present disclosure may be a biological sample or an environmental sample. Such samples may be obtained from any organism or environmental site desired. For example, the compositions, methods and devices of this disclosure may be used for detecting and quantifying bacterial cells in a sample obtained from, without limitation, soil, rock, plants, animals, cell or tissue culture, biofilms, organic debris, or water. In some embodiments, samples are obtained from mammals such as humans. In some embodiments, samples are obtained from a human's GI tract. In some embodiments, samples are body fluid samples including, but not limited to urine, blood, plasma, serum, saliva, semen, stool, sputum, cerebral spinal fluid, tears, mucus, and the like. In some embodiments, a single device collects multiple samples, for example, 2, 3, 4, 5, 6, 7, 8, 9, 10, 11, 12, 13, 14, 15, 16, 17, 18, 19, 20, 21, 22, 23, 24, 25, 30, 35, 40, 45, 50, 100 or more samples. In some embodiments, the sample is between 1-2000 µL (e.g., 1-1500 µL, 1-1900 µL, 1-1000 µL, 1-500 ul, 1-250 ul, 1-100 µl, 1-50 µl, 1-10 µl, and 1-5 µl).

A "colony-forming unit" or "CFU" refers to a unit used to estimate the number of viable bacteria or fungal cells in a sample. Viable is defined by the cell's ability to divide and form a population (or colony). In some embodiments, the viable bacterial cells in a sample may be derived from bacteria selected from the group consisting of: *Escherichia coli* (or *E. coli*), *Bacillus anthracis, Bacillus cereus, Bacteroides vulgatus, Clostridium botulinum, Clostridium butyricum, Yersinia pestis, Yersinia enterocolitica, Francisella tularensis, Brucella* species, *Clostridium perfringens, Clostridium sporogenes, Klebsiella pneumoniae, Enterobacter aerogenes, Burkholderia mallei, Burkholderia pseudomallei, Staphylococcus* species, *Staphylococcus aureus, Mycobacterium* species, *Enterococcus faecalis*, Group A *Streptococcus*, Group B *Streptococcus, Streptococcus pneumoniae, Streptococcus mutans, Proteus mirabilis, Helicobacter pylori, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsia, Rickettsia akari, Rickettsia prowazekii, Rickettsia canada, Bacillus subtilis, Bacillus subtilis niger, Bacillus thuringiensis* and *Coxiella burnetti*.

As used herein, the term "coupled" indicates that two elements can be directly coupled to one another or coupled to one another through one or more intermediate elements.

The term "saturate" means to permeate or be permeated with a liquid. In some embodiments, an absorptive sponge of the present disclosure may be fully saturated with an amount of a liquid such that no more liquid can be held. In some embodiments, an absorptive sponge of the present disclosure may be partially saturated with a liquid at an amount that is less than the maximum amount of the liquid that can be held by the sponge. For instance, in some embodiments, a sponge is half-saturated with a liquid at half of the maximum amount of the liquid that can be held by the sponge.

The term "semi-solid" means a material that is neither solid (elastic behavior) nor liquid (viscous behavior) and possesses the characteristics of both viscosity and elasticity. Examples of semi-solid materials include gels, ointments, creams, and highly viscous liquids.

As used herein "culturing" refers to maintaining cells in an environment that allows a population of one or more cells to increase in number through cell division. For example, in some embodiments "culturing" may include combining the cells with media in a dilution chamber at a temperature that permits cell growth, optionally a temperature found in vivo within the GI tract or reproductive tract of a subject. In some embodiments, the cells are cultured at a temperature between about 35° C. and 42° C. In some embodiments, the cells are cultured at a temperature of about 37° C.

As used herein "dilution fluid" refers to a fluid within the device for diluting a fluid sample from the GI tract or reproductive tract. In some embodiments, the dilution fluid is an aqueous solution. In some embodiments, the dilution fluid includes one or more agents that promote or inhibit the growth of an organism, such as a fungus or bacteria. In some embodiments, the dilution fluid includes one or more agents that facilitate the detection of an analyte, such as dyes or binding agents for analytes.

In some embodiments, a dilution fluid is a sterile media. As used herein, "sterile media" refers to media that does not contain any viable bacteria or other cells that would grow and increase in number through cell division. Media may be rendered sterile by various techniques known in the art such as, but not limited to, autoclaving and/or preparing the media using aseptic techniques. In some embodiments, the media is a liquid media. Examples of media suitable for culturing bacteria include nutrient broth, Lysogeny Broth (LB) (also known as Luria Broth), Wilkins chalgren, and Tryptic Soy Broth (TSB). Other growth or culture media known in the art may also be used in the methods and devices described herein. In some embodiments, the media has a carbon source, such as glucose or glycerol, a nitrogen source such as ammonium salts or nitrates or amino acids, as well as salts and/or trace elements and vitamins for microbial growth. In some embodiments, the media is suitable for maintaining eukaryotic cells. In some embodiments, the media includes one or more agents that promote or inhibit the growth of bacteria, optionally agents that promote or inhibit the growth of specific types of bacteria.

In some embodiments, the media is a selective media. As used herein, "selective media" refers to a media that allows certain types of cells to grow and inhibits the growth of other organisms. Accordingly, the growth of cells in a selective media indicates the presence of certain types of cells within the cultured sample. For example, in some embodiments the media is selective for Gram-positive or Gram-negative bacteria. In some embodiments, the media contains crystal violet and bile salts (such as found in MacConkey agar) that inhibit the growth of Gram-positive organisms and allows for the selection and isolation of Gram-negative bacteria. In another embodiment, the media contains a high concentration of salt (e.g., NaCl) (such as found in Mannitol salt agar) and is selective for Gram-positive bacteria. In some embodiments, the media selectively kills eukaryotic cells or only grows prokaryotic cells. In another embodiment, the media selectively kills prokaryotic cells (or alternatively only grows eukaryotic cells), for example, using a media that includes antibiotics.

In some embodiments, the media is an indicator media. As used herein, "indicator media" refers to a media that contains specific nutrients or indicators (such as, but not limited to neutral red, phenol red, eosin y, or methylene blue) that produce a detectable signal when a certain type of cells are cultured in the indicator media.

As used herein, "detecting bacteria" refers to determining the presence or absence of bacteria within a sample or estimating the concentration of bacteria within a sample. For example, in some embodiments, bacterial growth can be determined based on the concentration of bacteria within a sample. In some embodiments, the detection system detects and/or quantitates a particular bacterial genus, species or strain within a sample. In some embodiments, the detection system detects the products of bacterial growth within the cultured and/or diluted sample or a change in concentration of certain components within the media due to bacterial growth. In some embodiments, products of bacterial growth include analytes produced and/or secreted by the bacteria that are present in the media, including, but not limited to, bacterial toxins, exosomes, secreted proteins, and metabolites.

A "photosensitizer" as used herein refers to a sensitizer for generation of singlet oxygen usually by excitation with light. Exemplary photosensitizers suitable for use in the present application include those described in U.S. Pat. Nos. 6,251,581, 5,516,636, 8,907,081, 6,545,012, 6,331,530, 8,247,180, 5,763,602, 5,705,622, 5,516,636, 7,217,531, and U.S. Patent Publication No. 2007/0059316, all of which are herein expressly incorporated by reference in their entireties. The photosensitizer can be photoactivatable (e.g., dyes and aromatic compounds) or chemiactivated (e.g., enzymes and metal salts). When excited by light, the photosensitizer is usually a compound included of covalently bonded atoms, usually with multiple conjugated double or triple bonds. The compound should absorb light in the wavelength range of 200-1100 nm, usually 300-1000 nm, e.g., 450-950 nm, with an extinction coefficient at its absorbance maximum greater than 500 $M^{-1}$ $cm^{-1}$, e.g., at least 5000 $M^{-1}$ $cm^{-1}$, or at least 50,000 $M^{-1}$ $cm^{-1}$ at the excitation wavelength. The lifetime of an excited state produced following absorption of light in the absence of oxygen will usually be at least 100 nsec, e.g., at least 1 μsec. In general, the lifetime is desirably sufficiently long to permit energy transfer to oxygen, which will normally be present at concentrations in the range of $10^{-5}$ to $10^{-13}$M depending on the medium. The sensitizer excited state will usually have a different spin quantum number (S) than its ground state and will usually be a triplet (S=1) when, as is usually the case, the ground state is a singlet (S=O). In some embodiments, the sensitizer will have a high intersystem crossing yield. That is, photoexcitation of a sensitizer will produce the long lived state (usually triplet) with an efficiency of at least 10%, at least 40%, e.g., greater than 80%. The photosensitizer will usually be at most weakly fluorescent under the assay conditions (quantum yield usually less that 0.5, or less that 0.1).

GI Tract

As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts. The device may be used to detect, analyze and/or quantify an analyte, e.g., bacterial cells, in a sample from the GI tract (e.g., in one or more of the mouth, throat, esophagus, stomach, small intestine, large intestine, rectum, anus, sphincter, duodenum, jejunum, ileum, ascending colon, transverse colon, and descending colon) of a subject. The device may also be used to detect or quantify bacterial cells from outside the GI tract, including the female reproductive tract. In some embodiments, the samples from the subject are environmental samples that do not contain eukaryotic cells.

The GI tract is a large organ that extends from the buccal cavity to the anus. The primary function of the GI tract is to digest food, absorb nutrients and eliminated any waste. The GI tract is composed of the esophagus, the stomach, and the intestines. The different segments of the GI tract are generally associated with different characteristics. Chewed food flows through the esophagus, and into the stomach where it is temporarily stored and mixed with gastric acid. Involuntary muscle contractions, termed peristalsis, push the food out of the stomach and into the small intestine. The small intestine can be divided into the duodenum, the jejunum and the ileum. The majority of food digestion and absorption occurs in the ileum. Waste and unwanted products are passed into the colon, or large intestine. Typically, food resides for 10 to 14 seconds in the esophagus, and travels within the small intestine for 2 to 4 hours. Half of the contents of the stomach is emptied within 60 to 90 minutes (Khutoryanskiy (2015) Nature Materials 14: 963-964). While food enters the esophagus at approximately pH 7.0, foods are acidified within the stomach (pH 1-5). The pH in the proximal small intestine is between 6.8 and 7.88; between 5.26 and 6.72 in the distal small intestine, between 5.26-6.72 in the ascending colon, and between 5.20 and 7.02 in the descending colon (Khutoryanskiy (2015) Nature Materials 14: 963-964).

Over 1000 different microbial species have been identified that can live in the human GI tract, e.g., *Actinobacteria*, *Bifidobacterium* spp., *Coriobacteriales*, *Eggerthella*, *Slackia* spp., *Actinomycetales*, *Bacteroidetes*, *Firmicutes*, *Gemella*, *Clostridia*, *Lachnospiraceae*, *Negativicutes*, *Fusobacteria*, and *fungi* (e.g., *Eukarya*). See, e.g., Rajilic-Stojanovic and de Vos (2014) FEMS Microbiol. Rev. 38(5): 996-1047; and Carroll et al. (2015) Mamm. Genome 20(7): 395-403. Whereas the small intestine contains very few bacteria, the colon comprises between $10^{13}$ and $10^{14}$ commensal bacteria (Johansson et al. (2013) Nat. Rev. Gastroenterol. Hepatol. 10(6): 352-361).

The intestinal fluid can contain a variety of digestive enzymes (e.g., pepsin, lipase, amylase, enterokinase, sucrose, maltase, lactase, secretin, motilin). See, e.g., Ulleberg et al. (2011) Food Dig. 2(1-3): 52-61.

Diseases or Disorders

The detection and/or analysis of an analyte described herein may be used to determine whether the subject has or is at risk of developing a disease or disorder (e.g., a GI disorder). These diseases and disorders are not limited to diseases and disoders present in the GI tract of the subject, and can include diseases or disoders at sites other than the GI tract of the subject. For example, in some embodiments, analytes present in the GI tract may be indicative of a systemic disease or disorder. In some embodiments, the analytes are associated with a systemic disease or disorder. In some embodiments, analytes present in the GI tract may be indicative of a disease or disorder described herein, including, but not limited to an infectious disease, IBD, Crohn's disease, and cancer.

In some embodiments of any of the methods described herein, the subject has a GI disorder. In some embodiments, the analytes disclosed herein may be indicative of a GI disorder in a subject. Examples of such GI disorders include inflammatory bowel disease (IBD), Crohn's disease (e.g., active Crohn's disease, refractory Crohn's disease, or fistulizing Crohn's disease), ulcerative colitis, indeterminate colitis, infectious colitis, microscopic colitis, drug or chemical-induced colitis, diverticulitis, ischemic colitis, pseudomembranous colitis, hemorrhagic colitis, hemolytic-uremic syndrome colitis, collagenous colitis, colitis associated with disorders of innate immunity as in leukocyte adhesion deficiency-1, diversion colitis, gastritis, peptic ulcers, stress ulcers, bleeding ulcers, gastric hyperacidity, dyspepsia, gastroparesis, Zollinger-Ellison syndrome, gastroesophageal reflux disease, short-bowel (anastomosis) syndrome, mucositis (e.g., oral mucositis, gastrointestinal mucositis, nasal mucositis and proctitis), necrotizing enterocolitis, esophagitis, a hypersecretory state associated with systemic mastocytosis, basophilic leukemia, hyperhistaminemia, Celiac disease (e.g., nontropical Sprue), enteropathy associated with seronegative arthropathies, eosinophilic gastroenteritis, colitis associated with radiotherapy or chemotherapy (such as checkpoint inhibitor chemotherapy), colitis associated with disorders of innate immunity such as leukocyte adhesion deficiency-1, gastritis, chronic granulomatous disease, food allergies, infectious gastritis or enterocolitis (e.g., Helicobacter pylori-infected chronic active gastritis), other forms of gastrointestinal inflammation caused by an infectious agent, irritable colon syndrome, small intestinal bacterial overgrowth (SIBO) and pouchitis.

"Inflammatory Bowel Disease" or "IBD" is a chronic inflammatory autoimmune condition of the GI tract. Although the cause of IBD remains unknown, several factors such as genetic, infectious and immunologic susceptibility have been implicated. IBD is much more common in Caucasians, especially those of Jewish descent.

A chronic inflammatory autoimmune condition of the GI tract presents clinically as either ulcerative colitis (UC) or Crohn's disease (CD). Both IBD conditions are associated with an increased risk for malignancy of the GI tract. "Crohn's disease" ("CD") is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living. CD is frequently complicated by the development of malabsorption, strictures, and fistulae and may require repeated surgery. UC, less frequently, may be complicated by severe bloody diarrhea and toxic megacolon, also requiring surgery. The most prominent feature of Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual. Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

A "symptom" of a disease or disorder (e.g., an inflammatory bowel disease, e.g., ulcerative colitis or Crohn's disease) is any morbid phenomenon or departure from the normal in structure, function, or sensation, experienced by a subject and indicative of disease.

In certain embodiments, the subject has small intestinal bacterial overgrowth (SIBO). The small intestine houses less than $10^3$ bacteria/mL under healthy conditions. When the homeostasis of the gut microbiome is disrupted or aberrant, various functions of the gut microbiota are uncontrolled. See, e.g., Shreiner et al. (2016) Curr. Opin. Gastroenterol. 31(1): 69-75; Bures et al. (2010) World J. Gastroenterol. 16(24): 2978-2990. Excessive levels of bacteria (over $10^5$ bacteria/mL) and abnormal types of bacteria in the small intestine leads to the development of SIBO. SIBO is associated with chronic diarrhea, abdominal discomfort, bloating, malabsorption, flatulence, and unintentional weight loss. While Gram-positive bacteria are typically found in the small intestine, subjects suffering from SIBO have a variety of bacteria in the small intestine including Gram-negative bacteria, which are normally only present in very small numbers or not at all within the small intestine. For example, bacteria present in SIBO may secrete mucosal damaging toxins or metabolize bile salts, which can lead to malabsorption and bloating. A study comparing the prevalence of SIBO in subjects aged 24 to 50 and in subjects aged 61 or older found that SIBO was more prevalent in older subjects as compared to younger subjects (15.6% and 5.9% respectively) (Parlesak et al. (2003) J. Am. Geriatr. Soc. 51(6): 768-773). SIBO was also seen more frequently in subjects with reduced body weight. Risk factors for developing SIBO include: metabolic disorders (e.g., diabetes, hypochloryhydria), malnutrition, irritable bowel syndrome (IBS), Celiac disease, Crohn's disease, cirrhosis, renal failure, gastroparesis, small bowel dysmotility, structural abnormalities of the GI tract (e.g., jejunal diverticula), gastric resection and immuno-deficiency. Additional risk factors include the use of certain medications (e.g., antibiotics, gastric acid secretion inhibitors). See, e.g., Dukowicz et al. (2007) Gastronenterol. Hepatol. 3(2): 112-122. In some embodiments, subjects having SIBO have delayed intestinal transit times (Cuoco et al. (2002) Hepatogastroenterology 49: 1582-1586). In some embodiments, subjects having SIBO have accelerated intestinal transit times (Van Citters and Lin (2006) Clin. Nutrition in Gastrointestinal Disease. Thorofare: Slack Inc; 2006; 271-280).

As used herein, a subject has or is at risk of having SIBO if the subject has intestinal bacteria levels that are greater than $10^3$ colony forming units (CFU)/mL, e.g., greater than $10^4$ CFU/mL, greater than $10^5$ CFU/mL, greater than $10^6$ CFU/mL, greater than $10^7$ CFU/mL, greater than $10^8$ CFU/mL, greater than $10^9$ CFU/mL, greater than $10^{10}$ CFU/mL. In some embodiments, the bacteria are both Gram-positive and Gram-negative bacteria. In some embodiments, the bacteria are Gram-positive bacteria. In some embodiments, the bacteria are Gram-negative bacteria.

The prevalence of SIBO in healthy individuals varies from about 0-20% (see, e.g., Lombardo et at (2010) Clin. Gastroenterol. Hepatol. 8: 504-8; Sabaté et al. (2008) Obes. Surg. 18: 371-7; Posserud et al. (2007) Gut 56: 802-8; Teo (2004) J. Gastroenterol. Hepatol. 19: 904-9; Lewis et al. (1999) Age Ageing 28: 181-5; Pimentel et al. (2003) Am. J. Gastroenterol. 98: 412-9; Rana et al. (2011) Diabetes Technol. Ther. 13: 1115-20; Bratten et al. (2008) Am. J. Gastroenterol. 103: 958-63; and Scarpellini et al. (2009) J. Pediatr. 155: 416-20). Several clinical conditions are associated with SIBO and are referred to herein as "SIBO-related conditions." Exemplary SIBO-related conditions include, but are not limited to, coeliac disease (see, e.g., Rana et al. (2007) Trop. Gastroenterol. 28: 159-61; Rubio-Tapia et al. (2009) J.

*Clin. Gastroenterol.* 43: 157-61; and Tursi et al. (2003) *Am. J. Gastroenterol.* 98: 839-43), connective tissue diseases such as scleroderma (see, e.g., Levesque et al. (2009) *Rheumatology* 48: 1314-9; and Parodi et al. (2008) *Am. J. Gastroenterol.* 103: 1257-62), Crohn's disease (see, e.g., Fukushima et al. (1999) *Dis. Colon Rectum* 42: 1072-7; Klaus et al. (2009) *Gastroenterol.* 9: 61; and U.S. Publication No. 2002/0039599), diabetes mellitus (see, e.g., Rana et al. (2011) *Diabetes Technol Ther* 13: 1115-20, and Zaccardi et al. (2009) *Eur. Rev. Med. Pharmacol. Sci.* 13: 419-23), hypothyroidism (see, e.g., Lauritano et al. (2007) *J. Clin. Endocr. Metab.* 92: 4180-4), nonspecific dysmotility (see, e.g., Jacobs et al. (2013) *Aliment. Pharmacol. Ther.* 37: 1103-11), radiation enteropathy (see, e.g., Wedlake et al. (2008) *Eur. J Cancer* 44: 2212-7), ulcerative colitis (see, e.g., Ibanez et al. (2008) *Gastroenterology* 134: A-350), chronic fatigue syndrome (see, e.g., Ojetti et al. (2009) *Eur. Rev. Med. Pharmacol. Sci.* 13: 419-23), chronic pancreatitis (see, e.g., Mancilla et al. (2008) 136: 976-80; and Trespi et al (1999) *Curr. Med. Res. Opin.* 15: 47-52), drug-induced inhibition of acid secretion (see, e.g., Jacobs (2013) *Aliment. Pharmacol. Ther.* 37: 1103-11; Compare et al. (2010) *Eur. J Clin. Invest.* 41: 380-6; and Lombardo et al. (2010) *Clin. Gastroenterol. Hepatol.* 8: 504-8), end-stage renal failure (see, e.g., Strid et al. (2003) *Digestion* 67: 129-37), fibromyalgia (see, e.g., U.S. Publication No. 2002/0039599), irritable bowel syndrome (Posserud et al. (2007) *Gut* 56: 802-8; Bratten et al. (2008) *Am. J. Gastroenterol.* 103: 958-63; 30. Pimentel et al. (2000) *Am. J. Gastroenterol.* 95: 3503-6; Nucera et al. (2005) *Aliment. Pharmacol. Ther.* 21: 1391-5; Lupascu et al. (2005) *Aliment. Pharmacol. Ther.* 22: 1157-60; and Grover et al. (2008) *Neurogastroenterol. Motil.* 20: 998-1008), immunodeficiency syndromes such as HIV-infection and chronic lymphocytic leukaemia (see, e.g., Chave et al. *Am. J. Gastroenterol.* 89: 2168-71; and Smith et al. (1990) *J. Clin. Pathol.* 43: 57-9), liver cirrhosis (see, e.g., Yang et al. (1998) *Scand. J. Gastroenterol.* 33: 867-71; and Gunnarsdottir (2003) *Am. J. Gastroenterol.* 98: 1362-70), obesity (see, e.g., Sabaté et al. (2008) Obes. Surg. 18: 371-7; and Madrid et al. (2011) *Dig. Dis. Sci.* 56: 155-60), parenteral nutrition (see, e.g., Gutierrez et al. (2012) *J Pediatr. Surg.* 47: 1150-4), rosacea (Parodi et al. Clin. *Gastroenterol. Hepatol.* 6: 759-64), muscular dystrophy (see, e.g., Tarnopolsky et al. (2010) *Muscle Nerve* 42: 853-5), and Parkinson's disease (see, e.g., Gabrielli (2011) *Movement Disord.* 26: 889-92). Thus, in some embodiments of any of the methods described herein, the subject has a SIBO-related condition selected from the group consisting of coeliac disease, a connective tissue disease (e.g., scleroderma), Crohn's disease, diabetes mellitus, hypothyroidism, nonspecific dysmotility, radiation enteropathy, ulcerative colitis, chronic fatigue syndrome, chronic pancreatitis, drug-induced inhibition of acid secretion, end-stage renal failure, fibromyalgia, irritable bowel syndrome, an immunodeficiency syndrome (e.g., HIV-infection and chronic lymphocytic leukaemia), obesity, parenteral nutrition, rosacea, muscular dystrophy, and Parkinson's disease. For example, the methods described herein may be used to detect SIBO in a subject having a SIBO-related condition.

In some embodiment of any of the methods described herein, the subject is suspected of having SIBO or a SIBO-related condition. In some embodiments of any of the methods described herein, the subject has one or more symptoms selected from the group consisting of bloating, diarrhea, flatulence, abdominal pain, constipation, weight loss, fever, abdominal tenderness, nausea, gastric stasis, and steatorrhea.

In some embodiments of any of the methods described herein, the subject has been subjected to a surgical intervention. For example, SIBO is prevalent in subjects that have undergone abdominal surgery, bilateral vagotomy, gastrectomy, ileocaecal valve resection, and roux-en-Y reconstruction (see, e.g., Grace et al. (2013) *Aliment. Pharmacol. Ther.* 38(7):674-88, the entire contents of which are expressly incorporated herein by reference). In some embodiment of any of the methods described herein, the subject has been subjected to a surgical intervention selected from the group consisting of abdominal surgery, bilateral vagotomy, gastrectomy, ileocaecal valve resection, and roux-en-Y reconstruction.

In some embodiments, detection of analytes disclosed herein are indicative of disorders of the gastrointestinal tract associated with anomalous bacterial populations. The bacteria may include, but are not limited to, the types of bacteria present in the fluid sample or the concentration of bacteria in specific regions of the GI tract. Data obtained using the methods described herein may be used to determine whether a subject has an infection, such as Small Intestinal Bacterial Overgrowth (SIBO), or to characterize bacterial populations within the GI tract for diagnostic or other purposes. In some embodiments, detection of an analyte disclosed herein in a subject may be indicative of a disease or condition originating from the endoderm in a subject. In some embodiments of any of the methods described herein, the subject has a disease or condition orginating from the endoderm selected from the group of: gastritis, Celiac disease, hepatitis, alcoholic lever disease, fatty liver disease (hepatic steatosis), non-alcoholic fatty liver disease (NASH), cirrhosis, primary schlerosing cholangitis, pancreatitis, insterstitial cystitits, asthma, chronic obstructive pulmonary disease, pulmonary fibrosis, pharyngitis, thyroiditis, hyperthyroidism, parathyroiditis, nephritis, Hashimoto's disease, Addison's disease, Graves' disease, Sjögren syndrome, type 1 diabetes, pelvic inflammatory disease, auditory canal inflammation, tinnitus, vestibular neuritis, otitis media, auditory canal inflammation, tracheitis, cholestatic liver disease, primary biliary schlerosis, liver parenchyma, an inherited metabolic disorder of the liver, Byler syndrome, cerebrotendinous, xanthomatosis, Zellweger's syndrome, neonatal hepatitis, cystic fibrosis, ALGS (Alagilles syndrome), PFIC (progressive familial intrahepatic cholestasis), autoimmune hepatitis, primary biliary cirrhosis (PBC), liver fibrosis, NAFLD, portal hypertension, general cholestasis, such as in jaundice due to drugs or during pregnancy, intra- and extrahepatic cholestasis, such as hereditary forms of cholestasis, such as PFIC1, gall stones and choledocholithiasis, malignancy causing obstruction of the biliary tree, symptoms (scratching, pruritus) due to cholestasis/jaundice, chronic autoimmune liver disease leading to progressive cholestasis, and pruritus of cholestatic liver disease, duodenal ulcers, enteritis (radiation-, chemotherapy-, or infection-induced enteritis), diverticulitis, pouchitis, cholecystitis, and cholangitis. In some embodiments of any of the methods described herein, the inflammatory disease or condition that arises in a tissue originating from the endoderm is inflammation of the liver.

In some embodiments, the detection of analytes disclosed herein is indicative of diseases or disorders of the liver. In some embodiments, detection of an analyte disclosed herein in a subject may be indicative of a liver disease or disorder in a subject. For example, the methods, devices, and compositions described herein may be used to determine whether a subject has or is at risk of developing a liver disease or disorder, and/or to determine or monitor a course of treatment for a liver disease or disorder. A non-exhaustive list of liver diseases and disorders, include, but are not limited to fibrosis, cirrhosis, alcoholic lever disease, fatty liver disease (hepatic steatosis), non-alcoholic fatty liver disease (NASH), cholestatic liver disease, liver parenchyma, an inherited metabolic disorder of the liver, PFIC (progressive familial intrahepatic cholestasis), autoimmune hepatitis, primary biliary cirrhosis (PBC), liver fibrosis, NAFLD, chronic autoimmune liver disease leading to progressive cholestasis, pruritus of cholestatic liver disease, inflammation of the liver, and liver fibrosis.

Methods of Selecting and Optimizing Treatment

In some embodiments, the methods described herein include the administration of one or more treatments, e.g., antibiotics, to a subject identified as having or being at risk of developing a GI disorder (e.g., SIBO). The methods can also include selecting a treatment for a subject who has a GI disorder or is determined to be at risk for developing a GI disorder, based upon the presence or absence of an analyte, or based upon the amount of an analyte. The methods can also include administering a treatment selected by a method described hereinto a subject who has or is at risk of developing a GI disorder to treat, delay disease progression, or reduce the risk of developing of the disease. For example, in some embodiments, the methods described herein can include the administration of an antibiotic (e.g., rifaximin) to a subject identified as having or being at risk of developing SIBO. In some embodiments, the methods can also include selecting a subject having SIBO or who is at risk of developing SIBO (e.g., a subject having a SIBO-related condition), and treating the subject with an antibiotic (e.g., rifaximin) to treat, delay disease progression, or reduce the risk of developing SIBO.

In some embodiments of any of the methods described herein, the method can further include the step of monitoring a subject, e.g., for an increase or decrease in one or more analytes, or any other parameter associated with clinical outcome. In some embodiments, the step of monitoring includes providing the subject with an ingestible device to determining the presence or absence of an analyte and/or the levels or amount of an analyte. In some embodiments, the step of monitoring occurs prior to administering a treatment, during the course of a treatment, or after treatment. In some embodiments, the step of monitoring includes an additional step of ingesting an ingestible device that was previously provided to the subject to determine the presence or absence of an analyte and/or the levels or amounts of an analyte.

Also provided herein are methods of determining the efficacy of a GI disorder treatment. In some embodiments, providing an ingestible device can determine successful treatment of a GI disorder in a subject (e.g., the presence or absence of an analyte is determined; the levels of an analyte is decreased as compared to the levels of the analyte determined in the subject at an early period of time; the levels of an analyte is decreased as compared to the levels of the analyte determined in a control subject (e.g., a subject that does not have a GI disorder, or is not at risk of developing a GI disorder); the levels of an analyte is increased as compared to the levels of the analyte determined in the subject at an early period of time). In some embodiments, prior to the providing an ingestible device step, the subject received treatment for a GI disorder (e.g., any of the treatment described herein). For example, in some embodiments, the level of an analyte (e.g., any of the analytes described herein) is decreased as compared to the level of the analyte described herein prior to treatment for a GI disorder, and further treatment is discontinued. For example, in some embodiments, the level of an analyte (e.g., any of the analytes described herein) is increased as compared to the level of the analyte described herein prior to treatment for a GI disorder, and a different treatment is administered.

Non-limiting examples of such agents for treating or preventing a gastrointestinal disorder (e.g., Crohn's disease, ulcerative colitis) include substances that suppress cytokine production, downregulate or suppress self-antigen expression, or mask MHC antigens. Examples of such agents include 2-amino-6-aryl-5-substituted pyrimidines (see U.S. Pat. No. 4,665,077); non-steroidal anti-inflammatory drugs (NSAIDs); ganciclovir; tacrolimus; glucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-ME-DROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, antiinterleukin-2 (IL-2) antibodies and anti-IL-2 receptor antibodies, and anti-interleukin-6 (IL-6) receptor antibodies and antagonists; anti-LFA-1 antibodies, including anti-CD 11a and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al. Science, 251: 430-432 (1991); WO90/11294; Janeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002); biologic agents that interfere with T cell helper signals, such as anti-CD40 receptor or anti-CD40 ligand (CD 154), including blocking antibodies to CD40-CD40 ligand. (e.g., Dune et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP340,109) such as T10B9. Non-limiting examples of adjunct agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinylimidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TP1O; T Cell Sciences, Inc.); slow-release mesalazine; antagonists of platelet activating factor (PAF); ciprofloxacin; and lignocaine. In some embodiments, the agents for treating or preventing a gastrointestinal disorder (e.g., SIBO) include any antibiotic described herein (e.g., rifaximin). Examples of agents for UC are sulfasalazine and related salicylate-containing drugs for mild cases and corticosteroid drugs in severe cases.

Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

In some embodiments, the antibiotic selected for treatment is selected from the group consisting of: beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefinenoxime, cefinetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3', 4'dideoxykanamycin B, 1,2'-N-DL-isoserylkanamycin B, 1,2'-N—[(S)-4-amino-2-hydroxybutyryl]-3', 4'-dideoxykanamycin B,1,2'-N—[(S)-4-amino-2-hydroxybutyryl]kanamycin B, 1-N-(2-Aminobutanesulfonyl) kanamycin A, 1-N-(2-aminoethanesulfonyl)3', 4'-dideoxyribostamycin, 1-N-(2-aminoethanesulfonyl)3'-deoxyribostamycin, 1-N-(2-aminoethanesulfonyl)3'4'-dideoxykanamycin B, 1-N-(2-aminoethanesulfonyl) kanamycin A,1-N-(2 aminoethanesulfonyl)kanamycin B, 1-N-(2-aminoethanesulfony 1)ribostamycin, 1-N-(2-aminopropanesulfony 1)3'-deoxykanamycin B, 1-N-(2-aminopropanesulfony 1)3'4'-dideoxy kanamycin B, 1-N-(2-aminopropanesulfony 1) kanamycin A, 1-N-(2-aminopropanesulfony 1) kanamycin B, 1-N-(L-4-amino-2-hydroxy-butyryl)2, '3'-dideoxy-2'-fluorokanamycin A, 1-N-(L-4-amino-2-hydroxy-propionyl) 2,'3'-dideoxy-2'-fluorokanamycin A, 1-N-DL-3', 4'-dideoxy-isoserylkanamycin B,1-N-DL-isoserylkanamycin, 1-N-DL-isoserylkanamycin B, 1-N-[L-(−)-(alpha-hydroxygamma-aminobutyryl)]-XK-62-2,2', 3'-dideoxy-2'-fluorokanamycin A,2-hydroxygentamycin A 3,2-hydroxygentamycin B, 2-hydroxygentamycin B1, 2-hydroxygentamycin JI-20A, 2-hydroxygentamycin JI-20B, 3"-N-methyl-4"-C-methyl-3', 4'-dodeoxy kanamycin A, 3"-N-methyl-4"-C-methyl-3', 4'-dodeoxy kanamycin B, 3"-N-methyl-4"-C-methyl-3', 4'-dodeoxy-6'methyl kanamycin B, 3', 4'-Dideoxy-3'-enoribostamycin,3', 4'-dideoxyneamine,3', 4'dideoxyribostamycin, 3'-deoxy-6'-N-methyl-kanamycin B,3'-deoxyneamine, 3'deoxyribostamycin, 3'-oxysaccharocin,3,3'-nepotrehalosadiamine, 3-demethoxy-2"-Nformimidoylistamycin B disulfate tetrahydrate, 3-demethoxyistamycin B,3-0-demethyl-2-N-formimidoylistamycin B, 3-0-demethylistamycin B,3-trehalosamine,411,6 11-dideoxydibekacin, 4-N-glycyl-KA-6606VI, 5"-Amino-3', 4', 5"-trideoxy-butirosin A, 611-deoxydibekacin,61-epi-fortimicin A, 6-deoxy-neomycin (structure 6-deoxy-neomycin B),6-deoxy-neomycin B, 6-deoxy-neomycin C, 6-deoxy-paromomycin, acmimycin, AHB-3', 4'-dideoxyribostamycin, AHB-3'-deoxykanamycin B, AHB-3'-deoxyneamine, AHB-3'-deoxyribostamycin, AHB-411-611-dideoxydibekacin, AHB-611-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gammal, coumamidine gamma2,D,L-1-N-(alpha-hydroxy-betaaminopropionyl)-XK-62-2, dactimicin, de-O-methyl-4-N-glycyl-KA-6606VI, de-O-methyl-KA-66061, de-O-methyl-KA-70381, destomycin A, destomycin B, di-N6', 03-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KG1(stereoisomer KG1/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethy 1-7-0-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, omidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-0-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, arnfomycin, amythiamycin, antifungal from Zalerion arboricola, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from Zalerion sp., lysobactin, lysozyme, macromomycin, magainin, melittin, mersacidin, mikamycin, mureidomycin, mycoplanecin, mycosubtilin, neopeptifl uorin, neoviri dogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a Streptomyces compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-2 5 oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascoseroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Analytes

The compositions and methods described herein can be used to detect, analyze, and/or quantitate a variety of analytes in a human subject. "Analyte" as used in the present application refers to a compound or composition to be detected in a sample. Exemplary analytes suitable for use in the present application include those described in U.S. Pat. No. 6,251,581, which is incorporated by reference herein in its entirety. Broadly speaking, an analyte can be any substance (e.g., a substance with one or more antigens) capable of being detected. An exemplary and non-limiting list of analytes includes ligands, proteins and fragments thereof, blood clotting factors, hormones, cytokines, polysaccharides, nucleic acids, carbohydrates, mucopolysaccharides, lipids, fatty acids, microorganisms (e.g., bacteria), microbial antigens, and therapeutic agents (including fragments and metabolites thereof).

For instance, the analyte may be a substance that binds to an analyte-binding agent (e.g., a biomolecule) and forms a complex. In some embodiments, the analyte may bemonovalent (monoepitopic) or polyvalent (polyepitopic), usually antigenic or haptenic. In some embodiments, the analyte is a single compound or plurality of compounds. In some embodiments, the analyte is a plurality of compounds which share at least one common epitopic or determinant site. The analyte can be a part of a cell such as bacteria or a cell bearing a blood group antigen such as A, B, D, etc., a human leukocyte antigen (HLA), or other cell surface antigen. The analyte can also be a microorganism (e.g., bacterium (e.g. a pathogenic bacterium), a fungus, protozoan, or a virus), a protein, a nucleic acid, a lipid, or a hormone. In some embodiments, the analyte can be an exosome or a part of an exosome (e.g., a bacterial exosome). In some embodiments, the analyte is derived from a subject (e.g., a human subject). In some embodiments, the analyte is derived from a microorganism present in the subject. In some embodiments, the analyte is a nucleic acid (e.g., a DNA molecule or a RNA molecule), a protein (e.g., a soluble protein, a cell surface protein), or a fragment thereof, that can be detected using any of the devices and methods provided herein.

The polyvalent ligand analytes will normally be poly (amino acids), i.e., a polypeptide (i.e., protein) or a peptide, polysaccharides, nucleic acids (e.g., DNA or RNA), and combinations thereof. Such combinations include components of bacteria, viruses, chromosomes, genes, mitochondria, nuclei, cell membranes, and the like.

In some embodiments, the polyepitopic ligand analytes have a molecular weight of at least about 5,000 Da, more usually at least about 10,000 Da. In the poly(amino acid) category, the poly(amino acids) of interest may generally have a molecular weight from about 5,000 Da to about 5,000,000 Da, more usually from about 20,000 Da to 1,000,000 Da; among the hormones of interest, the molecular weights will usually range from about 5,000 Da to 60,000 Da.

In some embodiments, the monoepitopic ligand analytes generally have a molecular weight of from about 100 to 2,000 Da, more usually from 125 to 1,000 Da.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

In some embodiments, the analyte is a protein. In some embodiments, the analyte is a protein, e.g., an enzyme (e.g., a hemolysin, a protease, a phospholipase), a soluble protein, a membrane-bound protein, or an exotoxin. In some embodiments, the analyte is a fragment of a protein, a peptide, or an antigen. In some embodiments, the analyte is a peptide of at least 5 amino acids (e.g., at least 6, at least 7, at least 8, at least 9, at least 10, at least 25, at least, 50, or at least 100 amino acids). Exemplary lengths include 6, 7, 8, 9, 10, 11, 12, 13, 14, 15, 16, 17, 18, 19, 20, 21, 22, 23, 24, 25, 26, 27, 28, 29, 30, 50, 75, or 100 amino acids. Exemplary classes of protein analytes include, but are not limited to: protamines, histones, albumins, globulins, scleroproteins, phosphoproteins, antibodies, affimers, mucoproteins, chromoproteins, lipoproteins, nucleoproteins, glycoproteins, T-cell receptors, proteoglycans, cell surface receptors, membrane-anchored proteins, transmembrane proteins, secreted proteins, HLA, and unclassified proteins. In some embodiments, the analyte is an affimer (see, e.g., Tiede et al. (2017) *eLife* 6: e24903, which is expressly incorporated herein by reference).

Exemplary analytes include: Prealbumin, Albumin, $\alpha_1$-Lipoprotein, $\alpha_1$-Antitrypsin, $\alpha_1$-Glycoprotein, Transcortin, 4.6S-Postalbumin, $\alpha_1$-glycoprotein, $\alpha_{1X}$-Glycoprotein, Thyroxin-binding globulin, Inter-$\alpha$-trypsin-inhibitor, Gc-globulin (Gc 1-1, Gc 2-1, Gc 2-2), Haptoglobin (Hp 1-1, Hp 2-1, Hp 2-2), Ceruloplasmin, Cholinesterase, $\alpha_2$-Lipoprotein(s), Myoglobin, C-Reactive Protein, $\alpha_2$-Macroglobulin, $\alpha_2$-HS-glycoprotein, Zn-$\alpha_2$-glycoprotein, $\alpha_2$-Neuramino-glycoprotein, Erythropoietin, $\beta$-lipoprotein, Transferrin, Hemopexin, Fibrinogen, Plasminogen, $\beta_2$-glycoprotein I, $\beta_2$-glycoprotein II, Immunoglobulin G (IgG) or $\gamma$G-globulin, Immunoglobulin A (IgA) or $\gamma$A-globulin, Immunoglobulin M (IgM) or $\gamma$M-globulin, Immunoglobulin D (IgD) or $\gamma$D-Globulin ($\gamma$D), Immunoglobulin E (IgE) or $\gamma$E-Globulin ($\gamma$E), Free $\kappa$ and $\lambda$ light chains, and Complement factors: C'1, (C'1q, C'1r, C'1s, C'2, C'3 ($\beta_1$A, $\alpha_2$D), C'4, C'5, C'6, C'7, C'8, C'9.

Additional examples of analytes include tumor necrosis factor-$\alpha$ (TNF$\alpha$), interleukin-12 (IL-12), IL-23, IL-6, $\alpha$2$\beta$1 integrin, $\alpha$1$\beta$1 integrin, $\alpha$4$\beta$7 integrin, integrin $\alpha$4$\beta$1 (VLA-4), E-selectin, ICAM-1, $\alpha$5$\beta$1 integrin, $\alpha$4$\beta$1 integrin, VLA-4, $\alpha$2$\beta$1 integrin, $\alpha$5$\beta$3 integrin, $\alpha$5$\beta$5 integrin, $\alpha$IIb$\beta$3 integrin, MAdCAM-1, SMAD7, JAK1, JAK2, JAK3, TYK-2, CHST15, IL-1, IL-1$\alpha$, IL-1$\beta$, IL-18, IL-36$\alpha$, IL-36$\beta$, IL-36$\gamma$, IL-38, IL-33, IL-13, CD40L, CD40, CD3$\gamma$, CD3$\delta$, CD3$\epsilon$, CD3$\zeta$, TCR, TCR$\alpha$, TCR$\beta$, TCR$\delta$, TCR$\gamma$, CD14, CD20, CD25, IL-2, IL-2 $\beta$ chain, IL-2 $\gamma$ chain, CD28, CD80, CD86, CD49, MMP1, CD89, IgA, CXCL10, CCL11, an ELR chemokine, CCR2, CCR9, CXCR3, CCR3, CCR5, CCL2, CCL8, CCL16, CCL25, CXCR1m CXCR2m CXCL1, CXCL2, CXCL3, CXCL4, CXCL5, CXCL6, CXCL7, and CXCL8, and a nucleic acid (e.g., mRNA) encoding any of the same.

In some embodiments, the analyte is a blood clotting factor. Exemplary blood dotting factors include, but are not limited to:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

In some embodiments, the analyte is a hormone. Exemplary hormones include, but are not limited to: Peptide and Protein Hormones, Parathyroid hormone, (parathromone), Thyrocalcitonin, Insulin, Glucagon, Relaxin, Erythropoietin, Melanotropin (melancyte-stimulating hormone; intermedin), Somatotropin (growth hormone), Corticotropin (adrenocorticotropic hormone), Thyrotropin, Follicle-stimulating hormone, Luteinizing hormone (interstitial cell-stimulating hormone), Luteomammotropic hormone (luteotropin, prolactin), Gonadotropin (chorionic gonadotropin), Secretin, Gastrin, Angiotensin I and II, Bradykinin, and Human placental lactogen, thyroxine, cortisol, triiodothyronine, testosterone, estradiol, estrone, progestrone, luteinizing hormone-releasing hormone (LHRH), and immunosuppressants such as cyclosporin, FK506, mycophenolic acid, and so forth.

In some embodiments, the analyte is a peptide hormone (e.g., a peptide hormone from the neurohypophysis). Exemplary peptide hormones from the neurohypophysis include, but are not limited to: Oxytocin, Vasopressin, and releasing factors (RF) (e.g., corticotropin releasing factor (CRF), luteinizing hormone releasing factor (LRF), thyrotropin releasing factor (TRF), Somatotropin-RF, growth hormone releasing factor (GRF), follicle stimulating hormone-releasing factor (FSH-RF), prolactin inhibiting factor (PIF), and melanocyte stimulating hormone inhibiting factor (MIF)).

In some embodiments, the analyte is a cytokine or a chemokine. Exemplary cytokines include, but are not limited to: interleukin-1 (IL-1), interleukin-2 (IL-2), interleukin-6 (IL-6), epidermal growth factor (EGF), tumor necrosis factor (TNF, e.g., TNF-α or TNF-β), and nerve growth factor (NGF).

In some embodiments, the analyte is a cancer antigen. Exemplary cancer antigens include, but are not limited to: prostate-specific antigen (PSA), carcinoembryonic antigen (CEA), α-fetoprotein, Acid phosphatase, CA19.9, CA125, CD19, WT-1, CD22, L1-CAM, ROR-1, CD30, CD125, AFP, CEA, ETA, MAGE, and MUC16.

In some embodiments, the analyte is a tissue-specific antigen. Exemplary tissue specific antigens include, but are not limited to: alkaline phosphatase, myoglobin, CPK-MB, calcitonin, and myelin basic protein.

In some embodiments, the analyte is a mucopolysaccharide or a polysaccharide.

In some embodiments, the analyte is a microorganism, or a molecule derived from or produced by a microorganism (e.g., a bacteria, a virus, prion, or a protozoan). For example, in some embodiments, the analyte is a molecule (e.g., a protein or a nucleic acid) that is specific for a particular microbial genus, species, or strain (e.g., a specific bacterial genus, species, or strain). In some embodiments, the microorganism is pathogenic (i.e., causes disease). In some embodiments, the microorganism is non-pathogenic (e.g., a commensal microorganism). Exemplary microorganisms include, but are not limited to:

| | |
|---|---|
| Corynebacteria | |
| Corynebacterium diphtheria | |
| Pneumococci | |
| Diplococcus pneumoniae | |
| Streptococci | |
| Streptococcus pyrogenes | |
| Streptococcus salivarus | |
| Staphylococci | |
| Staphylococcus aureus | |
| Staphylococcus albus | |
| Neisseria | |
| Neisseria meningitidis | |
| Neisseria gonorrhea | |
| Enterobacteriaciae | |
| Escherichia coli | |
| Aerobacter aerogenes | The coliform bacteria |
| Klebsiella pneumoniae | |
| Salmonella typhosa | |
| Salmonella choleraesuis | The Salmonellae |
| Salmonella typhimurium | |
| Shigella dysenteria | |
| Shigella schmitzii | |
| Shigella arabinotarda | |
| | The Shigellae |
| Shigella flexneri | |
| Shigella boydii | |
| Shigella sonnei | |
| Other enteric bacilli | |
| Proteus vulgaris | |
| Proteus mirabilis | Proteus species |
| Proteus morgani | |
| Pseudomonas aeruginosa | |
| Alcaligenes faecalis | |
| Vibrio cholerae | |
| Hemophilus-Bordetella group | Rhizopus oryzae |
| Hemophilus influenza, H. ducryi | Rhizopus arrhizua |
| | Phycomycetes |
| Hemophilus hemophilus | Rhizopus nigricans |
| Hemophilus aegypticus | Sporotrichum schenkii |
| Hemophilus parainfluenza | Flonsecaea pedrosoi |
| Bordetella pertussis | Fonsecacea compact |
| Pasteurellae | Fonsecacea dermatidis |
| Pasteurella pestis | Cladosporium carrionii |
| Pasteurella tulareusis | Phialophora verrucosa |
| Brucellae | Aspergillus nidulans |
| Brucella melltensis | Madurella mycetomi |
| Brucella abortus | Madurella grisea |
| Brucella suis | Allescheria boydii |
| Aerobic Spore-forming Bacilli | Phialophora jeanselmei |
| Bacillus anthracis | Microsporum gypseum |
| Bacillus subtilis | Trichophyton mentagrophytes |
| Bacillus megaterium | Keratinomyces ajelloi |
| Bacillus cereus | Microsporum canis |
| Anaerobic Spore-forming Bacilli | Trichophyton rubrum |
| Clostridium botulinum | Microsporum adouini |
| Clostridium tetani | Viruses |
| Clostridium perfringens | Adenoviruses |
| Clostridium novyi | Herpes Viruses |
| Clostridium septicum | Herpes simplex |
| Clostridium histoyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-ike bacteria) | Picornaviruses |
| Actinomyces Isaeli | Poliovirus |

| | |
|---|---|
| Actinomyces bovis | Coxsackievirus |
| Actinomyces naeslundii | Echoviruses |
| Nocardia asteroides | Rhinoviruses |
| Nocardia brasiliensis | Myxoviruses |
| The Spirochetes | Influenza (A, B, and C) |
| Treponema pallidum | Parainfluenza (1-4) |
| Treponema pertenue | Mumps Virus |
| Spirillum minus | |
| Streptobacillus monoiliformis | Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial Virus |
| Trypanasomes | Rubella Virus |
| Mycoplasmas | Arboviruses |
| Mycoplasma pneumoniae | |
| Other pathogens | Eastern Equine Encephalitis Virus |
| Listeria monocytogenes | Western Equine Encephalitis Virus |
| Erysipeothrix rhusiopathiae | Sindbis Virus |
| Streptobacillus moniliformis | Chikugunya Virus |
| Donvania granulomatis | Semliki Forest Virus |
| Entamoeba histolytica | Mayora Virus |
| Plasmodium falciparum | St. Louis Encephalitis |
| Plasmodium japonicum | California Encephalitis Virus |
| Bartonella bacilliformis | Colorado Tick Fever Virus |
| Rickettsia (bacteria-like parasites) | Yellow Fever Virus |
| Rickettsia prowazekii | Dengue Virus |
| Rickettsia mooseri | Reoviruses |
| Rickettsia rickettsii | Reovirus Types 1-3 |
| Rickettsia conori | Retroviruses |
| Rickettsia australis | Human Immunodeficiency |
| Rickettsia sibiricus | Viruses I and II (HTLV) |
| Rickettsia akari | Human T-cell Lymphotrophic |
| Rickettsia tsutsugamushi | Virus I & II (HIV) |
| Rickettsia burnetti | Hepatitis |
| Rickettsia quintana | Hepatitis A Virus |
| Chlamydia (unclassifiable parasites bacterial/viral) | Hepatitis B Virus |
| | Hepatitis C Virus |
| Chlamydia agents (naming uncertain) | Tumor Viruses |
| Chlamydia trachomatis | |
| Fungi | Rauscher Leukemia Virus |
| Cryptococcus neoformans | Gross Virus |
| Blastomyces dermatidis | Maloney Leukemia Virus |
| Histoplasma capsulatum | |
| Coccidioides immitis | Human Papilloma Virus |
| Paracoccidioides brasliensis | |
| Candida albicans | |
| Aspergillus fumigatus | |
| Mucor corymbifer (Absidia corymbifera) | |

In some embodiments, the analyte is a bacterium. Exemplary bacteria include, but are not limited to: *Escherichia coli* (or *E. coli*), *Bacillus anthracis*, *Bacillus cereus*, *Clostridium botulinum*, *Clostridium difficile*, *Yersinia pestis*, *Yersinia enterocolitica*, *Francisella tularensis*, *Brucella* species, *Clostridium perfringens*, *Burkholderia mallei*, *Burkholderia pseudomallei*, *Staphylococcus* species, *Mycobacterium* species, Group A *Streptococcus*, Group B *Streptococcus*, *Streptococcus pneumoniae*, *Helicobacter pylori*, *Salmonella enteritidis*, *Mycoplasma hominis*, *Mycoplasma orale*, *Mycoplasma salivarium*, *Mycoplasma fermentans*, *Mycoplasma pneumoniae*, *Mycobacterium bovis*, *Mycobacterium tuberculosis*, *Mycobacterium avium*, *Mycobacterium leprae*, *Rickettsia rickettsia*, *Rickettsia akari*, *Rickettsia prowazekii*, *Rickettsia canada*, *Bacillus subtilis*, *Bacillus subtilis niger*, *Bacillus thuringiensis*, *Coxiella burnetti*, *Faecalibacterium prausnitzii* (also known as Bacteroides *prausnitzii*), *Roseburia hominis*, *Eubacterium rectale*, *Dialister invisus*, *Ruminococcus albus*, *Ruminococcus callidus*, and *Ruminococcus bromii*. Additional exemplary bacteria include bacteria of the *phyla* Firmicutes (e.g., *Clostridium* clusters XIVa and IV), bacteria of the phyla Bacteroidetes (e.g., *Bacteroides fragilis* or *Bacteroides vulgatus*), and bacteria of the phyla Actinobacteria (e.g., *Coriobacteriaceae* spp. or *Bifidobacterium adolescentis*). Bacteria of the Clostridium cluster XIVa includes species belonging to, for example, the *Clostridium, Ruminococcus, Lachnospira, Roseburia, Eubacterium, Coprococcus, Dorea,* and *Butyrivibrio* genera. Bacteria of the Clostridium cluster IV includes species belonging to, for example, the *Clostridium, Ruminococcus, Eubacterium* and *Anaerofilum* genera. In some embodiments, the analyte is *Candida*, e.g., *Candida albicans*. In some embodiments, the analyte is a byproduct from a bacterium or other microorganism, e.g., helminth ova, enterotoxin (*Clostridium difficile* toxin A; TcdA) or cytotoxin (*Clostridium difficile* toxin B; TcdB).

In some embodiments, the bacterium is a pathogenic bacterium. Non-limiting examples of pathogenic bacteria belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia*. Non-limiting examples of specific pathogenic bacterial species include a strain of Bacillus anthracis, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumoniae*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter sakazakii*, a strain of *Enterococcus faecalis*, a strain of *Enterococcus faecium*, a strain of *Escherichia coil* (e.g., *E. coli* O157 H7), a strain of *Francisella tularensis*, a strain of *Haemophilus influenza*, a strain of *Helicobacter pylori*, a strain of *Legionella pneumophila*, a strain of *Leptospira interrogans*, a strain of *Listeria monocytogenes*, a strain of *Mycobacterium leprae*, a strain of *Mycobacterium tuberculosis*, a strain of *Mycobacterium ulcerans*, a strain of *Mycoplasma pneumonia*, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes, a strain of Treponema pallidum*, a strain of *Vibrio cholera*, a strain of *Yersinia enterocolitica*, and, a strain of *Yersinia pestis*.

In some embodiments, the bacterium is a commensal bacterium (e.g., a probiotic). In some embodiments, the bacterium has been previously administered to a subject, e.g., as a live biotherapeutic agent. Exemplary commensal bacteria include, but are not limited to, *Faecalibacterium prausnitzii* (also referred to as Bacteroides praussnitzii), *Roseburia hominis, Eubacterium rectale, Dialister invisus, Ruminococcus albus, Ruminococcus gnavus, Ruminococcus torques, Ruminococcus callidus,* and *Ruminococcus bromii*.

In some embodiments, the analyte is a virus. In some embodiments, the virus is a pathogenic virus. Non-limiting examples of pathogenic viruses belong to the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In some embodiments, the analyte is a virus. In some embodiments, the virus is a pathogenic virus. Non-limiting examples of pathogenic viruses belong to the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In some embodiments, the analyte is a fungus. In some embodiments, the fungi is a pathogenic fungus. Non-limiting examples of pathogenic fungi belong to the genera *Asperfillus*, *Canidia*, *Cryptococcus*, *Histoplasma*, *Pneumocystis*, and *Stachybotrys*. Non-limiting examples of specific pathogenic fungi species include a strain of *Aspergillus clavatus*, *Aspergillus fumigatus*, *Aspergillus flavus*, *Canidia albicans*, *Cryptococcus albidus*, *Cryptococcus gattii*, *Cryptococcus laurentii*, *Cryptococcus neoformans*, *Histoplasma capsulatum*, *Pneumocystis jirovecii*, *Pneumoctystis carinii*, and *Stachybotrys chartarum*.

In some embodiments, the analyte is a protozoan. In some embodiments, the analyte is a pathogenic protozoan. Non-limiting examples of pathogenic protozoa belong to the genera *Acanthamoeba*, *Balamuthia*, *Cryptosporidium*, *Dientamoeba*, *Endolimax*, *Entamoeba*, *Giardia*, *Iodamoeba*, *Leishmania*, *Naegleria*, *Plasmodium*, *Sappinia*, *Toxoplasma*, *Trichomonas*, and *Trypanosoma*. Non-limiting examples of specific pathogenic protozoa species include a strain of *Acanthamoeba* spp., *Balamuthia mandrillaris*, *Cryptosporidium canis*, *Cryptosporidium felis*, *Cryptosporidium hominis*, *Cryptosporidium meleagridis*, *Cryptosporidium muris*, *Cryptosporidium parvum*, *Dientamoeba fragilis*, *Endolimax nana*, *Entamoeba dispar*, *Entamoeba hartmanni*, *Entamoeba histolytica*, *Entamoeba coli*, *Entamoeba moshkovskii*, *Giardia lamblia*, *Iodamoeba butschlii*, *Leishmania aethiopica*, *Leishmania braziliensis*, *Leishmania chagasi*, *Leishmania donovani*, *Leishmania infantum*, *Leishmania major*, *Leishmania mexicana*, *Leishmania tropica*, *Naegleria fowleri*, *Plasmodium falciparum*, *Plasmodium knowlesi*, *Plasmodium malariae*, *Plasmodium ovale*, *Plasmodium vivax*, *Sappinia diploidea*, *Toxoplasma gondii*, *Trichomonas vaginalis*, *Trypanosoma brucei*, and *Trypanosoma cruzi*.

In some embodiments, the analyte is secreted by or expressed on the cell surface of a microorganism (e.g., a bacterium, a colonic bacterium, a viable bacterium, a dead bacterium, a parasite (e.g., *Giardia lamblia*, *Cryptosporidium*, *Cystoisosporiasis belli*, and *Balantidium coli*), a virus (e.g., a herpes virus, a cytomegalovirus, a herpes simplex virus, an Epstein-Barr virus, a human papilloma virus, a rotavirus, a human herpesvirus-8; Goodgame (1999) Curr. Gastroenterol. Rep. 1(4): 292-300). In some embodiments, the analyte is secreted by or expressed on the cell surface of a Gram-negative bacterium (e.g., *E. coli*, *Helicobacter pylori*). In some embodiments, the analyte is secreted by or expressed on the cell surface (e.g., a bacterial surface epitope) of a Gram-positive bacterium (e.g., *Staphylococcus aureus*, *Clostridium botulinum*, *Clostridium difficile*).

In some embodiments, the analyte is a molecule expressed on the surface of a bacterial cell (e.g., a bacterial cell surface protein). In some embodiments, the analyte is a bacterial toxin (e.g., TcdA and/or TcdB from *Clostridium difficile*). In some embodiments, the analyte is CFA/I fimbriae, flagella, lipopolysaccharide (LPS), lipoteichoic acid, or a peptidoglycan. Non-limiting examples of bacterium that may express an analyte that can be detected using any of the devices and methods described herein include: *Bacillus anthraces*, *Bacillus cereus*, *Clostridium botulinum*, *Clostridium difficile*, *Escherichia coli*, *Yersinia pestis*, *Yersinia enterocolitica*, *Francisella tularensis*, *Brucella species*, *Clostridium perfringens*, *Burkholderia mallei*, *Burkholderia pseudomallei*, *Helicobacter pylori*, *Staphylococcus* species, *Mycobacterium* species, Group A *Streptococcus*, Group B *Streptococcus*, *Streptococcus pneumoniae*, *Francisella tularensis*, *Salmonella enteritidis*, *Mycoplasma hominis*, *Mycoplasma orale*, *Mycoplasma salivarium*, *Mycoplasma fermentans*, *Mycoplasma pneumoniae*, *Mycobacterium bovis*, *Mycobacterium tuberculosis*, *Mycobacterium avium*, *Mycobacterium leprae*, *Rickettsia rickettsia*, *Rickettsia akari*, *Rickettsia prowazekii*, *Rickettsia canada*, *Bacillus subtilis*, *Bacillus subtilis niger*, *Bacillus thuringiensis*, *Coxiella bumetti*, *Candida albicans*, *Bacteroides fragilis*, *Leptospira interrogans*, *Listeria monocytogenes*, *Pasteurella multocida*, *Salmonella typhi*, *Salmonella typhimurium*, *Shigella dysenteriae*, *Shigella flexneria*, *Shigella sonnei*, *Vibrio cholera*, and *Vibrio parahaemolyticus*.

In some embodiments, the analyte is a byproduct from a bacterium or another microorganism, e.g., helminth ova, enterotoxin (*Clostridium difficile* toxin A; TcdA), cytotoxin (*Clostridium difficile* toxin B; TcdB), and ammonia. In some embodiments, the analyte is an antigen from a microorganism (e.g., a bacteria, virus, prion, fungus, protozoan or a parasite).

In some embodiments, the analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

In some embodiments, the analyte is a steroid selected from the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

In some embodiments, the analyte is a bile acid or a bile salt (also known as a conjugated bile acid). Bile acids are products of cholesterol synthesis that are synthesized in the liver, conjugated to taurine or glycine, and stored in the gallbladder until released into the small intestine. The primary bile acids are cholic acid, and chenodeoxycholic acid, which are deconjugated and dehydroxylated by instestinal bacteria to form the secondary bile acids deoxycholic acid and lithocholic acid, respectively. The majority of bile acids (about 95%) are reabsorbed in the distal ileum and returned to the liver (see, e.g., U.S. Publication No. 2017/0343535, incorporated herein by reference). Impaired absorption of bile acids in the ileum can lead to excess bile acids in the colon which can cause symptoms of bile acid malabsorption (BAM; also known as bile acid diarrhea), including watery stool and fecal incontinence. Interestingly, up to 50% of patients with irritable bowel syndrome with diarrhea (IBS-D) also have BAM (see, e.g., Camilleri et al. (2009) *Neurogastroeterol. Motil.* 21(7): 734-43). In some embodiments, the presence, absence, and/or a specific level of one or more bile acids or bile salts in the GI tract of a subject is indicative of a condition or disease state (e.g., a GI disorder and/or a non-GI disorder (e.g., a systemic disorder or a liver disease)). In some embodiments, the compositions, devices, and methods described herein may be used to detect, analyze and/or quantify at least one bile acid or bile salt in the GI tract of the subject to diagnose a GI disorder such as BAM or IBS (e.g., IBS-D). In some embodiments, the devices, methods and compositions described herein can be used to detect, quantitate, and/or analyze a bile acid or a bile salt in the GI tract of a subject. For instance, the presence and/or absence, and/or the concentration of a bile acid, a bile salt, or a combination thereof, may be determined at a specific region of the GI tract of a subject (e.g., one or more of the duodenum, jejunum, ileum, ascending colon, transverse colon or descending colon) to determine whether the subject has or is at risk of developing a GI disorder, such as BAM or IBS-D. In some embodiments, the devices, methods and compositions described herein can be used to determine the ratio of two or more bile acids or bile acid salts in the GI tract of a subject (e.g., a specific region of the GI tract of a subject including one or more of the duodenum, jejunum, ileum, ascending colon, transverse colon or descending colon). In some embodiments, the presence and/or absence, and/or the concentration of a bile acid, a bile salt, or a combination thereof, is determined in the ileum of a subject. In some embodiments, the presence and/or absence, and/or the concentration of a bile acid, a bile salt, or a combination thereof, is determined in the colon of a subject. In some embodiments, the concentration of a bile acid, a bile salt, or a combination thereof, is determined in specific regions of the GI tract of the subject, and for example, compared to determine where along the GI tract the compounds are accumulating. In some embodiments, the detection of a concentration of a bile acid, bile salt, or a combination thereof, in a specific region of the GI tract of the subject (e.g., the colon or the ileum) that is above a reference level of a bile acid, bile salt, or a combination thereof (e.g., the average level of a bile acid in healthy subjects) may be indicative of BAM and/or IBS-D in a subject. In some embodiments, the bile acid is selected from the group consisting of chenodeoxycholic acid, cholic acid, deoxycholate, lithocholate, and ursodeoxycholic acid. In some embodiments, the bile acid comprises cholesten-3-one or a structural variant thereof. In some embodiments, the bile acid is cholesten-3-one or a structural variant thereof. In some embodiments, the bile acid is cholesten-3-one. In some embodiments, the bile acid is a structural variant of cholesten-3-one. In some embodiments, the bile salt is selected from the group consisting of glycocholic acid, taurocholic acid, glycodeoxycholic acid, glycochenodeoxycholic acid, taurodeoxycholic acid, taurochenodeoxycholic acid, glycolithocholic acid, and taurolithocholic acid.

In some embodiments, the analyte is 7α-hydroxy-4-cholesten-3-one (7αC4). The measurement of 7αC4 allows for the monitoring of the enzymatic activity of hepatic cholesterol 7α-hydroxylase, the rate limiting enzyme in the synthesis of bile acids and can be used as a surrogate to detect BAM (see, e.g., Galman et al. (2003) *J. Lipid. Res.* 44: 859-66; and Camilleri et al. (2009) Neurogastroeterol. Motil. 21(7): 734-43, incorporated herein by reference in their entirety).

In some embodiments, the analyte comprises cholesterol, a lipid, a fat soluble vitamin (e.g., ascorbic acid, cholecalciferol, ergocalciferol, a tocopherol, a tocotrienol, phylloquinone, and a menaquinone), bilirubin, fibroblast growth factor 19 (FGF19), TGR5 (also known as GP-BAR1 or M-BAR), glycine, taurine, or cholecystokinin (CCK or CCK-PZ). In some embodiments, the analyte comprises cholecystokinin. Cholecystokinin is a peptide hormone that contributes to control intestinal motility (see Rehfeld (2017) *Front. Endocrinol.* (*Lausanne*) 8: 47). In some embodiments, the analyte comprises secretin. Secretin is a peptide hormone that regulates the pH of the duodenal content by controlling gastric acid secretion, regulates bile acid and bicarbonate secretion in the duodenum, and regulates water homeostasis (see, e.g., Afroze et al. (2013) *Ann. Transl. Med.* 1(3): 29). In some embodiments, a subject has been administered cholecystokinin or secretin to induce the release of an analyte (e.g., from the liver and/or gall bladder into the GI tract).

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof 5-HT is a molecule that plays a role in the regulation of gastrointestinal motility, secretion, and sensation. Imbalances in the levels of 5-HT are associated with several diseases including inflammatory bowel syndrome (IBS), autism, gastric ulcer formation, non-cardiac chest pain, and functional dyspepsia (see, e.g., Faure et al. (2010) *Gastroenterology* 139(1): 249-58 and Muller et al. (2016) *Neuroscience* 321: 24-41, and International Publication No. WO 2014/188377, each of which are incorporated herein by reference). Conversion of metabolites within the serotonin, tryptophan and/or kynurenine pathways affects the levels of 5-HT in a subject. Therefore, measuring the levels of one or more of the metabolites in this pathway may be used for the diagnosis, management and treatment of a disease or disorder associated with 5-HT imbalance including but not limited to IBS, autism, carcinoid syndrome, depression, hypertension, Alzheimer's disease, constipation, migraine, and serotonin syndrome. One or more analytes in the serotonin, tryptophan and/or kynurenine pathways can be detected and/or quantitated using, for example, methods and analyte-binding agents that bind to these metabolites including, e.g., antibodies, known in the art (see, e.g., International Publication No. WO2014/188377, the entire contents of which are expressly incorporated herein by reference).

In some embodiments, the analyte is a lactam having from 5 to 6 annular members selected from barbituates, e.g., phenobarbital and secobarbital, diphenylhydantonin, primidone, ethosuximide, and metabolites thereof.

In some embodiments, the analyte is an aminoalkylbenzene, with alkyl of from 2 to 3 carbon atoms, selected from the amphetamines; catecholamines, which includes ephedrine, L-dopa, epinephrine; narceine; papaverine; and metabolites thereof.

In some embodiments, the analyte is a benzheterocyclic selected from oxazepam, chlorpromazine, tegretol, their derivatives and metabolites, the heterocyclic rings being azepines, diazepines and phenothiazines.

In some embodiments, the analyte is a purine selected from theophylline, caffeine, their metabolites and derivatives.

In some embodiments, the analyte is marijuana, cannabinol or tetrahydrocannabinol.

In some embodiments, the analyte is a vitamin such as vitamin A, vitamin B, e.g. vitamin $B_{12}$, vitamin C, vitamin D, vitamin E and vitamin K, folic acid, thiamine.

In some embodiments, the analyte is selected from prostaglandins, which differ by the degree and sites of hydroxylation and unsaturation.

In some embodiments, the analyte is a tricyclic antidepressant selected from imipramine, dismethylimipramine, amitriptyline, nortriptyline, protriptyline, trimipramine, chlomipramine, doxepine, and desmethyldoxepin.

In some embodiments, the analyte is selected from antineoplastics, including methotrexate.

In some embodiments, the analyte is an antibiotic as described herein, including, but not limited to, penicillin, chloromycetin, actinomycetin, tetracycline, terramycin, and metabolites and derivatives.

In some embodiments, the analyte is a nucleoside or nucleotide selected from ATP, NAD, FMN, adenosine, guanosine, thymidine, and cytidine with their appropriate sugar and phosphate substituents.

In some embodiments, the analyte is selected from methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

In some embodiments, the analyte is a metabolite related to a diseased state. Such metabolites include, but are not limited to spermine, galactose, phenylpyruvic acid, and porphyrin Type 1.

In some embodiments, the analyte is an aminoglycoside, such as gentamicin, kanamicin, tobramycin, or amikacin.

In some embodiments, the analyte is a pesticide. Among pesticides of interest are polyhalogenated biphenyls, phosphate esters, thiophosphates, carbamates, polyhalogenated sulfenamides, their metabolites and derivatives.

In some embodiments, the analyte has a molecular weight of about 500 Da to about 1,000,000 Da (e.g., about 500 to about 500,000 Da, about 1,000 to about 100,000 Da).

In some embodiments, the analyte is a receptor, with a molecular weight ranging from 10,000 to $2 \times 10^8$ Da, more usually from 10,000 to $10^6$ Da. For immunoglobulins, IgA, IgG, IgE and IgM, the molecular weights will generally vary from about 160,000 Da to about $10^6$ Da. Enzymes will normally range in molecular weight from about 10,000 Da to about 1,000,000 Da. Natural receptors vary widely, generally having a molecular weight of at least about 25,000 Da and may be $10^6$ or higher Da, including such materials as avidin, DNA, RNA, thyroxine binding globulin, thyroxine binding prealbumin, transcortin, etc.

In some embodiments, the term "analyte" further includes polynucleotide analytes such as those polynucleotides defined below. These include m-RNA, r-RNA, t-RNA, DNA, DNA-DNA duplexes, DNA-RNA duplexes, nucleic acid molecules comprising modified bases, locked nucleic acid molecules (LNA molecules), antagomirs, peptide nucleic acid molecules (PNA molecules), antisense RNA or DNA molecules (e.g., antisense molecules including modifications to the sugars, bases, backbone linkages that allow for specific detection), chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), etc. The term analyte also includes polynucleotide-binding agents, such as, for example, restriction enzymes, trascription factors, transcription activators, transcription repressors, nucleases, polymerases, histones, DNA repair enzymes, intercalating gagents, chemotherapeutic agents, and the like.

In some embodiments, the analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest (i.e., an analyte-binding agent), such as a specific binding pair member complementary to the analyte of interest, whose presence will be detected only when the analyte of interest is present in a sample. Thus, the agent probative of the analyte becomes the analyte that is detected in an assay.

In some embodiments, the analyte a nucleic acid (e.g., a bacterial DNA molecule or a bacterial RNA molecule (e.g., a bacterial tRNA, a transfer-messenger RNA (tmRNA)). See, e.g., Sjostrom et al. (2015) Scientific Reports 5: 15329; Ghosal (2017) Microbial Pathogenesis 104: 161-163; Shen et al. (2012) Cell Host Microbe. 12(4): 509-520.

In some embodiments, the analyte is a component of an outer membrane vesicle (OMV) (e.g., an OmpU protein, Elluri et al. (2014) PloS One 9: e106731). See, e.g., Kulp and Kuehn (2010) Annual Review of microbiology 64: 163-184; Berleman and Auer (2013) Environmental microbiology 15: 347-354; Wai et al. (1995) Microbiology and immunology 39: 451-456; Lindmark et al. (2009) BMC microbiology 9: 220; Sjostrom et al. (2015) Scientific Reports 5: 15329.

In some embodiments, the analyte is G-CSF, which can stimulate the bone marrow to produce granulocytes and stem cells and release them into the bloodstream.

In some embodiments, the analyte is an enzyme such as glutathione S-transferase. For example, the ingestible device can include P28GST, a 28 kDa helminth protein from Schistosoma with potent immunogenic and antioxidant properties. P28GST prevents intestinal inflammation in experimental colitis through a Th2-type response with mucosal eosinophils and can be recombinantly produced (e.g., in *S. cerevisiae*). See, for example, U.S. Pat. No. 9,593,313, Driss et al., *Mucosal Immunology*, 2016 9, 322-335; and Capron et al., *Gastroenterology*, 146(5):S-638.

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, analytes are therapeutic agents, fragments thereof, and metabolites thereof (e.g., antibiotics). In some embodiments, analytes are biomarkers. In some embodiments, the analytes are antibodies. In some embodiments, the analytes are antibiotics. Additional exemplary analytes (e.g., therapeutic agents (e.g., drugs), antibodies, antibiotics and biomarkers) are provided below.

A. Antibodies

In some embodiments, the analyte or the analyte-binding agent is an antibody. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv) and domain antibodies), and fusion proteins including an antibody portion, and any other modified configuration of the immunoglobulin molecule that includes an antigen recognition site. The term antibody includes antibody fragments (e.g., antigen-binding fragments) such as an Fv fragment, a Fab fragment, a F(ab')2 fragment, and a Fab' fragment. Additional examples of antigen-binding fragments include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies including the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Lazikani et al, 1997, J. Molec. Biol. 273:927-948). As used herein, a CDR may refer to CDRs defined by either approach or by a combination of both approaches.

As known in the art, a "constant region" of an antibody refers to the constant region of the antibody light chain or the constant region of the antibody heavy chain, either alone or in combination.

A "derivative" refers to any polypeptide (e.g., an antibody) having a substantially identical amino acid sequence to the naturally occurring polypeptide, in which one or more amino acids have been modified at side groups of the amino acids (e.g., an biotinylated protein or antibody). The term "derivative" shall also include any polypeptide (e.g., an antibody) which has one or more amino acids deleted from, added to, or substituted from the natural polypeptide sequence, but which retains a substantial amino acid sequence homology to the natural sequence. A substantial sequence homology is any homology greater than 50 percent.

In some embodiments, the antibody can be a humanized antibody, a chimeric antibody, a multivalent antibody, or a fragment thereof. In some embodiments, an antibody can be a scFv-Fc (Sokolowska-Wedzina et al., *Mol. Cancer Res.* 15(8):1040-1050, 2017), a VHH domain (Li et al., *Immunol. Lett.* 188:89-95, 2017), a VNAR domain (Hasler et al., *Mol. Immunol.* 75:28-37, 2016), a (scFv)2, a minibody (Kim et al., *PLoS One* 10(1):e113442, 2014), or a BiTE. In some embodiments, an antibody can be a DVD-Ig (Wu et al., *Nat. Biotechnol.* 25(11):1290-1297, 2007; WO 08/024188; WO 07/024715), and a dual-affinity re-targeting antibody (DART) (Tsai et al., *Mol. Ther. Oncolytics* 3:15024, 2016), a triomab (Chelius et al., *MAbs* 2(3):309-319, 2010), kih IgG with a common LC (Kontermann et al., *Drug Discovery Today* 20(7):838-847, 2015), a crossmab (Regula et al., *EMBO Mol. Med.* 9(7):985, 2017), an ortho-Fab IgG (Kontermann et al., *Drug Discovery Today* 20(7):838-847, 2015), a 2-in-1-IgG (Kontermann et al., *Drug Discovery Today* 20(7):838-847, 2015), IgG-scFv (Cheal et al., *Mol. Cancer Ther.* 13(7):1803-1812, 2014), scFv2-Fc (Natsume et al., *J. Biochem.* 140(3):359-368, 2006), a bi-nanobody (Kontermann et al., *Drug Discovery Today* 20(7):838-847, 2015), tanden antibody (Kontermann et al., *Drug Discovery Today* 20(7):838-847, 2015), a DART-Fc (Kontermann et al., *Drug Discovery Today* 20(7):838-847, 2015), a scFv-HSA-scFv (Kontermann et al., *Drug Discovery Today* 20(7):838-847, 2015), DNL-Fab3 (Kontermann et al., *Drug Discovery Today* 20(7):838-847, 2015), DAF (two-in-one or four-in-one), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H) IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody (e.g., antibodies derived from *Camelus bactriamus, Calelus dromaderius,* or *Lama paccos*) (U.S. Pat. No. 5,759,808; Stijlemans et al., *J. Biol. Chem.* 279:1256-1261, 2004; Dumoulin et al., *Nature* 424:783-788, 2003; and Pleschberger et al., *Bioconjugate Chem.* 14:440-448, 2003), nanobody-HSA, a diabody (e.g., Poljak, *Structure* 2(12): 1121-1123, 1994; Hudson et al., *J. Immunol. Methods* 23(1-2):177-189, 1999), a TandAb (Reusch et al., *mAbs* 6(3):727-738, 2014), scDiabody (Cuesta et al., *Trends in Biotechnol.* 28(7):355-362, 2010), scDiabody-CH3 (Sanz et al., *Trends in Immunol.* 25(2):85-91, 2004), Diabody-CH3 (Guo et al.), Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody (Huston et al., *Human Antibodies* 10(3-4):127-142, 2001; Wheeler et al., *Mol. Ther.* 8(3):355-366, 2003; Stocks, *Drug Discov. Today* 9(22):960-966, 2004), dock and lock bispecific antibody, ImmTAC, HSAbody, scDiabody-HSA, tandem scFv, IgG-IgG, Cov-X-Body, and scFv1-PEG-scFv2.

In some embodiments, an antibody can be an IgNAR, a bispecific antibody (Milstein and Cuello, *Nature* 305:537-539, 1983; Suresh et al., *Methods in Enzymology* 121:210, 1986; WO 96/27011; Brennan et al., *Science* 229:81, 1985; Shalaby et al., *J. Exp. Med.* 175:217-225, 1992; Kolstelny et al., *J. Immunol.* 148(5):1547-1553, 1992; Hollinger et al., *Proc. Natl. Acad. Sci. U.S.A.* 90:6444-6448, 1993; Gruber et al., *J. Immunol.* 152:5368, 1994; Tuft et al., *J. Immunol.* 147:60, 1991), a bispecific diabody, a triabody (Schoonooghe et al., *BMC Biotechnol.* 9:70, 2009), a tetrabody, scFv-Fc knobs-into-holes, a scFv-Fc-scFv, a (Fab'scFv)$_2$, a V-IgG, a IvG-V, a dual V domain IgG, a heavy chain immunoglobulin or a camelid (Holt et al., *Trends Biotechnol.* 21(11):484-490, 2003), an intrabody, a monoclonal antibody (e.g., a human or humanized monoclonal antibody), a heteroconjugate antibody (e.g., U.S. Pat. No. 4,676,980), a linear antibody (Zapata et al., *Protein Eng.* 8(10): 1057-1062, 1995), a trispecific antibody (Tuft et al., *J. Immunol.* 147:60, 1991), a Fabs-in-Tandem immunoglobulin (WO 15/103072), or a humanized camelid antibody.

In some embodiments, the antibody binds specifically to a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid. Exemplary antibodies that bind to metabolites in these pathways are disclosed, for example, in International Publication No. WO2014/188377, the entire contents of which are incorporated herein by reference.

In some embodiments, the antibody is specific for a particular genus, species, or strain of a microorganism, and may therefore be used for the detection, analysis and/or quantitation of the microorganism using the detection methods described below. In some embodiments, the antibody specifically binds to a surface-specific biomolecule (e.g., a pilus subunit or a flagella protein) present in a particular genus, species or strain of microorganism, and does not cross-react with other microorganisms. In some embodiments, these antibodies may be used in the methods described herein to diagnose a subject with a particular infection or disease, or to monitor an infection (e.g., during or after treatment). In some embodiments, the antibody specifically binds to an antigen present in a particular genera, species or strain of a microorganism. Exemplary antigens, the corresponding microorganism that can be detected, and the disease caused by the microorganism (in parentheticals) include: outer membrane protein A OmpA (*Acinetobacter baumannii, Acinetobacter infections*)); HIV p24 antigen, HIV Eenvelope proteins (Gp120, Gp41, Gp160) (HIV (Human immunodeficiency virus), AIDS (Acquired immunodeficiency syndrome)); galactose-inhibitable adherence protein GIAP, 29 kDa antigen Eh29, GaVGaINAc lectin, protein CRT, 125 kDa immunodominant antigen, protein M17, adhesin ADH112, protein STIRP (*Entamoeba histolytica*, Amoebiasis); protective Antigen PA, edema factor EF, lethal facotor LF, the S-layer homology proteins SLH (*Bacillus anthracis*, Anthrax); nucleocapsid protein NP, glycoprotein precursor GPC, glycoprotein GP1, glycoprotein GP2 (Junin virus, Argentine hemorrhagic fever); 41 kDa allergen Asp v13, allergen Asp f3, major conidial surface protein rodlet A, protease Peplp, GPI-anchored protein Ge1p, GPI-anchored protein Crf1p (*Aspergillus* genus, Aspergillosis); outer surface protein A OspA, outer surface protein OspB, outer surface protein OspC, decorin binding protein A DbpA, flagellar filament 41 kDa core protein Fla, basic membrane protein A precursor BmpA (Immunodominant antigen P39), outer surface 22 kDa lipoprotein precursor (antigen IPLA7), variable surface lipoprotein vIsE (*Borrelia* genus, *Borrelia* infection); OmpA-like transmembrane domain-containing protein Omp31, immunogenic 39-kDa protein M5 P39, 25 kDa outer-membrane immunogenic protein precursor Omp25, outer membrane protein MotY Omp16, conserved outer membrane protein D15, malate dehydrogenase Mdh, component of the Type-IV secretion system (T4SS) VirJ, lipoprotein of unknown function BAB1-0187 (*Brucella* genus, Brucellosis); major outer membrane protein PorA, flagellin FlaA, surface antigen CjaA, fibronectin binding protein CadF, aspartate/glutamate-binding ABC transporter protein Peb1A, protein FspA1, protein FspA2 (*Campylobacter* genus, Campylobacteriosis); glycolytic enzyme enolase, secreted aspartyl proteinases SAP1-10, glycophosphatidylinositol (GPI)-linked cell wall protein, adhesin Als3p, cell surface hydrophobicity protein CSH (usually *Candida albicans* and other *Candida* species, Candidiasis); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB (*Chlamydia trachomatis, Chlamydia*); major outer membrane protein MOMP, outer membrane protein 2 Omp2, (*Chlamydophila pneumoniae, Chlamydophila pneumoniae* infection); outer membrane protein U Porin ompU, (*Vibrio cholerae*, Cholera); surface layer proteins SLPs, Cell Wall Protein CwpV, flagellar protein FliC, flagellar protein FliD (*Clostridium difficile, Clostridium difficile* infection); acidic ribosomal protein P2 CpP2, mucin antigens Muc1, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); membrane protein pp15, capsid-proximal tegument protein pp150 (Cytomegalovirus, Cytomegalovirus infection); prion protein (vCJD prion, Variant Creutzfeldt-Jakob disease (vCJD, nvCJD)); cyst wall proteins CWP1, CWP2, CWP3, variant surface protein VSP, VSP1, VSP2, VSP3, VSP4, VSP5, VSP6, 56 kDa antigen (Giardia intestinalis, Giardiasis); minor pilin-associated subunit pilC, major pilin subunit and variants pilE, pilS (Neisseria gonorrhoeae, Gonorrhea); outer membrane protein A OmpA, outer membrane protein C OmpC, outer membrane protein K17 OmpK17 (*Klebsiella granulomatis, Granuloma inguinale* (Donovanosis)); fibronectin-binding protein Sfb (*Streptococcus pyogenes*, Group A streptococcal infection); outer membrane protein P6 (*Haemophilus influenzae, Haemophilus influenzae* infection); integral membrane proteins, aggregation-prone proteins, O-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and O104:H4, Hemolytic-uremic syndrome (HUS)); hepatitis A surface antigen HBAg (Hepatitis A Virus, Hepatitis A); hepatitis B surface antigen HBsAg (Hepatitis B Virus, Hepatitis B); envelope glycoprotein E1 gp32 gp35, envelope glycoprotein E2 NS1 gp68 gp70, capsid protein C, (Hepatitis C Virus, Hepatitis C); type IV pilin PilE, outer membrane protein MIP, major outer membrane protein MompS (*Legionella pneumophila*, Legionellosis (Legionnaires' disease, Pontiac fever)); minor pilin-associated subunit pi1C, major pilin subunit and variants pilE, pilS (*Neisseria meningitidis*, Meningococcal disease); adhesin P1, adhesion P30 (*Mycoplasma pneumoniae*, *Mycoplasma* pneumonia); F1 capsule antigen, outer membrane protease P1a, (*Yersinia pestis*, Plague); surface adhesin PsaA, cell wall surface anchored protein psrP (*Streptococcus pneumoniae*, Pneumococcal infection); flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA (*Salmonella* genus, Salmonellosis); collagen adhesin Cna, fibronectin-binding protein A FnbA, secretory antigen SssA (*Staphylococcus* genus, Staphylococcal food poisoning); collagen adhesin Can (*Staphylococcus* genus, *Staphylococcal* infection); fibronectin-binding protein A FbpA (Ag85A), fibronectin-binding protein D FbpD, fibronectin-binding protein C FbpC1, heat-shock protein HSP65, protein PST-S (*Mycobacterium tuberculosis*, Tuberculosis); and outer membrane protein FobA, outer membrane protein FobB, type IV pili glycosylation protein, outer membrane protein tolC, protein TolQ (*Francisella tularensis*, Tularemia). Additional exemplary microorganisms and corresponding antigens are disclosed, e.g., in U.S. Publication No. 2015/0118264, the entire contents of which are expressly incorporated herein by reference.

In some embodiments, a plurality of antibodies (e.g., 2, 3, 4, 5, 6, 7, 8, 9, 10, 15, 20, 25, 30, or more antibodies) are used as analyte-binding agents in any of the methods described herein (e.g., to detect the presence of one or more analytes in a sample). In some embodiments, the plurality of antibodies bind to the same analyte (e.g., an antigen). In some embodiments, the plurality of antibodies bind to the same epitope present on the analyte (e.g., an antigen). In some embodiments, the plurality of antibodies bind to different epitopes present on the same analyte. In some embodiments, the plurality of antibodies bind to overlapping epitopes present on the same analyte. In some embodiments, the plurality of antibodies bind to non-overlapping epitopes present on the same analyte.

B. Antibiotics

In some embodiments, the analyte or analyte-binding agent is an antibiotic. An "antibiotic" or "antibiotic agent" refers to a substance that has the capacity to inhibit or slow down the growth of, or to destroy bacteria and/or other microorganisms. In some embodiments, the antibiotic agent is a bacteriostatic antibiotic agent. In some embodiments, the antibiotic is a bacteriolytic antibiotic agent. Exemplary antibiotic agents are set forth in the U.S. Patent Publication US 2006/0269485, which is hereby incorporated by reference herein in its entirety.

In some embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In some embodiments, the antibiotic is rifaximin.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefinenoxime, cefinetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3', 4'-dideoxykanamycin B, 1,2'-N-DL-isoseryl-kanamycin B, 1,2'-N—[(S)-4-amino-2-hydroxybutyryl]-3', 4'-dideoxykanamycin B, 1,2'-N—[(S)-4-amino-2-hydroxybutyryl]-kanamycin B, 1-N-(2-Aminobutanesulfonyl) kanamycin A, 1-N-(2-aminoethanesulfonyl)3', 4'-dideoxyribostamycin, 1-N-(2-Aminoethanesulfonyl)3'-deoxyribostamycin, 1-N-(2-aminoethanesulfonyl)3'4'-dideoxykanamycin B, 1-N-(2-aminoethanesulfonyl)kanamycin A, 1-N-(2-aminoethanesulfonyl)kanamycin B, 1-N-(2-aminoethanesulfonyl)ribostamycin, 1-N-(2-aminopropanesulfonyl)3'-deoxykanamycin B, 1-N-(2-aminopropanesulfonyl)3'4'-dideoxykanamycin B, 1-N-(2-aminopropanesulfonyl)kanamycin A, 1-N-(2-aminopropanesulfonyl)kanamycin B, 1-N-(L-4-amino-2-hydroxy-butyryl)2,'3'-dideoxy-2'-fluorokanamycin A, 1-N-(L-4-amino-2-hydroxy-propionyl)2,'3'-dideoxy-2'-fluorokanamycin A, 1-N-DL-3', 4'-dideoxy-isoserylkanamycin B, 1-N-DL-isoserylkanamycin, 1-N-DL-isoserylkanamycin B, 1-N4L-(—)-(alpha-hydroxy-gamma-aminobutyryl)-XK-62-2,2', 3'-dideoxy-2'-fluorokanamycin A,2-hydroxygentamycin A3,2-hydroxygentamycin B, 2-hydroxygentamycin B1, 2-hydroxygentamycin JI-20A, 2-hydroxygentamycin JI-20B, 3"-N-methyl-4"-C-methyl-3', 4'-dodeoxy kanamycin A, 3"-N-methyl-4"-C-methyl-3', 4'-dodeoxy kanamycin B, 3"-N-methyl-4"-C-methyl-3', 4'-dodeoxy-6'-methyl kanamycin B, 3', 4'-Dideoxy-3'-eno-ribostamycin,3', 4'-dideoxyneamine,3', 4'-dideoxyribostamycin, 3'-deoxy-6'-N-methyl-kanamycin B,3'-deoxyneamine,3'-deoxyribostamycin, 3'-oxysaccharocin,3,3'-nepotrehalosadiamine, 3-demethoxy-2"-N-formimidoylistamycin B disulfate tetrahydrate, 3-demethoxyistamycin B,3-O-demethyl-2-N-formimidoylistamycin B, 3-O-demethylistamycin B,3-trehalosamine,4", 6"-dideoxydibekacin, 4-N-glycyl-KA-6606VI, 5"-Amino-3', 4', 5"-trideoxy-butirosin A, 6"-deoxydibekacin,6'-epifortimicin A, 6-deoxy-neomycin (structure 6-deoxy-neomycin B),6-deoxy-neomycin B, 6-deoxy-neomycin C, 6-deoxy-paromomycin, acmimycin, AHB-3', 4'-dideoxyribostamycin, AHB-3'-deoxykanamycin B, AHB-3'-deoxyneamine, AHB-3'-deoxyribostamycin, AHB-4"-6"-dideoxydibekacin, AHB-6"-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gammal, coumamidine gamma2,D,L-1-N-(alpha-hydroxy-beta-aminopropionyl)-XK-62-2, dactimicin, de-O-methyl-4-N-glycyl-KA-6606VI, de-O-methyl-KA-6606I, de-O-methyl-KA-7038I, destomycin A, destomycin B, di-N6',O3-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KG1 (stereoisomer KG1/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethyl-7-O-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Ansa-type antibiotics include, but are not limited to, 21-hydroxy-25-demethyl-25-methylth ioprotostreptovaricin, 3-methylth iorifamycin, ansamitocin, atropisostreptovaricin, awamycin, halomicin, maytansine, naphthomycin, rifabutin, rifamide, rifampicin, rifamycin, rifapentine, rifaximin (e.g., Xifaxan®), rubradirin, streptovaricin, tolypomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazole, ornidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-O-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, amfomycin, amythiamycin, antifungal from *Zalerion arboricola*, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from Zalerion sp., lysobactin, lysozyme, macromomycin, magainin, melittin, mersacidin, mikamycin, mureidomycin, mycoplanecin, mycosubtilin, neopeptifluorin, neoviridogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a *Streptomyces* compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfcarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Dicarboxylic acids, having between about 6 and about 14 carbon atoms in their carbon atom skeleton are particularly useful in the treatment of disorders of the skin and mucosal membranes that involve microbial. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments of the present disclosure, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred. It has antibacterial effects on both aerobic and anaerobic organisms, particularly *Propionibacterium acnes* and *Staphylococcus epidermidis*, normalizes keratinization, and has a cytotoxic effect on malignant or hyperactive melanocytes. In a preferred embodiment, the dicarboxylic acid is azelaic acid in a concentration greater than 10%. Preferably, the concentration of azelaic acid is between about 10% and about 25%. In such concentrates, azelaic acid is suitable for the treatment of a variety of skin disorders, such as acne, rosacea and hyperpigmentation.

In some embodiments, the antibiotic agent is an antibiotic metal. A number of metals ions have been shown to possess antibiotic activity, including silver, copper, zinc, mercury, tin, lead, bismutin, cadmium, chromium and ions thereof. It has been theorized that these antibiotic metal ions exert their effects by disrupting respiration and electron transport systems upon absorption into bacterial or fungal cells. Antimicrobial metal ions of silver, copper, zinc, and gold, in particular, are considered safe for in vivo use. Anti-microbial silver and silver ions are particularly useful due to the fact that they are not substantially absorbed into the body. Thus, in one or more embodiment, the antibiotic metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The antibiotic metal can further be intercalated in a chelating substrate.

In further embodiments, the antibiotic metal is ionic. The ionic antibiotic metal can be presented as an inorganic or organic salt (coupled with a counterion), an organometallic complex or an intercalate. Non-binding examples of counter inorganic and organic ions are sulfadiazine, acetate, benzoate, carbonate, iodate, iodide, lactate, laurate, nitrate, oxide, and palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

In one or more embodiments, the antibiotic metal or metal ion is embedded into a substrate, such as a polymer, or a mineral (such as zeolite, clay and silica).

In one or more embodiments, the antibiotic agent includes strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents, such as quinones, are also included. Such agents possess a potent broad-spectrum activity.

In one or more embodiments, the antibiotic agent is a cationic antimicrobial agent. The outermost surface of bacterial cells universally carries a net negative charge, making them sensitive to cationic substances. Examples of cationic antibiotic agents include: quaternary ammonium compounds (QAC's)—QAC's are surfactants, generally containing one quaternary nitrogen associated with at least one major hydrophobic moiety; alkyltrimethyl ammonium bromides are mixtures of where the alkyl group is between 8 and 18 carbons long, such as cetrimide (tetradecyltrimethylammonium bromide); benzalkonium chloride, which is a mixture of n-alkyldimethylbenzyl ammonium chloride where the alkyl groups (the hydrophobic moiety) can be of variable length; dialkylmethyl ammonium halides; dialkylbenzyl ammonium halides; and QAC dimmers, which bear bi-polar positive charges in conjunction with interstitial hydrophobic regions.

In one or more embodiments, the cationic antimicrobial agent is a polymer. Cationic antimicrobial polymers include, for example, guanide polymers, biguanide polymers, or polymers having side chains containing biguanide moieties or other cationic functional groups, such as benzalkonium groups or quarternium groups (e.g., quaternary amine groups). It is understood that the term "polymer" as used herein includes any organic material including three or more repeating units, and includes oligomers, polymers, copolymers, block copolymers, terpolymers, etc. The polymer backbone may be, for example a polyethylene, ploypropylene or polysilane polymer.

In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to poly(hexamethylenebiguanide), poly(hexamethylenebiguanide) hydrochloride, poly(hexamethylenebiguanide) gluconate, poly(hexamethylenebiguanide) stearate, or a derivative thereof. In one or more embodiments, the antimicrobial material is substantially water-insoluble.

In some embodiments, the antibiotic agent is selected from the group of biguanides, triguanides, bisbiguanides and analogs thereof.

Guanides, biguanides, biguanidines and triguanides are unsaturated nitrogen containing molecules that readily obtain one or more positive charges, which make them effective antimicrobial agents. The basic structures a guanide, a biguanide, a biguanidine and a triguanide are provided below.

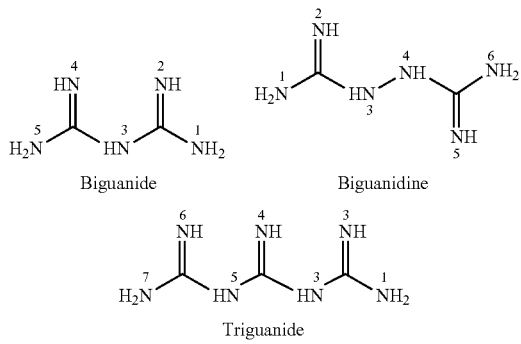

Biguanide

Biguanidine

Triguanide

In some embodiments, the guanide, biguanide, biguanidine or triguanide, provide bi-polar configurations of cationic and hydrophobic domains within a single molecule.

Examples of guanides, biguanides, biguanidines and triguanides that are currently been used as antibacterial agents include chlorhexidine and chlorhexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can conceivably be used according to the present disclosure are chlorproguanil hydrochloride, proguanil hydrochloride (currently used as antimalarial agents), mefformin hydrochloride, phenformin and buformin hydrochloride (currently used as antidiabetic agents).

Yet, in one or more embodiments, the antibiotic is a non-classified antibiotic agent, including, without limitation, aabomycin, acetomycin, acetoxycycloheximide, acetylnanaomycin, an *Actinoplanes* sp. compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis immune substance, anti-tuberculosis immune substance, an antibiotic from *Escherichia coli*, an antibiotic from *Streptomyces refuineus*, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosylbenanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2', 5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, prop-2-enylmonate, protomycin, *Pseudomonas* antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *Streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin and analogs, salts and derivatives thereof.

In one or more embodiments, the antibiotic agent is a naturally occurring antibiotic compound. As used herein, the term "naturally-occurring antibiotic agent" includes all antibiotics that are obtained, derived or extracted from plant or vertebrate sources. Non-limiting examples of families of naturally-occurring antibiotic agents include phenol, resorcinol, antibiotic aminoglycosides, anamycin, quinines, anthraquinones, antibiotic glycopeptides, azoles, macrolides, avilamycin, agropyrene, cnicin, aucubin antibioticsaponin fractions, berberine (isoquinoline alkaloid), arctiopicrin (sesquiterpene lactone), lupulone, humulone (bitter acids), allicin, hyperforin, echinacoside, coniosetin, tetramic acid, imanine and novoimanine.

Ciclopirox and ciclopiroxolamine possess fungicidal, fungistatic and sporicidal activity. They are active against a broad spectrum of dermatophytes, yeasts, moulds and other fungi, such as *Trichophytons* species, *Microsporum* species, *Epidermophyton* species and yeasts (*Candida albicans, Candida glabrata*, other candida species and *Cryptococcus neoformans*). Some *Aspergillus* species are sensitive to ciclopirox as are some *Penicillium*. Likewise, ciclopirox is effective against many Gram-positive and Gram-negative bacteria (e.g., *Escherichia coli, Proteus mirabilis, Pseudomonas aeruginosa, Staphylococcus* and *Streptococcus* species), as well as *Mycoplasma* species, *Trichomonas vaginalis* and *Actinomyces*.

Plant oils and extracts which contain antibiotic agents are also useful. Non-limiting examples of plants that contain agents include thyme, *Perilla*, lavender, tea tree, *Terfezia clayeryi, Micromonospora, Putterlickia verrucosa, Putterlickia pyracantha, Putterlickia retrospinosa, Maytenus ilicifolia, Maytenus evonymoides, Maytenus aquifolia, Faenia interjecta, Cordyceps sinensis*, couchgrass, holy thistle, plantain, burdock, hops, echinacea, buchu, chaparral, myrrh, red clover and yellow dock, garlic, and St. John's wort. Mixtures of the antibiotic agents as described herein may also be employed.

C. Biomarkers

In some embodiments, the analyte or analyte-binding agent is a biomarker. In general, biomarkers of diseases and disorders may be detected, analyzed and/or quantitated using the devices, compositions and methods described herein. The detection, analysis and quantification of a biomarker using the devices, methods and compositions described herein is particular useful in determining and monitoring the course of treatment that could be used to treat a condition in a subject (e.g., a human subject). Biomarkers can be detected and analyzed locally in the GI tract of a subject to determine whether the subject has or is at risk of developing a disease or disorder. In addition, biomarkers can be monitored using the compositions and methods described herein to determine whether a particular course of treatment in a subject diagnosed with a disease or disorder is effective or should be altered. For example, in some embodiments, inflammatory biomarker(s) is/are detected and analyzed in a subject using the ingestible devices described herein to determine whether a subject has or is at risk of developing IBD. As necessary, the subject can then be administered one or more courses of treatment (e.g., an anti-TNFα antibody) and the level of such inflammatory biomarker(s) can be monitored to assess efficacy of treatment.

In some embodiments, biomarkers are detected and analyzed in a subject to determine whether the subject has or is at risk of developing a disease or disorder. These diseases and disorders may occur in the GI tract of the subject or at a non-GI tract site in the subject. For example, biomarkers present in the GI tract may be indicative of a systemic disease or disorder. In some embodiments, the biomarkers are associated with a systemic disease or disorder. In some embodiments, the biomarkers are associated with one or more of a GI disorder, inflammation, cancer, an infectious disease, a liver disease, and an inflammatory disease. Exemplary clases of biomarkers include antibodies (e.g., therapeutic antibodies), antigens (e.g., bacterial antigens), and cytokines). In some embodiments, the analyte or the analytebinding agent is a biomarker, e.g., a biomarker of a GI disorder. An illustrative list of examples of biomarkers for detection, diagnosis or monitoring of treatment efficacy for GI disorders includes interferon-γ, IL-1β, IL-6, IL-22, IL-17A, TNFα, IL-2, memory cells ($CD44^+CD45RB^-CD4^+$ cells); α4β7; VEGF; ICAM; VCAM; SAA; Calprotectin; lactoferrin; FGF2; TGFb; ANG-1; ANG-2; PLGF; a biologic (e.g., infliximab (REMICADE); adalimumab (HUMIRA); ustekinumab (STELARA); vedolizumab (ENTYVIO); golimumab (SIMPONI); Jak inhibitors; and others); EGF; IL12/23p40; GMCSF; A4 B7; AeB7; CRP; SAA; ICAM; VCAM; AREG; EREG; HB-EGF; HRG; BTC; TGFα; SCF; TWEAK; MMP-9; MMP-6; Ceacam CD66; IL10; ADA; Madcam-1; CD166 (AL CAM); FGF2; FGF7; FGF9; FGF19; Anti-neutrophil cytoplasmic antibody (ANCA); Anti-*Saccharomyces cerevisiae* Antibody IgA (ASCAA); Anti-*Saccharomyces cerevisiae* Antibody IgG (ASCAG); Anti-*Clostridium* cluster XIVa flagellin CBir1 antibody (CBir1); Anti-*Clostridium* cluster XIVa flagellin 2 antibody (A4-Fla2); Anti-*Clostridium* cluster XIVa flagellin X antibody (FlaX); Anti-*Escherichia coli* Outer Membrane Protein C (OmpC); Perinuclear AntiNeutrophil Cytoplasmic Antibody (ANCA); Amphiregulin Protein (AREG); Betacellulin Protein (BTC); Epidermal Growth Factor (EGF); Epiregulin Protein (EREG); Heparin Binding Epidermal Growth Factors (HBEGF); Hepatocyte Growth Factor (HGF); Neuregulin-1 (HRG); Transforming Growth Factor alpha (TGFA); C-Reactive Protein (CRP); Serum Amyloid A (SAA); Intercellular Adhesion Molecule 1 (ICAM-1); Vascular Cell Adhesion Molecule 1 (VCAM-1); and fibroblasts underlying the intestinal epithelium.

In some embodiments, a biomarker is an IBD biomarker, such as, for example: anti-glycan; anti-*Saccharomyces cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbir1 flagellin; anti-I2 antibody; autoantibodies targeting the exocrine pancreas (PAB); and perinuclear anti-neutrophil antibody (pANCA); and calprotectin.

In some embodiments, a biomarker is associated with membrane repair, fibrosis, angiogenesis. In certain embodiments, a biomarker is an inflammatory biomarker, an anti-inflammatory biomarker, an MMP biomarker, an immune marker, or a TNF pathway biomarker. In some embodiments, a biomarker is gut-specific.

For tissue samples, HER2 can be used as a biomarker relating to cytotoxic T cells. Additionally, other cytokine levels can be used as biomarkers in tissue (e.g., phospho STAT 1, STAT 3 and STAT 5), in plasma (e.g., VEGF, VCAM, ICAM, IL-6), or both.

In some embodiments, the biomarker include one or more immunoglobulins, such as, for example, immunoglobulin M (IgM), immunoglobulin D (IgD), immunoglobulin G (IgG), immunoglobulin E (IgE) and/or immunoglobulin A (IgA). In some embodiments, IgM is a biomarker of infection and/or inflammation. In some embodiments, IgD is a biomarker of autoimmune disease. In some embodiments, IgG is a biomarker of Alzheimer's disease and/or for cancer. In some embodiments, IgE is a biomarker of asthma and/or allergen immunotherapy. In some embodiments, IgA is a biomarker of kidney disease.

In some embodiments, the biomarker is High Sensitivity C-reactive Protein (hsCRP); 7α-hydroxy-4-cholesten-3-one (7αC4); Anti-Endomysial IgA (EMA IgA); Anti-Human Tissue Transglutaminase IgA (tTG IgA); Total Serum IgA by Nephelometry; Fecal Calprotectin; or Fecal Gastrointestinal Pathogens.

In some embodiments, the biomarker is:

a) an anti-gliadin IgA antibody, an anti-gliadin IgG antibody, an anti-tissue transglutaminase (tTG) antibody, an anti-endomysial antibody;

b) i) a serological biomarker that is ASCA-A, ASCA-G, ANCA, pANCA, anti-OmpC antibody, anti-CBir1 antibody, anti-FlaX antibody, or anti-A4-Fla2 antibody;

b) ii) an inflammation biomarker that is VEGF, ICAM, VCAM, SAA, or CRP;

b) iii) the genotype of the genetic biomarkers ATG16L1, ECM1, NKX2-3, or STAT3;

c) a bacterial antigen antibody biomarker;

d) a mast cell biomarker;

e) an inflammatory cell biomarker;

f) a bile acid malabsorption (BAM) biomarker;

g) a kynurenine biomarker;

or h) a serotonin biomarker.

In some embodiments, the biomarker is a bacterial antigen antibody biomarker selected from the group consisting of an anti-Fla1 antibody, anti-Flat antibody, anti-FlaA antibody, anti-FliC antibody, anti-FliC2 antibody, anti-FliC3 antibody, anti-YBaN1 antibody, anti-ECFliC antibody, anti-Ec0FliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-EcOStx2A antibody, anti-CjcdtB/C antibody, anti-CdTcdA/B antibody, and combinations thereof.

In some embodiments, the biomarker is a mast cell biomarker selected from the group consisting of beta-tryptase, histamine, prostaglandin E2 (PGE2), and combinations thereof.

In some embodiments, the biomarker is an inflammatory biomarker is selected from the group consisting of CRP, ICAM, VCAM, SAA, GROα, and combinations thereof.

In some embodiments, the biomarker is a bile acid malabsorption biomarker selected from the group consisting of 7α-hydroxy-4-cholesten-3-one, FGF19, and a combination thereof.

In some embodiments, the biomarker is a kynurenine biomarker selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the biomarker is a serotonin biomarker selected from the group consisting of serotonin (5-HT), 5-hydroxyindoleacetic acid (5-HIAA), serotonin-O-sulfate, serotonin-O-phosphate, and combinations thereof.

Additional biomarkers are disclosed, e.g., at U.S. Pat. No. 9,739,786, the entire contents of which are incorporated herein by reference.

In some embodiments, the biomarker is associated with a liver disease or disorder. In some embodiments, the analyte or analyte-binding agent is a biomarker of a liver disease or a liver disorder. In some embodiments, the devices, compositions and methods disclosed herein may be used to detect, analyze and/or quantitate a biomarker associated with a liver disease or disorder, e.g., to determine whether a subject has or is at risk of developing a liver disease or disorder. In some embodiments, the devices, compositions, and methods described herein can be used to detect an analyte (e.g., a biomarker) in a sample from the gastrointestinal tract of the subject to determine whether the subject has or is at risk of developing a liver disease or disorder (e.g., NASH). In some embodiments, the detection, analysis and quantification of a liver disease biomarker using the devices, methods and compositions described herein may be used in determining and monitoring the course of treatment that could be used to treat a liver disease or disorder in a subject (e.g., a human subject). An illustrative list of examples of biomarkers that may be used for the detection, diagnosis, or monitoring of treatment efficacy for a liver disease or disorder includes bilirubin, gamma-glutamyl transferase (GGT), haptoglobin, apolipoprotein A1, alpha2-macroglobulin, cholesterol, triglycerides, alanine aminotransferase (ALT), aspartate aminotransferase (AST), glucose, cytokeratin-18 (CK18) fragment, hyaluronic acid, TGF-β, fatty acid binding protein, hydroxysteroid 17-beta dehydrogenase 13 (17β-HSD13), glutamyl dipeptides, glutamyl valine, glutamyl leucine, glutamyl phenylalanine, glutamyl tyrosine, carnitine, butylcarnitine, lysine, tyrosine, isoleucine, glycerophosphatidylcholine, glycerylphsphorylethanolamine, taurine, glycine conjugates, taurocholic acid, taurodeoxycholic acid, lactate, glutamate, cysteine-gluthatione disulfide, caprate, 10-undecenoate, oleoyl-lysophosphatidylcholine, oxidized and reduced gluthatione, glutamate, andenosine triphosphate, creatine, cholic acid, and glycodeoxycholic acid. Additional biomarkers, as well as therapeutic agents, for liver diseases and disorders are known in the art (see, e.g., Hirsova and Gores (2015) *Cell.*

*Mol. Gastroenterol. Hepatol.* 1(1): 17-27; Willebrords et al. (2015) *Progress in Lipid Research* 59: 106-125; Alkhouri et al. (2011) *Expert Rev. Gastroenterol. Hepatol.* 5(2): 201-12; Wang (2014) *Cell Death and Disease* 5: e996; and Alonso et al. (2017) *Gastroenterology* 152: 1449-61, incorporated herein by reference).

D. Therapeutic Agents

In some embodiments, the analyte or analyte-binding agent is a therapeutic agent, a fragment of a therapeutic agent and/or a metabolite of a therapeutic agent. The compositions and methods provided below may also be used to detect, analyze and/or quantitate a therapeutic agent, a fragment of a therapeutic agent, and/or a metabolite of a therapeutic agent. Exemplary therapeutic agents include antibodies, nucleic acids (e.g., inhibitory nucleic acids), small molecules, and live biotherapeutics such as probiotics. In some embodiments, the analyte or the analyte-binding agent used in any of the detection methods described herein is a drug or a therapeutic agent. In some embodiments, the drug or therapeutic agent is used for the treatment of inflammatory bowel disease (IBD), for example, Crohn's Disease or Ulcerative Colitis (UC). Nonlimiting examples of such agents for treating or preventing inflammatory bowel disease include substances that suppress cytokine production, down-regulate or suppress self-antigen expression, or mask the MHC antigens. Examples of such agents include CHST15 inhibitors (e.g., STNM01); IL-6 receptor inhibitora (e.g., tocilizumab); IL-12/IL-23 inhibitors (e.g., ustekinumab and brazikumab); integrin inhibitors (e.g., vedolizumab and natalizumab); JAK inhibitors (e.g., tofacitinib); SMAD7 inhibitors (e.g., Mongersen); IL-13 inhibitors; IL-1 receptor inhibitors; TLR agonists (e.g., Kappaproct); stem cells (e.g., Cx601); 2-amino-6-aryl-5-substituted pyrimidines (see U.S. Pat. No. 4,665,077); non-steroidal anti-inflammatory drugs (NSAIDs); ganciclovir; tacrolimus; glucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, antiinterleukin-2 (IL-2) antibodies and anti-IL-2 receptor antibodies, and anti-interleukin-6 (IL-6) receptor antibodies and antagonists; anti-LFA-1 antibodies, including anti-CD 11a and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002) and see also definition below); 10 biologic agents that interfere with T cell helper signals, such as anti-CD40 receptor or anti-CD40 ligand (CD 154), including blocking antibodies to CD40-CD40 ligand. (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Non-limiting examples of agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinylimidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TP1O; T Cell Sciences, Inc.); slow-release mesalazine; antagonists of platelet activating factor (PAF); ciprofloxacin; and lignocaine. Examples of agents for UC are sulfasalazine and related salicylate-containing drugs for mild cases and corticosteroid drugs in severe cases. Exemplary therapeutic agents that may be used for the treatment of a liver disease or disorder (e.g., liver fibrosis or NASH) include elafibranor (GFT 505; Genfit Corp.), obeticholic acid (OCA; Intercept Pharmaceuticals, Inc.), cenicriviroc (CVC; Allergan plc), selonsertib (formerly GS-4997; Gilead Sciences, Inc.), an anti-LOXL2 antibody (simtuzumab (formerly GS 6624; Gilead Sciences, Inc.)), GS-9450 (Gilead Sciences, Inc.), GS-9674 (Gilead Sciences, Inc.), GS-0976 (formerly NDI-010976; Gilead Sciences, Inc.), Emricasan (Conatus Pharmaceuticals, Inc.), Arachidyl-amido cholanoic acid (Aramchol™; Galmed Pharmaceuticals Ltd.), AKN-083 (Allergan plc (Akarna Therapeutics Ltd.)), TGFTX4 (Genfit Corp.), TGFTX5 (Genfit Corp.), TGFTX1 (Genfit Corp.), a RoRγ agonist (e.g., LYC-55716; Lycera Corp.), an ileal bile acid transporter (iBAT) inhibitor (e.g., elobixibat, Albireo Pharma, Inc.; GSK2330672, GlaxoSmithKline plc; and A4250; Albireo Pharma, Inc.), stem cells, a CCR2 inhibitor, bardoxolone methyl (Reata Pharmaceuticals, Inc.), a bone morphogenetic protein-7 (BMP-7) mimetic (e.g., THR-123 (see, e.g., Sugimoto et al. (2012) *Nature Medicine* 18: 396-404)), an anti-TGF-β antibody (e.g., fresolimumab; see also U.S. Pat. Nos. 7,527,791 and 8,383,780, incorporated herein by reference), pirfenidone (Esbriet®, Genentech USA Inc.), an anti-integrin αvβ6 antibody, an anti-connective tissue growth factor (CTGF) antibody (e.g., pamrevlumab; FibroGen Inc.), pentoxifylline, vascular endothelial growth factor (VEGF), a renin angiotensin aldosterone system (RAAS) inhibitor (e.g., a rennin inhibitor (e.g. pepstatin, CGP2928, aliskiren), or an ACE inhibitor (e.g., captopril, zofenopril, enalapril, ramipril, quinapril, perindopril, lisinopril, benazepril, imidapril, fosinopril, and trandolapril)), thrombospondin, a statin, bardoxolone, a PDES inhibitor (e.g., sidenafil, vardenafil, and tadalafil), a NADPH oxidase-1 (NOX1) inhibitor (see, e.g., U.S. Publication No. 2011/0178082, incorporated herein by reference), a NADPH oxidase-4 (NOX4) inhibitor (see, e.g., U.S. Publication No. 2014/0323500, incorporated herein by reference), an ETA antagonist (e.g., sitaxentan, ambrisentan, atrasentan, BQ-123, and zibotentan), nintedanib (Boehringer Ingelheim), INT-767 (Intercept Pharmaceuticals, Inc.), VBY-376 (Virobay Inc.), PF-04634817(Pfizer), EXC 001 (Pfizer), GM-CT-01 (Galectin Therapeutics), GCS-100 (La Jolla Pharmaceuticals), hepatocyte growth factor mimetic (Refanalin®; Angion Biomedica), SAR156597 (Sanofi), tralokinumab (AstraZeneca), pomalidomide (Celgene), STX-100 (Biogen IDEC), CC-930 (Celgene), anti-miR-21 (Regulus Therapeutics), PRM-151 (Promedior), BOT191 (BiOrion), Palomid 529 (Paloma Pharamaceuticals), IMD1041 (IMMD, Japan), serelaxin (Novartis), PEG-relaxin (Ambrx and Bristol-Myers Squibb), ANG-4011 (Angion Biomedica), FT011 (Fibrotech Therapeutics), pirfenidone (InterMune), F351 (pirfenidone derivative (GNI Pharma), vitamin E (e.g., tocotrienol (alpha, beta, gamma, and delta) and tocopherol (alpha, beta, gamma, and delta)), pentoxifylline, an insulin sensitizer (e.g., rosiglitazone and pioglitazone), cathepsin B inhibitor R-3020, etanercept and biosimilars thereof, peptides that block the activation of Fas (see, e.g., International Publication No. WO 2005/117940, incorporated herein by reference), caspase inhibitor VX-166, caspase inhibitor Z-VAD-fmk, fasudil, belnacasan (VX-765), and pralnacasan (VX-740).

Exemplary additional therapeutic agents are provided below and include exemplary drug classes, and exemplary embodiments for each, that may be detected and analyzed using the methods herein.

1. TNF Inhibitors

The term "TNFα inhibitor" refers to an agent which directly or indirectly inhibits, impairs, reduces, down-regulates, or blocks TNFα activity and/or expression. In some embodiments, a TNFα inhibitor is an inhibitory nucleic acid, an antibody or an antigen-binding fragment thereof, a fusion protein, a soluble TNFα receptor (a soluble TNFR1 or a soluble TNFR2), or a small molecule TNFα antagonist. In some embodiments, the inhibitory nucleic acid is a ribozyme, small hairpin RNA, a small interfering RNA, an antisense nucleic acid, or an aptamer.

Exemplary TNFα inhibitors that directly inhibit, impair, reduce, down-regulate, or block TNFα activity and/or expression can, e.g., inhibit or reduce binding of TNFα to its receptor (TNFR1 and/or TNFR2) and/or inhibit or decrease the expression level of TNFα or a receptor of TNFα (TNFR1 or TNFR2) in a cell (e.g., a mammalian cell). Non-limiting examples of TNFα inhibitors that directly inhibit, impair, reduce, down-regulate, or block TNFα activity and/or expression include inhibitory nucleic acids (e.g., any of the examples of inhibitory nucleic acids described herein), an antibody or fragment thereof, a fusion protein, a soluble TNFα receptor (e.g., a soluble TNFR1 or soluble TNFR2), and a small molecule TNFα antagonist.

Exemplary TNFα inhibitors that can indirectly inhibit, impair, reduce, down-regulate, or block TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: TRADD, TRAF2, MEKK1/4, MEKK4/7, JNK, AP-1, ASK1, RIP, MEKK 3/6, MAPK, NIK, IKK, and NF-κB in a mammalian cell), and/or decrease the level of TNFα-induced gene expression in a mammalian cell (e.g., decrease the transcription of genes regulated by, e.g., one or more transcription factors selected from the group of NF-κB, c-Jun, and ATF2). A description of downstream signaling of a TNFα receptor is provided in Wajant et al., *Cell Death Differentiation* 10:45-65, 2003 (incorporated herein by reference). For example, such indirect TNFα inhibitors can be an inhibitory nucleic acid that targets (decreases the expression) a signaling component downstream of a TNFα receptor (e.g., any one or more of the signaling components downstream of a TNFα receptor described herein or known in the art), a TNFα-induced gene (e.g., any TNFα-induced gene known in the art), or a transcription factor selected from the group of NF-κB, c-Jun, and ATF2.

In other examples, such indirect TNFα inhibitors can be a small molecule inhibitor of a signaling component downstream of a TNFα receptor (e.g., any of the signaling components downstream of a TNFα receptor described herein or known in the art), a small molecule inhibitor of a protein encoded by a TNFα-induced gene (e.g., any protein encoded by a TNFα-induced gene known in the art), and a small molecule inhibitor of a transcription factor selected from the group of NF-κB, c-Jun, and ATF2.

In other embodiments, TNFα inhibitors that can indirectly inhibit, impair, reduce, down-regulate, or block one or more components in a mammalian cell (e.g., a macrophage, a CD4+ lymphocyte, a NK cell, a neutrophil, a mast cell, a eosinophil, or a neuron) that are involved in the signaling pathway that results in TNFα mRNA transcription, TNFα mRNA stabilization, and TNFα mRNA translation (e.g., one or more components selected from the group of CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, and MK2). For example, such indirect TNFα inhibitors can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, and MK2). In other examples, an indirect TNFα inhibitors is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, MyD88, IRAK, lipopolysaccharide binding protein (LBP), TRAF6, ras, raf, MEK1/2, ERK1/2, NIK, IKK, rac, MEK4/7, JNK, c-jun, MEK3/6, p38, PKR, TTP, and MK2).

Inhibitory Nucleic Acids

Inhibitory nucleic acids that can decrease the expression of TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, rac, MEK4/7, JNK, c-jun, MEK3/6, p38, PKR, TTP, or MK2 mRNA expression in a mammalian cell include antisense nucleic acid molecules, i.e., nucleic acid molecules whose nucleotide sequence is complementary to all or part of a TNFα, TNFR1, TNFR2, TRADD, TRAF2, MEKK1/4, MEKK4/7, JNK, AP-1, ASK1, RIP, MEKK 3/6, MAPK, NIK, IKK, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 mRNA.

An antisense nucleic acid molecule can be complementary to all or part of a non-coding region of the coding strand of a nucleotide sequence encoding a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB rac, MEK4/7, JNK, c-jun, MEK3/6, p38, PKR, TTP, or MK2 protein (e.g., specificity for a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 mRNA.

An inhibitory nucleic acid can also be a nucleic acid molecule that forms triple helical structures. For example, expression of a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 polypeptide can be inhibited by targeting nucleotide sequences complementary to the regulatory region of the gene encoding the TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

In some embodiments, a TNFα inhibitor can be a siRNA molecule used to decrease expression of a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 mRNA.

Exemplary TNFα inhibitors that are inhibitory nucleic acids targeting TNFα include, e.g., antisense DNA (e.g., Myers et al., *J Pharmacol Exp Ther.* 304(1):411-424, 2003; Wasmuth et al., Invest. Opthalmol. Vis. Sci, 2003; Dong et al., *J. Orthop. Res.* 26(8):1114-1120, 2008; U.S. Patent Application Serial Nos. 2003/0083275, 2003/0022848, and 2004/0770970; ISIS 104838; U.S. Pat. Nos. 6,180,403, 6,080,580, and 6,228,642; Kobzik et al., Inhibition of TNF Synthesis by Antisense Oligonucleotides, in Manual of Antisense Methodology, Kluwer Academic Publishers, Vol. 4, pp. 107-123, 1999; Taylor et al., *Antisense Nucleic Acid Drug Develop.* 8(3):199-205, 1998; Mayne et al., *Stroke* 32:240-248, 2001; Mochizuki et al., *J. Controlled Release* 151(2):155-161, 2011; Dong et al., *J. Orthopaedic Res.* 26(8):1114-1120, 2008; Dong et al., *Pharm. Res.* 28(6): 1349-1356, 2011; and Pampfer et al., *Biol. Reproduction* 52(6):1316-1326, 1995), antisense RNA, short interfering RNA (siRNA) (e.g., Taishi et al., *Brain Research* 1156:125-132, 2007; Presumey et al., *Eur. J. Pharm. Biopharm.* 82(3):457-467, 2012; Laroui et al., *J. Controlled Release* 186:41-53, 2014; D'Amore et al., *Int. J. Immunopathology Pharmacol.* 21:1045-1047, 2008; Choi et al., *J. Dermatol. Sci.* 52:87-97, 2008; Qin et al., *Artificial Organs* 35:706-714, 2011; McCarthy et al., *J. Controlled Release* 168: 28-34, 2013; Khoury et al., *Current Opin. Mol. Therapeutics* 9(5):483-489, 2007; Lu et al., *RNA Interference Technology From Basic Science to Drug Development* 303, 2005; Xie et al., *PharmaGenomics* 4(6):28-34, 2004; Aldawsari et al., *Current Pharmaceutical Design* 21(31):4594-4605, 2015; Zheng et al., *Arch. Med. Sci.* 11:1296-1302, 2015; Peng et al., *Chinese J. Surgery* 47(5):377-380, 2009; Aldayel et al., *Molecular Therapy. Nucleic Acids* 5(7):e340, 2016; Bai et al., *Current Drug Targets* 16:1531-1539, 2015; U.S. Patent Application Publications Nos. 2008/0097091, 2009/0306356, and 2005/0227935; and WO 14/168264), short hairpin RNA (shRNA) (e.g., Jakobsen et al., *Mol. Ther.* 17(10): 1743-1753, 2009; Ogawa et al., *PLoS One* 9(3): e92073, 2014; Ding et al., *Bone Joint* 94-6 (Suppl. 11):44, 2014; and Hernandez-Alejandro et al., *J. Surgical Res.* 176(2):614-620, 2012), and microRNAs (see, e.g., WO 15/26249). In some embodiments, the inhibitory nucleic acid blocks pre-mRNA splicing of TNFα (e.g., Chiu et al., *Mol. Pharmacol.* 71(6): 1640-1645, 2007).

In some embodiments, the inhibitory nucleic acid, e.g., an aptamer (e.g., Orava et al., *ACS Chem Biol.* 2013; 8(1): 170-178, 2013), can block the binding of a TNFα protein with its receptor (TNFR1 and/or TNFR2).

In some embodiments, the inhibitory nucleic acid can down-regulate the expression of a TNFα-induced downstream mediator (e.g., TRADD, TRAF2, MEKK1/4, MEKK4/7, JNK, AP-1, ASK1, RIP, MEKK 3/6, MAPK, NIK, IKK, NF-κB, p38, JNK, IκB-α, or CCL2). Further teachings of downstream TNFα-induced mediators can be found in, e.g., Schwamborn et al., *BMC Genomics* 4:46, 2003; and Zhou et al., *Oncogene* 22: 2034-2044, 2003, incorporated by reference herein. Additional aspects of inhibitory nucleic acids are described in Aagaard et al., *Adv. Drug Delivery Rev.* 59(2):75-86, 2007, and Burnett et al., *Biotechnol. J.* 6(9):1130-1146, 2011.

In certain embodiments, the inhibitory nucleic acid targets a nucleic acid encoding a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2.

Antibodies

In some embodiments, the TNFα inhibitor is an antibody or an antigen-binding fragment thereof (e.g., a Fab or a scFv). In some embodiments, an antibody or antigen-binding fragment described herein binds specifically to any one of TNFα, TNFR1, or TNFR2. In some embodiments, an antibody or antigen-binding fragment of an antibody described herein can bind specifically to TNFα. In some embodiments, an antibody or antigen-binding fragment of an antibody described herein can bind specifically to a TNFα receptor (TNFR1 or TNFR2).

Non-limiting examples of TNF inhibitors that are antibodies that specifically bind to TNFα are described in Elliott et al., *Lancet* 1994; 344: 1125-1127, 1994; Rankin et al., *Br. Rheumatol.* 2:334-342, 1995; Butler et al., *Eur. Cytokine Network* 6(4):225-230, 1994; Lorenz et al., *J. Immunol.* 156(4):1646-1653, 1996; Hinshaw et al., *Circulatory Shock* 30(3):279-292, 1990; Wanner et al., *Shock* 11(6):391-395, 1999; Bongartz et al., *JAMA* 295(19):2275-2285, 2006; Knight et al., *Molecular Immunol.* 30(16):1443-1453, 1993; Feldman, *Nature Reviews Immunol.* 2(5):364-371, 2002;

Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Ordas et al., *Clin. Pharmacol. Therapeutics* 91(4):635-646, 2012; Cohen et al., *Canadian J Gastroenterol. Hepatol.* 15(6):376-384, 2001; Feldmann et al., *Ann. Rev. Immunol.* 19(1):163-196, 2001; Ben-Horin et al., *Autoimmunity Rev.* 13(1):24-30, 2014; and U.S. Pat. Nos. 6,090,382; 6,258,562; and 6,509,015).

In certain embodiments, the TNFα inhibitor can include or is infliximab (Remicade™), CDP571, CDP 870, golimumab (Golimumab™), adalimumab (Humira™), or certolizumab pegol (Cimzia™). In certain embodiments, the TNFα inhibitor can be a TNFα inhibitor biosimilar. Examples of approved and late-phase TNFα inhibitor biosimilars include, but are not limited to, infliximab biosimilars such as Remsima™ and Inflectra® (CT-P13) from Celltrion/Pfizer, GS071 from Aprogen, Flixabi™ (SB2) from Samsung Bioepis, PF-06438179 from Pfizer/Sandoz, NI-071 from Nichi-Iko Pharmaceutical Co., and ABP 710 from Amgen; adalimumab biosimilars such as Exemptia™ (ZRC3197) from Zydus Cadila, India, Solymbic® and Amgevita® (ABP 501) from Amgen, Imraldi (SB5) from Samsung Bioepis, GP-2017 from Sandoz, Switzerland, ONS-3010 from Oncobiologics, M923/Viropro, U.S.A., from Momenta Pharmaceuticals/Baxalta (Baxter spinoff USA), PF-06410293 from Pfizer, BMO-2 or MYL-1401-A from Biocon/Mylan, CHS-1420 from Coherus, FKB327 from Fujifilm/Kyowa Hakko Kirin (Fujifilm Kyowa Kirin Biologics), and Cyltezo (BI 695501) from Boehringer Ingelheim, CT-P17 from Celltrion, BAX 923 from Baxalta (now a part of Shire), MSB11022 from Fresenius Kabi (bought from Merck kGaA (Merck Group) in 2017), LBAL from LG Life Sciences/Mochida Pharmaceutical, South Korea/Japan, PBP1502 from Prestige Biopharma, Adfrar from Torrent Pharmaceuticals, India, a biosimilar of adalimumab in development by Adello Biologics, a biosimilar of adalimumab in development by AET Biotech/BioXpress Therapeutics, Germany/Switzerland, a biosimilar of adalimumab from mAbxience, Spain, a biosimilar of adalimumab in development by Plant-Form, Canada; and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, and CHS-0214 from Coherus.

In some embodiments, a biosimilar is an antibody or antigen-binding fragment thereof that has a light chain that has the same primary amino acid sequence as compared to a reference antibody (e.g., adalimumab) and a heavy chain that has the same primary amino acid sequence as compared to the reference antibody. In some examples, a biosimilar is an antibody or antigen-binding fragment thereof that has a light chain that includes the same light chain variable domain sequence as a reference antibody (e.g., adalimumab) and a heavy chain that includes the same heavy chain variable domain sequence as a reference antibody. In some embodiments, a biosimilar can have a similar glycosylation pattern as compared to the reference antibody (e.g., adalimumab). In other embodiments, a biosimilar can have a different glycosylation pattern as compared to the reference antibody (e.g., adalimumab). Changes in the N-linked glycosylation profile of a biosimilar as compared to a reference antibody (e.g., adalimumab) can be detected using 2-anthranilic acid (AA)-derivatization and normal phase liquid chromatography with fluorescence detection, as generally described in Kamoda et al., *J. Chromatography J.* 1133:332-339, 2006. For example, a biosimilar can have changes in one or more (e.g., two, three, four, five, six, seven, eight, nine, ten, or eleven) of the following types of N-glycosylation as compared to the reference antibody (e.g., adalimumab): neutrally-charged oligosaccharides; monosialylated fucose-containing oligosaccharides; monosialylated oligosaccharides; bisialylated fucose-containing oligosaccharide; bisialylated oligosaccharides; triantennary, trisiaylated oligosaccharides of form 1; triantennary, trisialylated oligosaccharides of form 2; mannose-6-phosphate oligosaccharides; monophosphorylated oligosaccharides; tetrasialylated oligosaccharides; monosialylated and monophosphorylated oligosaccharides; and bis-mannose-6-phosphate oligosaccharides.

In some embodiments, the biosimilar can have a change in one, two, or three of: the percentage of species having one C-terminal lysine, the percentage of species having two C-terminal lysines, and the percentage of species having three C-terminal lysines as compared to the reference antibody (e.g., adalimumab).

In some embodiments, the biosimilar can have a change in the level of one, two, or three of acidic species, neutral species, and basic species in the composition as compared to the reference antibody (e.g., adalimumab).

In some embodiments, the biosimilar can have a change in the level of sulfation as compared to the reference antibody.

In some embodiments, the TNFα inhibitor can be SAR252067 (e.g., a monoclonal antibody that specifically binds to TNFSF14, described in U.S. Patent Application Publication No. 2013/0315913) or MDGN-002 (described in U.S. Patent Application Publication No. 2015/0337046). In some embodiments, the TNFα inhibitor can be PF-06480605, which binds specifically to TNFSF15 (e.g., described in U.S. Patent Application Publication No. 2015/0132311). Additional examples of TNFα inhibitors include DLCX105 (described in Tsianakas et al., *Exp. Dermatol.* 25:428-433, 2016) and PF-06480605, which binds specifically to TNFSF15 (described in U.S. Patent Application Publication No. 2015/0132311).

Fusion Proteins

In some embodiments, the TNFα inhibitory agent is a fusion protein (e.g., an extracellular domain of a TNFR fused to a partner peptide, e.g., an Fc region of an immunoglobulin, e.g., human IgG) (see, e.g., Peppel et al., *J. Exp. Med.* 174(6):1483-1489, 1991; Deeg et al., *Leukemia* 16(2): 162, 2002) or a soluble TNFR (e.g., TNFR1 or TNFR2) that binds specifically to TNFα. In some embodiments, the TNFα inhibitor includes or is etanercept (Enbrel™) (see, e.g., WO 91/03553 and WO 09/406,476, incorporated by reference herein). In some embodiments, the TNFα inhibitor includes or is r-TBP-I (e.g., Gradstein et al., *J. Acquir. Immune Defic. Syndr.* 26(2): 111-117, 2001). In some embodiments, the TNFα inhibitor includes or is a soluble TNFα receptor (e.g., Watt et al., *J Leukoc Biol.* 66(6):1005-1013, 1999; Tsao et al., *Eur Respir J.* 14(3):490-495, 1999; Kozak et al., *Am. J. Physiol. Reg. Integrative Comparative Physiol.* 269(1):R23-R29, 1995; Mohler et al., *J. Immunol.* 151(3):1548-1561, 1993; Nophar et al., *EMBO J.* 9(10): 3269, 1990; Bjornberg et al., *Lymphokine Cytokine Res.* 13(3):203-211, 1994; Piguet et al., *Eur. Respiratory J* 7(3): 515-518, 1994; and Gray et al., *Proc. Natl. Acad. Sci. U.S.A.* 87(19):7380-7384, 1990).

Small Molecules

In some embodiments, the TNFα inhibitor is a small molecule. In some embodiments, the TNFα inhibitor is C87

(Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the small molecule is a tumor necrosis factor-converting enzyme (TACE) inhibitor (e.g., Moss et al., *Nature Clinical Practice Rheumatology* 4: 300-309, 2008). In some embodiments, the TACE inhibitor is TMI-005 and BMS-561392. Additional examples of small molecule inhibitors are described in, e.g., He et al., *Science* 310(5750):1022-1025, 2005.

In some examples, the TNFα inhibitor is a small molecule that inhibits the activity of one of TRADD, TRAF2, MEKK1/4, MEKK4/7, JNK, AP-1, ASK1, RIP, MEKK 3/6, MAPK, NIK, IKK, and NF-κB, in a mammalian cell.

In some examples, the TNFα inhibitor is a small molecule that inhibits the activity of one of CD14, MyD88 (see, e.g., Olson et al., *Scientific Reports* 5:14246, 2015), IRAK (Chaudhary et al., *J. Med. Chem.* 58(1):96-110, 2015), lipopolysaccharide binding protein (LBP) (see, e.g., U.S. Pat. No. 5,705,398), TRAF6 (e.g., 3-[(2,5-Dimethylphenyl) amino]-1-phenyl-2-propen-1-one), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, R05126766 (CH5126766), PLX7904, and MLN2480), MEK1/2 (e.g., Facciorusso et al., *Expert Review Gastroenterol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, JNK (e.g., AEG 3482, BI 78D3, CEP 1347, c-JUN peptide, IQ 1S, JIP-1 (153-163), SP600125, SU 3327, and TCS JNK60), c-jun (e.g., AEG 3482, BI 78D3, CEP 1347, c-JUN peptide, IQ 1S, JIP-1 (153-163), SP600125, SU 3327, and TCS JNK60), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), and MK2 (PF 3644022 and PHA 767491).

2. IL-12/IL-23 Inhibitors

The term "IL-12/IL-23 inhibitors" refers to an agent which decreases IL-12 or IL-23 expression and/or the ability of IL-12 to bind to an IL-12 receptor or the ability of IL-23 to bind to an IL-23 receptor. IL-12 is a heterodimeric cytokine that includes both IL-12A (p35) and IL-12B (p40) polypeptides. IL-23 is a heterodimeric cytokine that includes both IL-23 (p19) and IL-12B (p40) polypeptides. The receptor for IL-12 is a heterodimeric receptor includes IL-12R β1 and IL-12R β2. The receptor for IL-23 receptor is a heterodimeric receptor that includes both IL-12R β1 and IL-23R.

In some embodiments, the IL-12/IL-23 inhibitor can decrease the binding of IL-12 to the receptor for IL-12. In some embodiments, the IL-12/IL-23 inhibitor can decrease the binding of IL-23 to the receptor for IL-23. In some embodiments, the IL-12/IL-23 inhibitor decreases the expression of IL-12 or IL-23. In some embodiments, the IL-12/IL-23 inhibitor decreases the expression of a receptor for IL-12. In some embodiments, the IL-12/IL-23 inhibitor decreases the expression of a receptor for IL-23.

In some embodiments, the IL-12/IL-23 inhibitory agent targets IL-12B (p40) subunit. In some embodiments, the IL-12/IL-23 inhibitory agent targets IL-12A (p35). In some embodiments, the IL-12/IL-23 inhibitory agent targets IL-23 (p19). In some embodiments, the IL-12/IL-23 inhibitory agent targets the receptor for IL-12 (one or both of IL-12R β1 or IL-12R β2). In some embodiments, the IL-12/IL-23 inhibitory agent targets the receptor for IL-23 (one or both of IL-12R β1 and IL-23R).

In some embodiments, an IL-12/IL-23 inhibitor can be an inhibitory nucleic acid. In some embodiments, the inhibitory nucleic acid can be an antisense nucleic acid, a ribozyme, and a small interfering RNA (siRNA).

Inhibitory nucleic acids that can decrease the expression of IL-12A (p35), IL-12B (p40), IL-23 (p19), IL-12R β1, IL-12R β2, or IL-23R mRNA expression in a mammalian cell include antisense nucleic acid molecules, i.e., nucleic acid molecules whose nucleotide sequence is complementary to all or part of an IL-12A (p35), IL-12B (p40), IL-23 (p19), IL-12R β1, IL-12R β2, or IL-23R mRNA. An antisense nucleic acid molecule can be complementary to all or part of a non-coding region of the coding strand of a nucleotide sequence encoding an IL-12A (p35), IL-12B (p40), IL-23 (p19), IL-12R β1, IL-12R β2, or IL-23R protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding an IL-12A (p35), IL-12B (p40), IL-23 (p19), IL-12R (31, IL-12R (32, or IL-23R protein (e.g., specificity for an IL-12A (p35), IL-12B (p40), IL-23 (p19), IL-12R (31, IL-12R (32, or IL-23R mRNA).

An inhibitor nucleic acid can also be a nucleic acid molecule that forms triple helical structures. For example, expression of an IL-12A (p35), IL-12B (p40), IL-23 (p19), IL-12R β1, IL-12R β2, or IL-23R protein can be inhibited by targeting nucleotide sequences complementary to the regulatory region of the gene encoding the IL-12A (p35), IL-12B (p40), IL-23 (p19), IL-12R β1, IL-12R β2, or IL-23R protein (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

Other examples of a IL-12/IL-23 inhibitor include siRNA that decrease the level of IL-12A (p35), IL-12B (p40), IL-23 (p19), IL-12R β1, IL-12R β2, or IL-23R mRNA.

Non-limiting examples of siRNAs targeting IL-12A (p35), IL-12B (p40), IL-23 (p19), IL-12R β1, IL-12R β2, or IL-23R are described in Tan et al., *J. Alzheimers Dis.* 38(3): 633-646, 2014; Niimi et al., *J. Neuroimmunol.* 254(1-2):39-45, 2013. Non-limiting examples of short hairpin RNA (shRNA) targeting IL-12A (p35), IL-12B (p40), IL-23 (p19), IL-12R β1, IL-12R β2, or IL-23R are described in Bak et al., *BMC Dermatol.* 11:5, 2011.

Non-limiting examples of inhibitory nucleic acids are microRNAs (e.g., microRNA-29 (Brain et al., *Immunity* 39(3):521-536, 2013), miR-10a (Xue et al., *J. Immunol.* 187(11):5879-5886, 2011), microRNA-155 (Podsiad et al., *Am. J. Physiol. Lung Cell Mol. Physiol.* 310(5):L465-75, 2016).

Antibodies

In some embodiments, the IL-12/IL-23 inhibitor is an antibody or an antigen-binding fragment thereof (e.g., a Fab or a scFv). In some embodiments, an antibody or antigen-binding fragment described herein binds specifically to any one of IL-12A (p35), IL-12B (p40), IL-23 (p19), IL-12R β1, IL-12R β2, or IL-23R, or a combination thereof.

In some embodiments, the antibody is ustekinumab (CNTO 1275, Stelara®) or a variant thereof (Krueger et al., *N Engl. J. Med.* 356(6):580-592, 2007; Kauffman et al., *J. Invest. Dermatol.* 123(6):1037-1044, 2004; Gottlieb et al., *Curr. Med. Res. Opin.* 23(5):1081-1092, 2007; Leonardi et al., *Lancet* 371(9625):1665-1674, 2008; Papp et al., *Lancet* 371(9625):1675-1684, 2008). In some embodiments, the antibody is briakinumab (ABT-874, J-695) or a variant thereof (Gordon et al., *J. Invest. Dermatol.* 132(2):304-314, 2012; Kimball et al., *Arch Dermatol.* 144(2): 200-207, 2008).

In some embodiments, the antibody is guselkumab (CNTO-1959) (Callis-Duffin et al., *J. Am. Acad. Dermatol.* 70(5 Suppl 1), 2014); AB162 (Sofen et al., *J. Allergy Clin. Immunol.* 133: 1032-40, 2014); tildrakizumab (MK-3222, SCH900222) (Papp et al. (2015) *Br. J. Dermatol.* 2015); Langley et al., Oral Presentation at: American Academy of Dermatology, March 21-25, Denver Colo., 2014); AMG 139 (MEDI2070, brazikumab) (Gomollon, *Gastroenterol. Hepatol.* 38(Suppl. 1):13-19, 2015; Kock et al., *Br. J. Pharmacol.* 172(1):159-172, 2015); FM-202 (Tang et al., *Immunology* 135(2):112-124, 2012); FM-303 (Tang et al., *Immunology* 135(2):112-124, 2012); ADC-1012 (Tang et al., *Immunology* 135(2):112-124, 2012); LY-2525623 (Gaffen et al., *Nat. Rev. Immunol.* 14:585-600, 2014; Sands, *Gastroenterol. Hepatol.* 12(12):784-786, 2016), LY-3074828 (Coskun et al., *Trends Pharmacol. Sci.* 38(2):127-142, 2017), BI-655066 (risankizumab) (Singh et al., *MAbs* 7(4):778-791, 2015; Krueger et al., *J. Allergy Clin. Immunol.* β6(1):116-124, 2015) or a variant thereof.

See e.g., Tang et al., *Immunology* β5(2):112-124, 2012. Further teachings of IL-12/IL-23 antibodies and antigen-binding fragments thereof are described in U.S. Pat. Nos. 6,902,734; 7,247,711; 7,252,971; and 7,491,391; US 2012/0288494; and US 2013/0302343, each of which is incorporated by reference in its entirety.

In some embodiments, the IL-12/IL-23 inhibitor is PTG-200, an IL-23R inhibitor currently in preclinical development by Protagonist Therapeutics.

In some embodiments, the IL-12/IL-23 inhibitor is Mirikizumab (LY 3074828), an IL-23R inhibitor currently in clinical development (Phase II) by Eli Lilly.

Fusion Proteins

In some embodiments, the IL-12/IL-23 inhibitor is a fusion protein, a soluble antagonist, or an antimicrobial peptide. In some embodiments, the fusion protein comprises a soluble fragment of a receptor of IL-12 or a soluble fragment of a receptor of IL-23. In some embodiments, the fusion protein comprises an extracellular domain of a receptor of IL-12 or an extracellular domain of a receptor of IL-23.

In some embodiments, the fusion protein is adnectin or a variant thereof (Tang et al., *Immunology* β5(2):112-124, 2012). In some embodiments, the soluble antagonist is a human IL-23Ra-chain mRNA transcript (Raymond et al., *J. Immunol.* 185(12):7302-7308, 2010). In some embodiments, the IL-12/IL-23 is an antimicrobial peptide (e.g., MP-196 (Wenzel et al., *PNAS* 111(14):E1409-E1418, 2014)).

Small Molecules

In some embodiments, the IL-12/IL-23 inhibitor is a small molecule. In some embodiments, the small molecule is STA-5326 (apilimod) or a variant thereof (Keino et al., *Arthritis Res. Ther.* 10: R122, 2008; Wada et al., *Blood* 109(3):1156-1164, 2007; Sands et al., *Inflamm. Bowel Dis.* 16(7):1209-1218, 2010).

3. IL-6 Receptor Inhibitors

The term "IL-6 receptor inhibitor" refers to an agent which decreases IL-6 receptor expression and/or the ability of IL-6 to bind to an IL-6 receptor. In some embodiments, the IL-6 receptor inhibitor targets the IL-6 receptor β-subunit, glycoprotein 130 (sIL6gp130). In other embodiments, the IL-6 receptor inhibitor targets the IL-6 receptor subunit (IL6R). In other embodiments, the IL-6 receptor inhibitor targets the complex consisting of both the IL-6 receptor subunit (IL6R) and the IL-6 receptor β-subunit, glycoprotein 130 (sIL6gp130). In some embodiments, the IL-6 receptor inhibitor targets IL-6.

In some embodiments, an IL-6 receptor inhibitor is an inhibitory nucleic acid, an antibody or an antigen-binding fragment thereof, a fusion protein, a IL-6 receptor antagonist, or a small molecule. In some embodiments, the inhibitory nucleic acid is a small interfering RNA, an antisense nucleic acid, an aptamer, or a microRNA. Exemplary IL-6 receptor inhibitors are described herein. Additional examples of IL-6 receptor inhibitors are known in the art.

Exemplary aspects of different inhibitory nucleic acids are described below. Any of the examples of inhibitory nucleic acids that can decrease expression of an IL6R, sIL6gp130, or IL-6 mRNA. Inhibitory nucleic acids that can decrease the expression of IL6R, sIL6gp130, or IL-6 mRNA in a mammalian cell include antisense nucleic acid molecules, i.e., nucleic acid molecules whose nucleotide sequence is complementary to all or part of an IL6R, sIL6gp130, or IL-6 mRNA.

Inhibitory Nucleic Acids

An antisense nucleic acid molecule can be complementary to all or part of a non-coding region of the coding strand of a nucleotide sequence encoding an IL6R, sIL6gp130, or IL-6 protein. Non-coding regions (5' and 3' untranslated regions) are the 5' and 3' sequences that flank the coding region in a gene and are not translated into amino acids. Exemplary antisense nucleic acids that are IL-6 receptor inhibitors are described in Keller et al., *J. Immunol.* 154(8): 4091-4098, 1995; and Jiang et al., *Anticancer Res.* 31(9): 2899-2906, 2011.

Another example of an inhibitory nucleic acid is a ribozyme that has specificity for a nucleic acid encoding an IL6R, sIL6gp130, or IL-6 protein (e.g., specificity for an IL6R, sIL6gp130, or IL-6 mRNA).

An inhibitory nucleic acid can also be a nucleic acid molecule that forms triple helical structures. For example, expression of an IL6R, sIL6gp130, or IL-6 polypeptide can be inhibited by targeting nucleotide sequences complementary to the regulatory region of the gene encoding the IL6R, sIL6gp130, or IL-6 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

Additional examples of IL-6 receptor inhibitors include siRNA that decrease the level of IL6R, sIL6gp130, or IL-6 mRNA. Non-limiting examples of short interfering RNA (siRNA) that are IL-6 receptor inhibitors are described in Yi et al., *Int. J. Oncol.* 41(1):310-316, 2012; and Shinriki et al., *Clin. Can. Res.* 15(17):5426-5434, 2009). Non-limiting examples of microRNAs that are IL-6 receptor inhibitors are described in miR34a (Li et al., *Int. J. Clin. Exp. Pathol.* 8(2):1364-1373, 2015) and miR-451 (Liu et al., *Cancer Epidemiol.* 38(1):85-92, 2014).

Non-limiting examples of aptamers that are IL-6 receptor inhibitors are described in Meyer et al., *RNA Biol.* 11(1): 57-65, 2014; Meyer et al., *RNA Biol.* 9(1):67-80, 2012; and Mittelberger et al., *RNA Biol.* 12(9):1043-1053, 2015. Additional examples of inhibitory nucleic acids that are IL-6 receptor inhibitors are described in, e.g., WO 96/040157.

Antibodies

In some embodiments, the IL-6 receptor inhibitor is an antibody or an antigen-binding fragment thereof (e.g., a Fab or a scFv). In some embodiments, an antibody or antigen-binding fragment described herein binds specifically to IL-6. In some embodiments, an antibody or antigen-binding fragment described herein binds specifically to IL-6 receptor (e.g., one or both of IL6R and sIL6gp130).

In certain embodiments, the antibody comprises or consists of an antigen-binding fragment or portion of tocilizumab (artlizumab, Actemra®; Sebba, *Am. J. Health Syst. Pharm.* 65(15):1413-1418, 2008; Tanaka et al., *FEBS Letters* 585(23):3699-3709, 2011; Nishimoto et al., *Arthritis Rheum.* 50:1761-1769, 2004; Yokota et al., *Lancet* 371 (9617):998-1006, 2008; Emery et al., *Ann. Rheum. Dis.* 67(11):1516-1523, 2008; Roll et al., *Arthritis Rheum.* 63(5): 1255-1264, 2011); clazakizumab (BMS945429; ALD518, a humanized monoclonal antibody that binds circulating IL-6 cytokine rather than the IL-6 receptor, blocking both classic signaling and trans-signaling (Weinblatt, Michael E., et al. "The Efficacy and Safety of Subcutaneous Clazakizumab in Patients With Moderate-to-Severe Rheumatoid Arthritis and an Inadequate Response to Methotrexate: Results From a Multinational, Phase IIb, Randomized, Double-Blind, Placebo/Active-Controlled, Dose-Ranging Study." Arthritis & Rheumatology 67.10 (2015): 2591-2600.)); sarilumab (REGN88 or SAR153191; Huizinga et al., *Ann. Rheum. Dis.* 73(9):1626-1634, 2014; Sieper et al., *Ann. Rheum. Dis.* 74(6):1051-1057, 2014; Cooper, *Immunotherapy* 8(3): 249-250, 2016); MR-16 (Hartman et al., *PLosOne* 11(12): e0167195, 2016; Fujita et al., *Biochim. Biophys. Acta.* 10:3170-80, 2014; Okazaki et al., *Immunol. Lett.* 84(3):231-40, 2002; Noguchi-Sasaki et al., *BMC Cancer* 16:270, 2016; Ueda et al., *Sci. Rep.* 3:1196, 2013); rhPM-1 (MRA; Nishimoto et al., *Blood* 95: 56-61, 2000; Nishimoto et al., *Blood* 106: 2627-2632, 2005; Nakahara et al., *Arthritis Rheum.* 48(6): 1521-1529, 2003); NI-1201 (Lacroix et al., *J. Biol. Chem.* 290(45):26943-26953, 2015); EBI-029 (Schmidt et al., Eleven Biotherapeutics Poster #B0200, 2014). In some embodiments, the antibody is a nanobody (e.g., ALX-0061 (Van Roy et al., *Arthritis Res. Ther.* 17: 135, 2015; Kim et al., *Arch. Pharm. Res.* 38(5):575-584, 2015)). In some embodiments, the antibody is NRI or a variant thereof (Adachi et al., *Mol. Ther.* 11(1):5262-263, 2005; Hoshino et al., *Can. Res.* 67(3): 871-875, 2007). In some embodiments, the antibody is PF-04236921 (Pfizer) (Wallace et al., *Ann. Rheum. Dis.* 76(3):534-542, 2017).

In some embodiments, the antibody is siltuximab (Sylvant®), also known as CNTO 328, a chimeric, human-murine, immunoglobulin (Ig) Gκ mAb that binds and neutralizes human IL-6 with high affinity and specificity. The variable region of siltuximab is derived from a murine anti-IL-6 antibody, CLB8, and the constant region is derived from a human IgG1κ molecule. Sylvant® is approved for the treatment of patients with multicentric Castleman's disease (MCD).

In some embodiments, the IL-6R inhibitor is AMG220, also known as C326, an avimer that displays bi-specificity to its interleukin target, as well as binding to the Fc domain of IgG (resulting in reduced renal clearance and FcRn recycling). The compound has subpicomolar affinity for IL-6 and displays a moderate serum half-life (~30 h). Phase I clinical trials of AMG220 in Crohn's disease revealed dose-dependent reduction in serum C-reactive protein, an inflammation biomarker synthesized by hepatocytes in response to IL-6. Despite its apparent efficacy, Amgen has suspended the clinical development of the compound.

Fusion Proteins

In some embodiments, the IL-6 receptor inhibitor is a fusion protein, a soluble receptor, or a peptide (see e.g., U.S. Pat. No. 5,591,827). In some embodiments, the IL-6 receptor fusion protein comprises or consists of soluble gp130 (Jostock et al., *Eur. J. Biochem.* 268(1):160-167, 2001; Richards et al., *Arthritis Rheum.* 54(5):1662-1672, 2006; Rose-John et al., *Exp. Opin. Ther. Targets* 11(5):613-624, 2007).

In some embodiments, the IL-6 receptor fusion protein comprises or consists of FE999301 (Jostock et al., *Eur. J. Biochem.* 268(1):160-167, 2001) or sgp130Fc protein (Jones et al., *J. Clin. Invest.* 121(9):3375-3383, 2011). In some embodiments, the IL-6 receptor inhibitor is a peptide (e.g., S7 (Su et al., *Cancer Res.* 65(11):4827-4835, 2005). In some embodiments, the IL-6 receptor inhibitor is a triterpenoid saponin (e.g., chikusetsuaponin IVa butyl ester (CS-Iva-Be) (Yang et al., *Mol. Cancer. Ther.* 15(6):1190-200, 2016).

Small Molecules

In some embodiments, the IL-6 receptor inhibitor is a small molecule (see, e.g., U.S. Pat. No. 9,409,990). In some embodiments, the small molecule is LMT-28 (Hong et al., *J. Immunol.* 195(1): 237-245, 2015); ERBA (Enomoto et al., *Biochem. Biophys. Res. Commun.* 323:1096-1102, 2004; Boos et al., *J. Nat. Prod.* 75(4):661-668, 2012), ERBF (TB-2-081) (Hayashi et al., *J. Pharmacol. Exp. Ther.* 303: 104-109, 2002; Vardanyan et al., *Pain* 151(2):257-265, 2010; Kino et al., *J. Allergy Clin. Immunol.* 120(2):437-444, 2007), or a variant thereof 4. Integrin Inhibitors The term "integrin inhibitor" refers to an agent which decreases the expression of one or more integrins and/or decreases the binding of an integrin ligand to one or more integrins that play a role in the recruitment, extravasation, and/or activation of a leukocyte. In some embodiments, the integrin inhibitor specifically binds to at least a portion of a ligand binding site on a target integrin. In some embodiments, the integrin inhibitor specifically binds to a target integrin at the same site as an endogenous ligand. In some embodiments, the integrin inhibitor decreases the level of expression of the target integrin in a mammalian cell. In some embodiments, the integrin inhibitor specifically binds to an integrin ligand.

Non-limiting examples of integrins that can be targeted by any of the integrin inhibitors described herein include: α2β1 integrin, α1β1 integrin, α4β7 integrin, integrin α4β1 (VLA-4), E-selectin, ICAM-1, α5β1 integrin, α4β1 integrin, VLA-4, α2β1 integrin, α5β3 integrin, α5β5 integrin, αIIbβ3 integrin, and MAdCAM-1. A non-limiting example of integrin inhibitor that can decrease the expression and/or activity of α4β7 integrin is FTY720. A non-limiting example of an integrin inhibitor that specifically targets MAdCAM is PF-547659 (Pfizer). Non-limiting examples of an integrin inhibitor that specifically targets α4β7 is AJM300 (Ajinomoto), etrolizumab (Genentech), and vedolizumab (Millenium/Takeda).

In some embodiments, the integrin inhibitor is an αIIbβ3 integrin inhibitor. In some embodiments, the αIIbβ3 integrin inhibitor is abciximab (ReoPro®, c7E3; Kononczuk et al., *Curr. Drug Targets* 16(13):1429-1437, 2015; Jiang et al., *Appl. Microbiol. Biotechnol.* 98(1):105-114, 2014), eptifibatide (Integrilin®; Scarborough et al., *J. Biol. Chem.* 268:1066-1073, 1993; Tcheng et al., *Circulation* 91:2151-2157, 1995) or tirofiban (Aggrastat®; Hartman et al., *J. Med. Chem.* 35:4640-4642, 1992; Pierro et al., *Eur. J. Ophthalmol.* 26(4):e74-76, 2016; Guan et al., *Eur. J. Pharmacol* 761:144-152, 2015). In some embodiments, the integrin inhibitor is an αL-selective integrin inhibitor. In some embodiments, the integrin inhibitor is a β2 integrin inhibitor.

In some embodiments, the integrin inhibitor is an α4 integrin (e.g., an α4β1 integrin (e.g., Very Late Antigen-4 (VLA-4), CD49d, or CD29)) inhibitor, an α4β7 integrin inhibitor. In some embodiments, the integrin inhibitor targets endothelial VCAM1, fibronectin, mucosal addressin cellular adhesion molecule-1 (MAdCAM-1), vitronectin, tenascin-C, osteopontin (OPN), nephronectin, agiostatin, tissue-type transglutaminase, factor XIII, Von Willebrand factor (VWF), an ADAM protein, an ICAM protein, collagen, e-cadherin, laminin, fibulin-5, or TGFβ. In some embodiments, the α4 integrin inhibitor is natalizumab (Tysabri®; Targan et al., *Gastroenterology* β2(5):1672-1683, 2007; Sandborn et al., *N Engl. J. Med.* 353(18):1912-1925, 2005; Nakamura et al., *Intern. Med.* 56(2):211-214, 2017; and Singh et al., *J. Pediatr. Gastroenterol. Nutr.* 62(6):863-866, 2016). In some embodiments, the integrin inhibitor is an endogenous integrin inhibitor (e.g., SHARPIN (Rantala et al., *Nat. Cell. Biol.* 13(11):1315-1324, 2011).

In some embodiments, the integrin inhibitor is an αv integrin (e.g., an α5β1 integrin, an α5β3 integrin, an α5β5 integrin inhibitor, and/or an α5β6 integrin) inhibitor.

In some embodiments, the integrin inhibitor is an α5β1 integrin inhibitor.

In some embodiments, an integrin inhibitor is an inhibitory nucleic acid, an antibody or antigen-binding fragment thereof, a fusion protein, an integrin antagonist, a cyclic peptide, a disintegrin, a peptidomimetic, or a small molecule. In some embodiments, the inhibitory nucleic acid is a small hairpin RNA, a small interfering RNA, an antisense, an aptamer, or a microRNA.

Inhibitory Nucleic Acids

In some embodiments, the inhibitory nucleic acid can be an antisense nucleic acid, a ribozyme, a small interfering RNA, a small hairpin RNA, or a microRNA. Inhibitory nucleic acids that can decrease the expression of target integrin mRNA or a target integrin ligand mRNA (e.g., any of the exemplary integrins described herein or any of the exemplary integrin ligands described herein) in a mammalian cell include antisense nucleic acid molecules, i.e., nucleic acid molecules whose nucleotide sequence is complementary to all or part of target integrin mRNA or a target integrin ligand mRNA. An antisense nucleic acid molecule can be complementary to all or part of a non-coding region of the coding strand of a nucleotide sequence encoding a target integrin or a target integrin ligand (e.g., any of the exemplary target integrins or any of the exemplary integrin ligands described herein). Non-coding regions (5' and 3' untranslated regions) are the 5' and 3' sequences that flank the coding region in a gene and are not translated into amino acids. Exemplary integrin inhibitors that are antisense nucleic acids include ATL1102 (e.g., Limmroth et al., *Neurology* 83(20):1780-1788, 2014; Li et al., *Dig. Liver Dis.* 39(6):557-565, 2007; Goto et al., *Inflamm. Bowel Dis.* 12(8):758-765, 2006).

Another example of an inhibitory nucleic acid is a ribozyme that has specificity for a nucleic acid encoding a target integrin (e.g., any of the exemplary target integrins described herein) or an integrin ligand (e.g., any of the exemplary integrin ligands described herein).

An inhibitory nucleic acid can also be a nucleic acid molecule that forms triple helical structures. For example, expression of a target integrin (e.g., any of the exemplary target integrins described herein) or an integrin ligand (e.g., any of the exemplary integrin ligands described herein) can be inhibited by targeting nucleotide sequences complementary to the regulatory region of the gene encoding the target integrin (e.g., any of the exemplary target integrins described herein) or the integrin ligand (e.g., any of the exemplary integrin ligands described herein) (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

In some embodiments, an integrin inhibitor is a siRNA that decreases the level of a target integrin (e.g., any of the exemplary target integrins described herein) mRNA or an integrin ligand (e.g., any of the exemplary integrin ligands described herein) mRNA. Non-limiting examples of integrin inhibitors that are short interfering RNAs (siRNAs) are described in Wang et al., *Cancer Cell Int* 16:90, 2016). In some embodiments, the integrin inhibitor is a short hairpin RNA (shRNA).

Non-limiting examples of integrin inhibitors that are microRNA include miR-124 (Cai et al., *Sci. Rep.* 7:40733, 2017), miR-β4 (Qin et al., *Oncol. Rep.* 37(2):823-830, 2017), miR-92b (Ma et al., *Oncotarget* 8(4):6681-6690, 2007), miR-17 (Gong et al., *Oncol. Rep.* 36(4), 2016), miR-338 (Chen et al., *Oncol. Rep.* 36(3):1467-74, 2016), and miR-30a-5p (Li et al., *Int. J. Oncol.* 48(3):1155-1164, 2016).

Antibodies

In some embodiments, the integrin inhibitor is an antibody or an antigen-binding fragment thereof (e.g., a Fab or a scFv). In some embodiments, the antibody can be a humanized antibody, a chimeric antibody, a multivalent antibody, or a fragment thereof.

In some embodiments, the antibody is a pan-β1 antibody (e.g., OS2966 (Carbonell et al., *Cancer Res.* 73(10):3145-3154, 2013). In some embodiments, the integrin antibody is a monoclonal antibody (e.g., 17E6 (Castel et al., *Eur. J. Cell. Biol.* 79(7):502-512, 2000); Mitjans et al., *Int. J. Cancer* 87(5):716-723, 2000)). In some embodiments, the monoclonal antibody is vedolizumab (e.g., Entyvio®) or a variant thereof (Feagan et al., *N. Engl. J. Med* 369:699-710, 2013; Sandborn et al., *N. Engl. J. Med.* 369:711-721, 2013; Sands et al., *Gastroenterology* 147:618-627, 2014; and Milch et al., *Neuroimmunol.* 264:123-126, 2013; Wyant et al., *J. Crohns Colitis* 10(12):1437-1444, 2016; and Feagan et al., *Gastroenterology* 142(5):5160-5161, 2012).

In some embodiments, the antibody can be a Fab fragment of a monoclonal chimeric mouse-human antibody (e.g., abciximab (ReoPro, c7E3), Kononczuk et al., *Curr. Drug Targets* 16(13):1429-1437, 2015; Jiang et al., *Appl. Microbiol. Biotechnol.* 98(1):105-114, 2014), or a variant thereof. In some embodiments, the integrin antibody is a humanized monoclonal antibody. In some embodiments, the humanized monoclonal antibody is natalizumab (Tysabri®) (Targan et al., *Gastroenterology* 132(5):1672-1683, 2007; Sandborn et al., *N. Engl. J. Med.* 353(18):1912-1925, 2005; Nakamura et al., *Intern Med.* 56(2):211-214, 2017; Singh et al., *J. Pediatr. Gastroenterol. Nutr.* 62(6):863-866, 2016). In some embodiments, the humanized monoclonal antibody is vitaxin (MEDI-523) or a variant thereof (Huveneers et al., *Int, J.*

Radiat. Biol. 81(11-12):743-751, 2007; Coleman et al., Circ. Res. 84(11):1268-1276, 1999). In some embodiments, the humanized monoclonal antibody is etaracizumab (Abegrin®, MEDI-522, LM609) or a variant thereof (Hersey et al., Cancer 116(6):1526-1534, 2010; Delbaldo et al., Invest New Drugs 26(1):35-43, 2008). In some embodiments, the humanized monoclonal antibody is CNTO95 (Intetumumab®) or a variant thereof (Jia et al., Anticancer Drugs 24(3):237-250, 2013; Heidenreich et al., Ann. Oncol. 24(2): 329-336, 2013; Wu et al., J. Neurooncol. 110(1):27-36, 2012). In some embodiments, the humanized monoclonal antibody is efalizumab (Raptiva®) or a variant thereof (Krueger et al., J. Invest. Dermatol. 128(11):2615-2624, 2008; Li et al., PNAS 106(11):4349-4354, 2009; Woolacott et al., Health Technol. Assess 10:1-233, 2006). In some embodiments, the humanized monoclonal antibody is STX-100 (Stromedix®) or a variant thereof (van Aarsen et al., Cancer Res. 68:561-570, 2008; Lo et al., Am. J. Transplant. 13(12):3085-3093, 2013). In some embodiments, the humanized monoclonal antibody is 264RAD or a variant thereof (Eberlein et al., Oncogene 32(37):4406-4417, 2013).

In some embodiments, the humanized monoclonal antibody is rovelizumab or a variant thereof (Goodman et al., Trends Pharmacol. Sci 33:405-412, 2012). In some embodiments, the humanized monoclonal antibody is Cytolin® or a variant thereof (Rychert et al., Virology J. 10:120, 2013). In some embodiments, the humanized monoclonal antibody is etrolizumab or a variant thereof (Vermeire et al., Lancet 384:309-318, 2014; Rutgeerts et al., Gut 62:1122-1130, 2013; Lin et al., Gastroenterology 146:307-309, 2014; Ludviksson et al., J. Immunol. 162(8):4975-4982, 1999; Stefanich et al., Br. J. Pharmacol. 162(8):1855-1870, 2011). In some embodiments, the humanized monoclonal antibody is abrilumab (AMG 181; MEDI-7183) or a variant thereof (Pan et al., Br. J. Pharmacol. 169(1):51-68, 2013; Pan et al., Br. J. Clin. Pharmacol. 78(6):β15-β33, 2014). In some embodiments, the humanized monoclonal antibody is PF-00547659 (SHP647) or a variant thereof (Vermeire et al., Gut 60(8):1068-1075, 2011; Sandborn et al., Gastroenterology 1448(4):S-162, 2015). In some embodiments, the humanized monoclonal antibody is SAN-300 (hAQC2) or a variant thereof (Karpusas et al., J. Mol. Biol. 327:1031-1041, 2003). In some embodiments, the humanized monoclonal antibody is DI176E6 (EMD 5257) or a variant thereof (Goodman et al., Trends Pharmacol. Sci 33:405-412, 2012; and Sheridan et al., Nat. Biotech. 32:205-207, 2014).

In some embodiments, the integrin antibody is a chimeric monoclonal antibody. In some embodiments, the chimeric monoclonal antibody is volociximab or a variant thereof (Kuwada et al., Curr. Opin. Mol. Ther. 9(1):92-98, 2007; Ricart et al., Clin. Cancer Res. 14(23):7924-7929, 2008; Ramakrishnan et al., J Exp. Ther. Oncol. 5(4):273-86, 2006; Bell-McGuinn et al., Gynecol. Oncol. 121:273-279, 2011; Almokadem et al., Exp. Opin. Biol. Ther. 12:251-7, 2012).

In some embodiments, the antibody specifically binds one or more (e.g., 1, 2, 3, 4, or 5) integrin. In some embodiments, the antibody specifically binds an integrin dimer (e.g., MLN-00002, MLN02 (Feagan et al., Clin. Gastroenterol. Hepatol. 6(12):1370-1377, 2008; Feagan et al., N Engl. J. Med. 352(24):2499-2507, 2005). In certain embodiments, the antibody comprises or consists of an antigen-binding fragment of abciximab (Reopro™) (Straub et al., Eur. J. Cardiothorac Surg. 27(4):617-621, 2005; Kim et al., Korean J. Intern. Med. 19(4):220-229, 2004). In some embodiments, the integrin inhibitor is an antibody-drug conjugate (e.g., IMGN388 (Bendell et al., EJC Suppl 8(7):152, 2010).

Further examples of antibodies and antigen-binding fragments thereof are described in U.S. Pat. Nos. 5,919,792; 6,214,834; 7,074,408; 6,833,373; 7,655,624; 7,465,449; 9,558,899; 7,659,374; 8,562,986; 8,398,975; and 8,853,149; US 2007/0117849; US 2009/0180951; US 2014/0349944; US 2004/0018192; WO 11/137418; and WO 01/068586; each of which is incorporated by reference in its entirety.

Fusion Proteins

In some embodiments, the integrin inhibitor is a fusion protein (e.g., an Fc fusion protein of an extracellular domain of an integrin or an integrin receptor), a soluble receptor (e.g., the extracellular domain of an integrin or an integrin receptor), or a recombinant integrin binding protein (e.g., an integrin ligand). See, e.g., Lode et al., PNAS 96(4):1591-1596, 1999; Stephens et al., Cell Adhesion Comm. 7:377-390, 2000; and US 2008/0739003; incorporated by reference herein). Non-limiting examples of fusion proteins that are integrin inhibitors include Ag25426 (Proteintech).

Small Molecules Antagonists

In some embodiments, the integrin inhibitor is a small molecule. In some embodiments, the small molecule is a non-peptide small molecule. In some embodiments, the non-peptide small molecule is a RGD (ArgGlyAsp)-mimetic antagonist (e.g., tirofiban (Aggrastat®); Pierro et al., Eur. J Ophthalmol. 26(4):e74-76, 2016; Guan et al., Eur. J. Pharmacol 761:144-152, 2015. In some embodiments, the small molecule is α4 antagonist (e.g., firategrast (Miller et al., Lancet Neurol. 11(2):131-139, 2012) AJM300 (Yoshimura et al., Gastroenterology 149(7):1775-1783, 2015; Takazoe et al., Gastroenterology β6(5):A-181, 2009; Sugiura et al., J. Crohns Colitis 7(11):e533-542, 2013)). In some embodiments, the small molecule is α4β1 antagonist (e.g., IVL745 (Norris et al., J. Allergy Clin. Immunol. 116(4):761-767, 2005; Cox et al., Nat. Rev. Drug Discov. 9(10):804-820, 2010)), BIO-1211 (Abraham et al., Am. J. Respir. Crit. Care Med. 162:603-611, 2000; Ramroodi et al., Immunol. Invest. 44(7):694-712, 2015; Lin et al., J. Med. Chem. 42(5):920-934, 1999), HMR 1031 (Diamant et al., Clin. Exp. Allergy 35(8):1080-1087, 2005); valategrast (R411) (Cox et al., Nat. Rev. Drug Discov. 9(10):804-820, 2010), GW559090X (Ravensberg et al., Allergy 61(9):1097-1103, 2006), TR14035 (Sircar et al., Bioorg. Med. Chem. 10(6):2051-2066, 2002; Cortijo et al., Br. J. Pharmacol. 147(6):661-670, 2006)). In some embodiments, the small molecule is αvβ3 antagonist (e.g., L0000845704, SB273005). In some embodiments, the small molecule is α5β1 antagonist (e.g., JSM6427). In some embodiments, the small molecule is GLPG0974 (Vermeire et al., J. Crohns Colitis Suppl. 1:S39, 2015). In some embodiments, the small molecule is MK-0429 (Pickarksi et al., Oncol. Rep. 33(6):2737-45, 2015; Rosenthal et al., Asia Pac J. Clin. Oncol. 6:42-8, 2010). In some embodiments, the small molecule is JSM-6427 or a variant thereof (Zahn et al., Arch. Ophthalmol. 127(10):β29-β35, 2009; Stragies et al., J. Med. Chem. 50:3786-94, 2007).

In some embodiments, the small molecule targets a β2 integrin. In some embodiments, the small molecule is SAR-118 (SAR1118) or a variant thereof (Zhong et al., ACS Med. Chem. Lett. 3(3):203-206, 2012; Suchard et al., J. Immunol. 184:3917-3926, 2010; Yandrapu et al., J. Ocul. Pharmacol. Ther. 29(2):236-248, 2013; Semba et al., Am. J. Ophthalmol. 153:1050-60, 2012). In some embodiments, the small molecule is BMS-587101 or a variant thereof (Suchard et al., J. Immunol. 184(7):3917-3926, 2010; Potin et al., J. Med. Chem. 49:6946-6949, 2006). See e.g., Shimaoka et al., Immunity 19(3):391-402, 2003; U.S. Pat. Nos. 7,138,417; 7,928,113; 7,943,660; and 9,216,174; US 2008/0242710; and US 2008/0300237.

In some embodiments, the small molecule integrin inhibitor can be PTG-100, which is described in, e.g., Shames et al., "Pharmakokinetics and Pharmacodynamics of the Novel Oral Peptide Therapeutic PTG-100 (α4β7 Integrin Antagonist) in Normal Healthy Volunteers," 24th United European Gastroentrology Week, October 15-19, Vienna, Austria, 2016.

Cyclic Peptides

In some embodiments, the integrin inhibitor is a cyclic peptide. In some embodiments, the cyclic peptide comprises or consists of an amino acid sequence as set forth in the amino acid sequence of a ligand recognition sequence of an endogenous integrin ligand. In some embodiments, the cyclic peptide competes for a target integrin ligand binding site with an endogenous integrin ligand. In some embodiments, the cyclic peptide includes one or more (e.g., 1, 2, 3, 4, 5, 6, 7, 8) D-amino acids. In some embodiments, the cyclic peptide is a synthetic cyclic peptide. In some embodiments, the synthetic cyclic peptide is a heptapeptide. In some embodiments, the synthetic cyclic peptide is eptifabitide (Integrilin™), or a variant thereof. In some embodiments, the cyclic peptide comprises a heterocyclic nucleic (e.g., a benzodiazepinone, a piperazine, a benzoazepinone, a nitroaryl, an isoxazoline, an indazole, or a phenol; Spalluto et al., Curr. Med. Chem. 12:51-70, 2005). In some embodiments, the cyclic peptide is a macrocycle (see, e.g., Halland et al., ACS Med. Chem. Lett. 5(2):193-198, 2014). In some embodiments, the peptide is ALG-1001 or a variant thereof (Mathis et al., Retin. Phys. 9:70, 2012). In some embodiments, the cyclic peptide is an imidazolone-phenylalanine derivative, a heteroaryl, hetrocyclic, and aryl derivative, a bicyclic-aromatic amino acid derivative, a cyclohexanecarboxylic acid derivative, a di-aryl substituted urea derivative, a multimeric L-alanine derivative, a L-alanine derivative, or a pyrimidyl-sulfonamide derivative (see, e.g., U.S. Pat. Nos. 6,630,492; 6,794,506; 7,049,306; 7,371,854; 7,759,387; 8,030,328; 8,129,366; 7,820,687; 8,350,010; and 9,345,793).

Peptidomimetics

In some embodiments, the integrin inhibitor is a peptidomimetic. In some embodiments, the peptidomimetic has an integrin-ligand recognition motif (e.g., RGD, KTS, or MLD). See, e.g., Carron et al., Cancer Research 58:1930-1935, 1998; Fanelli et al., Vascular Cell 6:11, 2014; and De Marco et al., Curr. Top. Med. Chem. 16(3):343-359, 2016.

In some embodiments, the peptidomimetic is an RGD (ArgGlyAsp)-based peptide (U.S. Pat. No. 8,809,338, incorporated by reference in its entirety herein). In some embodiments, the RGD-based peptide can be cilengitide or a variant thereof (EMD 12974) (Mas-Moruno et al., Anticancer Agents Med. Chem. 10:753-768, 2010; Reardon et al., Future Oncol. 7(3):339-354, 2011; Beekman et al., Clin. Genitourin Cancer 4(4):299-302, 2006; SC56631 (e.g., Engleman et al., Am Soc. Clin. Invest. 99(9):2284-2292, 1997; Peng et al., Nature Chem Biol. 2:381-389, 2006). In some embodiments, the peptidomimetic can be a Lys-Gly-Asp (KGD)-based peptide. In some embodiments, the peptidomimetic can be vipegitide or a variant thereof (Momic et al., Drug Design Devel. Therapy 9:291-304, 2015). In some embodiments, the peptidomimetic can be a peptide conjugated with an antimicrobial synthetic peptide. (e.g., ACDCRGDCFC conjugated with (KLAKLAK)$_2$ (Ellerby et al., Nat. Med. 5(9):1032-1038, 1999). See, e.g., U.S. Pat. No. 8,636,977.

Disintegrins

In some embodiments, the integrin inhibitor can be a disintegrin. The term "disintegrin" as used herein refers to a low molecular weight peptide integrin inhibitor derived from a snake venom (e.g., pit viper venom). In some embodiments, the disintegrin is a RGD(ArgGlyAsp)-, a KTS- or an MLD-based disintegrin.

Non-limiting examples of disintegrins include accutin, accurhagin-C, albolabrin, alternagin-c, barbourin, basilicin, bitisgabonin-1, bitisgabonin-2, bitistatin, cerastin, cereberin, cumanastatin 1, contortrostatin, cotiarin, crotatroxin, dendroaspin, disba-01, durissin, echistatin, EC3, elegantin, eristicophin, eristostatin, EMS11, EO4, EO5, flavoridin, flavostatin, insularin, jarastatin, jerdonin, jerdostatin, lachesin, lebein (e.g., lebein-1, lebein-2), leberagin-C, lebestatin, lutosin, molossin, obtustatin, ocellatusin, rhodocetin, rhodostomin, R-mojastin 1, salmosin, saxatilin, schistatin, tablysin-15, tergeminin, triflavin, trigramin, trimestatin, VA6, vicrostatin, viridin, viperstatin, VB7, VLO4, and VLO5, or a variant thereof. See, e.g., Arruda Macedo et al., Curr. Protein. Pept. Sci. 16(6):532-548, 2015; Hsu et al., Sci. Rep. 6:23387, 2016; Kele et al. Curr. Protein Pept. Sci. 6:532-548, 2015; Koh et al., Toxicon 59(4):497-506, 2012; Scarborough et al., J. Biol. Chem. 268:1058-1065, 1993; Kisiel et al., FEBSLett. 577:478-482, 2004; Souza et al., Arch. Biochem. Biophys. 384:341-350, 2000; Eble et al., J. Biol. Chem. 278:26488-26496, 2003; Marcinkiewicz et al., J. Biol. Chem. 274:12468-12473, 1999; Calvete et al., J. Proteome Res. 6:326-336, 2007; Scibelli et al., FEMS Microbiol. Lett. 247:51-57, 2005; Oliva et al., Toxicon 50:1053-1063, 2007; Minea et al., Toxicon 59:472-486, 2012; Smith et al., FEBS Lett. 512:111-115, 2002; Tselepis et al., J. Biol. Chem. 272:21341-21348, 1997; Da Silva et al., Tromb. Res. 123:731-739, 2009; Thibault et al., Mol. Pharmacol. 58:1137-1145, 2000; Lu et al., Biochem. J. 304:818-825, 1994; Yeh et al., Biochim. Biophys. Acta. 1425:493-504, 1998; Huang et al., Exp. Hematol. 36:1704-1713, 2008; Shih et al., Matrix Biol. 32:152-159, 2013; Wang et al., Br. J. Pharmacol. 160:1338-β51, 2010; Della-Casa et al., Toxicon 57:125-β3, 2011; Sheu et al., Biochim. Biophys. Acta. β36:445-454, 1997; Fujii et al., J. Mol. Biol. 332:115-122, 2003; Bilgrami et al., J. Mol. Biol. 341:829-837, 2004; Zhou et al., Toxicon 43:69-75, 2004; Scarborough et al., J. Biol. Chem. 268:1066-1073, 1993; Shebuski et al., J. Biol. Chem. 264:21550-21556, 1989; Lu et al., Biochem. J. 304:929-936, 1994; McLane et al., Biochem. J. 301:429-436, 1994; Juarez et al., Toxicon 56:1052-1058, 2010; Olfa et al., Lab. Invest. 85:1507-1516, 2005; Elbe et al., Matrix Biol. 21:547-558, 2002; Bazan-Socha et al., Biochemistry 43:1639-1647, 2004; Danen et al., Exp. Cell. Res. 238:188-196, 1998; Marcinkiewicz et al., Biochemistry 38(40):β302-β309, 1999; Calvete et al., Biochem. J. 372:725-734, 2003; Swenson et al., Pathophysiol. Haemost. Thromb. 34:169-176, 2005; Kwon et al., PLoS One 8; e81165, 2013; Yang et al., Toxicon 45:661-669, 2005; Limam et al., Matrix Biol. 29:117-126, 2010; Gan et al., J. Biol. Chem. 263:19827-19832, 1988; Ma et al., Thromb. Haemost. 105(6):1032-1045, 2011; and U.S. Pat. No. 7,074,408, incorporated in their entirety herein.

5. TLR Agonists/Antagonists

The term "TLR agonist" is an agent that binds to and activates a toll-like receptor (TLR) expressed in a mammalian cell (e.g., a human cell). In some embodiments, the TLR agonist binds to and activates TLR1. In some embodiments, the TLR agonist binds to and activates TLR2. In some embodiments, the TLR agonist binds to and activates TLR3. In some embodiments, the TLR agonist binds to and activates TLR4. In some embodiments, the TLR agonist binds to and activates TLR5. In some embodiments, the TLR agonist binds to and activates TLR6. In some embodiments, the TLR agonist binds to and activates TLR7. In some embodiments, the TLR agonist binds to and activates TLR8. In some embodiments, the TLR agonist binds to and activates TLR9. In some embodiments, the TLR agonist binds to and activates TLR10. In some embodiments, the TLR agonist binds to and activates TLR11. In some embodiments, the TLR agonist binds to and activates two or more (e.g., three, four, five, six, seven, eight, nine, ten, or eleven) TLRs (e.g., two or more of any of TLR1, TLR2, TLR3, TLR4, TLR5, TLR6, TLR7, TLR8, TLR9, TLR10, and TLR11 (in any combination)).

In some embodiments, the TLR agonist is a synthetic TLR agonist, a TLR mimic, or a small molecule. Non-limiting examples of TLR agonists are described in Bhardwaj et al., Cancer J. 16(4):382-391, 2010; Meyer et al., Exp. Opin. Investig. Drugs 17(7):1051-1065, 2008; Adams, Immunotherapy 1(6):949-964, 2009; Hennessy et al., Nat. Rev. Drug Discov. 9:293-307, 2010; and U.S. Pat. Nos. 7,498,409; 9,421,254; 8,409,813; 8,361,986; 8,795,678; 8,728,486; 8,636,979; 8,999,946; 9,359,360; 9,050,376; and 9,556,167; US 2014/0322271; US 2016/0206690; US 2009/0253622; US 2011/0135669; US 2011/0250175; US 2014/0220074; and US 2012/0219615; each incorporated in its entirety herein. In some embodiments, the TLR agonist is a peptide or a fusion protein (Huleatt et al., Vaccine 25: 763-775, 2007).

In some embodiments, a TLR agonist specifically binds to and activates a single TLR (e.g., TLR4, TLR7, TLR8, or TLR9; Zhu et al., J. Clin. Invest. 120:607-616, 2010; Zhu et al., PNAS 105:16260-16265, 2008; Wang et al., J. Virol. 79(22):14355-14370, 2005). In some embodiments, the TLR agonist binds to and activates more than one TLR (e.g., Bacillus of Calmette-Guerin, Myobacterium bovis (BCG); Morton et al., Ann. Surg. 180(4):635-643, 1974; Mortoon et al., J. Clin. Oncol. ASCO Ann. Meeting Proceedings Part I 25(18 Suppl), 2007). In some embodiments, the TLR agonist is a TLR2/TLR6 agonist (e.g., Pam2CSK4 or MALP-2 (Agnihotri et al., J. Med. Chem. 54: 8148-8160, 2011; Wu et al., J. Med. Chem. 53: 3198-3213, 2010)).

In some embodiments, the TLR agonist is an endogenous molecule released from dead cells (e.g., a heat shock protein (HSP) and mobility group box 1 (HMGB1); Asea et al., J. Biol. Chem. 277:15028-15034, 2002; Kepp et al., Cancer Metastasis 30: 61-69, 2011).

TLR3 Agonists

In some embodiments, the TLR agonist specifically binds and activates TLR3 (e.g., a synthetic agonist). Non-limiting examples of TLR agonists that bind and activate TLR3 are described in Nicodemus et al., Immunotherapy 2:137-140, 2010. In some embodiments, the TLR3 agonist is a synthetic double-stranded RNA (dsRNA) complex (e.g., polyribosinic: polyribocytidic acid (polyI:C); Sivori et al., PNAS 101:10116-10121, 2004; Sloat et al., Pharmaceutical Res. 23:1217-1226, 2006; Ichinohe et al., Microbes and infection/Institut Pasteur 9:1333-β40, 2007; Robinson et al., J. Natl. Cancer Inst. 57(3):599-602, 1976). In some embodiments, the TLR3 agonist is a TLR3 mimic (e.g., polyadenosine-polyuridylic acid (poly A:U) (Veyrat et al., Oncotarget 7(50):82580-82593, 2016; Alizadeh et al., Iran J. Allergy Asthma Immunol. 12(2):161-167, 2013); rintatolimod (polyI: polyCU, Ampligen®) (Steinman et al., Nature 449: 419-426, 2007; Jasani et al., Vaccine 27(25-26):3401-3404, 2009; Strayer et al., PLoS One 7(3): e31334, 2012). In some embodiments, the TLR3 mimic is polyionisinic-polycytidylic acid stabilized with poly-L-lysine and carboxymethylcellulose (Poly-ICLC, Hiltonol®; Hawkins et al., J. Biol. Resp. Mod. 4:664-668, 1985; Butowski et al., J. Neurooncol. 91:175-182, 2009; Jeong et al., J. Neurochem. doi.10.1111, 2015). In some embodiments, the TLR3 agonist is RGC100 (Naumann et al., Clin. Dev. Immunol. 283649, 2013), IPH-3102 (Basith et al., Exp. Opin. Ther. Pat. 21: 927-944, 2011), or a variant thereof. In some embodiments, the TLR3 agonist is CQ-07001 (Clinquest). In some embodiments, the TLR3 agonist is Ampligen poly(I):poly(C12U) (Hemispherx Biopharma). In some embodiments, the TLR3 agonist is IPH-31XX (Innate Pharma). In some embodiments, the TLR3 agonist is MCT-465-dsRNA (MultiCell Technologies).

TLR4 Agonists

In some embodiments, the TLR agonist specifically binds to and activates TLR4 (Peri et al., J. Med. Chem. 57(9): 3612-3622, 2014). In some embodiments, the TLR4 agonist is bacterial lipopolysaccharide (LPS) or a variant thereof. In some embodiments, the TLR4 agonist is monophosphoryl lipid A (MPL, MPLA, GLA, GLA-SE) (Ribi et al., J. Immunol. 6:567-572, 1984; Okemoto et al., J. Immunol. 176:1203-1208, 2006; Matzner et al., Int. J. Cancer β8:1754-1764, 2016; Cauwelaert et al., PLoS One 11(1): e0146372, 2016). In some embodiments, the TLR agonist is AS15 or AS02b (Brichard et al., Vaccine 25(Suppl. 2):B61-B71, 2007; Kruit et al., J. Clin. Oncol. 26(Suppl): Abstract 9065, 2008). In some embodiments, the TLR agonist is an aminoalkyl glucosaminide 4-phosphate (e.g., RC-529, Ribi.529, E6020) or a variant thereof (Baldridge et al., J. Endotoxin Res. 8:453-458, 2002; Morefield et al., Clin. Vaccine Immunol. 14: 1499-1504, 2007). In some embodiments, the TLR agonist is picibanil (OK-432) (Hazim et al., Med. J. Malaysia 71(6):328-330, 2016; Tian et al., Asian Pac J. Cancer Prev. 16(11):4537-4542, 2015; Rebuffini et al., Dent Rese. J. 9(Suppl. 2):S192-S196, 2012). In some embodiments, the TLR4 agonist is Spirulina complex polysaccharide (Kwanishi et al., Microbiol. Immunol. 57:63-73, 2013). In some embodiments, the TLR4 agonist is chitohexaose or a variant thereof (Panda et al., 8:e1002717, 2012; Barman et al., Cell Death Dis. 7:e2224, 2016). In some embodiments, the TLR4 agonist is E5564 (Eritoran) (Eisai). In some embodiments, the TLR4 agonist is CRX-675 or CRX-527 (GSK).

TLR5 Agonists

In some embodiments, the TLR agonist binds and activates TLR5. In some embodiments, the TLR5 agonist is flagellin or a variant thereof (e.g., entolimod (CBLB502)) (Yoon et al., Science 335: 859-864, 2012; Fukuzawa et al., J. Immunol. 187:3831-3839, 2011; Brackett et al., PNAS 113(7):E874-E883, 2015; Leigh et al., PLoS One 9(1): e85587, 2014; Hossain et al., Blood 120:255, 2012). In some embodiments, the TLR5 agonist is flagellin HuHa (Vaxinate) or flagellin HuM2e (Vaxinate).

TLR7/8 Agonists

In some embodiments, the TLR agonist binds and activates TLR7/8 (e.g., TLR7 agonist, TLR8 agonist, or a TLR7 and TLR8 agonist). In some embodiments, the TLR7/8 agonist is ANA975 (isotorabine) (Anadys/Novartis), ANA773 (Anadys/Novartis), In some embodiments, the TLR7/8 agonist is an imidazoquinoline or a variant thereof (e.g., imiquimod (Aldara™; Kaspari et al., British J. Dermatology 147: 757-759, 2002; Smorlesi et al., Gene Therapy 12: 1324-β3, 2005; Prins et al., J. Immunol. 176: 157-164, 2006; Shackleton et al., Cancer Immun. 4:9, 2004; Green et al., Br. J. Dermatol. 156(2):337-345, 2007; Geisse et al., Am. Acad. Dermatol. 50(5):722-733, 2004; Wolf et al., Arch. Dermatol. β9(3): 273-276, 2003), resiquimod (R848; Hemmi et al., Nat. Immunol. 3:196-200, 2002; Jurk et al., Nat. Immunol. 3:49, 2002; Rook et al., Blood 126(12):1452-1461, 2015; Dovedi et al., *Blood* 121: 251-259, 2013). In some embodiments, the TLR agonist is a synthetic imiadzoquinoline mimicking viral single stranded RNA (ssRNA) (852A) or a variant thereof (Dudek et al., *Clin. Cancer Res.* β(23):7119-7125, 2007; Dummer et al., *Clin. Cancer Res.* 14(3):856-864, 2008; Weigel et al., *Am. J. Hematol.* 87(10):953-956, 2012; Geller et al., *Cancer Immunol. Immunother.* 59(12):1877-1884, 2010; Inglefield et al., *J. Interferon Cytokine Res.* 28(4):253-263, 2008). In some embodiments, the TLR agonist is a small molecule. In some embodiments, the small molecule mimics viral ssRNA (e.g., motolimod (VTX-2337)) or a variant thereof (Dietsch et al., *Clin. Cancer Res.* 21(24):5445-5452, 2015; Northfelt et al., *Clin. Cancer Res.* 20(14):3683-3691, 2014; Lu et al., *Clin. Cancer Res.* 18(2): 499-509, 2012). In some embodiments, the small molecule is GS-9620 or a variant thereof (Bam et al., *Antimicrob Agents Chemother.* 61(1):e01369, 2016; Rebbapragada et al., *PLoS One* 11(1):e0146835, 2016; Gane et al., *J. Hepatol.* 63(2): 320-328, 2015; Fosdick et al., *J. Med. Chem.* 56(18): 7324-7333, 2013). In some embodiments, the small molecule is SC1 (Wiedemann et al., *Oncoimmunology* 5(7): e1189051, 2016; Hamm et al., *J. Immunol.* 6(4):257-265, 2009). In some embodiments, the small molecule is gardiquimod (Ma et al., *Cell. Mol. Immunol.* 7:381-388, 2010; Hjelm et al., *Hum. Vaccin. Immunother.* 10(2): 410-416, 2014; Buitendijk et al., *AIDS Res. Hum. Retroviruses* 29(6):907-918, 2013), CL075 (Philbin et al., *J. Allergy Clin. Immunol.* β0:195-204, 2012; Dowling et al., *PLoS One* 8(3): e58164, 2013), CL097 (Gorden et al., *J. Immunol.* 174: 1259-1268, 2005; Gorski et al., *Int. Immunol.* 18:1115, 2006; Levy et al., *Blood* 108:1284-1289, 2006; Wille-Reece et al., *J. Exp. Med.* 203: 1249-1258, 2006), loxoribine (Pope et al., *Cell Immunol.* 162:333, 1995; Heil et al., *Eur. J. Immunol.* 33:2987-2997, 2003; Lee et al., *PNAS* 100:6646-6651, 2003), or VTX-294 (Dowling et al., *PLoS One* 8(3): e58164, 2013). In some embodiments, the TLR7/8 agonist is IMO-9200. In some embodiments, the TLR7 agonist is IPH-32XX (Innate Pharma).

TLR9 Agonists

In some embodiments, the TLR agonist binds and activates TLR9. In some embodiments, the TLR9 agonist is a synthetic oligonucleotide. In some embodiments, the synthetic oligonucleotide contains unmethylated CpG dinucleotide (CpG-ODN) (Krieg, *J. Clin. Invest.* 117:1184-1194, 2007; Carpentier et al., *Neuro-oncol.* 8(1):60-66, 2006; Link et al., *J. Immunother.* 29(5): 558-568, 2006; Pashenkov et al., *J. Clin. Oncol.* 24(36): 5716-5724, 2006; Meng et al., *BMC Biotechnol.* 11:88, 2011). In some embodiments, the TLR9 agonist is PF-3512676 or a variant thereof (Hofmann et al., *J. Immunother.* 31(5):520-527, 2008; Molenkamp et al., *Clin. Caner. Res.* 14(14):4532-4542, 2008). In some embodiments, the TLR9 agonist is IMO-2055 (EMD1201801) or a variant thereof (Machiels et al., *Investig. New Drugs* 31:1207-1216, 2013). In some embodiments, the TLR9 agonist is DIMS0150 (Atreya et al., *J. Crohns Colitis* 10(11):1294-β02, 2016). In some embodiments, the TLR9 agonist is CpG7909 (Vaximmune) (Coley, GSK, Novartis, DARPA). In some embodiments, the TLR9 agonist is IMO-9200. In some embodiments, the TLR9 agonist is AVE0675 (Coley, Sanofi Aventis). In some embodiments, the TLR9 agonist is Amplivax (Idera).

Microbial Products as TLR Agonists

In some embodiments, the TLR agonist is a bacterial or viral component. In some embodiments, the TLR agonist is derived from the cell wall *Mycobacterium bovis* (BCG). In some embodiments, the *Mycobacterium bovis* cell wall component is a TLR2 and/or TLR4 agonist (e.g., SMP105 (Murata et al., *Cancer Sci.* 99:1435-1440, 2008; Miyauchi et al., *Drug Discov. Ther.* 6: 218-225, 2013; Tsuji et al., *Infect Immun.* 68: 6883-6890, 2000; Smith et al., *Cancer Immunol. Immunother.* 63(8):787-796, 2014). Additional examples of TLR agonists are known in the art.

TLR Antagonists

By the term "TLR antagonist" means an agent that decreases the binding of a TLR agonist to TLR4 or TLR9 expressed in a mammalian cell (e.g., a human cell). For example, a TLR antagonist can be a TLR4 antagonist. In other examples, a TLR antagonist is a TLR9 antagonist. Non-limiting examples of TLR antagonists are described in Fukata et al., *Mucosal Immunity* 6:451-463, 2013.

A non-limiting example of a TLR4 antagonist is 1A6 (Ungaro et al., *Am. J. Physiol. Gastrointest. Liver Physiol.* 296:G1167-G1179, 2009) or CRX-526 (Fort et al., *J. Immunol.* 174:6416-6423, 2005). Additional examples of TLR4 antagonists include eritoran tetrasodium (E5564) (Sun et al., *Investigative Ophthalmol. Visual Sci.* 50(3):1247-1254, 2009), small heat shock protein B8 (HSP22) (Roelofs et al., *J. Immunol.* 176(11):7021-7027, 2006), CRX-527 (Bazin et al., *Bioorganic Med Chem. Letters* 18(2):5350-5354, 2008), E5564 (Kitazawa et al., *J. Gastroentrol. Hepatol.* 25(5): 1009-1012, 2010), IAXO-102 (Huggins et al., *Atherosclerosis* 242(2):563-570, 2015), AG-411 (Kondo et al., *Trends Immunol.* 33(9):449-458, 2012), CRX-52624 (Alderson et al., *J. Endotoxin Res.* 12(5):313-319, 2006), E5531 (Becker et al., *Toxicol. Appl. Pharmacol.* 207(2):269-275, 2005).

A non-limiting example of a TLR9 antagonist is adenoviral oligodeoxynucleotides (AV-ODN) (Obermeier et al., *Gastroenterology* 129:913-927, 2005). Additional examples of TLR9 antagonists include ODN 2088, ODN 4084-F, ODN INH-1, ODN INH-18, ODN TTAGGG (A151), and G-ODN (each commercially available from InvivoGen). In some embodiments, the TLR9 antagonist is CpG-ODN c41 (Li et al., *Vaccine* 29:2193-2198, 2011). In some embodiments, the TLR9 antagonist is COV08-0064 (Shaker et al., *Biochemical Pharmacol.* 112:90-101, 2016; Hoque et al., *J. Immunol.* 190(8):4297-4304, 2013); ODN 1585, ODN 1826, ODN 2395, and ODN 2088 (Boivin et al., *Antiviral Res.* 96(3):414-421, 2012); IMO-8400 (Zhu et al., *J. Immunol.* 188(1):119, 2012); IRS869 (Mandl et al., *Nature Med.* 14(10:1077-1087, 2008); IMO-3100 (Hennessy et al., *Nature Rev. Drug Discov.* 9(4):293-307, 2010); TTAGGG (Carvalho et al., *PLoS One* 6(11):e28256, 2011); and CpG ODN 2088 (David et al., *J. Neurotrauma* 31(21):1800-1806, 2014).

6. SMAD7 Inhibitors

The term "SMAD7 inhibitor" refers to an agent which decreases SMAD7 expression, decreases SMAD7's ability to decrease formation of Smad2/Smad4 complexes, and/or decreases the ability of SMAD7 to bind to TGF-β type I receptor. In some embodiments, the SMAD7 inhibitor decreases SMAD7 expression in a mammalian cell. In some embodiments, the SMAD7 inhibitor decreases SMAD7's ability to decrease formation of Smad2/Smad4 complexes in a mammalian cell. In some embodiments, the SMAD7 inhibitor decreases the ability of SMAD7 to bind to a TGF-β type I receptor in a mammalian cell. In some embodiments, the SMAD7 inhibitor decreases SMAD7 expression in a mammalian cell.

In some embodiments, a SMAD7 inhibitory agent is an inhibitory nucleic acid. In some embodiments, the inhibitory nucleic acid is an antisense nucleic acid, a small interfering RNA, or a microRNA. Examples of aspects of these different inhibitory nucleic acids are described below.

Inhibitory nucleic acids that can decrease the expression of SMAD7 expression in a mammalian cell include antisense nucleic acid molecules, i.e., nucleic acid molecules whose nucleotide sequence is complementary to all or part of SMAD7 mRNA. An antisense nucleic acid molecule can be complementary to all or part of a non-coding region of the coding strand of a nucleotide sequence encoding a SMAD7 protein. Non-coding regions (5' and 3' untranslated regions) are the 5' and 3' sequences that flank the coding region in a gene and are not translated into amino acids. Non-limiting examples of SMAD7 inhibitors that are antisense nucleic acids include mongersen (GED0301) (Monteleon et al., *N Engl. J. Med.* 372:1104-1113, 2015) and Smad7-as (Kleiter et al., *J. Neuroimmunol.* 187(1-2):61-73, 2007; and Boirivant et al., *Gastroenterology* β1(6):1786-1798, 2006).

Another example of an inhibitory nucleic acid is a ribozyme that has specificity for a nucleic acid encoding a SMAD7 protein (e.g., specificity for a SMAD7 mRNA).

An inhibitory nucleic acid can also be a nucleic acid molecule that forms triple helical structures. For example, expression of a SMAD7 polypeptide can be inhibited by targeting nucleotide sequences complementary to the regulatory region of the gene encoding the SMAD7 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can be a siRNA that decreases the level of a SMAD7 mRNA. Non-limiting examples of short interfering RNA (siRNA) that target nucleic acid that encodes SMAD7 are described in, e.g., Su et al., *Mol. Vis.* 18:1881-1884, 2012.

Inhibitory nucleic acids targeting SMAD7 also include microRNAs (e.g., miR-497 (Hu et al., *Am. J. Transl. Res.* 8(7): 3023-3031, 2016; Liu et al., *DNA Cell Biol.* 35(9): 521-529, 2016), miR-21 (Lin et al., *Cell Physiol. Biochem.* 38(6): 2152-2162, 2016; He et al., *Heart Vessels* 31(10): 1696-1708, 2016).

7. Inhibitory Agents of Janus Kinase (JAK) Activity and/or Expression

The term "JAK inhibitor" refers to an agent which decreases the expression of Janus kinase 1 (JAK1), JAK2, JAK3, or non-receptor protein tyrosine kinase 2 (TYK-2) and/or the kinase activity of at least one of JAK1, JAK2, JAK3, and TYK-2. In some embodiments, the JAK inhibitor decreases the expression of JAK1. In some embodiments, the JAK inhibitor decreases the expression of JAK2. In some embodiments, the JAK inhibitor decreases the expression of JAK3. In some embodiments, the JAK inhibitor decreases the expression of TYK-2.

In some embodiments, the JAK inhibitor decreases the kinase activity of JAK1. In some embodiments, the JAK inhibitor decreases the kinase activity of JAK2. In some embodiments, the JAK inhibitor decreases the kinase activity of JAK3. In some embodiments, the JAK inhibitor decreases the kinase activity of TYK-2. In some embodiments, the JAK inhibitor is a decreases the kinase activity of JAK1, JAK2, JAK3, and TYK2. In some embodiments, the JAK inhibitor decreases the kinase activity of two or more (e.g., 3 or 4) of: JAK1, JAK2, JAK3 and TYK2. In some embodiments, the JAK inhibitor decreases the kinase activity of a single JAK isoform (e.g., JAK1, JAK2, JAK3, or TYK2).

In some embodiments, the JAK inhibitor decreases the kinase activity of JAK1 and JAK2. In some embodiments, the JAK inhibitor decreases the kinase activity of JAK1 and JAK3. In some embodiments, the JAK inhibitor decreases the kinase activity of JAK2 and JAK3. In some embodiments, the JAK inhibitor decreases the kinase activity of JAK1, JAK2 and JAK3.

In some embodiments, a JAK inhibitory agent is an inhibitory nucleic acid or a small molecule. In some embodiments, the inhibitory nucleic acid is an antisense nucleic acid, a ribozyme, a small interfering RNA, a small hairpin RNA, or a microRNA. Examples of aspects of these different inhibitory nucleic acids are described below.

Inhibitory nucleic acids that can decrease the expression of JAK1, JAK2, JAK3, or TYK2 mRNA expression in a mammalian cell include antisense nucleic acid molecules, i.e., nucleic acid molecules whose nucleotide sequence is complementary to all or part of a JAK1, JAK2, JAK3, or TYK2 mRNA.

Inhibitory Nucleic Acids

An antisense nucleic acid molecule can be complementary to all or part of a non-coding region of the coding strand of a nucleotide sequence encoding a JAK1, JAK2, JAK3, or TYK2 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding a JAK1, JAK2, JAK3, or TYK2 protein (e.g., specificity for a JAK1, JAK2, JAK3, or TYK2 mRNA).

An inhibitory nucleic acid can also be a nucleic acid molecule that forms triple helical structures. For example, expression of a JAK1, JAK2, JAK3, or JAK4 polypeptide can be inhibited by targeting nucleotide sequences complementary to the regulatory region of the gene encoding the JAK1, JAK2, JAK3, or TYK2 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can also be a siRNA that decreases the level of a JAK1, JAK2, JAK3, or TYK2 mRNA. Non-limiting examples of JAK inhibitors that are short interfering RNAs (siRNAs) are described in Cook et al., *Blood* 123:2826-2837, 2014. Non-limiting examples of JAK inhibitors that are short hairpin RNAs (shRNAs) are described in Koppikar et al., *Nature* 489(7414):155-159, 2012).

Small Molecules

In some embodiments, the JAK inhibitor is a small molecule. In some embodiments, the JAK inhibitory agent is a pan-JAK inhibitor (e.g., 3-O-methylthespesilactam (Li et al., *Biochem. Pharmacol.* 86(10):1411-8, 2013)).

In some embodiments, the JAK inhibitor is a JAK1 and JAK2 inhibitor. In some embodiments, the JAK1 and JAK2 inhibitor is ruxolitinib (Jakafi®, Jakavi®, INCB018424) (Harrison et al., *N. Engl. J Med.* 366:787-798, 2012; Pieri et al., *Am. J Hematol.* 92(2):187-195, 2017; Mackay-Wiggan et al., *JCI Insight* 1(15):e89790, 2016; Rudolph et al., *Leukemia* 30(10):2119-2123, 2016; Furqan et al., *Biomark Res.* 1(1):5, 2013), baricitinib (INCB028050, LY3009104) (Gras, *Drugs Today (Barc)* 52(10):543-550, 2016; Smolen et al., *Ann. Rheum. Dis.* 76(4):694-700, 2016; Kubo et al., *Expert. Rev. Clin. Immunol.* 12(9):911-919, 2016; Fridman et al., *J Immunol.* 84(9):5298-5307, 2010), AZD1480 (Guschin et al., *EMBO* 14:1421-1429, 1995; Ioannidis et al., *J Med. Chem.* 54: 262-276, 2011; Moisan et al., *Nat. Cell Biol.* 17(1):57-67, 2015; Qin et al., *J. Neurosci.* 36(18):5144059, 2016; Jiang et al., *Biochem. Biophys. Res. Commun.* 458(4): 908-912, 2015; Verstovsek et al., *Leuk. Res.* 39(2):157-163, 2015; Plimack et al., *Oncologist* 18(7): 819-820, 2013; Yan et al., *Oncotarget* 4(3):433-445, 2013), filgotinib (GLPG0634, G146034) (Vermeire et al., *Lancet* 389 (10066):266-275, 2017; Menet et al., *J. Med. Chem.* 57(22): 9323-9342, 2014; Van Rompaey et al., *J. Immunol.* 191(7): 3568-3577, 2013; Namour et al., *Clin. Pharmacokinet.* 54(8):859-874, 2015), momelotinib (GS-0387, CYT387) (Pardanani et al., *Leukemia* 23: 1441-1445, 2009; Gupta et al., *Haematologica* 102(1):94-102, 2017; Hu et al., *Mol. Pharm.* 13(2):689-697, 2016; Abubaker et al., *BMC Cancer* 14: 317, 2014; Durmus et al., *Pharmacol. Res.* 76:9-16, 2013; Pardanani et al., *Leukemia* 27(6): 1322-1327, 2013; Monaghan et al., *Leukemia* 25(12):1891-1899, 2011; Tyner et al., *Blood* 115(25):5232-5240, 2010).

In some embodiments, the JAK inhibitory agent is a JAK1 inhibitor (e.g., GSK2586184 (Kahl et al., *Lupus* 25(13): 1420-1430, 2016; Ludbrook et al., *Br. J. Dermatol.* 174(5): 985-995, 2016; van Vollenhoven et al., *Lupus* 24(6): 648-649, 2015), oclacitinib (PF03394197, Apoque®) (Gonzales et al., *J. Vet. Pharmacol. Ther.* 37(4):317-324, 2014; Collard et al., *J. Vet. Pharmacol. Ther.* 37(3):279-285, 2014; Cosgrove et al., *Vet. Dermatol.* 24(6):587-597, 2013), upadacitinib (ABT494) (Kremer et al., *Arthritis Rheumatol.* 68(12): 2867-2877, 2016; Mohamed et al., *Clin. Pharmaco.* 55(12): 1547-1558, 2016), GLG0778 (O'Shea et al., *Ann. Rev. Med.* 66(1):311-28, 2015; Schwartz et al., *Nat. Rev. Rheum.* 12: 25-36, 2016), INCB039110 (Mascarenhas et al., *Haematologica* 102(2):327-335, 2017; Bissonnette et al., *J. Dermatolog. Treat.* 27(4):332-338, 2016; Rosenthal et al., *Exp. Opin. Pharmacother.* 15(9):1265-1276, 2014), PF04965842 (Gadina et al., *Curr. Opin. Rheumatol.* 26(2):237-243, 2014; Degryset et al., *J. Hematol. Oncol.* 8:91, 2015); SAR-20347 (Works et al., *J. Immunol.* 193(7):3278-3287, 2014)).

In some embodiments, the JAK inhibitory agent is a JAK2 inhibitor (e.g., CEP-33779 (Dugan et al., *J. Med. Chem.* 55(11):5243-5254, 2012; Seavey et al., *Mol. Cancer Ther.* 11(4):984-993, 2012; Stump et al., *Arthritis Res. Ther.* 13(2):R68, 2011), fedratinib (TG101348, SAR302503) (Pardanani et al., *J. Clin. Oncol.* 29:789-796, 2011; Jamieson et al., *J. Transl. Med.* 13:294, 2015; Zhang et al., *Oncotarget* 6(16):14329-14343, 2015; Wernig et al., *Blood* 105:4508-4515, 2008); lestaurtinib (CEP-701) (Hexnet et al., *Blood* 111:5663-5671, 2008; Santos et al., *Blood* 115: 1131-1136, 2010; Smith et al., *Blood* 103: 3669-3676, 2004; Hexner et al., *Leuk. Lymphoma.* 56(9):2543, 2015; Geyer et al., *Hematology* 17(Suppl1):S129-132, 2012; Diaz et al., *PLoS One* 6(4):e18856, 2011; Minturn et al., *Cancer Chemother. Pharmacol.* 68(4):1057-1065, 2011), AC-430 (O'Shea et al., *Immunity* 36(4):542-550, 2012; Patterson et al., *Clin. Exp. Immunol.* 176:1-10, 2014), pacritinib (SB1518) (Deeg et al., *J. Clin. Oncol.* 29: Abstract 6515, 2011; Verstovsek et al., *J. Hematol. Oncol.* 9(1):137, 2016; Chow et al., *Onco Targets. Ther.* 9:2655-2665, 2016; Komrokji et al., *Blood* 125(17): 2649-2655, 2015; Jayaraman et al., *Drug Metab. Lett.* 9(1): 28-47, 2015), BMS-911543 (Mace et al., *Oncotarget* 6(42): 44509-44522, 2015; Wan et al., *ACS Med. Chem. Lett.* 6(8):850-855, 2015; Purandare et al., *Leukemia* 26(2):280-288, 2012), XL019 (Verstovsek et al., *Leuk. Res.* 38(3):316-322, 2014; Forsyth et al., *Bioorg. Med. Chem. Lett.* 22(24): 7653-7658, 2012), INCB039110 (Mascarenhas et al., *Haematologica* 102(2):327-335, 2017; Bissonnette et al., *J. Dermatol. Treat.* 27(4):332-338, 2016), Gandotinib® (LY-2784544) (Ma et al., *Blood Cancer J.* 3:e109, 2013; Verstovsek et al., *Blood* 122: 665, 2013; Mitchell et al., *Org. Process Res. Dev.* 16(1):70-81. 2012); R723 (Shide et al., *Blood* 117(25): 6866-6875, 2011)); Z3 (Sayyah et al., *Mol. Cancer. Ther.* 7(8):2308-2318, 2008)) or a variant thereof.

In some embodiments, the JAK inhibitory agent is a JAK3 inhibitor (e.g., decernotinib (VX-509) (Elwood et al., *J. Pharmacol. Exp. Ther.* 2017; Genovese et al., *Ann Rheum Dis.* 75(11):1979-1983, 2016; Gadina et al., *Arthritis Rheumatol.* 68(1):31-34, 2016; Farmer et al., *J. Med. Chem.* 58(18):7195-7216, 2015; Fleischmann et al., *Arthritis Rheumatol.* 67(2):334-343, 2015; Mahajan et al., *J. Pharmacol.* 353(2):405-414, 2015), R348 or a variant thereof (Velotta et al., *Transplantation* 87(5):653-659, 2009; Deuse et al., *Transplantation* 85(6):885-892, 2008)). In some embodiments, the small molecule is R256 or a variant thereof (Ashino et al., *J. Allergy Clin. Immunol.* 133(4):1162-1174, 2014). In some embodiments, the small molecule is R333 or a variant thereof. In some embodiments, the small molecule is INCB047986 or a variant thereof (Norman, *Exp. Opin. Investig. Drugs* 23(8):1067-1077, 2014). In some embodiments, the small molecule is INCB16562 or a variant thereof (Koppikar et al., *Blood* 115(4):2919-2927, 2010; Li et al., *Neoplasia* 12(1):28-38, 2010). In some embodiments, the small molecule is NVP-BSK805 or a variant thereof (Ringel et al., *Acta Haematol.* 132(1):75-86, 2014; Baffert et al., *Mol. Cancer. Ther.* 9(7):1945-1955, 2010). In some embodiments, the small molecule is peficitinib (ASP015K, JNJ-54781532) or a variant thereof (Genovese et al., *Arthritis Rheumatol.*, 2017; Ito et al., *J. Pharmacol. Sci.* β3(1):25-33, 2017; Cao et al. (2016) *Clin. Pharmacol. Drug Dev.* 5(6): 435-449, 2016; Takeuchi et al., *Ann. Rheum. Dis.* 75(6): 1057-1064, 2016). In some embodiments, the small molecule is tofacitinib (Xeljanz®, Jakvinus®, CP-690, 500) or a variant thereof (Ghoreschi et al., *J. Immunol.* 186(7):4234-4243, 2011; Yoshida et al., *Biochem. Biophys. Res. Commun* 418(2):234-240, 2012; Calama et al., *Pulm. Pharmacol. Ther.* S1094-5539(16):30060-30068, 2017; Cutolo et al., *J. Inflamm. Res.* 6:129-β7, 2013). In some embodiments, the small molecule is cucurbitacin I (JSI-124) or a variant thereof (Oi et al., *Int. J. Oncol.* 49(6):2275-2284, 2016; Qi et al., *Am. J. Chin. Med.* 43(2):337-347, 2015; Seo et al., *Food Chem. Toxicol.* 64:217-224, 2014). In some embodiments, the small molecule is CHZ868 or a variant thereof (Wu et al., *Cancer Cell* 28(1):29-41, 2015; Meyer et al., *Cancer Cell* 28(1):15-28, 2015).

In some embodiments, the small molecule is a TYK2 inhibitor (e.g., Masse et al., *J. Immunol.* 194(1):67, 2015; Menet, *Pharm. Pat. Anal.* 3(4):449-466, 2014; Liang et al., *Euro. J. Med. Chem.* 67: 175-187, 2013; Jang et al., *Bioorg. Med. Chem. Lett.* 25(18):3947-3952, 2015); U.S. Pat. Nos. 9,296,725 and 9,309,240; US 2013/0231340; and US 2016/0251376). In some embodiments, the TYK2 inhibitor is Ndi-031301 (Akahane et al., *Blood* 128:1596, 2016); BMS-986165 (Gillooly et al., 2016 *ACR/ARHP Annual Meeting*, Abstract 11L, 2016); SAR-20347 (Works et al., *J. Immunol.* 193(7):3278-3287, 2014); tyrphostin A1 (Ishizaki et al., *Int. Immunol.* 26(5):257-267, 2014); a triazolopyridine (US 2013/0143915); or a variant thereof.

Additional examples of JAK inhibitors that are small molecules are described in, e.g., Furomoto et al., *BioDrugs* 27(5):431-438, 2013; O'Shea et al., *Ann. Rheum. Dis.* 72(2): ii111-ii-115, 2013; Sonbol et al., *Ther. Adv. Hematol.* 4(1): 15-35, 2013; and Tanaka et al. (2015) *J. Biochem.* 158(3): 173-179, 2015.

In some embodiments, the JAK inhibitor is a pan-JAK inhibitor. As used herein, the term "pan-JAK inhibitor" is an agent that has an $IC_{50}$ of about 500 nM to 4 μM (e.g., about 500 nM to about 2 μM) for each of human JAK1, human JAK2, and human JAK3 isoforms, when the $IC_{50}$ is determined for each of wildtype human JAK1, wildtype human JAK2, and wildtype human JAK3 using similar assay conditions (e.g., the same assay conditions). In some embodiments, a pan-JAK inhibitor can be an agent that has an $IC_{50}$ for wildtype human JAK1, wildtype human JAK2, and wildtype human JAK3 that are within ±10% of each other, when each of the $IC_{50}$ values is assays under similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the pan-JAK inhibitor is tofacitinib (Xeljanz®, Jakvinus®, tasocitinib, CP-690550; Yokoyama et al., *J. Clin. Immunol.* 33(3):586-594, 2013; and Thoma et al., *J. Med. Chem.* 54(1):284-288, 2011); cerdulatinib (PRT2070; Coffey et al. (2014) *J. Pharmacol. Exp. Ther.* 351(3):538-548, 2014; and Ma et al., *Oncotarget* 6(41):43881-43896, 2015); Pyridone 6 (P6; Nakagawa et al., *J. Immunol.* 187(9): 4611-4620, 2011; and Pedranzini et al., *Cancer Res.* 66(19):9714-9721, 2006); PF-06263276 (Jones et al. "Design and Synthesis of a Pan-Janus Kinase Inhibitor Clinical Candidate (PF-06263276) Suitable for Inhaled and Topical Delivery for the Treatment of Inflammatory Diseases of the Lungs and Skin" J. Med. Chem., 2017, 60 (2), pp 767-786); JAK inhibitor 1 (CAS 457081-03-07; JAKi; Wang et al., *Antimicrob. Agents Chemother.* 60(5):2834-48, 2016; Bordonaro et al., *PLoS One* 9:e115068, 2014; and Osorio et al., *PLoS Pathogens* 10(6):e1004165, 2014); or baricitinib (Olumiant; LY3009104; INCB-28050; and Hsu and Armstrong, *J. Immunol. Res.* Article ID 283617, 2014).

In some embodiments, the JAK inhibitor is a selective JAK1/JAK3 inhibitor. As used herein, the term "selective JAK1/JAK3 inhibitor" means an agent that has an $IC_{50}$ for wildtype human JAK1 and wildtype human JAK3, that are each at least 5-fold (e.g., at least 10-fold or at least 20-fold) lower than the $IC_{50}$ for wildtype human JAK2, when the $IC_{50}$ is determined for each of wildtype human JAK1, wildtype human JAK2, and wildtype human JAK3 using similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the JAK inhibitor is a selective JAK1 inhibitor. As used herein, the term "selective JAK1 inhibitor" means an agent that has an $IC_{50}$ for wildtype human JAK1 that is at least 10-fold (e.g., at least 20-fold) lower than each of the $IC_{50}$ for wildtype human JAK2 and the $IC_{50}$ for wildtype human JAK3 when measured using similar assay conditions (e.g., the same assay, e.g., the human wildtype JAK1, wildtype human JAK2, and wildtype human JAK3 assay described in Kim et al., *J. Med. Chem.* 58(18):7596-5602, 2015). In some embodiments, the JAK1 inhibitor is (31S,4R)-3-ethyl-4-(3H-imidazo[1,2-a]pyrrolo[2,3-e]pyrazin-8-yl)-N-(2,2,2-trifluoroethyl)pyrrolidine-1-carboxamide as disclosed in international patent application PCT/US2014/062145, incorporated by reference herein in its entirety.

In some embodiments, the JAK inhibitor is a selective JAK3 inhibitor. As used herein, the term "selective JAK3 inhibitor" means an agent that has an $IC_{50}$ for wildtype human JAK3 that is at least 10-fold (e.g., at least 20-fold) lower than each of the $IC_{50}$ for wildtype human JAK2 and the $IC_{50}$ for wildtype human JAK1 when measured using similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the JAK inhibitor is a JAK1 and JAK3 inhibitor (e.g., a selective JAK1/JAK3 inhibitor). In some embodiments, the selective JAK1/JAK3 inhibitor is ZM 39923 (Brown et al., *Bioorg. Med. Chem. Lett.* 10(6): 575-579, 2000; and Lai et al., *Chem. Biol.* 15(9):969-978, 2008); or peficitinib (ASP015K; JNJ-54781532; Ito et al., *J. Pharmacol. Sci.* 133(1):25-33, 2017; Cao et al., *Clin. Pharmacol. Drug Dev.* 5(6):435-449, 2016; Takeuchi et al., *Ann. Rheum. Dis.* 75(6):1057-1064, 2016); and Papp et al., *Br. J. Dermatol.* 173(3):767-776, 2015).

In some embodiments, the kinase inhibitor is TOP-1288 from TopiVert Pharma Ltd., which is described in "The Pharmacological Profile of TOP1288, a Narrow Spectrum Kinase Inhibitor (NSKI) in Clinical Development as an Anti-Inflammatory Treatment for Ulcerative Colitis" Foster, Martyn et al. Gastroenterology, Volume 152, Issue 5, 5766.

8. Immunosuppressants

An "immunosuppressant" as disclosed is a low molecular weight immunosuppressants, with low molecular weight defined as <1500 Da, such as <1000 Da. The term "immunosuppressant" refers to a corticosteroid, a direct calcineurin inhibitor, a cytostatic, or a direct mTOR inhibitor that can suppress, restrict, or reduce the response of the immune system of a subject (e.g., one or both of the innate and adaptive immune system). In some examples, an immunosuppressant drug can decrease the level of activation and/or migration of a leukocyte (e.g., a T lymphocyte or a B lymphocyte, a macrophage, a mononcyte, a natural killer cell, a neutrophil, an eosinophil, or a basophil).

In some embodiments, the immunosuppressant is methotrexate, sulfasalazine, minocycline, or leflunomide) (Zink et al., *Annals of the Rheumatic Diseases* 64: 1274-1279, 2005).

Non-limiting examples of FDA-approved immunosuppressant drugs include: CellCept®, Rapamune®, Velcade®, Protopic®, Afinitor®, Arava®, Zenapax®, Sandimmune®, Advagraf®, Protopic®, Prograf®, Astagraf XL®, Elidel®, Myfortic®, Imuran®, and Azasan®.

Non-limiting examples of immunosuppressants are described in: Bakr et al., *Exp. Clin. Transplant* 15(Suppl. 1):16-23, 2017; Palmer et al., *Am. J. Kidney Dis.* S0272-6386(17):30036-7, 2017; Moran et al., *Semin Hematol* 49(3):270-276, 2012; Kamel et al., *World J. Transplant* 6(4):697-702, 2016; Shrestha et al., *Exp. Clin. Transplant.* 15(1):1-9, 2017; Liu et al., *PLoS One* 12(1):e0170246, 2017; Chon and Josephson, *Expert Rev. Clin. Immunol.* 7(3): 273-281, 2011; Sollinger et al., *Transplantation* 60: 225-232, 1995; Salvardori et al., *Am. J. Transplant* 4: 231-236, 2004; Webster et al., *Cochrane Database Syst. Rev.* 19(2): CD004290, 2006; Nashan et al., *Transplantation* 78: 1332-β40, 2004; and Hardinger et al., *Am. J. Transplant* 2: 867-871, 2002.

Exemplary corticosteroids, cytostatics, calcineurin inhibitors, and mTOR inhibitors, are described below.

Corticosteroids

In some embodiments, the immunosuppressant drug is a corticosteroid. In some embodiments, the immunosuppressant drug can be a glucocorticosteroid (Coutinho et al., *Mol. Cell. Endocrinol.* 335(1): 2-13, 2011; van Staa et al., *QJM* 93: 105-111, 2000; Wust et al., *J. Immunol.* 180: 8434-8443, 2008) or glucocorticoid. Non-limiting examples of corticosteroids include: 11-dehydrocorticosterone (also called 11-oxocorticosterone and 17-deoxycortisone); 11-deoxycorticosterone (also called deoxycortone, desoxycortone, and 21-hydroxyprogesterone); 11-deoxycortisol (also called cortodoxone and cortexolone); 11-ketoprogesterone (also called 11-oxoprogesterone and ketogestin); 11β-hydroxypregnenolone; 11β-hydroxyprogesterone (also known as 21-deoxycorticosterone); 11β,17α,21-trihydroxypregnenolone; 17α,21-dihydroxypregnenolone; 17α-hydroxypregnenolone; 17α-hydroxyprogesterone; 18-hydroxy-11-deoxycorticosterone; 18-hydroxycorticosterone; 18-hydroxyprogesterone; 21-deoxycortisol; 21-doxycortisone; 21-hydroxypregnenolone (also known as prebediolone); aldosterone; corticosterone (also known as 17-deoxycortisol); cortisol (also known as hydrocortisone); cortisone; pregnenolone; progesterone; flugestone (also known as flurogestone); fluorometholone; medrysone (also known as hydroxymethylprogesterone); prebediolone acetate (also known as 21-acetoxypregnenolone); chlormadinone acetate; cyproterone acetate; medrogestone; medroxyprogesterone acetate; megastrol acetate; segesterone acetate; chloropredisone; cloprednol; difluprednate; fludrocortisone; fluocinolone; fluperolone; fluprednisolone; loteprednol; methylprednisolone; prednicarbate; prednisolone; prednisone; tixocortol; triamcinolone; methasone; alclometasone; beclomethasone; betamethasone; clobetasol; clobetasone; clocortolone; desoximetasone; dexamethasone; diflorasone; difluocortolone; fluclorolone; flumetasone; fluocortin; fluocortolone; fluprednidene; fluticasone; fluticasone furoate; halometasone; mepredisone; mometasone; mometasone furoate; paramethasone; prednylidene; rimexolone; ulobetasol (also known as halobetasol); amcinonide; budesonide; ciclesonide; deflazacort; desonide; formocortal (also known as fluoroformylone); fluclorolone acetonide (also known as flucloronide); fludroxycortide (also known as flurandrenolone and flurandrenolide); flunisolide; fluocinolone acetonide; fluocinonide; halcinonide; triamcinolone acetonide; cortivazol; and RU-28362. In some embodiments, the corticosteroid can be budesonide (e.g., Entocort®), dexamethasone, hydrocortisone (e.g., Cortef®, Cortenema®, and Proctofoam®), methylprednisolone, prednisolone (e.g., Orapred®), and prednisone. Additional examples of corticosteroids are known in the art.

Cytostatics

In some embodiments, the immunosuppressant drug is a cytostatic (e.g., an alkylating agent or an antimetabolite) (Mor et al., BioDrugs 8(6): 469-88, 1997). In some embodiments, the cytostatic is an antimetabolite drug (e.g., a folic acid analogue, (e.g., methotrexate), a purine analogue (e.g., azathioprine or mercaptopurine), a pyrimidine analogue (e.g., fluorouracil), a protein synthesis inhibitors, and cytotoxic antibiotics (e.g., dactinomycin, an anthracycline, mitomycin C, bleomycin, and mithramycin).

In some embodiments, the cytostatic can be an inhibitor of de novo purine synthesis (e.g., azathioprine (AZA, Imuran®, or Azasan®), mycophenolate mofetil (MMF, CellCept®), mycophenolate acid (MPA, Myfortic®), mizoribin, or methotrexate). In some embodiments, the cytostatic is an inhibitor of de novo pyrimidine synthesis (e.g., leflunomide, brequinar, or methotrexate).

In some embodiments, the cytostatic is an alkylating agent. In some embodiments, the alkylating agent is cyclophosphamide (Luznik et al., Blood 115(16): 3224-330, 2010). In some embodiments, the cytostatic is chlorambucil (Chen et al., Clin. J. Am. Soc. Nephrol. 8(5):787-796, 2013). In some embodiments, the cytostatic is mycophenolate mofetil (MMF, CellCept®) (Mor et al., BioDrugs 8(6):469-88, 1997). In some embodiments, the cytostatic is mycophenolate sodium (Albano et al., Ann Transplant 21: 250-261, 2016). In some embodiments, the cytostatic is azathioprine (Imuran®) (Maley et al., J. Am. Acad Dermatol 73(3): 439-43, 2015). In some embodiments, the immunosuppressant drug is 6-mercaptopurine (e.g., Purinethol®) (Kombluth et al., Gastroenterologist 2(3): 239-46, 1994). In some embodiments, the cytostatic is an inhibitor of inosine monophosphate dehydrogenase (e.g., VX-148; Jain et al., J. Pharmacol Exper Ther 302(2): 1272-1277, 2002).

In some embodiments, the cytostatic is a vitamin D analog (e.g., MC1288). See, e.g., Binderup et al., Biochem. Pharmacol. 42:1569-1575, 1991; and Johnsson et al., Transplant Int. 7:392-397, 1994).

In some embodiments, the cytostatic is brequinar (Crramer et al., Transplantation 53:303-308, 1992; Xu et al., J. Immunol. 160(2):846-53, 1998). In some embodiments, the cytostatic is mizoribine (Bredinin) (Aikawa et al., Transplant. Proc. 37(7):2947-50, 2005). In some embodiments, the cytostatic is gusperimus (Perenyei et al., Rheumatology (Oxford) 53(10):1732-1741, 2014).

Calcineurin Inhibitors

In some embodiments, the immunosuppressant is a calcineurin inhibitor. See, e.g., Beland et al., Transpl. Int doi: 10.1111/tri 12934, 2017. In some embodiments, the calcineurin inhibitor is voclosporin (Luveniq®) (Busque et al., Am. J. Transplant 11(12):2675-2684, 2011). Voclosporin is a structural analog of cyclosporine A, with an additional single carbon extension that has a double-bond on one side chain. The binding affinities of voclosporin and cyclosporine A for cyclophilin are comparable; however, upon binding, the ethynyl side chain of voclosporin induces structural changes in calcineurin that may result in increased immunosuppressive activity relative to cyclosporine A. In some embodiments, the calcineurin inhibitor is cyclosporin A (e.g., gengraf, Neural®, or Sandimmune®) (Canafax and Ascher, Clin. Pharm. 2(6):515-524, 1983; Goring et al., Curr. Med. Res. Opin. 30(8): 1473-87, 2014), a cyclosporin analogue (see, e.g., Wenger et al., Transplant Proc. 18:213-218, 1986; Jeffery, Clin. Biochem. 24:15-21, 1991; Wenger, Angewandte Chem. 24:77-85, 1985; Lazarova et al., Expert Opin. Ther. Patents 13(9):1327-1332, 2003; Thomson, Lancet 338:195, 1991; U.S. Pat. Nos. 4,885,276, 7,511,013, 8,367,053, 8,481,483, 9,175,042, 9,200,038, and 9,226,927; US 2011/0092669, US 2006/0069016, US 2010/0708671, US 2012/0088734, WO 12/051193, WO 15/31381, WO 12/51194, and WO 12/051193), or a cyclosporin analogue (see, e.g., Rothbard et al., Nature 6(11):1253-1257, 2000; Cho et al., Arch. Pharm. Res. 27:662, 2004; US 2012/0157385; and U.S. Pat. No. 6,316,405). In some embodiments, the calcineurin inhibitor is tacrolimus, also called FK-506 or fujimycin (e.g., Hecoria®, Prograf®, Astagraf XL®, or Protopic®) (Helmschrott et al., Drug Des. Devel. Ther. 9:1217-1224, 2015; Bloom et al., Clin. Transplant 27(6):E685-93, 2013; Riva et al., Fam. Hosp. 41(2):150-168, 2017; McCormack, Drugs 74917, 2014); Cryan et al., Biochem. Biophys. Res. Commun. 180(2): 846-852, 1991; and Graf et al., J. Clin. Rheumatol. 9(5):310-315, 2003). In some embodiments, the calcineurin inhibitor is pimecrolimus (Elidel®) (Malachowski et al., Pediatr. Dermatol. 33(6): e360-e361, 2016; Eichenfiled and Eichenfield, J. Pediatr. 167(5):1171-1172, 2015). In some embodiments, the calcineurin inhibitor is Sanglifehrin A (SFA) (see, e.g., Hartel et al., Scand. J. Immunol. 63(1):26-34, 2006; Zhang et al., J. Immunol. 166(9):5611-5618, 2001; and Woltman et al., J. Immunol. 172(10): 6482-6489, 2004). Additional examples of calcineurin inhibitors are described in U.S. Pat. No. 7,041,283.

mTOR Inhibitors

In some embodiments, an mTOR inhibitor can be rapamycin (mTOR) inhibitor (e.g., sirolimus (Rapamune®), everolimus) (Forster et al., Transplantation 100(11):2461-2470, 2016; Opelz et al., Nephrol. Dial. Transplant. 31(8): β60-β67, 2016; and Baroja-Mazo et al., World J. Transplant. 6(1): 183-92, 2016. Another example of an mTOR inhibitor is everolimus (e.g., Afinitor® or Zortress®). Another example of an mTOR inhibitor is dactolisib (also called BEZ235 or NVP-BEZ235). Another example of an mTOR inhibitor is temsirolimus (also called CCI-779) (e.g., Torisel®).

In some embodiments, the low molecular weight immunosuppressant is selected from (molecular weights are shown in parenthesis):
   a. Cyclosporine (1202 Da);
   b. Tacrolimus (804 Da);
   c. Methotrexate (454 Da);
   d. Sirolimus (914 Da);
   e. Everolimus (958 Da);
   f. Corticosteroids (360-430 Da);
   g. Voclosporin (1214 Da);
   h. Azathioprine (277 Da); and
   i. Purinethol or 6-MP (6-mercaptopurine) (152 Da).

9. Live Biotherapeutics

In some embodiments, a live biotherapeutic (also can be referred to as a live cell therapy) can be detected and analyzed by the methods herein.

In some embodiments, the live biotherapeutic includes populations of live bacteria and/or yeast, optionally in combination with a prebiotic such as a non-digestible carbohydrate, oligosaccharide, or short polysaccharide (e.g., one or more of inulin, oligofructose, galactofructose, a galacto-oligosaccharides, or a xylo-oligosaccharide) and/or an antibiotic or antifungal agent, or both an antibiotic and antifungal agent. The bacteria or the yeast can be recombinant. The populations of live bacteria and/or yeast can be used to selectively alter beneficial species within the GI tract and/or to reduce detrimental species within the GI tract of the subject. See, for example, U.S. Patent Publication No. 20070258953; U.S. Patent Publication No. 20080003207; WO2007076534; WO2007136719; and WO2010099824.

In some embodiments, the live biotherapeutic includes one or more species of bacteria (e.g., two or more, three or more, four or more, five or more, six or more, or seven or more species) that are underrepresented in patients with IBD. The microbiotas of Crohn's disease (CD) and ulcerative colitis (UC) patients have statistically significant differences from those of non-inflammatory bowel disease controls, including a reduction in beneficial commensal bacteria in IBD patients relative to non-inflammatory bowel disease patients. For example, members of the phyla Firmicutes (e.g., *Clostridium* clusters XIVa and IV), Bacteroidetes (e.g., *Bacteroides fragilis* or *Bacteroides vulgatus*), and Actinobacteria (e.g., *Coriobacteriaceae* spp. or *Bifidobacterium adolescentis*) are reduced in CD and UC patients. See, e.g., Frank, et al., *Proc Natl Acad Sci USA*, 2007, 104:13780-13785; Forbes, et al., *Front Microbiol.*, 2016; 7: 1081, and Nagao-Kitamoto and Kamada, *Immune Netw.* 2017 17(1): 1-12. *Clostridium* cluster XIVa includes species belonging to, for example, the *Clostridium, Ruminococcus, Lachnospira, Roseburia, Eubacterium, Coprococcus, Dorea*, and *Butyrivibrio* genera. *Clostridium* cluster IV includes species belonging to, for example, the *Clostridium, Ruminococcus, Eubacterium* and *Anaerofilum* genera. For example, *Faecalibacterium prausnitzii* (also referred to as *Bacteroides praussnitzii*), *Roseburia hominis, Eubacterium rectale, Dialister invisus, Ruminococcus albus, Ruminococcus callidus*, and *Ruminococcus bromii* are less abundant in CD or UC patients. See, e.g., Nagao-Kitamoto and Kamada, 2017, supra.

In some embodiments, the live biotherapeutic includes one or more species of bacteria (e.g., two or more, three or more, four or more, five or more, six or more, or seven or more species) that produce a desired product such as a short chain fatty acid (SCFA) (e.g., butyrate, acetate, or propionate) or induce production (e.g., *Clostridium butyricum* or *F. prausnitzii*) of an anti-inflammatory agent such as interleukin-10 in host cells. See, e.g., Hayashi, et al., *Cell Host Microbe* (2013) β:711-722.

In some embodiments, the live biotherapeutic includes one or more species of bacteria (e.g., two or more, three or more, four or more, five or more, six or more, or seven or more species) that are underrepresented in patients with IBD and one or more probiotics (e.g., two or more, three or more, four or more, five or more, six or more, seven or more, or eight or more probiotics).

In some embodiments, the live biotherapeutic is FIN-524 (Finch Therapeutics, Somerville, Mass.), a cocktail of cultured microbial strains that are linked to positive outcomes among IBD patients.

In some embodiments, the live biotherapeutic includes one or more species of bacteria from a healthy donor (e.g., as collected from a stool sample). See, e.g., Vermeire, *J Crohns Colitis*, 2016, 10(4): 387-394. For example, the live biotherapeutic can be FIN-403 (Finch Therapeutics, Somerville, Mass.), a candidate for *Clostridium difficile* treatment.

In some embodiments, the live biotherapeutic includes one or more agents for inhibiting the growth of a fungus (e.g., a yeast such as a species of *Candida*). In some subjects with Crohn's disease, the bacterial species of *E. coli* and *Serratia marcescens* and the yeast species *Candida tropicalis* are found at higher concentrations versus that of healthy relatives, indicating that the bacteria and fungus may interact in the intestines. In some embodiments, the agent inhibiting the growth of a fungus (i.e., an anti-fungal agent) is amphotericin B, an echinocandin such as Caspofungin, Micafungin, or Anidulafungin, or an extended-spectrum triazole. In some embodiments, the therapeutic includes about 2.5 mg/L of Amphotericin B.

In some embodiments, the live biotherapeutic is a bacteriophage or prophage (i.e., the genetic material of a bacteriophage incorporated into the genome of a bacterium or existing as an extrachromosomal plasmid of the bacterium, and able to produce phages if specifically activated). The bacteriophage can be lytic or lysogenic. In some embodiments, the bacteriophage can infect bacteria commonly found in the GI tract. For example, the bacteriophage can infect one or more, two or more, three or more, four or more, five or more, six or more, seven or more, eight or more, nine or more, or ten or more species of bacteria within the GI tract. See, for example, Wang, et al., *Inflamm Bowel Dis.*, 2015; 21(6): 1419-1427. In some embodiments, the bacteriophage can be lytic bacteriophage and infect one or more detrimental bacterial species in the GI tract to reduce the detrimental species in the GI tract. For example, the bacteriophage can infect two or more, three or more, four or more, five or more, six or more, or seven or more detrimental bacterial species. In some embodiments, bacteriophage can be a member of the families from the order Caudovirales such as Siphoviridae, Myroviridae, Podoviridae, or Microviridae. See, e.g., Babickova and Gardlik, *World J. Gastroentrol.* 2015; 21(40):11321-11330. In some embodiments, the bacteriophage can include one or more of bacteriophage K (such as ATCC strain 19685-B1), bacteriophage 17 (such as ATCC strain 23361-B 1), and Stab8. See, e.g., WO2016172380A1. In some embodiments, the live biotherapeutic includes one or more bacteriophages, and one or more probiotics or prebiotics, optionally in combination with an antibiotic.

In some embodiments, the live biotherapeutic can include bacteriophage or prophage that are genetically modified to produce one or more products that are anti-inflammatory and/or that can enhance intestinal barrier function.

In some embodiments, the live biotherapeutic includes regulatory T cells (Treg cells). Autologous Treg cells can be prepared by isolating peripheral blood mononuclear cells (PBMCs) from the subject's blood and then expanding ova-specific T cells by culturing the PBMCs in the presence of ovalbumin using *Drosophila* derived artificial antigen presenting cells transfected with specific stimulatory molecules. See, e.g., Brun, et al., *Int Immunopharmacol.*, 2009, 9(5):609-13. T cells can be cloned and Ova-Treg clones can be selected based on an ovalbumin-specific IL-10 production. A phase 1/2a study in 20 patients showed that a single injection of antigen-specific (ovalbumin) Treg cells was safe in CD and about 40% of the patients show a clinical response after treatment. See, e.g., Neurath, 2014, supra; and Desreumaux, et al., *Gastroenterology,* 2012, 143:1207-1217.

In some embodiments, the live biotherapeutic can be bacteriophage or bacteria carrying plasmids that encode a targeted antimicrobial. A targeted antimicrobial can include RNA-guided nucleases (RGNs) targeting specific DNA sequences within a target bacteria. For example, a targeted antimicrobial can couple a phage vector with the CRISPR (clustered regularly interspaced short palindromic repeats)/Cas system (e.g., the biological nanobots from Eligo Bioscience (Eligobiotics)). The biological nanobots can be composed of a capsid from a bacteriophage virus (modified to not multiply) that infect targeted bacteria and deliver the CRISPR/Cas9 system into the targeted bacteria, resulting in the targeted bacteria being killed by cleavage of the bacterial genome by Cas9 enzyme within a predetermined pathogenic sequence. See, for example, WO2017/009399A1 and Citorik, et al., *Nat Biotechnol.*, 2014, 32(11): 1141-1145.

In some embodiments, the live biotherapeutic can comprise stem cells. The term "stem cell" is used herein to refer to a cell that is capable of differentiating into a two or more different cell types. As used herein, the term "a stem cell" may refer to one or more stem cells.

In some embodiments, the stem cells can be hematopoietic stem cells (HSC) capable of differentiating into different types of blood cells, including myeloid and lymphoid lineages of blood cells. HSC can be obtained from bone marrow, cord blood, or peripheral blood, and are commonly used for bone marrow transfusions in combination with chemotherapy to restart the immune system. HSC are $CD34^+$ cells. Cell-surface markers can be identified by any suitable conventional technique, including, for example, positive selection using monoclonal antibodies against cell-surface markers.

In some embodiments, the stem cells are capable of differentiating into two or more different cell types other than blood cells. In some embodiments, the stem cells are capable of differentiating into cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. The capacity of the cells to differentiate into at least two cell types can be assayed by methods known in the art.

Non-limiting examples of stem cells include embryonic stem cells or adult stem cells such as mesenchymal stem cells (MSC) (also can be referred to as mesenchymal stromal cells) or other multipotent stem cells; endothelial progenitor cells; stem cells from a particular tissue or organ such as intestinal stem cells, adipose stem cells, or testes stem cells; or induced pluripotent stem cells (iPSC). In some embodiments, stem cells from a particular tissue also can be classified as MSC.

In some embodiments, the stem cells are MSC, which can differentiate into bone, muscle, cartilage, or adipose type cells. MSC can down-regulate inflammation and have a strong immunoregulatory potential. MSC can be obtained from various tissues, including from, for example, bone marrow, placenta, amniotic fluid, Wharton's jelly, amniotic membrane, chorionic villi, umbilical cord, umbilical cord blood, adipose tissue, dental pulp, synovial membrane, or peripheral blood. Depending on the source of MSC and the stemness (i.e., multipotency), the MSC can express a variety of different markers, including, for example, one or more of CD105, CD73, CD90, CD13, CD29, CD44, CD10, Stro-1, CD271, SSEA-4, CD146, CD49f, CD349, GD2, 3G5, SSEA-3, SISD2, Stro-4, MSCA-1, CD56, CD200, PODX1, Sox11, or TM4SF1 (e.g., 2 or more, 3 or more, 4 or more, 5 or more, 6 or more, 7 or more, 8 or more, 9 or more, or 10 or more of such markers), and lack expression of one or more of CD45, CD34, CD14, CD19, and HLA-DR (e.g., lack expression of two or more, three or more, four or more, or five or more such markers). In some embodiments, MSC can express CD105, CD73, and CD90. In some embodiments, MSC can express CD105, CD73, CD90, CD13, CD29, CD44, and CD10. In some embodiments, MSC can express CD105, CD73, and CD90 and one or more stemness markers such as Stro-1, CD271, SSEA-4, CD146, CD49f, CD349, GD2, 3G5, SSEA-3. SISD2, Stro-4, MSCA-1, CD56, CD200, PODX1, Sox11, or TM4SF1. In some embodiments, MSC can express CD105, CD73, CD90, CD13, CD29, CD44, and CD10 and one or more stemness markers such as Stro-1, CD271, SSEA-4, CD146, CD49f, CD349, GD2, 3G5, SSEA-3. SISD2, Stro-4, MSCA-1, CD56, CD200, PODX1, Sox11, or TM4SF1. See, e.g., Lv, et al., *Stem Cells,* 2014, 32:1408-1419.

Intestinal stem cells (ISC) can be positive for one or more biomarkers such as Musashi-1 (Msi-1), Asc12, Bmi-1, Doublecortin and Ca2+/calmodulin-dependent kinase-like 1 (DCAMKL1), and Leucin-rich repeat-containing G-protein-coupled receptor 5 (Lgr5). See, e.g., Mohamed, et al., Cytotechnology, 2015 67(2): 177-189.

In some embodiments, MSCs are commercially available. See, e.g. Prochymal® from Osiris Therapeutics.

In some embodiments, the stem cells can be PF-05285401 cells (Multistem® cells), which are human stem cells obtained from adult bone marrow or other nonembryonic tissue sources. Multistem® cells are commercially available from Athersys Inc.

In some embodiments, the stem cells can be autologous adipose derived stem cells such as Cx401 cells.

In some embodiments, the stem cells can be human iPSCs, which can be generated from adult somatic cells (e.g., fibroblasts, keratinocytes, dental pulp cells, cord blood, or peripheral blood mononuclear cells) or MSC. iPSCs can be generated using retroviral or non-retroviral methods. See, for example, Loh, et al., *Blood* 2009, 113: 5476-5479, Okita, et al., *Nat Methods*. 2011, 8(5):409-12, or Okita, et al., *Stem Cells,* 2013, 31(3): 458-466. In some embodiments, p53 suppression and nontransforming L-Myc can be used to generate human induced pluripotent stem cells (iPSCs) with episomal plasmid vectors encoding OCT3/4, SOX2, KLF4, and LIN28. In some embodiments, adult somatic cells can be transduced with retroviruses encoding four pluripotency factors (SOX2, KLF4, c-MYC, and OCT4). Fully reprogrammed iPSCs have similar properties to embryonic stem cells (ESCs). Patient's cells can be used to derive iPSCs, which can then be induced to undergo differentiation into various types of somatic cells, all with the same genetic information as the patient. See, Azizeh-Mitra, et al., *Stem Cells Int* 2016; 6180487. In other embodiments, allogenic cells are used to derive iPSCs.

In some embodiments, the stem cells can be intestinal stem cells (ISC), which can differentiate into intestinal cell subtypes such as globet cells, Paneth cells, and enterocytes. ISC are located at the crypt base within the intestine and can be positive for one or more markers such as Musashi-1 (Msi-1), Asc12, Bmi-1, Doublecortin and $Ca^{2+}$/calmodulin-dependent kinase-like 1 (DCAMKL1), and Leucin-rich repeat-containing G-protein-coupled receptor 5 (Lgr5). See, e.g., Mohamed, et al., *Cytotechnology*, 2015 67(2): 177-189. In addition, ISC or crypts can be used to produce intestinal organoids using a biodegradable scaffold (e.g., poly-glycolic acid), growth factors such as epidermal growth factor (EGF), R-spondin, Jagged-1 peptide, or Noggin, and extracellular matrix. In some embodiments, mesenchymal cells are included in the culture to support the growth. The intestinal organoid can include a central lumen lined by a villus-like epithelium. See, e.g., US20160287670A1 and WO2015183920A2. Pre-clinical studies have demonstrated the intestinal organoid efficacy in differentiating into all GI cell lineages and regrowing parts of the intestine, muscle layer included. See, Agopian, et al., *J Gastrointest Surg.*, 2009, 13(5):971-82; Kuratnik and Giardina, *Biochem Pharmacol.*, 2013, 85:1721-1726; and Belchior et al., *Semin Pediatr Surg.*, 2014, 23:141-149.

In some embodiments, the stem cells can be allogeneic adipose-derived stem cells (ASC) such as ALLO-ASC cells or expanded ASC (eASC) (e.g., Cx601 cells). See, for example, Panes et al., Lancet; 2016, 388: 1281-90; and U.S. Patent Publication No. 20120020930. Cx601 cells are commercially available from TiGenix. Cx601 cells have been used for treating complex perianal fistulas in Crohn's disease patients. ALLO-ASC cells are commercially available from Anterogen Co., Ltd., and have been used for treating Crohn's disease.

In some embodiments, the stem cells can be human placental derived stem cells such as PDA-001 cells from Celgene. PDA-001 cells are a culture-expanded, plastic adherent, undifferentiated in vitro cell population that express the nominal phenotype CD34−, CD10+, CD105+ and CD200+. PDA-001 cells constitutively express moderate levels of HLA Class I and undetectable levels of HLA Class II, and they do not express the co-stimulatory molecules CD80 and CD86. PDA-001 is genetically stable, displaying a normal diploid chromosome count, normal karyotype and exhibit normal senescence after prolonged in vitro culture. See, e.g., U.S. Pat. No. 8,916,146.

10. Carbohydrate Sulfotransferase 15 (CHST15) Inhibitor

The term "CHST15 inhibitor" refers to an agent which decreases CHST15 activity and/or expression. A non-limiting example of CHST15 activity is the transfer of sulfate from 3'-phosphoadenosine 5'-phosphosulfate (PAPS) to the C-6 hydroxyl group of the GalNAc 4-sulfate residue of chondroitin sulfate A.

In some embodiments, a CHST15 inhibitor can be an inhibitory nucleic acid. In some embodiments, the inhibitory nucleic acid can be an antisense nucleic acid, a ribozyme, and a small interfering RNA (siRNA). Examples of aspects of these different oligonucleotides are described below. Any of the examples of inhibitory nucleic acids that can decrease expression of CHST15 mRNA in a mammalian cell can be synthesized in vitro.

Inhibitory nucleic acids that can decrease the expression of CHST15 mRNA expression in a mammalian cell include antisense nucleic acid molecules, i.e., nucleic acid molecules whose nucleotide sequence is complementary to all or part of an CHST15 mRNA.

An antisense nucleic acid molecule can be complementary to all or part of a non-coding region of the coding strand of a nucleotide sequence encoding a CHST15 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding a CHST15 protein (e.g., specificity for a CHST15 mRNA).

An inhibitory nucleic acid can also be a nucleic acid molecule that forms triple helical structures. For example, expression of a CHST15 polypeptide can be inhibited by targeting nucleotide sequences complementary to the regulatory region of the gene encoding the CHST15 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid is a siRNA molecule that decreases the level of a CHST15 mRNA. Non-limiting examples of siRNAs targeting CHST15 are described in Takakura et al., *PLosOne* 10(12):e0142981, 2015; Watanabe et al., *Cell Signal.* 27(7):1517-1524, 2015; Suzuki et al., *PLos One* 11(7):e0158967, 2016; Kai et al., *Mol. Ther. Nucl. Acids* 6: 163-172, 2017). In some embodiments, the siRNA targeting CHST15 is STNM01 or a variant thereof (Suzuki et al., *J. Crohns Colitis* 11(2):221-228, 2017; Atreya et al., *Eur. Crohn's Colitis Organisation*, Congress Abstract DOP073, 2017; US 2016/0355818; US 2017/0067058; US 2016/0348118).

Additional examples of CHST15 inhibitory nucleic acids are described in US 2015/0337313 and US 2016/0348118, which are incorporated by reference in its entirety.

11. IL-1 Inhibitors

The term "IL-1 inhibitor" refers to an agent that decreases the expression of an IL-1 cytokine or an IL-1 receptor and/or decreases the ability of an IL-1 cytokine to bind specifically to an IL-1 receptor. Non-limiting examples of IL-1 cytokines include IL-1α, IL-1β, IL-18, IL-36α, IL-36β, IL-36γ, IL-38, and IL-33. In some examples, an IL-1 cytokine is IL-1α. In some examples, an IL-1 cytokine is IL-1β.

As is known in the art, IL-1α and IL-1β each binds to a complex of IL-1R1 and IL1RAP proteins; IL-18 binds to IL-18Rα; IL-36α, IL-36β, and IL-36γ each binds to a complex of IL-1RL2 and IL-1RAP proteins; and IL-33 binds to a complex of IL1RL1 and IL1RAP proteins. IL-1Ra is an endogenous soluble protein that decreases the ability of IL-1α and IL-1β to bind to their receptor (e.g., a complex of IL-1R1 and IL1RAP proteins). IL-36Ra is an endogenous soluble protein that decreases the ability of IL-36α, IL-36β, and IL-36γ to bind to their receptor (e.g., a complex of IL-1RL2 and IL-1RAP proteins).

In some embodiments, the IL-1 inhibitor mimicks native human interleukin 1 receptor antagonist (IL1-Ra).

In some embodiments, the IL-1 inhibitor targets IL-1α. In some embodiments, the IL-1 inhibitor targets IL-1β. In some embodiments, the IL-1 inhibitor targets one or both of IL-1R1 and IL1RAP. For example, an IL-1 inhibitor can decrease the expression of IL-1α and/or decrease the ability of IL-1α to bind to its receptor (e.g., a complex of IL-1R1 and IL1RAP proteins). In another example, an IL-1 inhibitor can decrease the expression of IL-1β and/or decrease the ability of IL-1β to binds to its receptor (e.g., a complex of IL-1R1 and IL1RAP proteins). In some embodiments, an IL-1 inhibitor can decrease the expression of one or both of IL-1R1 and IL1RAP.

In some embodiments, the IL-1 inhibitor targets IL-18. In some embodiments, the IL-1 inhibitor targets IL-18Rα. In some embodiments, the IL-1 inhibitor decreases the ability of IL-18 to bind to its receptor (e.g., IL-18Rα). In some embodiments, the IL-1 inhibitor decreases the expression of IL-18. In some embodiments, the IL-1 inhibitor decreases the expression of IL-18Rα.

In some embodiments, the IL-1 inhibitor targets one or more (e.g., two or three) of IL-36α, IL-36β, and IL-36γ. In some embodiments, the IL-1 inhibitor targets one or both of IL-1RL2 and IL-1RAP. In some embodiments, the IL-1 inhibitor decreases the expression of one or more (e.g., two or three) of IL-36α, IL-36β, and IL-36γ. In some embodiments, the IL-1 inhibitor decreases the expression of one or both of IL-1RL2 and IL-1RAP proteins. In some embodiments, the IL-1 inhibitor decreases the ability of IL-36a to bind to its receptor (e.g., a complex including IL-1RL2 and IL-1RAP). In some examples, the IL-1 inhibitor decreases the ability of IL-36β to bind to its receptor (e.g., a complex including IL-1RL2 and IL-1RAP). In some examples, the IL-1 inhibitor decreases the ability of IL-36γ to bind to its receptor (e.g., a complex including IL-1RL2 and IL-1RAP).

In some embodiments, the IL-1 inhibitor targets IL-33. In some embodiments, the IL-1 inhibitor targets one or both of IL1RL1 and IL1RAP. In some embodiments, the IL-1 inhibitor decreases the expression of IL-33. In some embodiments, the IL-1 inhibitor decreases the expression of one or both of IL1RL1 and IL1RAP. In some embodiments, the IL-1 inhibitor decreases the ability of IL-33 to bind to its receptor (e.g., a complex of IL1RL1 and IL1RAP proteins).

In some embodiments, an IL-1 inhibitory agent is an inhibitory nucleic acid, an antibody or fragment thereof, or a fusion protein. In some embodiments, the inhibitory nucleic acid is an antisense nucleic acid, a ribozyme, or a small interfering RNA.

Inhibitory Nucleic Acids

Inhibitory nucleic acids that can decrease the expression of IL-1α, IL-1β, IL-18, IL-36α, IL-36β, IL-36γ, IL-38, IL-33, IL-1R1, IL1RAP, IL-18Rα, IL-1RL2, or IL1RL1 mRNA in a mammalian cell include antisense nucleic acid molecules, i.e., nucleic acid molecules whose nucleotide sequence is complementary to all or part of an IL-1α, IL-1β, IL-18, IL-36α, IL-36β, IL-36γ, IL-38, IL-33, IL-1R1, IL1RAP, IL-18Rα, IL-1RL2, or IL1RL1 mRNA.

An antisense nucleic acid molecule can be complementary to all or part of a non-coding region of the coding strand of a nucleotide sequence encoding an IL-1α, IL-113, IL-18, IL-36α, IL-36β, IL-36γ, IL-38, IL-33, IL-1R1, IL1RAP, IL-18Rα, IL-1RL2, or IL1RL1 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding an IL-1α, IL-1β, IL-18, IL-36α, IL-36β, IL-36γ, IL-38, IL-33, IL-1R1, IL1RAP, IL-18Rα, IL-1RL2, or IL1RL1 protein (e.g., specificity for an IL-1α, IL-1β, IL-18, IL-36α, IL-36β, IL-36γ, IL-38, IL-33, IL-1R1, IL1RAP, IL-18Rα, IL-1RL2, or IL1RL1 mRNA).

An inhibitory nucleic acid can also be a nucleic acid molecule that forms triple helical structures. For example, expression of an IL-1α, IL-1β, IL-18, IL-36α, IL-36β, IL-36γ, IL-38, IL-33, IL-1R1, IL1RAP, IL-18Rα, IL-1RL2, or IL1RL1 polypeptide can be inhibited by targeting nucleotide sequences complementary to the regulatory region of the gene encoding the IL-1α, IL-1β, IL-18, IL-36α, IL-36β, IL-36γ, IL-38, IL-33, IL-1R1, IL1RAP, IL-18Rα, IL-1RL2, or IL1RL1 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can be a siRNA that decreases the expression of an IL-1α, IL-1β, IL-18, IL-36α, IL-36β, IL-36γ, IL-38, IL-33, IL-1R1, IL1RAP, IL-18Rα, IL-1RL2, or IL1RL1 mRNA.

As described herein, inhibitory nucleic acids preferentially bind (e.g., hybridize) to a nucleic acid encoding IL-1α, IL-1β, IL-18, IL-36α, IL-36β, IL-36γ, IL-38, IL-33, IL-1R1, IL1RAP, IL-18Rα, IL-1RL2, or IL1RL1 protein to treat allergic diseases (e.g., asthma (Corren et al., *N. Engl. J. Med.* 365: 1088-1098, 2011)), radiation lung injury (Chung et al., *Sci. Rep.* 6: 39714, 2016), ulcerative colitis (Hua et al., *Br. J. Clin. Pharmacol.* 80:101-109, 2015), dermatitis (Guttman-Yassky et al., *Exp. Opin. Biol. Ther.* β(4):1517, 2013), and chronic obstructive pulmonary disease (COPD) (Walsh et al. (2010) *Curr. Opin. Investig Drugs* 11(11):β05-β12, 2010).

Exemplary IL-1 inhibitors that are antisense nucleic acids are described in Yilmaz-Elis et al., *Mol. Ther. Nucleic Acids* 2(1): e66, 2013; Lu et al., *J. Immunol.* 190(12): 6570-6578, 2013), small interfering RNA (siRNA) (e.g., Ma et al., *Ann. Hepatol.* 15(2): 260-270, 2016), or combinations thereof.

Antibodies

In some embodiments, the IL-1 inhibitor is an antibody or an antigen-binding fragment thereof (e.g., a Fab or a scFv). In some embodiments, an antibody or antigen-binding fragment described herein binds specifically to any one of IL-1α, IL-1β, IL-18, IL-36α, IL-36β, IL-36γ, IL-38, and IL-33. In some embodiments, an antibody or antigen-binding fragment of an antibody described herein can bind specifically to one or both of IL-1R1 and IL1RAP. In some embodiments, an antibody or antigen-binding fragment of an antibody described herein can bind specifically to IL-18Rα. In some embodiments, an antibody or antigen-binding fragment of an antibody described herein can bind specifically to one or both of IL1RL1 and IL1RAP. In some embodiments, an antibody or antigen-binding fragment of an antibody described herein can bind to one or both of IL-1RL2 and IL-1RAP.

In some embodiments, the IL-1 inhibitor is canakinumab (ACZ885, Ilaris® (Dhimolea, MAbs 2(1): 3-β, 2010; Yokota et al., *Clin. Exp. Rheumatol.* 2016; Torene et al., *Ann. Rheum. Dis.* 76(1):303-309, 2017; Gram, *Curr. Opin. Chem. Biol.* 32:1-9, 2016; Kontzias et al., *Semin. Arthritis Rheum* 42(2):201-205, 2012). In some embodiments, the IL-1 inhibitor is anakinra (Kineret®; Beynon et al., *J. Clin. Rheumatol.* 23(3):181-183, 2017; Stanam et al., *Oncotarget* 7(46):76087-76100, 2016; Nayki et al., *J. Obstet Gynaecol. Res.* 42(11):1525-1533, 2016; Greenhalgh et al., *Dis. Model Mech.* 5(6):823-833, 2012), or a variant thereof. In some embodiments, the IL-1 inhibitor is gevokizumab (XOMA 052; Knicklebein et al., *Am. J. Ophthalmol.* 172:104-110, 2016; Roubille et al., *Atherosclerosis* 236(2):277-285, 2014; Issafras et al., *J. Pharmacol. Exp. Ther.* 348(1):202-215, 2014; Handa et al., *Obesity* 21(2):306-309, 2013; Geiler et al., *Curr. Opin. Mol. Ther.* 12(6):755-769, 2010), LY2189102 (Bihorel et al., *AAPS J.* 16(5):1009-1117, 2014; Sloan-Lancaster et al., *Diabetes Care* 36(8):2239-2246, 2013), MABp1 (Hickish et al., *Lancey Oncol.* 18(2):192-201, 2017; Timper et al., *J. Diabetes Complications* 29(7): 955-960, 2015), CDP-484 (Braddock et al., *Drug Discov.* 3:330-339, 2004), or a variant thereof (Dinarello et al., *Nat. Rev. Drug Discov.* 11(8): 633-652, 2012).

Further teachings of IL-1 inhibitors that are antibodies or antigen-binding fragments thereof are described in U.S. Pat. Nos. 5,075,222; 7,446,175; 7,531,166; 7,744,865; 7,829,093; and 8,273,350; US 2016/0326243; US 2016/0194392, and US 2009/0191187, each of which is incorporated by reference in its entirety.

Fusion Proteins or Soluble Receptors

In some embodiments, the IL-1 inhibitor is a fusion protein or a soluble receptor. For example, a fusion can include an extracellular domain of any one of IL-1R1, IL1RAP, IL-18Rα, IL-1RL2, and IL1RL1 fused to a partner amino acid sequence (e.g., a stabilizing domain, e.g., an IgG Fc region, e.g., a human IgG Fc region). In some embodiments, the IL-1 inhibitor is a soluble version of one or both of IL-1RL1 and IL1RAP. In some embodiments, the IL-1 inhibitor is a soluble version of IL-18Rα. In some embodiments, the IL-1 inhibitor is a soluble version of one or both of IL-1RL2 and IL-1RAP.

In some embodiments, the IL-1 inhibitor is a fusion protein comprising or consisting of rilonacept (IL-1 Trap, Arcalyst®) (see, e.g., Kapur & Bonk, P. T. 34(3):β8-141, 2009; Church et al., *Biologics* 2(4):733-742, 2008; McDermott, Drugs Today (Bare) 45(6):423-430, 2009). In some embodiments, the IL-1 inhibitor is a fusion protein that is chimeric (e.g., EBI-005 (Isunakinra®) (Furfine et al., *Invest. Ophthalmol. Vis. Sci.* 53(14):2340-2340, 2012; Goldstein et al., *Eye Contact Lens* 41(3):145-155, 2015; Goldstein et al., Eye Contact Lens, 2016)).

In some embodiments, the IL-1 inhibitor is a soluble receptor that comprises or consists of sIL-1RI and/or sIL-1RII (Svenson et al., *Eur. J. Immunol.* 25(10): 2842-2850, 1995).

Endogenous IL-1 Inhibitor Peptides

In some embodiments, the IL-1 inhibitor can be an endogenous ligand or an active fragment thereof, e.g., IL-1Ra or IL-36Ra. IL-1Ra is an endogenous soluble protein that decreases the ability of IL-1α and IL-1β to bind to their receptor (e.g., a complex of IL-1R1 and IL1RAP proteins). IL-36Ra is an endogenous soluble protein that decreases the ability of IL-36α, IL-36β, and IL-36γ to bind to their receptor (e.g., a complex of IL-1RL2 and IL-1RAP proteins).

12. IL-13 Inhibitors

The term "IL-13 inhibitor" refers to an agent which decreases IL-13 expression and/or decreases the binding of IL-13 to an IL-13 receptor. In some embodiments, the IL-13 inhibitor decreases the ability of IL-13 to bind an IL-13 receptor (e.g., a complex including IL-4Rα and IL-13Rα1, or a complex including IL-13Rα1 and IL-13Rα2).

In some embodiments, the IL-13 inhibitor targets the IL-4Rα subunit. In some embodiments, the IL-13 inhibitor targets the IL-13Rα1. In some embodiments, the IL-13 inhibitor targets IL-13Rα2. In some embodiments, the IL-13 inhibitor targets an IL-13 receptor including IL-4Rα and IL-13Rα1. In some embodiments, the IL-13 inhibitor targets an IL-13 receptor including IL-13Rα1 and IL-13Rα2. In some embodiments, the IL-13 inhibitor targets IL-β.

In some embodiments, an IL-13 inhibitor is an inhibitory nucleic acid, an antibody or an antigen-binding fragment thereof, or a fusion protein. In some embodiments, the inhibitory nucleic acid can be an antisense nucleic acid, a ribozyme, a small interfering RNA, a small hairpin RNA, or a microRNA. Examples of aspects of these different inhibitory nucleic acids are described below.

Inhibitory nucleic acids that can decrease the expression of IL-13, IL-13Rα1, IL-13Ra2, or IL-4Rα mRNA expression in a mammalian cell include antisense nucleic acid molecules, i.e., nucleic acid molecules whose nucleotide sequence is complementary to all or part of an IL-13, IL-13Rα1, IL-13Rα2, or IL-Rα mRNA.

An antisense nucleic acid molecule can be complementary to all or part of a non-coding region of the coding strand of a nucleotide sequence encoding an IL-13, IL-13Rα1, IL-13Rα2, or IL-4Rα protein. Non-coding regions (5' and 3' untranslated regions) are the 5' and the 3' sequences that flank the coding region in a gene and are not translated into amino acids. Non-limiting examples of an inhibitors that are antisense nucleic acids are described in Kim et al., *J. Gene Med.* 11(1):26-37, 2009; and Mousavi et al., *Iran J. Allergy Asthma Immunol.* 2(3):β1-β7, 2003.

Another example of an inhibitory nucleic acid is a ribozyme that has specificity for a nucleic acid encoding an IL-13, IL-13Rα1, IL-13Rα2, or IL-4Rα (e.g., specificity for an IL-13, IL-13Rα1, IL-13Rα2, or IL-4Rα mRNA).

An inhibitory nucleic acid can also be a nucleic acid molecule that forms triple helical structures. For example, expression of an IL-13, IL-13Rα1, IL-13Rα2, or IL-4Rα polypeptide can be inhibiting by targeting nucleotide sequences complementary to the regulatory region of the gene encoding the IL-13, IL-13Rα1, IL-13Rα2, or IL-4Rα polypeptide (e.g., the promoter and/or enhancer, e.g., a sequence that is at least 1 kb, 2 kb, 3 kb, 4 kb, or 5 kb upstream of the transcription initiation start site) to form triple helical structures that prevent transcription of the gene in target cells.

As described herein, inhibitory nucleic acid preferentially bind (e.g., hybridize) to a nucleic acid encoding IL-13, IL-13Rα1, IL-13Rα2, or IL-4Rα protein to treat allergic diseases (e.g., asthma (Corren et al., *N. Engl. J. Med.* 365:1088-1098, 2011), radiation lung injury (Chung et al., *Sci. Rep.* 6:39714, 2016), ulcerative colitis (Hua et al., *Br. J. Clin. Pharmacol.* 80:101-109, 2015), dermatitis (Guttman-Yassky et al., *Exp. Opin. Biol. Ther.* 13(4):1517, 2013), and chronic obstructive pulmonary disease (COPD) (Walsh et al., *Curr. Opin. Investig. Drugs* 11(11):β05-β12, 2010)).

An inhibitory nucleic acid can be a siRNA molecule that decreases the level of an IL-13, IL-13Rα1, IL-13Rα2, or IL-4Rα mRNA. Non-limiting examples of siRNAs that are IL-13 inhibitors are described in Lively et al., *J. Allergy Clin. Immunol.* 121(1):88-94, 2008. Non-limiting examples of short hairpin RNA (shRHA) that are IL-13 inhibitors are described in Lee et al., *Hum. Gene Ther.* 22(5):577-586, 2011, and Shilovskiy et al., *Eur. Resp. J.* 42:P523, 2013.

In some embodiments, an inhibitory nucleic acid can be a microRNA. Non-limiting examples of microRNAs that are IL-13 inhibitors are let-7 (Kumar et al., *J. Allergy Clin. Immunol.* 128(5):1077-1085, 2011).

Antibodies

In some embodiments, the IL-13 inhibitor is an antibody or an antigen-binding fragment thereof (e.g., a Fab or a scFv). In some embodiments, an antibody or antigen-binding fragment described herein binds specifically to any one of IL-13, IL-13Rα1, IL-13Rα2, or IL-4Rα, or a combination thereof. In some embodiments, an antibody or antigen-binding fragment of an antibody described herein can bind specifically to IL-13. In some embodiments, an antibody or antigen-binding fragment of an antibody described herein can bind specifically to an IL-13 receptor (e.g., a complex including IL-4Rα and IL-13Rα1, or a complex including IL-13Rα1 and IL-13Rα2).

In some embodiments, the IL-13 inhibitor is a monoclonal antibody (Bagnasco et al., *Int. Arch. Allergy Immunol.* 170:122-131, 2016). In some embodiments, the IL-13 inhibitor is QAX576 (Novartis) or an antigen-binding fragment thereof (see, e.g., Kariyawasam et al., *B92 New Treatment Approaches for Asthma and Allergery San Diego,* 2009; Rothenberg et al., *J. Allergy Clin. Immunol.* β5:500-507, 2015). In some embodiments, the IL-13 inhibitor is ABT-308 (Abbott) or an antigen-binding fragment thereof (see, e.g., Ying et al., American Thoracic Society 2010 International Conference, May 14-19, 2010, New Orleans; Abstract A6644). In some embodiments, the IL-13 inhibitor is CNTO-5825 (Centrocore) or an antigen-binding fragment thereof (see, e.g., van Hartingsveldt et al., *British J. Clin. Pharmacol.* 75:1289-1298, 2013). In some embodiments, the IL-13 inhibitor is dupilumab (REGN668/SAR231893) or an antigen-binding fragment thereof (see, e.g., Simpson et al., *N Eng. J. Med.* 375:2335-2348, 2016; Thaci et al., *Lancet* 387:40-52, 2016). In some embodiments, the IL-13 inhibitor is AMG317 (Amgen) or an antigen-binding fragment thereof (Polosa et al., *Drug Discovery Today* 17:591-599, 2012; Holgate, *British J. Clinical Pharmacol.* 76:277-291, 2013). In some embodiments, the IL-13 inhibitor is an antibody that specifically binds to IL-13Rα1 (see, e.g., U.S. Pat. No. 7,807,158; WO 96/29417; WO 97/15663; and WO 03/080675).

In some embodiments, the IL-13 inhibitor is a humanized monoclonal antibody (e.g., lebrikizumab (TNX-650) (Thomson et al., *Biologics* 6:329-335, 2012; and Hanania et al., *Thorax* 70(8):748-756, 2015). In some embodiments, the IL-13 inhibitor is an anti-IL-13 antibody, e.g., GSK679586 or a variant thereof (Hodsman et al., *Br. J. Clin. Pharmacol.* 75(1):118-128, 2013; and De Boever et al., *J. Allergy Clin. Immunol.* β3(4):989-996, 2014). In some embodiments, the IL-13 inhibitor is tralokinumab (CAT-354) or a variant thereof (Brightling et al., *Lancet* 3(9): 692-701, 2015; Walsh et al. (2010) *Curr. Opin. Investig. Drugs* 11(11):β05-β12, 2010; Piper et al., *Euro. Resp. J.* 41:330-338, 2013; May et al., *Br. J. Pharmacol.* 166(1): 177-193, 2012; Singh et al., *BMC Pulm Med.* 10:3, 2010; Blanchard et al., *Clin. Exp. Allergy* 35(8): 1096-1103, 2005). In some embodiments, the 11-13 inhibitor is anrukinzumab (IMA-638) (Hua et al., *Br. J. Clin. Pharmacol.* 80: 101-109, 2015; Reinisch et al., *Gut* 64(6): 894-900, 2015; Gauvreau et al., *Am. J. Respir. Crit. Care Med.* 183(8):1007-1014, 2011; Bree et al., *J. Allergy Clin. Immunol.* 119(5):1251-1257, 2007). Further teachings of IL-13 inhibitors that are antibodies or antigen-binding fragments thereof are described in U.S. Pat. Nos. 8,067,199; 7,910,708; 8,221,752; 8,388,965; 8,399,630; and 8,734,801; US 2014/0341913; US 2015/0259411; US 2016/0075777; US 2016/0130339, US 2011/0243928, and US 2014/0105897 each of which is incorporated by reference in its entirety.

Fusion Proteins

In some embodiments, the IL-13 inhibitor is a fusion protein or a soluble antagonist. In some embodiments, the fusion protein comprises a soluble fragment of a receptor of IL-13 (e.g., a soluble fragment of a complex including IL-13Rα1 and IL-4Rα, a soluble fragment of a complex including IL-13Rα1 and IL-13Rα2, a soluble fragment of IL-13Rα1, a soluble fragment of IL-13Rα2, or soluble fragment of IL-4Rα). In some embodiments, the fusion protein comprises an extracellular domain of a receptor of IL-13 (e.g., a fusion protein including an extracellular domain of both IL-13Rα1 and IL-4Rα, a fusion protein including an extracellular domain of both IL-13Rα1 and IL-13Rα2, a fusion protein including an extracellular domain of IL-13Rα1, a fusion protein including an extracellular domain of IL-13Rα2, or a fusion protein including an extracellular domain of IL-4Rα).

In some embodiments, the fusion protein comprises or consists of sIL-13Rα2-Fc (see, e.g., Chiaramonte et al., *J. Clin. Invest.* 104(6):777-785, 1999; Kasaian et al., *Am. J. Respir. Cell. Mol. Biol.* 36(3):368-376, 2007; Miyahara et al., *J. Allergy Clin. Immunol.* 118(5):1110-1116, 2006; Rahaman et al., *Cancer Res.* 62(4):1103-1109, 2002; incorporated by reference herein). In some embodiments, the fusion protein comprises or consists of an IL-13 fusion cytotoxin (e.g., IL-13/diphtheria toxin fusion protein (Li et al., *Protein Eng.* 15(5):419-427, 2002), IL-13-PE38QQR (IL-13-PE) (Blease et al. (2001) *J. Immunol.* 167(11):6583-6592, 2001; and Husain et al., *J. Neuro-Oncol.* 65(1):37-48, 2003)).

13. IL-10 and IL-10 Receptor Agonists

The term "IL-10 receptor agonist" is any molecule that binds to and activates a receptor for IL-10 expressed on a mammalian cell or a nucleic acid that encodes any such molecule. A receptor for IL-10 can include, e.g., a complex of two IL-10 receptor-1 (IL-10R1) proteins and two IL-10 receptor 2 (IL-10122) proteins. In some examples, an IL-10 receptor agonist is an antibody or an antigen-binding antibody fragment that specifically binds to and activates a receptor for IL-10 (e.g., a human receptor for IL-10). In some examples, an IL-10 receptor agonist is a recombinant IL-10 (e.g., human recombinant IL-10). In some examples, an IL-10 receptor agonist is a pegylated recombinant IL-10 (e.g., pegylated recombinant human IL-10). In some examples, an IL-10 receptor agonist is a fusion protein. In some examples, an IL-10 receptor agonist is an IL-10 peptide mimetic.

Further teachings of IL-1 inhibitors that are antibodies or antigen-binding fragments thereof are described in U.S. Pat. Nos. 5,075,222; 7,446,175; 7,531,166; 7,744,865; 7,829,093; and 8,273,350; US 2016/0326243; US 2016/0194392, and US 2009/0191187, each of which is incorporated by reference in its entirety.

Recombinant IL-10

In some examples, an IL-10 receptor agonist is a recombinant IL-10 protein. In some examples, a recombinant IL-10 protein has an amino acid sequence that is identical to a human IL-10 protein. Non-limiting commercial sources of recombinant human IL-10 protein are available from Peprotech (Rocky Hill, N.J.), Novus Biologicals (Littleton, Colo.), Stemcell™ Technologies (Cambridge, Mass.), Millipore Sigma (Billerica, Mass.), and R&D Systems (Minneapolis, Minn.). In some examples, a recombinant human IL-10 protein can be Tenovil™ (Schering Corporation).

In some examples, a recombinant IL-10 protein is a functional fragment of human IL-10 protein. In some examples, a functional fragment of human IL-10 is a fragment of a human IL-10 protein that is able to specifically bind to and activate a human receptor of IL-10. A functional fragment of a human IL-10 protein can have one, two, three, four, five, six, seven, eight, nine, ten, eleven, twelve, thirteen, fourteen, fifteen, sixteen, seventeen, eighteen, nineteen, or twenty amino acids removed from the N- and/or C-terminus of the wildtype mature human IL-10 protein. In some embodiments, the recombinant human IL-10 can include a sequence that is at least 80% identical (e.g., at least 82% identical, at least 84% identical, at least 86% identical, at least 88% identical, at least 90% identical, at least 92% identical, at least 94% identical, at least 95% identical, at least 96% identical, at least 98% identical, or at least 99% identical) to the sequence of wildtype, mature human IL-10, and is able to specifically bind to and activate a human receptor of IL-10. Mutation of amino acids that are not conserved between different mammalian species is less likely to have a negative effect on the activity of a recombinant IL-10 protein.

In some embodiments, the IL-10 receptor agonist is rhuIL-10 (Tenovil) or a variant thereof. See, e.g., McHutchison et al., *J. Interferon Cytokine Res.* 1:1265-1270, 1999; Rosenblum et al., *Regul. Toxicol. Pharmacol.* 35:56-71, 2002; Schreiber et al., *Gastroenterology* 119(6):1461-1472, 2000; Maini et al., *Arthritis Rheum.* 40(Suppl):224, 1997.

Exemplary methods of making a recombinant human IL-10 are described in Pajkrt et al., *J. Immunol.* 158: 3971-3977, 1997). Additional exemplary methods of making recombinant IL-10 are described herein and are known in the art.

In some embodiments, a recombinant IL-10 is a pegylated recombinant IL-10 (e.g., pegylated recombinant human IL-10) (e.g., a 5 kDa N-terminally PEGylated form of IL-10; AM0010) (Infante et al., *ASCO Meeting Abstracts* 33(15_suppl):3017, 2015; Chan et al., *PLoS One* 11(6): e0156229, 2016; Mumm et al., *Cancer Cell* 20(6):781-796, 2011; Teng et al., *Cancer Cell* 20(6):691-693, 2011; U.S. Pat. Nos. 8,691,205; 8,865,652; 9,259,478; and 9,364,517; and U.S. Patent Application Publication Nos. 2008/0081031; 2009/0214471; 2011/0250163; 2011/0091419; 2014/0227223; 2015/0079031; 2015/0086505; 2016/0193352; 2016/0367689; 2016/0375101; and 2016/0166647).

In some embodiments, a recombinant IL-10 is a stabilized isoform of a recombinant IL-10. In some embodiments, the stabilized isoform of a recombinant IL-10 is a viral IL-10 protein (e.g., a human cytomegalovirus IL10 (e.g., cmv-IL10, LA-cmv-IL-10 (e.g., Lin et al., *Virus Res.* β1(2):213-223, 2008; Jenkins et al., *J. Virol.* 78(3):1440-1447, 2004; Kotenko et al., *Proc. Natl. Acad. Sci. U.S.A.* 97(4):1695-1700, 2000; Jones et al., *Proc. Natl. Acad. Sci. U.S.A.* 99(14):9404-9409, 2002) or a latency-associated viral IL-10 protein (e.g., Poole et al., *J. Virol.* 88(24):β947-β955, 2014).

In some embodiments, the recombinant IL-10 is a mammalian IL-10 homolog (see, e.g., WO 00/073457). In some embodiments, a mammalian IL-10 homolog is BCRF1, an EBV homolog of human IL-10, also known as viral IL-10, or a variant thereof (Liu et al., *J. Immunol.* 158(2):604-613, 1997).

Fusion Proteins

In some embodiments, the IL-10 receptor agonist is a fusion protein. In some embodiments, the fusion protein comprises the amino acid sequence of an IL-10 protein (or a functional fragment thereof) and a fusion partner (e.g., an Fc region (e.g., human IgG Fc) or human serum albumin). In some embodiments the fusion partner can be an antibody or an antigen-binding antibody fragment (e.g., an scFv) that targets IL-10 receptor agonist to an inflamed tissue. In some embodiments, the antibody or antigen-binding fragment that is a fusion partner can bind specifically, or preferentially, to inflamed gastrointestinal cells by, e.g., CD69. In some embodiments, an IL-10 receptor agonist that is a fusion protein can be, e.g., F8-IL-10, such as Dekavil (Philogen).

In some embodiments, the fusion protein is a L19-IL-10 fusion protein, a HyHEL10-IL-10 fusion protein, or a variant thereof. See, e.g., Trachsel et al., *Arthritis Res. Ther.* 9(1):R9, 2007, and Walmsley et al., *Arthritis Rheum.* 39: 495-503, 1996.

IL-10 Peptide Mimetic

In some embodiments, the IL-10 receptor agonist is an IL-10 peptide mimetic. A non-limiting example of an IL-10 peptide mimetic is IT 9302 or a variant thereof (Osman et al., *Surgery* 124(3):584-92, 1998; Lopez et al., *Immunobiology* 216(10):1117-1126, 2011). Additional examples of IL-10 peptide mimetics are described in DeWitt, *Nature Biotech.* 17:214, 1999, and Reineke et al., *Nature Biotech.* 17:271-275, 1999.

Antibodies

In some embodiments, the IL-10 receptor agonist is an antibody or an antigen-binding antibody fragment that binds to and activates an IL-10 receptor (e.g., a human IL-10 receptor). In some embodiments, the antibody or antigen-binding antibody fragment that specifically binds to an epitope on IL-10R-1 protein (e.g., human IL-10R-1 protein). In some embodiments, the antibody or antigen-binding antibody fragment that specifically binds to an epitope on IL-10R-2 protein (e.g., a human IL-10R-2 protein). In some embodiments, the antibody or the antigen-binding antibody fragment that specifically binds to an epitope on IL-10R-1 and IL-10R-2 proteins (e.g., human IL-10R-1 and human IL-10R-2 proteins).

In some embodiments, the IL-10 receptor agonist is an antibody (e.g., F8-IL10 (also known as DEKAVIL) or a variant thereof (see, e.g., Schwager et al., *Arthritis Res. Ther.* 11(5):R142, 2009; Franz et al., *Int. J. Cardiol.* 195:311-322, 2015; Galeazzi et al., *Isr. Med. Assoc. J.* 16(10):666, 2014).

Cells Producing a Recombinant IL-10

In some embodiments, a recombinant cell (e.g., a recombinant mammalian cell) secretes a recombinant IL-10 (e.g., any of the recombinant IL-10 proteins described herein). In some embodiments, a cell (e.g., a mammalian cell) secretes IL-10 (e.g., human IL-10). In some embodiments, the mammalian cell can be a mammalian cell obtained from the subject, after the introduction of a nucleic acid encoding the recombinant IL-10 (e.g., any of the recombinant IL-10 proteins described herein) into the cell obtained from the subject.

In some examples, the recombinant mammalian cell can be a Chinese Hamster Ovary (CHO) cell, a B cell, a $CD8^+$ T cell, a dendritic cell, a keratinocyte or an epithelial cell. See, e.g., Mosser et al., *Immunol. Rev.* 226:205-218, 2009; Fillatreau et al., *Nat. Rev. Immunol.* 8:391-397, 2008; Ryan et al., *Crit. Rev. Immunol.* 27:15-32, 2007; Moore et al., *Annu. Rev. Immunol.* 19:683-765, 2001. In some embodiments, the recombinant mammalian cell can be a mesenchymal stem cell (e.g., Gupte et al., *Biomed. J.* 40(1):49-54, 2017).

Nucleic Acids and Vectors the Encode an IL-10 Receptor Agonist

In some examples, an IL-10 receptor agonist can be a nucleic acid (e.g., a vector) that includes a sequence encoding an IL-10 receptor agonist (e.g., any of the IL-10 proteins described herein). In some embodiments, the nucleic acid includes a sequence encoding IL-10 (e.g., human IL-10). In some embodiments, the nucleic acid includes a sequence encoding a recombinant IL-10 (e.g., a recombinant human IL-10).

The nucleic acid can be, e.g., a vector. In some embodiments, a vector can be a viral vector (e.g., an adenovirus vector, a herpes virus vector, a baculovirus vector, or a retrovirus vector). A vector can also be, e.g., a plasmid or a cosmid. Additional examples of vectors are known in the art. A vector can include a promoter sequence operably linked to the sequence encoding an IL-10 receptor agonist (e.g., any of the recombinant IL-10 proteins described herein).

A non-limiting example of a composition including a nucleic acid that encodes an IL-10 receptor agonist is XT-150 (Xalud Therapeutics).

Additional Examples of IL-10 Receptor Agonists

In some embodiments, the recombinant cell is a recombinant Gram-positive bacterial cell (e.g., a genetically modified Lactococcus lactis (LL-Thy12) (see, e.g., Steidler et al., Science 289:1352-β55, 2000; Braat et al., Clin. Gastroenterol. Heptal. 4:754-759, 2006). In some embodiments, the recombinant cell is a recombinant Gram-negative bacterial cell (e.g., a Shigella flexneri cell) that secretes an IL-10 receptor agonist (e.g., a recombinant IL-10 protein) (Chamekh et al., J. Immunol. 180(6): 4292-4298, 2008).

In some embodiments, the IL-10 receptor agonist is a cell (e.g., a Clostridium butyricum cell) that induces IL-10 production and secretion by a different cell (e.g., a macrophage) (e.g., Hayashi et al., *Cell Host Microbe* 13:711-722, 2013). In some embodiments, the IL-10 receptor agonist is a recombinant bacterial cell (e.g., a Lactobacillus acidophilus cell) that is deficient in lipoteichoic acid and induces IL-10 production and secretion by a different cell (e.g., a dendritic cell) (e.g., Mohamadzadeh et al., *Proc. Natl. Acad. Sci. U.S.A.* 108(Suppl. 1):4623-4630, 2011; Konstantinov et al., *Proc. Natl. Acad. Sci. U.S.A.* 105(49):19474-9, 2008). In some embodiments, the IL-10 receptor agonist is a bacterial cell or a fragment of a bacterial cell that is maintained in the supernatant that induces IL-10 secretion in a different cell (e.g., an immune cell) (e.g., a *Faecalibacterium prausnitzii* cell or a *Faecalibacterium prausnitzii* supernatant) (see, e.g., Sokol et al., *Proc. Natl. Acad. Sci. U.S.A.* 105(43):16731-16736, 2008).

Additional examples of other IL-10 receptor agonists are described in, e.g., U.S. Pat. No. 6,936,586; WO 96/01318; WO 91/00349; WO 13/130913; each incorporated in its entirety herein.

14. Glatiramer Acetate

Glatiramer acetate, formerly known as copolymer-1, consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecule weight of glatiramer acetate is 4,700-11,000 daltons.

Chemically, glatiramer acetate is designated L-glutamic acid polymer with L-alanine, L-lysine and L-tyrosine, acetate (salt). The CAS number for glatiramer acetate is CAS-147245-92-9. The IUPAC name for glatiramer acetate is acetic acid; (2S)-2-amino-3-(4-hydroxyphenyl)propanoic acid; (2S)-2-aminopentanedioic acid; (2S)-2-aminopropanoic acid; (2S)-2,6-diaminohexanoic acid.

Glatiramer acetate is marketed as the active ingredient of Copaxone® by Teva Pharmaceuticals Ltd., Israel. Copaxone® is a clear, colorless to slightly yellow, sterile, nonpyrogenic solution. Each 1 mL of Copaxone® solution contains 20 mg or 40 mg of glatiramer acetate and 40 mg of mannitol. The pH of Copaxone® solution is approximately 5.5 to 7.0. Copaxone® 20 mg/mL is an FDA-approved product. Copaxone® 40 mg/mL in a prefilled syringe was developed as a newer formulation of the active ingredient glatiramer acetate.

Glatiramer acetate is known as being useful for the treatment of inflammatory and autoimmune diseases, in addition to its uses for treating multiple sclerosis, see, e.g., U.S. Pat. Nos. 7,033,582, 7,053,043, 7,074,580, 7,279,172, and 7,425,332, hereby incorporated by reference in their entirety. Glatiramer acetate has been shown to therapeutically reduce inflammation and ameliorate the pathological manifestations of inflammatory bowel disease (IBD) in numerous murine models (see, e.g., Aharoni et al., *J. of Pharmacology and Experimental Therapeutics* 318:68-78, 2006; Yao et al., *Eur. J. Immunol.* 43:125-β6, 2013; and Yablecovitch et al., *J. of Pharmacology and Experimental Therapeutics* 337:391-399, 2011, each of which is hereby incorporated by reference in its entirety).

Various glatiramer acetate formulations and methods of preparing glatiramer acetate and glatiramer acetate formulations have been described in, for example, U.S. Pat. Nos. 8,399,413, 8,859,489, 8,920,373, 8,921,116, 8,969,302, 8,993,722, 9,018,170, 9,029,507, 9,155,775, and 9,402,874, which are hereby incorporated by reference in their entirety.

15. CD40/CD40L Inhibitors

The term "CD40/CD40L inhibitors" refers to an agent which decreases CD40 or CD40L (CD154) expression and/or the ability of CD40 to bind to CD40L (CD154). CD40 is a costimulatory receptor that binds to its ligand, CD40L (CD154).

In some embodiments, the CD40/CD40L inhibitor can decrease the binding between CD40 and CD40L by blocking the ability of CD40 to interact with CD40L. In some embodiments, the CD40/CD40L inhibitor can decrease the binding between CD40 and CD40L by blocking the ability of CD40L to interact with CD40. In some embodiments, the CD40/CD40L inhibitor decreases the expression of CD40 or CD40L. In some embodiments, the CD40/CD40L inhibitor decreases the expression of CD40. In some embodiments, the CD40/CD40L inhibitor decreases the expression of CD40L.

In some embodiments, the CD40/CD40L inhibitor is an inhibitory nucleic acid, an antibody or an antigen-binding fragment thereof, a fusion protein, or a small molecule. In some embodiments, the inhibitory nucleic acid is a small interfering RNA, an antisense nucleic acid, an aptamer, or a microRNA. Exemplary CD40/CD40L inhibitors are described herein. Additional examples of CD40/CD40L inhibitors are known in the art.

Exemplary aspects of different inhibitory nucleic acids are described below. Any of the examples of inhibitory nucleic acids that can decrease expression of CD40 or CD40L mRNA in a mammalian cell can be synthesized in vitro. Inhibitory nucleic acids that can decrease the expression of CD40 or CD40L mRNA in a mammalian cell include antisense nucleic acid molecules, i.e., nucleic acid molecules whose nucleotide sequence is complementary to all or part of a CD40 or CD40L mRNA.

Inhibitory Nucleic Acids

An antisense nucleic acid molecule can be complementary to all or part of a non-coding region of the coding strand of a nucleotide sequence encoding a CD40 or CD40L protein. Non-coding regions (5' and 3' untranslated regions) are the 5' and 3' sequences that flank the coding region in a gene and are not translated into amino acids.

Some exemplary antisense nucleic acids that are CD40 or CD40L inhibitors are described, e.g., in U.S. Pat. Nos. 6,197,584 and 7,745,609; Gao et al., Gut 54(1):70-77, 2005; Arranz et al., *J. Control Release* 165(3):163-172, 2012; Donner et al., *Mol. Ther. Nucleic Acids* 4:e265, 2015.

Another example of an inhibitory nucleic acid is a ribozyme that has specificity for a nucleic acid encoding a CD40 or CD40L protein (e.g., specificity for a CD40 or CD40L mRNA).

An inhibitory nucleic acid can also be a nucleic acid molecule that forms triple helical structures. For example, expression of a CD40 or CD40L polypeptide can be inhibited by targeting nucleotide sequences complementary to the regulatory region of the gene encoding the CD40 or CD40L polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can be a siRNA molecule that decreases the level of a CD40 or CD40L mRNA. Non-limiting examples of short interfering RNA (siRNA) that are CD40/CD40L inhibitors are described in, e.g., Pluvinet et al., *Blood* 104:3642-3646, 2004; Karimi et al., *Cell Immunol.* 259(1):74-81, 2009; and Zheng et al., *Arthritis Res. Ther.* 12(1):R13, 2010. Non-limiting examples of short hairpin RNA (shRNA) targeting CD40/CD40L are described in Zhang et al., *Gene Therapy* 21:709-714, 2014. Non-limiting examples of microRNAs that are CD40/CD40L inhibitors include, for example, miR146a (Chen et al., *FEBS Letters* 585(3):567-573, 2011), miR-424, and miR-503 (Lee et al., *Sci. Rep.* 7:2528, 2017).

Non-limiting examples of aptamers that are CD40/CD40L inhibitors are described in Soldevilla et al., *Biomaterials* 67:274-285, 2015.

Antibodies

In some embodiments, the CD40/CD40L inhibitor is an antibody or an antigen-binding fragment thereof (e.g., a Fab or a scFv). In some embodiments, an antibody or antigen-binding fragment described herein binds specifically to CD40 or CD40L, or to both CD40 and CD40L.

In certain embodiments, the antibody comprises or consists of an antigen-binding fragment or portion of PG102 (Pangenetics) (Bankert et al., *J. Immunol.* 194(9):4319-4327, 2015); 2C10 (Lowe et al., *Am. J. Transplant* 12(8): 2079-2087, 2012); ASKP1240 (Bleselumab) (Watanabe et al., *Am. J. Transplant* 13(8):1976-1988, 2013); 4D11 (Imai et al., *Transplantation* 84(8):1020-1028, 2007); BI 655064 (Boehringer Ingelheim) (Visvanathan et al., 2016 American College of Rheumatology Annual Meeting, Abstract 1588, Sep. 28, 2016); 5D12 (Kasran et al., *Aliment. Pharmacol. Ther.*, 22(2):111-122, 2005; Boon et al., *Toxicology* 174(1): 53-65, 2002); ruplizumab (hu5c8) (Kirk et al., *Nat. Med.* 5(6):686-693, 1999); CHIR12.12 (HCD122) (Weng et al., *Blood* 104(11):3279, 2004; Tai et al., *Cancer Res.* 65(13): 5898-5906, 2005); CDP7657 (Shock et al., *Arthritis Res. Ther.* 17(1):234, 2015); BMS-986004 domain antibody (dAb) (Kim et al., *Am. J. Transplant.* 17(5):1182-1192, 2017); 5c8 (Xie et al., *J. Immunol.* 192(9):4083-4092, 2014); dacetuzumab (SGN-40) (Lewis et al., *Leukemia* 25(6):1007-1016, 2011; and Khubchandani et al., *Curr. Opin. Investig. Drugs* 10(6):579-587, 2009); lucatumumab (HCD122) (Bensinger et al., *Br. J. Haematol.* 159: 58-66, 2012; and Byrd et al., *Leuk. Lymphoma* 53(11): 10.3109/10428194.2012.681655, 2012); PG102 (FFP104) (Bankert et al., *J. Immunol.* 194(9):4319-4327, 2015); Chi Lob 7/4 (Johnson et al., *J. Clin. Oncol.* 28:2507, 2019); and ASKP1240 (Okimura et al., *Am. J. Transplant.* 14(6): 1290-1299, 2014; and Ma et al., *Transplantation* 97(4): 397-404, 2014).

Further teachings of CD40/CD40L antibodies and antigen-binding fragments thereof are described in, for example, U.S. Pat. Nos. 5,874,082; 7,169,389; 7,271,152; 7,288,252; 7,445,780; 7,537,763; 8,277,810; 8,293,237; 8,551,485; 8,591,900; 8,647,625; 8,784,823; 8,852,597; 8,961,976; 9,023,360, 9,028,826; 9,090,696, 9,221,913; US2014/0093497; and US2015/0017155, each of which is incorporated by reference in its entirety.

Fusion and Truncated Proteins and Peptides

In some embodiments, the CD40/CD40L inhibitor is a fusion protein, a truncated protein (e.g., a soluble receptor) or a peptide. In some embodiments, the CD40/CD40L inhibitor is a truncated protein as disclosed in, for example, WO 01/096397. In some embodiments, the CD40/CD40L inhibitor is a peptide, such as a cyclic peptide (see, e.g., U.S. Pat. No. 8,802,634; Bianco et al., *Org. Biomol. Chem.* 4:1461-1463, 2006; Deambrosis et al., *J. Mol. Med.* 87(2): 181-197, 2009; Vaitaitis et al., *Diabetologia* 57(11):2366-2373, 2014). In some embodiments, the CD40/CD40L inhibitor is a CD40 ligand binder, for example, a Tumor Necrosis Factor Receptor-associated Factor (TRAF): TRAF2, TRAF3, TRAF6, TRAF5 and TTRAP, or E3 ubiquitin-protein ligase RNF128.

Small Molecules

In some embodiments, the CD40/CD40L inhibitor is a small molecule (see, e.g., U.S. Pat. No. 7,173,046, U.S. Patent Application No. 2011/0065675). In some embodiments, the small molecule is Bio8898 (Silvian et al., *ACS Chem. Biol.* 6(6):636-647, 2011); Suramin (Margolles-Clark et al., *Biochem. Pharmacol.* 77(7):1236-1245, 2009); a small-molecule organic dye (Margolles-Clark et al., *J. Mol. Med.* 87(11):1133-1143, 2009; Buchwald et al., *J. Mol. Recognit.* 23(1):65-73, 2010), a naphthalenesulphonic acid derivative (Margolles-Clark et al., *Chem. Biol. Drug Des.* 76(4):305-313, 2010), or a variant thereof.

16. CD3 Inhibitors

The term "CD3 inhibitor" refers to an agent which decreases the ability of one or more of CD3γ, CD3δ, CD3ε, and CD3ζ to associate with one or more of TCR-α, TCR-β, TCR-δ, and TCR-γ. In some embodiments, the CD3 inhibitor can decrease the association between one or more of CD3γ, CD3δ, CD3ε, and CD3ζ and one or more of TCR-α, TCR-13, TCR-δ, and TCR-γ by blocking the ability of one or more of CD3γ, CD3δ, CD3ε, and CD3ζ to interact with one or more of TCR-α, TCR-13, TCR-δ, and TCR-γ.

In some embodiments, the CD3 inhibitor is an antibody or an antigen-binding fragment thereof, a fusion protein, or a small molecule. Exemplary CD3 inhibitors are described herein. Additional examples of CD3 inhibitors are known in the art.

Antibodies

In some embodiments, the CD3 inhibitor is an antibody or an antigen-binding fragment thereof (e.g., a Fab or a scFv). In some embodiments, the CD3 inhibitor is an antibody or antigen-binding fragment that binds specifically to CD3γ. In some embodiments, the CD3 inhibitor is an antibody or antigen-binding fragment that binds specifically to CD3δ. In some embodiments, the CD3 inhibitor is an antibody or antigen-binding fragment that binds specifically to CD3ε. In some embodiments, the CD3 inhibitor is an antibody or antigen-binding fragment that binds specifically to CD3ζ. In some embodiments, the CD3 inhibitor is an antibody or an antigen-binding fragment that can bind to two or more (e.g., two, three, or four) of CD3γ, CD3δ, CD3ε, and CD3ζ.

In certain embodiments, the antibody comprises or consists of an antigen-binding fragment or portion of visiluzumab (Nuvion; HuM-291; M291; SMART anti-CD3 antibody) (Carpenter et al., *Biol. Blood Marrow Transplant* 11(6): 465-471, 2005; Trajkovic *Curr. Opin. Investig. Drugs* 3(3): 411-414, 2002; Malviya et al., *J. Nucl. Med.* 50(10): 1683-1691, 2009; muromonab-CD3 (orthoclone OKT3) (Hori et al., *Surg. Today* 41(4): 585-590, 2011; Norman *Ther. Drug Monit* 17(6): 615-620, 1995; and Gramatzki et al., *Leukemia* 9(3): 382-390, 19); otelixizumab (TRX4) (Vossenkamper et al., *Gastroenterology* 147(1): 172-183, 2014; and Wiczling et al., *J. Clin. Pharmacol.* 50(5): 494-506, 2010); foralumab (NI-0401) (Ogura et al., *Clin. Immunol.* 183: 240-246; and van der Woude et al., *Inflamm. Bowel Dis.* 16: 1708-1716, 2010); ChAgly CD3; teplizumab (MGA031) (Waldron-Lynch et al., *Sci. Transl. Med.* 4(118): 118ra12, 2012; and Skelley et al., *Ann. Pharmacother.* 46(10): 1405-1412, 2012); or catumaxomab (Removab®) (Linke et al., Mabs 2(2): 129-β6, 2010; and Bokemeyer et al., *Gastric Cancer* 18(4): 833-842, 2015).

Additional examples of CD3 inhibitors that are antibodies or antibody fragments are described in, e.g., U.S. Patent Application Publication Nos. 2017/0204194, 2017/0137519, 2016/0368988, 2016/0333095, 2016/0194399, 2016/0168247, 2015/0166661, 2015/0118252, 2014/0193399, 2014/0099318, 2014/0088295, 2014/0080147, 2013/0115213, 2013/0078238, 2012/0269826, 2011/0217790, 2010/0209437, 2010/0183554, 2008/0025975, 2007/0190045, 2007/0190052, 2007/0154477, 2007/0134241, 2007/0065437, 2006/0275292, 2006/0269547, 2006/0233787, 2006/0177896, 2006/0165693, 2006/0088526, 2004/0253237, 2004/0202657, 2004/0052783, 2003/0216551, and 2002/0142000, each of which is herein incorporated by reference in its entirety (e.g., the sections describing the CD3 inhibitors). Additional CD3 inhibitors that are antibodies or antigen-binding antibody fragments are described in, e.g., Smith et al., *J. Exp. Med.* 185(8):1413-1422, 1997; Chatenaud et al., *Nature* 7:622-632, 2007.

In some embodiments, the CD3 inhibitor comprises or consists of a bispecific antibody (e.g., JNJ-63709178) (Gaudet et al., *Blood* 128(22): 2824, 2016); JNJ-64007957 (Girgis et al., *Blood* 128: 5668, 2016); MGD009 (Tolcher et al., *J. Clin. Oncol.* 34:15, 2016); ERY974 (Ishiguro et al., *Sci. Transl. Med.* 9(410): pii.eaa14291, 2017); AMV564 (Hoseini and Cheung *Blood Cancer J.* 7:e522, 2017); AFM11 (Reusch et al., *MAbs* 7(3): 584-604, 2015); duvortuxizumab (JNJ 64052781); RO6958688; blinatumomab (Blincyto®; AMG103) (Ribera *Expert Rev. Hematol.* 1:1-11, 2017; and Mori et al., *N Engl. J. Med.* 376(23):e49, 2017); XmAb13676; or REGN1979 (Bannerji et al., Blood 128: 621, 2016; and Smith et al., *Sci. Rep.* 5:17943, 2015)).

In some embodiments, the CD3 inhibitor comprises or consists of a trispecific antibody (e.g., ertumaxomab (Kiewe and Thiel, *Expert Opin. Investig. Drugs* 17(10): 1553-1558, 2008; and Haense et al., *BMC Cancer* 16:420, 2016); or FBTA05 (Bi20; Lymphomun) (Buhmann et al., *J. Transl. Med.* 11:160, 2013; and Schuster et al., *Br. J. Haematol.* 169(1): 90-102, 2015)).

Fusion and Truncated Proteins and Peptides

In some embodiments, the CD3 inhibitor is a fusion protein, a truncated protein (e.g., a soluble receptor), or a peptide. In some embodiments, the CD3 inhibitor can be a fusion protein (see, e.g., Lee et al., *Oncol. Rep.* 15(5): 1211-1216, 2006).

Small Molecules

In some embodiments, the CD3 inhibitor comprises or consists of a bispecific small molecule-antibody conjugate (see, e.g., Kim et al., *PNAS* 110(44): 17796-17801, 2013; Viola et al., *Eur. J. Immunol.* 27(11):3080-3083, 1997).

17. CD14 Inhibitors

The term "CD14 inhibitors" refers to an agent which decreases the ability of CD14 to bind to lipopolysaccharide (LPS). CD14 acts as a co-receptor with Toll-like receptor 4 (TLR4) that binds LPS in the presence of lipopolysaccharide-binding protein (LBP).

In some embodiments, the CD14 inhibitor can decrease the binding between CD14 and LPS by blocking the ability of CD14 to interact with LPS.

In some embodiments, the CD14 inhibitor is an antibody or an antigen-binding fragment thereof. In some embodiments, the CD14 inhibitor is a small molecule. Exemplary CD14 inhibitors are described herein. Additional examples of CD14 inhibitors are known in the art.

Antibodies

In some embodiments, the CD14 inhibitor is an antibody or an antigen-binding fragment thereof (e.g., a Fab or a scFv). In some embodiments, the CD14 inhibitor is an antibody or antigen-binding fragment that binds specifically to CD14.

In certain embodiments, the antibody comprises or consists of an antigen-binding fragment or portion of IC14 (Axtelle and Pribble, *J. Endotoxin Res.* 7(4): 310-314, 2001; Reinhart et al., *Crit. Care Med.* 32(5): 1100-1108, 2004; Spek et al., *J. Clin. Immunol.* 23(2): 132-140, 2003). Additional examples of anti-CD14 antibodies and CD14 inhibitors can be found, e.g., in WO 2015/140591 and WO 2014/122660, incorporated in its entirety herein.

Additional examples of CD14 inhibitors that are antibodies or antibody fragments are described in, e.g., U.S. Patent Application Serial No. 2017/0107294, 2014/0050727, 2012/0227412, 2009/0203052, 2009/0029396, 2008/0286290, 2007/0106067, 2006/0257411, 2006/0073145, 2006/0068445, 2004/0092712, 2004/0091478, and 2002/0150882, each of which is herein incorporated by reference (e.g., the sections that describe CD14 inhibitors).

Small Molecules

In some embodiments, the CD14 inhibitor is a small molecule. Non-limiting examples of CD14 inhibitors that are small molecules are described in, e.g., methyl 6-deoxy-6-N-dimethyl-N-cyclopentylammonium-2, 3-di-O-tetradecyl-α-D-glucopyranoside iodide (IAXO-101); methyl 6-Deoxy-6-amino-2,3-di-O-tetradecyl-α-D-glucopyranoside (IAXO-102); N-(3,4-bis-tetradecyloxy-benzyl)-N-cyclopentyl-N,N-dimethylammonium iodide (IAXO-103); and IMO-9200.

Additional examples of CD14 inhibitors that are small molecules are known in the art.

18. CD20 Inhibitors

The term "CD20 inhibitors" refers to an agent that binds specifically to CD20 expressed on the surface of a mammalian cell.

In some embodiments, the CD20 inhibitor is an antibody or an antigen-binding fragment thereof, or a fusion protein or peptide. Exemplary CD20 inhibitors are described herein. Additional examples of CD20 inhibitors are known in the art.

Antibodies

In some embodiments, the CD20 inhibitor is an antibody or an antigen-binding fragment thereof (e.g., a Fab or a scFv).

In certain embodiments, the antibody comprises or consists of an antigen-binding fragment or portion of rituximab (Rituxan®, MabThera®, MK-8808) (Ji et al., *Indian J. Hematol. Blood Transfus.* 33(4): 525-533, 2017; and Calderon-Gomez and Panes *Gastroenterology* 142(1): 1741-76, 2012); —PF-05280586; ocrelizumab (Ocrevus™) (Sharp *N. Engl. J. Med.* 376(17): 1692, 2017); ofatumumab (Arzerra®; HuMax-CD20) (AlDallal *Ther. Clin. Risk Manag.* β:905-907, 2017; and Furman et al., *Lancet Haematol.* 4(1): e24-e34, 2017); PF-05280586 (Williams et al., *Br. J. Clin. Pharmacol.* 82(6): 1568-1579, 2016; and Cohen et al., *Br. J. Clin. Pharmacol.* 82(1): 129-138, 2016); obinutuzumab (Gazyva®) (Reddy et al., *Rheumatology* 56(7): 1227-1237, 2017; and Marcus et al., *N. Engl. J Med.* 377(14): 1331-1344, 2017); ocaratuzumab (AME-133v; LY2469298)

(Cheney et al., Mabs 6(3): 749-755, 2014; and Tobinai et al., *Cancer Sci.* 102(2): 432-8, 2011); GP2013 (Jurczak et al., *Lancet Haenatol.* 4(8): e350-e361, 2017); IBI301; HLX01; veltuzumab (hA20) (Kalaycio et al., *Leuk. Lymphoma* 57(4): 803-811, 2016; and Ellebrecht et al., *JAMA Dermatol.* 150(12): β31-β35, 2014); SCT400 (Gui et al., *Chin. J Cancer Res.* 28(2): 197-208); ibritumomab tiuxetan (Zevalin®) (Philippe et al., *Bone Marrow Transplant* 51(8): 1140-1142, 2016; and Lossos et al., *Leuk. Lymphoma* 56(6): 1750-1755, 2015); ublituximab (TG1101) (Sharman et al., *Blood* 124: 4679, 2014; and Sawas et al., *Br. J. Haematol.* 177(2): 243-253, 2017); LFB-R603 (Esteves et al., *Blood* 118: 1660, 2011; and Baritaki et al., *Int. J. Oncol.* 38(6): 1683-1694, 2011); or tositumomab (Bexxar) (Buchegger et al., *J. Nucl. Med.* 52(6): 896-900, 2011; and William and Bierman *Expert Opin. Biol. Ther.* 10(8): 1271-1278, 2010). Additional examples of CD20 antibodies are known in the art (see, e.g., WO 2008/156713).

In certain embodiments, the antibody comprises or consists of an antigen-binding fragment or portion of a bispecific antibody (e.g., XmAb13676; REGN1979 (Bannerji et al., *Blood* 128: 621, 2016; and Smith et al., *Sci. Rep.* 5: 17943, 2015); PRO131921 (Casulo et al., *Clin. Immnol.* 154(1): 37-46, 2014; and Robak and Robak *BioDrugs* 25(1): 13-25, 2011); or Acellbia).

In some embodiments, the CD20 inhibitor comprises or consists of a trispecific antibody (e.g., FBTA05 (Bi20; Lymphomun) (Buhmann et al., *J. Transl. Med.* 11:160, 2013; and Schuster et al., *Br. J. Haematol.* 169(1): 90-102, 2015)).

Additional examples of CD20 inhibitors that are antibodies or antigen-binding fragments are described in, e.g., U.S. Patent Application Publication Nos. 2017/0304441, 2017/0128587, 2017/0088625, 2017/0037139, 2017/0002084, 2016/0362472, 2016/0347852, 2016/0333106, 2016/0271249, 2016/0243226, 2016/0115238, 2016/0108126, 2016/0017050, 2016/0017047, 2016/0000912, 2016/0000911, 2015/0344585, 2015/0290317, 2015/0274834, 2015/0265703, 2015/0259428, 2015/0218280, 2015/0125446, 2015/0093376, 2015/0079073, 2015/0071911, 2015/0056186, 2015/0010540, 2014/0363424, 2014/0356352, 2014/0328843, 2014/0322200, 2014/0294807, 2014/0248262, 2014/0234298, 2014/0093454, 2014/0065134, 2014/0044705, 2014/0004104, 2014/0004037, 2013/0280243, 2013/0273041, 2013/0251706, 2013/0195846, 2013/0183290, 2013/0089540, 2013/0004480, 2012/0315268, 2012/0301459, 2012/0276085, 2012/0263713, 2012/0258102, 2012/0258101, 2012/0251534, 2012/0219549, 2012/0183545, 2012/0100133, 2012/0034185, 2011/0287006, 2011/0263825, 2011/0243931, 2011/0217298, 2011/0200598, 2011/0195022, 2011/0195021, 2011/0177067, 2011/0165159, 2011/0165152, 2011/0165151, 2011/0129412, 2011/0086025, 2011/0081681, 2011/0020322, 2010/0330089, 2010/0310581, 2010/0303808, 2010/0183601, 2010/0080769, 2009/0285795, 2009/0203886, 2009/0197330, 2009/0196879, 2009/0191195, 2009/0175854, 2009/0155253, 2009/0136516, 2009/0130089, 2009/0110688, 2009/0098118, 2009/0074760, 2009/0060913, 2009/0035322, 2008/0260641, 2008/0213273, 2008/0089885, 2008/0044421, 2008/0038261, 2007/0280882, 2007/0231324, 2007/0224189, 2007/0059306, 2007/0020259, 2007/0014785, 2007/0014720, 2006/0121032, 2005/0180972, 2005/0112060, 2005/0069545, 2005/0025764, 2004/0213784, 2004/0167319, 2004/0093621, 2003/0219433, 2003/0206903, 2003/0180292, 2003/0026804, 2002/0039557, 2002/0012665, and 2001/0018041, each herein incorporated by reference in their entirety (e.g., sections describing CD20 inhibitors).

Peptides and Fusion Proteins

In some embodiments, the CD20 inhibitor is an immunotoxin (e.g., MT-3724 (Hamlin *Blood* 128: 4200, 2016).

In some embodiments, the CD20 inhibitor is a fusion protein (e.g., TRU-015 (Rubbert-Roth *Curr. Opin. Mol. Ther.* 12(1): 115-123, 2010). Additional examples of CD20 inhibitors that are fusion proteins are described in, e.g., U.S. Patent Application Publication Nos. 2012/0195895, 2012/0034185, 2009/0155253, 2007/0020259, and 2003/0219433, each of which are herein incorporated by reference in their entirety (e.g., sections describing CD20 inhibitors).

19. CD25 Inhibitors

The term "CD25 inhibitors" refers to an agent which decreases the ability of CD25 (also called interleukin-2 receptor alpha chain) to bind to interleukin-2. CD25 forms a complex with interleukin-2 receptor beta chain and interleukin-2 common gamma chain.

In some embodiments, the CD25 inhibitor is an antibody or an antigen-binding fragment thereof, or a fusion protein. Exemplary CD25 inhibitors are described herein. Additional examples of CD25 inhibitors are known in the art.

Antibodies

In some embodiments, the CD25 inhibitor is an antibody or an antigen-binding fragment thereof (e.g., a Fab or a scFv). In some embodiments, a CD25 inhibitor is an antibody or an antigen-binding fragment thereof that specifically binds to CD25. In some embodiments, a CD25 inhibitor is an antibody that specifically binds to IL-2.

In certain embodiments, the antibody comprises or consists of an antigen-binding fragment or portion of basiliximab (Simulect™) (Wang et al., *Clin. Exp. Immunol.* 155(3): 496-503, 2009; and Kircher et al., *Clin. Exp. Immunol.* β4(3): 426-430, 2003); daclizumab (Zenapax; Zinbryta®) (Berkowitz et al., *Clin. Immunol.* 155(2): 176-187, 2014; and Bielekova et al., *Arch Neurol.* 66(4): 483-489, 2009); or IMTOX-25.

In some embodiments, the CD25 inhibitor is an antibody-drug-conjugate (e.g., ADCT-301 (Flynn et al., *Blood* 124: 4491, 2014)).

Additional examples of CD25 inhibitors that are antibodies are known in the art (see, e.g., WO 2004/045512). Additional examples of CD25 inhibitors that are antibodies or antigen-binding fragments are described in, e.g., U.S. Patent Application Publication Nos. 2017/0240640, 2017/0233481, 2015/0259424, 2015/0010539, 2015/0010538, 2012/0244069, 2009/0081219, 2009/0041775, 2008/0286281, 2008/0171017, 2004/0170626, 2001/0041179, and 2010/0055098, each of which is incorporated herein by reference (e.g., sections that describe CD25 inhibitors).

Fusion Proteins

In some embodiments, the CD25 inhibitor is a fusion protein. See, e.g., Zhang et al., *PNAS* 100(4): 1891-1895, 2003.

20. CD28 Inhibitors

The term "CD28 inhibitors" refers to an agent which decreases the ability of CD28 to bind to one or both of CD80 and CD86. CD28 is a receptor that binds to its ligands, CD80 (also called B7.1) and CD86 (called B7.2).

In some embodiments, the CD28 inhibitor can decrease the binding between CD28 and CD80 by blocking the ability of CD28 to interact with CD80. In some embodiments, the CD28 inhibitor can decrease the binding between CD28 and CD86 by blocking the ability of CD28 to interact with CD86. In some embodiments, the CD28 inhibitor can decrease the binding of CD28 to each of CD80 and CD86.

In some embodiments, the CD28 inhibitor is an antibody or an antigen-binding fragment thereof, a fusion protein, or peptide. Exemplary CD28 inhibitors are described herein. Additional examples of CD28 inhibitors are known in the art.

Antibodies

In some embodiments, the CD28 inhibitor is an antibody or an antigen-binding fragment thereof (e.g., a Fab or a scFv).

In some embodiments, the CD28 inhibitor is a monovalent Fab' antibody (e.g., CFR104) (Poirier et al., *Am. J Transplant* 15(1): 88-100, 2015).

Additional examples of CD28 inhibitors that are antibodies or antigen-binding fragments are described in, e.g., U.S. Patent Application Publication Nos. 2017/0240636, 2017/0114136, 2016/0017039, 2015/0376278, 2015/0299321, 2015/0232558, 2015/0150968, 2015/0071916, 2013/0266577, 2013/0230540, 2013/0109846, 2013/0078257, 2013/0078236, 2013/0058933, 2012/0201814, 2011/0097339, 2011/0059071, 2011/0009602, 2010/0266605, 2010/0028354, 2009/0246204, 2009/0117135, 2009/0117108, 2008/0095774, 2008/0038273, 2007/0154468, 2007/0134240, 2007/0122410, 2006/0188493, 2006/0165690, 2006/0039909, 2006/0009382, 2006/0008457, 2004/0116675, 2004/0092718, 2003/0170232, 2003/0086932, 2002/0006403, 2013/0197202, 2007/0065436, 2003/0180290, 2017/0015747, 2012/0100139, and 2007/0148162, each of which is incorporated by reference in its entirety (e.g., sections that described CD28 inhibitors).

Fusion Proteins and Peptides

In some embodiments, the CD28 inhibitor is a fusion protein (see, e.g., U.S. Pat. No. 5,521,288; and US 2002/0018783). In some embodiments, the CD28 inhibitor is abatacept (Orencia®) (Herrero-Beaumont et al., *Rheumatol. Clin.* 8: 78-83, 2012; and Korhonen and Moilanen *Basic Clin. Pharmacol. Toxicol.* 104(4): 276-284, 2009).

In some embodiments, the CD28 inhibitor is a peptide mimetic (e.g., AB103) (see, e.g., Bulger et al., *JAMA Surg.* 149(6): 528-536, 2014), or a synthetical peptoid (see, e.g., Li et al., *Cell Mol. Immunol.* 7(2): β3-142, 2010).

21. CD49 Inhibitors

The term "CD49 inhibitors" refers to an agent which decreases the ability of CD49 to bind to one of its ligands (e.g., MMP1). In some embodiments, the CD49 inhibitor is an antibody or an antigen-binding fragment thereof. Exemplary CD49 inhibitors are described herein. Additional examples of CD49 inhibitors are known in the art.

Antibodies

In some embodiments, the CD49 inhibitor is an antibody or an antigen-binding fragment thereof (e.g., a Fab or a scFv).

In certain embodiments, the antibody comprises or consists of an antigen-binding fragment or portion of natalizumab (Tysabri®; Antegren®) (see, e.g., Pagnini et al., *Expert Opin. Biol. Ther.* 17(11): 1433-1438, 2017; and Chataway and Miller Neurotherapeutics 10(1): 19-28, 2013; or vatelizumab (ELND-004)).

22. CD89 Inhibitors

The term "CD89 inhibitors" refers to an agent which decreases the ability of CD89 to bind to IgA. CD89 is a transmembrane glycoprotein that binds to the heavy-chain constant region of IgA. In some embodiments, the CD89 inhibitor can decrease the binding between CD89 and IgA by blocking the ability of CD89 to interact with IgA. In some embodiments, the CD89 inhibitor is an antibody or an antigen-binding fragment thereof. Exemplary CD89 inhibitors are described herein. Additional examples of CD89 inhibitors are known in the art.

Antibodies

In some embodiments, the CD89 inhibitor is an antibody or an antigen-binding fragment thereof (e.g., a Fab or a scFv).

In certain embodiments, the antibody comprises or consists of an antigen-binding fragment or portion of HF-1020. Additional examples of CD89 antibodies are known in the art (see, e.g., WO 2002/064634).

23. Chemokine/Chemokine Receptor Inhibitors

The term "chemokine/chemokine receptor inhibitors" refers to an agent which decreases the ability of a chemokine to bind to its receptor, where the chemokine is one of CXCL10 (IL-10), CCL11, or an ELR chemokine, or the chemokine receptor is CCR2 or CCR9.

CXCL10 (IP-10) Inhibitors

As used herein "CXCL10", "interferon gamma-induced protein 10" and "IP-10" can be used interchangeably. CXCL10 binds to the CXCR3 receptor (e.g., CXCR3-A or CXCR3-B).

The term "CXCL10 inhibitor" refers to an agent which decreases the ability of CXCL10 to bind to a CXCR3 receptor (e.g., CXCR3-A and/or CXCR3-B).

In some embodiments, the CXCL10 inhibitor can decrease the binding between CXCL10 and CXCR3-A by blocking the ability of CXCL10 to interact with CXCR3-A. In some embodiments, the CXCL10 inhibitor can decrease the binding between CXCL10 and CXCR3-B by blocking the ability of CXCL10 to interact with CXCR3-B.

In some instances, the CXCL10 inhibitor that decreases the binding between CXCL10 and a CXCR3 (e.g., CXCR3-A and/or CXCR3-B) is a small molecule. In some instances, the CXCL10 inhibitor that decreases the binding between CXCL10 and a CXCR3 (e.g., CXCR3-A and/or CXCR3-B) is an antibody or an antigen-binding antibody fragment. In some instances, the CXCL10 inhibitor that decreases the binding between CXCL10 and a CXCR3 (e.g., CXCR3-A and/or CXCR3-B) is a peptide (e.g., a peptide antagonist of a CXCR3 receptor, e.g., one or both of CXCR-A and/or CXCR-B).

CXCL10 Inhibitors—Antibodies

In some embodiments, the CXCL10 inhibitor is an antibody or an antigen-binding fragment thereof (e.g., a Fab or a scFv). In some embodiments, an antibody or antigen-binding fragment described herein binds specifically to CXCL10 or a CXCR3 receptor (e.g., CXCR3-A and/or CXCR3-B), or both a CXCL10 and a CXCR3 receptor (e.g., CXCR3-A and/or CXCR3-B). In some embodiments, a CXCL10 inhibitor can bind to both CXCR3-A and CXCR3-B.

In other instances, the CXCL10 inhibitor is a monoclonal antibody (mAb) (see, e.g., WO 05/58815). For example, the CXCL10 inhibitor can be Eldelumab® (MDX-1100 or BMS-936557), BMS-986184 (Bristol-Meyers Squibb), or NI-0801 (NovImmune). See, e.g., Kuhne et al., *J. Immunol.* 178(1):5241, 2007; Sandborn et al., *J. Crohns Colitis* 11(7): 811-819, 2017; and Danese et al., *Gastroenterology* 147(5): 981-989, 2014. Additional examples of CXCL10 inhibitors that are antibodies are described in U.S. Patent Application Publication Nos. 2017/0158757, 2017/0081413, 2016/0009808, 2015/0266951, 2015/0104866, 2014/0127229, 2014/0065164, 2013/0216549, 2010/0330094, 2010/0322941, 2010/0077497, 2010/0021463, 2009/0285835, 2009/0169561, 2008/0063646, 2005/0191293, 2005/0112119, 2003/0158392, 2003/0031645, and 2002/

0018776; and WO 98/11218, each of which is incorporated by reference in its entirety (e.g., the description of CXCL10 inhibitors).

CCL11 Inhibitors

The term "CCL11 inhibitor" refers to an agent which decreases the ability of CCL11 to bind to one or more of CCR2, CCR3, and CCR5.

In some embodiments, the CCL11 inhibitor can decrease the binding between CCL11 and CCR2 by blocking the ability of CCL11 to interact with CCR2. In some embodiments, the CCL11 inhibitor can decrease the binding between CCL11 and CCR3 by blocking the ability of CCL11 to interact with CCR3. In some embodiments, the CCL11 inhibitor can decrease the binding between CCL11 and CCR5 by blocking the ability of CCL11 to interact with CCR5.

In some embodiments, a CCL11 inhibitor is an antibody or an antigen-binding fragment thereof.

CCL11 Inhibitors—Antibodies

In some embodiments, the CCL11 inhibitor is an antibody or an antigen-binding fragment thereof (e.g., a Fab or a scFv). In some embodiments, an antibody or antigen-binding fragment described herein binds specifically to CCL11, CCR2, CCR3, or CCR5, or can specifically bind to two or more of CCL11, CCR2, CCR3, and CCR5. In some embodiments, a CCL11 inhibitor can bind to two or more of CCR2, CCR3, and CCR5.

In some examples the chemokine/chemokine receptor inhibitor is bertilimumab (Immune Pharmaceuticals), an anti-eotaxin-1 monoclonal antibody that targets CCL11, and is currently in a Phase II clinical study for ulcerative colitis. Additional examples of CCL11 inhibitors are described in U.S. Patent Application Publication Nos. 2016/0289329, 2015/0086546, 2014/0342450, 2014/0178367, 2013/0344070, 2013/0071381, 2011/0274696, 2011/0038871, 2010/0074886, 2009/0297502, 2009/0191192, 2009/0169541, 2009/0142339, 2008/0268536, 2008/0241923, 2008/0241136, 2005/0260139, 2005/0048052, 2004/0265303, 2004/0132980, 2004/0126851, 2003/0165494, 2002/0150576, 2002/0150570, 2002/0051782, 2002/0051781, 2002/0037285, 2002/0028436, 2002/0015700, 2002/0012664, 2017/0131282, 2016/0368979, 2016/0208011, 2011/0268723, 2009/0123375, 2007/0190055, 2017/0049884, 2011/0165182, 2009/0226434, 2009/0110686, 2009/0047735, 2009/0028881, 2008/0107647, 2008/0107595, 2008/0015348, 2007/0274986, 2007/0231327, 2007/0036796, 2007/0031408, 2006/0229336, 2003/0228306, 2003/0166870, 2003/0003440, 2002/0019345, and 2001/0000241, each of which is incorporated by reference in its entirety (e.g., the description of CCL11 inhibitors).

CXCL10 Inhibitors—Small Molecules and Peptides

In some instances, the CXCL10 inhibitor is a small molecule. For example, the CXCL10 inhibitor can be ganodermycin (see, e.g., Jung et al., *J. Antiobiotics* 64:683-686, 2011). Additional exemplary small molecule CXCL10 inhibitors are described in: U.S. Patent Application Publication No. 2005/0075333; U.S. Patent Application Publication No. 2004/0242498; U.S. Patent Application Publication No. 2003/0069234; U.S. Patent Application Publication No. 2003/0055054; U.S. Patent Application Publication No. 2002/0169159; WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25):15687-15692 (1998); and Howard et al., *J. Med. Chem.* 41(13):2184-2193 (1998).

In some examples, the CXCL10 inhibitor is a peptide antagonist of a CXCR3 receptor (e.g., as described in U.S. Patent Application Publication No. 2007/0116669, 2006/0204498, and WO 98/09642). In some examples, the CXCL10 inhibitor is a chemokine mutant or analogue, e.g., those described in U.S. Pat. No. 5,739,103, WO 96/38559, and WO 98/06751. Additional examples of CXCL10 inhibitors that are small molecules or peptides are known in the art.

CCR2 Inhibitors

As used herein "CCR2," "CC chemokine receptor 2," or "MCP-1" can be used interchangeably. CCL2, CCL8, and CCL16 each individually bind to CCR2.

The term "CCR2 inhibitor" refers to an agent which decreases the ability of CCR2 to bind to one or more (e.g., two, or three) of CCL2, CCL8, and CCL16.

In some embodiments, the CCR2 inhibitor can decrease the binding between CCL2 and CCR2 by blocking the ability of CCL2 to interact with CCR2. In some embodiments, the CCR2 inhibitor can decrease the binding between CCL8 and CCR2 by blocking the ability of CCL8 to interact with CCR2. In some embodiments, the CCR2 inhibitor can decrease the binding between CCL16 and CCR2 by blocking the ability of CCL16 to interact with CCR2.

In some embodiments, the CCR2 inhibitor decreases the ability of CCR2 to bind to each of CCL2 and CCL8. In some embodiments, the CCR2 inhibitor decreases the ability of CCR2 to bind to each of CCL2 and CCL16. In some embodiments, the CCR2 inhibitor decreases the ability of CCR2 to bind to each of CCL8 and CCL16. In some embodiments, the CCR5 inhibitor decreases the ability of CCR2 to bind to each of CCL2, CCL8, and CCL16.

In some instances, the CCR2 inhibitor is a small molecule. In some instances, the CCR2 inhibitor is an antibody or an antigen-binding antibody fragment. In some instances, the CCR2 inhibitor is a peptide.

CCR2 Inhibitors—Antibodies

In some embodiments, the CCR2 inhibitor is an antibody or an antigen-binding fragment thereof (e.g., a Fab or a scFv). In some embodiments, an antibody or antigen-binding fragment described herein binds specifically to CCR2. In some embodiments, an antibody or antigen-binding fragment described herein binds specifically to CCL2. In some embodiments, an antibody or antigen-binding fragment described herein binds specifically to CCL8. In some embodiments, an antibody or antigen-binding fragment described herein binds specifically to CCL16. In some embodiments, an antibody or antigen-binding fragment described herein binds specifically to CCR2 and one or more of (e.g., one, two, or three) of CCL2, CCL8, and CCL16.

In some embodiments, the CCR2 inhibitor is a monoclonal antibody. For example, the CCR2 inhibitor can be MLN1202 (Millennium Pharmaceuticals), C775, STI-B0201, STI-B0211, STI-B0221, STI-B0232, carlumab (CNTO 888; Centocor, Inc.), or STI-B0234, or an antigen-binding fragment thereof. See also, e.g., Vergunst et al., *Arthritis Rheum.* 58(7):1931-1939, 2008. Additional examples of CCR2 inhibitors that are antibodies or antigen-binding antibody fragments are described in, e.g., U.S. Patent Application Publication Nos. 2015/0086546, 2016/0272702, 2016/0289329, 2016/0083482, 2015/0361167; 2014/0342450, 2014/0178367, 2013/0344070, 2013/0071381, 2011/0274696, 2011/0059107, 2011/0038871, 2009/0068109, 2009/0297502, 2009/0142339, 2008/0268536, 2008/0241923, 2008/0241136, 2007/0128112, 2007/0116708, 2007/0111259, 2006/0246069, 2006/0039913, 2005/0232923, 2005/0260139, 2005/0058639, 2004/0265303, 2004/0132980, 2004/0126851, 2004/0219644, 2004/0047860, 2003/0165494, 2003/0211105, 2002/0150576, 2002/0051782, 2002/0042370, and 2002/0015700; and U.S. Pat. Nos. 6,312,689, 6,084,075, 6,406,694, 6,406,865, 6,696,550, 6,727,349, 7,442,775, 7,858,318, 5,859,205, 5,693,762, and 6,075,181, each of which is incorporated by reference (e.g., the description of the CCR2 inhibitors). Additional examples of CCR2 inhibitors are described in, e.g., WO 00/05265. Additional examples of CCR2 inhibitors that are antibodies or antigen-binding antibodies fragments are described in, e.g., Loberg et al., *Cancer Res.* 67(19):9417, 2007.

CCR2 Inhibitors—Small Molecules and Peptides

In some examples, the CCR2 inhibitor is a small molecule. For example, the CCR2 inhibitor can be elubrixin, PF-04634817, BMS-741672, or CCX872. See, e.g., U.S. Pat. No. 9,434,766; U.S. Patent Application Publication No. 20070021466; Deerberg et al., *Org. Process Rev. Dev.* 20(11): 1949-1966, 2016; and Morganti et al., *J. Neurosci.* 35(2):748-760, 2015.

Additional non-limiting examples of CCR2 inhibitors that are small molecules include, e.g., the phenylamino substituted quaternary salt compounds described in U.S. Patent Application Publication No. 2009/0112004; the biaryl derivatives described in U.S. Patent Application Publication No. 2009/0048238; the pyrazol derivatives described in U.S. Patent Application Publication No. 2009/0029963; the heterocyclic compounds described in U.S. Patent Application Publication No. 2009/0023713; the imidazole derivatives described in U.S. Patent Application Publication No. 2009/0012063; the aminopyrrolidines described in U.S. Patent Application Publication No. 2008/0176883; the heterocyclic cyclopentyl tetrahydroisoquinolones and tetrahydropyridopyridines described in U.S. Patent Application Publication No. 2008/0081803; the heteroaryl sulfonamides described in U.S. Patent Application Publication No. 2010/0056509; the triazolyl pyridyl benzenesulfonamides described in U.S. Patent Application Publication No. 2010/0152186; the bicyclic and bridged nitrogen heterocycles described in U.S. Patent Application Publication No. 2006/0074121; the fused heteroaryl pyridyl and phenyl benzenesulfonamides described in WO 09/009740; and the 3-aminopyrrolidene derivatives described in WO 04/050024.

Additional non-limiting examples of CCR2 inhibitors include: N-((1R,3S)-3-isopropyl-3-{[3-(trifluoromethyl)-7,8-dihydro-1,6-naph-thyri-din-6(5H)-yl]carbonyl}cyclopentyl)-N-[(3S,4S)-3-methoxytetrahydro-2H-pyran-4-yl]amine; 3[(3S,4R)-1-((1R,3S)-3-isopropyl-2-oxo-3-{[6-(trifluoromethyl)-2H-1,3-ben-z-oxazin-3(4H)-yl]methyl}cyclopentyl)-3-methylpiperidin-4-yl]benzoic acid; (3S,4S)-N-((1R,3S)-3-isopropyl-3-{[7-(trifluoromethyl)-3,4-dihydroisoquin-olin-2(1B)-yl]carbonyl}cyclopentyl)-3-methyltetrahydro-2H-p-yran-4-aminium; 3-[(3S,4R or 3R,4S)-1-((1R,3S)-3-Isopropyl-3-{[6-(trifluoromethyl)-2H-1,3-benzoxazin-3-(4H)-yl]carbonyl}cyclopentyl)-3-methylpiperidin-4-yl]benzoic acid; INCB3284; Eotaxin-3; PF-04178903 (Pfizer), and pharmaceutically acceptable salts thereof.

Additional non-limiting examples of CCR2 inhibitors include: bindarit (2-((1-benzyl-1H-indazol-3-yl)methoxy)-2-methylpropionic acid); AZD2423 (AstraZeneca); the indole describes described in U.S. Pat. Nos. 7,297,696, 6,962,926, 6,737,435, and 6,569,888; the bicyclic pyrrole derivatives described in 6,441,004 and 6,479,527; the CCR2 inhibitors described in U.S. Patent Application Publications Nos. 2005/0054668, 2005/0026975, 2004/0198719, and 2004/0047860, and Howard et al., *Expert Opin. Ther. Patents* 11(7):1147-1151 (2001).

Additional non-limiting examples of CCR2 inhibitors that are small molecules are described in, e.g., WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25): 15687-15692, 1998; and Howard et al., *J. Med. Chem.* 41(13):2184-2193, 1998.

In some embodiments, the CCR2 inhibitor is a small nucleic acid, e.g., NOX-E36 (a 40-nucleotide L-RNA oligonucleotide that is linked to a 40-kDa PEG; NOXXON Pharma AG).

In some embodiments, the CCR2 inhibitor is a peptide, e.g., a dominant negative peptide described in, e.g., Kiyota et al., *Mol. Ther.* 17(5):803-809, 2009, and U.S. Patent Application Publication No. 20070004906, or an antagonistic peptide, e.g., the antagonistic peptides described in WO 05/037305 and Jiang-Hong Gong, et al., *J. Exp. Med.* 186:131, 1997. Additional examples of CCR2 inhibitors that are peptides are described in, e.g., U.S. Pat. No. 5,739,103; WO 96/38559; WO 98/06751; and WO 98/09642. In some embodiments, a CCR2 inhibitor is a CCR2 mutein (e.g., U.S. Patent Application Publication No. 2004/0185450).

Additional examples of CCR2 inhibitors that are small molecules and peptides are known in the art.

CCR9 Inhibitors

As used herein "CCR9" or "CC chemokine receptor 9" can be used interchangeably. CCR9 specifically binds to CCL25.

The term "CCR9 inhibitor" refers to an agent which decreases the ability of CCR9 to bind to CCL25.

In some embodiments, the CCR9 inhibitor can decrease the binding between CCL25 and CCR9 by blocking the ability of CCL25 to interact with CCR9. In some instances, the CCR9 inhibitor is a small molecule. In some instances, the CCR9 inhibitor is an antibody or an antigen-binding antibody fragment.

CCR9 Inhibitors—Antibodies

In some embodiments, the CCR9 inhibitor is an antibody or an antigen-binding fragment thereof (e.g., a Fab or a scFv). In some embodiments, an antibody or antigen-binding fragment described herein binds specifically to CCR9. In some embodiments, an antibody or antigen-binding fragment described herein binds specifically to CCL25. In some embodiments, an antibody or antigen-binding fragment described herein binds specifically to both CCR9 and CCL25.

In other instances, the CCR9 inhibitor is a monoclonal antibody. For example, the CCR9 antibody can be 91R, see, e.g., Chamorro et al., *MAbs* 6(4): 1000-1012, 2014. Additional non-limiting examples of CCR9 inhibitors are described in, e.g., U.S. Patent Application Publication Nos. 2012/0100554, 2012/0100154, 2011/0123603, 2009/0028866, and 2005/0181501.

CCR9 Inhibitors—Small Molecules

In some instances, the CCR9 inhibitor is a small molecule. For example, the CCR9 inhibitor can be Traficet-EN® (also called Vercirnon, CCX282, and GSK1605786) or Tu1652 CCX507. See, e.g., Eksteen et al., *IDrugs* 13(7): 472-481, 2010; and Walters et al., *Gastroenterology* 144(5): S-815, 2013.

Additional examples of CCR9 inhibitors that are small molecules are known in the art.

ELR Chemokine Inhibitors

ELR chemokines are CXC chemokines that have a glutamic acid-leucine-arginine (ELR) motif. See, e.g., Strieter et al., *J. Biol. Chem.* 270:27348-27357, 1995.

The term "ELR chemokine inhibitor" refers to an agent which decreases the ability of CXCR1 and/or CXCR2 to bind to one or more (e.g., two, three, four, five, six, seven, or eight) of CXCL1, CXCL2, CXCL3, CXCL4, CXCL5, CXCL6, CXCL7, and CXCL8.

In some embodiments, the ELR chemokine inhibitor can decrease the binding between CXCR1 and CXCL8 by blocking the ability of CXCR1 to interact with CXCL8. In some embodiments, the ELR chemokine inhibitor can decrease the binding between CXCR1 and CXCL6 by blocking the ability of CXCR1 to interact with CXCL6. In some embodiments, the ELR chemokine inhibitor can decrease the binding between CXCR1 and each of CXCL8 and CXCL6.

In some embodiments, the ELR chemokine inhibitor can decrease the binding between CXCR2 and CXCL1 by blocking the ability of CXCR2 to interact with CXCL1. In some embodiments, the ELR chemokine inhibitor can decrease the binding between CXCR2 and CXCL2 by blocking the ability of CXCR2 to interact with CXCL2. In some embodiments, the ELR chemokine inhibitor can decrease the binding between CXCR2 and CXCL3 by blocking the ability of CXCR2 to interact with CXCL3. In some embodiments, the ELR chemokine inhibitor can decrease the binding between CXCR2 and CXCL4 by blocking the ability of CXCR2 to interact with CXCL4. In some embodiments, the ELR chemokine inhibitor can decrease the binding between CXCR2 and CXCL5 by blocking the ability of CXCR2 to interact with CXCL5. In some embodiments, the ELR chemokine inhibitor can decrease the binding between CXCR2 and CXCL6 by blocking the ability of CXCR2 to interact with CXCL6. In some embodiments, the ELR chemokine inhibitor can decrease the binding between CXCR2 and CXCL7 by blocking the ability of CXCR2 to interact with CXCL7. In some embodiments, the ELR chemokine inhibitor can decrease the binding between CXCR2 and one or more (e.g., two, three, four, five, six, or seven) of CXCL1, CXCL2, CXCL3, CXCL4, CXCL5, CXCL6, and CXCL7.

In some embodiments, the ELR chemokine inhibitor can decrease the binding of CXCR1 to one or both of CXCL6 and CXCL8, and can decrease the binding to CXCR2 to one or more (e.g., two, three, four, five, six, or seven) of CXCL1, CXCL2, CXCL3, CXCL4, CXCL5, CXCL6, and CXCL7.

In some instances, the ELR chemokine inhibitor is a small molecule. In some instances, the ELR chemokine inhibitor is an antibody or an antigen-binding antibody fragment.

ELR Chemokine Inhibitors—Antibodies

In some embodiments, the ELR chemokine inhibitor is an antibody or an antigen-binding fragment thereof (e.g., a Fab or a scFv). In some embodiments, an antibody or antigen-binding fragment described herein binds specifically to CXCR1 and/or CXCR2. In some embodiments, an antibody or antigen-binding fragment described herein binds specifically to one or more (e.g., two, three, four, five, six, seven, or eight) of: CXCL1, CXCL2, CXCL3, CXCL4, CXCL5, CXCL6, CXCL7, and CXCL8 (IL-8).

An ELR chemokine inhibitor can be, e.g., a monoclonal antibody. A non-limiting example of an ELR inhibitor is TAB-099MZ. Additional examples of ELR chemokine inhibitors that are antibodies or antigen-binding antibody fragments are described in, e.g., U.S. Pat. No. 9,290,570; and U.S. Patent Application Publication Nos. 2004/0170628, 2010/0136031, 2015/0160227, 2015/0224190, 2016/0060347, 2016/0152699, 2016/0108117, 2017/0131282, 2016/0060347, 2014/0271647, 2014/0170156, 2012/0164143, 2010/0254941, 2009/0130110, 2008/0118517, 2004/0208873, 2003/0021790, 2002/0082396, and 2001/0006637, each of which is herein incorporated by reference (e.g., the portions describing ELR chemokine inhibitors).

ELR Chemokine Inhibitors—Small Molecules

In some instances, the ELR chemokine inhibitor is, e.g., a small molecule. For example, the ELR chemokine inhibitor can be, e.g., LY-3041658 or repertaxin (Reparixin; DF 1681Y). Additional non-limiting examples of ELR chemokine inhibitors that are small molecules are described in, e.g., U.S. Patent Application Publication Nos. 2007/0248594, 2006/0014794, 2004/0063709, 2004/0034229, 2003/0204085, 2003/0097004, 2004/0186142, 2004/0235908, 2006/0025453, 2017/0224679, 2017/0190681, 2017/0144996, and 2017/0128474, each of which are incorporated by reference (e.g., the portions describing the ELR chemokine inhibitors).

In some embodiments, the ELR chemokine inhibitor is a peptide, e.g., any of the peptides described in U.S. Patent Application Publication Nos. 2009/0270318, 2009/0118469, and 2007/0160574, 2007/0021593, 2003/0077705, and 2007/0181987, each of which is incorporated by reference (e.g., the portions describing the ELR chemokine inhibitors).

Combination Detection

Any combination of the analytes, e.g., bacteria, biomarkers, and/or drugs disclosed herein can be detected using any of the methods described herein. For example, the methods and devices disclosed herein can be used to detect combinations of analytes such as a biomarker indicative of a GI disorder and a drug used to treat the GI disorder. The methods and devices can be used to detect a drug disclosed above and another drug, e.g., another drug used in combination with the first drug. Examples of such drugs include 2-amino-6-aryl-5-substituted pyrimidines (see U.S. Pat. No. 4,665,077); non-steroidal antiinflammatory drugs (NSAIDs); ganciclovir; tacrolimus; lucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-ME-DROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD 11a and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002) and see also definition below); biologic agents that interfere with T cell helper signals, such as anti-CD40 receptor or anti-CD40 ligand (CD 154), including blocking antibodies to CD40-CD40 ligand. (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Non-limiting examples of drugs that may be detected using any of the methods described herein also include: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinyl-imidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TP1O; T Cell Sciences, Inc.); slow-release mesalazine; antagonists of platelet activating factor (PAF); ciprofloxacin; and lignocaine. Examples of drugs that can be detected using the presently claimed methods include sulfasalazine, related salicylate-containing drugs, and corticosteroids. In some embodiments, the methods described herein can be used to detect iron, antidiarrheal agents, azathioprine, 6-mercaptopurine, and/or methotrexate.

In other embodiments, the methods described herein can provide for detection of a TNF inhibitor as described herein and one or more of: a CHST15 inhibitor, a IL-6 receptor inhibitor, an IL-12/IL-23 inhibitor, an integrin inhibitor, a JAK inhibitor, a SMAD7 inhibitor, a IL-13 inhibitor, an IL-1 receptor inhibitor, a TLR agonist, an immunosuppressant, a live biotherapeutic (e.g., bacteria of the species *Roseburia hominis*, *Eubacterium rectale*, *Dialister invisus*, *Ruminococcus albus*, *Ruminococcus callidus*, and *Ruminococcus bromii*), or a stem cell.

Analyte-Binding Agents

Certain detection methods described below can utilize at least one analyte-binding agent in order to detect an analyte in a sample. An "analyte-binding agent" is a molecule that binds to a specific analyte. Some analyte-binding agents may comprise analytes (e.g., the analytes described above) in accordance with the ability of the analyte to bind to another molecule to be detected using the methods described below. For example, in some embodiments, the analyte-binding agent comprises an antibody when used as a reagent to detect and/or quantify an antigen that the antibody specifically binds to. However, in some embodiments, the antibody is an analyte (e.g., an antibody which is a drug, such as a TNFα antibody) and the analyte-binding agent comprises an antigen to which the antibody specifically binds, thereby allowing for its use as a reagent to detect and/or quantify the antibody. In some embodiments, the analyte-binding agent binds to analyte that is specific to a particular genus, species, or strain of a microorganism (e.g., a pathogenic bacteria). In some embodiments, an analyte-binding agent has an area on the surface or in a cavity which specifically binds to and is thereby defined as complementary with a particular spatial and polar organization of the analyte. In some embodiments, the analyte-binding agent and the corresponding analyte form a binding pair, such as, but not limited to, an immunological pair (such as antigen-antibody), a biotin-avidin pair, a hormone-hormone receptor pair, a nucleic acid duplex, IgG-protein A pair, a polynucleotide pair such as DNA-DNA, DNA-RNA, and the like. In some embodiments, the analyte-binding agent comprises an antibody (e.g., a monoclonal antibody), an affimer, an aptamer, an antigen, a receptor, a small molecule, and a nucleic acid (e.g., a DNA molecule or an RNA molecule). In some embodiments, either member of the binding pair (e.g., the analyte-binding agent and/or the analyte) can be detectably labeled as described herein.

In some embodiments, the analyte-binding agent comprises a portion of a nucleic acid that is complementary to the nucleic acid sequence of the target analyte. As used herein, "complementary" refers to the capacity for pairing through hydrogen binding between two nucleic acid sequences. For example, if a nucleic acid base at one position of the target analyte is capable of hydrogen bonding with a nucleic acid base at a corresponding position of an analyte-binding agent, then the bases are considered to be complementary to each other at that position. In some embodiments, 100% complementarity is not required. In some embodiments, 100% complementarity is required. Routine methods can be used to design an analyte-binding agent that binds to a nucleic acid sequence of a target analyte. In some embodiments, the analyte-binding agent comprises a nucleic acid sequence that is complementary to at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65 or more contiguous nucleotides or nucleosides present in the nucleic acid sequence of the target analyte (e.g., a DNA molecule or an RNA molecule). In general, the analyte-binding agents useful in the devices and methods described herein have at least 80% sequence complementarity to a nucleic acid sequence of a target analyte, e.g., at least 85%, at least 90%, at last 92%, at least 94%, at least 95%, at least 96%, at least 97%, at least 98%, at least 99%, or are 100% complementary to a nucleic acid sequence of a target analyte).

In some embodiments, the analyte-binding agent comprises a detectable moiety such as a photosensitizer, a fluorescent compound, and/or chemiluminescent compound described herein. In some embodiments, the analyte-binding agent is capable of being detected by a detection system of a device described herein, e.g., an optical detection system.

Ingestible Devices

Ingestible devices and their use are described, for example, in the following U.S. patent applications, each of which is hereby incorporated by reference: U.S. Ser. No. 14/460,893, entitled "Ingestible Medical Device," and filed Aug. 15, 2014; U.S. Ser. No. 15/514,413, entitled "Electromechanical Pill Device with Localization Capabilities," and filed Mar. 24, 2017; U.S. Ser. No. 15/680,400, entitled "Systems and Methods for Obtaining Samples using Ingestible Devices," filed on Aug. 18, 2017; U.S. Ser. No. 15/680,430, entitled "Sampling Systems and Related Materials and Methods," filed on Aug. 18, 2017; U.S. Ser. No. 15/699,848, entitled "Electromechanical Ingestible Delivery of a Dispensable Substance," filed on Sep. 8, 2017; U.S. Ser. No. 62/480,187, entitled "Localization Systems and Methods for an Optoelectromechanical Pill Device," filed on Mar. 31, 2017; and U.S. Ser. No. 62/540,873, entitled "Localization Systems and Methods for an Ingestible Device," filed on Aug. 3, 2017.

In general, an ingestible device is configured to be able to enter the GI tract (e.g., via the mouth) and collect one or more samples while passing through one or more regions of the GI tract. Optionally, the device can include one or more additional functionalities, including the ability to analyze the sample while in the GI tract of the subject (in vivo), the ability to deliver a substance (e.g., a therapeutic agent) while in the GI tract of the subject (in vivo) and/or the ability to locate the device outside the GI tract of the subject (ex vivo).

The ingestible device described herein may generally be in the shape of a capsule, like a conventional pill. In some embodiments, the device is an ingestible device. In some embodiment, the device is for insertion and removal from the reproductive tract. Accordingly, the shape of the device provides for easier ingestion, or insertion and removal, and is also familiar to healthcare practitioners and patients.

Unlike a conventional pill, the device is designed to withstand the chemical and mechanical environment of the GI tract (e.g., effects of muscle contractile forces and concentrated hydrochloric acid in the stomach) or reproductive tract. However, unlike other devices that are intended to stay inside a patient's body (e.g., medical implants), the ingestible device is designed (in general) to only temporarily travel within the body, or to be selectively inserted and removed from the body in the case of the female reproductive tract. Accordingly, the regulatory rules governing the materials and manufacture of the ingestible device may be less strict than for the devices that are intended to stay inside the body. Nevertheless, since the ingestible device still enters the body, the material(s) used to manufacture the ingestible device are generally selected to at least comply with the standards for biocompatibility (e.g., ISO 10993). Furthermore, components inside the ingestible device are free of any restricted and/or toxic metals and are lead-free pursuant to the Directive 2002/95/EC, which is also known as the Restriction of Hazardous Substances (RoHS).

There is a broad range of materials that may be used for manufacturing the ingestible device. Different materials may be used for each of the different components of the ingestible device. Examples of these materials include, but are not limited to, thermoplastics, fluoropolymers, elastomers, stainless steel and glass complying with ISO 10993 and USP Class VI specifications for biocompatibility. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Use of different materials for different components may enable functionalization of certain surfaces for interaction with proteins, antibodies, and other biomarkers. For example, Teflon® may be used as a material in the ingestible device for any movable components in order to reduce friction between these components. Other example materials may include other materials commonly used in micro-fabrication, such as polydimethylsiloxane (PDMS), borosilicate glass, and/or silicon.

Generally, an enclosure of the ingestible device may be manufactured from a type of plastic, such as a photosensitive acrylic polymer material. The enclosure may be formed by coupling two enclosure ends together. The enclosure, in effect, protects the interior of the ingestible device from its external environment and also protects the external environment (e.g., the GI tract or reproductive tract) from components inside the device.

Furthermore, the device may include one or more additional layers of protection. The additional protection may protect the patient against any adverse effects arising from any structural problems associated with the enclosure (e.g., the two enclosure ends falling apart or a fracture developing in the enclosure). For example, a power supply inside the device may be coated with an inert and pliable material (e.g., a thin layer of silicone polymer) so that only electrical contacts on the power supply are exposed. This additional protection to the power supply may prevent chemicals inside the device from seeping into the patient's body.

Also, a surface of the device and surfaces of the different components in the device may receive different treatments that vary according to their intended use. For example, the surface of the device may receive plasma activation for increasing hydrophilic behavior. Dilution chambers, storage components, ports, valves, pumps and/or conduits that are intended to come into contact with a fluid such as biological fluid or dilution fluid during normal operation of the device may also receive hydrophilic treatment while certain other components may receive hydrophobic treatments.

FIG. 1 illustrates an example ingestible device 100 with multiple openings in the housing. The ingestible device 100 has an outer housing with a first end 102A, a second end 102B, and a wall 104 extending longitudinally from the first end 102A to the second end 102B. Ingestible device 100 has a first opening 106 in the housing, which is connected to a second opening 108 in the housing. The first opening 106 of the ingestible device 100 is oriented substantially perpendicular to the second opening 108, and the connection between the first opening 106 and the second opening 108 forms a curved chamber 110 within the ingestible device 100.

The overall shape of the ingestible device 100, or any of the other ingestible devices discussed in this disclosure, may be similar to an elongated pill or capsule. This may make the ingestible device 100 easy to consume, and allow it to travel easily through the GI tract. In certain portions of the GI tract, such as the stomach, the ingestible device 100 may be free to move or rotate in any direction. In other portions of the GI tract, the movement of the ingestible device 100 may be restricted. For example, in the relatively narrow confines of the small intestine, the walls of the small intestine may squeeze down on the ingestible device, forcing the ingestible device 100 to orient itself longitudinally along the length of the small intestine. In this case, the walls of the small intestine wrap around the longitudinally extending wall 104 of the ingestible device 100, and the ingestible device 100 travels through the small intestine with one of the ends 102A or 102B in front.

For illustrative purposes, the ingestible device 100 of FIG. 1 shows the first opening 106 located in a portion of the wall 104 and oriented radially, and the second opening 108 located near the first end 102A and oriented longitudinally. However, in some embodiments, the exact location and orientation of the first opening 106 and the second opening 108 may be different from that shown in FIG. 1. During transit through the GI Tract, natural contractions within the small intestine may apply pressure radially to different portions of the wall 104 of the ingestible device 100, which may force solids or fluids into the first opening 106. As new material (e.g., fluid and solid particulates from the small intestine or other portions of the GI tract) enters the curved chamber 110 through the first opening 106, older material already located in the curved chamber 110 may be naturally forced out of the curved chamber 110 through the second opening 108.

In some embodiments, a portion of the curved chamber 110 may be used as a sampling chamber, which may hold samples obtained from the GI tract. In some embodiments the curved chamber 110 is subdivided into sub-chambers, each of which may be separated by a series of one or more valves or interlocks. For example, sub-chambers may be used to retain multiple samples within different portions of the curved chamber 110. In some embodiments, the curved chamber 110 is connected to other chambers within the ingestible device 100, or other openings located on the housing of the ingestible device 100. This may allow new samples to be acquired in the curved chamber 110 while older samples of interest are still stored within the ingestible device 100. In some embodiments, the ingestible device 100 is equipped with sensors to detect the properties a sample contained in the sampling chamber, or the results of an assay technique applied to the sample. In some embodiments, the ingestible device 100 is configured to obtain and retain a sample within the sampling chamber, which may be retrieved at a later time.

In some embodiments, the first opening 106, the second opening 108, or the curved chamber 110 include one or more of a hydrophilic or hydrophobic material, a sponge, a valve, or an air permeable membrane. For example, a one-way valve may prevent material from entering the curved chamber 110 through the second opening 108. As an alternate example, placing an air permeable membrane within the curved chamber 110 near the second opening 108 may allow unwanted gasses and air bubbles to pass through the air permeable membrane and exit the curved chamber 110, while solid or liquid samples may be prevented from passing through the air permeable membrane, and are retained within the curved chamber 110. The air permeable membrane may also prevent solid or liquid samples from entering the curved chamber 110 through the second opening 108.

The use of a hydrophilic material or sponge may allow samples to be retained within the curved chamber 110, and may reduce the amount of pressure needed for fluid to enter through the first opening 106 and dislodge air or gas in the curved chamber 110. Examples of hydrophilic materials that may be incorporated into the ingestible device 100 include hydrophilic polymers such as polyvinyl alcohol, polyvinyl pyrrolidone, and the like. Similarly, materials that have undergone various types of treatments, such as plasma treatments, may have suitable hydrophilic properties, and may be incorporated into the investible device 100. Sponges may be made of any suitable material or combination of materials, such as fibers of cotton, rayon, glass, polyester, polyethylene, polyurethane, and the like. Sponges generally may be made from commercially available materials, such as those produced by Porex®.

In some embodiments, the sponges may be treated in order to change their absorbency or to help preserve samples. Examples of materials which may be used to treat the sponges, alone or in combination, include sorbic acid, propyl parabene, citric acid, surfactants such as Tween® (polysorbate), DNA inhibitors and stabilizers, RNA inhibitors and stabilizers, protein inhibitors and stabilizers, and the like. In some embodiments, the sponges may be cut or abraded to change their absorbency or other physical properties.

Hydrophobic materials located near the second opening 108 may repel liquids, discouraging liquid samples from entering or exiting the curved chamber 110 through the second opening 108. This may serve a similar function as an air permeable membrane. Examples of hydrophobic materials which may be incorporated into the ingestible device 100 include polycarbonate, acrylics, fluorocarbons, styrenes, certain forms of vinyl, and the like.

The various materials listed above are provided as examples, and are not limiting. In practice, any type of suitable hydrophilic, hydrophobic, or sample preserving material may be used in the ingestible device 100, and the teachings discussed in relation to ingestible device 100 may be incorporated into any of the other ingestible devices described in this disclosure. Various methods for taking samples, controlling the movement of samples, or removing unwanted gasses, are discussed in detail in relation to FIGS. 2-9, and any of the various structures or techniques described in connection with FIGS. 2-9 may be incorporated into the ingestible device 100.

Figure 2:
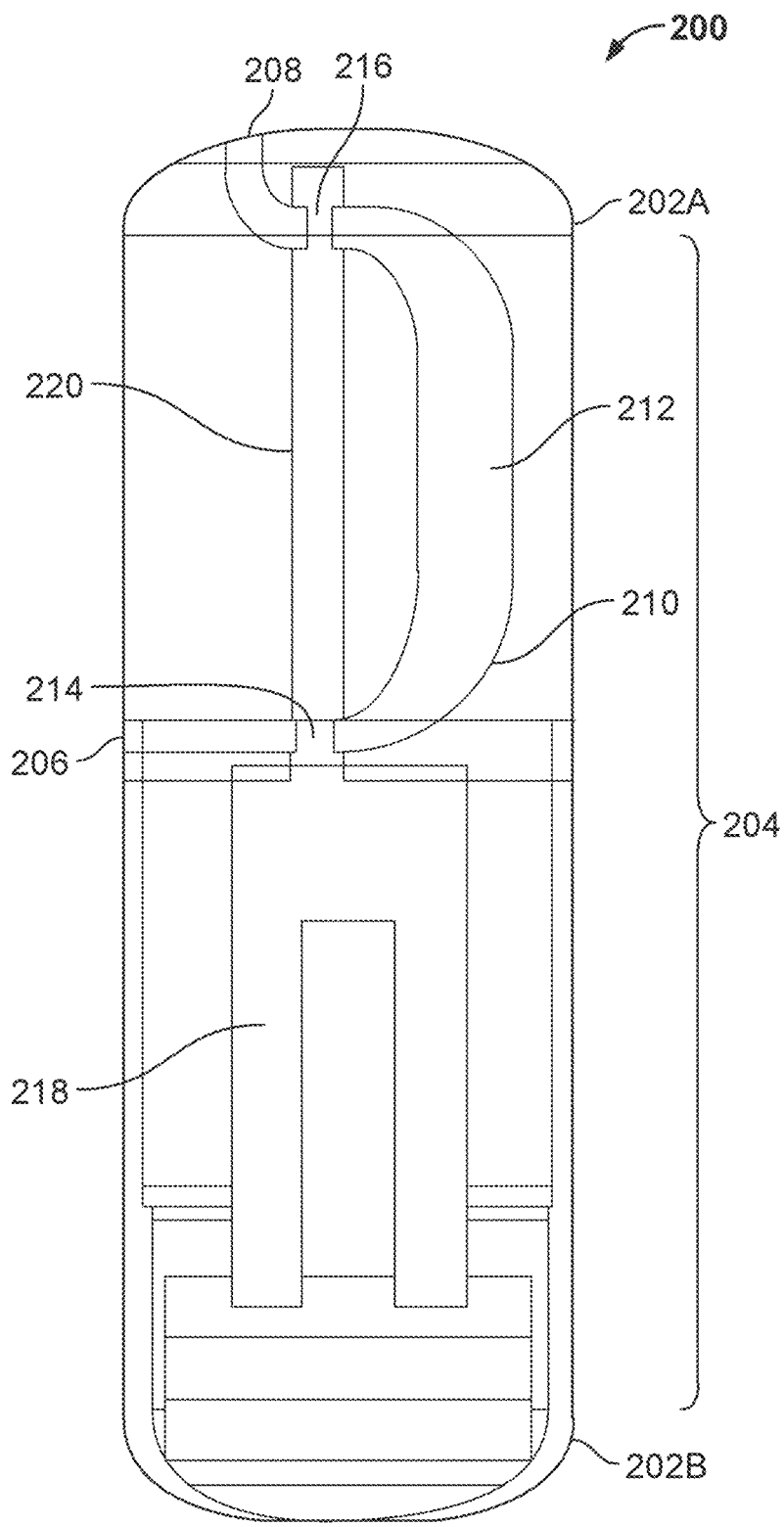
FIG. 2 shows an ingestible device.

FIG. 2 illustrates an example ingestible device 200 with multiple openings in the housing and various modifications that may be made to the ingestible device 100 (FIG. 1). Similar to the ingestible device 100, the ingestible device 200 has an outer housing with a first end 202A, a second end 202B, and a wall 204 extending longitudinally from the first end 202A to the second end 202B. Also similar to the ingestible device 100, the ingestible device 200 has a first opening 206 in the housing, which is connected to a second opening 208 in the housing. The connection between the first opening 206 and the second opening 208 forms a curved chamber 210 within the ingestible device 200.

In the ingestible device 200, a portion of the curved chamber 210 forms a sampling chamber 212. In some embodiments, the ingestible device 200 may include a sensor (not shown) within or proximate to the sampling chamber. This sensor may be used to detect a property of the sample. In some embodiments, an assay technique is applied to a sample within the sampling chamber, and the sensor may be used to detect the results of the assay technique. A first valve 214 is located between the first opening 206 and the sampling chamber 212. Similarly, a second valve 216 is located between the second opening 208 and the sampling chamber 212. In some embodiments, the valves 214 and 216 prevent a fluid from entering or exiting the sampling chamber 212, or may be used to isolate a sample within the sampling chamber 212.

The ingestible device 200 includes a mechanical actuator 218 coupled to the valves 214 and 216. In some embodiments, the mechanical actuator 218 is used to move one or both of the valves 214 and 216 between an open and a closed position. In some embodiments, the mechanical actuator 218 is controlled by a microcontroller, microprocessor, or other circuitry inside the ingestible device 200. In an open position, the first valve 214 may allow a sample to pass in and out of the sampling chamber 212 through the portion of the curved chamber 210 connected to the first opening 206. Similarly, in an open position, the second valve 216 may allow a sample to pass in and out of the sampling chamber 212 from the portion of the curved chamber 210 connected to the second opening 208. When the valves 214 and 216 are in the closed positions, they may not allow a sample to pass into or out of the sampling chamber 212.

In some embodiments, the valves 214 and 216 are rotary valves, pin valves, flap valves, butterfly valves, ball valves, plug valves, or any other suitable type of one-way or two-way valves, and may be the same or different types of valves. In some embodiments, one or both of the valves 214 and 216 are automatic valves that reseal themselves after a sample has been obtained, similar to the osmotic valve mechanism discussed in relation to FIG. 3. In some embodiments, one or both of the valves 214 and 216 include a pumping mechanism, such as the pumping mechanism discussed in relation to FIG. 9. For illustrative purposes, the ingestible device 200 is depicted with both of the valves 214 and 216 as moveable two-way valves coupled to the mechanical actuator 218. However, in some embodiments, the mechanical actuator 218 is coupled to only one of the valves, and the other valve may be replaced with a passive one-way valve. For example, the mechanical actuator 218 may be coupled to only the first valve 214, and the second valve 216 may be replaced with a passive one-way valve that allows gases, fluids, or solids to exit the sampling chamber 212 through the portion of the curved chamber 210 connected to the second opening 208. This may restrict fluid from entering the sampling chamber 212 from the second opening 208, but allow unwanted material to be removed from the sampling chamber 212 as the sample is obtained.

In some embodiments, the ingestible device 200 may be able to detect the approximate location of the ingestible device 200 within the GI tract. For example, it may be possible to use various combinations of light emitting diodes and sensors positioned along the ingestible device 200 to determine whether the device is in the stomach, small intestine, or large intestine. Methods for determining the location of an ingestible device within a GI tract are described in greater detail elsewhere herein. In these embodiments, the ingestible device 200 may be configured to use the mechanical actuator 218 to move the valves 214 and 216 into an open position in response to determining that the ingestible device 200 has reached a predetermined location within the GI tract. For example, a microcontroller on board the ingestible device 200 may be configured to open the valves 214 and 216 only when the ingestible device 200 is within the small intestine, thereby obtaining a sample from within the small intestine.

For illustrative purposes, the ingestible device 200 is depicted with the mechanical actuator 218, the first valve 214, and the second valve 216 oriented in a substantially straight line, with a single shaft 220 being used to couple the mechanical actuator 218 to the valves 214 and 216. However, in some embodiments, the orientation and/or positioning of the valves 214 and 216 relative to the position of the mechanical actuator 218 may be different than that shown, and the coupling of the mechanical actuator 218 to the valves 214 and 216 may also be different. In some embodiments, the mechanical actuator 218 simultaneously moves the valves 214 and 216. For example, in some embodiments the valves 214 and 216 are rotary valves, and they may be simultaneously opened and closed by rotating the shaft 220 that extends from the mechanical actuator 218 along the length of the ingestible device 200. As an alternate example, the valves 214 and 216 may be pin valves, and the pins may be attached to the shaft 220 that extends from the mechanical actuator 218 along the length of the ingestible device 200. In this case, the mechanical actuator 218 may open and close the valves by moving the shaft 220 linearly. This may be accomplished either by configuring mechanical actuator 218 to be a linear actuator, such as a solenoid. Alternately, the mechanical actuator 218 may be a rotary actuator, and the rotation may be converted into a linear motion. One skilled in the art will understand that this may be done any number of ways, for example, by coupling the mechanical actuator 218 to a ball screw mechanism, a threaded lead nut and lead screw mechanism, a rack and pinion mechanism, or the like.

In some embodiments, the ingestible device 200 does not include the second valve 216 at all. In this case, fluids and solids contained within the sampling chamber 212 may be free to exit through the second opening 208. Alternately, the second valve 216 near the second opening 208 may be replaced by an air-permeable membrane, which may allow gasses and unwanted air bubbles to exit the sampling chamber 212 through the second opening 208, while still retaining fluids and/or solids within the sampling chamber 212. Alternately, the second valve 216 near the second opening 208 may be replaced with a hydrophobic material. Similar to an air permeable membrane, an appropriately positioned hydrophobic material may be used to line the walls of the curved chamber 210 proximate to the second opening 208, which may allow gasses or unwanted air bubbles to exit the sampling chamber 212 through the second opening 208, while restricting some fluids from entering or exiting the sampling chamber 212 through the second opening 208. In some embodiments, one or more of the above described mechanisms may be combined in the same ingestible device. For example, the ingestible device 200 may implement the second valve 216 as a two-way valve, and also have hydrophobic material and an air-permeable membrane located near the second opening 208.

In some embodiments, the curved chamber 210 is connected to one or more sub-chambers (not shown). Each of these sub-chambers may be configured to hold one or more samples, and isolate the samples from both the sampling chamber 212, and the other sub-chambers. For example, each sub-chamber may be connected to the curved chamber 210 through a one-way valve, allowing samples to enter the sub-chamber from the curved chamber 210, but preventing the obtained samples from exiting the sub-chamber and re-entering either the curved chamber 210 or the sampling chamber 212. In general, any type of valve or other suitable mechanism may be used to isolate samples contained in the sub-chambers. In some embodiments, the ingestible device 200 distributes different samples into different sub-chambers at different times, or from different locations of the GI tract. For example, the ingestible device 200 may obtain a sample from the duodenum and distribute it into a first sub-chamber, and the ingestible device 200 may later obtain a sample from the ileum and distribute it into a second sub-chamber. In some embodiments, different types of assay techniques or diagnostics are applied to some of the samples contained in the different sub-chambers.

Figure 3:
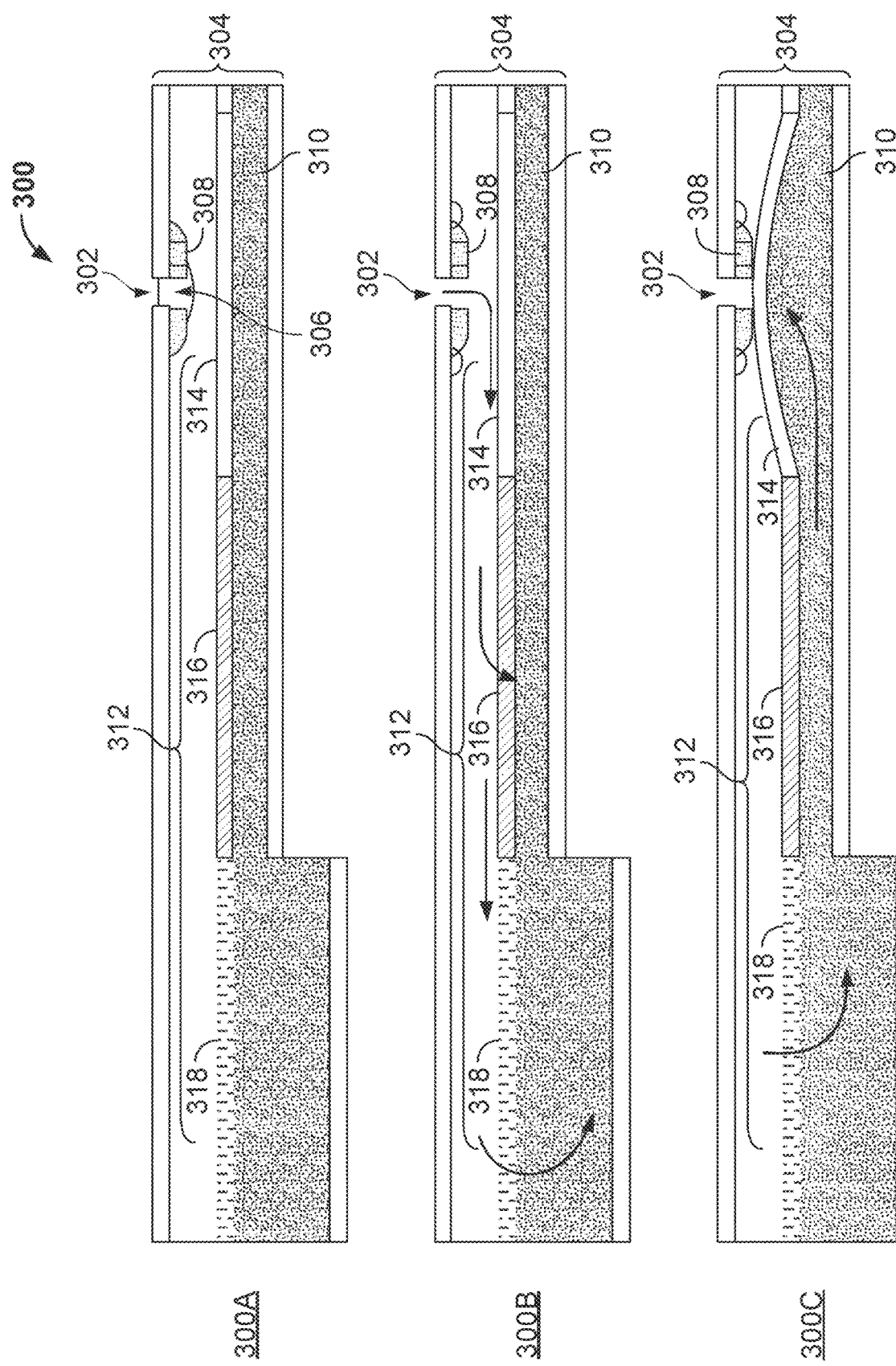
FIG. 3 shows a valve.

FIG. 3 illustrates an example of an osmotic valve mechanism 300, which may be incorporated into an ingestible device in order to obtain samples. The osmotic valve mechanism 300 may be used in an ingestible device that features a first end, a second end, and a wall extending longitudinally between the first end and the second end, similar to the shape of the ingestible devices 100 (FIG. 1) and 200 (FIG. 2).

The osmotic valve mechanism 300 includes an inlet port 302, which is connected to a sampling chamber 304. In some embodiments, the inlet port 302 connects sampling chamber 304 directly or indirectly to an opening in the housing of an ingestible device.

The initial state of the osmotic valve mechanism 300 is shown in diagram 300A. As shown in diagram 300A, the inlet port 302 of the osmotic valve mechanism 300 is sealed using a single use sealing device 306 positioned within the inlet port 302. The single use sealing device 306 is positioned adjacent to a heating element 308. When it is time for the osmotic valve mechanism 300 to be opened (which may be determined by a localization mechanism that determines the ingestible device is located in a desirable portion of the GI tract), the heating element 308 applies heat to the sealing device 306, causing the sealing device 306 to deform and unseal the inlet port 302.

Figure 4:
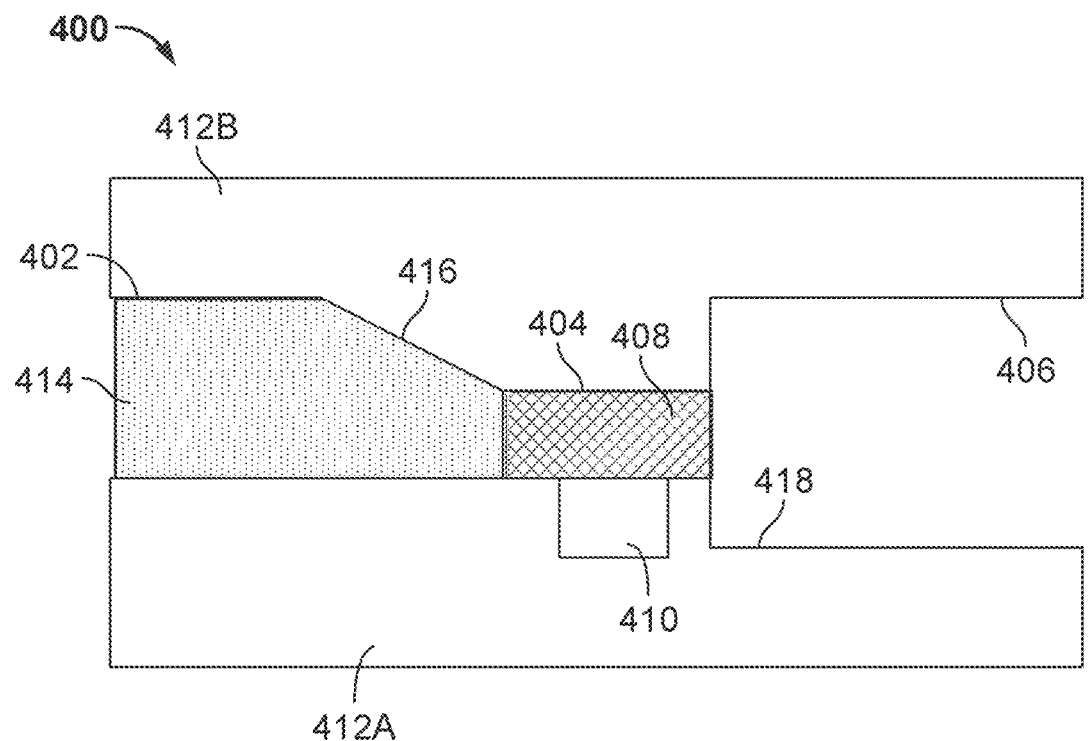
FIGS. 4 and 5 illustrate operation of a valve.
Figure 5:
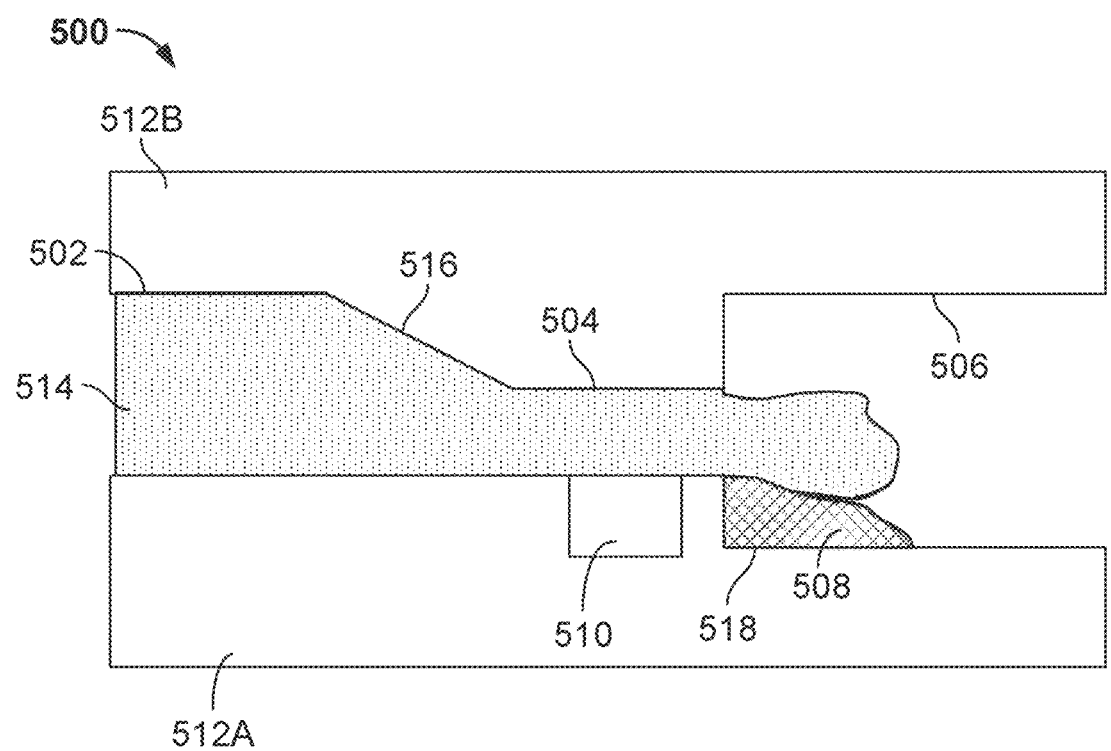

In some embodiments, the sealing device 306 may be a plug made out of a material that is meltable, deformable, and/or destroyable through the use of the heating element 308, such as wax. For example, in some embodiments, the heating element 308 may be a resistive heater that undergoes ohmic heating as an electrical current is passed through it, and the sealing device 306 is a wax plug. In some embodiments, the type of wax used to form the wax plug has a melting point between 38 degrees and 80 degrees Celsius, which is above the ambient temperature of a human body, but which may be easily achieved using the heating element 308. Some embodiments of the osmotic valve mechanism 300 may use a sealing device 306 that is melted or deformed at temperatures outside of the range described above, but practical considerations may be made to ensure that the osmotic valve mechanism 300 does not cause unwanted damage or burning to the GI tract. In some embodiments, a microprocessor is configured to control the heating element 308, causing it to generate heat. For example, the microprocessor may be configured to activate the heating element 308 once the ingestible device reaches a particular location within the GI tract. An example mechanism for unsealing the inlet port 302 is described in greater detail in relation to FIGS. 4 and 5. Although FIGS. 3, 4, and 5 depict the sealing device 306 as a type of plug, any type of suitable sealing device may be used. For example, in some embodiments, the sealing device includes a breakable membrane, which may be destroyed when heat is applied to the membrane. In some embodiments, the osmotic valve mechanism 300 does not include a heating element 308, and the sealing device 306 is melted, deformed, destroyed, or dislodged from the inlet port 302 by a mechanical actuator, or through electromagnetic fields. For example, the sealing device 306 may be a membrane that will rupture when a sufficiently large electrical current or magnetic field is applied to the membrane.

Inside the sampling chamber 304 of the osmotic valve mechanism 300 is made of a member including an absorptive material 310, and at least a portion of the absorptive material 310 is located near the inlet port 302. The absorptive material 310 may include any suitable sponge material or hydrophilic material, such as any of the materials described in relation to FIG. 1. The portion of the absorptive material 310 located near the inlet port 302 may have a tendency to expand when it comes into contact with fluids. The osmotic valve mechanism 300 has a barrier 312 inside the sampling chamber 304, which is divided into three portions. The first portion of the barrier 312 is a flexible membrane 314, the second portion of the barrier 312 adjacent to the flexible membrane 314 is a rigid portion 316, and the third portion of the barrier 312 adjacent to the rigid portion 316 is a semi-permeable membrane 318.

The barrier 312 within the sampling chamber 304 is positioned between the inlet port 302 and the absorptive material 310, covering a surface of the absorptive material 310. When the inlet port 302 is unsealed, a sample (e.g., a fluid sample containing solid particulates taken from the GI tract) enters the sampling chamber 304 through the inlet port 302, and begins to fill the sampling chamber 304. The absorptive material 310 may have a natural tendency to expand when it comes into contact with a fluid sample. However, by covering a surface of the absorptive material 310, the barrier 312 may allow only certain portions of absorptive material 310 to expand. The barrier 312 may also direct the flow of a fluid sample as it enters the sampling chamber 304, and allow the fluid sample to come into contact with only certain parts of the absorptive material 310.

Diagram 300B shows the osmotic valve mechanism 300 shortly after the inlet port 302 is unsealed. Once the inlet port 302 is unsealed, the sampling chamber 304 may be opened, and a sample may enter the sampling chamber 304 through the inlet port 302. In some embodiments, the sample cannot cross the flexible membrane 314 and contact the absorptive material 310. As a result, the flexible membrane 314 may be used to guide the sample as it enters the sampling chamber 304. Similarly, in some embodiments the sample cannot cross the rigid portion 316 of the barrier 312, and the rigid portion 316 may also be used to guide the sample as it enters the sampling chamber 304. The semi-permeable membrane 318 allows at least a portion of the sample to pass through the semi-permeable membrane and contact the absorptive material 310. This may allow the sample to be absorbed by the absorptive material 310 after the sample has filled the top portion of the sampling chamber 304, which in turn may cause the absorptive material 310 to begin to expand.

Diagram 300C shows the state of the osmotic valve mechanism 300 after the absorptive material 310 has absorbed a portion of the sample. The portion of the absorptive material 310 under the flexible membrane 314 expands when the absorptive material 310 absorbs the sample. As the absorptive material 310 expands, the flexible membrane 314 is forced up against the inlet port 302, effectively sealing the inlet port 302 from the sampling chamber 304. In some embodiments, the rigid portion 316 prevents the portion of the absorptive material 310 under the rigid portion 316 from expanding. In some embodiments, the semi-permeable membrane 318 may be rigid, and prevent the portion of the absorptive material 310 adjacent to the semi-permeable membrane 318 from expanding.

After the absorptive material 310 expands, causing the inlet port 302 to be resealed, a portion of the sample may be confined within the sampling chamber 304. Once a sample has been properly confined, it may be possible to apply a wide range of assay techniques or diagnostics to the sample. In some embodiments, the portion of the sampling chamber 304 between the rigid portion 316 and the wall of the sampling chamber forms a testing area. For example, a sensor may be placed within or proximate to the sampling chamber 304 in order to study the portion of the sample contained within the testing area located above the rigid portion 316. This sensor may be used to study properties of the sample, or it may be used to detect the results of an assay technique applied to the sample.

Diagram 300C is shown for illustrative purposes only, and is not limiting. In some embodiments, the osmotic valve mechanism 300 does not include the barrier 312, or one or more portions of the barrier 312 are excluded or rearranged within the sampling chamber 304. For example, the location of the rigid portion 316 and the semi-permeable membrane 318 may be reversed, or the rigid portion 316 may be removed and the semi-permeable membrane 318 extended so that it connects directly with the flexible membrane 314. When the osmotic valve mechanism 300 does not include a barrier 312 or does not include the flexible membrane 314, a portion of the absorptive material 310 near the inlet port 302 may expand and clog the inlet port 302, effectively resealing the inlet port 302.

In some embodiments, the material used to form the absorptive material 310 expands at a controlled rate, which may ensure that sufficient time has passed for the sample to enter the sampling chamber 304 and for the sampling chamber 304 to be filled before the inlet port 302 is resealed. This may be particularly useful for embodiments where the osmotic valve mechanism 300 does not include a flexible membrane 314 and/or the semi-permeable membrane 318. In some embodiments, a portion of the absorptive material 310 is covered by a dissolvable film or membrane, which may prevent the absorptive material 310 from expanding until a sufficient amount of time has passed for the film to dissolve.

In some embodiments, the sampling chamber 304 is connected to one or more sub-chambers (not shown). Each of these sub-chambers may be configured to hold samples, and isolate the samples from both the sampling chamber 304, and the other sub-chambers. For example, each sub-chamber may be connected to the sampling chamber 304 through a one-way valve, allowing samples to enter the sub-chamber from the sampling chamber, but preventing the obtained samples from exiting the sub-chamber. As an alternate example, each of the sub-chambers may employ a sealing device, heating element, and member made of absorptive material arranged similar to osmotic valve mechanism 300. In these embodiments, each of the sub-chambers may be opened by activating their respective heating elements, and may be automatically sealed off from the sampling chamber 304 after a sufficient amount of the sample has been obtained. In general, any type of valve or other suitable mechanism may be used to isolate samples contained in the sub-chambers. In some embodiments, similar to ingestible device 200, an ingestible device employing multiple sub-chambers in conjunction with the osmotic valve mechanism 300 may distribute different samples into different sub-chambers at different times, or from different locations of the GI tract.

It will be understood by one skilled in the art that variations of the osmotic valve mechanism 300 may be combined with any of the other ingestible devices described in this disclosure. For example, in some embodiments of the ingestible device 200 shown and described in relation to FIG. 2, one or both of the valves 214 and 216 may be replaced with certain embodiments of the osmotic valve mechanism 300. One or both of the valves 214 and 216 may include a sealing device that can be destroyed or deformed (e.g., by the mechanical actuator 218 or through a heating element), and one or both of the valves 214 and 216 may be automatically resealed by the expansion of absorptive material located within the sampling chamber 212.

FIGS. 4 and 5 illustrate in detail how some embodiments of the osmotic valve mechanism 300 (FIG. 3) may be operated in order to obtain a sample.

FIG. 4 shows a detailed view of an inlet port 400, which may be incorporated into osmotic valve mechanism 300, prior to being unsealed. The inlet port 400 features an exterior portion 402, which is separated by a middle portion 404 from an interior portion 406. The middle portion 404 of the inlet port 400 contains a sealing device 408, which may be the same as sealing device 306 shown and described in relation to FIG. 3. A heating element 410 is located near the middle portion 404, and adjacent to the sealing device 408. The sides of the inlet port 412A and 412B form the shape of the inlet port 400, and may be constructed from an insulating material, such as insulating ceramic, or polymers such as polyamide-imide, polyphenylene sulfide, polyphenylene oxide, and the like. For illustrative purposes, the exterior portion 402 of the inlet port 400 is depicted as being filled with a sample 414, which may be a fluid sample obtained from the GI tract. However, in some embodiments, the inlet port 400 may be operated regardless of whether a sample 414 is actually contained in the exterior portion 402. The exterior portion 402 and the interior portion 406 are wider than the middle portion 404. A sloped wall 416 gradually reduces the width of the exterior portion 402, to transition from the wider width of the exterior portion 402 to the narrower width of the middle portion 404. This configuration may reduce the overall volume of the sealing device 408 (compared to a configuration with a wider middle portion 404), and reduce the surface area of the sealing device 408 exposed to the sample 414, which may reduce the amount of heat lost from the sealing device 408 to the sample 414. In turn, this may make it easier to raise the temperature of the sealing device 408 using the heating element 410. In some embodiments, the geometry of the inlet port 400 may allow an air pocket (not shown) to form in the exterior portion 402, separating the sealing device 408 from fluid contained within the GI tract. This may act as an insulating barrier around the sealing device 408, and also make it easier to raise the temperature of the sealing device 408 using the heating element 410. Moreover, the larger width of the interior portion 406 relative to the middle portion 404 forms a remnant capture area 418, which may hold the remnants of the sealing device 408 after the inlet port 400 is unsealed.

In some embodiments, the exterior portion 402 of the inlet port 400 may be connected directly or indirectly to an opening in the housing of an ingestible device. In some embodiments, there is nothing to restrict a sample from entering the opening, and, at any given time, the exterior portion 402 of the inlet port 400 may be filled with a fluid sample 414 gathered from whatever portion of the GI tract the ingestible device is located within.

Sealing device 408 prevents the fluid sample 414 contained within the exterior portion 402 of the inlet port 400 from entering the interior portion 406 of the inlet port 400. For simplicity, FIGS. 4 and 5 depict the sealing device 408 as a plug, which forms a seal that may be broken by using a heating element 410. However, in some embodiments the sealing device 408 may be any other type of breakable seal or valve used within the middle portion 404 to separate the exterior portion 402 of the inlet port 400 and the interior portion 406 of the inlet port 400.

In some embodiments, the heating element 410 may be operated by a microcontroller. For example, the microcontroller may be configured to operate the heating element 410 and unseal the inlet port 400 when the ingestible device is in a certain portion of the GI tract. The sides of the inlet port 412A and 412B may be formed from an insulating material, which may shield the ingestible device and the fluid sample 414 from the heat generated by the heating element 410. This may also help to focus the heat produced by heating element 410 in the direction of the sealing device 408, and may reduce the total amount of power to drive the heating element 410 to melt, deform, or destroy the sealing device 408.

In some embodiments, the dimensions of the inlet port 400 are chosen such that a fluid sample 414 is naturally drawn into the exterior portion 402, and ultimately through the middle portion 404 into the interior portion 406, through capillary action. Typically, the cross-section of the exterior portion 402, the middle portion 404, and the interior portion 406 will be square, circular, or rectangular, but any type of cross-section may be used. The overall cross-sectional area of the exterior portion 402, the middle portion 404, and the interior portion 406 of the inlet port 400 is typically less than 50 square millimeters given the size constraints of the ingestible device, with 0.2 to 2 square millimeters being common. However, the cross-sectional areas listed above are only examples, and any cross-sectional area may be chosen in order to better draw in samples from the different portions of the GI tract. One skilled in the art will understand that the exact shape and dimensions will depend on the physical properties of the sample to be acquired, and some embodiments may use cross-sections other than the ones mentioned above.

FIG. 5, shows a detailed view of an inlet port 500, which may be incorporated into osmotic valve mechanism 300, after it has been unsealed.

After the heating element 510 has heated the sealing device 508 sufficiently, the sealing device 508 may deform, melt, or otherwise be destroyed, effectively unsealing the inlet port 500. Once the inlet port 500 is unsealed, the fluid sample 514 is able to flow naturally from the exterior portion 502 of the inlet port 500 to the interior portion 506 of the inlet port 500 through the middle portion 504. Similar to the embodiments described in relation to FIG. 4, the sides 512A and 512B of the inlet port may be made of an appropriate insulating material, and form the shape of the inlet port 500, the exterior portion 502 with the sloped wall 516, the middle portion 504, and the interior portion 506 along with the remnant capture area 518. As the fluid sample 514 enters the interior portion 506 of the inlet port 500, the natural flow of the fluid sample 514 may carry any of the remnants of the sealing device 508 into the remnant capture area 518 located within the interior portion 506. In some embodiments, once the melted or deformed remnants of the sealing device 508 cease to be in contact with the heating element 510 and instead come into contact with the insulating material that make up the walls of the remnant capture area 518, the remnants of the sealing device 508 re-solidifies or re-forms along the walls of the remnant capture area 518. As a result, the remnant capture area 518 may provide a location for the re-solidified remnants of the sealing device 508 to be stored, and may prevent the remnants of the sealing device 508 from impeding the flow of the sample 514.

In some embodiments, electromagnetic forces are used to attract the remnants of the sealing device 508 to the remnant capture area 518. For example, the sealing device (e.g., the sealing device 408) may be made from a magnetic material, and an induced or permanent magnetic field may be used to attract the remnants of the sealing device 508 to the remnant capture area 518. This magnetic field may be applied after the heating element 510 is activated, and until the remnants of the sealing device 508 re-solidify or re-form within the remnant capture area 518.

It will be understood that the embodiments described by FIGS. 3, 4, and 5, are merely illustrative, and they may be modified and combined with other techniques for drawing in or pumping fluid samples without departing from the spirit and scope of this disclosure. For example, to encourage samples to be drawn into the sampling chamber 304, the sampling chamber 304 may contain a low-pressure vacuum, and samples may be forcibly drawn into the sampling chamber 304 when the inlet port 302 is unsealed. A similar effect may also be produced by connecting the sampling chamber 304 to a sub-chamber containing a low-pressure vacuum, or by using by using a mechanical actuator to either pump the fluid samples or to increase the volume of the sampling chamber 304. In some embodiments, the geometry and relative size of the exterior portions 402 and 502, the middle portions 404 and 504, and interior portions 406 and 506, may be different from those depicted in FIGS. 4 and 5. For example, the different portions 402, 404, 406, 502, 504, and 506 may have a uniform width, and the sloped walls 416 and 516 and/or the remnant capture areas 418 and 518 are not included. As another example, a sloped wall may be used to form the remnant capture areas 418 and 518.

Figure 6:
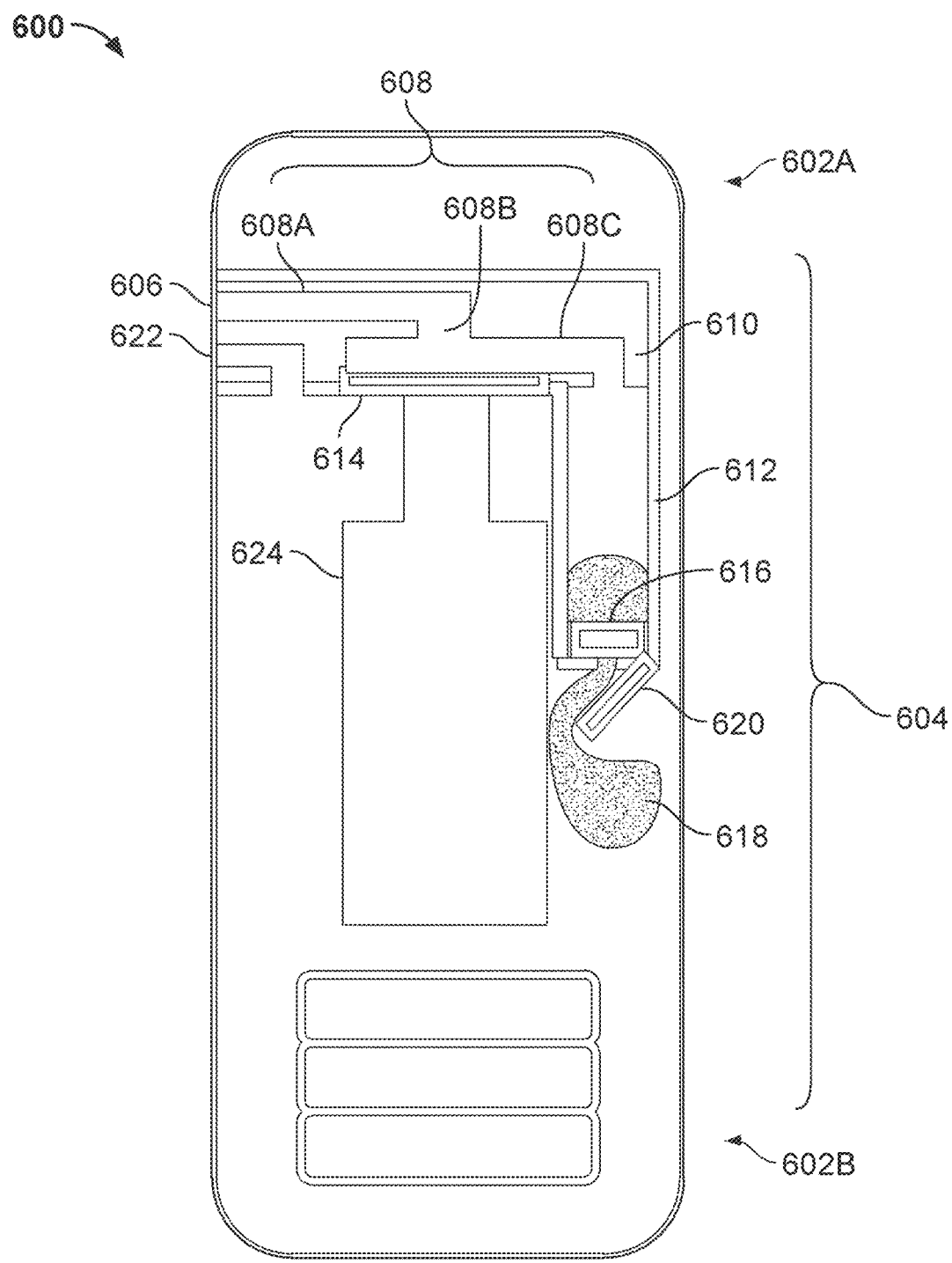
FIG. 6 shows an ingestible device.

FIG. 6 illustrates another example of an ingestible device 600 with a sampling chamber that includes an exit port. Similar to the ingestible devices 100 and 200, the ingestible device 600 is designed to have an outer housing with a first end 602A, a second end 602B, and a wall 604 extending longitudinally from the first end 602A to the second end 602B. The ingestible device 600 has an opening 606 in the housing, which allows samples to enter the ingestible device 600 from the surrounding environment. The ingestible device 600 has an inlet region 608 connected to the opening 606. The inlet region 608 is connected to an entry port 610 of a sampling chamber 612. The inlet region 608 is divided into three portions. A first portion 608A of the inlet region 608 is connected to the opening 606 and a second portion 608B, and a third portion 608C is connected to the entry port 610 of the sampling chamber 612. The second portion 608B connects the first portion 608A to the third portion 608C, and may contain a moveable valve 614 that is used to prevent samples from flowing through the inlet region 608, and isolate the first portion 608A of the inlet region 608 from the third portion 608C of the inlet region 608.

The ingestible device 600 has a mechanical actuator 624 coupled to the moveable valve 614. In some embodiments, a microprocessor or microcontroller is configured to control the mechanical actuator 624 and move the moveable valve 614 between an open and a closed position. For example, the microcontroller may be configured to move the moveable valve 614 into an open position after the ingestible device reaches a particular location within the GI tract. In some embodiments, the mechanical actuator may be driven by a set of batteries or other power source located within the ingestible device 600. When the moveable valve 614 is moved into an open position, a sample may be allowed to flow through the inlet region 608, and enter the sampling chamber 612 through the entry port 610. When the moveable valve 614 is in a closed position, the sample is prevented from flowing through the inlet region 608 and reaching the sampling chamber 612 from the opening 606.

For illustrative purposes, FIG. 6 depicts the moveable valve 614 as a diaphragm valve, which uses a mechanical actuator 624 to move a flexible diaphragm in order to seal or unseal an aperture in the second portion 608B of the inlet region 608, which may effectively block or unblock the inlet region 608. However, it will be understood that, in some embodiments, the moveable valve 614 may be a different type of valve. For example, in some embodiments the moveable valve 614 may be replaced by a pumping mechanism, such as the pumping mechanism described in relation to FIG. 9. As another example, in some embodiments the moveable valve 614 is replaced with an osmotic valve, similar to the embodiments described in relation to FIGS. 3, 4, and 5. Several examples of other different valve types are described in relation to FIG. 7.

The sampling chamber 612 of the ingestible device 600 has an exit port 616 located on the opposite end of the sampling chamber 612 from the entry port 610. In general, the exit port 616 may be located anywhere within the sampling chamber 612. The exit port 616 is configured to allow air or gas 618 to exit the sampling chamber 612, while preventing at least a portion of the sample obtained by the ingestible device 600 from exiting the sampling chamber 612. For example, the exit port 616 may include a gas-permeable membrane, which allows the gas 618 to exit the sampling chamber 612, but which would prevent a liquid or solid sample from leaving the sampling chamber 612 through the exit port 616. Allowing the gas 618 to exit the sampling chamber 612 may prevent pressure from building up within the sampling chamber 612 as the sample enters through the entry port 610. This may result in the sample being drawn into the sampling chamber 612 more easily, and result in increasing the overall volume of the sample able to be collected by the ingestible device 600, and increasing the ease with which the sample is brought into the sampling chamber 612.

The ingestible device 600 includes a one-way valve 620 as part of the exit port 616. This valve may prevent the gas 618 from re-entering the sampling chamber 612. However, in some embodiments the one-way valve 620 may be excluded from the ingestible device 600. In some embodiments, the exit port 616 includes a gas permeable membrane. This gas permeable membrane may lose its permeability when it is placed in contact with the sample. For example, the gas permeable membrane may include a spongy material that allows the gas 618 to exit the sampling chamber 612 through the exit port 616. Once the spongy material becomes moist through contact with the sample, it may become no longer gas permeable, or the permeability may be greatly reduced, thereby preventing the gas 618 from reentering the sampling chamber 612. In some embodiments, the gas permeable membrane may include expanded polytetrafluorethylene, polypropylene, or the like. In some embodiments, the material used to make the gas permeable membrane may be filter-like, as opposed to sponge-like materials. Generally, the gas permeable membrane may be made of any material that allow gas to permeate, but which prevents liquid from flowing through the membrane due to sufficient resistance or surface tension effects.

In the ingestible device 600, the exit port 616 is connected to a volume within the housing of ingestible device 600 outside of the sampling chamber. Depending on the manufacturing process used to produce the ingestible device 600, the volume within the housing of the ingestible device 600 may contain air or some other type of gas.

The ingestible device 600 includes an outlet port 622, which is connected to the volume within housing of the ingestible device 600. The outlet port 622 may provide a path for the gas 618 to exit the ingestible device 600 and be released into the environment surrounding the ingestible device 600. This may be advantageous when the volume of gas 618 is relatively large, since it may prevent pressure from building up within the housing of the ingestible device 600. In some embodiments, the ingestible device 600 does not include an outlet port 622, and the gas 618 stays inside the volume of the ingestible device 600. In some embodiments, the outlet port 622 is directly or indirectly connected to the exit port 616, for example, by a tube or channel. In some embodiments, the exit port 616 leads directly from the sampling chamber 612 to an opening in the ingestible device 600, and the exit port 616 may effectively replace the outlet port 622. In some embodiments, the outlet port 622 may contain a gas permeable membrane, a one-way valve, a hydrophobic channel, or some other mechanism to avoid unwanted material, (e.g., fluids and solid particulates from within the GI tract), from entering the ingestible device 600 through the outlet port 622.

In some embodiments, the ingestible device 600 may include a sensor within or proximate to the sampling chamber 612. For example, this sensor may be used to detect various properties of a sample contained within the sampling chamber 612, or this sensor may be used to detect the results of an assay technique applied to the sample contained within the sampling chamber 612.

In some embodiments, a hydrophilic sponge is located within the sampling chamber 612, and the hydrophilic sponge may be configured to absorb the sample as the sample enters the sampling chamber 612. In some embodiments, the hydrophilic sponge fills a substantial portion of the sampling chamber 612, and holds the sample for an extended period of time. This may be particularly advantageous if the sample is collected from the ingestible device 600 after the ingestible device 600 exits the body. In some embodiments, the hydrophilic sponge is placed on only certain surfaces or fills only certain portions of the sampling chamber 612. For example, it may be possible to line certain walls (or all walls) of the sampling chamber 612 with a hydrophilic sponge to assist in drawing in the sample, while leaving some (or none) of the walls of the sampling chamber 612 uncovered. Leaving walls uncovered may allow the use of diagnostics or assay techniques that involve a relatively un-obscured optical path. An example of such an embodiment is described in detail in relation to FIG. 8. In some embodiments, the sponge material may be placed on all walls of the sampling chamber 612. This may prevent unwanted ambient light from entering the sampling chamber 612, which may be useful for certain types of low light detection assays. In some embodiments, an opaque material is used to cover some or all sides of the sampling chamber 612. This may also prevent unwanted ambient light from entering the sampling chamber 612.

In some embodiments, the ingestible device 600 may include a sealed vacuum chamber connected to the exit port 616, or connected directly or indirectly to the sampling chamber 612. The sealed vacuum chamber may have an internal pressure that is substantially lower than ambient pressure of the sampling chamber 612 and/or the inlet region 608. In these embodiments, the ingestible device 600 unseals the vacuum chamber in order to reduce the pressure within the sampling chamber. This change in pressure may force the sample to be sucked into the sampling chamber, or allow the sample to be drawn into the sampling chamber quickly.

For simplicity, FIG. 6 depicts only a single sampling chamber 612, but it will be understood that the inlet region 608 may be connected to multiple sampling chambers arranged throughout the device, each of which may be controlled independently through the use of one or more valves. For example, in some embodiments there may be one or more sub-chambers connected to the inlet region 608. Each of the sub-chambers may be configured to hold samples gathered from within the GI tract, and keep those samples isolated. In general, any type of valve or other suitable mechanism may be used to isolate samples contained in the sub-chambers, including any of the valves or mechanisms described in relation to FIGS. 1-5. In some embodiments, the ingestible device 600 distributes different samples into each of the different sub-chambers at different times, or from different locations within the GI tract. For example, the ingestible device 600 may accomplish this by opening up a valve to connect the interior of inlet region 608 to the appropriate sub-chamber before opening up the inlet region 608 to draw in the sample from the opening 606 in the housing.

Figure 7:
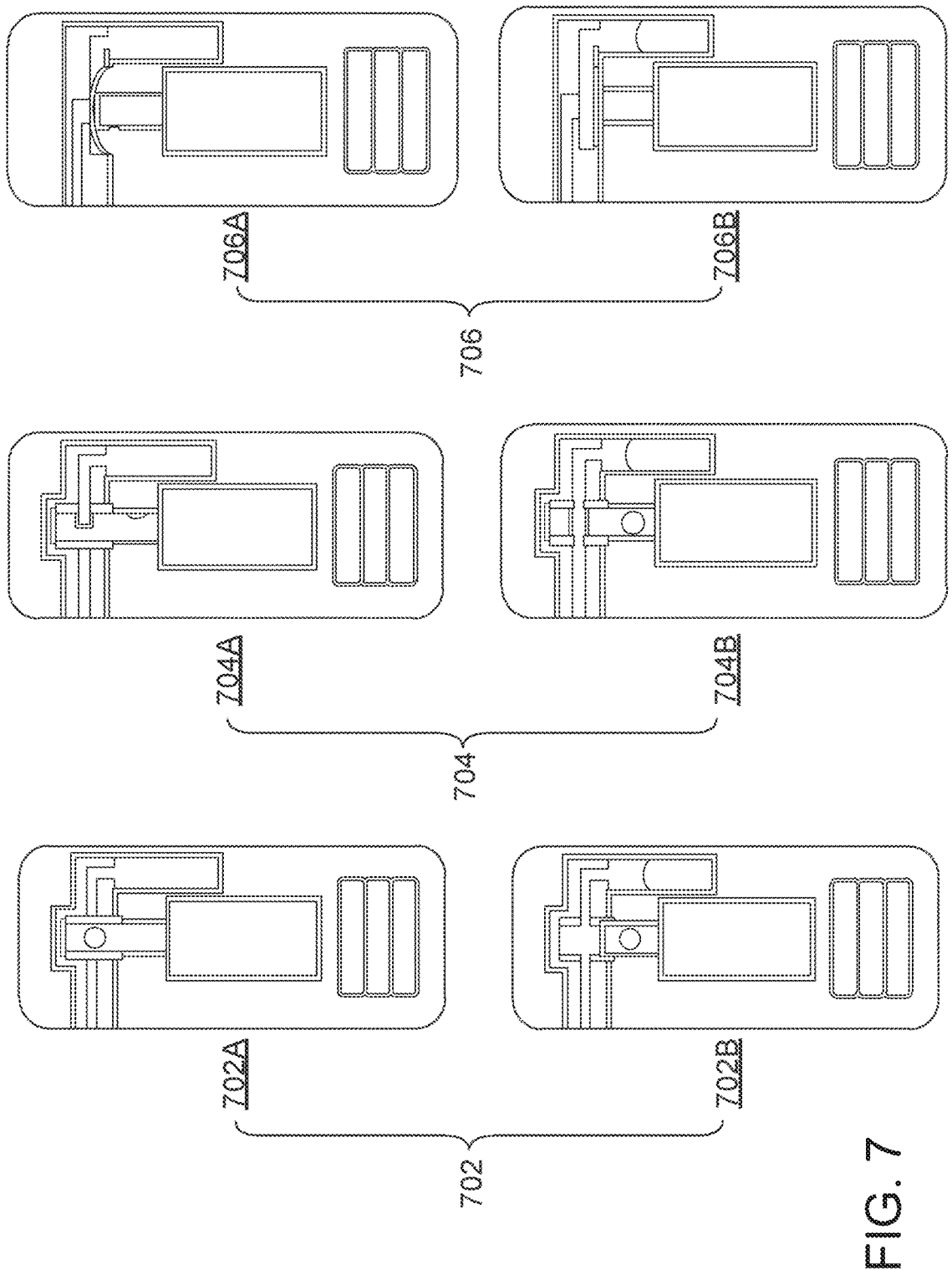
FIG. 7 shows valve designs.

FIG. 7 depicts different types of moveable valves that may be incorporated into an ingestible device, such as the ingestible devices 100, 200 or 600. The ingestible device 702 illustrates how a pin valve may be used as a moveable valve (e.g., as moveable valve 614 of ingestible device 600 (FIG. 6)), with diagram 702A showing the pin valve in a closed position, and diagram 702B showing the pin valve in an open position. In the ingestible device 702, a mechanical actuator may be configured to move the pin valve linearly in order to switch between an open position and a closed position. For example, in diagram 702A, the ingestible device 702 has a pin inserted into the inlet port, thereby preventing the sample from flowing into the sampling chamber from the opening in the ingestible device 702. In diagram 702B, the ingestible device 702 has a pin that has been removed from the inlet port, allowing the sample to flow freely into the sampling chamber from the opening in the ingestible device 702. In order to generate linear motion, the mechanical actuator may be a linear actuator, such as a solenoid. Alternately, the mechanical actuator may be a rotatory actuator, and the rotation may be converted into a linear motion. One skilled in the art will understand that this may be done any number of ways, for example, by coupling the mechanical actuator to a ball screw mechanism, a threaded lead nut and lead screw mechanism, a rack and pinion mechanism, or the like.

Ingestible device 704 illustrates how a rotary valve may be used as a moveable valve (e.g., as moveable valve 614 of ingestible device 600 (FIG. 6)), with diagram 704A showing the rotary valve in a closed position, and diagram 704B showing the rotary valve in an open position. In diagram 704A, the ingestible device 704 has a rotary pin oriented such that the sample is prevented from entering the sampling chamber from the opening in the ingestible device 704. In diagram 704B, the ingestible device 704 has a rotary pin that has been rotated into an orientation where the sample is free to flow into the sampling chamber from the opening in the ingestible device 704. In order to operate the rotary valve, the mechanical actuator in ingestible device 704 may be a rotatory actuator, which is capable of rotating the rotary pin to switch between the open position and the closed position.

Ingestible device 706 illustrates how a flexible diaphragm, or diaphragm valve, may be used as a moveable valve (e.g., as moveable valve 614 of ingestible device 600 (FIG. 6)), with diagram 706A showing the diaphragm valve in a closed position, and diagram 706B showing the diaphragm valve in an open position. In diagram 706A, the ingestible device 706 has a diaphragm valve in a closed position, with the flexible diaphragm being pressed against an aperture in the inlet region due to the pressure generated by the mechanical actuator against the flexible diaphragm. This may effectively block a sample from flowing through the inlet region, and thereby preventing a sample from entering the sampling chamber from the opening in the ingestible device 706. In diagram 706B, the ingestible device 706 has a diaphragm valve in an open position, with the pressure removed from the flexible diaphragm. The diaphragm returns to a position away from the aperture in the inlet region, allowing a sample to flow freely into the sampling chamber from the opening the in ingestible device 706.

In some embodiments, ingestible device 706 has a spring mechanism near the diaphragm or in direct contact with the diaphragm. The spring mechanism may apply pressure to the diaphragm to oppose the pressure applied by the mechanical actuator, which may cause the flexible diaphragm to be moved into an open position when the mechanical actuator is not applying pressure to the flexible diaphragm. Additionally, this may ensure that the diaphragm valve remains open when the mechanical actuator is not applying pressure across the flexible diaphragm.

In some embodiments, moving the mechanical actuator from a closed position to an open position causes a volume of the inlet region within the ingestible device to increase. This may cause the pressure within the inlet region to be reduced, generating suction to draw a sample into the inlet region. Similarly, moving the mechanical actuator from an open position to a closed position may cause the volume of the inlet region to be reduced. This may cause the pressure within the inlet region to be increased, pushing the sample out of the inlet region. Depending on the design of the inlet region, the mechanical actuator, and the moveable valve, this may push the sample into the sampling chamber rather than pushing the sample back through the opening in the ingestible device. An example of such a design is described in greater detail in relation to FIG. 9.

Figure 8:
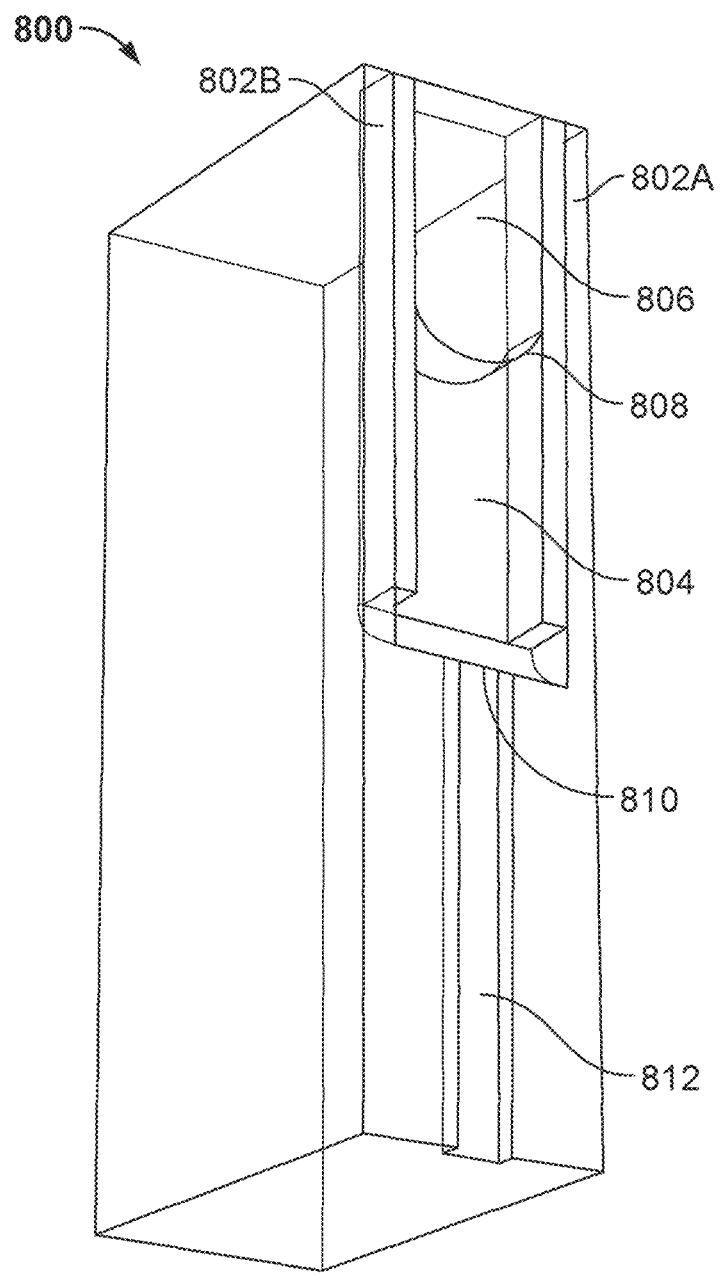
FIG. 8 shows a sampling chamber.

FIG. 8 illustrates an example of a sampling mechanism that may be incorporated into an ingestible device, such as the ingestible devices 100, 200, 600, and 702-706. The sampling mechanism 800 is partially lined with hydrophilic sponges 802A and 802B. In between the hydrophilic sponges 802A and 802B is a testing region 804 within the sampling mechanism 800. The hydrophilic sponges 802A and 802B attract a liquid or fluid sample 806, and may draw the sample 806 into the sampling mechanism 800. As the hydrophilic sponges 802A and 802B are saturated with the sample 806, a meniscus 808 is formed at the end of the sample 806, between the hydrophilic sponges 802A and 802B. This system may be useful for acquiring particularly viscous samples, which may have difficulty flowing into the sampling mechanism 800 naturally.

The sampling mechanism 800 includes an exit port 810 connected to a channel 812. As the sample 806 is drawn into the sampling mechanism 800, air or gas contained in the sampling mechanism 800 may be pushed out of the sampling mechanism 800 through the exit port 810 and into the channel 812. This may avoid gas being trapped within the sampling mechanism 800, which in turn may avoid pressure building inside of the sampling mechanism 800 and preventing the sample 806 from being drawn into the testing region 804.

In some embodiments, the sampling mechanism 800 may not include an exit port 810 or a channel 812, and any air or gas in the sampling mechanism 800 may be allowed to remain within the sampling mechanism 800. In some embodiments, the sampling mechanism 800 may be filled with a low pressure vacuum, attached to a pump or other mechanism to create a vacuum, or attached to a sealed chamber containing a low pressure vacuum that may be unsealed. The use of a vacuum may allow the sampling mechanism 800 to forcibly draw in a sample.

In some embodiments, an ingestible device may include sensors or diagnostics to study the sample 806 contained within the sampling mechanism 800. Because there is no sponge material on the front and back walls of the testing region 804, information about the sample 806 contained within the testing region 804 may be gathered by using sensors and/or assay techniques that involve a clear optical path, which would otherwise be obscured by a sponge (e.g., the hydrophilic sponges 802A and 802B). For example, light sources and/or optical sensors may be placed near the front and/or back walls in order to test optical properties of the sample, or to detect the results of certain assay techniques.

It will be understood by those skilled in the art that the sampling mechanism 800 depicted in FIG. 8 is merely illustrative, and the general techniques described in relation to FIG. 8 may be applied to a wide range of different chambers, channels, and fluid pathways, and incorporated into a wide range of different ingestible devices. Furthermore, in some embodiments, the overall geometry of FIG. 8 and the positioning of the sponges and the testing area may be altered. For example, the sponge may be formed in the shape of hollow tubes, with testing areas located in the middle of each tube. In this case, there would be a clear optical path from one end of the tube to the other.

Figure 9:
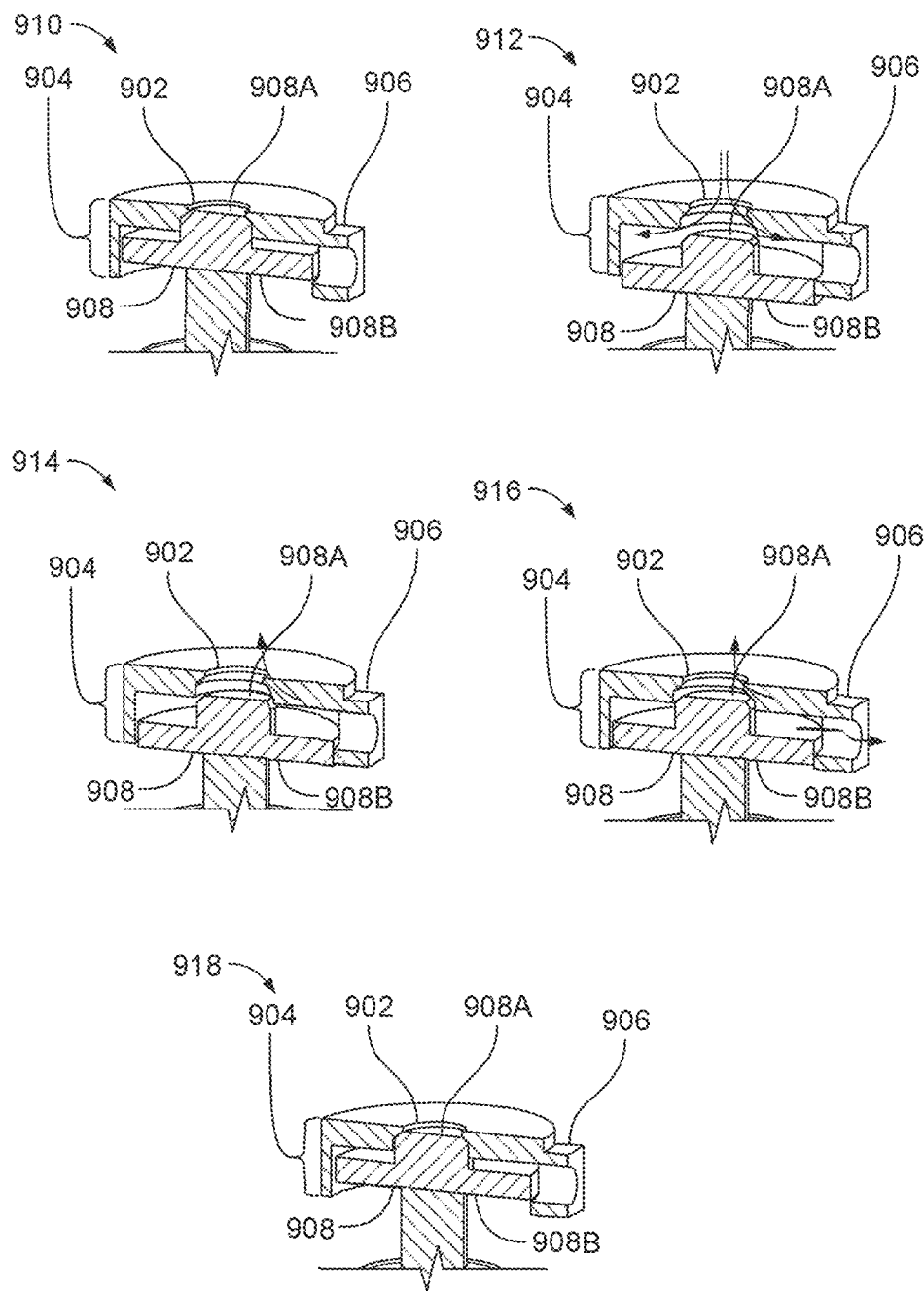
FIG. 9 shows a pumping mechanism.

FIG. 9 illustrates a pumping mechanism 900 that may be incorporated into an ingestible device, including certain embodiments of ingestible devices 100, 200, 600, and 702-706. For illustrative purposes, the pumping mechanism 900 may be described in the context of an ingestible device similar to ingestible device 600 (FIG. 6). When it is incorporated into an ingestible device similar to ingestible device 600, the pumping mechanism 900 may function as a moveable valve (e.g., moveable valve 614 of ingestible device 600), and control the ability of samples to flow between the opening 606 in the housing and the entry port 610 of the sampling chamber 612. Additionally, the pumping chamber 904 of the pumping mechanism 900 may form part of the second portion 608B of the inlet region 608. However, the general structure and principles of pumping mechanism 900 are not limited to the ingestible devices described in this disclosure, and they may be applied to a wide range of ingestible devices.

Pumping mechanism 900 is designed to draw in a sample through a first opening 902 into a pumping chamber 904, and push a portion of the sample out of the pumping chamber 904 through a second opening 906. In some embodiments, the first opening 902 may be connected directly or indirectly to an opening in the housing of an ingestible device. For example, an inlet region (e.g., the first portion 608A of the inlet region 608 of the ingestible device 600 (FIG. 6)) may connect an opening in the housing of an ingestible device (e.g., the opening 606 in the housing of ingestible device 600 (FIG. 6)) to the first opening 902. In some embodiments, the second opening 906 is connected directly or indirectly to a sampling chamber of an ingestible device. For example, the second opening 906 may be connected to an entry port of a sampling chamber (e.g., connected via the third portion 608C of the inlet region 608 to the entry port 610 of the sampling chamber 612 of the ingestible device 600 (FIG. 6)).

The pumping mechanism 900 features a moveable pump head 908 contained within the pumping chamber 904. The protrusion 908A of the moveable pump head 908 is shaped to fit within the first opening 902, or otherwise block the first opening 902. The base 908B of the moveable pump head 908 is able to cover the second opening 906 or otherwise block the second opening 906. Moreover, the protrusion 908A and the base 908B of the moveable pump head 908 are sized and oriented from each other in such a manner such that when the protrusion 908A blocks the first opening 902, the base 908B may simultaneously block the second opening 906 or leave the second opening 906 unblocked. Furthermore, when the base 908B blocks the second opening 906, the protrusion 908A may always be configured to also block the first opening 902.

As the moveable pump head 908 is moved up and down, the openings 902 and 906 may be sealed or unsealed, switching the pumping mechanism 900 across an open position, a partially closed position, and a closed position. In the open position (as is shown in the diagram 912), both the first opening 902 and the second opening 906 are unsealed or open. In the partially closed position (as is shown in the diagram 914, the moveable pump head 908 is positioned to only seal the first opening 902, while leaving the second opening 906 open. Finally, in the closed position (as is shown in the diagrams 910 and 918), both the first opening 902 and the second opening 906 are sealed.

In some embodiments, the moveable pump head 908 may be connected to a mechanical actuator (e.g., the mechanical actuator 624 of the ingestible device 600 (FIG. 6)), which may be configured to move the moveable pump head 908 linearly up and down. For example, the moveable pump head 908 may be located on the end of a shaft that is attached to the mechanical actuator. In some embodiments, the mechanical actuator and the positioning of the moveable pump head 908 may be controlled by a microcontroller or microprocessor located within the ingestible device. For example, a microcontroller may be configured to move the pump head 908 and begin pumping a sample through the pumping chamber 904 only after the ingestible device has reached a particular location within the GI tract.

Diagram 910 depicts the pumping mechanism 900 in a fully closed position. When the pumping mechanism 900 is in the fully closed position, the protrusion 908A of the moveable pump head 908 may be positioned within the first opening 902, and the base 908B of the moveable pump head 908 may be positioned adjacent to the second opening 906. In the fully closed position, the positioning of the moveable pump head 908 may effectively prevent a sample from entering or exiting the pumping chamber 904 from the openings 902 or 906.

Diagram 912 depicts the pumping mechanism 900 in an open position. When the pumping mechanism 900 is in the open position, the moveable pump head 908 is moved away from the first opening 902, moving the protrusion 908A of the moveable pump head 908 out of the first opening 902, and moving the base 908B of the moveable pump away from the second opening 906. In this position, the pumping mechanism 900 may allow one or more samples to enter the pumping chamber 904 through the first opening 902, and exit the pumping chamber 904 through the second opening 906. Because the effective volume of the pumping chamber 904 increases when the moveable pump head 908 is moved away from the first opening 902, the pumping mechanism 900 may draw a sample into the sampling chamber through the first opening 902 when transitioning from a closed position depicted in the diagram 910 to an open position depicted in the diagram 912. In some embodiments, a one-way valve may be incorporated into an ingestible device to prevent samples from being drawn into the pumping chamber 904 through the second opening 906 when the pumping mechanism 900 transitions between the closed position and the open position. This may ensure that the only sample entering the pumping chamber 904 is drawn in through the first opening 902.

Diagram 914 depicts the pumping mechanism 900 in a partially closed position. When the pumping mechanism 900 is in the partially closed position, the protrusion 908A of the moveable pump head 908 is positioned adjacent to the first opening 902, or just inside the first opening 902. In this position, the protrusion 908A of the moveable pump head 908 effectively seals off the first opening 902, preventing any of the sample remaining in the pumping chamber 904 from exiting pumping chamber 904 via the first opening 902. In this position, the base 908B of the moveable pump head 908 is positioned away from the second opening 906. This may allow any sample remaining in the pumping chamber 904 to exit the pumping chamber 904 through the second opening 906. For example, if the second opening 906 is connected to an entry port of a sampling chamber (e.g., connected via the third portion 608C of the inlet region 608 to the entry port 610 of the sampling chamber 612 of the ingestible device 600 (FIG. 6)), this may allow the sample to flow freely from the pumping mechanism 900 into the sampling chamber via the entry port.

Diagram 916 depicts the pumping mechanism 900 as it transitions between the partially closed position to the fully closed position. As the pumping mechanism 900 moves into the fully closed position, the moveable pump head 908 forces any of remaining sample contained within the pumping chamber 904 out of the pumping chamber 904 through the second opening 906. As this happens, the protrusion 908A of the moveable pump head 908 remains within the first opening 902, blocking it off and preventing the sample from exiting the pumping chamber 904 through first opening 902. By comparison, the base 908B of the moveable pump head 908 does not fully cover the second opening 906, and the sample is free to exit the pumping chamber 904 through the second opening 906. In combination, this may result in a majority of the sample remaining in the sampling chamber being forced through the second opening 906 as the pumping mechanism 900 moves from the partially closed position depicted in diagram 914 to the fully closed position depicted in diagram 918.

Diagram 918 depicts the pumping mechanism 900 in the fully closed position, similar to diagram 910. As noted before, in the fully closed position the moveable pump head 908 is positioned to seal off the openings 902 and 906, which may prevent a sample from entering or exiting the pumping chamber 904 from the openings 902 or 904. In general, the pumping mechanism 900 may cycle between the closed position depicted in diagrams 910 and 918 and the open position depicted in diagram 912 any number of times in order to draw additional samples into the pumping chamber 904 through the first opening 902, and force the samples out of the pumping chamber 904 through the second opening 906.

Although FIG. 9 depicts the protrusion 908A of the moveable pump head 908 located in the center of the moveable pump head 908, the location of the protrusion 908A may be anywhere on the moveable pump head 908. For example, the protrusion 908A of the moveable pump head 908 and the first opening 902 may be positioned on the side of the pumping chamber 904. In some embodiments, the moveable pump head 908 is split into two pieces, which may be controlled by one or more actuators. For example, the protrusion 908A and the base 908B may be two separate pieces, each of which is moved using a different actuator. This may allow the first opening 902 to be sealed and unsealed independently from the volume of the pumping mechanism 900 being increased or decreased.

For illustrative purposes, the diagrams 910-918 depict the base 908B of the moveable pump head 908 being used to cover or otherwise block the second opening 906. However, in some embodiments, the moveable pump head 908 may not cover, fit within, or otherwise block the second opening 906, and it will be understood by one skilled in the art that the second opening 906 does not need to be partially or fully blocked in order to push a sample through the second opening 906. For example, the moveable pump head 908 may not include a base 908B at all. Instead, the moveable pump head 908 may be made of a flexible material that forms a seal with the underside of the pumping chamber 904. In this case, the moveable pump head 908 may be moved up and down in a manner similar to a plunger in order to change the effective volume of the pumping chamber 904. When the volume decreases, the sample is at least partially forced out of the pumping chamber 904 through the second opening 906.

In general, incorporating the pumping mechanism 900 into an ingestible device may not impair the function of the openings, ports, valves, membranes, sampling chambers, or other structures of the ingestible device, and any of the teachings or embodiments described in conjunction with the ingestible devices 100, 200, 600, or 702-706 may be combined in different embodiments of an ingestible device along with the pumping mechanism 900. For example, the pumping mechanism 900 may replace the first valve 214 in the ingestible device 200 (FIG. 2), and may be used to force the sample into the sampling chamber 212. As an alternate example, the pumping mechanism 900 may be used to force samples into the sampling chamber 304 of the osmotic valve mechanism 300 (FIG. 3). As another example, the pumping mechanism 900 may be incorporated into an embodiment of the ingestible device 600 (FIG. 6) where the exit port 616 is not included, and the pumping mechanism 900 may be used to force the sample into the sampling chamber 612 despite the pressure that may result from air or gas 618 being trapped within the sampling chamber 612.

For illustrative purposes, the examples provided by this disclosure focus primarily on a number of different example embodiments of an ingestible device, such as the ingestible devices 100, 200, 600, and 702-706. However, it is understood that variations in the general shape and design of one or more embodiments of the ingestible devices described in relation to FIGS. 1-9 may be made without significantly changing the functions and operations of the device. Furthermore, it should be noted that the features and limitations described in any one embodiment may be applied to any other embodiment herein, and the descriptions and examples relating to one embodiment may be combined with any other embodiment in a suitable manner. For example, any of the valves described in relation to FIG. 7 may be used as the valves 214 and 216 described in relation to FIG. 2. As an alternate example, the absorptive material 310 and flexible membrane 314 described in relation to FIG. 3 may be incorporated into any of the various sampling chambers described in various embodiments of ingestible devices 100, 200, 600, and 702-706 in order to automatically seal the sampling chamber. Moreover, the figures and examples provided in disclosure are intended to be only exemplary, and not limiting. Only the claims that follow are meant to set bounds as to what the present invention includes. It should also be noted that the systems and/or methods described above may be applied to, or used in accordance with, other systems and/or methods, including systems and/or methods that may or may not be directly related to ingestible devices.

Figure 10:
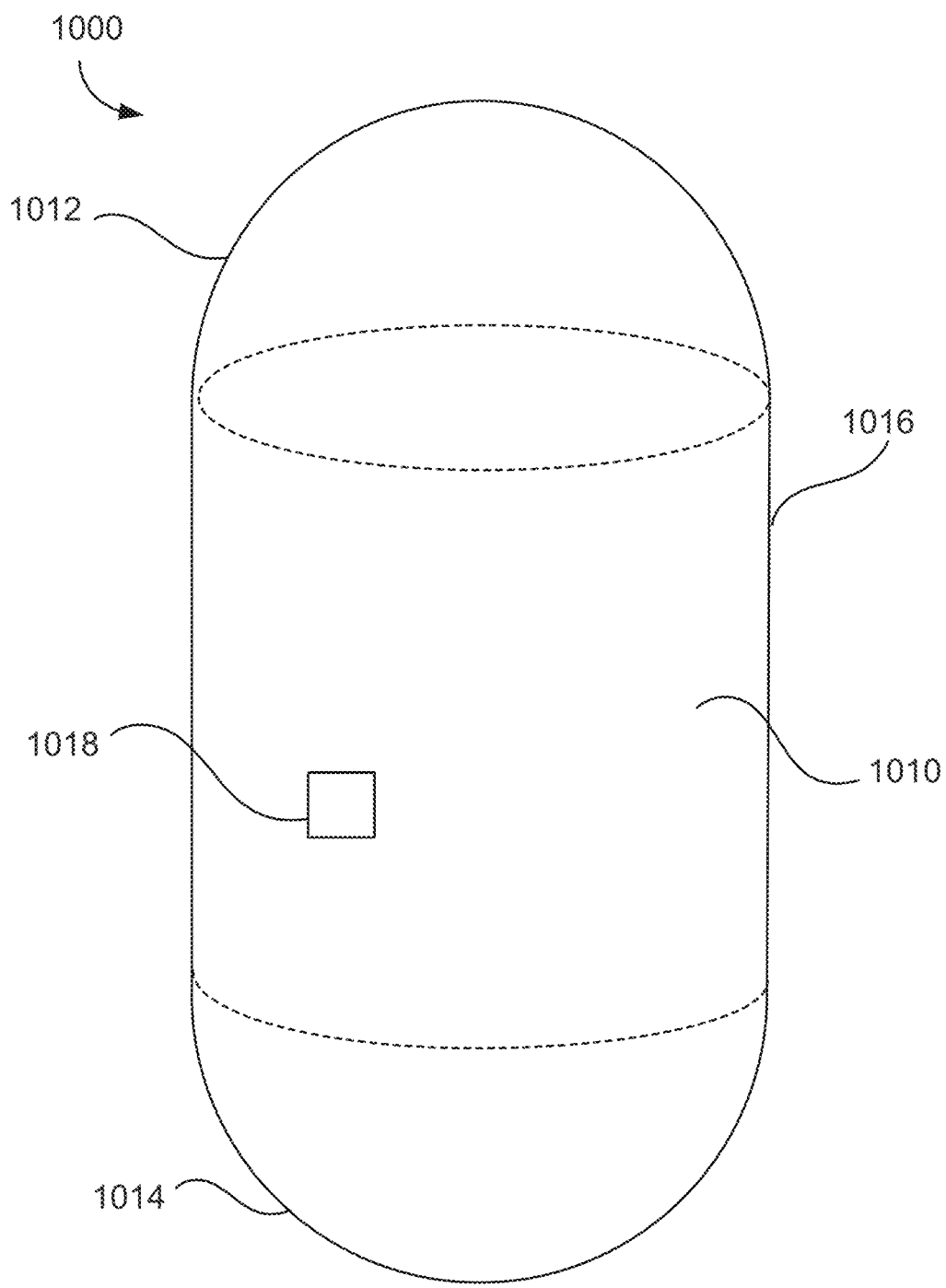
FIG. 10 shows an ingestible device.

FIG. 10 illustrates, in a highly schematic fashion, an ingestible device 1000 having a housing 1010 that includes a first end 1012 and a second end 1014 opposite first end 1012. Housing 1010 also includes a wall 1016 that connects first end 1012 and second end 1014. Wall 1016 has an opening 1018 that allows fluid from an exterior of the ingestible device 1000 (e.g., from the GI tract) and into an interior of ingestible device 1000.

Figure 11:
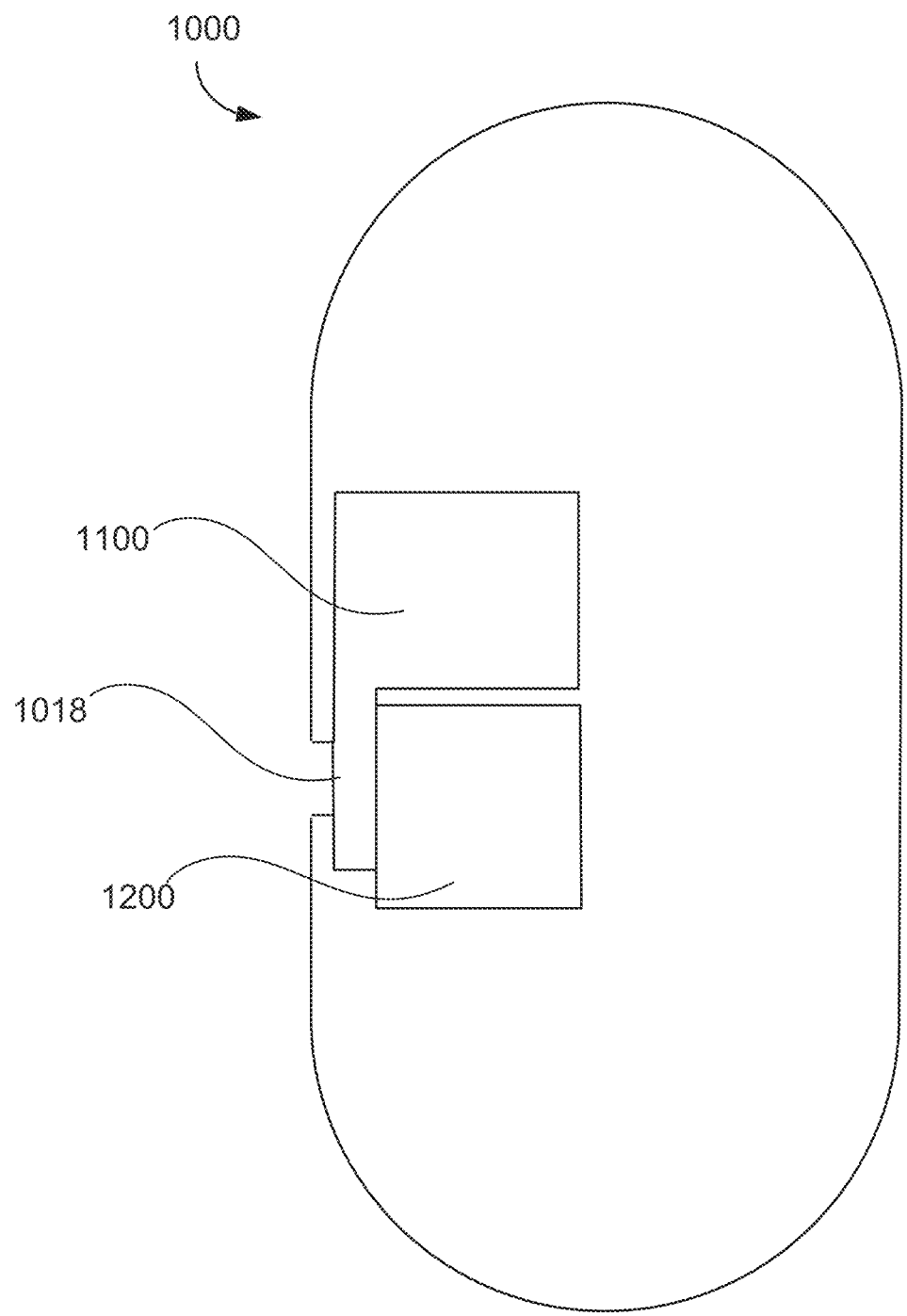
FIG. 11 shows an ingestible device.

FIG. 11 depicts a cross-sectional view of a portion of the interior of ingestible device 1000. As shown in FIG. 11, the interior of ingestible device 1000 includes a valve system 1100 and a sampling system 1200. Valve system 1100 is depicted as having a portion that is flush with the opening 1018 so that valve system 1100 prevents fluid exterior to ingestible device 1000 from entering sampling system 1200. However, as described in more detail below with reference to FIGS. 12-16, valve system 1100 can change position so that valve system 1100 allows fluid exterior to ingestible device 1000 to enter sampling system 1200.

Figure 12:
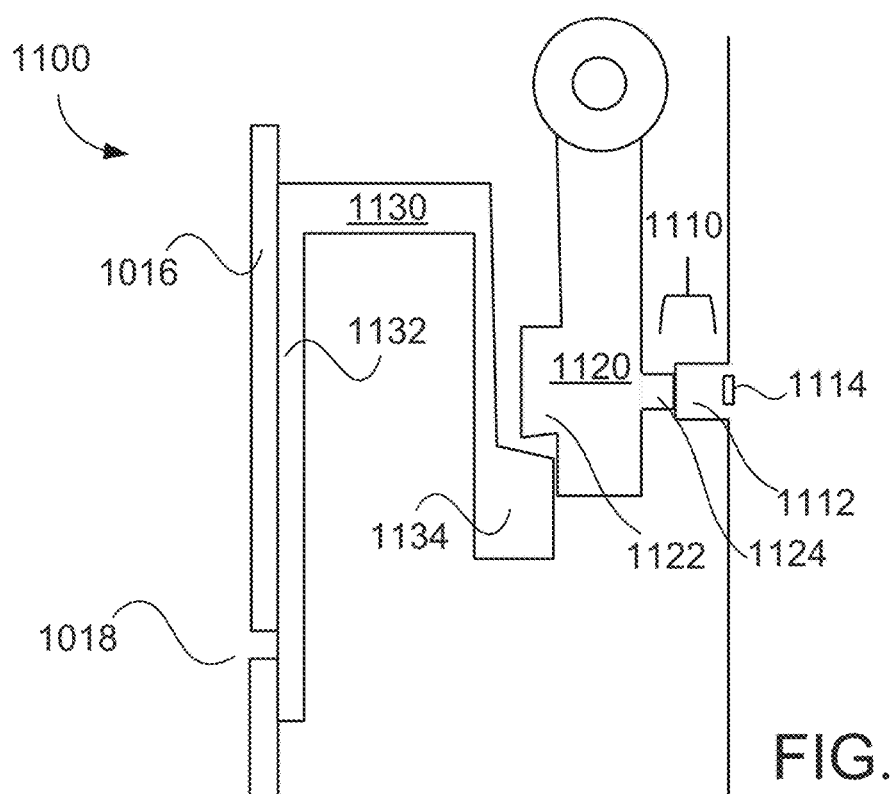
FIG. 12 illustrates a valve system.
Figure 16:
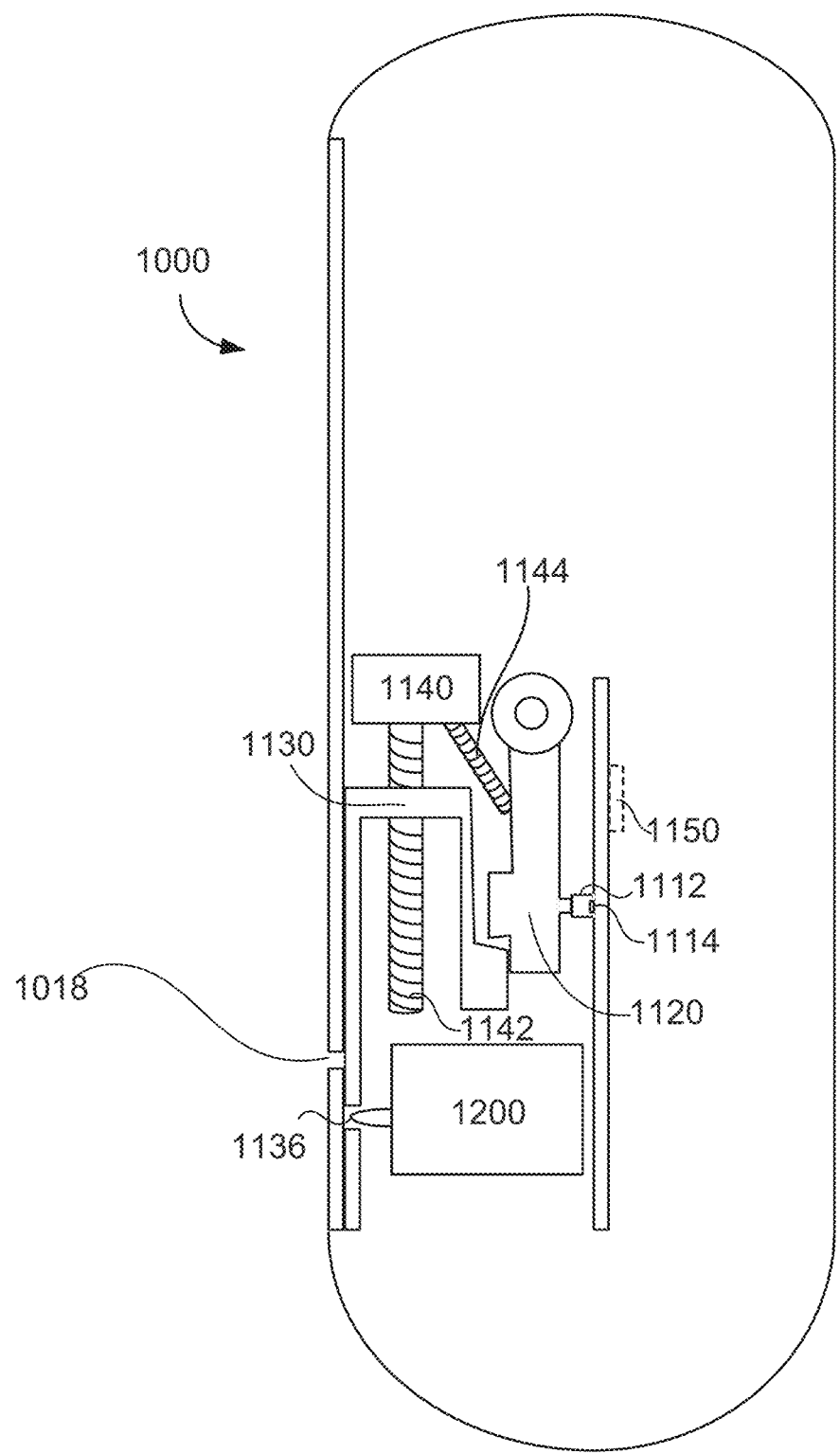
FIG. 16 illustrates a more detailed view of an ingestible device.

FIGS. 12 and 16 illustrate valve system 1100 in more detail. As shown in FIG. 12, valve system 1100 includes an actuation mechanism 1110, a trigger 1120, and a gate 1130. In FIGS. 12 and 16, a leg 1132 of gate 1130 is flush against, and parallel with, housing wall 1016 so that gate leg 1132 covers opening 1018 to prevent fluid exterior to ingestible device 1000 (e.g., fluid in the GI tract) from entering the interior of ingestible device 1000. A protrusion 1134 of gate 1130 engages a lip 1122 of trigger 1120. A peg 1124 of trigger 1120 engages a wax pot 1112 of actuation mechanism 1110. Referring to FIG. 16, a biasing mechanism 1140 includes a compression spring 1142 that applies an upward force on gate 1130. Biasing mechanism 1140 also includes a torsion spring 1144 that applies a force on trigger 1120 in the counter-clockwise direction. In FIGS. 12 and 16, the force applied by torsion spring 1144 is counter-acted by the solid wax in pot 1112, and the force applied by compression spring 1142 is counter-acted by lip 1122.

Figure 13A:
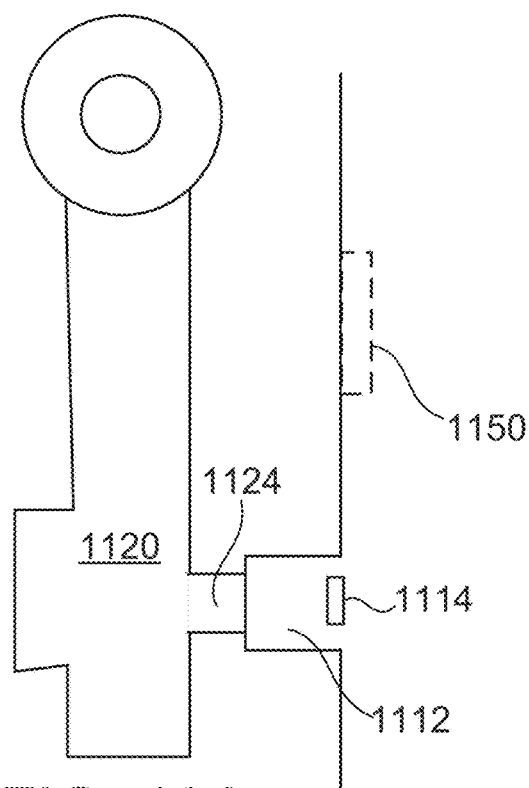
FIGS. 13A and 13B illustrate a portion of a two-stage valve system in its first and second stages, respectively.
Figure 13B:
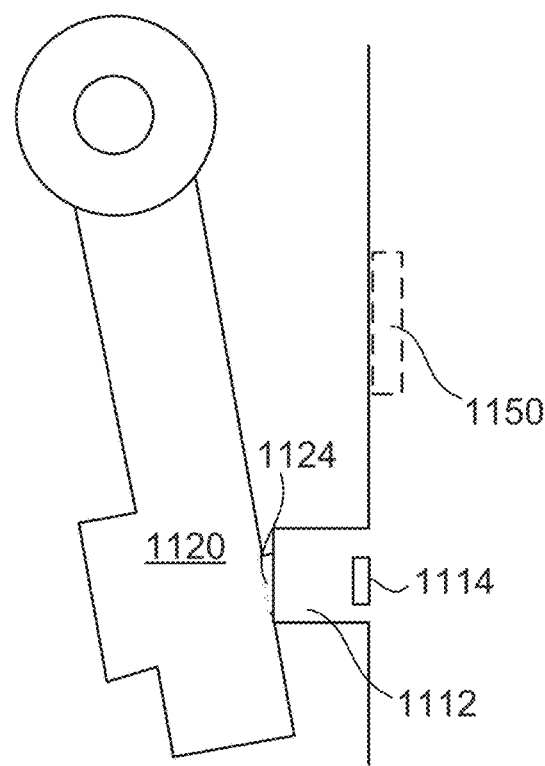

FIGS. 13A and FIG. 13B show an embodiment of the manner in which actuation mechanism 1110 actuates movement of trigger 1120. Similar to FIGS. 12 and 16, FIG. 13A shows a configuration in which peg 1124 applies a force against solid wax pot 1112 due to torsion spring 1144, and in which the solid nature of wax pot 1112 resists the force applied by peg 1124. A control unit 1150 is in signal communication with valve system 1100. During use of ingestible device 1000, a control unit 1150 receives a signal, indicating that the position of valve system 1100 should change, e.g., so that ingestible device 1000 can take a sample of a fluid in the GI tract. Control unit 1150 sends a signal that causes a heating system 1114 of actuation system 1100 to heat the wax in pot 1112 so that the wax melts. As shown in FIG. 13B, the melted wax is not able to resist the force applied by peg 1124 so that, under the force of torsion spring 1144, trigger 1120 moves in a counter-clockwise fashion.

FIGS. 14A and 14B illustrate the interaction of trigger 1120 and gate 1130 before and after actuation. As shown in FIG. 14A, when wax pot 1112 is solid (corresponding to the configuration shown in FIG. 13A), protrusion 1134 engages lip 1122, which prevents the force of compression spring 1142 from moving gate 1130 upward. As shown in FIG. 14B, when the wax in pot 1112 melts (FIG. 13B), trigger 1120 moves counter-clockwise, and lip 1122 disengages from protrusion 1134. This allows the force of compression spring 1142 to move gate 1130 upward. As seen by comparing FIG. 14A to FIG. 14B, the upward movement of gate 1130 results in an upward movement of an opening 1136 in gate leg 1132.

FIGS. 15A and 15B illustrate the impact of the upward movement of opening 1136 on the ability of ingestible device 1000 to obtain a sample. As shown in FIG. 15A, when the wax in pot 1112 is solid (FIGS. 13A and 14A), opening 1136 in is not aligned with opening 1018 in wall 1016 of ingestible device 1000. Instead, gate leg 1132 covers opening 1018 and blocks fluid from entering the interior of ingestible device 1000. As shown in FIG. 15B, when the wax in pot 1112 is melted and trigger 1120 and gate 1130 have moved (FIGS. 13B and 14B), opening 1136 in gate 1130 is aligned with opening 1018 in wall 1016. In this configuration, fluid that is exterior to ingestible device 1000 (e.g., in the GI tract) can enter the interior of ingestible device 1000 via openings 1018 and 1036.

Figure 17A:
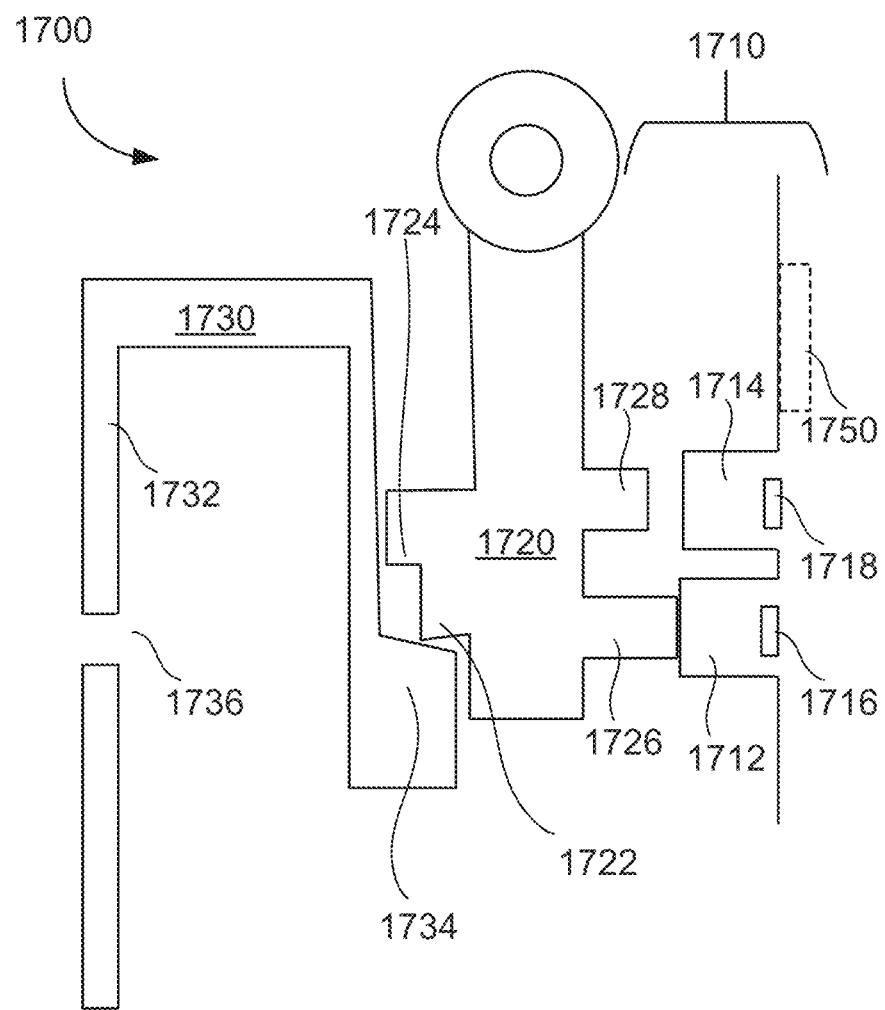
FIGS. 17A-17C illustrate a portion of a three-stage valve system in its first, second and third stages, respectively.
Figure 17C:
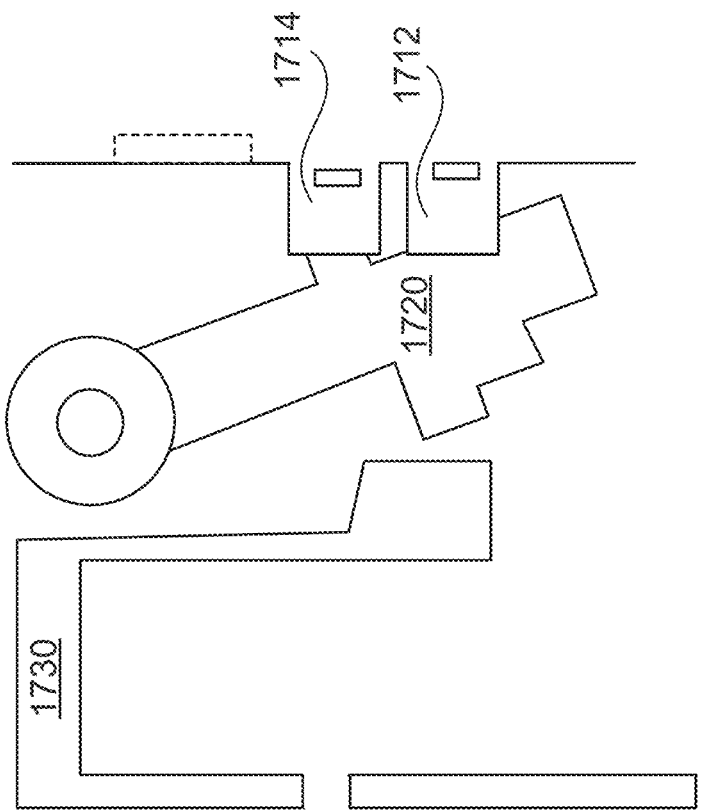
Figure 17B:
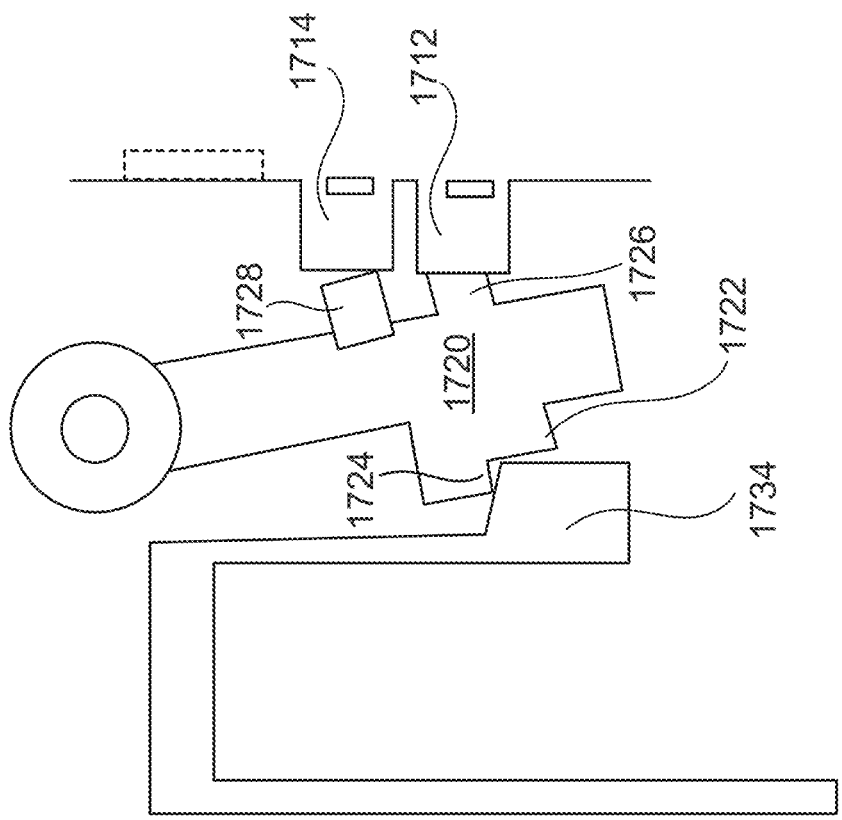
Figure 18C:
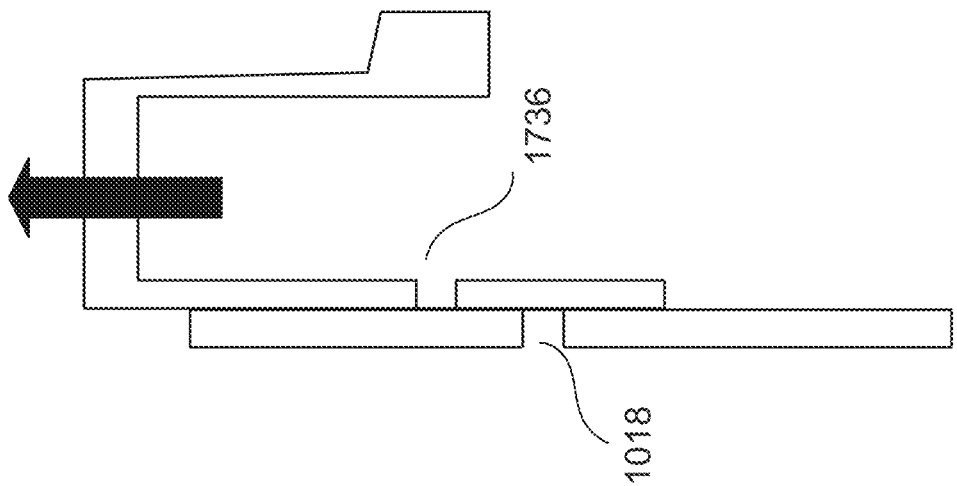
FIGS. 18A-18C illustrate a portion of a three-stage valve system in its first, second and third stages, respectively.
Figure 18B:
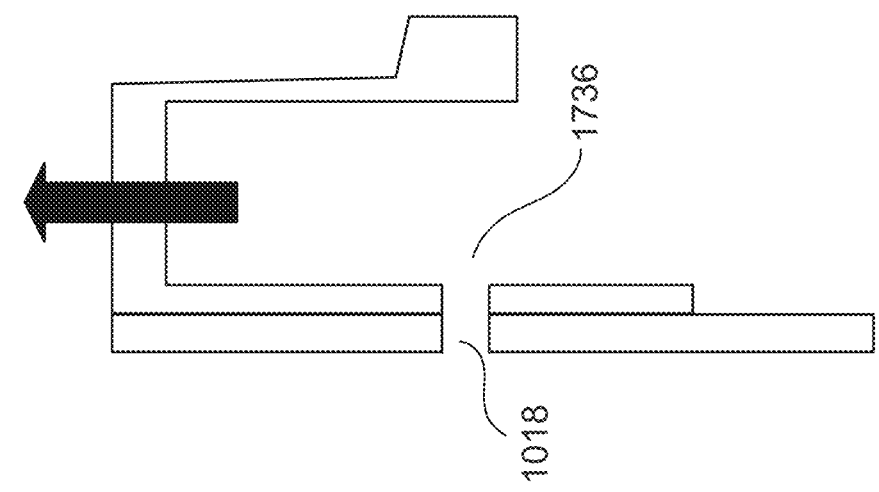
Figure 18A:
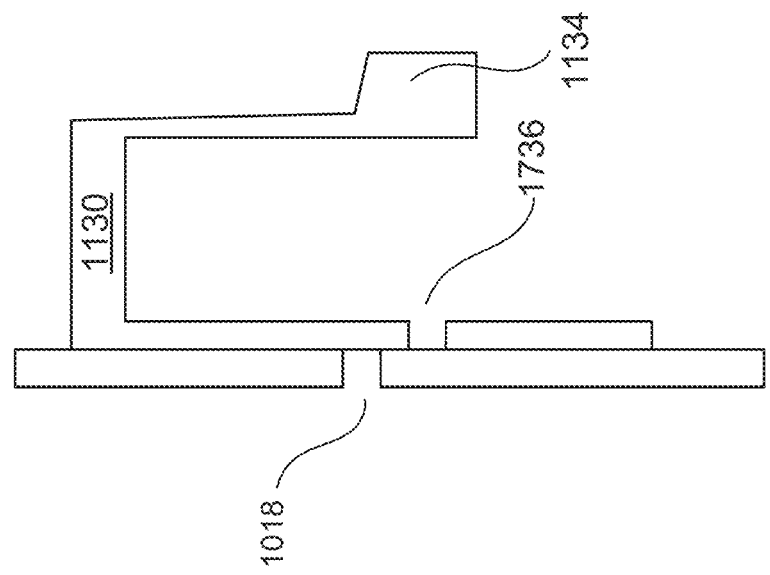
Figure 19A:
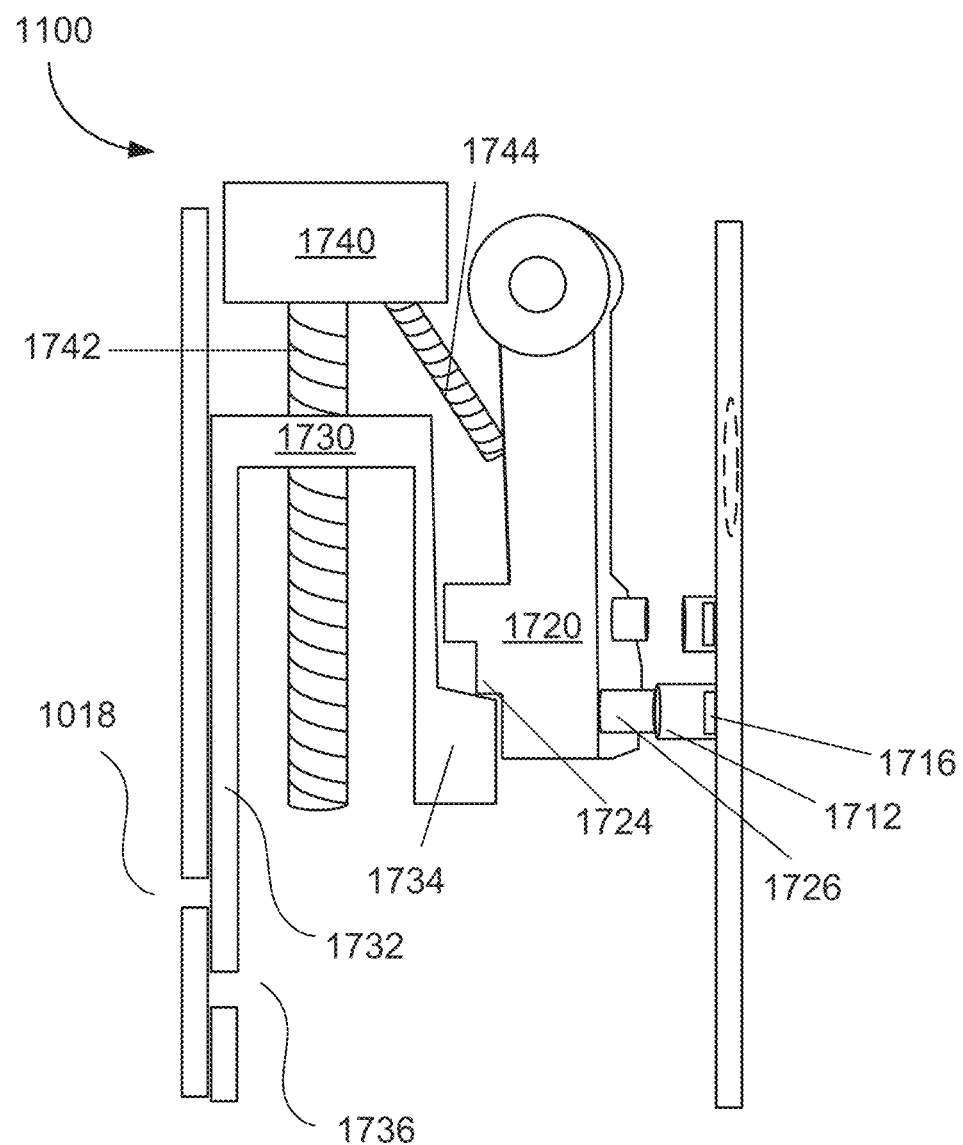
FIGS. 19A-19C illustrate a portion of a three-stage valve system in its first, second and third stages, respectively.
Figure 19B:
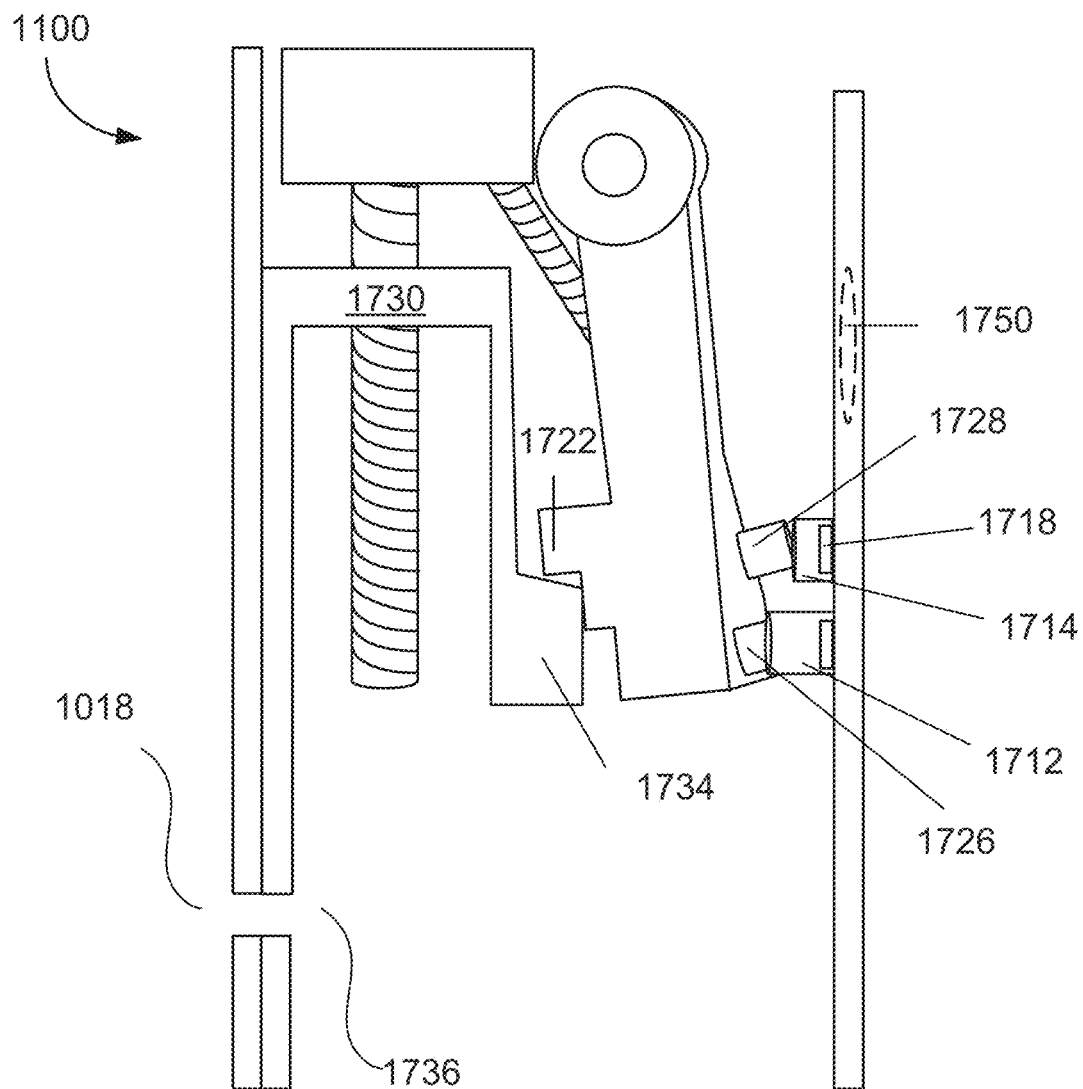
Figure 19C:
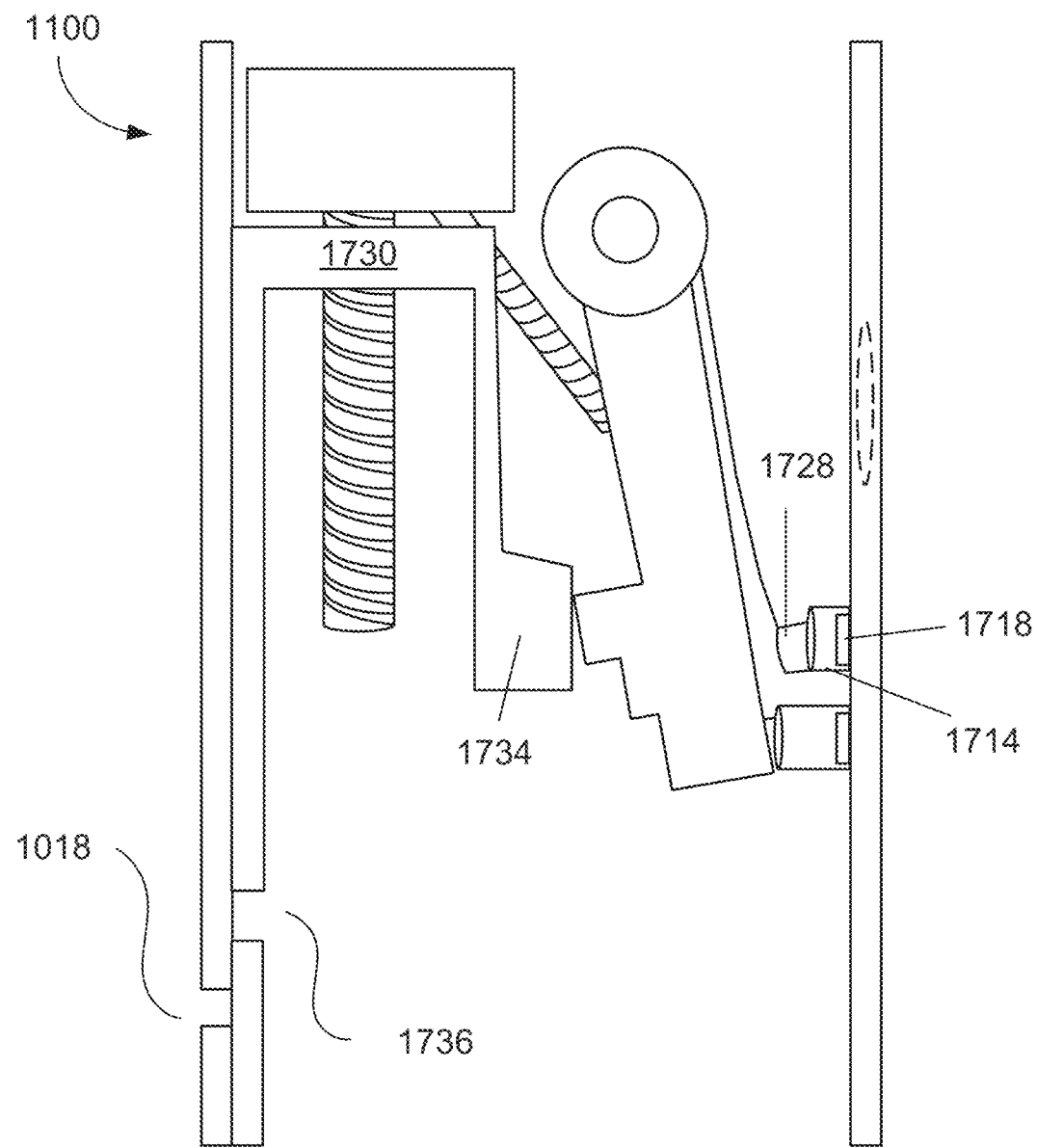

While the foregoing description is made with regard to a valve system having one open position and one closed position (e.g., a two-stage valve system), the disclosure is not limited in this sense. Rather, the concepts described above with regard to a two stage valve system can be implemented with a valve system have more than two stages (e.g., three stages, four stages, five stages, etc.). For example, FIGS. 17A-19C illustrate cross-sectional views of a three-stage valve system 1700. FIGS. 17A, 18A and 19A illustrate different views of components of valve system 1700 in the same position. FIGS. 17B, 18B and 19B illustrate different views of components of valve system 1700 in the same position. FIGS. 17C, 18C and 19C illustrate different views of components of valve system 1700 in the same position.

As shown in FIGS. 17A-19C, valve system 1700 includes an actuation system 1710, a trigger 1720, a gate 1730 and a biasing system 1740. Actuation system 1710 includes a first wax pot 1712, a second wax pot 1714, a first heating system 1716 and a second heating system 1718. Trigger 1720 includes a first lip 1722, a second lip 1724, a first peg 1726 and a second peg 1728. Gate 1730 includes a gate leg 1732 and a protrusion 1734. Gate leg 1732 has an opening 1736. Biasing system 1740 includes a compression spring 1742 and a torsion spring 1744. In addition, the ingestible device includes a control unit 1750.

As shown in FIGS. 17A, 18A and 19A, in the first stage, protrusion 1734 engages first lip 1722, and first peg 1726 engages first wax pot 1712. Compression spring 1742 applies an upward force on gate 1730, and torsion spring 1744 applies a force on trigger 1720 in the counter-clockwise direction. The force applied by torsion spring 1744 is counter-acted by the solid wax in first pot 1712, and the force applied by compression spring 1742 is counter-acted by first lip 1722. Opening 1736 is not aligned with opening 1018.

FIGS. 17B, 18B and 19B illustrate the configuration in a second stage, after control unit 1750 sends a signal to first heating system 1716 to melt the wax in first pot 1712. In the second stage, trigger 1720 has moved counter-clockwise relative to its position in the first stage. First peg 1726 is positioned in first pot 1712 because the melted wax cannot prevent this movement. Further counter-clockwise movement of trigger 1720 is prevented by the engagement of second peg 1728 with the solid wax in second pot 1714. With the counter-clockwise movement of trigger 1720, first lip 1722 disengages from protrusion 1734, and gate 1730 moves upward so that opening 1736 in leg 1732 is aligned with opening 1018. Further upward movement of gate 1730 is prevented by the engagement of protrusion 1734 with second lip 1724.

FIGS. 17C, 18C and 19C illustrate the configuration in a third stage, after control unit 1750 sends a signal to second heating system 1718 to melt the wax in second pot 1714. In the third stage, trigger 1720 has moved counter-clockwise relative to its position in the second stage. Second peg 1728 is positioned in second pot 1714 because the melted wax cannot prevent this movement. Further counter-clockwise rotation is prevented by the engagement of first and second pegs 1726 and 1728, respectively with first and second pots 1712 and 1714, respectively. Protrusion 1734 is disengaged from second lip 1724, allowing the force of compression spring 1742 to move gate 1730 upward so that opening 1736 is no longer aligned with opening 1018.

Figure 20:
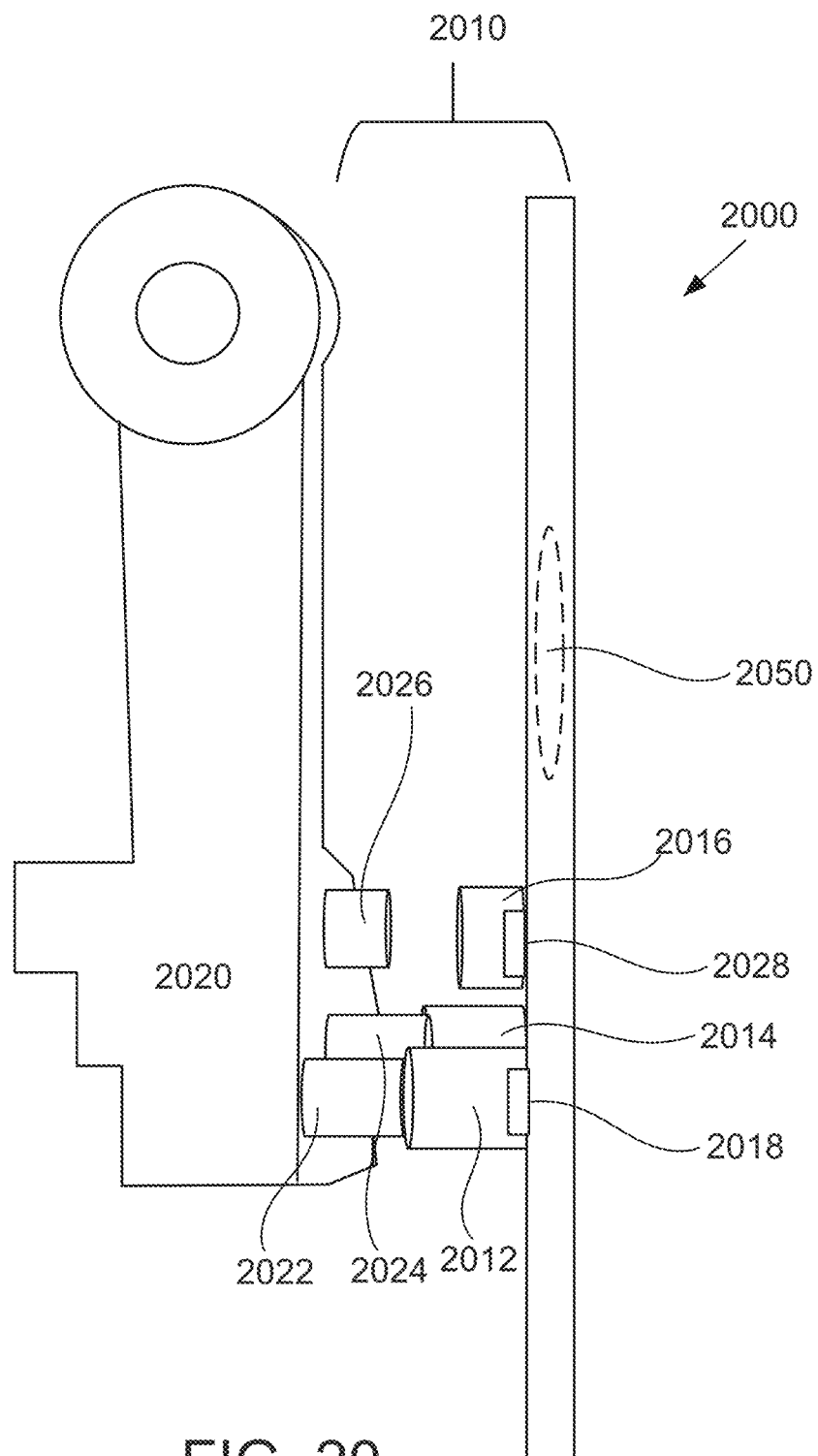
FIG. 20 illustrates a three-stage valve system in its first stage.

FIG. 20 illustrates another embodiment of a three stage valve system 2000 that can be used in an ingestible device. Valve system 2000 that is similar to valve system 1700 except that actuation system 2010 includes three includes wax pots 2012, 2014 and 2016, respectively, that define a triangle, and trigger 2020 includes three pegs 2022, 2024 and 2026, respectively, that define a corresponding triangle. Actuation system 2010 is controlled using a control unit 2050. Actuation system 2010 also includes a first heating system 2018 that heats the wax in pots 2012 and 2014 and so that pegs 2022 and 2024 enters their corresponding pot, causing valve system 2000 to move from its first stage to its second stage. Actuation system 2010 also includes a second heating system 2028 that heats the wax in pot 2016 so that pegs 2026 enters pot 2016, causing valve system 2000 to move from its second stage to its third stage.

In the foregoing discussion, embodiments actuating systems are described that include one or more wax pots and corresponding heating systems. But the disclosure is not limited to such actuating systems. Generally, any actuating system can be used that will provide an appropriate force to resist counter-clockwise movement of the trigger when desired and to remove that force when desired. Examples of such actuation systems include a pot with a silicon or wax seal. A control unit may be used to rupture the seal and allow counter clock-wise movement of the trigger. Additionally, or alternatively, the actuation mechanism may use dissolvable coating to that dissolves over time or in the presence of a substance. As the coating dissolves, the trigger may move further in the counter clock-wise direction. Other actuation mechanisms may also apply an attractive force rather than remove a resistive force. For example, the actuation mechanism may include magnetic pegs and slidable magnets The magnets may be located behind the pots or may slide to a position behind the pots when the valve system should change stages. As the magnets behind the pots slide into range of the magnetic trigger pegs, the trigger moves in the counterclockwise direction due to the attractive force between the magnetic peg and the magnets. The sliding mechanism to move the slidable magnets may be powered by an osmotic pump, a pressurized chamber, or any other applicable method of movement previously described in other embodiments.

In the discussion above, embodiments of triggers are disclosed that include one or more lips and one or more pegs. However, the disclosure is not limited to such triggers. In general, for example, any trigger design can be used that is capable of providing the step-wise movement of the trigger. Such trigger designs include, for example, a releasable latch coupling or a saw toothed engagement wall. A different embodiment may utilize a ball in socket joint to engage the trigger and gate, in which the "socket" is located on the trigger. It is to be noted that such designs need not be based on counter-clockwise movement and may be, for example, designed for the controlled movement of the trigger in one or more of various degrees of freedom. For example, rather than rotate, the trigger may be configured to slide laterally to push a peg of the trigger into a melted wax pot.

The discussion above describes embodiments of gates that include a protrusion and a leg with an opening. The disclosure is not limited to such designs. Generally, any appropriate arrangement can be used so long as it provides the desired step-wise controlled movement of an opening to the interior of the ingestible device. Exemplary designs include a gate that is capable of responding to or applying magnetic forces on the trigger. A saw toothed pattern may also provide a step-wise gate movement. Additionally, embodiments include a latch designed to releasably couple the gate to the trigger. A different embodiment may utilize a ball in socket joint in which the "ball" is located on the gate. Optionally, a gate can include one or regions that include one or more appropriate sealing materials positioned to cover the opening in the housing of the ingestible device when the gate is positioned to prevent fluid exterior to the ingestible device from entering the interior of the device via the opening in the housing of the ingestible device.

In the foregoing discussion, embodiments of biasing systems are described that include a compression spring and a biasing spring. However, the disclosure is not limited in this sense. In general, any biasing elements can be used to provide the counter-clockwise force to the trigger and/or to provide the upward force to the gate. Exemplary biasing elements include elastic bands, wherein a stretched elastic band acts similar to a stretched compression spring as described. Additional basing mechanisms may include magnets and/or magnetic forces to induce trigger or gate movement. For example, a magnet may be located above the gate, where, like the constant force of the stretched compression spring, the magnet also applies a constant attractive force on the gate.

Figure 21A:
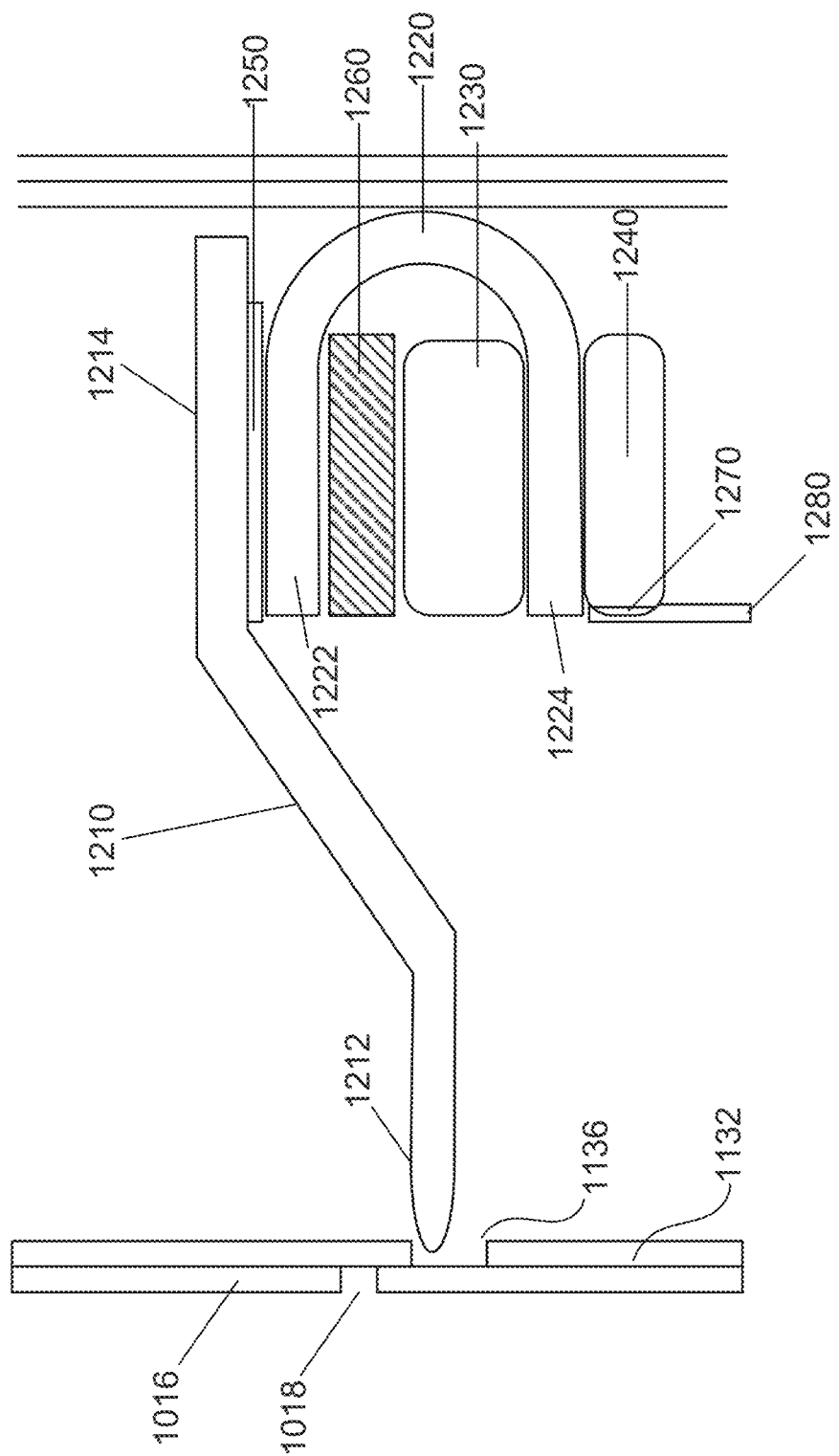
FIG. 21A illustrates a portion of an ingestible device.
Figure 21B:
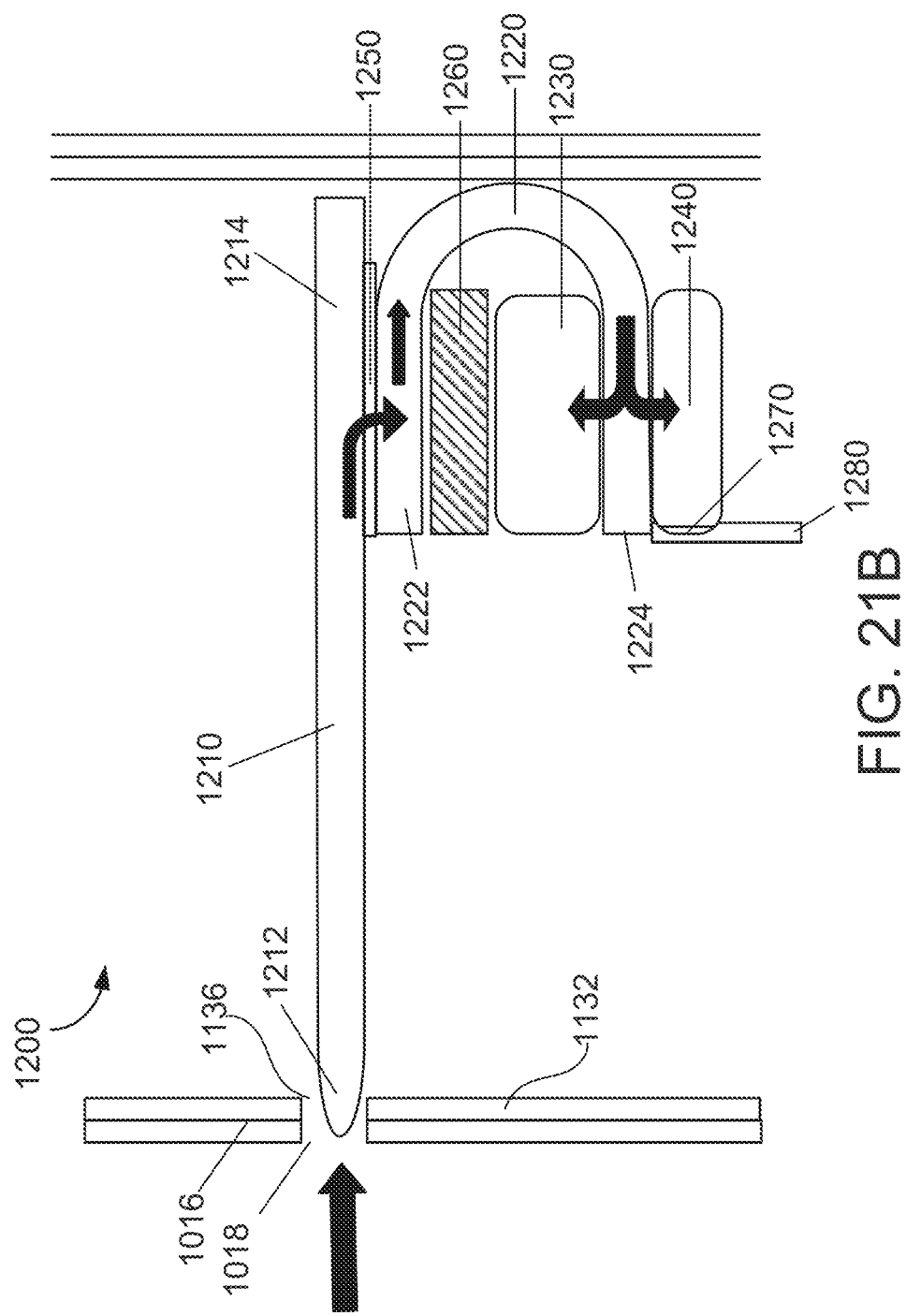
FIG. 21B illustrates a portion of an ingestible device.

As noted above in addition to a valve system, an ingestible device includes a sampling system. FIGS. 21A and 21B illustrate a partial cross sectional view of ingestible device 1000 with sampling system 1200 and certain components of valve system 1100. Sampling system 1200 includes a series of sponges configured to absorb fluid from an opening, move the fluid to a location within the housing, and prepare the fluid for testing. Preparation for testing may include filtering the fluid and combining the fluid with a chemical assay. The assay may be configured to dye cells in the filtered sample. The series of sponges includes a wicking sponge 1210, a transfer sponge 1220, a volume sponge 1230, and an assay sponge 1240.

Wicking sponge 1210 is made of an absorptive material that absorbs the fluid form the opening in the housing when the valve is open i.e. when the inlet and the housing are aligned. The wicking sponge transfers the fluid from the opening to a filter. Wicking sponge 1210 includes a wicking tongue 1212 extended towards the housing 1016. As shown in FIG. 21A, before actuation of the actuation system (FIGS. 13A, 14A, 15A), wicking tongue 1212 is not adjacent opening 1018 in wall 1016 of ingestible device 1000 so that wicking tongue 1212 does not absorb fluid exterior to ingestible device 1000. However, as shown in FIG. 21B, after actuation of the actuation system (FIGS. 13B, 14B, 15B), wicking tongue 1212 is adjacent opening 1018 so that wicking sponge 1212 is made of an absorptive material that absorbs fluid that passes through opening 1018, e.g., fluid from the GI tract. Fluid absorbed by wicking tongue 1212 can travel through wicking sponge 1210 to a distal end 1214 of wicking sponge 1210. The wicking sponge 1210 and wicking tongue 1212 may be made of a VF2 sponge, an Ahlstrom M13 sponge, MF/F material, a Carwild Ivalon Polyvinyl Alcohol material, or another suitable absorptive material. Optionally, the dimensions of the sponge material may be selected to enable all its desired functions while remaining precisely packaged within the capsule. In some embodiments, Carwild Ivalon Polyvinyl Alcohol material is cut to the dimensions 1.4 millimeters (height)×6 millimeters (width)×8.5 millimeters (length). In certain embodiments, one or more of the following parameters can be considered when selecting an appropriate material and/or its dimension: ability to load one more preservative materials; desired preservative material(s) to be loaded; capacity to hold one or more dried preservatives; ability to facilitate hydration of one or more dried preservative materials upon contact with one or more GI fluids; capacity to capture fluid (e.g., GI fluid); and swelling properties upon fluid uptake (generally, it is desirable to have little or no swelling upon fluid uptake). Typically, the preservative(s) is (are) selected based on the analyte of interest.

Nucleic acid preservatives can be used to prevent or reduce the rate of nucleic acid degradation or denaturation, and/or increase the stability of nucleic acids, e.g., to maintain nucleic acid structure. In some embodiments, the nucleic acid preservative is nuclease inhibitor (deoxyribonuclease inhibitor). In some embodiments, the nucleic acid preservative is a ribonuclease inhibitor. Nuclease inhibitors and ribonuclease inhibitors are known in the art, and have been described in, e.g., U.S. 6,224,379, herein incorporated by reference in its entirety. In some embodiments, the nucleic acid preservative mixture can include EDTA, sodium citrate, an ammonium sulphate. In some embodiments, the RNA preservative mixture includes 2 mL of 0.5M EDTA, 1.25 ml of 1 M sodium citrate, 35 g of ammonium sulphate, and 46.8 mL of dH20. In some embodiments, the RNA preservative is an RNAlater™ stabilization solution (ThermoFisher Scientific), as described in U.S. Pat. No. 7,056,673, which is herein incorporated by reference in its entirety. In some embodiments, an RNA preservative can include one or more of triphenylmethane dyes (such as methyl green, crystal violet, pararosaniline, or tris-(4-aminophenyl)methane), cresyl violet, polyamines, and cobalt ions. In some embodiments, an RNA preservative can include one or more of spermine, spermidine, 1,10-diamino-4,7-diazadecane, 1,11-diamino-4,8-diazaundecane, 1,13-diamino-4,10-diazatridecane, 1,14-diamino-4,11-diazatetradecane, 1,15-diamino-4,12-diazapentadecane, 1,16-diamino-4,13-diazahexadecane, 1,17-diamino-4,14-diazaheptadecane, 1,18-diamino-4,15-diazanonadecane, 1,19-diamino-4,16-diazaeicosane, and 1,20-diamino-4,17-diazaheneicosane.

Protein preservatives can be used to prevent or reduce the rate of protein degradation or denaturation, and/or increase the stability of proteins, e.g., to maintain protein structure. Preservatives can include, by way of example, protease inhibitors, surfactants (e.g., nonionic surfactants), emulsifiers, acids, parabens, esters and protein stabilizers.

In some embodiments, the preservative can prevent or reduce the digestion or degradation of proteins by one or more proteases. In some embodiments, the preservative can be a protease inhibitor. In some embodiments, the protease inhibitor is a serine protease inhibitor, a metalloprotease inhibitor, an aminopeptidase inhibitor, a cysteine peptidase inhibitor, or an aspartyl protease inhibitor. In some embodiments, the protease inhibitor can prevent or reduce digestion by proteases such as, but not limited to, trypsin, chymotrypsin, plasmin kallikrein, thrombin, papain, cathepsin B, cathepsin L, calpain and staphopain, endoproteinase Lys-C, Kallikrein, and thrombin. In some embodiments, the protease inhibitor can be 4-(2-aminoethyl)benzenesulfonyl fluoride hydrochloride (AEBSF, CAS 30827-99-7), aprotinin (CAS 9087-70-1), bestatin (CAS 58970-76-6), E-64 (CAS 66701-25-5), leupeptin (CAS 103476-89-7), pepstatin A (CAS 26305-03-3), or N-p-Tosyl-L-phenylalanine chloromethyl ketone (TPCK). In some embodiments, the protein biomarker preservative includes 4-(2-aminoethyl)benzenesulfonyl fluoride hydrochloride (AEBSF, CAS 30827-99-7), aprotinin (CAS 9087-70-1), bestatin (CAS 58970-76-6), E-64 (CAS 66701-25-5), leupeptin (CAS 103476-89-7), pepstatin A (CAS 26305-03-3), DMSA, and bovine serum albumin, and, optionally, N-p-Tosyl-L-phenylalanine chloromethyl ketone (TPCK).

In some embodiments, the preservative can be a protein stabilizer such as, for example, Trehalose or Dextran.

A preservative as disclosed herein can be an acid. In some embodiments, the preservative can be an acid with a pKa between 3 and 7. In some embodiments, the preservative can be citric acid, or sorbic acid.

In some embodiments, the preservative can be a surfactant such as a polysorbate. Exemplary polysorbates include, for example, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), sorbitan monolaurate, sorbitan monopalmitate, sorbitan monostearate, sorbitan tristearate, and sorbitan monooleate.

In some embodiments, the preservative is a paraben, parahydroxybenzoate, or ester of parahydroxybenzoic acid (4-hydroxybenzoic acid). In some embodiments, the preservative can be propyl paraben.

In some embodiments, the preservative can include dimethyl sulfoxide (DMSA). In some embodiments, the preservative can include bovine serum albumin.

The preservative can be a mixture of two or more of a protease inhibitor, a surfactant, an emulsifier, an acid, a paraben, and an ester. For example, a preservative as described herein can include a mixture of two or more protease inhibitors. In some embodiments, a preservative as described herein can include a mixture of one or more protease inhibitors, and one or more acids. In some embodiments, a preservative as described herein can include a mixture of one or more protease inhibitors, one or more acids, and an ester, e.g., a paraben. In some embodiments, a preservative as described herein can include a mixture of one or more protease inhibitors, one or more acids, one or more esters, and one or more surfactants. In some embodiments, the preservative can include the HALT™ protease inhibitor cocktail (Thermo Fisher). In some embodiments, the preservative can include the HALT™ protease inhibitor cocktail (Thermo Fisher) and TPCK. In some embodiments, the preservative can be bactericidal to preserve a protein, e.g., a protein biomarker. In some embodiments, the preservative mixture that is bactericidal includes citric acid (CAS 77-92-9), sorbic acid (CAS 110-44-1), propylparaben (CAS 94-13-3), tween 80 (CAS 9005-65-6), ethanol, bovine serum albumin, and TPCK (CAS 402-71-1).

In some embodiments, a preservative mixture containing one or more protease inhibitors can be contacted with a protein in the gastrointestinal tract to stabilize the protein. In some embodiments, the protein is an immunoglobulin. In some embodiments, the protein is an IgA or IgM. In some embodiments, the protein is a secretory IgA. In an exemplary embodiment, a preservative mixture containing AEBSF, aprotinin, bestatin, E-64, leupeptin and pepstatin A protease inhibitors (HALT™, Thermo Fisher), and N-p-Tosyl-L-phenylalanine chloromethyl ketone (TPCK, Sigma Aldrich) can be used to stabilize one or more immunoglobulin proteins in the gastrointestinal tract, e.g., secretory IgA.

In some embodiments, a preservative mixture containing one or more protease inhibitors, acids, parabens, and surfactants can be contacted with a protein in the gastrointestinal tract to stabilize the protein. In some embodiments, the protein is not an immunoglobulin. In an exemplary embodiment, a preservative mixture containing AEBSF, aprotinin, bestatin, E-64, leupeptin and pepstatin A protease inhibitors (HALT™, Thermo Fisher), N-p-Tosyl-L-phenylalanine chloromethyl ketone (TPCK, Sigma Aldrich), citric acid, sorbic acid, propyl paraben, polysorbate 80 (Tween 80), BSA can be used to stabilize one or more non-immunoglobulin proteins in the gastrointestinal tract, e.g., a cytokine, calprotectin, S100A12, lactoferrin, M2-pyruvate kinase, neopterin, a metalloproteinase, a myeloperoxidase, polymorphonuclear elastase, and/or alpha 1 antitrypsin eosinophilic protein X.

In some embodiments, one or more internal controls are included in an ingestible device, as described herein, that is used to collect one or more analytes. The internal control can be used to monitor the stability and degradation of small molecules, nucleic acids, and/or proteins in the device over time. In some embodiments, the internal control can be a small molecule, a nucleic acid, and/or a protein. In some embodiments, the small molecule internal control can be 2,4 dinitrophenol (2,4, DNP), femocene, and/or a deuterium-labeled cholesterol. In some embodiments, the nucleic acid internal control can be a DNA internal control. In some embodiments, the nucleic acid internal control can be a RNA internal control. In some embodiments, the RNA internal control can be a G+C-rich (60%) RNA molecule with extensive secondary structure, based on a modified delta virus genome, as described in Dingle et al., J. Clin. Microbiol. 42(3):1003-1011, 2004, herein incorporated by reference in its entirety. In some embodiments, the protein internal control can be human serum albumin (HSA), fluorescein isothiocyanate, and/or biotin.

In some embodiments, the preservative is a microbial preservative. In exemplary embodiments, the preservative prevents, inhibits, or reduces the growth and/or multiplication of a microorganism. In some embodiments, the preservative permanently prevents, inhibits, or reduces the growth and/or multiplication of a microorganims. In exemplary embodiments, the preservative prevents, inhibits, or reduces the growth and/or multiplication of bacteria. In some embodiments, the preservative permanently prevents, inhibits, or reduces the growth and/or multiplication of bacteria. In some embodiments, the preservative is one or more of a bacteriostatic, bacteriocidal, and/or fixative compound.

Bacteriostatic preservatives arrest the growth or multiplication of the bacteria. In some embodiments, the preservative kills the bacteria, thereby preventing growth and multiplication. Bactericidal preservatives kill bacteria. Bacteria enter a device as described herein in the GI tract of a subject, and are contacted with a bacteriostatic preservative that arrests bacterial growth and multiplication, or a bactericidal preservative that kills the bacteria. As a result, the numbers of bacteria in the device are representative of the bacterial microflora that was present in the GI tract at the time the bacteria first entered the device.

In some embodiments, the preservative can be a bacteriostatic food preservative, such as, but not limited to, sorbic acid, citric acid, propyl paraben, nisin, dimethyl dicarbonate, and ethylenediaminetetraacetic acid (EDTA). In some embodiments, the preservative can be sodium azide, hydroxyurea, fusidic acid, diazolidinyl urea, imidazolidinyl urea, salicylic acid, barium and nickle chloride, metallic copper, thimerosal, 2-phenoxyethanol, or ProClin™. In some embodiments, the preservative can be one or more of sorbic acid, citric acid, propyl paraben, nisin, dimethyl dicarbonate, ethylenediaminetetraacetic acid (EDTA), sodium azide, hydroxyurea, fusidic acid, diazolidinyl urea, imidazolidinyl urea, salicylic acid, barium and nickle chloride, metallic copper, thimerosal, 2-phenoxyethanol, and ProClin™.

In some embodiments, the preservative prevents or reduces nucleic acid degradation, in addition to preventing or inhibiting the growth and/or multiplication of bacteria. The preservation of nucleic acid integrity allows for the quantification of bacteria using PCR-based DNA or RNA analysis methods, e.g., 16S ribosomal RNA PCR and sequencing. In some embodiments, the preservative includes EDTA.

In some embodiments, the bactericidal preservative can include one or more of citric acid (CAS 77-92-9), sorbic acid (CAS 110-44-1), propylparaben (CAS 94-13-3), Tween 80 (CAS 9005-65-6), ethanol, bovine serum albumin, and TPCK (CAS 402-71-1). In some embodiments, the bactericidal preservative is a mixture of citric acid, sorbic acid, propyl-paraben, and Tween 80, e.g., the bactericidal preservative can include 2.5% (m/v) citric acid, 2.5% (m/v) sorbic acid, 2.5% (m/v) propyl-paraben), and 3.13% (m/v) Tween 80. In some embodiments, the bactericidal preservative is a mixture of sorbic acid, Tris, EDTA, Tween 80, and NaCl, e.g., the bactericidal preservative can include 2.0% (m/v) sorbic acid, tris, EDTA, 1.0% (m/v) Tween 80, and 1.0% (m/v) NaCl. In some embodiments, the bactericidal preservative is a heavy metal bactericidal mixture. In some embodiments, the bactericidal preservative is a mixture that includes barium chloride and nickel chloride. In some embodiments, the bactericidal preservative is thimerosal, e.g., a stabilizer that includes 0.1% thimerosal.

A cell filter 1250 is located between distal end 1214 of wicking sponge 1210 and a first end 1222 of transfer sponge 1220. The cell filter 1250 is configured to prevent undesired cells, such as Hela cells, from entering one or more downstream sponges in sampling system 1200, particularly sponges used in testing. In some embodiments, the filter can be used to filter and/or selectively kill eukaryotic cells. Excluding such undesired cells enhances the accuracy of various analytical results.

Fluid that passes from wicking sponge 1210 and through cell filter 1250 can enter transfer sponge 1220 via its first end first end 1222. Transfer sponge 1220 is configured to move the filtered fluid from cell filter 1250 to volume sponge 1230 and/or assay sponge 1240.

To allow transfer sponge 1220 (made of an absorptive material) to absorb a relatively large volume of fluid, transfer sponge 1220 is shaped (e.g., arc-shaped) to provide a relatively long distance between first end 1222 of transfer sponge 1220 and a second end 1224 of transfer sponge 1220. Second end 1224 contacts both volume sponge 1230 and assay sponge 1240 while preventing volume sponge 1230 and assay sponge 1240 from directly contacting each other. A barrier 1260 is located between first end 1222 and volume sponge 1230 to ensure that fluid absorbed in transfer sponge 1220 at first end 1222 travels to second end 1224 before being absorbed by volume sponge 1230. Although depicted as being arc-shaped, transfer sponge 1220 can have one or more different configurations, such as, for example, an extended straight line or multiple curves, depending, for example, on the desired volume of sample and/or desired transfer speed. In general, the shorter and/or thinner the path of transfer sponge 1220, the quicker the transfer speed from first end 1222 to second end 1224. The transfer sponge 1220 may be made of a VF2 sponge, an Ahlstrom M13 sponge, MF/F material, or another suitable absorptive material.

Volume sponge 1230 is made of an absorptive material that absorbs additional fluid for testing and is in fluid communication with assay sponge 1240 via second end 1224 of transfer sponge 1220. Volume sponge 1230 can be particularly useful when fluorescent or optical testing is used. In some embodiments, assay sponge 1240 and transfer sponge 1224 may not individually contain a sufficient volume of the sample to attain a confident test result. The volume of volume sponge 1230, assay sponge 1240, and second end 1224 of the transfer sponge 1220 sum to a sufficient testing volume for optical, and other, tests. Assay sponge 1240 contains a chemical assay that is used to test the sample or to prepare the sample for a test. Once assay sponge 1240 is saturated, the assay chemicals are free to flow from assay sponge 1240 and interact with sample absorbed by transfer sponge 1220 and volume sponge 1230. Volume sponge 1230 and the assay sponge 1240 may be made of a VF2 sponge, an Ahlstrom M13 sponge, MF/F material, or another suitable absorptive material. Preferably, the wicking sponge, wicking tongue, transfer sponge, and assay sponge are Ahlstrom M13 sponges, and the volume sponge is a VF2 sponge.

Cell filter 1250 can be made from any appropriate material and have any appropriate dimensions. Exemplary materials include polycarbonate (PCTE), polyethersulfone (PES), polyester (PETE) and polytetrafluoroethylene (PTFE). In some embodiments, the dimensions of cell filter 1250 can be about 9.5 millimeters by about 6.5 millimeters by about 0.05 millimeter.

Sampling system 1200 also includes a membrane 1270 located between assay sponge 1240 and a vent 1280 for gases to leave sampling system 1200. Membrane 1270 is configured to allow one or more gases to leave sampling system 1200 via an opening 1280, while maintaining liquid in sampling system 1200.

Figure 22:
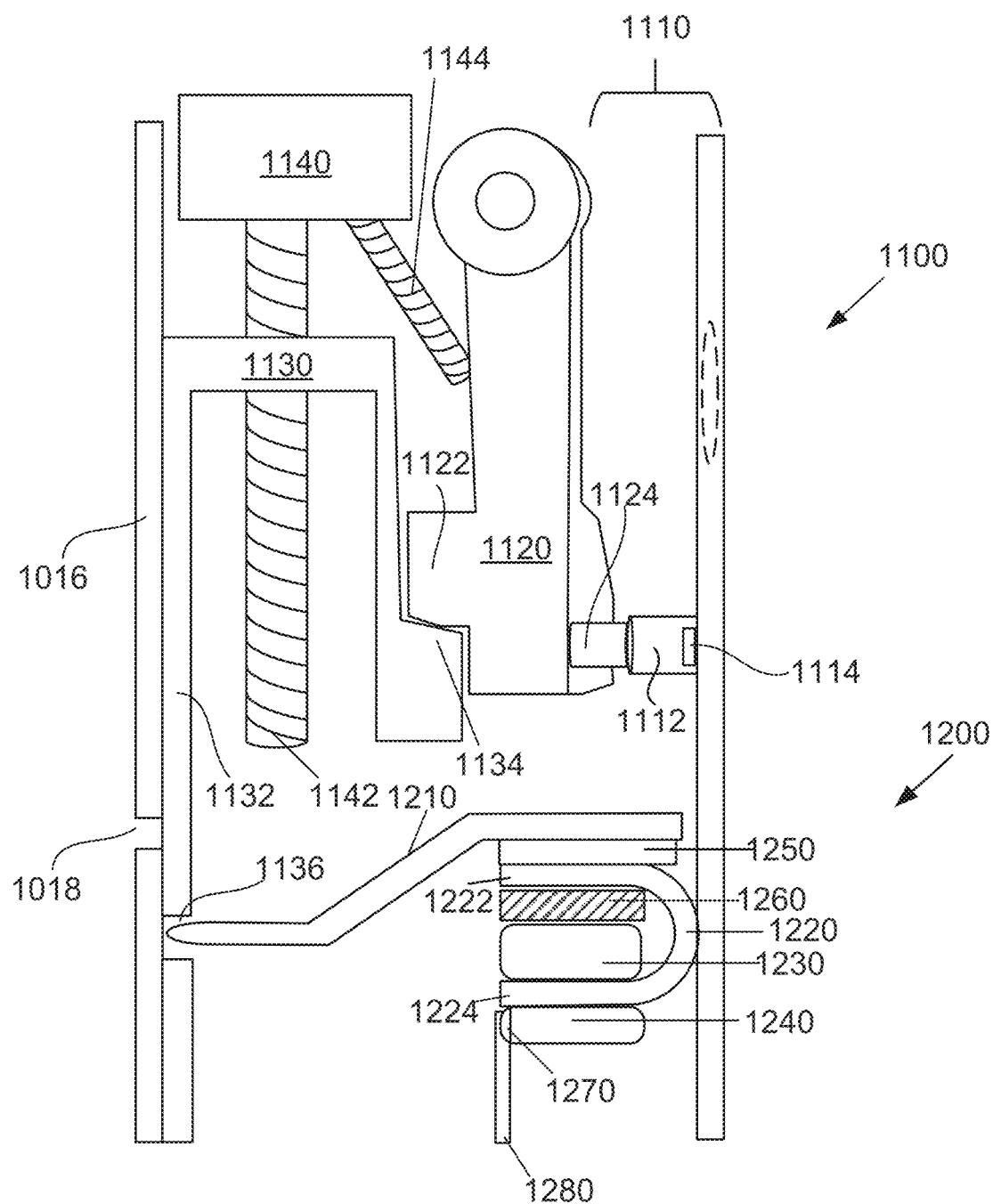
FIG. 22 illustrates an ingestible device.

FIG. 22 illustrates an embodiment of ingestible device 1000 with a relatively detailed view of both valve system 1100 and sampling system 1200. FIG. 22 shows valve system 1100 positioned prior to actuation of actuation system 1110 (e.g., when configured as shown in FIGS. 13A, 14A, 15A and 20A).

Figure 23:
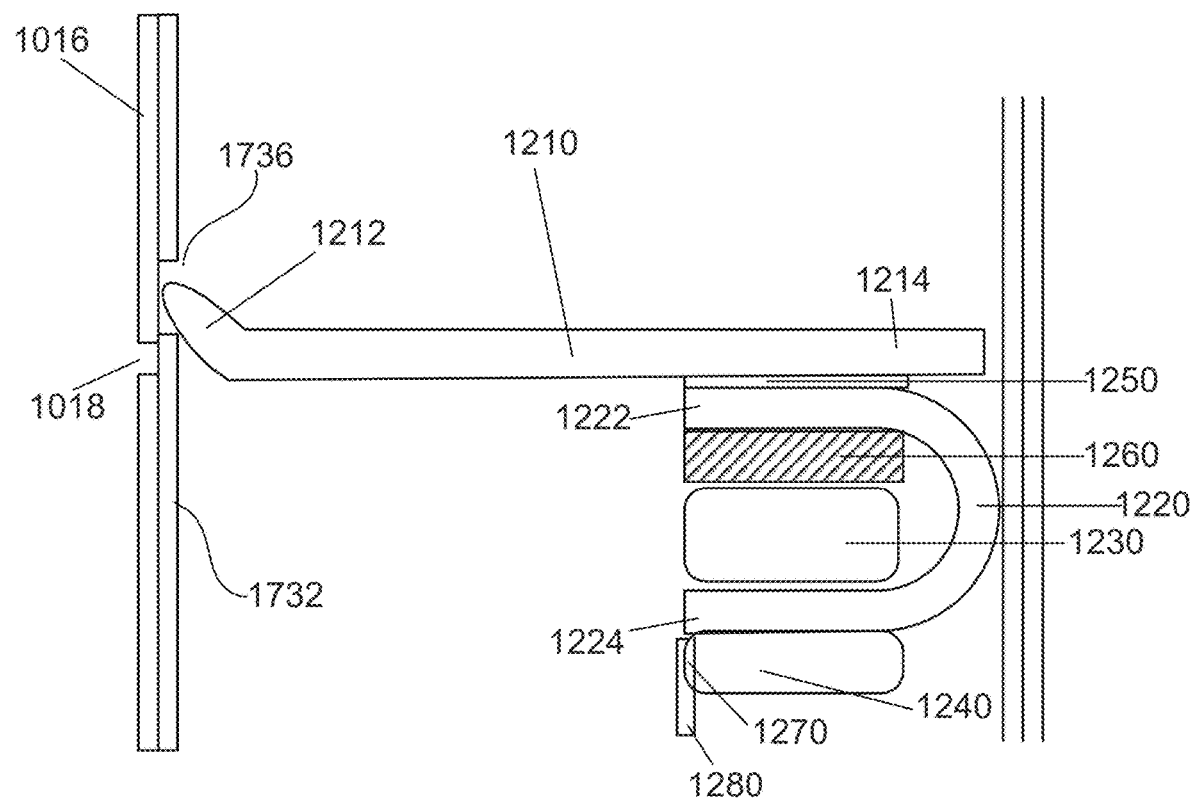
FIG. 23 illustrates an ingestible device.

FIG. 23 illustrates an embodiment of an ingestible device including sampling system 1200 and three-stage valve system 1700 positioned in its third stage.

Figure 24:
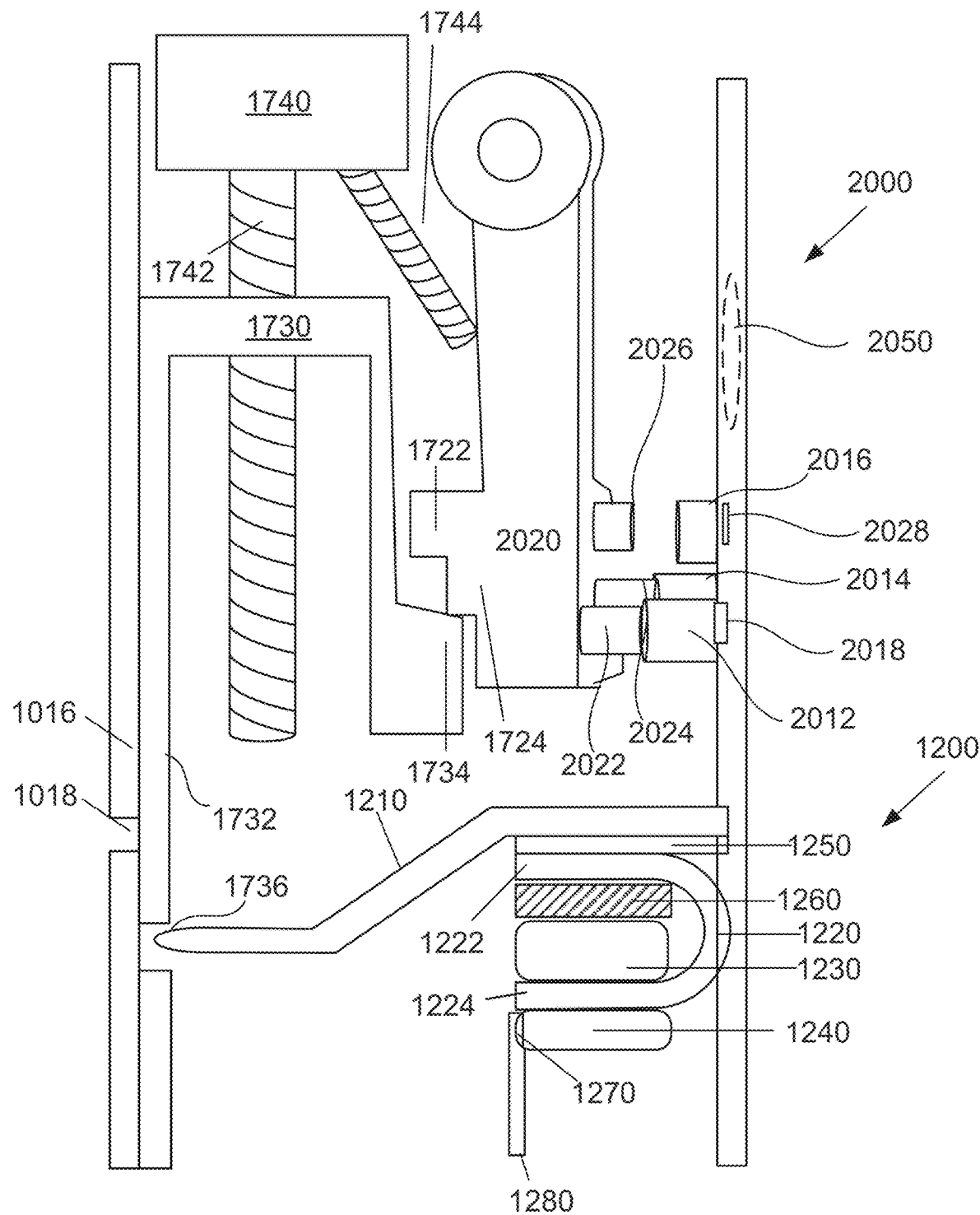
FIG. 24 illustrates an ingestible device.

FIG. 24 illustrates an embodiment of an ingestible device 1000 including sampling system 1200 and valve system 2000 positioned in its third stage.

Figure 25:
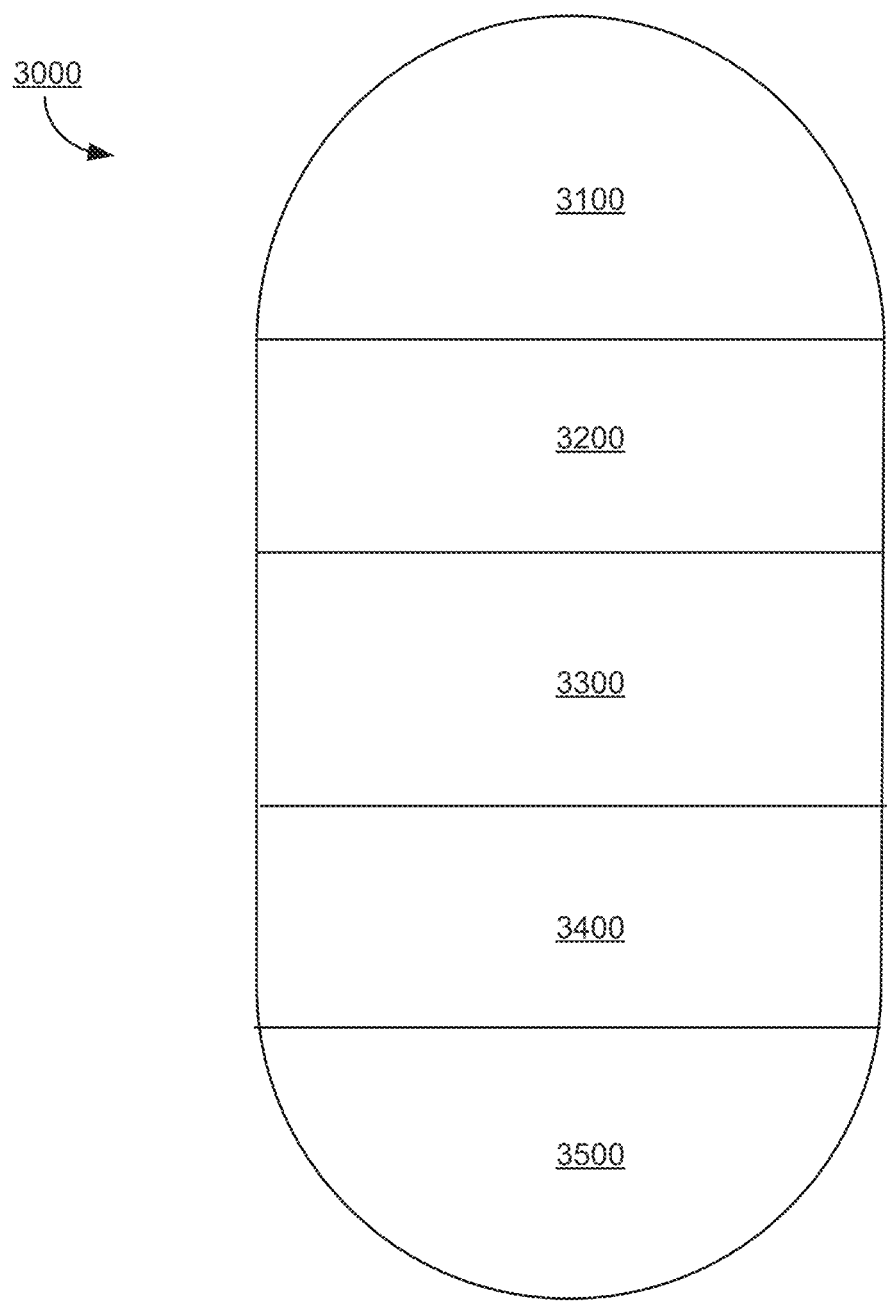
FIG. 25 illustrates an ingestible device.

FIG. 25 is a highly schematic illustration of an ingestible device 3000 that contains multiple different systems that cooperate for obtaining a sample and analyzing a sample, e.g., within the GI tract of a subject. Ingestible device 3000 includes a power system 3100 (e.g., one or more batteries), configured to power an electronics system 3200 (e.g., including a control system, optionally in signal communication with an external base station), and an analytic system 3500.

Exemplary analytical systems include assay systems, such as, for example, optical systems containing one or more sources of radiation and/or one more detectors. Such systems may use, for example, a light source that illuminates and a sample and a detector configured to detect light that is emitted by the sample (e.g., fluorescence spectroscopy), optical density (e.g., the portion of light that passes through the sample), and/or light that is diffracted by sample (e.g., diffraction optics). An analytical system may use, for example, ELISA (enzyme-linked immunosorbent assay). An analytical system may use, for example, LOCI (luminescent oxygen channeling) or LOCI (fluorescent oxygen channeling). An analytical technique may involve incubating and/or diluting a sample before or during the analysis/assaying of the sample. An analytical technique may involve the use of staining/dyeing a live cell.

Ingestible device 3000 also includes a sampling system 3400 for taking in a sample from the environment exterior to ingestible device 3000, and a valve system 3300 that regulates the ability of a fluid to access sampling system 3400.

Figure 26:
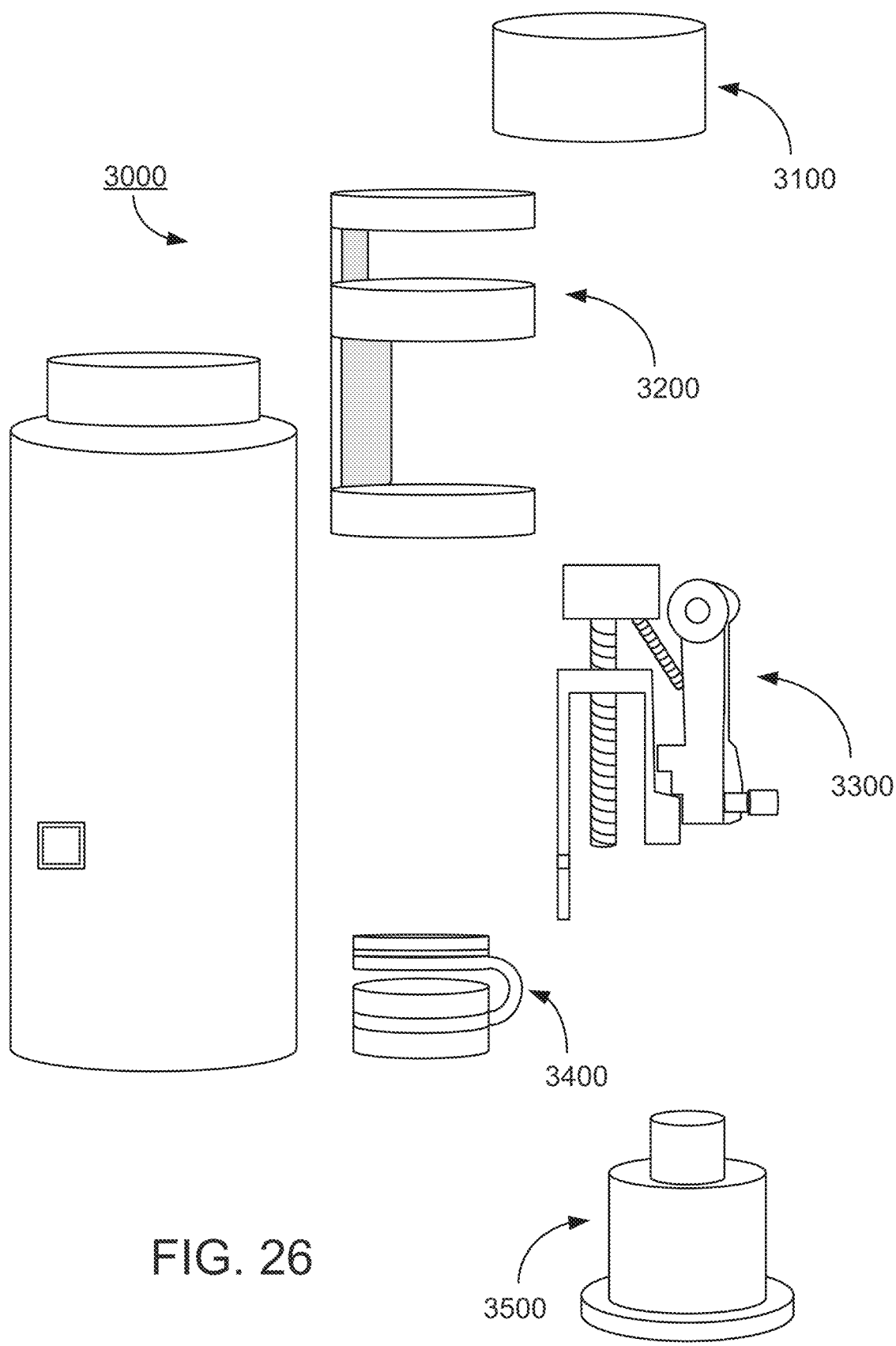
FIG. 26 is an exploded view of an ingestible device.

FIG. 26 provides an exploded view of the ingestible device 3000. FIG. 26 includes the exploded view of ingestible device 3000, showing a general configuration of the systems in FIG. 25. FIG. 26 includes power system 3100 (e.g., a stack of batteries), electronic system 3200 (e.g., a PCB and associated wiring), valve system 3300, sampling system 3400, and analytic system 3500.

Figure 27:
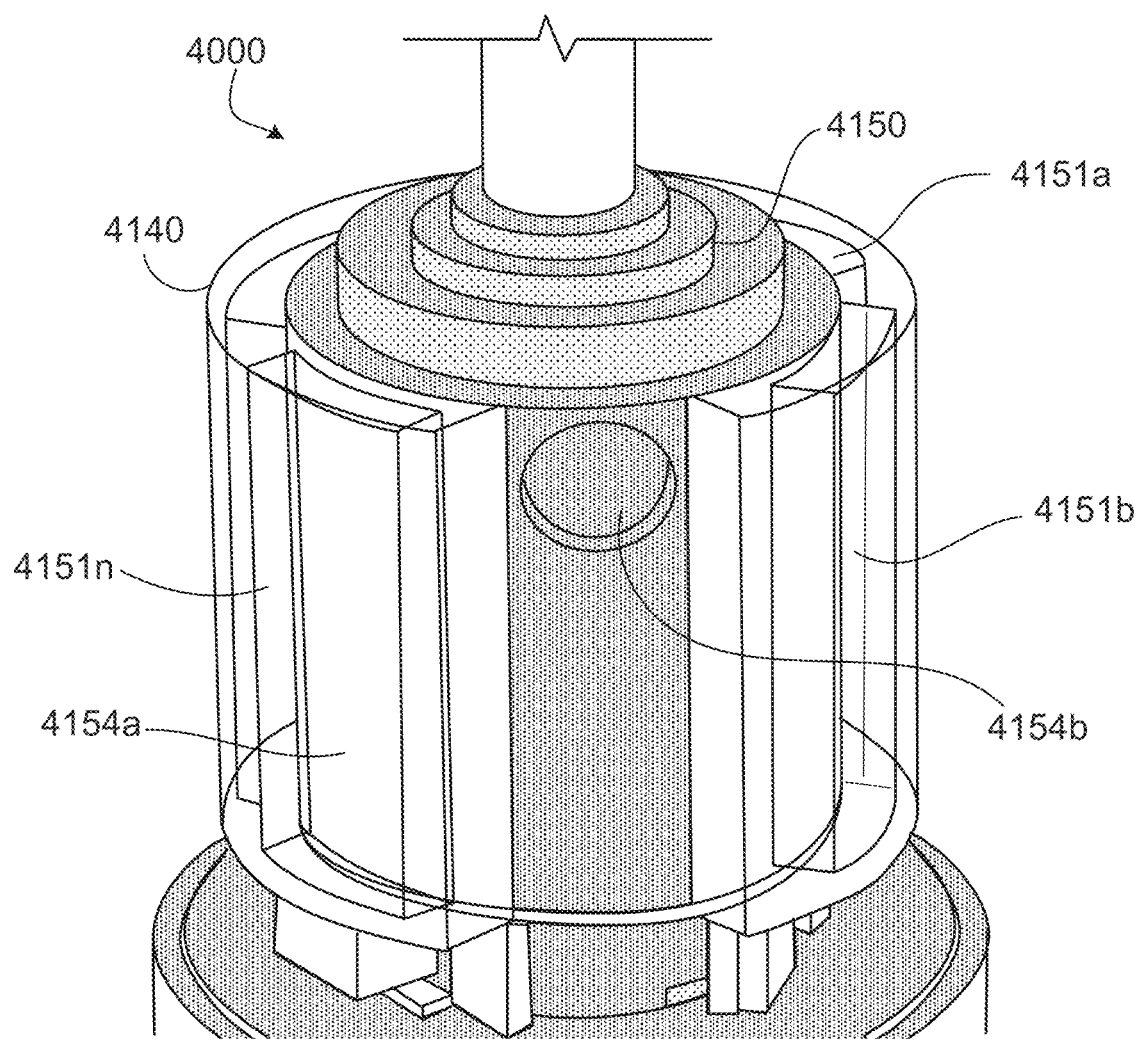
FIG. 27 illustrates a portion of an ingestible device.

FIG. 27 illustrates a portion of an ingestible device 4000 with a port 4154*b* in an open position to the exterior of the ingestible device 4000. The ingestible device 4000 may include a cylinder-shaped rotatable element 4150 that includes sampling ports on the wall of the rotatable element 4150. The sampling chamber 4150 is wrapped by a shell element 4140 with dividers to form a series of dilution chambers 4151*a-n* between the shell element 4140 and the rotatable element 4150. In operation, when the ingestible device 4000 determines the device itself arrives at a target location within the GI tract, the rotatable element 4150 may be rotated into an open position such that an aperture of the shell element 4140 is aligned with the port 4154*b* on the wall of the rotatable element 4150 and the port 4154*b* is exposed to the exterior of the ingestible device 4000 through the aperture. In this way, fluid from the GI tract can enter the port 4154*b* and occupy the volume defined by the port 154*b*. In the embodiment shown in FIG. 24, the port 4154*b* may be a depression on the surface of a rotatable element 4150 and a number of dilution chambers 4151*a-n* are positioned circumferentially around the axis of rotation of the rotatable element 4150. As previously discussed, each of the dilution chambers 4151*a-n* may store a dilution fluid. In some embodiments, the depression is a cylindrical depression. Optionally, the depression may be a rectangular depression, or any concave depression forming a regular or irregular shape. In another embodiment, the port 4154*b* may be connected to a chamber (not shown) within the rotatable element 4150 to create an enlarged space to store the GI fluid sample from the external environment of the ingestible device.

In some embodiments, the ingestible device 4000 may further include a controller and an actuator. The controller may determine that the ingestible device 4000 is located at a target location of the GI tract, and then the actuator may trigger the rotation of the rotatable element 4150 to align the port 4154*b* at the open position to initiate the sampling. For example, the housing of ingestible device 4000 may have a pH-sensitive enteric coating to detect or otherwise be sensitive to a pH level of the environment external to the ingestible device 4000, based on which the controller may determine whether the ingestible device has arrived at a target location. For another example, the ingestible device 4000 may include an optical sensing unit that transmits an illumination to the environment and collects a reflectance, based on which, the regio-specific location of the ingestible device 4000 may be identified based on optical characteristics of the reflectance.

Figure 28:
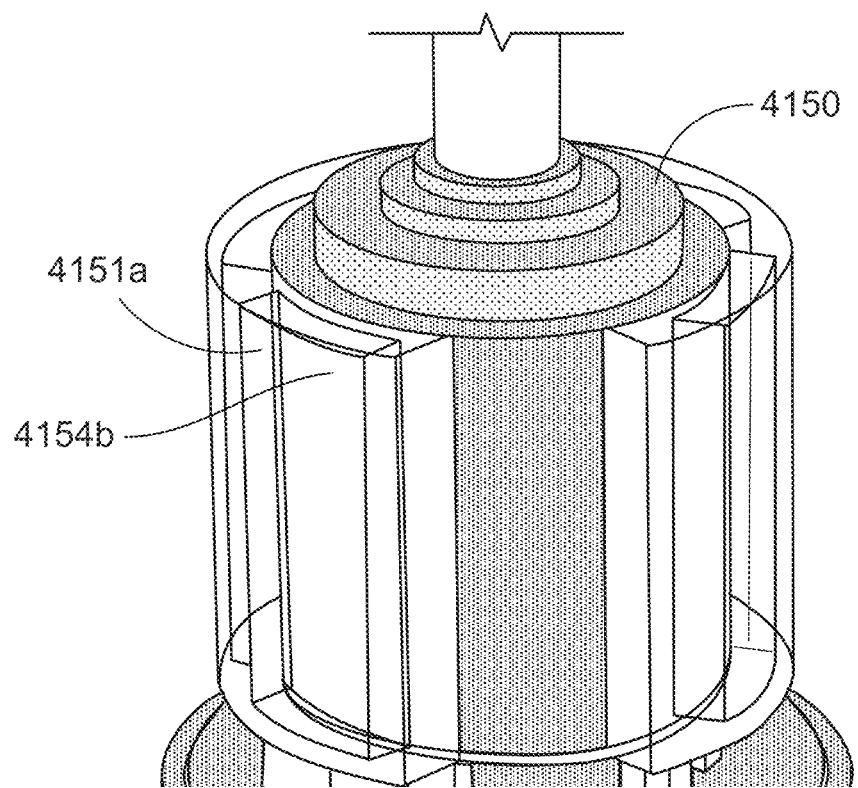
FIG. 28 illustrates a portion of an ingestible device.

FIG. 28 shows one embodiment of a portion of an ingestible device with a port 4154*b* at a first position aligned with a first dilution chamber 4151*a*. In operation, the rotatable element 4150 may be rotated to align the sampling port 4154*b* and the first dilution chamber 4151*a* such that the fluid sample from the GI tract stored within the volume of the sampling port 4154*b* can be combined with dilution fluid in the first dilution chamber to form a first dilution. The first dilution may then occupy the combined volume of the port 4154*b* and first dilution chamber 4151*a*. Optionally, the rotatable element 4150 may be subsequently rotated to a second position such that the port 4154*b* containing a portion of the first dilution is then moved to be aligned and in fluid communication with another dilution chamber, e.g., a second dilution chamber that is next to the first dilution chamber along the rotational direction. In this way, the first dilution stored within the port 4154*b* may then again be diluted with the dilution fluid stored within the second dilution chamber. Similarly, if the rotatable element 4150 keeps rotating and allows the port 4154*b* to be serially aligned with each dilution chamber, then the original GI fluid sample may be diluted serially and each dilution chambers 4151*a-n* may be left with a diluted GI fluid sample at a different dilution ratio.

Figure 29:
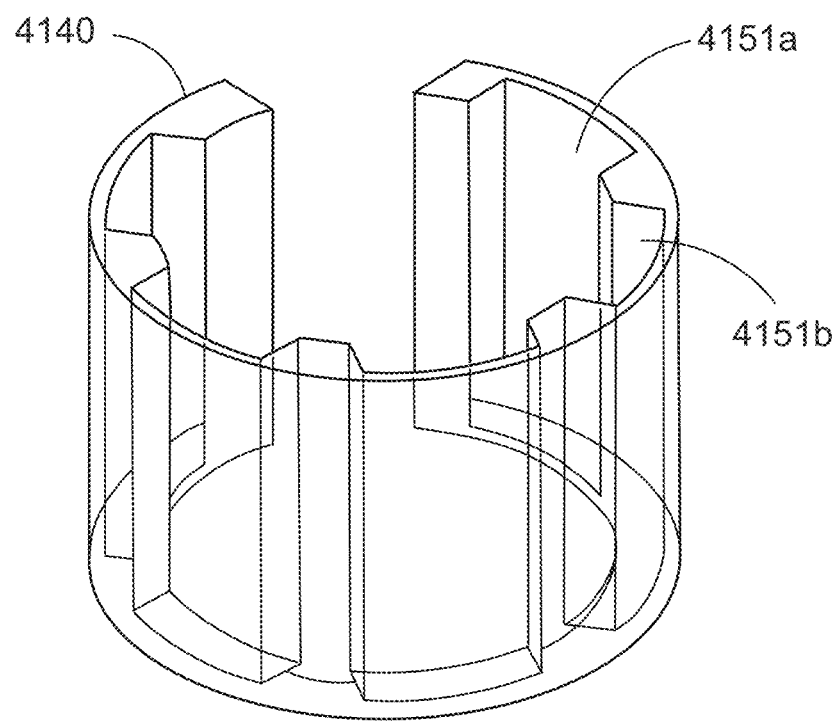
FIG. 29 illustrates a member forming part of a set of five incubation chambers suitable for an ingestible device.

FIG. 29 shows an embodiment of an element 4140 forming part of a set of five dilution chambers (e.g., including 4151*a-b*) for surrounding a rotatable element (e.g., 4150 in FIGS. 21-22) in an ingestible device as described herein. In some embodiments, the device may contain a single dilution chamber. Alternatively, the device may contain 2, 3, 4, 5, 6, 7, 8 or greater than 8 dilution chambers.

In some embodiments, each dilution chamber 4151*a-n* may be filled with a dilution fluid prior to the ingestible device 4000 being administered. In another embodiment, the dilution fluid may be stored in a separate reservoir (not shown) within the ingestible device 4000. At the time when the ingestible device 4000 is determined to be at a target location within the GI tract, a pumping mechanism may pump the dilution fluid into one or more dilution chambers 4151*a-b* via one or more outlet (not shown) of the reservoir.

In some embodiments, the shell element 4140 may have valves or pumps (not shown) between the dilution chambers 4151*a-n*. For example, the diluted fluid from a first dilution chamber may be pumped into a second dilution chamber via a valve between the two chambers.

Devices of the type depicted in FIGS. 27-29 optionally can include a sampling system as disclosed herein.

Figure 30:
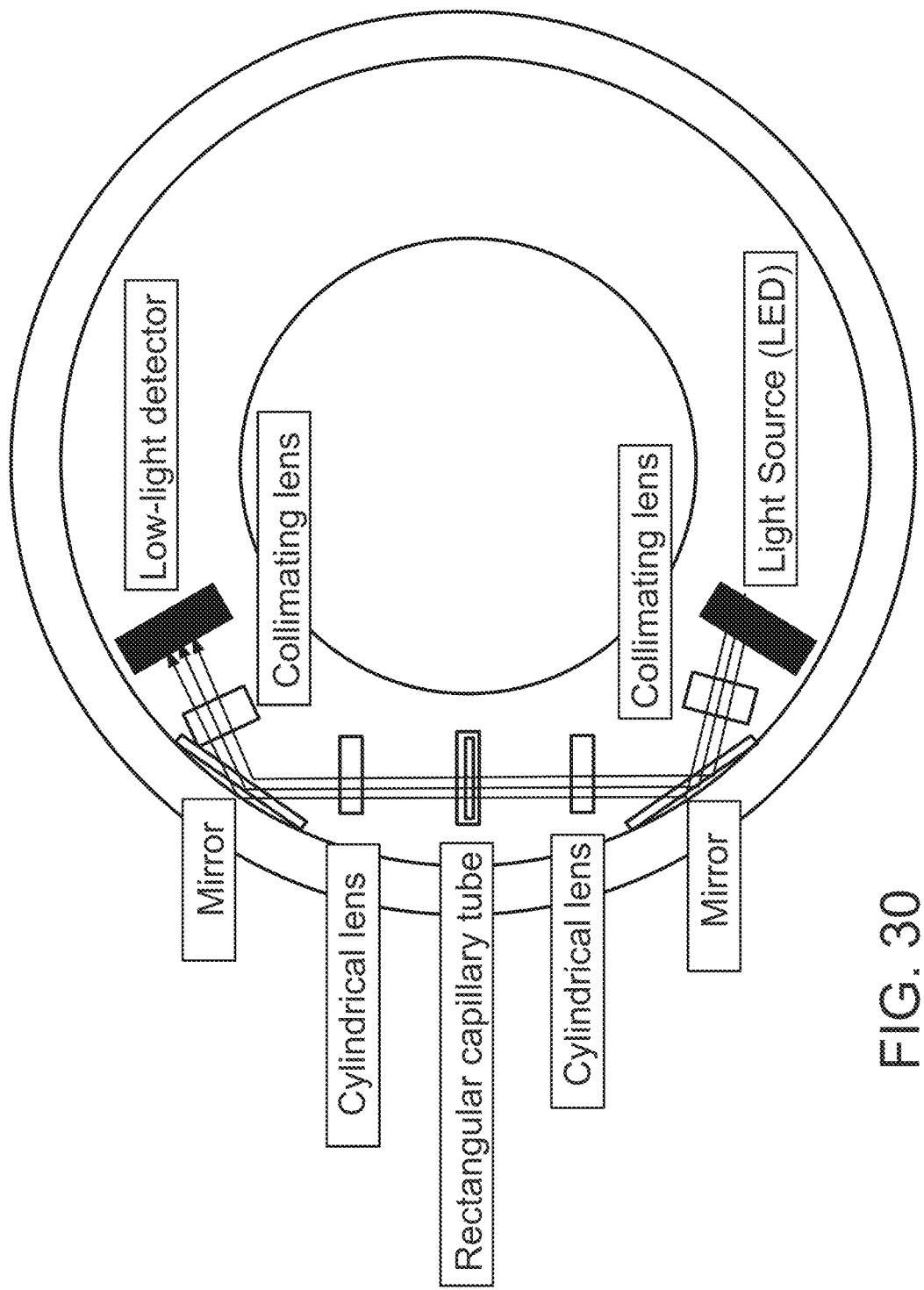
FIG. 30 illustrates a partial cross-sectional view of optics in an ingestible device.

In certain embodiments, an ingestible device includes a microscopic evaluation system. In some embodiments, bacterial cells in a sample may be first labeled with fluorescent dyes (such as those described herein), and the fluorescently-labeled cells may be imaged and counted by the microscopic evaluation using an ingestible device as described herein. For example, in some embodiments, the bacterial cells in a sample may be labeled with multiple analyte-binding reagents (e.g., multiple antibodies each specific for different types of analytes (e.g., bacteria of different genera, species, and/or strains)), each conjugated to a different dye, thereby allowing for the imaging, detection and counting of the different types of analytes (e.g., bacteria) present in the sample. In other embodiments, the fluorescently-labeled cells are counted as they pass through an onboard flow system (e.g., microfluidic single cell channeling). Examples of flow cytometry systems include hydrodynamic focusing, small diameter capillary tube flow, and rectangular capillary tube flow. As described herein, live bacteria cells are labeled, and the principles of flow cytometry are used to quantify labeled cells. Generally speaking, the photons from an incident laser beam are absorbed by the fluorophore and raised to a higher, unstable energy level. Within less than a nanosecond, the fluorophore re-emits the light at a longer representative wavelength where it is passed through a series of dichroic filters. This reemitted light can be collected and interpreted as proportional to the number of labeled bacteria cells. In some embodiments, a sheath fluid is not used as part of the flow system to help accommodate the volume restrictions of the device. In some embodiments, a rectangular capillary tube is used to achieve a sufficiently large cross-sectional area and relatively thin inspection area. The flow cytometry optical system operates parallel to the fluidics system and serves to observe the redirection of light passing through the cell and delivers information about the bacterial cells. In some embodiments, rather than using a conventional laser and spherical lenses to focus the light to a point, an LED and cylindrical lenses are used to focus the light to a line across a rectangular capillary tube. In other embodiments, collimating lenses are used to make the light source parallel, while cylindrical lenses are used to refine the inspection area. An exemplary optical configuration for this arrangement can be seen in FIG. 30. In some embodiments, optical filters can be added to permit the use of fluorophores. The characteristic wavelength of reemitted light from the fluorophores can be isolated and detected with the use of dichroic, bandpass, and short or long wave pass filters. Generally, multiple dichroic lenses and photomultipliers are used, however, due to space limitations, only a single side-scatter detector and forward scatter detector may be used in certain embodiments.

One of the design challenges of integrating flow cytometry into the device is to provide a pumping mechanism. Without moving fluid, individual bacteria cells cannot be identified and accounted for by flow cytometry within a fixed volume of fluid. In some embodiments, a gear motor is to move fluid through the device. For example, a micromotor including a planetary gearhead (e.g., with a 25:1 reduction) can provide the desired amount of torque to create fluid flow. In another embodiment, a series of piezoelectric resistors embedded in the surface of a microfabricated plate is used to create flow. In yet another embodiment, a micropump that includes a pair of one-way valves and uses a magnetic pump membrane actuated by an external magnetic field is used to create flow.

Figure 31:
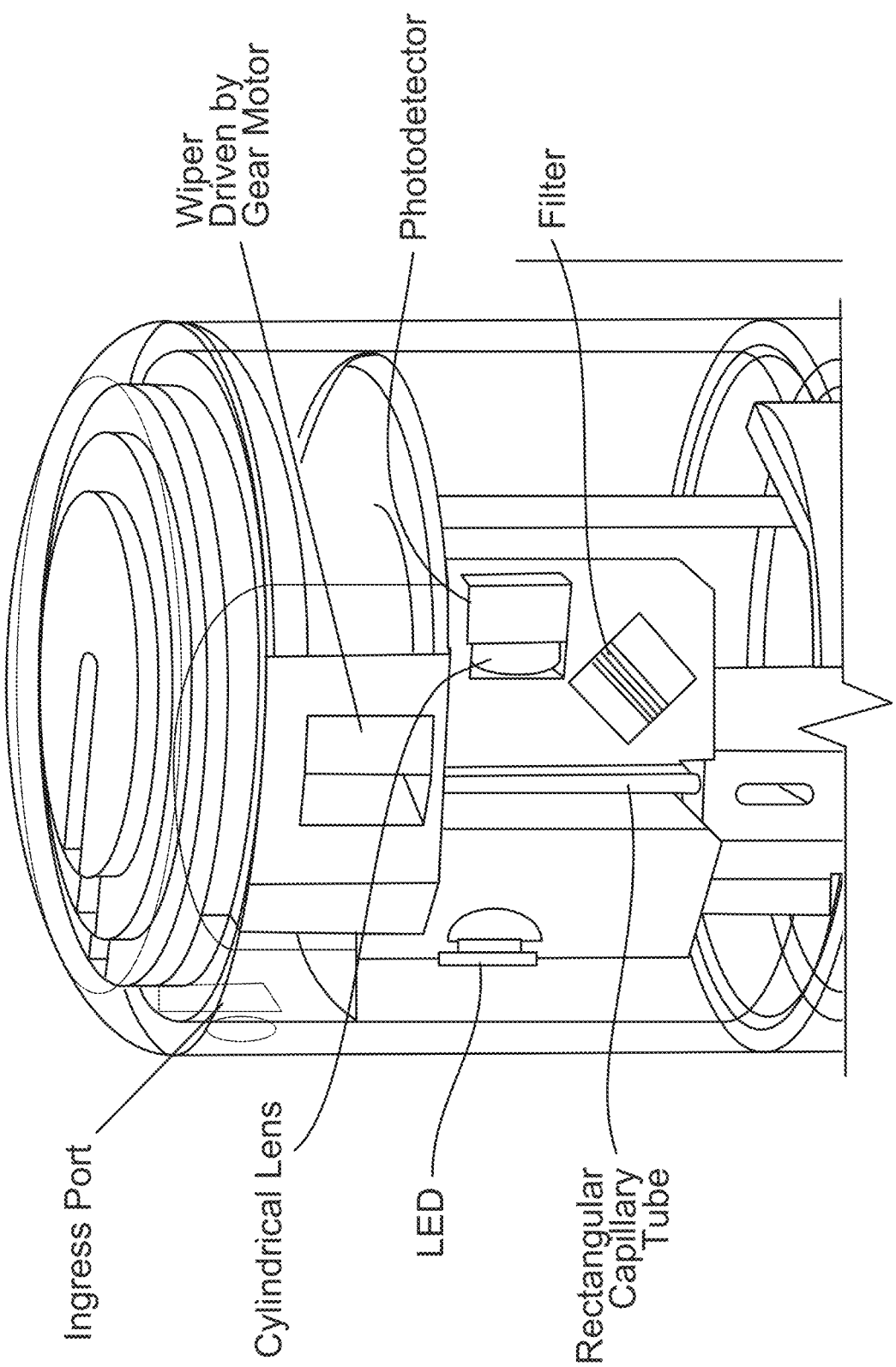
FIG. 31 illustrates components of the optics and flow chamber systems in an ingestible device.

In some embodiments, the system architecture includes an opening and sealing mechanism combined with a rotary wiper which creates a pressure driven flow via a gear motor. The gear motor can be used for other functions in the device. As shown in FIG. 31, the components of the optics and flow chamber systems fit within the device. In some embodiments, the sample fluid is absorbed via a flexible membrane at the top of the capsule. In some embodiments, the gear motor has 270° of permissible travel which serves to open and fill the fluid chamber. During closure, the motor closes the ingress port while simultaneously pushing the fluid through the rectangular capillary tube where the optical system is located. The threaded component allows the flexible membrane to close and seal the ingress channel without changing the wiper height. In some embodiments, the volume of the sample chamber is 25 µL, 50 µL, 75 µL or more. In some embodiments, two or more samples are taken from the GI tract to procure a sufficient sample size. Referring to FIG. 31, an LED on the left side of the capillary tube and the low-light photodetector on the right for capturing forward and side scatter are shown. Once the fluid passes through the capillary tube, it exits the capsule via a one-way valve. In certain embodiments, the flow system allows for the detection of cell size and internal cell complexity, in addition to cell quantitation.

The foregoing discussion is not exhaustive with respect to various ingestible device designs, either with respect to sampling componentry or absorbent (sponge) design.

As an example, while ingestible devices have been described that include one or more optical systems incorporated into the ingestible device, in some embodiments, an ingestible device does not include an optical system. Optionally, such ingestible devices may also not include any other analytical componentry. In embodiments of an ingestible device, which do not include an optical system and/or other analytical componentry, there may be more room inside the ingestible device to store one or more samples.

Figure 32:
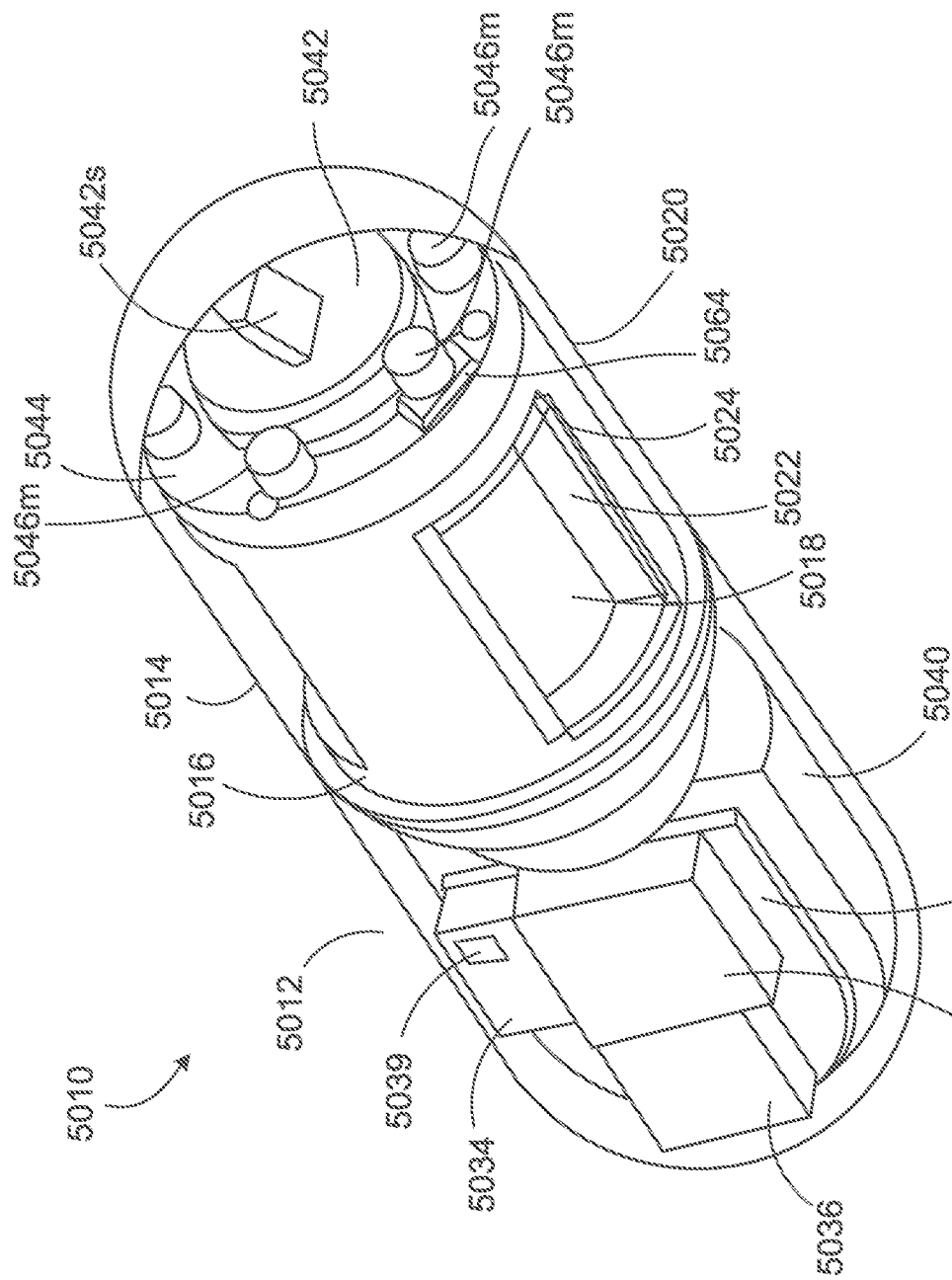
FIG. 32 shows a partial view of an ingestible device

FIG. 32 shows a partial view of an exemplary embodiment of an ingestible device 5010 in which a portion of the enclosure of ingestible device 5010 has been removed. Ingestible device 5010 may be used for collecting substances. Ingestible device 5010 may generally be in the shape of a capsule, like a conventional pill. Accordingly, the shape of ingestible device 5010 provides for easier ingestion and is also familiar to healthcare practitioners and patients.

The structure of ingestible device 5010 includes first portion 5012 and second portion 5014. First portion 5012 includes control electronics, a power supply, and a communication system. Second portion 5014 is generally configured to interact with the GI tract, such as, for example but not limited to, sample collection, substance delivery and environmental monitoring. Second portion 5014 includes a storage sub-unit 5016 with one or more chambers 5018 and a chamber enclosure 5020 that encloses or overlays a storage sub-unit 5016. Each chamber 5018 has a corresponding chamber opening 5022. Chamber enclosure 5020 has an access port 5024. In this example embodiment, ingestible device 5010 includes three chambers 5018, but there can be other embodiments that have one, two or more than three chambers.

Figures 33A, 33B, 33C:
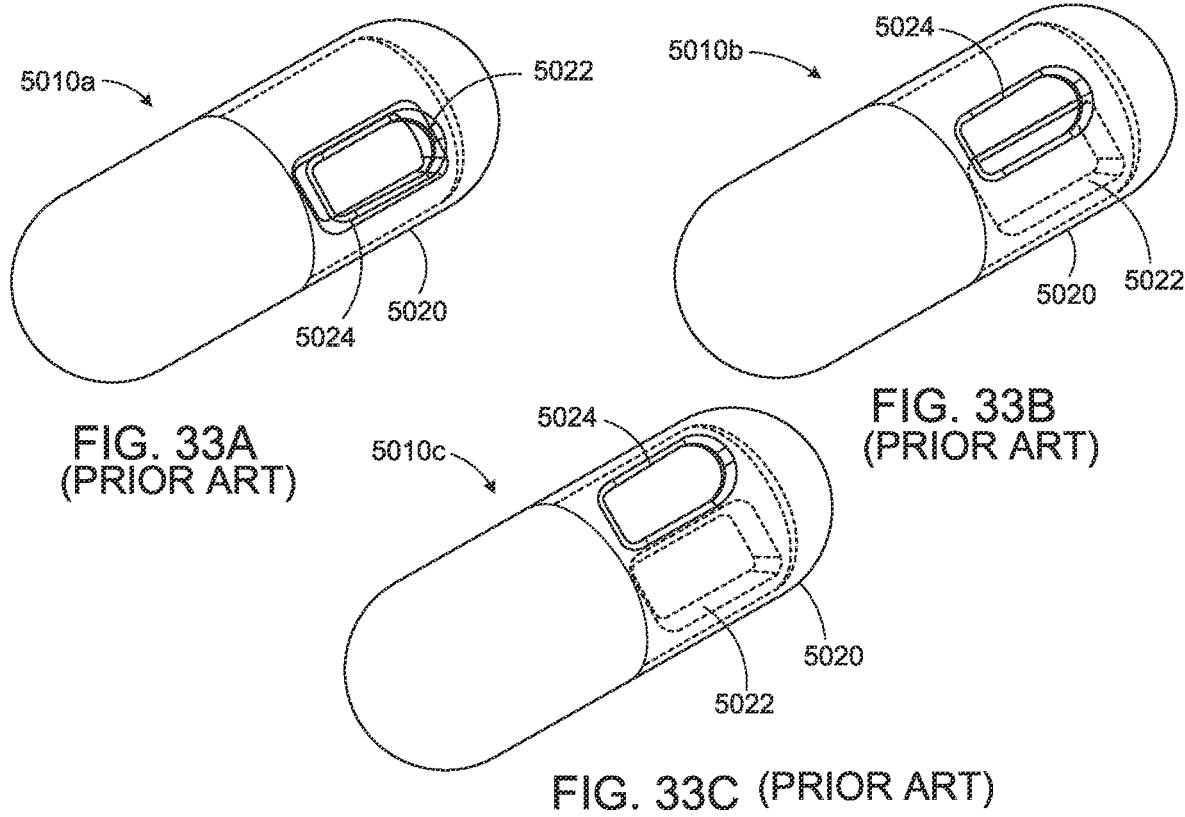
FIGS. 33A, 33B and 33C illustrate operation of ingestible device.

FIGS. 33A-33C illustrate operation of ingestible device 5010. Generally, chamber enclosure 5020 operates as a "closed-loop" revolver mechanism. Chamber enclosure 5020 rotates, in a controlled manner, to align the access port 5024 with each of chamber openings 5022 for collecting, at targeted locations, samples of the contents in the GI into corresponding chambers 5018 (shown in FIG. 32), and/or for delivering substances stored in chambers 5018 (shown in FIG. 32) to targeted locations within the body.

Generally, during collection of samples, the rotation of chamber enclosure 5020 may be described as a "closed-loop" revolver mechanism because each chamber opening 5022 is exposed only once during the passage of ingestible device 5010 within the body in order to avoid cross-contamination of the collected samples. In other words, in some embodiments, chamber enclosure 5020 ideally rotates only once when collecting samples during each usage of ingestible device 5010 so that access port 5024 aligns with each of chamber openings 5022 serially and only once. That is, during collection of samples, access port 2224 does not bypass any chamber opening 5022 and also does not return to a previous chamber opening 5022 during its rotation.

In some embodiments, chamber enclosure 5020 can rotate in a bidirectional motion before completing one revolution and/or perform multiple revolutions during one usage of the ingestible device 5010 so that at least one chamber opening 5022 is exposed multiple times. A chamber opening 5022 may need to be exposed multiple times if its corresponding chamber stores solids or semi-solid reagents, sensors or cleaning agents for cleaning the GI tract.

As illustrated in FIG. 33A, shown therein generally is ingestible device 5010 in an open position 5010a in which access port 5024 on chamber enclosure 5020 is aligned with a chamber opening 5022. In this configuration, ingestible device 5010 may collect substances through chamber opening 5022. In other words, the contents of the GI tract may be forced into exposed chamber 5018 (shown in FIG. 32) through muscular contractions (e.g., peristalsis).

Thereafter, chamber enclosure 5020 may rotate to seal chamber opening 5022. FIG. 33B shows ingestible device 5010 with a partially open/partially closed position 5010b in which access port 5024 has been rotated such that chamber enclosure 5020 partially seals chamber opening 5022.

FIG. 33C shows ingestible device 5010 in a closed position 5010c, in which the chamber enclosure 5020 has been rotated a distance such that access port 5024 completely seals chamber opening 5022. If chamber enclosure 5020 has not rotated one revolution, chamber enclosure 5020 may continue to rotate in the same direction in order to align access port 5024 with another chamber opening 5022 depending if ingestible device 5010 has been configured to perform another operation (i.e. sampling or distribution).

In another example embodiment, chamber enclosure 5020 may be stationary and storage sub-unit 5016 (shown in FIG. 32) may instead rotate to align its one or more chamber openings 5022 with access port 5024. Rotating storage sub-unit 5016 instead of chamber enclosure 5020 may provide greater control over the rotation motion and a more constant motion since storage sub-unit 5016 would not be subjected to a varying viscosity arising from the contents in the GI tract. This arrangement, however, may limit a volume of at least one of chambers 5018.

In some embodiments, chamber enclosure 5020 or storage sub-unit 5016 may rotate in a predetermined sequence of bidirectional rotational motions. As described above, when storage sub-unit 5016 is configured to rotate instead of chamber enclosure 5020, the volume of at least one of chambers 5018 can be limited. In order to avoid having to limit the volume of the chambers 5018, non-recess areas that may be used to separate different chambers 5018 in storage sub-unit 5016 may be minimized in volume or removed. Ingestible device 5010 can rotate in a first direction for aligning access port 5024 with one of the two adjacent chambers. Ingestible device 5010 can be configured to rotate in a second direction that is opposite to the first direction in order to avoid cross contamination between samples collected into or substances released from those two adjacent chambers.

Ingestible device 5010 may be used for collecting usable samples from the contents of the GI tract (e.g., 100 µL sized samples) and maintaining each sample in isolation from one another until the samples are extracted.

In some embodiments, ingestible device 5010 may also be configured to conduct in-vivo measurements. Ingestible device 5010 is introduced into the body with some of chambers 5018 being empty and some of chambers 5018 carrying at least one reagents. At a predefined location in the body, ingestible device 5010 is configured to collect a sample from the GI tract and to store the sample into a chamber carrying at least one reagent. After collection, in-vivo analysis may be conducted based on how the collected sample interacts with the reagent inside chamber 5018. For example, ingestible device 5010 may use a biochemistry assay, such as an enzyme-linked immunosorbent assay (ELISA), for performing in-situ experiments on collected samples. Alternatively, peripherals can be included into chambers 5018 for changing the dynamics of several in-vivo analysis and measurements. The peripherals may include a light source, a receiver, a transducer, a heater, and the like. In general, the in-vivo experiments vary according to the type of information that is being sought.

Figure 34:
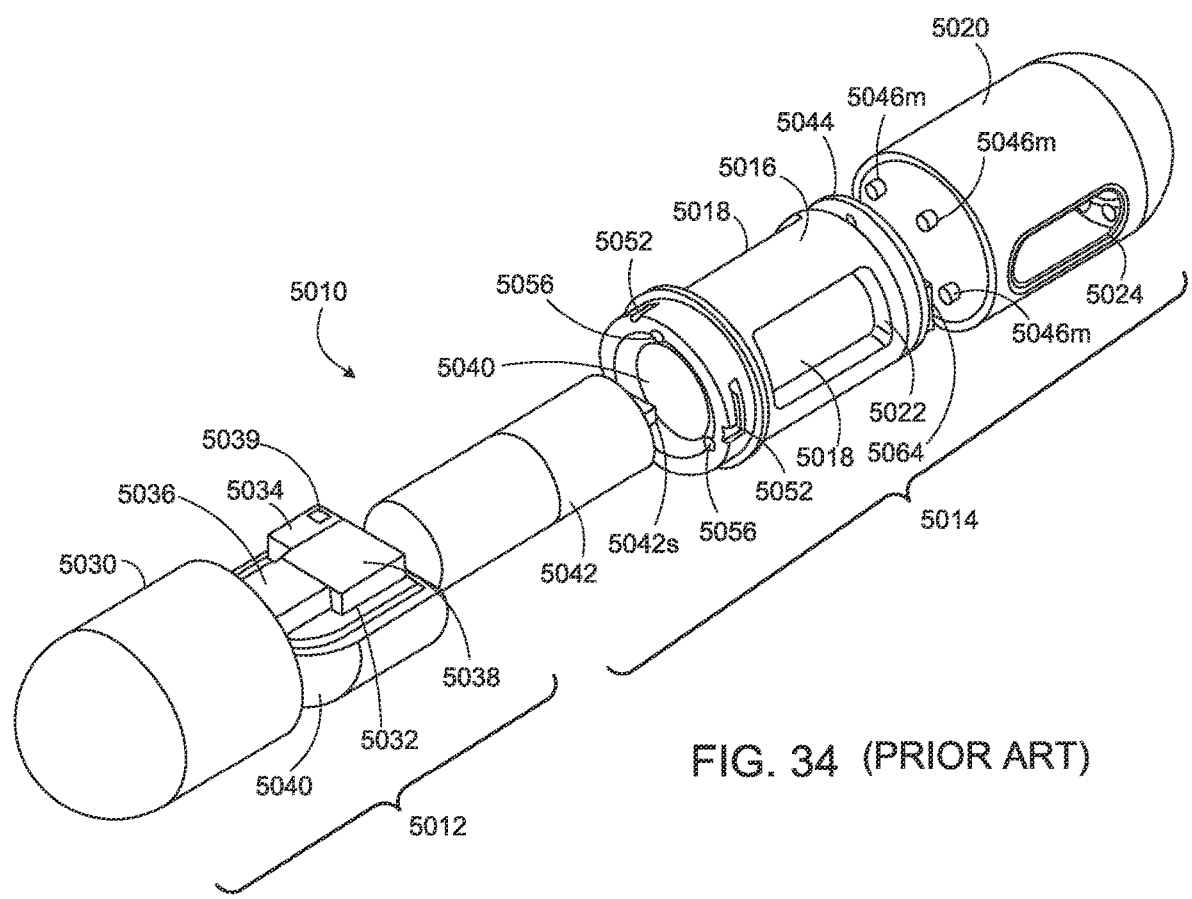
FIG. 34 illustrates an exploded view of the components of ingestible device.

FIG. 34 illustrates an exploded view of the components of ingestible device 5010 in one example embodiment. First portion 5012 of ingestible device 5010 includes an end closure 5030, and electronic components embedded on a main printed circuit board (PCB) 5032 including a communication subsystem having communication peripherals 5034 and a transceiver 5036, a main microcontroller (i.e. processor) 5038, a power supply 5040 and other peripheral components, including a magnetic switch 5039, described in further detail below. Second portion 5014 of ingestible device 5010 generally includes a motor 5042 with a shaft 5042s protruding from motor 5042, storage sub-unit 5016, a secondary PCB 5044, an encoding magnet arrangement 5046m and the chamber enclosure 5020. Generally, by placing main PCB 5032 and secondary PCB 5044 in distinct regions inside ingestible device 5010, they may be prevented from experiencing the same electrical or physical hazards. Motor 5042 is inserted into a motor compartment 5054 that is located in the center of storage sub-unit 5016. PCB 5044 is annular and includes one or more peripheral electronic components (e.g., a capacitor and a resistor, which can be used as a pull-up resistor), and a sensor 5064. Storage sub-unit 5016 further includes chambers 5018, with chamber openings 5022, for storing one or more collected samples and/or for storing one or more dispensable substances. Access holes 5056 are also located on storage sub-unit 5016 oriented towards the first portion 5030.

End enclosure 5030 provides a hollow space defined by an inner wall that is cylindrical with a domed end portion. End enclosure 5030 also includes engagement members for aligning and releasably engaging with storage sub-unit 5016 to releasably lock end enclosure 5030 in place during operation. In particular, engagement members releasably engage complementary structures 5052 in storage sub-unit 5016. When end enclosure 5030 locks with storage sub-unit 5016, end enclosure 5030 overlaps with a rear of storage sub-unit 5016 and creates a seal. In some embodiments, the overlap between end enclosure 5030 and storage sub-unit 5016 may span a width of 3 millimeters.

Some or all of the sponges of the above-described sampling systems may contain one or more preservatives (see discussion above). Typically, the assay sponge and/or the volume sponge and/or the transfer sponge contain one or more preservatives. Typically, the preservative(s) are selected based on the analyte of interest, e.g., an analyte (such as a nucleic acid or protein biomarker) for a GI disorder.

In some embodiments, an ingestible is configured to delivery one or more substances (e.g., one more therapeutic substances). FIGS. 35-55 provide illustrative and non-limiting examples of such ingestible devices. It is to be understood that one more features from such an ingestible device can be combined with one or more features of an ingestible device configured to take one more samples, such as, for example, described above with regarding to FIGS. 1-34.

Figure 35:
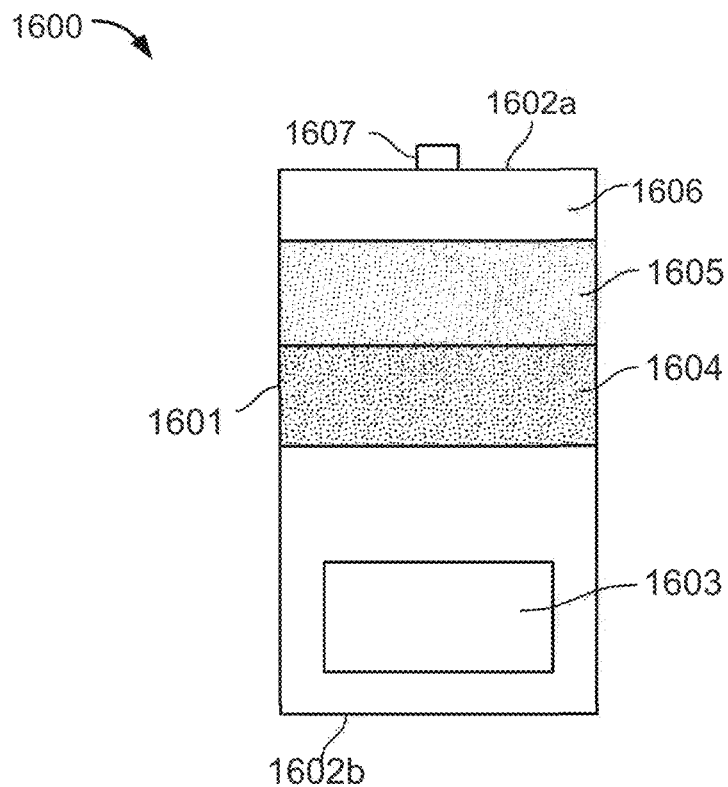
FIG. 35 illustrates an ingestible device.

FIG. 35 provides an example mock-up diagram illustrating aspects of a structure of an ingestible device 1600 for delivering a dispensable substance, according to some embodiments described herein. In some embodiments, the ingestible device 1600 may generally be in the shape of a capsule, a pill or any swallowable form that may be orally consumed by an individual. In this way, the ingestible device 1600 may be ingested by a patient and may be prescribed by healthcare practitioners and patients.

The ingestible device 1600 includes a housing 1601 that may take a shape similar to a capsule, a pill, and/or the like, which may include two ends 1602a-b. The housing 1601 may be designed to withstand the chemical and mechanical environment of the GI tract (e.g., effects of muscle contractile forces and concentrated hydrochloric acid in the stomach). A broad range of materials that may be used for the housing 1601. Examples of these materials include, but are not limited to, thermoplastics, fluoropolymers, elastomers, stainless steel and glass complying with ISO 10993 and USP Class VI specifications for biocompatibility; and any other suitable materials and combinations thereof.

In some embodiment, the wall of the housing 1601 may have a thickness of 0.5 mm-1 mm, which is sufficient to sustain an internal explosion (e.g., caused by hydrogen ignition or over pressure inside the housing).

The housing 1601 may or may not have a pH-sensitive enteric coating to detect or otherwise be sensitive to a pH level of the environment external to the ingestible device. As discussed elsewhere in the application in more detail, the ingestible device 1600 may additionally or alternatively include one more sensors, e.g., temperature sensor, pH sensor, impedance sensor, optical sensor.

The housing 1601 may be formed by coupling two enclosure portions together. The ingestible device 1600 may include an electronic component within the housing 1600. The electronic component may be placed proximally to an end 1602b of the housing, and includes a printed circuit board (PCB), a battery, an optical sensing unit, and/or the like.

The ingestible device 1600 further includes a gas generating cell 1603 that is configured to generate gas and thus cause an internal pressure within the housing 1601. In some embodiments, the gas generating cell may include or be connected to a separate channel or valve of the ingestible device such that gas may be release through the channel or valve to create a motion to alter the position of the ingestible device within the GI tract. Such gas release can also be used to position the ingestible device relative to the intestinal lining. In another embodiment, gas may be released through the separate channel or valve to alter the surface orientation of the intestinal tissue prior to delivery of the dispensable substance.

A traveling plunger 1604 may be placed on top of the gas generating cell 1603 within the housing 1601. The traveling plunger 1604 is a membrane that separates the gas generating cell 1603 and a storage reservoir that stores the dispensable substance 1605. In some embodiments, the traveling plunger 1604 may be a movable piston. In some embodiments, the traveling plunger 1604 may instead be a flexible membrane such as but not limited to a diaphragm. In some embodiments, the traveling plunger 1604, which may have the form of a flexible diaphragm, may be placed along an axial direction of the housing 1601, instead of being placed on top of the gas generating cell 1603. The traveling plunger or the membrane 1604 may move (when the membrane 1604 is a piston) or deform (when the membrane 1604 is a diaphragm) towards a direction of the end 1602a of the housing, when the gas generating cell 1603 generates gas to create an internal pressure that pushes the membrane 1604. In this way, the membrane or traveling plunger 1604 may push the dispensable substance 1605 out of the housing via a dispensing outlet 1607.

The housing 1601 may include a storage reservoir storing one or more dispensable substances 1605 adjacent to the traveling plunger 1604. The dispensable substance 1605 may take the form of a powder, a compressed powder, a fluid, a semi-liquid gel, or any other dispensable or deliverable form. The delivery of the dispensable substance 1605 may take a form such as but not limited to bolus, semi-bolus, continuous, systemic, burst delivery, and/or the like.

In some embodiments, the storage reservoir may include multiple chambers, and each chamber stores a different dispensable substance. For example, the different dispensable substances can be released at the same time via the dispensing outlet 1607. Alternatively, the multiple chambers may take a form of different layers within the storage reservoir such that the different dispensable substance from each chamber is delivered sequentially in an order. In one example, each of the multiple chambers is controlled by a separate traveling plunger, which may be propelled by gas generation. The electronic component may control the gas generating cell 1603 to generate gas to propel a specific traveling plunger, e.g., via a separate gas generation chamber, etc., to delivery the respective substance. In some embodiments, the content of the multiple chambers may be mixed or combined prior to release.

The ingestible device 1600 may include a dispensing outlet 1607 at one end 1602a of the housing 1601 to direct the dispensable substance 1605 out of the housing. The dispensing outlet 1607 may include an exit valve, a slit or a hole, a jet injection nozzle with a syringe, and/or the like. When the traveling plunger 1604 moves towards the end 1602a of the housing 1601, an internal pressure within the storage reservoir may increase and push the dispensing outlet to be open to let the dispensable substance 1605 be released out of the housing 1601.

In an embodiment, a pressure relief device 1606 may be placed within the housing 1601, e.g., at the end 1602a of the housing 1601.

In some embodiments, the housing 1601 may include small holes (e.g., with a diameter smaller than 2 mm), e.g., on the side of the housing 1601, or at the end 1602a to facilitate loading the dispensable substance into the storage reservoir.

In some embodiments, a feedback control circuit (e.g., a feedback resistor, etc.) may be added to send feedback from the gas generating cell 1603 to the electronic component such that when the internal pressure reaches a threshold level, the electronic component may control the gas generating cell 1603 to turn off gas generation, or to activate other safety mechanism (e.g., feedback-controlled release valve, etc.). For example, an internal pressure sensor may be used to measure the internal pressure within the ingestible device and generate feedback to the feedback control circuit.

Figure 36:
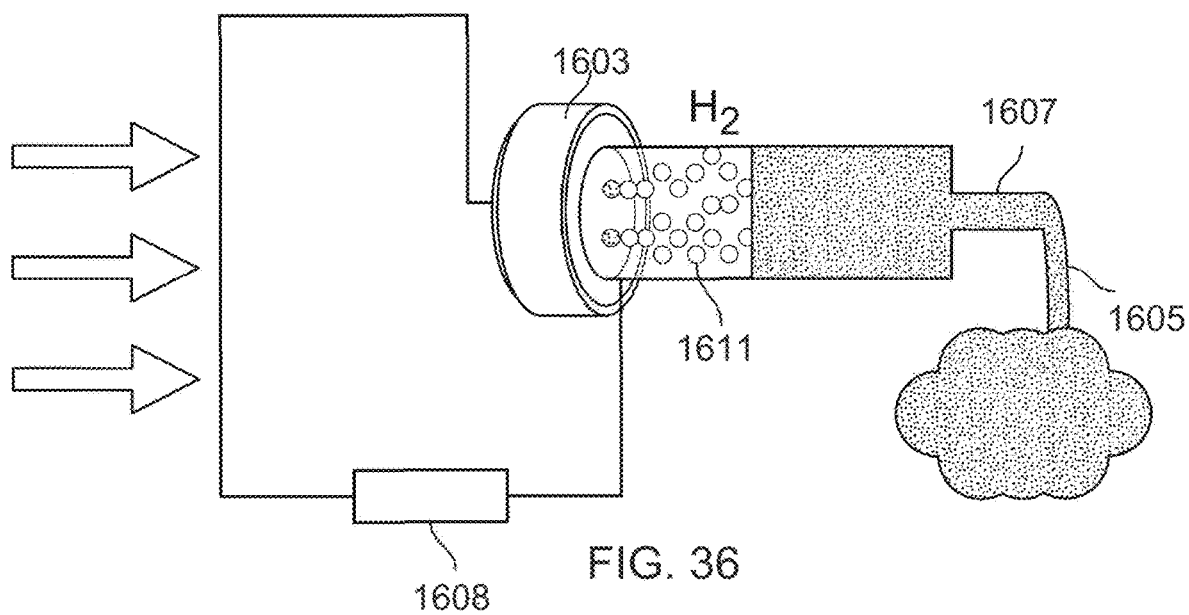
FIG. 36 illustrates aspects of a mechanism for an ingestible device.

FIG. 36 provides an example diagram illustrating aspects of a mechanism for a gas generating cell 1603 configured to generate a gas to dispense a substance, according to some embodiments described herein. As shown in FIG. 36, the gas generating cell 1603 generates a gas 1611 which can propel the dispensable substance 1605 out of the dispensing outlet 1607. A variable resistor 1608 may be connected to a circuit with the gas generating cell 1603 such that the variable resistor 1608 may be used to control an intensity and/or an amount of gas 1611 (e.g., hydrogen) generated by the cell 1603. Specifically, the gas generating cell 1603 may be a battery form factor cell that is capable of generating hydrogen when a resistor is applied. In this way, as the gas generating cell 1603 only needs the use of a resistor only without any active power requirements, the gas generating cell 1603 may be integrated into an ingestible device such as a capsule with limited energy/power available. For example, the gas generating cell 1603 may be compatible with a capsule at a size of 26 mm×13 mm or smaller.

In some embodiments, based on the elution rate of gas from the cell, and an internal volume of the ingestible device, it may take time to generate sufficient gas 1611 to deliver the substance 1605, and the time may be 30 seconds or longer. For example, the time to generate a volume of hydrogen equivalent to 500 µL of fluid would be approximately 5 minutes. A longer period of time may be needed based upon non-ideal conditions within the ingestible device, such as friction, etc. Thus, given that the production of gas (e.g., hydrogen) may take time, gas generation may need to start prior to the ingestible device arriving at the site of delivery to build pressure up within the device. The ingestible device may then need to know when it is approaching the site of delivery. For example, the device may start producing gas on an "entry transition," which is determined by temperature, so as to produce enough gas to be close to the pressure high enough to deliver the dispensable substance. The ingestible device may then only start producing gas again when it arrives at the site of delivery, which will cause the internal pressure within the ingestible device to reach a level required by the dispensing outlet to release the dispensable substance. Also, for regio-specific delivery, the ingestible device may estimate the time it takes to build up enough pressure to deliver the dispensable substance before the ingestible device arrives at a specific location, to activate gas generation.

Figure 37:
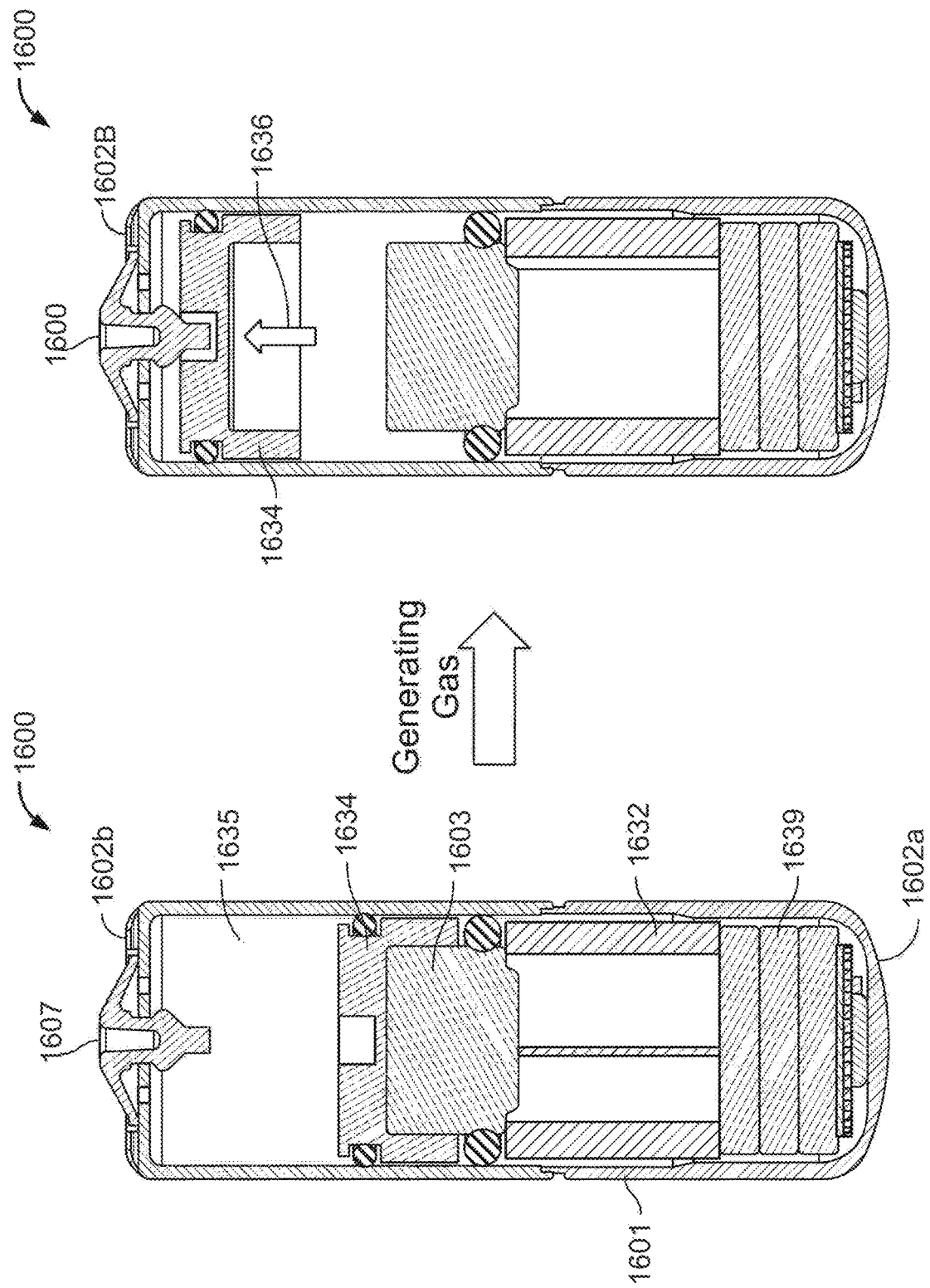
FIG. 37 illustrates an ingestible device.
Figure 38:
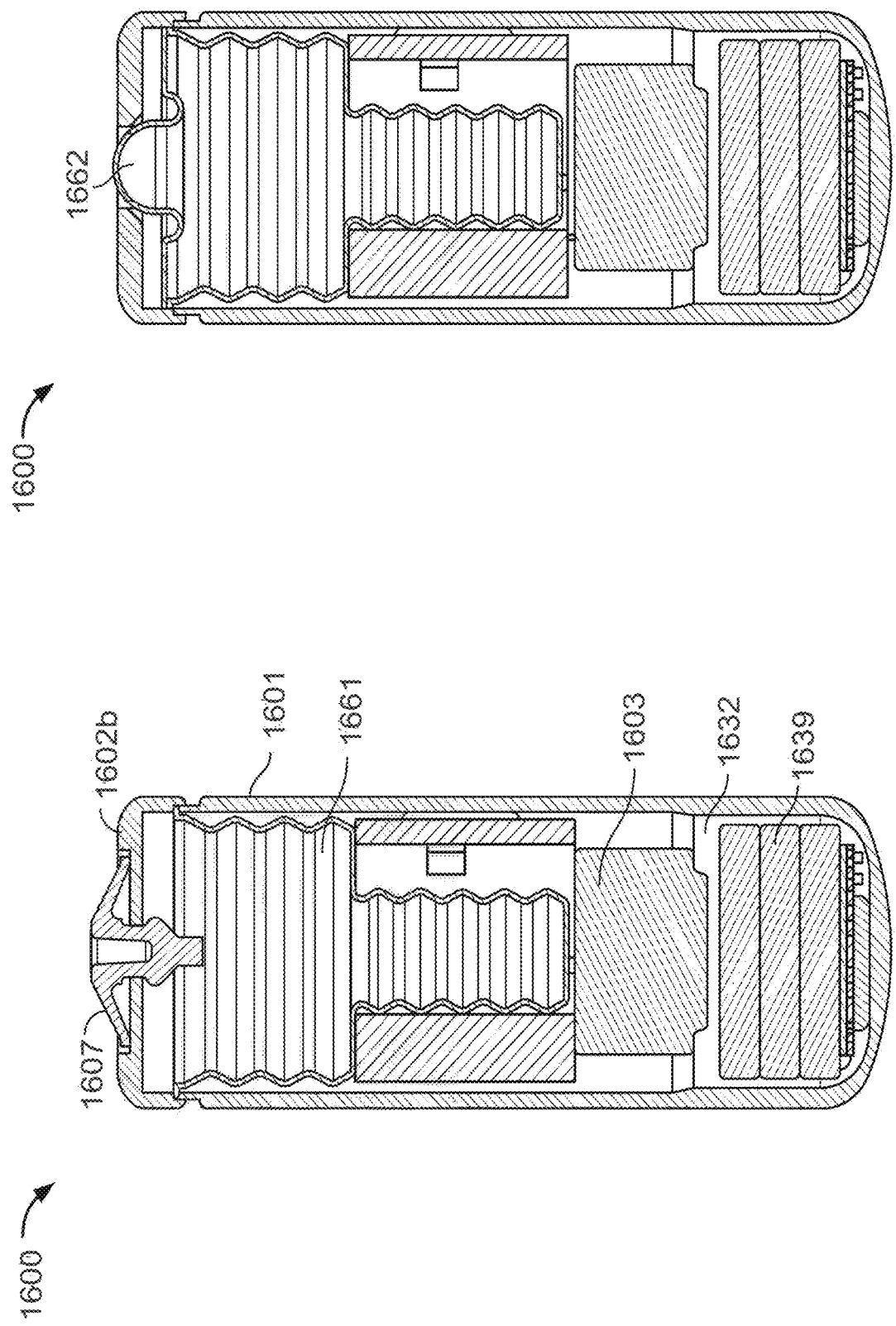
FIG. 38 illustrates an ingestible device.
Figure 39:
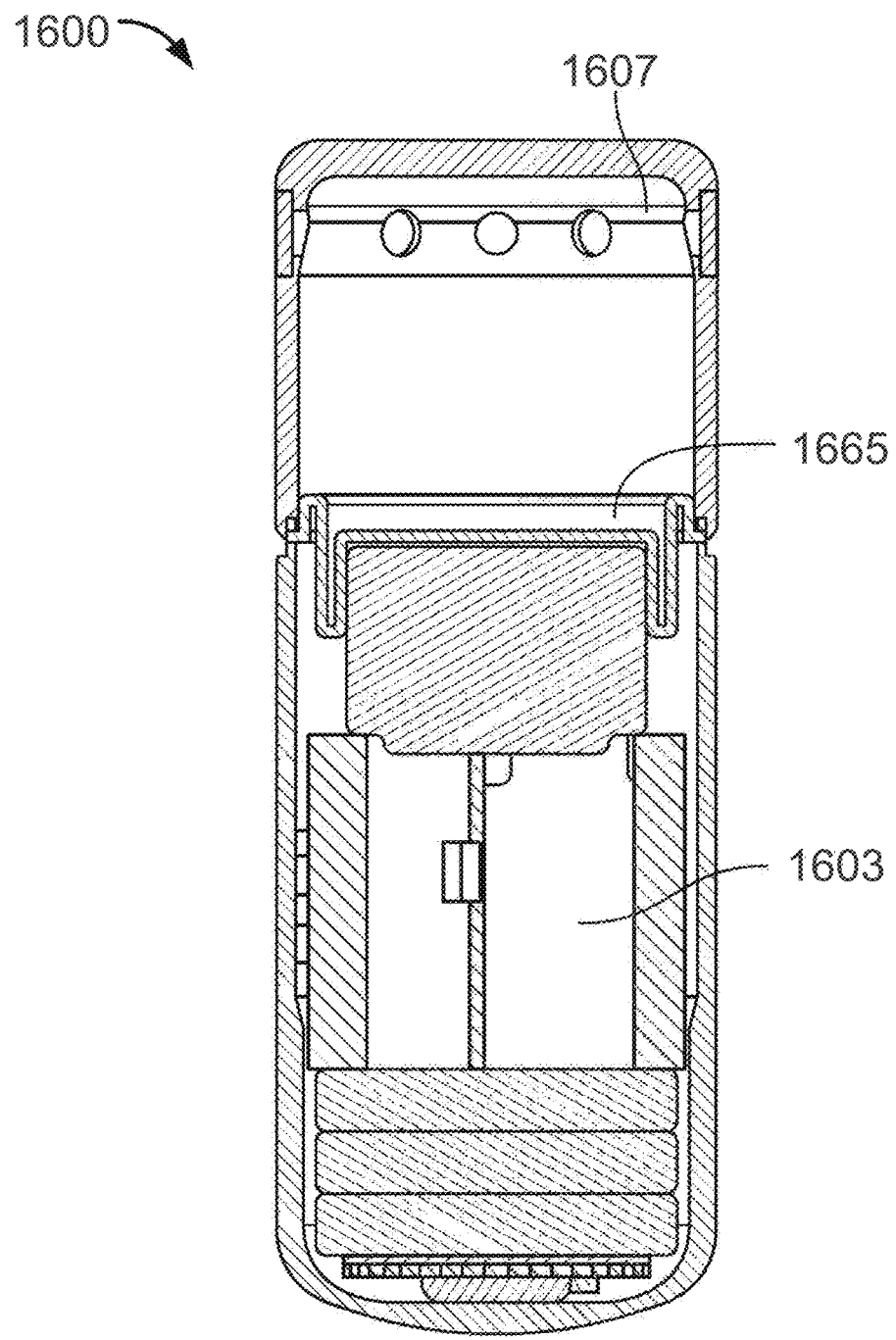
FIG. 39 illustrates an ingestible device.

FIGS. 37-39 illustrate an example of an ingestible device for localized delivery of a dispensable substance. The ingestible device 1600 includes a piston or drive element 1634 to push for substance delivery, in accordance with particular implementations described herein. The ingestible device 1600 may have one or more batteries 1639 placed at one end 1602a of a housing 1601 to provide power for the ingestible device 1600. A printed circuit board (PCB) 1632 may be placed adjacent to a battery or other power source 1639, and a gas generating cell 1603 may be mounted on or above the PCB 1632. The gas generating cell 1603 may be sealed from the bottom chamber (e.g., space including 1639 and 1632) of the ingestible device 1600. A movable piston 1634 may be placed adjacent to the gas generating cell 1603. In this way, gas generation from the gas generating cell 1603 may propel a piston 1634 to move towards another end 1602b of the housing 1601 such that the dispensable substance in a reservoir compartment 1635 can be pushed out of the housing through a dispensing outlet 1607, e.g., the movement is shown at 1636, with the piston 1634 at a position after dispensing the substance. The dispensing outlet 1607 may include a plug. The reservoir compartment 1635 can store the dispensable substance, or alternatively the reservoir compartment can house a storage reservoir 1661 which includes the dispensable substance. The reservoir compartment 1635 or storage reservoir 1661 may have a volume of approximately 6004 or even more dispensable substance, which may be dispensed in a single bolus, or gradually over a period of time.

Figure 40:
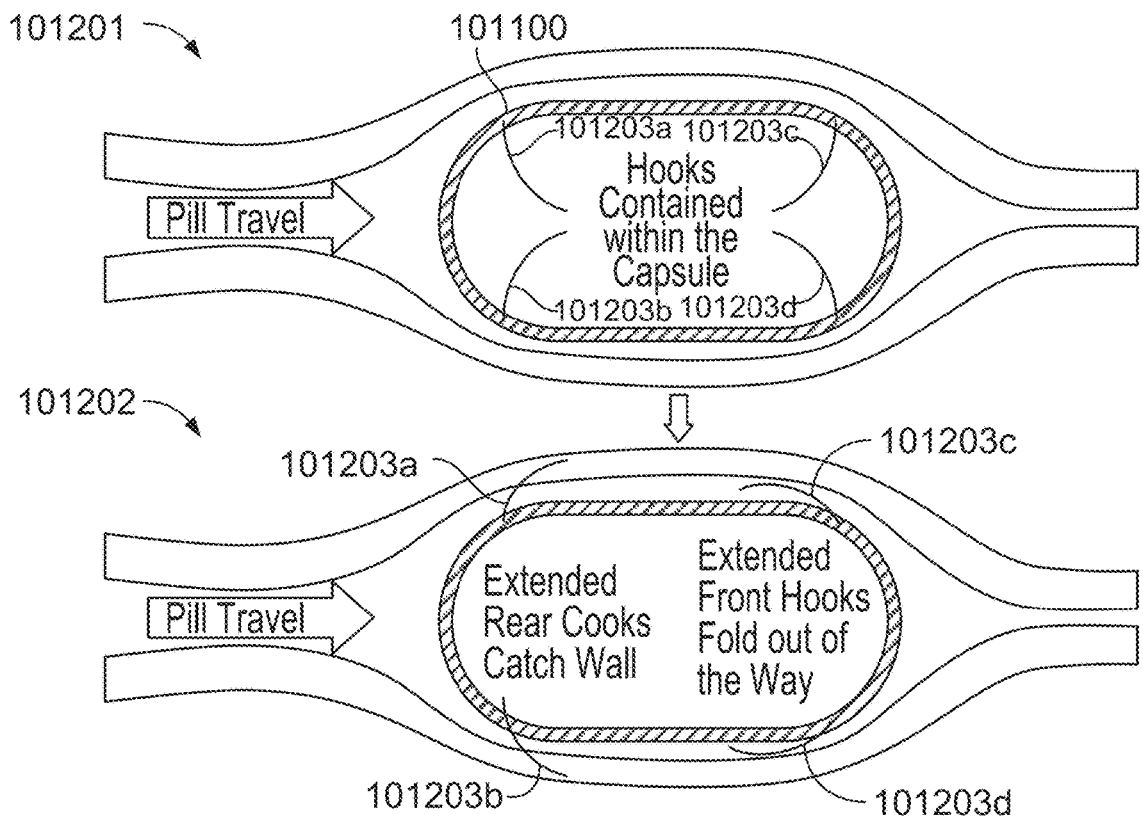
FIGS. 40, 41 and 42 illustrate exemplary anchoring mechanisms of an ingestible device.
Figure 41:
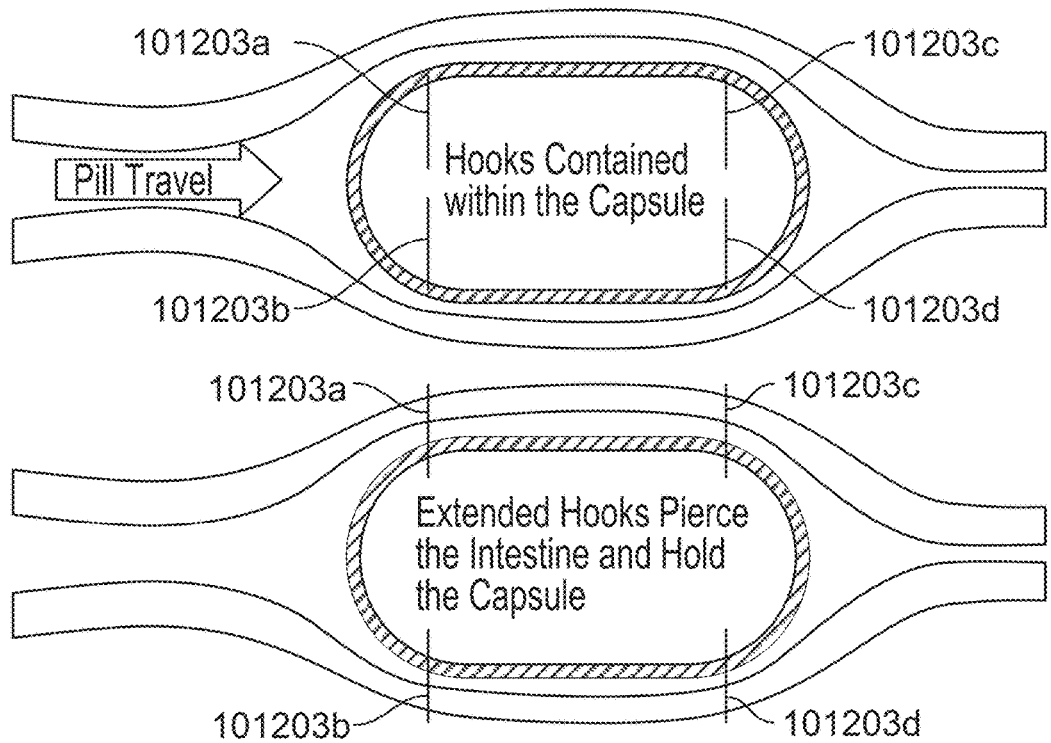
Figure 42:
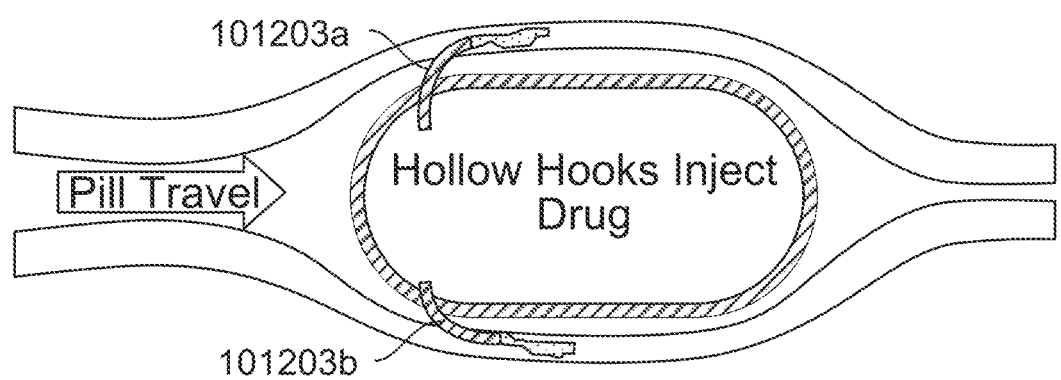

FIGS. 40-42 provide example structural diagrams illustrating aspects of anchoring mechanisms of an ingestible device to anchor the ingestible device to the intestine for dispensable substance delivery. As shown in FIG. 40, the ingestible device 101100 can be anchored within the intestine by extending hooks 101203a-d from the ingestible device 101100 after it has entered the region of interest. At 101201, as the ingestible device 101100 travels along the GI tract, the hooks 101203a-d are contained within the ingestible device. At 101202, when the ingestible device 101100 determines it has arrived at a location within the GI tract, the hooks 101203a-d can be actuated to extend outside of the ingestible device 101100 to catch in the intestinal wall and hold the ingestible device 101100 in the respective location. The hooks 101203a-d can be oriented to catch the intestinal wall regardless of the instant orientation of the ingestible device 101100. The hooks 101203a-d can also retract, dissolve, or detach from the intestinal wall after the dispensable substance has been delivered at the anchored location.

As shown in FIG. 41, the hooks 101203a-d could also extend radially from the ingestible device, and pierce into the intestinal wall to hold the ingestible device 101100 in place. As shown in FIG. 42, if the extending hooks (e.g., 101203*a*-*b*) are hollow, the hooks can be used to both anchor the ingestible device and inject the dispensable substance into the intestinal wall.

Figure 43:
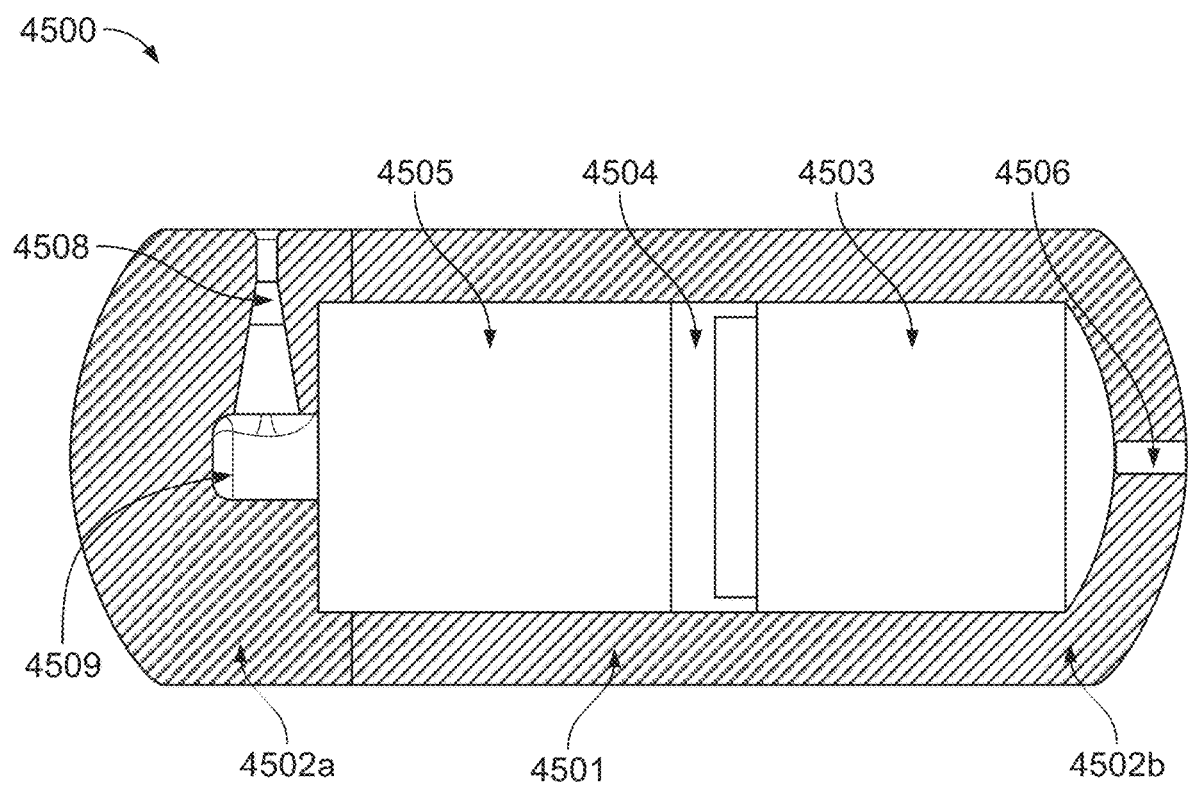
FIG. 43 illustrates an ingestible device.

FIG. 43 illustrates an ingestible device 4500 including a pre-pressurized actuator chamber 4503 and a sliding piston 4504, according to some embodiments described herein.

Ingestible device 4500 includes a device housing 4501. The device housing 4501 is composed of a cap portion 4502*a* and a base portion 4502*b* in the illustrated embodiments. Ingestible device 4500 also includes a pre-pressurized actuator chamber 4503 that is pressurized to a target pressure, for example during manufacture or via air fill port 4506 prior to ingestion. The capsule incorporates an active release mechanism that activates as the capsule reaches the target location. As the release mechanism activates, sliding piston 4504 will rapidly move to the left, pushing a high pressure jet of dispensable substance through the nozzle.

Depending on the material used to form the walls of the device housing 4501, the material could diffuse the compressed gas in the pre-pressurized actuator chamber 4503 over time, decreasing the internal pressure. To ensure that pressure is maintained in the ingestible device 4500 over a period between fabrication and patient use, packaging could be pressurized to equal the internal pressure of the pill in certain embodiments; therefore, preventing the permeation of compressed gas from the ingestible device 4500. Assuming the gas expansion within the capsule occurs very fast and an adiabatic polytropic process takes place, gas laws are used to correlate the initial and final pressure of the gas with its volume change ratio.

Figure 44A:
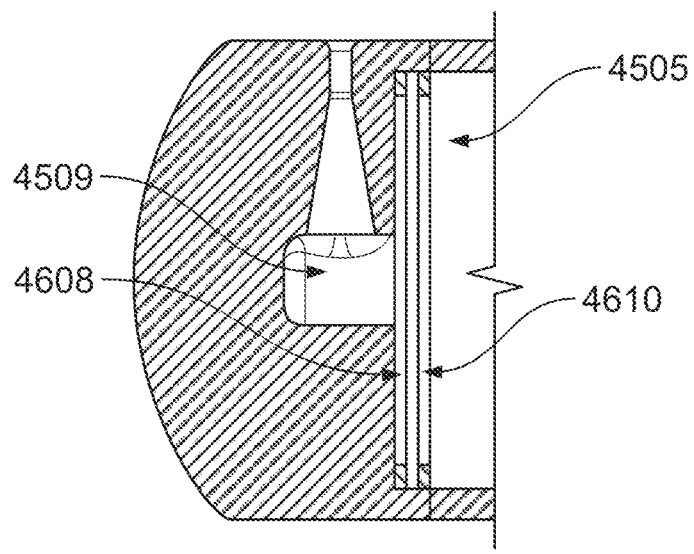
FIG. 44A illustrates a portion of an ingestible device.
Figure 44B:
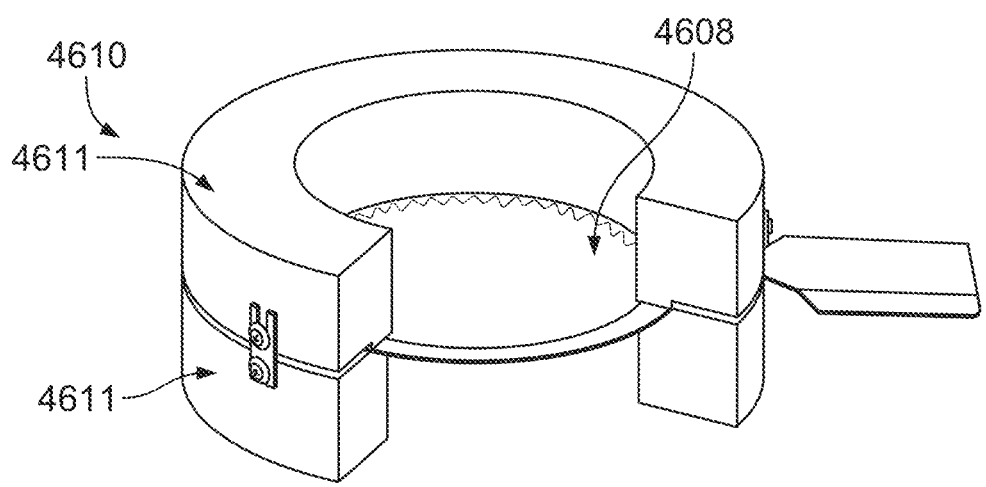
FIG. 44B illustrates a partial sectional view of a burst disc holder.

FIG. 44A illustrates a burst disc 4608 with an in line nozzle 4509. FIG. 44B illustrates a partial sectional view of a burst disc holder 4610, according to some embodiments described herein. A burst disc 4608 may enable the release of a dispensable substance, (for example from reservoir 4505) by purposefully fracturing at a targeted pressure allowing the dispensable substance to exit a nozzle 4509 to a target location within the GI tract. A burst disc 4608 can be used as the sole occlusion component in certain embodiments and can be used to provide isolation between upstream contamination and the dispensable substance payload in embodiments including another occlusion component. The burst disc 4608 can be held in place via clamped outer rings 4611 of disc holder 4610 as demonstrated in FIG. 44B.

Figure 45:
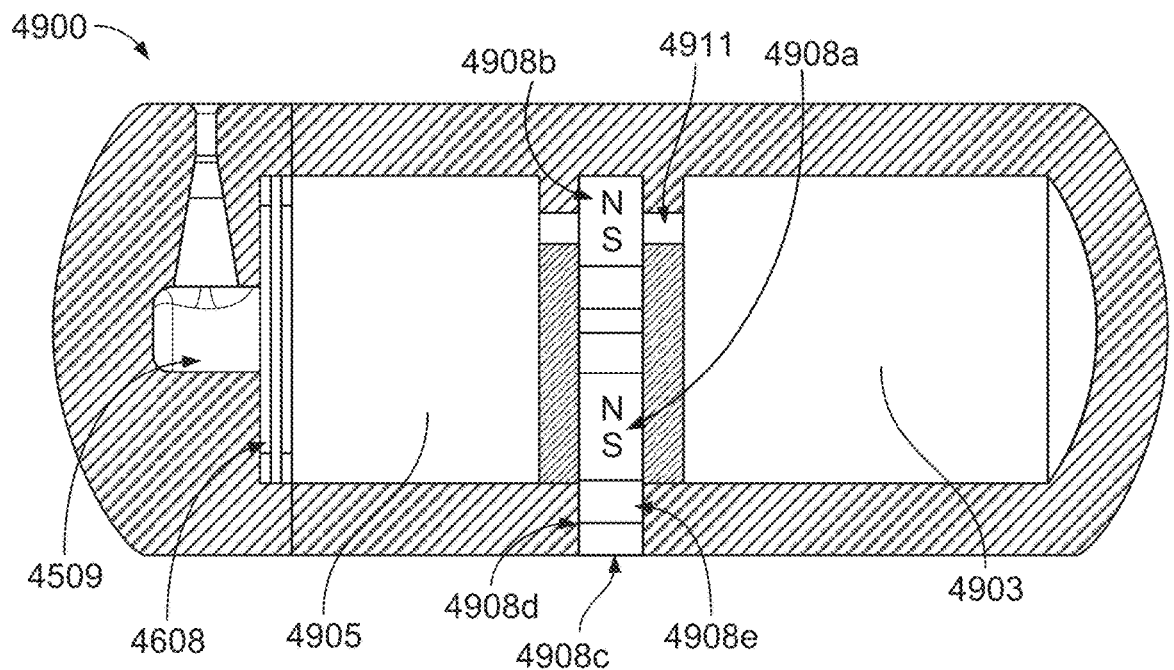
FIG. 45 illustrates an ingestible device.
Figure 46:
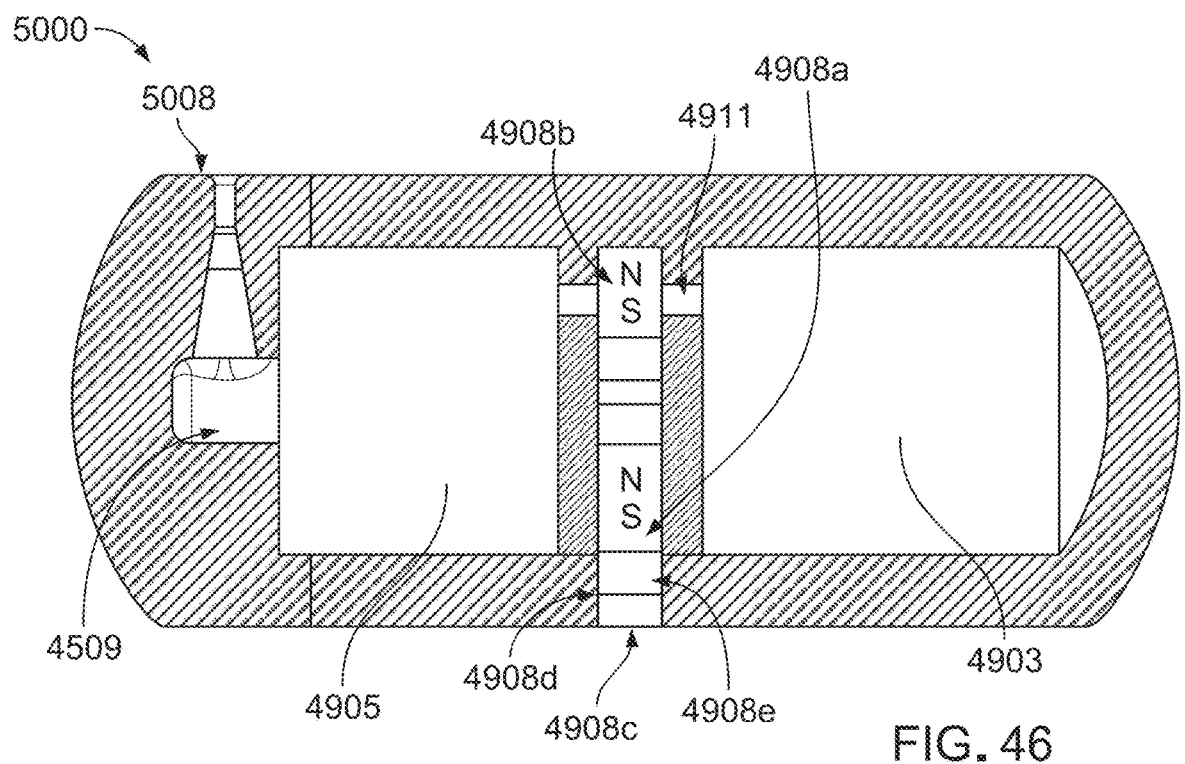
FIG. 46 illustrates an ingestible device.

FIG. 45 illustrates an ingestible device 4900 including a magnetic occlusion component 4908*b*, a burst disc 4608, and a pre-pressurized actuator chamber 4903, according to some embodiments described herein. FIG. 46 illustrates an ingestible device 5000 including a magnetic occlusion component, a pre-pressurized actuator chamber 4903 and a bioabsorbable plug 5008, according to some embodiments described herein. A magnetic stack, which upon peristaltic or osmotic pressure application releases pneumatic pressure, allowing for the delivery of a jet of dispensable substance through a conduit 4509. Osmotic pressure may be used to reconfigure the occlusion component that includes magnets 4908*a* and 4908*b*. The enteric coating 4908*c* dissolves when exposed to luminal fluid, exposing the membrane 4908*d* and osmogen 4908*e*. The membrane 4908*d* and osmogen 4908*e* facilitate the movement of liquid to create osmotic pressure on the magnet 4908*a*. As the osmotic pressure builds up, magnet 4908*a* will be pushed up in proximity to magnet 4908*b*. Magnet 4908*b* will be pulled down providing a flow through path for a gas from pressurized chamber 4905 to interact with the reservoir 4905 via connecting conduit 4911. The advantage of this system is that the mechanism may be completely sealed from the exterior of the capsule, allowing for pressure to only project into the chamber 4905. Note that an enteric coating/membrane stack 4908*c*, 4908*d* could be replaced by a method of leveraging peristalsis for pushing magnet 4908*a*. FIG. 45 is implemented with a burst disc 4608 as the sealing/release mechanism once the chamber 4905 is exposed to the pressurized chamber 4903. FIG. 46 is implemented with a bioabsorbable plug 5008 (e.g. enteric coating) that is dissolved and expelled once the reservoir 4905 is exposed to the pressurized actuator chamber 4903.

Figure 47:
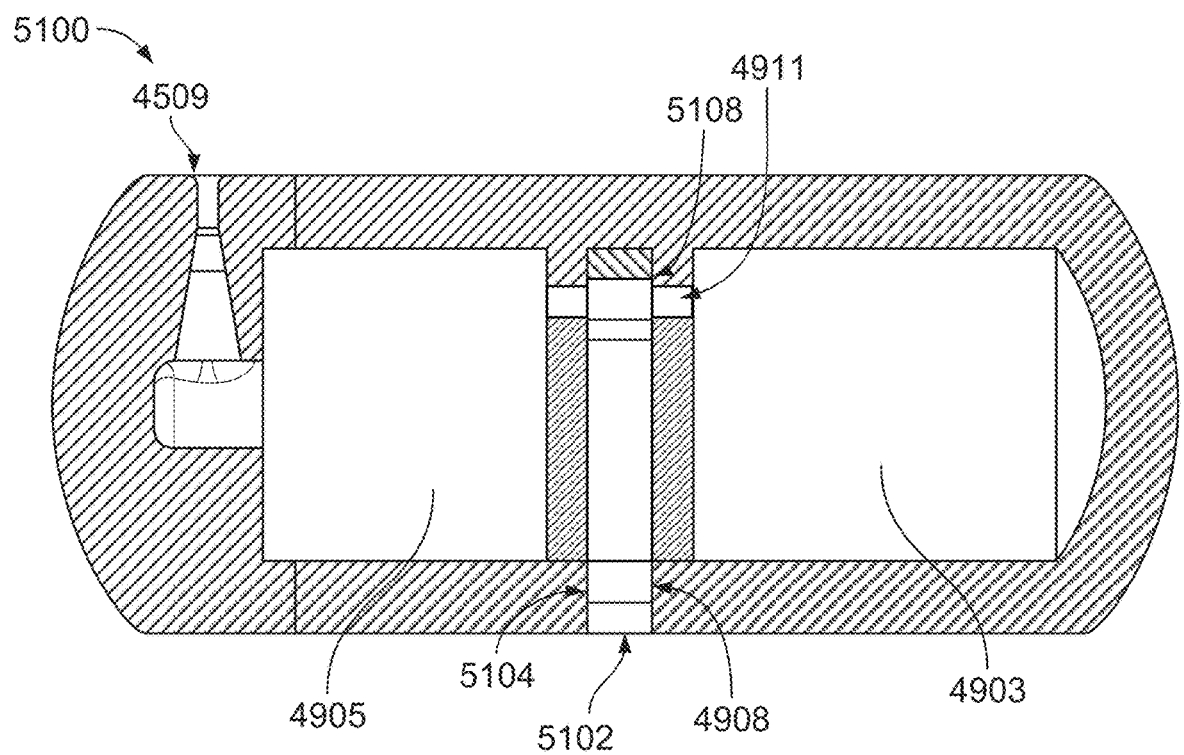
FIG. 47 illustrates an ingestible device.

FIG. 47 illustrates an ingestible device 5100 including enteric sliding occlusion component 5102, a pre-pressurized actuator chamber 4903 and a sliding component 5108, according to some embodiments described herein. An osmotic drive 4908, including an enteric coating 5102 and semipermeable membrane 5104, is configured to move a sliding component 5108. The sliding component 5108, once pushed by the osmotic drive 4908, will allow a flow-through port 4911 to connect the pressurized actuator chamber 4903 to the reservoir 4905, providing dispensable substance delivery through the nozzle 5108.

Figure 48:
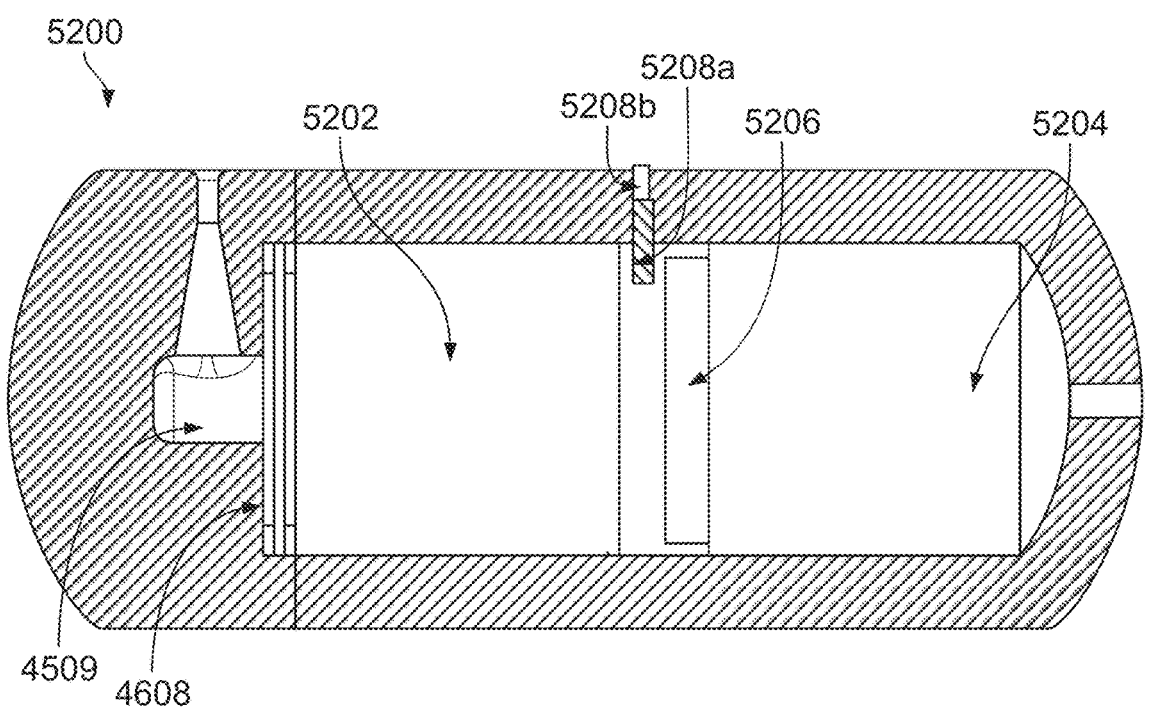
FIG. 48 illustrates an ingestible device.

FIG. 48 illustrates an ingestible device 5200 including dissolvable pin occlusion component, a chamber 5202, a pre-pressurized chamber 5204 and a sliding piston 5206, according to some embodiments described herein. In another embodiment, an enteric coating 5208*b* is dissolved, exposing a structural pin 5208*a* (such as a glucose spike or hydrogel) that dissolves in the presence of intestinal luminal fluid. With this design, as long as the pin 5208*a* is in place, the force exerted on the piston 5206 and the chamber 5202 is not large enough for the burst disk 4608 to rupture. The enteric coating 5208*b* and pin 5208*a* will dissolve as the capsule 5200 is ingested and as a result, the pressure force on the piston 5206 will increase. The full force of the pre-pressurized chamber 5204 translated onto the chamber 5202 via the piston 5206 is large enough to rupture the burst disk 4608. The rupture of the burst disk 4608 results in a pressurized jet of liquid being delivered from the chamber 5202 through the nozzle 4509.

Figure 49:
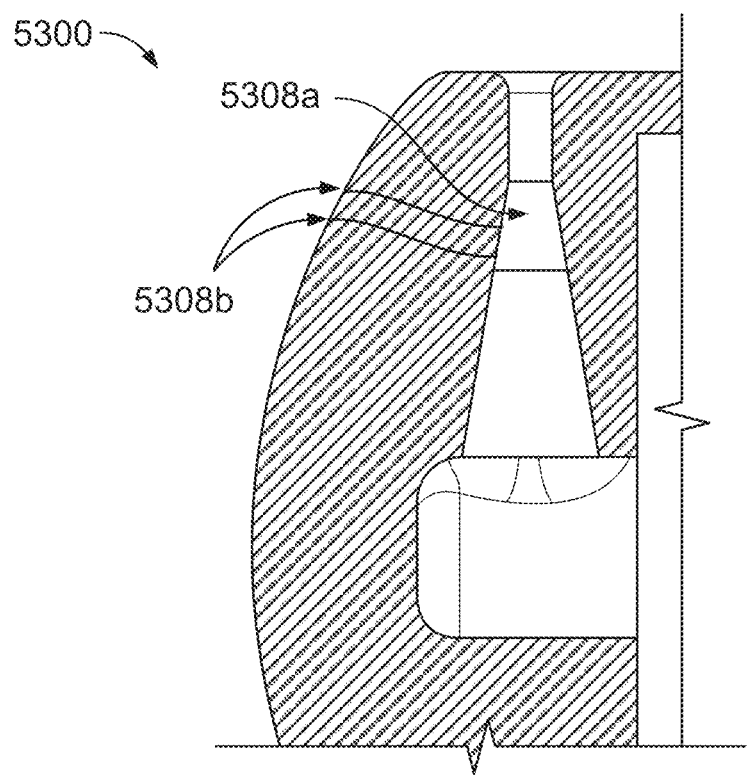
FIG. 49 illustrates an ingestible device.

FIG. 49 illustrates an ingestible device 5300 including wax plug 5308*a* with wire lead activators 5308*b*, according to some embodiments described herein. In this method, the dispensing site is identified based on collected reflected light. The reflectance of light in green and red spectrums (with iterations to this methodology and algorithm actively being pursued) are measured and an algorithm is used to correlate the measured reflectance with the location in the Gastrointestinal (GI) tract. This method provides a non-pH based system to determine the anatomical locations of the capsule during fasted transit. As the capsule 5300 reaches the target location, a signal is generated which will be used to activate an alternative release mechanism.

Figure 50:
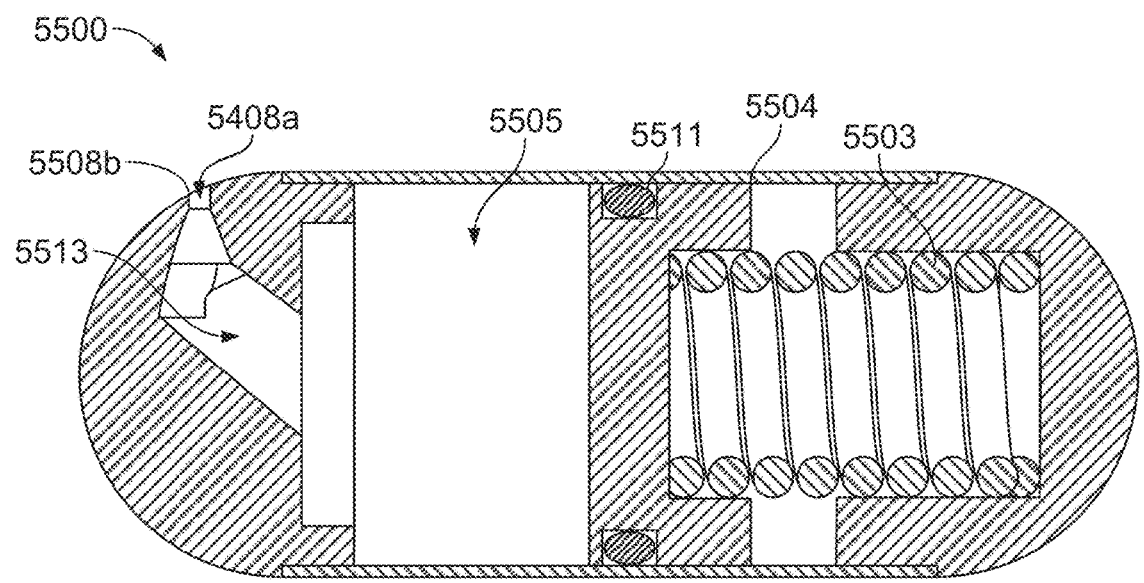
FIG. 50 illustrates an ingestible device.

FIG. 50 illustrates an ingestible 5500 device including a spring actuator 5503 and a sliding piston 5504, according to some embodiments described herein. Ingestible device 5500 uses the potential energy stored in a spring 5503 when compressed as the driving or actuating mechanism for jet delivery of the dispensable substance. The occlusion component or release mechanism consists of bioabsorbable plug 5508*a* separated from the reservoir 5505 by a protectant layer 5508*b*. In this embodiment, the inner volume of the capsule 5500 is divided into two sections separated by a sliding piston 5504. The left section (e.g., reservoir 5505) is filled with dispensable substance and a spring 5503 is mounted in the right section. The piston 5504 can freely move to the right or left depending on the net force exerted on the piston 5504. An O-ring 5511 is used to provide the sealing desired between the two sections, with alternative sealing means possible. Compressed spring 5503 applies a force on the piston 5504 and the piston 5504 transfers this force to the liquid dispensable substance in form of pressure. The same pressure will be transferred to the plug 5508a sealing the nozzle 5513. However, this pressure acts on a small area (area of the plug 5508a). Therefore, the large force exerted by the spring 5503 translates into a small force on the sealing plug 5508a. As the capsule 5500 is digested, it moves through GI tract and the bioabsorbable sealing plug 5508a will start dissolving. After certain amount of time, the plug will weaken or fully dissolve in GI fluid. As soon as the plug 5508a weakens to the design threshold, the pressure inside the reservoir 5503 drops, the spring 5503 will expand delivering dispensable substance (e.g., in the form of a high-pressure jet of fluid) through the opening.

Figure 51:
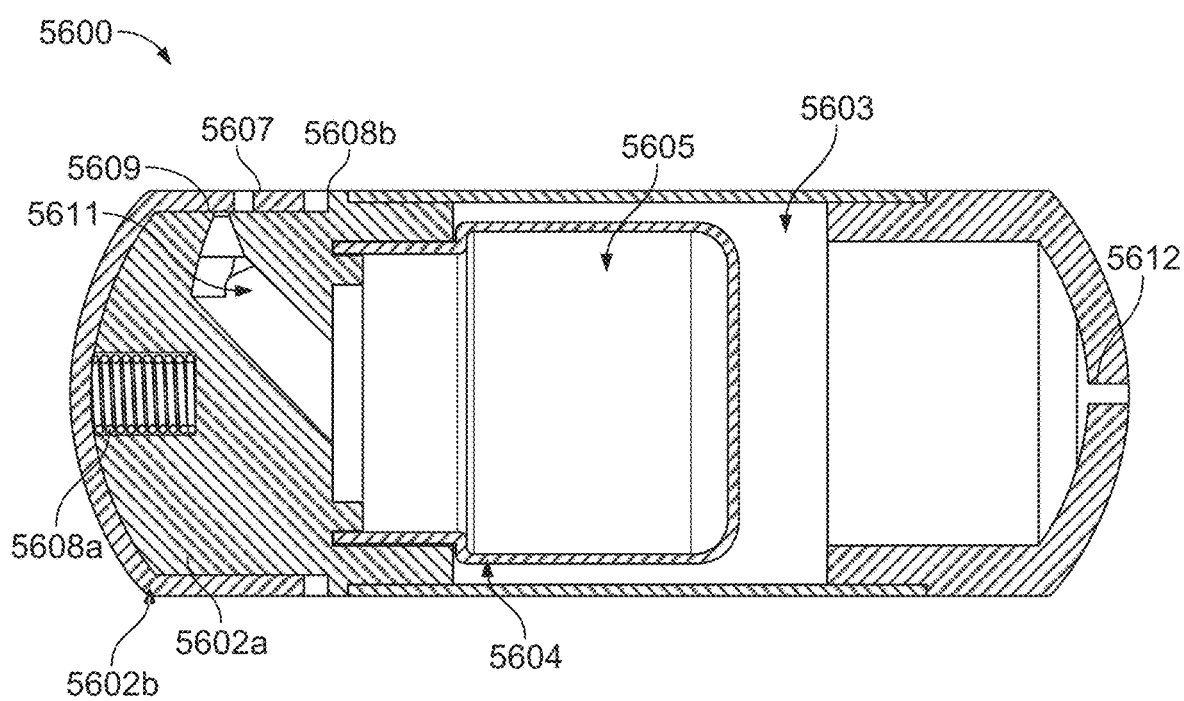
FIG. 51 illustrates an ingestible device.

FIG. 51 illustrates an ingestible device 5600 including a spring actuated slidable housing portion 5602b, according to some embodiments described herein. Ingestible device 5600 consists of a pressurized actuator 5603 chamber, a reservoir 5605 separated from the pressure actuator chamber 5603 by a deformable body 5604 such as bellows and a spring/enteric coating release mechanism The spring 5608a is mounted on the polycarbonate cap 5602a from one end and to a sliding cap 5602b on the other end. The stainless steel top slider 5602b can slide to the left and right opening and closing the nozzle 5611. An enteric ring 5608b is used to keep the top slider closed. An O-ring and a bioabsorbable plug 5609 are used to provide the desired sealing. An adhesive seal 5612 is located on the housing, on the opposite end of the capsule 5600 from the spring 5608a. Compressed gas applies a force on the bellows 5604 and the bellows 5604 transfer this force to the liquid dispensable substance in form of pressure. The same pressure will be transferred to the slider 5602b in form of a radial force. However, this pressure acts on a small area (area of the exit orifice 5607). Therefore, the transverse load on the slider 5602b is relatively small. When the capsule 5600 is assembled, the spring 5608a is compressed (slider 5602b in closed mode), and the enteric coating 5608b keeps the slider 5602b in position. As the capsule 5600 is digested, it moves through GI tract. The enteric coating 5608b will dissolve when the capsule 5600 passes through the intestinal fluid. With the dissolution of the enteric coating 5608b, the spring 5608a will push the slider 5602b back away from the capsule 5600 (open mode). As a result, the exit orifice 5607 becomes concentric with the nozzle 5611 and the jet of fluid will be released.

Figure 52:
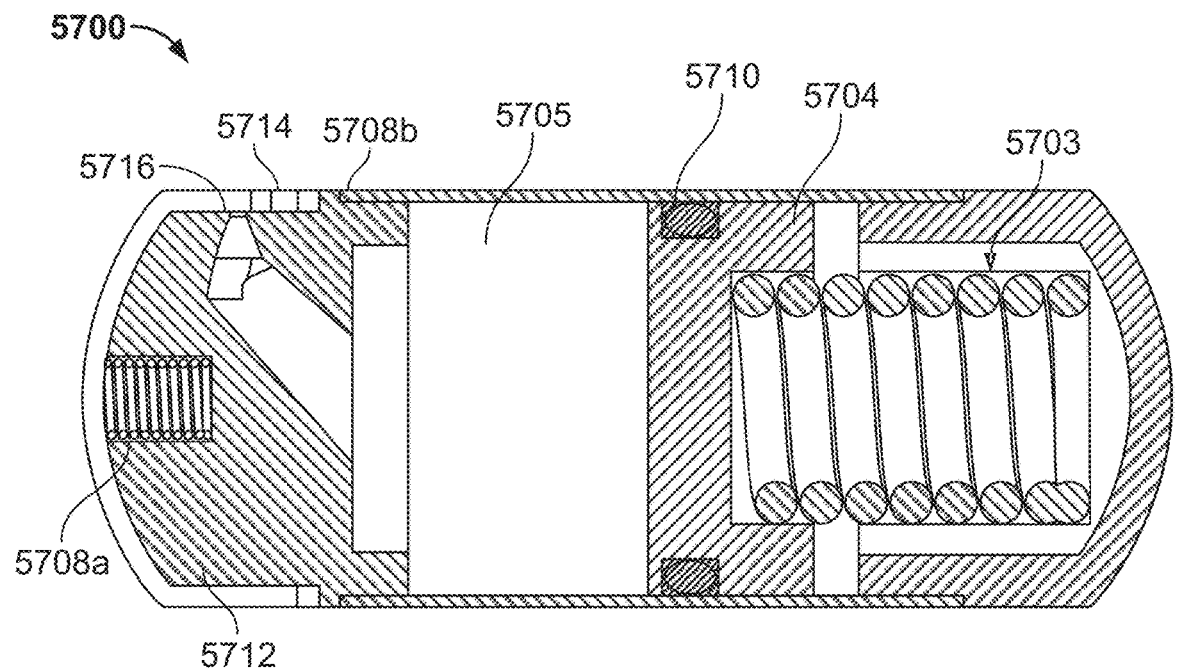
FIG. 52 illustrates an ingestible device.

FIG. 52 illustrates an ingestible device 5700 with another spring actuated slidable housing portion 5712, according to some embodiments described herein. Ingestible device 5700 uses a compressed spring (spring 5703) as the drive mechanism and a compressed spring 5708a (spring with sliding top cap 5712 as the release mechanism. A piston 5704 separates the reservoir 5705 from the spring chamber and an enteric coating 5708b is used to initiate the release mechanism. An O-ring 5710 is used to provide sealing between the piston 5704 and cylinder. Compressed spring 5703 applies a force on the piston 5704 and the piston 5704 transfers this force to the liquid dispensable substance in the form of pressure. The same pressure will be transferred to the top cap slider 5712 in form of a radial force. However, this pressure acts on a small area (area of the exit orifice 5714) resulting in a small transverse force on the top slider 5712. When the capsule 5700 is assembled, spring 5703 is left in compressed mode (slider 5712 in closed position). As the capsule 5700 is digested, it moves through GI tract. The enteric coating 5708b will dissolve when the capsule 5700 passes through the intestinal fluid. With the dissolution of the enteric coating 5708b, the spring 5708a will push the slider 5712 back away from the capsule 5700 (open mode). As a result, the exit orifice 5714 becomes concentric with the nozzle 5716 and the jet of fluid will be released.

Figure 53:
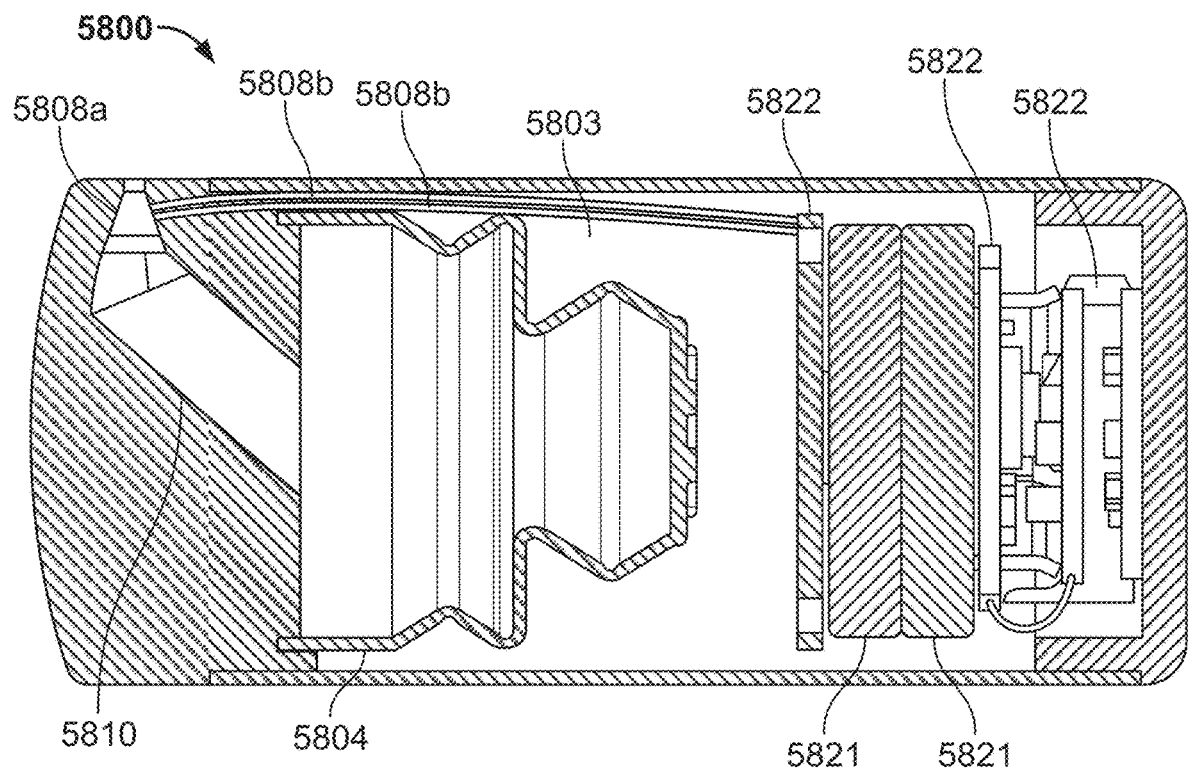
FIG. 53 illustrates an ingestible device.

FIG. 53 illustrates an ingestible device 5800 including a melt away occlusion component 5808a and a pressurized chamber 5803, according to some embodiments described herein. Ingestible device 5800 consists of two chambers, one chamber is filled with dispensable substance and the other chamber is filled with pressurized gas. A wax valve 5808a actuated by localization board 5822 is used as the occlusion component. A large section of the pressure chamber 5803 is occupied by the release mechanism and the batteries 5821. Wax valve wires 5808b are connected to the wax valve 5808a and will melt the wax using an electric current. The timing of this operation is controlled by the localization board 5822. In this embodiment, a fully controlled release mechanism is used. As the capsule 5800 reaches target area, the localization kit will activate and direct a predetermined electric current toward the wax valve 5808a. A heating element will receive this current and will melt or weaken the wax valve 5808a. With weakening or removal of the wax from the nozzle 5810, gas pressure from the pressurized chamber 5803 will push the bellows 5804 resulting in a pressurized jet of liquid dispensable substance exiting the nozzle 5810, thus delivering the dispensable substance.

Figure 54:
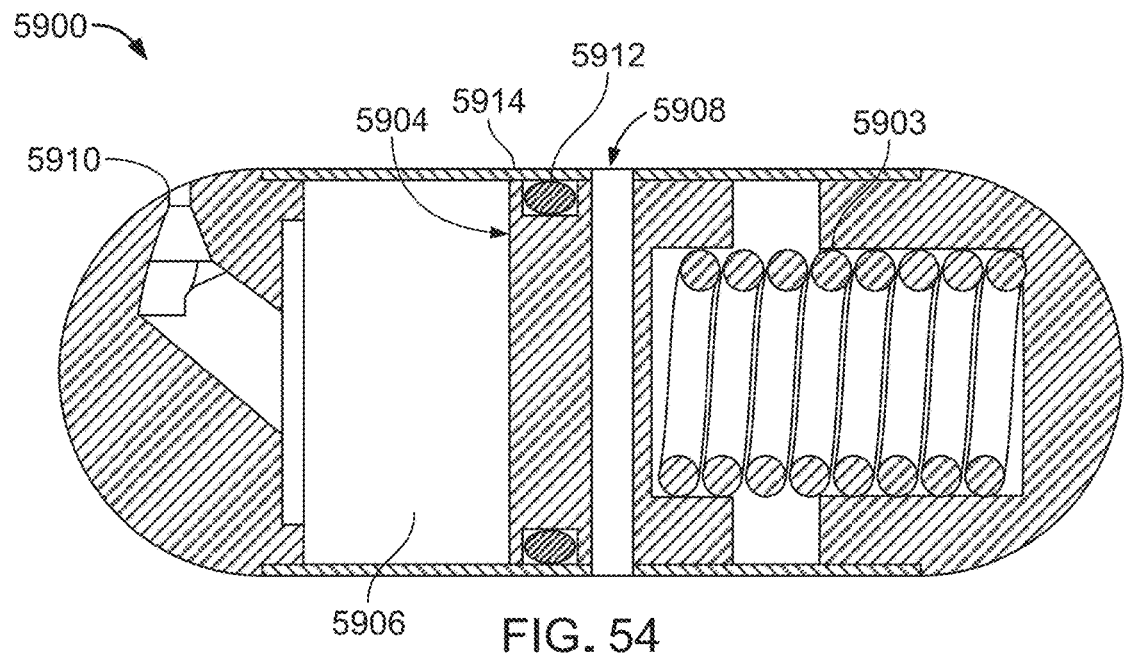
FIG. 54 illustrates an ingestible device.

FIG. 54 illustrates an ingestible device 5900 including a dissolvable pin occlusion component 5908 and a spring actuated sliding piston 5914, according to some embodiments described herein. One of the main challenges of designing an effective capsule is the sealing between the two chambers inside the capsule since there is a significant pressure difference between the two chambers, the dispensable substance tends to move from the dispensable substance chamber into the pressure or spring chamber. Certain embodiments address this by reducing the pressure difference between the two chambers during the shelf life and before jet delivery. For example, ingestible device 5900 includes a compressed spring 5903 is retained using a dissolvable pin 5908. Additionally, an O-ring 5912 is used to provide sealing between the piston 5914 and housing. With this design, as long as the pin 5908 is in place, there is no force exerted on the piston 5904 and the liquid in chamber 5906. The force exerted by the spring 5903 will result in shear stress on the pin 5908. The pin 5908 will dissolve as the capsule 5900 is ingested and as a result, the spring force will translate into a pressurized jet of liquid. An enteric coating on the ends of the pin 5908 could further enhance the specificity of the triggering location. During the shelf life and before ingestion of the capsule 5900, there is not a significant amount of pressure acting on the dispensable substance and consequently, sealing challenges are easier to address. With a 200-psi design pressure, the pin would be expected to hold approximately 20 lbf, and would involve design consideration to the shear strength of the dissolvable pin. As the capsule 5900 passes through the GI tract, the pin 5908 will start dissolving. As the pin 5908 dissolves, there is no support for the piston 5904 to keep the piston 5904 in place. The force of the spring 5903 will result in a significant pressure in the fluid. At a certain point the pin 5908 will fail and the piston 5904 will move to the left releasing a high-pressure jet of fluid through the nozzle 5910.

Figure 55:
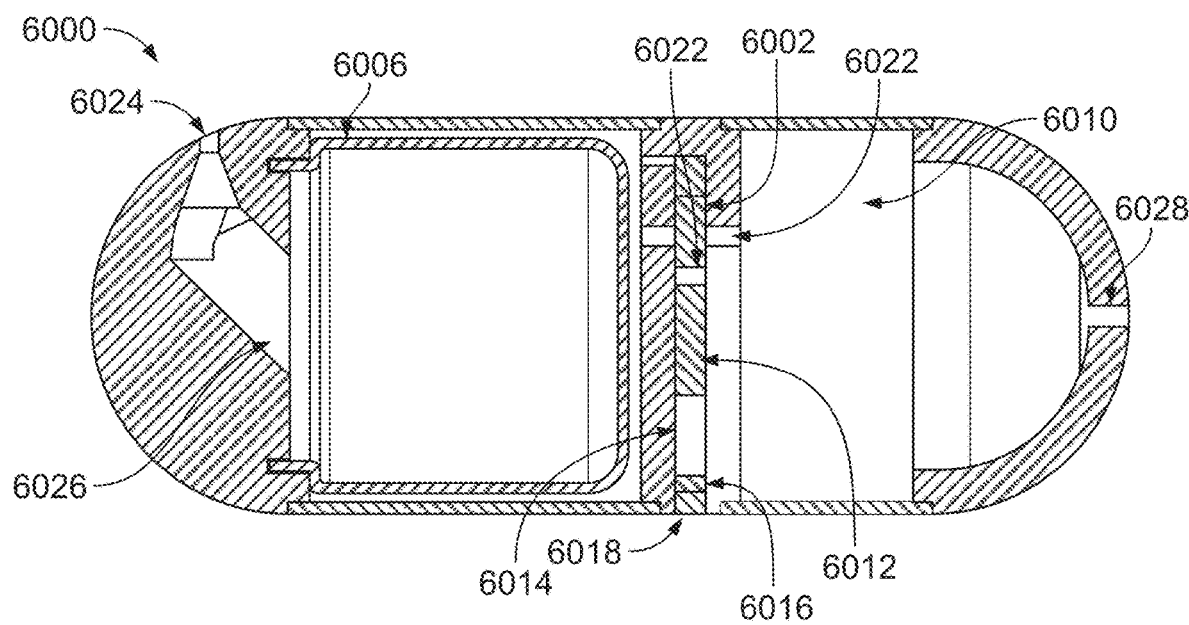
FIG. 55 illustrates an ingestible device.

FIG. 55 illustrates an ingestible device 6000 including shuttle slider occlusion component 6012 and a pressurized chamber 6010, according to some embodiments described herein. Ingestible device 6000 includes two chambers separated by a wall 6002 made of polycarbonate. The right chamber is an adhesive seal 6028 and a pressurized chamber 6010, pressurized with gas, and a bellows 6006 is installed in the left chamber. There are no openings connecting the two chambers 6006, 6010. An osmotic release mechanism is used to connect the two chambers 6006, 6010 through a sliding valve 6012. Osmogen 6014 is contained within a small container below the sliding valve 6012. Osmogen 6014 is separated from the GI fluid by a water permeable membrane 6016 covered with enteric coating 6018. On the top of the osmogen 6014, a shuttle slider 6012 is mounted. The slider 6012 has an opening 6020 in the middle. The slider shuttle 6012 is sandwiched between two slabs of polycarbonate with a pressure through port 6022. When the slider shuttle 6012 is in closed form, the holes on the polycarbonate slabs are not concentric with the hole on the slider shuttle 6012. When the slider shuttle 6012 is in open mode, the holes of the slider and polycarbonate slabs surrounding it all will be concentric letting gas and pressure exchange between the two chambers 6006, 6010.

In certain embodiments, an ingestible device is configured to determine its location (e.g., within the GI tract of a subject). FIGS. 56-70 provide illustrative and non-limiting examples of such ingestible devices and associated methods. It is to be understood that one more features from such embodiments can be combined with one or more features of an ingestible device configured to take one more samples, such as, for example, described above with regarding to FIGS. 1-34, and/or with one or more features of an ingestible device configured to deliver one or more substances (e.g., one or more therapeutic substances), such as, for example, described above with respect to FIGS. 35-55.

In some embodiments, the location of the ingestible device within the GI tract of the subject can be determined to an accuracy of at least 85%, e.g., at least 90%, at least 95%, at least 97%, at least 98%, at least 99%, 100%. In such embodiments, the portion of the portion of the GI tract of the subject can include, for example, the esophagus, the stomach, duodenum, the jejunum, and/or the terminal ileum, cecum and colon.

In certain embodiments, the location of the ingestible device within the esophagus of the subject can be determined to an accuracy of at least 85%, e.g., at least 90%, at least 95%, at least 97%, at least 98%, at least 99%, 100%.

In some embodiments, the location of the ingestible device within the stomach of the subject can be determined to an accuracy of at least 85%, e.g., at least 90%, at least 95%, at least 97%, at least 98%, at least 99%, 100%.

In certain embodiments, the location of the ingestible device within the duodenum of the subject can be determined to an accuracy of at least 85%, e.g., at least 90%, at least 95%, at least 97%, at least 98%, at least 99%, 100%.

In some embodiments, the location of the ingestible device within the jejunum of the subject can be determined to an accuracy of at least 85%, e.g., at least 90%, at least 95%, at least 97%, at least 98%, at least 99%, 100%.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Figure 56:
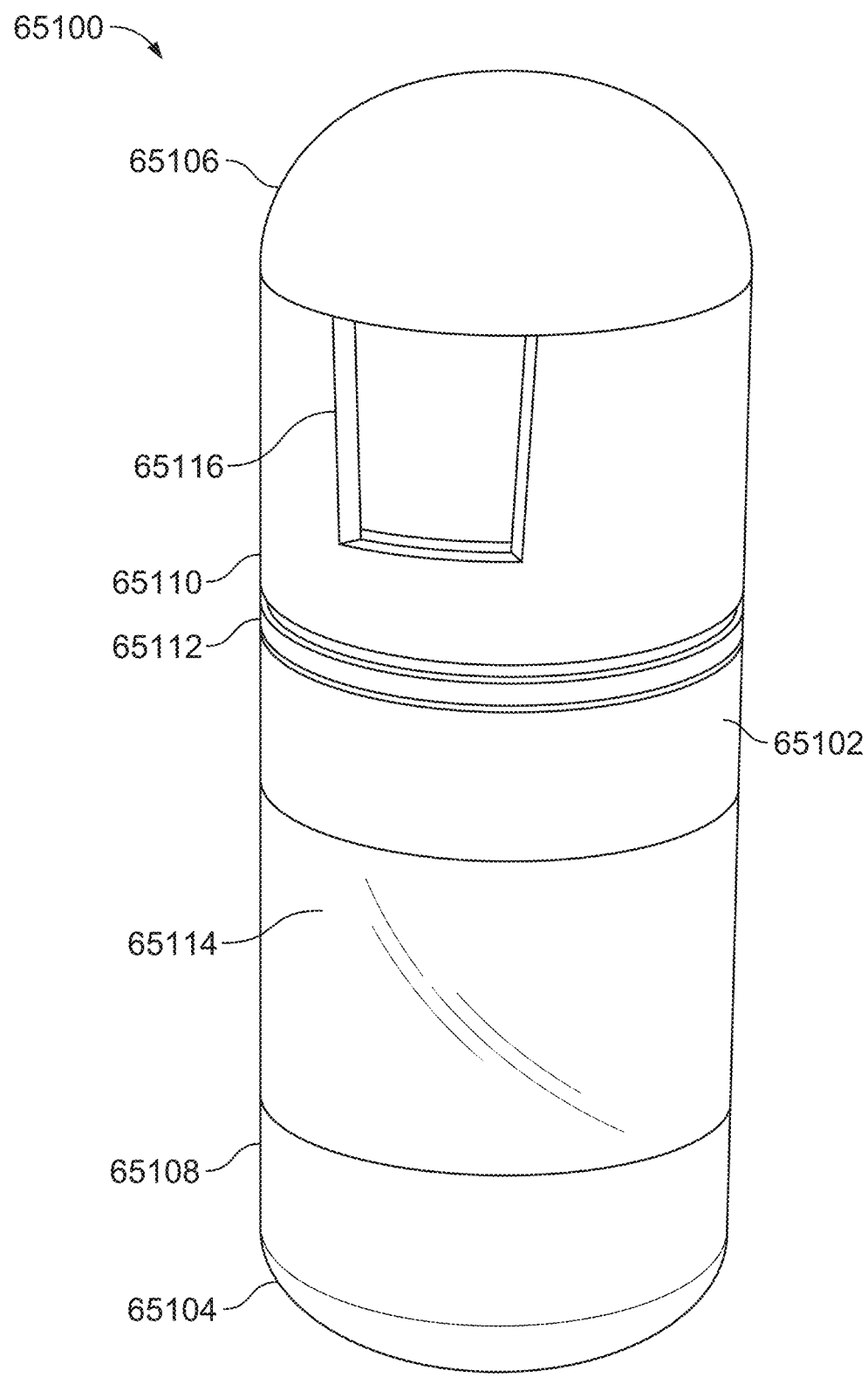
FIG. 56 is a view of an ingestible device.

Referring now to FIG. 56, shown therein is a view of an example embodiment of an ingestible device 65100, which may be used to identify a location within a gastrointestinal (GI) tract. It is to be understood that certain details regarding the design of ingestible device 65100 are not shown in FIG. 56 and the following figures, and that, in general, various aspect of ingestible devices described elsewhere herein can be implemented in ingestible device 65100 and the ingestible devices shown in the following figures.

In some embodiments, ingestible device 65100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 65100 may be configured to autonomously determine whether it is located within certain portions of the small intestine or large intestine, such as the duodenum, the jejunum, the cecum, or the colon.

Ingestible device 65100 may have a housing 65102 shaped similar to a pill or capsule. The housing 65102 of ingestible device 65100 may have a first end portion 65104, and a second end portion 65106. The first end portion 65104 may include a first wall portion 65108, and second end portion 65106 may include a second wall portion 65110. In some embodiments, first end portion 65104 and second end portion 65106 of ingestible device 65100 may be manufactured separately, and may be affixed together by a connecting portion 65112.

In some embodiments, ingestible device 65100 may include an optically transparent window 65114. Optically transparent window 65114 may be transparent to various types of illumination in the visible spectrum, infrared spectrum, or ultraviolet light spectrum, and ingestible device 65100 may have various sensors and illuminators located within the housing 65102, and behind the transparent window 65114. This may allow ingestible device 65100 to be configured to transmit illumination at different wavelengths through transparent window 65114 to an environment external to housing 65102 of ingestible device 65100, and to detect a reflectance from a portion of the illumination that is reflected back through transparent window 65114 from the environment external to housing 65102. Ingestible device 65100 may then use the detected level of reflectance in order to determine a location of ingestible device 65100 within a GI tract. In some embodiments, optically transparent window 65114 may be of any shape and size, and may wrap around the circumference of ingestible device 65100. In this case, ingestible device 65100 may have multiple sets of sensors and illuminators positioned at different locations azimuthally behind window 65114.

In some embodiments, ingestible device 65100 may optionally include an opening 65116 in the second wall portion 65110. In some embodiments, the second wall portion 65110 may be configured to rotate around the longitudinal axis of ingestible device 65100 (e.g., via a suitable motor or other actuator housed within ingestible device 65100). This may allow ingestible device 65100 to obtain a fluid sample from the GI tract, or release a substance into the GI tract, through opening 65116.

Figure 57:
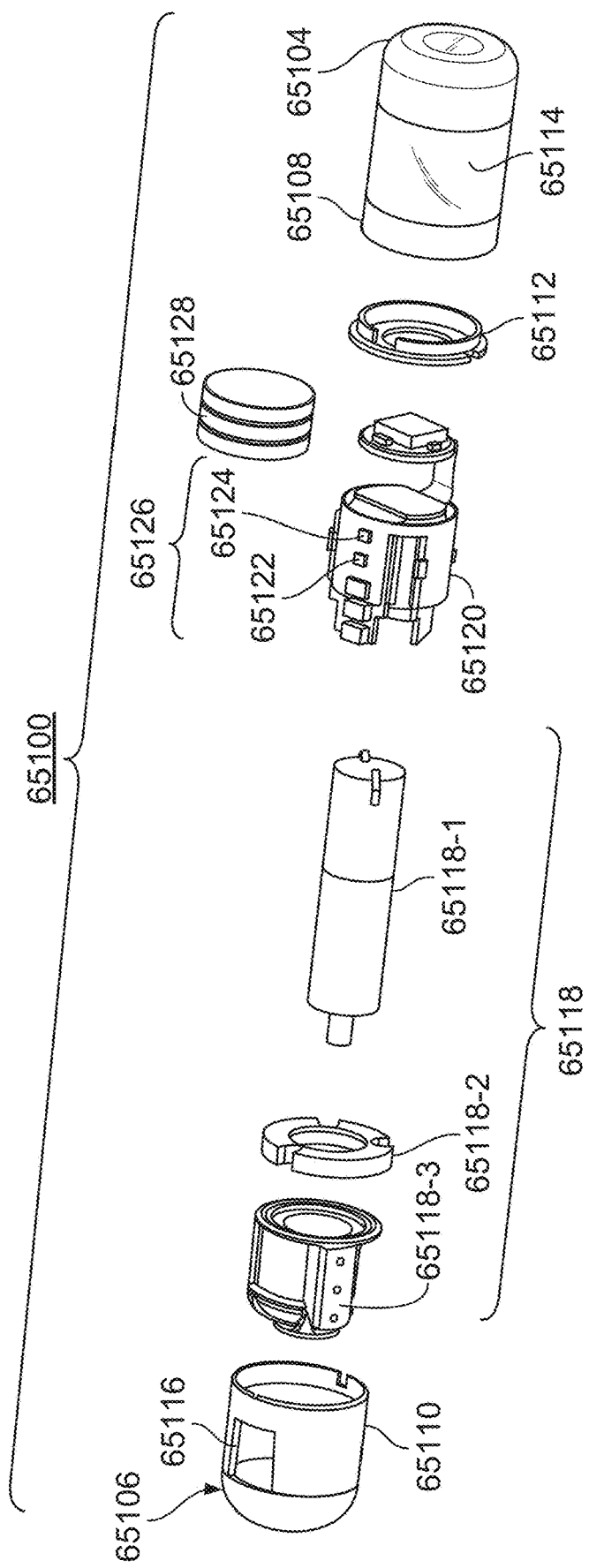
FIG. 57 is an exploded view of an ingestible device.

FIG. 57 shows an exploded view of ingestible device 65100. In some embodiments, ingestible device 65100 may optionally include a rotation assembly 65118. Optional rotation assembly 65118 may include a motor 65118-1 driven by a microcontroller (e.g., a microcontroller coupled to printed circuit board 65120), a rotation position sensing ring 65118-2, and a storage sub-unit 65118-3 configured to fit snugly within the second end portion 65104. In some embodiments, rotation assembly 65118 may cause second end portion 65104, and opening 65116, to rotate relative to the storage sub-unit 65118-3. In some embodiments, there may be cavities on the side of storage sub-unit 65118-3 that function as storage chambers. When the opening 65116 is aligned with a cavity on the side of the storage sub-unit 65118-3, the cavity on the side of the storage sub-unit 65118-3 may be exposed to the environment external to the housing 65102 of ingestible device 65100. In some embodiments, the storage sub-unit 65118-3 may be loaded with a medicament or other substance prior to the ingestible device 65100 being administered to a subject. In this case, the medicament or other substance may be released from the ingestible device 65100 by aligning opening 65116 with the cavity within storage sub-unit 65118-3. In some embodiments, the storage sub-unit 65118-3 may be configured to hold a fluid sample obtained from the GI tract. For example, ingestible device 65100 may be configured to align opening 65116 with the cavity within storage sub-unit 65118-3, thus allowing a fluid sample from the GI tract to enter the cavity within storage sub-unit 65118-3. Afterwards, ingestible device 65100 may be configured to seal the fluid sample within storage sub-unit 65118-3 by further rotating the second end portion 65106 relative to storage sub-unit 65118-3. In some embodiments, storage sub-unit 118-3 may also contain a hydrophilic sponge, which may enable ingestible device 65100 to better draw certain types of fluid samples into ingestible device 65100. In some embodiments, ingestible device 65100 may be configured to either obtain a sample from within the GI tract, or to release a substance into the GI tract, in response to determining that ingestible device 65100 has reached a predetermined location within the GI tract. For example, ingestible device 65100 may be configured to obtain a fluid sample from the GI tract in response to determining that the ingestible device has entered the jejunum portion of the small intestine (e.g., as determined by process 65900 discussed elsewhere herein). It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 65100 may include a printed circuit board (PCB) 65120, and a battery 65128 configured to power PCB 65120. PCB 65120 may include a programmable microcontroller, and control and memory circuitry for holding and executing firmware or software for coordinating the operation of ingestible device 65100, and the various components of ingestible device 65100. For example, PCB 65120 may include memory circuitry for storing data, such as data sets of measurements collected by sensing sub-unit 65126, or instructions to be executed by control circuitry to implement a localization process, such as, for example, one or more of the processes, discussed herein, including those discussed below in connection with one or more of the associated flow charts. PCB 65120 may include a detector 65122 and an illuminator 65124, which together form sensing sub-unit 65126. In some embodiments, control circuitry within PCB 65120 may include processing units, communication circuitry, or any other suitable type of circuitry for operating ingestible device 65100. For illustrative purposes, only a single detector 65122 and a single illuminator 65124 forming a single sensing sub-unit 65126 are shown. However, it is understood that in some embodiments there may be multiple sensing sub-units, each with a separate illuminator and detector, within ingestible device 65100. For example, there may be several sensing sub-units spaced azimuthally around the circumference of the PCB 65120, which may enable ingestible device 65100 to transmit illumination and detect reflectances or ambient light in all directions around the circumference of the device. In some embodiments, sensing sub-unit 65126 may be configured to generate an illumination using illuminator 65124, which is directed through the window 65114 in a radial direction away from ingestible device 65100. This illumination may reflect off of the environment external to ingestible device 65100, and the reflected light coming back into ingestible device 65100 through window 65114 may be detected as a reflectance by detector 65122.

In some embodiments, window 65114 may be of any suitable shape and size. For example, window 65114 may extend around a full circumference of ingestible device 65100. In some embodiments there may be a plurality of sensing sub-units (e.g., similar to sensing sub-unit 65126) located at different positions behind the window. For example, three sensing sub-units may be positioned behind the window at the same longitudinal location, but spaced 120 degrees apart azimuthally. This may enable ingestible device 65100 to transmit illuminations in all directions radially around ingestible device 65100, and to measure each of the corresponding reflectances.

In some embodiments, illuminator 65124 may be capable of producing illumination at a variety of different wavelengths in the ultraviolet, infrared, or visible spectrum. For example, illuminator 65124 may be implemented by using Red-Green-Blue Light-Emitting diode packages (RGB-LED). These types of RGB-LED packages are able to transmit red, blue, or green illumination, or combinations of red, blue, or green illumination. Similarly, detector 65122 may be configured to sense reflected light of the same wavelengths as the illumination produced by illuminator 65124. For example, if illuminator 65124 is configured to produce red, blue, or green illumination, detector 65122 may be configured to detect different reflectances produced by red, blue, or green illumination (e.g., through the use of an appropriately configured photodiode). These detected reflectances may be stored by ingestible device 65100 (e.g., within memory circuitry of PCB 65120 (FIG. 57)), and may then be used by ingestible device 65100 in determining a location of ingestible device 65100 within the GI tract (e.g., through the use of one or more processes described herein).

It is understood that ingestible device 65100 is intended to be illustrative, and not limiting. It will be understood that modifications to the general shape and structure of the various devices and mechanisms described in relation to FIG. 56 and FIG. 57 may be made without significantly changing the functions and operations of the devices and mechanisms. For example, ingestible device 65100 may have a housing formed from a single piece of molded plastic, rather than being divided into a first end portion 65104 and a second end portion 65106. As an alternate example, the location of window 65114 within ingestible device 65100 may be moved to some other location, such as the center of ingestible device 65100, or to one of the ends of ingestible device 65100. Moreover, the systems and methods discussed in relation to FIGS. 56-70 may be implemented on any suitable type of ingestible device, provided that the ingestible device is capable of detecting reflectances or levels of illumination in some capacity. For example, in some embodiments ingestible device 65100 may be modified to replace detector 65122 with an image sensor, and the ingestible device may be configured to measure relative levels of red, blue, or green light by decomposing a recorded image into its individual spectral components. It should be noted that the features and limitations described in any one embodiment may be applied to any other embodiment herein, and the descriptions and examples relating to one embodiment may be combined with any other embodiment in a suitable manner.

Figure 58:
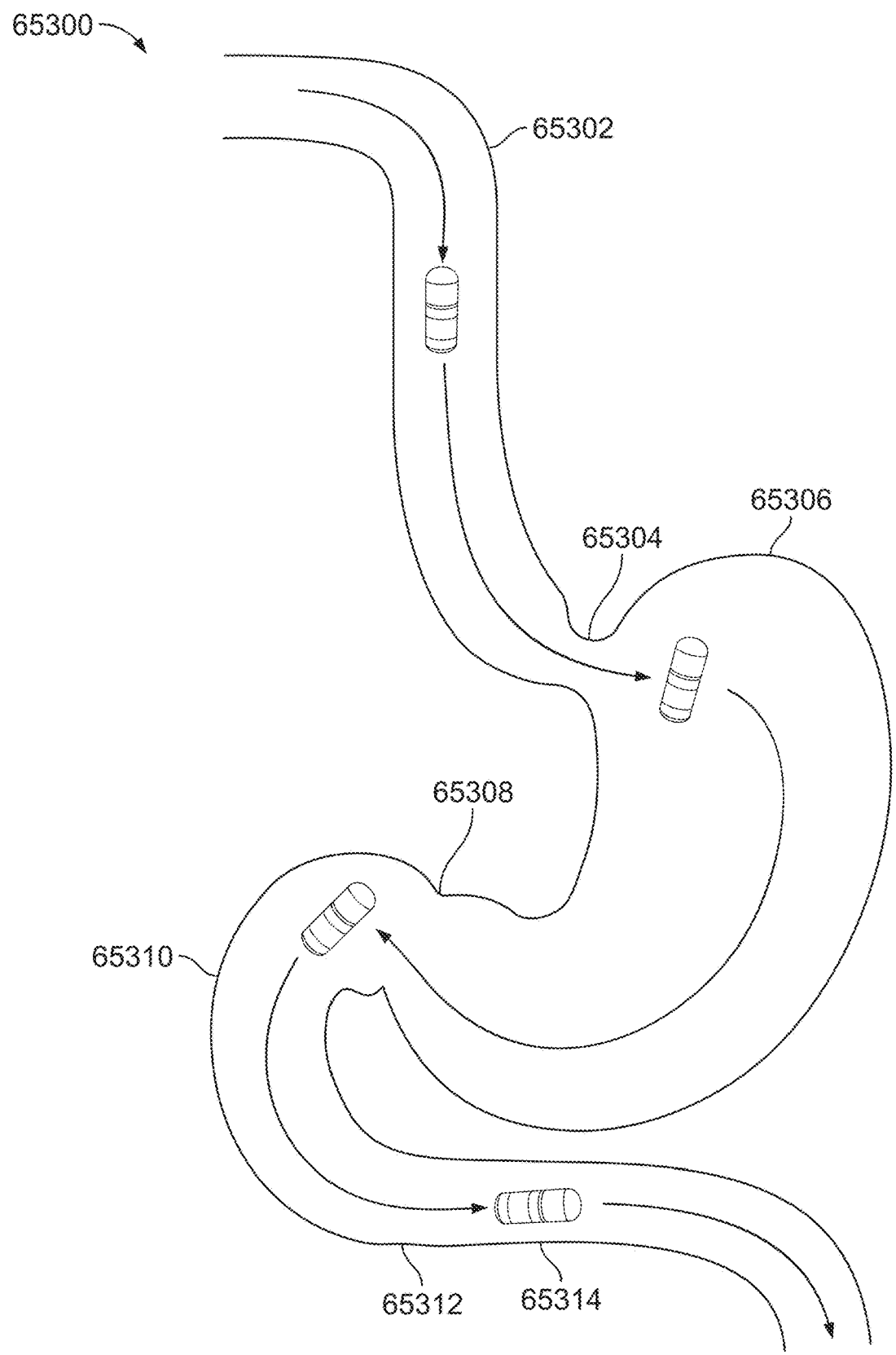
FIG. 58 is a diagram of an ingestible device during an example transit through a GI tract.

FIG. 58 is a diagram of an ingestible device during an example transit through a gastrointestinal (GI) tract, in accordance with some embodiments of the disclosure. The ngestible device may include any portion of any other ingestible device discussed in this disclosure, and may be any suitable type of ingestible device with localization capabilities. For example, the ingestible device may be without an optional opening for sampling or optional rotation assembly for sampling. In some embodiments, the ingestible device may be ingested by a subject, and as the ingestible device traverses the GI tract, the ingestible device determines its location within the GI tract. For example, the movement of the ingestible device and the amount of light detected by the ingestible device (e.g., via a detector as described elsewhere herein) may vary substantially depending on the location of the ingestible device within the GI tract, and the ingestible device may be configured to use this information to determine a location of the ingestible device within the GI tract. For instance, the ingestible device may detect ambient light from the surrounding environment, or reflectances based on illumination generated by the ingestible device (e.g., generated by an illuminator as described elsewhere herein), and use this information to determine a location of the ingestible device through processes, such as described herein. The current location of the ingestible device, and the time that the ingestible device detected each transition between the various portions of the GI tract, may then be stored by the ingestible device (e.g., in memory circuitry of a PCB as described elsewhere herein), and may be used for any suitable purpose.

Shortly after the ingestible device is ingested, the ingestible device will traverse the esophagus 65302, which may connect the subject's mouth to a stomach 65306. In some embodiments, the ingestible device may be configured to determine that it has entered the esophagus portion GI tract by measuring the amount and type of light (e.g., via a detector as described elsewhere herein) in the environment surrounding the the ingestible device. For instance, the ingestible device may detect higher levels of light in the visible spectrum (e.g., via a detector as described elsewhere herein) while outside the subject's body, as compared to the levels of light detected while within the GI tract. In some embodiments, the ingestible device may have previously stored data (e.g., on memory circuitry of a PCB as described elsewhere herein) indicating a typical level of light detected when outside of the body, and the the ingestible device may be configured to determine that entry to the body has occurred when a detected level of light (e.g., detected via a detector as described elsewhere herein) has been reduced beyond a threshold level (e.g., at least a 20-30% reduction) for a sufficient period of time (e.g., 5.0 seconds).

In some embodiments, the ingestible device may be configured to detect a transition from esophagus 65302 to stomach 65306 by passing through sphincter 65304. In some embodiments, ingestible device 65300 may be configured to determine whether it has entered stomach 65306 based at least in part on a plurality of parameters, such as but not limited to the use of light or temperature measurements (e.g., via a detector as described elsewhere herein or via a thermometer within the ingestible device), pH measurements (e.g., via a pH meter within the ingestible device), time measurements (e.g., as detected through the use of clock circuitry included within a PCB as described elsewhere herein), or any other suitable information. For instance, the ingestible device may be configured to determine that the ingestible device has entered stomach 65306 after detecting that a measured temperature of the ingestible device exceeds 31 degrees Celsius. Additionally, or alternately, the ingestible device may be configured to automatically determine it has entered stomach 65306 after one minute (or another pre-set time duration parameter, 80 seconds, 90 seconds, etc.) has elapsed from the time that the ingestible device was ingested, or one minute (or another pre-set time duration parameter, 80 seconds, 90 seconds, etc.) from the time that the ingestible device detected that it has entered the GI tract.

Stomach 65306 is a relatively large, open, and cavernous organ, and therefore the ingestible device may have a relatively large range of motion. By comparison, the motion of the ingestible device is relatively restricted within the tube-like structure of the duodenum 65310, the jejunum 65314, and the ileum (not shown), all of which collectively form the small intestine. Additionally, the interior of stomach 65306 has distinct optical properties from duodenum 65310 and jejunum 65314, which may enable the ingestible device to detect a transition from stomach 65306 to duodenum 65310 through the appropriate use of measured reflectances (e.g., through the use of reflectances measured by a detector as described elsewhere herein), as used in conjunction with a process 65600).

In some embodiments, the ingestible device may be configured to detect a pyloric transition from stomach 65306 to duodenum 65310 through the pylorus 65308. For instance, in some embodiments, the ingestible device may be configured to periodically generate illumination in the green and blue wavelengths (e.g., via an illuminator as described elsewhere herin), and measure the resulting reflectances (e.g., via a detector as described elsewhere herein). The ingestible device may be configured to then use a ratio of the detected green reflectance to the detected blue reflectance to determine whether the ingestible device is located within the stomach 65306, or duodenum 65310 (e.g., via process 65600). In turn, this may enable the ingestible device to detect a pyloric transition from stomach 65306 to duodenum 65310, an example of which is discussed in relation to FIG. 61.

Similarly, in some embodiments, the ingestible device may be configured to detect a reverse pyloric transition from duodenum 65310 to stomach 65306. The ingestible device will typically transition naturally from stomach 65306 to duodenum 65310, and onward to jejunum 65314 and the remainder of the GI tract. However, similar to other ingested substances, the ingestible device may occasionally transition from duodenum 65310 back to stomach 65306 as a result of motion of the subject, or due to the natural behavior of the organs with the GI tract. To accommodate this possibility, the ingestible device may be configured to continue to periodically generate illumination in the green and blue wavelengths (e.g., via an illuminator as described elsewhere herein), and measure the resulting reflectances (e.g., via a detector as described elsewhere herein) to detect whether or not the ingestible device has returned to stomach 65306. An exemplary detection process is described in additional detail in relation to FIG. 61.

After entering duodenum 65310, the ingestible device may be configured to detect a transition to the jejunum 65314 through the duodenojejunal flexure 65312. For example, the ingestible device may be configured to use reflectances to detect peristaltic waves within the jejunum 65314, caused by the contraction of the smooth muscle tissue lining the walls of the jejunum 65314. In particular, the ingestible device may be configured to begin periodically transmitting illumination (and measuring the resulting reflectances (e.g., via a detector and an illuminator of a sensing sub-unit as described elsewhere herein) at a sufficiently high frequency in order to detect muscle contractions within the jejunum 65314. The ingestible device may then determine that it has entered the jejunum 65314 in response to having detected either a first muscle contraction, or a predetermined number of muscle contractions (e.g., after having detected three muscle contractions in sequence). The interaction of the ingestible device with the walls of jejunum 65314 is also discussed in relation to FIG. 59, and an example of this detection process is described in additional detail in relation to FIG. 64.

Figure 59:
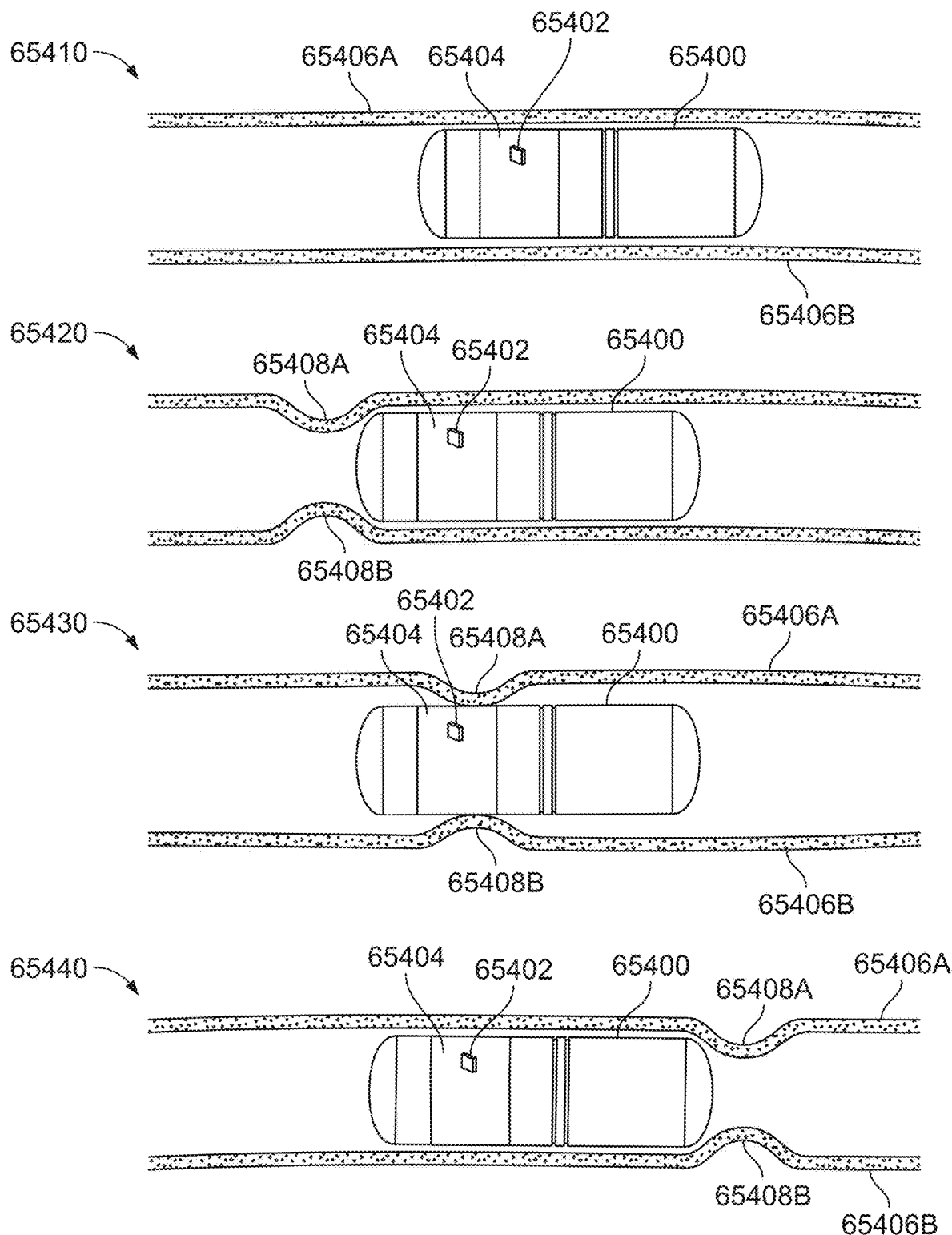
FIG. 59 is a diagram of an ingestible device during an example transit through a jejunum.

FIG. 59 is a diagram of an ingestible device during an example transit through a jejunum, in accordance with some embodiments of the disclosure. Diagrams 65410, 65420, 65430, and 65440 depict ingestible device 65400 as it traverses through a jejunum (e.g., jejunum 65314), and how ingestible device 65400 interacts with peristaltic waves formed by walls 65406A and 65406B (collectively, walls 65406) of the jejunum. In some implementations, ingestible device 65400 may include any portion of any other ingestible device discussed in this disclosure, and may be any suitable type of ingestible device with localization capabilities.

Diagram 65410 depicts ingestible device 65400 within the jejunum, when the walls 65406 of the jejunum are relaxed. In some embodiments, the confined tube-like structure of the jejunum naturally causes ingestible device 65400 to be oriented longitudinally along the length of the jejunum, with window 65404 facing walls 65406. In this orientation, ingestible device 65400 may use sensing sub-unit 65402 to generate illumination (e.g., via an illuminator as described elsewhere herein) oriented towards walls 65406, and to detect the resulting reflectances (e.g., via a detector as described elsewhere herein) from the portion of the illumination reflected off of walls 65406 and back through window 65404. In some embodiments, ingestible device 65400 may be configured to use sensing sub-unit 65402 to generate illumination and measure the resulting reflectance with sufficient frequency to detect peristaltic waves within the jejunum. For instance, in a healthy human subject, peristaltic waves may occur at a rate of approximately 0.05 Hz to 0.33 Hz. Therefore, the ingestible device 65400 may be configured to generate illumination and measure the resulting reflectance at least once every 2.5 seconds (i.e., potentially minimum rate to detect a 0.2 Hz signal), and preferably at a higher rate, such as once every 0.5 seconds, which may improve the overall reliability of the detection process due to more data points being available. It is understood that the ingestible device 65400 need not gather measurements at precise intervals, and in some embodiments the ingestible device 65400 may be adapted to analyze data gathered at more irregular intervals, provided that there are still a sufficient number of appropriately spaced data points to detect 0.05 Hz to 0.33 Hz signals.

Diagram 65420 depicts ingestible device 65400 within the jejunum, when the walls 65406 of the jejunum begin to contract and form a peristaltic wave. Diagram 65420 depicts contracting portion 65408A of wall 65406A and contracting portion 65408B of wall 65406B (collectively, contracting portion 65408 of wall 65406) that form a peristaltic wave within the jejunum. The peristaltic wave proceeds along the length of the jejunum as different portions of wall 65406 contract and relax, causing it to appear as if contracting portions 65408 of wall 65406 proceed along the length of the jejunum (i.e., as depicted by contracting portions 65408 proceeding from left to right in diagrams 65410-65430). While in this position, ingestible device 65400 may detect a similar level of reflectance (e.g., through the use of an illuminator and a detector of a sensing sub-unit as described elsewhere herein) as detected when there is no peristaltic wave occurring (e.g., as detected when ingestible device 65400 is in the position indicated in diagram 65410).

Diagram 65430 depicts ingestible device 65400 within the jejunum, when the walls 65406 of the jejunum continue to contract, squeezing around ingestible device 65400. As the peristaltic wave proceeds along the length of the jejunum, contracting portions 65408 of wall 65406 may squeeze tightly around ingestible device 65400, bringing the inner surface of wall 65406 into contact with window 65404. While in this position, ingestible device 65400 may detect a change in a reflectance detected as a result of illumination produced by sensing sub-unit 65402. The absolute value of the change in the measured reflectance may depend on several factors, such as the optical properties of the window 65404, the spectral components of the illumination, and the optical properties of the walls 65406. However, ingestible device 65400 may be configured to store a data set with the reflectance values over time, and search for periodic changes in the data set consistent with the frequency of the peristaltic waves (e.g., by analyzing the data set in the frequency domain, and searching for peaks between 0.05 Hz to 0.33 Hz). This may enable ingestible device 65400 to detect muscle contractions due to peristaltic waves without foreknowledge of the exact changes in reflectance signal amplitude that may occur as a result of detecting the muscle contractions of the peristaltic wave. An example procedure for detecting muscle contractions is discussed further in relation to FIG. 64, and an example of a reflectance data set gathered while ingestible device 65400 is located within the jejunum is discussed in relation to FIG. 65.

Diagram 65440 depicts ingestible device 65400 within the jejunum, when the peristaltic wave has moved past ingestible device 65400. Diagram 65440 depicts contracting portions 65408 that form the peristaltic wave within the jejunum having moved past the end of ingestible device 65400. The peristaltic wave proceeds along the length of the jejunum as different portions of wall 65406 contract and relax, causing it to appear as if contracting portions 65408 of wall 65406 proceed along the length of the jejunum (i.e., as depicted by contracting portions 65408 proceeding from left to right in diagrams 65410-65430). While in this position, ingestible device 65400 may detect a similar level of reflectance (e.g., through the use of an illuminator and a detector of a sensing sub-unit as described elsewhere herein) as detected when there is no peristaltic wave occurring (e.g., as detected when ingestible device 65400 is in the position indicated in diagram 65410, or diagram 65420).

Depending on the species of the subject, peristaltic waves may occur with relatively predictable regularity. After the peristaltic wave has passed over ingestible device 65400 (e.g., as depicted in diagram 65440), the walls 65406 of the jejunum may relax again (e.g., as depicted in diagram 65410), until the next peristaltic wave begins to form. In some embodiments, ingestible device 65400 may be configured to continue to gather reflectance value data while it is within the GI tract, and may store a data set with the reflectance values over time. This may allow ingestible device 65400 to detect each of the muscle contractions as the peristaltic wave passes over ingestible device 65400 (e.g., as depicted in diagram 65430), and may enable ingestible device 65400 to both count the number of muscle contractions that occur, and to determine that a current location of the ingestible device 65400 is within the jejunum. For example, ingestible device 65400 may be configured to monitor for possible muscle contractions while is inside either the stomach or the duodenum, and may determine that ingestible device 65400 has moved to the jejunum in response to detecting a muscle contraction consistent with a peristaltic wave.

Figure 60:
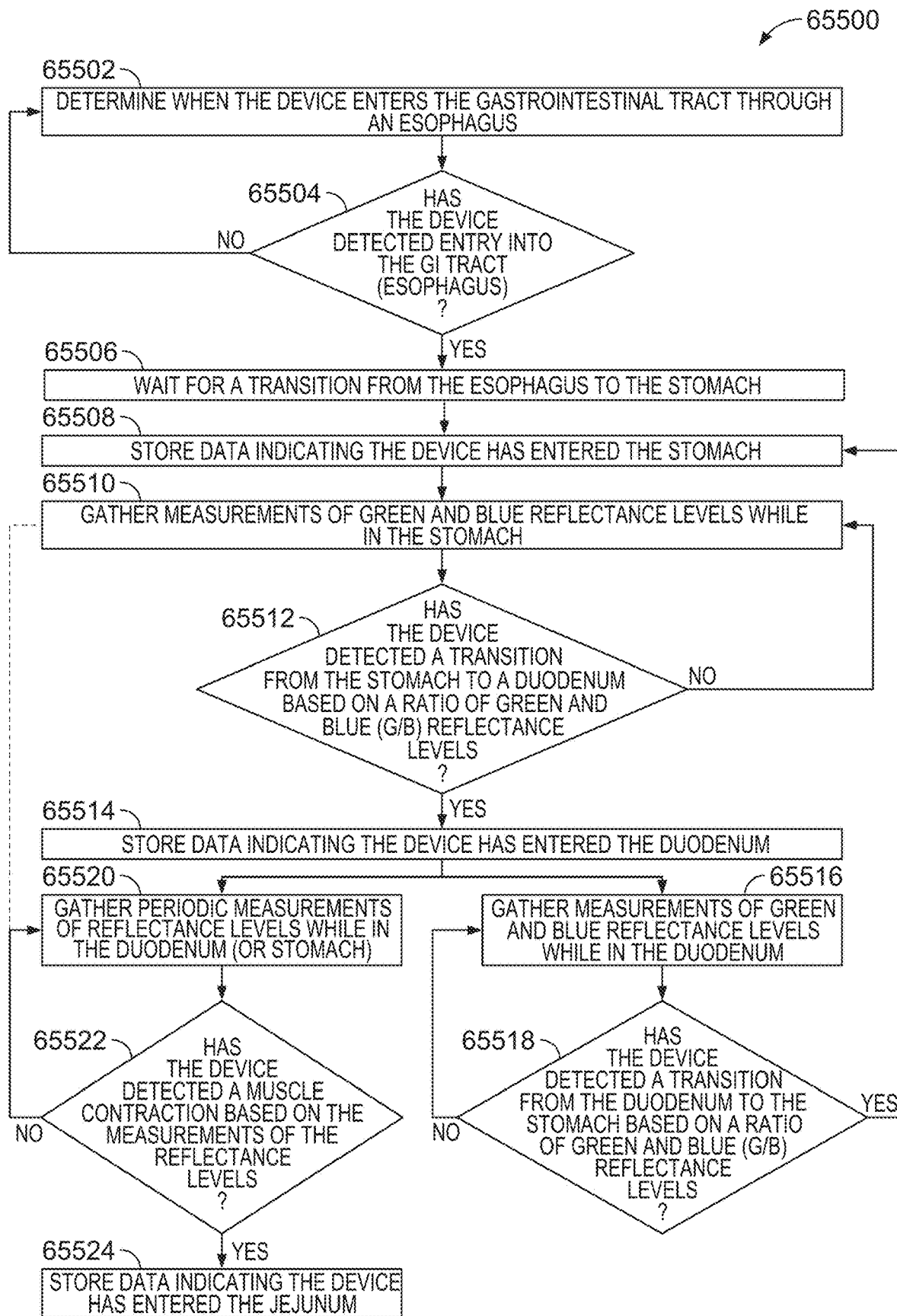
FIG. 60 is a flowchart of illustrative steps for determining a location of an ingestible device as it transits through a GI tract.

FIG. 60 is a flowchart illustrating some aspects of a localization process used by the ingestible device. In general, the process described in FIG. 60 can be used with any ingestible device disclosed herein. Furthermore, the features of FIG. 60 may be combined with any other systems, methods or processes described in this application. For example, portions of the process in FIG. 60 may be integrated into or combined with the pyloric transition detection procedure described by FIG. 61, or the jejunum detection process described by FIG. 64.

At 65502, the ingestible device gathers measurements (e.g., through a detector as described elsewhere herein) of ambient light. For example, the ingestible device may be configured to periodically measure (e.g., through a detector as described elsewhere herein) the level of ambient light in the environment surrounding the ingestible device. In some embodiments, the type of ambient light being measured may depend on the configuration of the detector within the ingestible device. For example, if the detector is configured to measure red, green, and blue wavelengths of light, the ingestible device may be configured to measure the ambient amount of red, green, and blue light from the surrounding environment. In some embodiments, the amount of ambient light measured by the ingestible device will be larger in the area external to the body (e.g., a well-lit room where the ingestible device is being administered to a subject) and in the oral cavity of the subject, as compared to the ambient level of light measured by the ingestible device when inside of an esophagus, stomach, or other portion of the GI tract (e.g., esophagus, stomach, duodenum, or jejunum).

At 65504, the ingestible device determines (e.g., via control circuitry within a PCB as described elsewhere herein) whether the ingestible device has detected entry into the GI tract. For example, the ingestible device may be configured to determine when the most recent measurement of ambient light (e.g., the measurement gathered at 65502) indicates that the ingestible device has entered the GI tract. For instance, the first time that the ingestible device gatherers a measurement of ambient light at 65502, the ingestible device may store that measurement (e.g., via storage circuitry within a PCB) as a typical level of ambient light external to the body. The ingestible device may be configured to then compare the most recent measurement of ambient light to the typical level of ambient light external to the body (e.g., via control circuitry within a PCB as described elsewhere herein), and determine that the ingestible device has entered the GI tract when the most recent measurement of ambient light is substantially smaller than the typical level of ambient light external to the body. For example, the ingestible device may be configured to detect that it has entered the GI tract in response to determining that the most recent measurement of ambient light is less than or equal to 20% of the typical level of ambient light external to the body. If the ingestible device determines that it has detected entry into the GI tract (e.g., that the ingestible device has entered at least the esophagus), process 65500 proceeds to 65506. Alternately, if the ingestible device determines that it has not detected entry into the GI tract (e.g., as a result of the most recent measurement being similar to the typical level of ambient light external to the body), process 65500 proceeds back to 65502 where the ingestible device gathers further measurements. For instance, the ingestible device may be configured to wait a predetermined amount of time (e.g., five seconds, ten seconds, etc.), and then gather another measurement of the level of ambient light from the environment surrounding the ingestible device.

At 65506, the ingestible device waits for a transition from the esophagus to the stomach (e.g., from the esophagus to the stomach). For example, the ingestible device may be configured to determine that it has entered the stomach (e.g., the stomach) after waiting a predetermined period of time after having entered the GI tract. For instance, a typical esophageal transit time in a human patient may be on the order of 15-30 seconds. In this case, after having detected that the ingestible device has entered the GI tract at 65504 (i.e., after detecting that the ingestible device has reached at least the esophagus), the ingestible device may be configured to wait one minute, or a similar amount of time longer than the typical esophageal transmit time (e.g., ninety-seconds), before automatically determining that the ingestible device has entered at least the stomach (e.g., the stomach).

In some embodiments, the ingestible device may also determine whether it has entered the stomach based on measurements of pH or temperature. For example, the ingestible device may be configured to determine that it has entered the stomach if a temperature of ingestible device has increased to at least 31 degrees Celsius (i.e., consistent with the temperature inside the stomach), or if a measured pH of the environment surrounding the ingestible device is sufficiently acidic (i.e., consistent with the acidic nature of gastric juices that may be found inside the stomach).

At 65508, the ingestible device (stores data indicating the ingestible device has entered the stomach (e.g., the stomach). For example, after having waited a sufficient amount of time at 65506, the ingestible device may store data (e.g., within storage circuitry of a PCB 65120 as described elsewhere herein) indicative of the ingestible device having entered at least the stomach. Once the ingestible device reaches at least the stomach, process 65500 proceeds to 65510 where the ingestible device may be configured to gather data to detect entry into the duodenum (e.g., the duodenum).

In some embodiments, process 65500 may also simultaneously proceed from 65508 to 65520, where the ingestible device may be configured to gather data in order to detect muscle contractions and detect entry into the jejunum (e.g., the jejunum). In some embodiments, the ingestible device may be configured to simultaneously monitor for entry into the duodenum at 65516-65518, as well as detect for entry into the jejunum at 65520-65524. This may allow the ingestible device to determine when it has entered the jejunum (e.g., as a result of detecting muscle contractions), even when it fails to first detect entry into the duodenum (e.g., as a result of very quick transit times of the ingestible device through the duodenum).

At 65510, the ingestible device gathers measurements of green and blue reflectance levels (e.g., through the use of an illuminator and a detector of a sensing sub-unit as described elsewhere herein) while in the stomach. For example, the ingestible device may be configured to periodically gather measurements of green and blue reflectance levels while in the stomach. For instance, the ingestible device may be configured to transmit a green illumination and a blue illumination (e.g., via an illuminator as described elsewhere herein) every five to fifteen seconds, and measure the resulting reflectance (e.g., via a detector as described elsewhere herein). Every time that the ingestible device gathers a new set of measurements, the measurements may be added to a stored data set (e.g., stored within memory circuitry of a PCB as described elsewhere herein). The ingestible device may then use this data set to determine whether or not the ingestible device is still within a stomach or a duodenum.

In some embodiments, the ingestible device may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable the ingestible device to sufficiently distinguish between the two wavelengths when detecting the reflectances (e.g., via a detector as described elsewhere herein). It is understood that the separation of 50 nm is intended to be illustrative, and not limiting, and depending on the accuracy of the detectors within the ingestible device, smaller separations may be possible to be used.

At 65512, the ingestible device determines (e.g., using control circuitry within a PCB as described elsewhere herein) whether the ingestible device has detected a transition from the stomach to a duodenum based on a ratio of green and blue (G/B) reflectance levels. For example, the ingestible device may obtain (e.g., from memory circuitry of a PCB as described elsewhere herein) a data set containing historical data for the respective ratio of the green reflectance to the blue reflectance as measured at a respective time. Generally speaking, a duodenum of a human subject reflects a higher ratio of green light to blue light, as compared to the ratio of green light to blue light that is reflected by a stomach. Based on this, the ingestible device may be configured to take a first set of ratios from the data set, representing the result of recent measurements, and compare them to a second set of ratios from the data set, representing the results of past measurements. When the the ingestible device determines that the mean value of the first set of ratios is substantially larger than the mean value of the second set of ratios (i.e., that the ratio of reflected green light to reflected blue light has increased), the ingestible device may determine that it has entered the duodenum (from the stomach. If the ingestible device detects a transition from the stomach to a duodenum (process 65500 proceeds to 65514, where the ingestible device stores data indicating that the ingestible device has entered the duodenum. Alternatively, if the ingestible device determines that the ingestible device has not transitioned from the stomach to the duodenum, process 65500 proceeds back to 65510 to gather more measurements of green and blue reflectance levels while still in the stomach. An example procedure for using measurements of green and blue reflectances to monitor for transitions between the stomach and the duodenum is discussed in greater detail in relation to FIG. 61.

In some embodiments, the first time that detects a transition from the stomach to the duodenum, the ingestible device may be configured to take a mean of the second set of data, (e.g., the set of data previously recorded while in the stomach) and store this as a typical ratio of green light to blue light detected within the stomach (e.g., the stomach) (e.g., within memory circuitry of a PCB 65120 (FIG. 57) as described elsewhere herein). This stored information may later be used by the ingestible device to determine when the ingestible device re-enters the stomach from the duodenum as a result of a reverse pyloric transition.

At 65514, the ingestible device stores data indicating that the ingestible device has entered the duodenum. For example, the ingestible device may store a flag within local memory (e.g., memory circuitry of a PCB as described elsewhere herein) indicating that the the ingestible device is currently in the duodenum. In some embodiments, the ingestible device may also store a timestamp indicating the time when the ingestible device entered the duodenum. Once the ingestible device reaches the duodenum, process 65500 proceeds to 65520 where the ingestible device may be configured to gather data in order to detect muscle contractions and detect entry into the jejunum. Process 65500 also proceeds from 65514 to 65516, where the ingestible device may be configured to gather data additional data in order to detect re-entry into the stomach from the duodenum.

At 65516, the ingestible device gathers measurements (e.g., via a sensing sub-unit as described elsewhere herein) of green and blue reflectance levels while in the duodenum. For example, the ingestible device may be configured to periodically gather measurements (e.g., via a sensing sub-unit as described elsewhere herein) of green and blue reflectance levels while in the duodenum, similar to the measurements made at 65510 while in the stomach. For instance, the ingestible device may be configured to transmit a green illumination and a blue illumination (e.g., via an illuminator as described elsewhere herein) every five to fifteen seconds, and measure the resulting reflectance (e.g., via a detectoras described elsewhere herein). Every time that the ingestible device gathers a new set of measurements, the measurements may be added to a stored data set (e.g., stored within memory circuitry of a PCB). The the ingestible device may then use this data set to determine whether or the ingestible device is still within the duodenum, or if the ingestible device has transitioned back into the stomach).

At 65518, the ingestible device determines a transition from the duodenum to the stomach based on a ratio of the measured green reflectance levels to the measured blue reflectance levels. In some embodiments, the ingestible device may compare the ratio of the measured green reflectance levels to the measured blue reflectance levels recently gathered by the ingestible device (e.g., measurements gathered at 65516), and determine whether or not the ratio of the measured green reflectance levels to the measured blue reflectance levels is similar to the average ratio of the measured green reflectance levels to the measured blue reflectance levels seen in the stomach. For instance, the ingestible device may retrieve data (e.g., from memory circuitry of a PCB (FIG. 57)) indicative of the average ratio of the measured green reflectance levels to the measured blue reflectance levels seen in the stomach, and determine that the ingestible device has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum to the stomach, process 65500 proceeds to 65508 to store data indicating the ingestible device has entered the stomach, and continues to monitor for further transitions. Alternatively, if the ingestible device does not detect a transition from the duodenum to the stomach, process 65500 proceeds to 65516 to gather additional measurements of green and blue reflectance levels while in the duodenum, which may be used to continuously monitor for possible transitions back into the stomach. An example procedure for using measurements of green and blue reflectances to monitor for transitions between the stomach and the duodenum is discussed in greater detail in relation to FIG. 61.

At 65520, the ingestible device gathers periodic measurements of the reflectance levels (e.g., via a sensing sub-unit) while in the duodenum. In some embodiments, the ingestible device may gather similar periodic measurements while in the stomach as well. In some embodiments, these periodic measurements may enable the ingestible device to detect muscle contractions (e.g., muscle contractions due to a peristaltic wave as discussed in relation to FIG. 59), which may be indicative of entry into a jejunum. The ingestible device may be configured to gather periodic measurements using any suitable wavelength of illumination (e.g., by generating illumination using an illuminator and detecting the resulting reflectance using a detector), or combinations of wavelengths of illumination. For example, in some embodiments, the ingestible device may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by the ingestible device at 65520 may be sufficiently fast as to detect peristaltic waves in a subject. For instance, in a healthy human subject, peristaltic waves may occur at a rate of approximately 0.05 Hz to 0.33 Hz. Therefore, the ingestible device may be configured to generate illumination and measure the resulting reflectance at least once every 2.5 seconds (i.e., potentially minimum rate to detect a 0.2 Hz signal), and preferably at a higher rate, such as once every 0.5 seconds or faster, and store values indicative of the resulting reflectances in a data set (e.g., within memory circuitry of a PCB). After gathering additional data (e.g., after gathering one new data point, or a predetermined number of new data points), process 65500 proceeds to 65522, where the ingestible device determines whether or not a muscle contraction has been detected.

At 65522, the ingestible device determines (e.g., via control circuitry within a PCB) whether the ingestible device detects a muscle contraction based on the measurements of reflectance levels (e.g., as gathered by a sensing sub-unit). For example, the ingestible device may obtain a fixed amount of data stored as a result of measurements made at 65520 (e.g., retrieve the past minute of data from memory circuitry within a PCB. The ingestible device may then convert the obtained data into the frequency domain, and search for peaks in a frequency range that would be consistent with peristaltic waves. For example, in a healthy human subject, peristaltic waves may occur at a rate of approximately 0.05 Hz to 0.33 Hz, and the ingestible device may be configured to search for peaks in the frequency domain representation of the data between 0.05 Hz to 0.33 Hz above a threshold value. If the ingestible device detects a contraction based on the reflectance levels (e.g., based on detecting peaks in the frequency domain representation of the data between 0.05 Hz to 0.33 Hz), process 65500 proceeds to 65524 to store data indicating that the device has entered the jejunum. Alternatively, if the ingestible device does not detect a muscle contraction, process 65500 proceeds to 65520 to gather periodic measurements of the reflectance levels while in the duodenum. In some embodiments, the ingestible device may store data (e.g., within memory circuitry of a PCB) indicating that a muscle contraction was detected, and process 65500 will not proceed from 65522 to 65524 until a sufficient number of muscle contractions have been detected.

At 65524, the ingestible device stores data (e.g., within memory circuitry of a PCB) indicating that the device has entered the jejunum). For example, in response to detecting that muscle contraction has occurred at 65522, the ingestible device may determine that it has entered the jejunum 65314, and is no longer inside of the duodenum or the stomach. In some embodiments, the ingestible device may continue to measure muscle contractions while in the jejunum, and may store data indicative of the frequency, number, or strength of the muscle contractions over time (e.g., within memory circuitry of a PCB). In some embodiments, the ingestible device may also be configured to monitor for one or more transitions. Such transitions can include a transition from the jejunum to the ileum, an ileoceacal transition from the ileum to the cecum, a transition from the cecum to the colon, or detect exit from the body (e.g., by measuring reflectances, temperature, or levels of ambient light).

In some embodiments, the ingestible device may also determine that it has entered the jejunum after a predetermined amount of time has passed after having detected entry into the duodenum. For example, barring a reverse pyloric transition from the duodenum back to the stomach, the typical transit time for an ingestible device to reach the jejunum from the duodenum in a healthy human subject is less than three minutes. In some embodiments, the ingestible device may therefore be configured to automatically determine that it has entered the jejunum after spending at least three minutes within the duodenum. This determination may be made separately from the determination made based on measured muscle contractions (e.g., the determination made at 65522), and in some embodiments, the ingestible device may determine that it has entered the jejunum in response to either detecting muscle contractions, or after three minutes has elapsed from having entered the duodenum (e.g., as determined by storing data at 65514 indicative of the time that ingestible device entered the duodenum).

For illustrative purposes, 65512-65518 of process 65500 describe the ingestible device measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 60, are merely illustrative. Any of the steps and descriptions of the flowcharts, including FIG. 60, may be modified, omitted, rearranged, and performed in alternate orders or in parallel, two or more of the steps may be combined, or any additional steps may be added, without departing from the scope of the present disclosure. For example, the ingestible device may calculate the mean and the standard deviation of multiple data sets in parallel in order to speed up the overall computation time. As another example, the ingestible device may gather data periodic measurements and detect possible muscle contractions (e.g., at 65520-65522) while simultaneously gathering green and blue reflectance levels to determine transitions to and from the stomach and duodenum (e.g., at 65510-65518). Furthermore, it should be noted that the steps and descriptions of FIG. 60 may be combined with any other system, device, or method described in this application, including processes 65600 and 65900, and any of the ingestible devices or systems discussed in this application could be used to perform one or more of the steps in FIG. 60.

Figure 61:
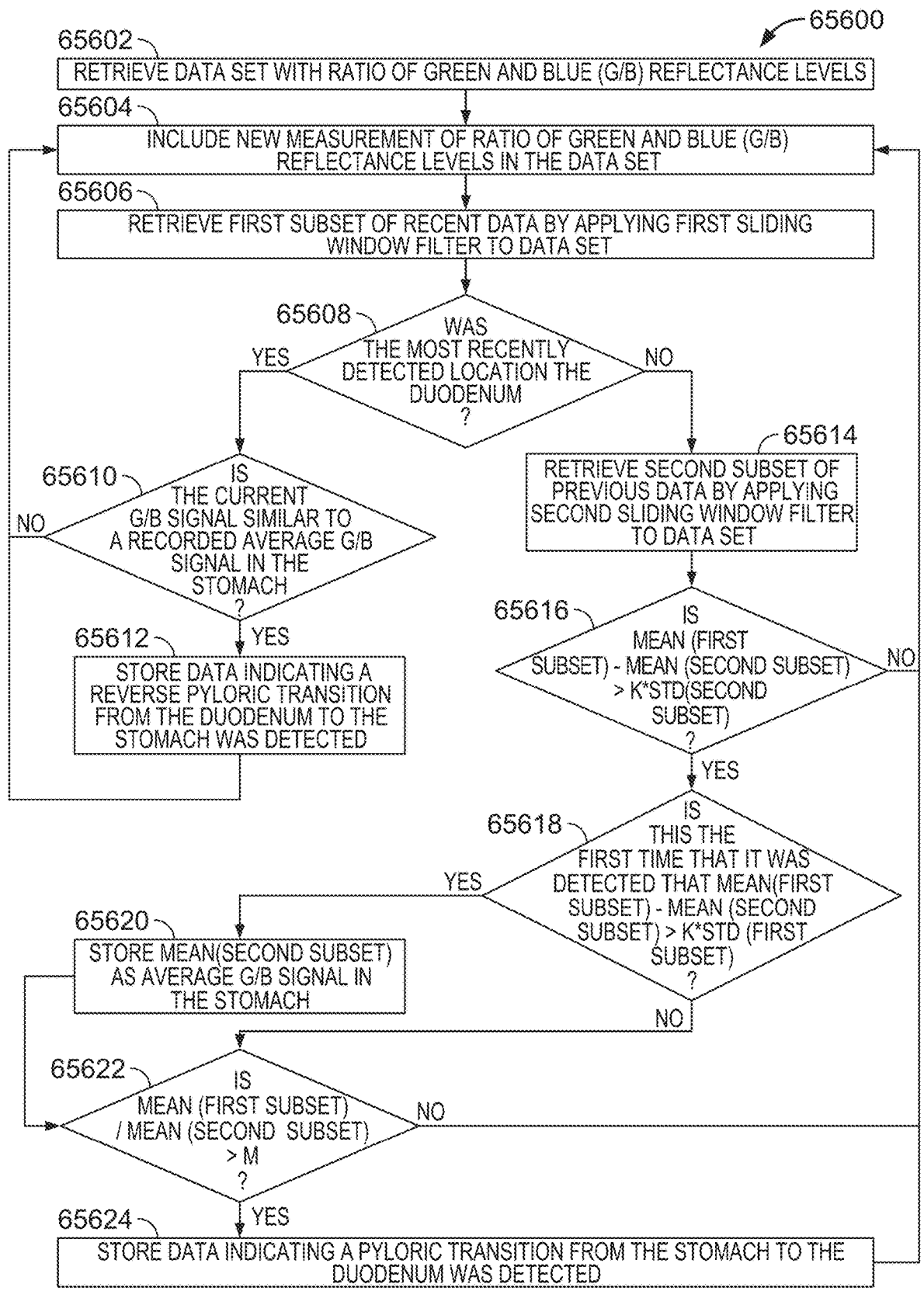
FIG. 61 is a flowchart of illustrative steps for detecting transitions from a stomach to a duodenum and from a duodenum back to a stomach.

FIG. 61 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 65600 may begin when an ingestible device first detects that it has entered the stomach, and will continue as long as the ingestible device determines that it is within the stomach or the duodenum. In some embodiments, process 65600 may only be terminated when an ingestible device determines that it has entered the jejunum, or otherwise progressed past the duodenum and the stomach. The duodenum detection process 65600 described in FIG. 61 may be applied to any device discussed in this application, and any of the ingestible devices may be used to perform one or more parts of the process described in FIG. 61. Furthermore, the features of FIG. 61 may be combined with any other systems, methods or processes described in this application. For example, portions of the process described by the process in FIG. 61 may be integrated into process 65500 discussed in relation to FIG. 60.

At 65602, the ingestible device retrieves a data set (e.g., from memory circuitry within a PCB) with ratios of the measured green reflectance levels to the measured blue reflectance levels over time. For example, the ingestible device may retrieve a data set from a PCB containing recently recorded ratios of the measured green reflectance levels to the measured blue reflectance levels (e.g., as recorded at 65510 or 65516 of process 65500). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 62 and FIG. 63.

At 65604, the ingestible device includes a new measurement (e.g., as made with a sensing sub-unit) of a ratio of the measured green reflectance level to the measured blue reflectance level in the data set. For example, the ingestible device may be configured to occasionally record new data by transmitting green and blue illumination (e.g., via an illuminator), detecting the amount of reflectance received due to the green and blue illumination (e.g., via a detector), and storing data indicative of the amount of the received reflectance (e.g., in memory circuitry of a PCB). The ingestible device may be configured to record new data every five to fifteen seconds, or at any other convenient interval of time. For illustrative purposes, the ingestible device is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be "1.0" at that given time); however, it is understood that the green reflectance data and the blue reflectance data may be stored separately within the memory of the ingestible device (e.g., stored as two separate data sets within memory circuitry of a PCB).

At 65606, the ingestible device retrieves a first subset of recent data by applying a first sliding window filter to the data set. For example, the ingestible device may use a sliding window filter to obtain a predetermined amount of the most recent data within the data set, which may include any new values of the ratio of the measured green reflectance level to the measured blue reflectance level obtained at 65604. For instance, the ingestible device may be configured to select between ten and forty data points from the data set, or the ingestible device may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 65614).

In some embodiments, the ingestible device may also be configured to remove outliers from the data set, or to smooth out unwanted noise in the data set. For example, the ingestible device may select the first subset of data, or any other subset of data, by first obtaining a raw set of values by applying a window filter to the data set (e.g., selecting a particular range of data to be included). The ingestible device may then be configured to identify outliers in the raw set of values; for instance, by identifying data points that are over three standard deviations away from the mean value of the raw set of values, or any other suitable threshold. The ingestible device may then determine the subset of data by removing outliers from the raw set of values. This may enable the ingestible device to avoid spurious information when determining whether or not it is located within the stomach or the duodenum.

At 65608, the ingestible device determines whether the most recently detected location was the duodenum. In some embodiments, the ingestible device may store a data flag (e.g., within memory circuitry of a PCB 65120 (FIG. 57)) indicating the most recent portion of the GI tract that the ingestible device detected itself to be within. For instance, every time the ingestible device detects entry to the stomach (e.g., detects entry into stomach 65306 as a result of the decision made at 65610), a flag is stored in memory indicating the ingestible device is in the stomach (e.g., as part of storing data at 65612). If the ingestible device subsequently detects entry into the duodenum (e.g., detects entry into the duodenum 65310 as a result of a decision made at 65624), another different flag is stored in memory indicating that the ingestible device is in the duodenum (e.g., as part of storing data at 65624). In this case, the ingestible device may retrieve the most recently stored flag at 65608, and determine whether or not the flag indicates that the ingestible device was most recently within the duodenum. If the ingestible device detects that it was most recently in the duodenum, process 65600 proceeds to 65610 where the ingestible device compares the recent measurements of the ratios of the measured green reflectance levels to the measured blue reflectance levels (e.g., measurements that include the recent measurement made at 65606) to the typical ratios measured within the stomach, and uses this information to determine whether a reverse pyloric transition from the duodenum back to the stomach has occurred. Alternately, if the ingestible device detects that it was not most recently in the duodenum (e.g., because it was in the stomach instead), process 65600 proceeds to 65614 where the ingestible device compares the recent measurements of the ratios of the measured green reflectance levels to the measured blue reflectance levels (e.g., measurements that include the recent measurement made at 65606) to past measurements, and uses this information to determine whether a pyloric transition from the stomach to the duodenum has occurred.

Process 65600 proceeds from 65608 to 65610 when the ingestible device determined that it was most recently in the duodenum. At 65610, the ingestible device determines (e.g., via control circuitry within a PCB) whether the current G/B signal is similar to a recorded average G/B signal in the stomach. For example, the ingestible device may be configured to have previously stored data (e.g., within memory circuitry of a PCB 65120 (FIG. 57)) indicative of the average ratio of the measured green reflectance levels to the measured blue reflectance levels measured in the stomach. The ingestible device may then retrieve this stored data indicative of the average ratio of the measured green reflectance levels to the measured blue reflectance levels in the stomach, and compare this against the recent measurements in order to determine whether or not the ingestible device has returned back to the stomach from the duodenum. For instance, the ingestible device may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was "1," with a standard deviation of "0.2," ingestible device may determine whether or not the mean value of the first subset of data is less than "1.0+k*0.2," where "k" is a number between zero and five. It is understood that, in some embodiments, the ingestible device may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 65600 proceeds to 65612 where the ingestible device stores data indicating that it has re-entered the stomach from the duodenum. Alternately, in response to determining that the recent ratio of measured green and blue reflectance levels is sufficiently different from the average ratio of measured green and blue reflectance levels seen in the stomach, the ingestible device proceeds directly to 65604, and continues to obtain new data on an ongoing basis.

At 65612, the ingestible device stores data indicating a reverse pyloric transition from the duodenum to the stomach was detected. For example, the ingestible device may store a data flag (e.g., within memory circuitry of a PCB) indicating that the ingestible device most recently detected itself to be within the stomach portion of the GI tract. In some embodiments, the ingestible device may also store data (e.g., within memory circuitry of a PCB) indicating a time that the ingestible device detected the reverse pyloric transition from the duodenum to the stomach. This information may be used by the ingestible device at 65608, and as a result process 65600 may proceed from 65608 to 65614, rather than proceeding from 65618 to 65610. After the ingestible device stores the data indicating a reverse pyloric transition from the duodenum to the stomach was detected, process 65600 proceeds to 65604 where the ingestible device continues to gather additional measurements, and continues to monitor for further transitions between the stomach and the duodenum.

Process 65600 proceeds from 65608 to 65614 when the ingestible device determined that it was not most recently in the duodenum (e.g., as a result of having most recently been in the stomach instead). At 65614, the ingestible device retrieves a second subset of previous data by applying a second sliding window filter to the data set. For example, the ingestible device may use a sliding window filter to obtain a predetermined amount of older data from a past time range, which may be separated from recent time range used to select the first subset of data gathered at 65606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, the ingestible device may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, the ingestible device may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if the ingestible device recently transitioned to the stomach from the duodenum (e.g., as determined by checking for recent data stored within the ingestible device at 65612), the ingestible device may select the second subset of data at 65614 from a time frame when the ingestible device is known to be within the stomach. In some embodiments, the ingestible device may alternately select a previously recorded average and standard deviation for ratios of green reflectances and blue reflectances within the stomach (e.g., an average and standard deviation typical of data recorded within the stomach, as previously recorded within memory circuitry of a PCB at 65620) in place of the second subset of data. In this case, the ingestible device may simply use the previously recorded average and previously recorded standard deviation when making a determination at 65616, rather than expending resources to calculate the mean and standard deviation of the second subset.

At 65616, the ingestible device determines whether the difference between the mean of the second subset and the mean of the first subset is greater than a predetermined multiple of the standard deviation of the first subset. For example, the ingestible device may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 65600 proceeds to 65618. Otherwise, process 65600 proceeds back to 65604, where the ingestible device 65604 continues to gather new data to be used in monitoring for transitions between the stomach and the duodenum.

At 65618, the ingestible device determines (e.g., via control circuitry within a PCB) whether the determination made at 65616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 65600 proceeds to 65620 to store the mean of the second subset of past data as an average G/B signal in the stomach. Alternatively, if the ingestible device determines that the immediately preceding determination made at 65616 is not the first time that the difference between the mean of the first subset of recent data and the mean of the second subset of past data is calculated to be greater than the standard deviation of the second subset, process 65600 proceeds directly to 65622.

At 65620, the ingestible device stores the mean of the second subset as an average G/B signal in the stomach. For example, the ingestible device may be configured to store the mean of the second subset of past data (e.g., store within memory circuitry of a PCB 65120) as the average ratio of the measured green reflectance levels to the measured blue reflectance levels measured in the stomach. In some embodiments, the ingestible device may also store the standard deviation of the second subset of past data as a typical standard deviation of the ratios of the measured green reflectance levels to the measured blue reflectance levels detected within the stomach. This stored information may be used by the ingestible device later on (e.g., at 65610) to compare against future data, which may enable the ingestible device to detect reverse pyloric transitions from the duodenum back to the stomach, and may generally be used in place of other experimental data gathered from the stomach (e.g., in place of the second subset of data at 65616). After storing the mean of the second subset as an average G/B signal in the stomach, process 65600 proceeds to 65622.

At 65622, the ingestible device determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable the ingestible device to ensure that it detected an actual transition to the duodenum. This may be particularly advantageous when the determination made at 65616 is potentially unreliable due to the standard deviation of the second subset of past data being abnormally small. For example, a typical value of the predetermined threshold "M," may be on the order of 0.1 to 0.5. If the ingestible device determines that the difference of the mean of the first subset of recent data to the second subset of past data is greater than a predetermined threshold, process 65600 proceeds to 65624 to store data indicating that a pyloric transition from the stomach to the duodenum was detected. Alternatively, if the ingestible device determines that the ratio of the mean of the first subset to the second subset is less than or equal to the predetermined threshold, "M" (i.e., determines that a transition to the duodenum has not occurred), process 65600 proceeds directly to 65604 where the ingestible device continues to make new measurements and monitor for possible transitions between the stomach and the duodenum.

In some embodiments, instead of using a difference of the mean of the first subset of recent data to the mean of the second subset of past data, the ingestible device determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable the ingestible device to ensure that it detected an actual transition to the duodenum. This may be particularly advantageous when the determination made at 65616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 65624, the ingestible device stores data indicating a pyloric transition from the stomach to the duodenum was detected. For example, the ingestible device may store a data flag (e.g., within memory circuitry of a PCB) indicating that the ingestible device most recently detected itself to be within the duodenum portion of the GI tract. In some embodiments, the ingestible device may also store data (e.g., within memory circuitry of a PCB) indicating a time that the ingestible device detected the pyloric transition from the stomach to the duodenum. This information may be used by the ingestible device at 65608, and as a result process 65600 may proceed from 65608 to 65610, rather than proceeding from 65618 to 65614. After the ingestible device stores the data indicating a pyloric transition from the stomach to the duodenum was detected, process 65600 proceeds to 65604 where the ingestible device continues to gather additional measurements, and continues to monitor for further transitions between the stomach and the duodenum.

It will be understood that the steps and descriptions of the flowcharts of this disclosure, including FIG. 61, are merely illustrative. Any of the steps and descriptions of the flowcharts, including FIG. 61, may be modified, omitted, rearranged, and performed in alternate orders or in parallel, two or more of the steps may be combined, or any additional steps may be added, without departing from the scope of the present disclosure. For example, the ingestible device may calculate the mean and the standard deviation of multiple data sets in parallel in order to speed up the overall computation time. Furthermore, it should be noted that the steps and descriptions of FIG. 61 may be combined with any other system, device, or method described in this application, and any of the ingestible devices or systems discussed in this application could be used to perform one or more of the steps in FIG. 61. For example, portions of process 65600 may be incorporated into 65508-65516 of process 65500, and may be part of a more general process for determining a location of the ingestible device. As another example, the ratio of detected blue and green light (e.g., as measured and added to the data set at 65604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 62 and FIG. 62 below.

Figure 62:
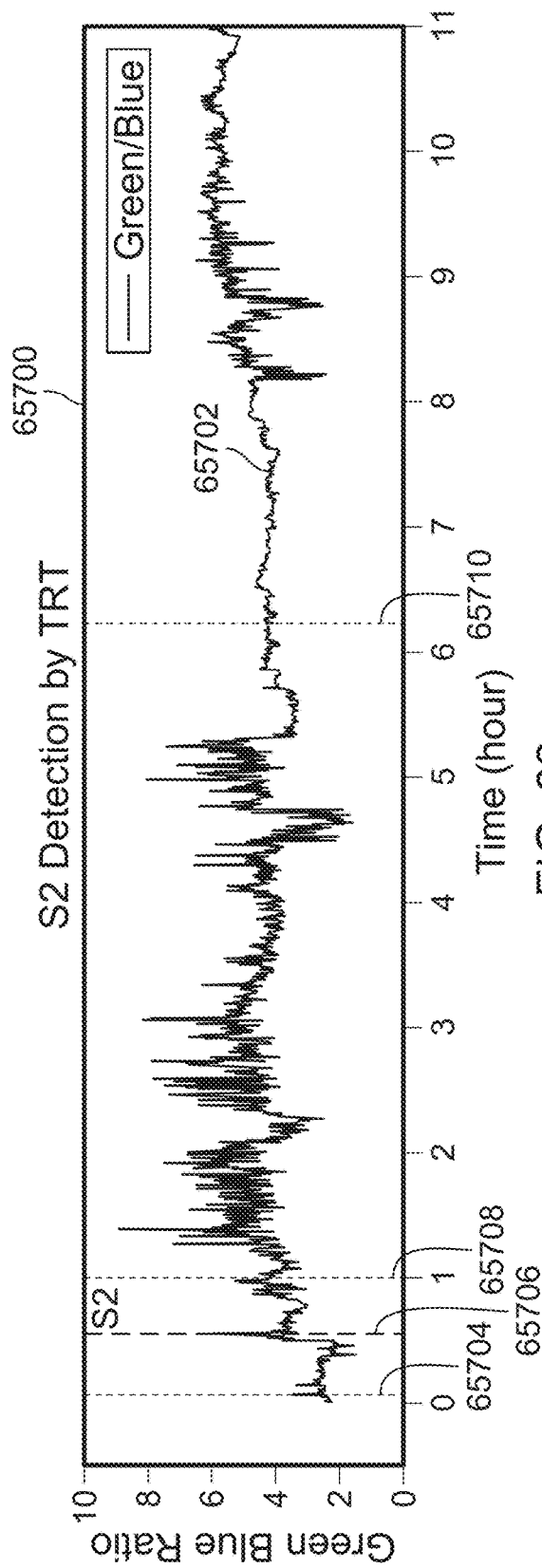
FIG. 62 is a plot illustrating data collected during an example operation of an ingestible device.

FIG. 62 is a plot illustrating data collected during an example operation of an ingestible device, which may be used when determining a location of an ingestible device as it transits through a gastrointestinal (GI) tract, in accordance with some embodiments of the disclosure.

Although FIG. 62 may be described in connection with the ingestible device for illustrative purposes, this is not intended to be limiting, and plot 65700 and data set 65702 may be typical of data gathered by any device discussed in this application. Plot 65700 depicts the ratios of the measured green reflectance levels to the measured blue reflectance levels over time. For example, the ingestible device may have computed the value for each point in the data set 65702 by transmitting green and blue illumination at a given time (e.g., via a illuminator), measuring the resulting green and blue reflectances (e.g., via a detector), calculating the ratio of the resulting reflectances, and storing the ratio in the data set along with a timestamp indicating the time that the reflectances were gathered.

At 65704, shortly after the ingestible device begins operation, the ingestible device determines that it has reached at least the stomach (e.g., as a result of making a determination similar to the determination discussed in relation to 65506 in process 65500). The ingestible device continues to gather additional measurements of green and blue reflectance levels, and at 65706 the ingestible device determines that a pyloric transition has occurred from the stomach to the duodenum (e.g., as a result of making a determination similar to the determinations discussed in relation to 65616-65624 of process 65600). Notably, the values in data set 65702 around 65706 jump up precipitously, which is indicative of the higher ratios of measured green reflectance levels to measured blue reflectance levels typical of the duodenum.

The remainder of the data set 65702 depicts the ratios of the measured green reflectance levels to the measured blue reflectance levels throughout the remainder of the GI tract. At 65708, the ingestible device has reached the jejunum (e.g., as determined through measurements of muscle contractions, as discussed in relation to FIG. 64), and by 65710, the ingestible device has reached the cecum. It is understood that, in some embodiments, the overall character and appearance of data set 65702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum the ingestible device may measure a relatively stable ratio of the measured green reflectance levels to the measured blue reflectance levels. In some embodiments, the ingestible device may be configured to determine transitions from the small intestine to the cecum based on these differences. For example, the ingestible device may compare recent windows of data to past windows of data, and detect a transition to the cecum in response to determining that the standard deviation of the ratios in the recent window of data is substantially less than the standard deviation of the ratios in the past window of data.

Figure 63:
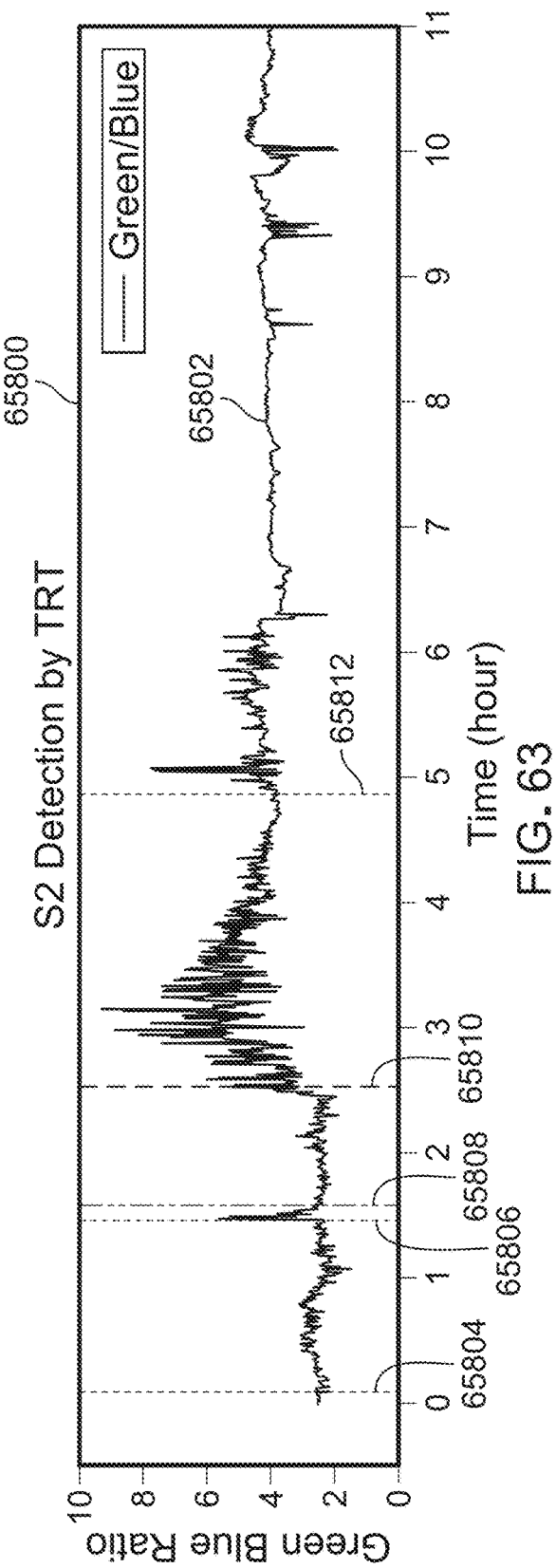
FIG. 63 is another plot illustrating data collected during an example operation of an ingestible device.

FIG. 63 is another plot illustrating data collected during an example operation of an ingestible device, which may be used when determining a location of an ingestible device as it transits through a gastrointestinal (GI) tract, in accordance with some embodiments of the disclosure. Similar to FIG. 62, FIG. 63 may be described in connection with the ingestible device for illustrative purposes. However, this is not intended to be limiting, and plot 65800 and data set 65802 may be typical of data gathered by any device discussed in this application.

At 65804, shortly after the ingestible device begins operation, the ingestible device determines that it has reached at least the stomach (e.g., as a result of making a determination similar to the determination discussed in relation to 65506 in process 65500). The ingestible device continues to gather additional measurements of green and blue reflectance levels (e.g., via a sensing sub-unit), and at 65806 the ingestible device determines that a pyloric transition has occurred from the stomach to the duodenum (e.g., as a result of making a determination similar to the determinations discussed in relation to 65616-65624 of process 65600). Notably, the values in data set 65802 around 65806 jump up precipitously, which is indicative of the higher ratios of measured green reflectance levels to measured blue reflectance levels typical of the duodenum, before falling shortly thereafter. As a result of the reduced values in data set 65802, the ingestible device determines that a reverse pyloric transition has occurred from the duodenum back to the stomach at 65808 (e.g., as a result of making a determination similar to the determinations discussed in relation to 65610-65612 of process 65600). At 65810, as a result of the values in data set 65802 increasing again, the ingestible device determines that another pyloric transition has occurred from the stomach to the duodenum, and shortly thereafter the ingestible device proceeds onwards to the jejunum, ileum, and cecum.

The remainder of the data set 65802 depicts the ratios of the measured green reflectance levels to the measured blue reflectance levels throughout the remainder of the GI tract. Notably, at 65812, ingestible device reaches the transition point between the ileum and the cecum. As discussed above in relation to FIG. 62, the transition to the cecum is marked by a reduced standard deviation in the ratios of measured green reflectances and measured blue reflectances over time, and the ingestible device may be configured to detect a transition to the cecum based on determining that the standard deviation of a recent set of measurements is substantially smaller than the standard deviation of past measurements taken from the jejunum or ileum.

Figure 64:
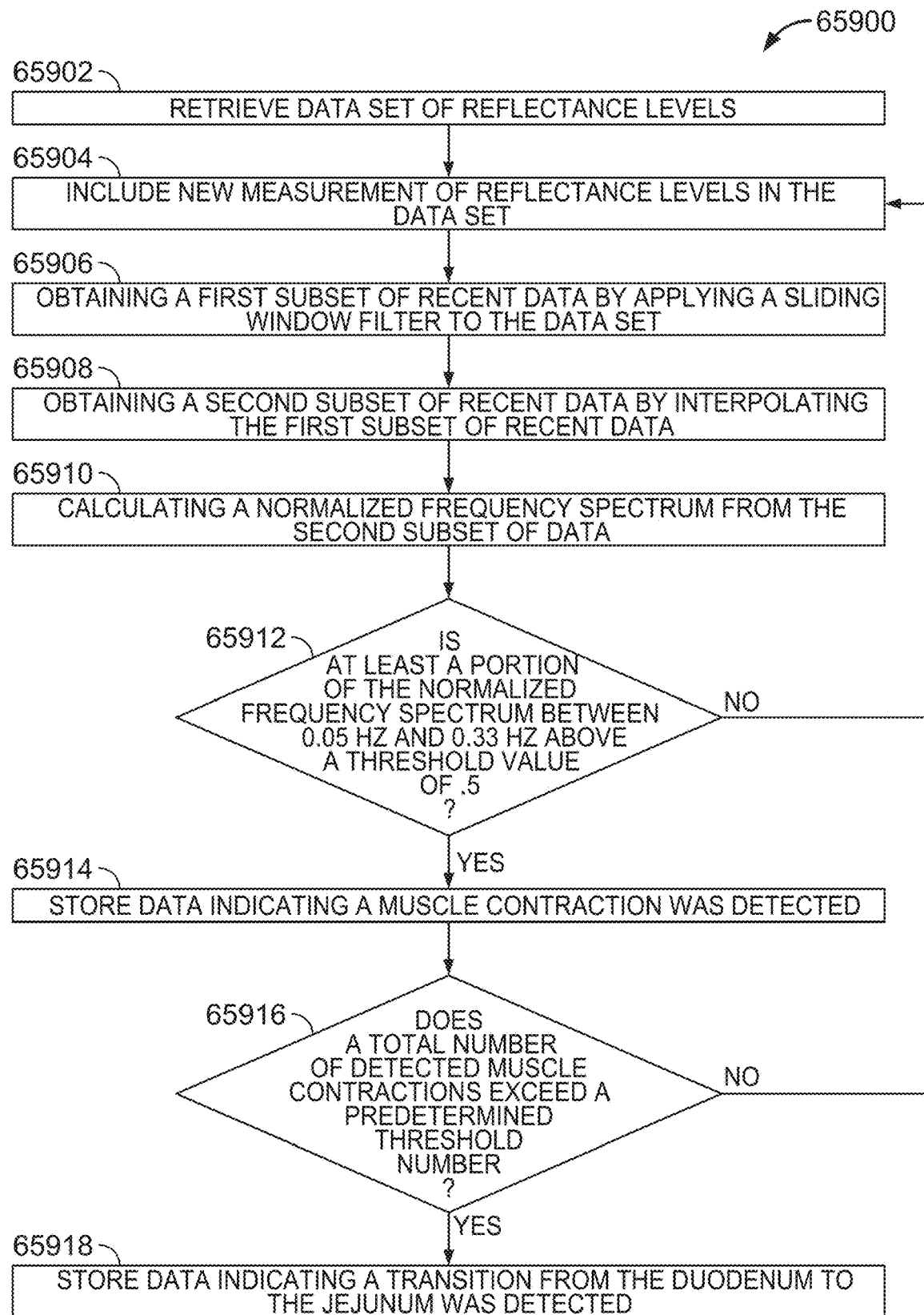
FIG. 64 is a flowchart of illustrative steps for detecting a transition from a duodenum to a jejunum.

FIG. 64 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 64 may be described in connection with the ingestible device for illustrative purposes, this is not intended to be limiting, and either portions or the entirety of process 65900 described in FIG. 64 may be applied to any device discussed in this application, and any of these ingestible devices may be used to perform one or more parts of the process described in FIG. 64. Furthermore, the features of FIG. 64 may be combined with any other systems, methods or processes described in this application. For example, portions of the process described by the process in FIG. 64 may be integrated into the localization process 65500 (e.g., as part of 65520-65524). In some embodiments, the ingestible device may perform process 65900 while in the duodenum, or in response to detecting entry to the duodenum. In other embodiments, the ingestible device may perform process 65900 while in the stomach, or in response to detecting entry into the GI tract. It is also understood that process 65900 may be performed in parallel with any other process described in this disclosure (e.g., process 65600), which may enable the ingestible device to detect entry into various portions of the GI tract, without necessarily detecting entry into a preceding portion of the GI tract.

For illustrative purposes, FIG. 64 may be discussed in terms of the ingestible device generating and making determinations based on a single set of reflectance levels generated at a single wavelength by a single sensing sub-unit (e.g., sensing sub-unit 65126). However, it is understood that the ingestible device may generate multiple wavelengths of illumination from multiple different sensing sub-units positioned around the circumference of ingestible device (e.g., multiple sensing sub-units positioned at different locations behind window 65114 of the ingestible device, and each of the resulting reflectances may be stored as a separate data set. Moreover, each of these sets of reflectance levels may be used to detect muscle contractions by running multiple versions of process 65900, each one of which processes data for a different set of reflectances corresponding to data sets obtained from measurements of different wavelengths or measurements made by different sensing sub-units.

At 65902, the ingestible device retrieves a set of reflectance levels. For example, the ingestible device may retrieve a data set of previously recorded reflectance levels from memory (e.g., from memory circuitry of a PCB). Each of the reflectance levels may correspond to reflectances previously detected by the ingestible device (e.g., via a detector) from illumination generated by the ingestible device (e.g., via an illuminator), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by the ingestible device at periodic intervals.

At 65904, the ingestible device includes new measurements of reflectance levels in the data set. For example, the ingestible device may be configured to detect a new reflectance (e.g., transmit illumination and detect the resulting reflectance using a sensing sub-unit) at regular intervals, or with sufficient speed as to detect peristaltic waves. For example, the ingestible device may be configured to generate illumination and measure the resulting reflectance once every three seconds (i.e., potentially minimum rate to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time the ingestible device makes a new reflectance level measurement at 65904, the new data is included to the data set (e.g., a data set stored within memory circuitry of a PCB).

At 65906, the ingestible device obtains a first subset of recent data by applying a sliding window filter to the data set. For example, the ingestible device may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.05 Hz to 0.33 Hz for healthy human subjects). In some embodiments, the ingestible device may also clean the data, for example, by removing outliers from the first subset of data obtained through the use of the sliding window filter.

At 65908, the ingestible device obtains a second subset of recent data by interpolating the first subset of recent data. For example, the ingestible device may interpolate the first subset of data in order to generate a second subset of data with a sufficient number of data points (e.g., data points spaced every 0.5 seconds or greater). In some embodiments, this may enable the ingestible device to also replace any outlier data points that may have been removed as part of applying the window filter at 65906.

At 65910, the ingestible device calculates a normalized frequency spectrum from the second subset of data. For example, the ingestible device may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and the ingestible device may be configured to have pre-stored values of a normalized discreet Fourier transform (DFT) matrix, or the rows of the DFT matrix corresponding to the 0.05 Hz to 0.33 Hz frequency components of interest, within memory (e.g., memory circuitry of a PCB). In this case, the ingestible device may use matrix multiplication between the DFT matrix and the data set to generate an appropriate frequency spectrum. An example data set and corresponding frequency spectrum that may be obtained by the ingestible device is discussed in greater detail in relation to FIG. 65.

At 65912, the ingestible device determines whether at least a portion of the normalized frequency spectrum is between 00.05 Hz to 0.33 Hz above a threshold value of 0.5 Hz. Peristaltic waves in a healthy human subject occur at a rate between 0.05 Hz to 0.33 Hz, and an ingestible device experiencing peristaltic waves (e.g., an ingestible device detecting contractions in the walls of the jejunum) may detect sinusoidal variations in the amplitude of detected reflectances levels that follow a similar 0.05 Hz to 0.33 Hz frequency. If the ingestible device determines that a portion of the normalized frequency spectrum between 0.05 Hz to 0.33 Hz is above a threshold value of 0.5 Hz, this measurement may be consistent with peristaltic waves in a healthy human subject, and process 65900 proceeds to 65914 where the ingestible device stores data indicating a muscle contraction was detected. Alternatively, if the ingestible device determines that no portion of the normalized frequency spectrum between 0.05 Hz to 0.33 Hz above a threshold value of 0.5, process 65900 proceeds directly to 65904 to make new measurements and to continue to monitor for new muscle contractions. It is understood that a threshold value other than 0.5 may be used, and that the exact threshold may depend on the sampling frequency and type of frequency spectrum used by the ingestible device.

At 65914, the ingestible device stores data indicating a muscle contraction was detected. For example, the ingestible device may store data in memory (e.g., memory circuitry of a PCB) indicating that a muscle contraction was detected, and indicating the time that the muscle contraction was detected. In some embodiments, the ingestible device may also monitor the total number of muscle contractions detected, or the number of muscle contractions detected in a given time frame. In some embodiments, detecting a particular number of muscle contractions may be consistent with the ingestible device being within the jejunum) of a healthy human subject. After detecting a muscle contraction, process 65900 proceeds to 65916.

At 65916, the ingestible device determines whether a total number of muscle contractions exceeds a predetermined threshold number. For example, the ingestible device may retrieve the total number of muscle contractions detected from memory (e.g., from memory circuitry of a PCB), and compare the total number to a threshold value. In some embodiments, the threshold value may be one, or any number larger than one. The larger the threshold value, the more muscle contractions need to be detected before the ingestible device stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 65900 proceeds to 65918 to store data indicating detection of a transition from the duodenum to the jejunum. Alternatively, if the total number of contractions does not exceed a predetermined threshold number, process 65900 proceeds to 65904 to include new measurements of reflectance levels in the data set. An example plot of the muscle contractions detected over time is discussed in greater detail in relation to FIG. 66.

At 65918, the ingestible device stores data indicating detection of a transition from the duodenum to the jejunum. For example, the ingestible device may store data in memory (e.g., from memory circuitry of a PCB) indicating that the jejunum has been reached. In some embodiments, if the ingestible device is configured to perform all or part of process 65900 while in the stomach, the ingestible device may store data at 65918 indicating detection of a transition from the stomach directly to the jejunum (e.g., as a result of transitioning too quickly through the duodenum for the pyloric transition to be detected using process 65600).

In some embodiments, the ingestible device may be configured to obtain a fluid sample from the environment external to a housing of the ingestible device in response to identifying a change in the location of the ingestible device. For example, the ingestible device may be configured to obtain a fluid sample from the environment external to the housing of the ingestible device (e.g., through the use of optional opening 65116 and optional rotating assembly 65118) in response to determining that the ingestible device is located within the jejunum. In some embodiments, the ingestible device may also be equipped with appropriate diagnostics to detect certain medical conditions based on the retrieved fluid sample, such as small intestinal bacterial overgrowth (SIBO).

In some embodiments, the ingestible device may be configured to deliver a dispensable substance that is pre-stored within the ingestible device from the ingestible device into the GI tract in response to identifying the change in the location of the ingestible device. For example, the ingestible device may have a dispensable substance pre-stored within the ingestible device (e.g., within a storage chamber or cavity on an optional storage sub-unit GI and the ingestible device may be configured to dispense the substance into the gastrointestinal tract (e.g., through the use of an optional opening and an optional rotating assembly) when the ingestible device detects that the ingestible device is located within the jejunum. In some embodiments, this may enable the ingestible device to deliver substances (e.g., therapeutics and medicaments) at targeted locations within the GI tract.

In some embodiments, the ingestible device may be configured to perform an action based on the total number of detected muscle contractions. For example, the ingestible device may be configured to retrieve data indicative of the total number of muscle contractions (e.g., from memory circuitry of a PCB), and compare that to an expected number of muscle contractions in a healthy individual. In response, the ingestible device may either dispense a substance into the GI tract (e.g., through the use of an optional opening and an optional rotating assembly), or may obtain a fluid sample from the environment external to the housing of the ingestible device (e.g., through the use of an optional opening and an optional rotating assembly). For instance, the ingestible device may be configured to obtain a sample in response to determining that a number of detected muscle contractions is abnormal, and differs greatly from the expected number. As another example, the ingestible device may be configured to deliver a substance into the GI tract (such as a medicament), in response to determining that the detected muscle contractions are consistent with a functioning GI tract in a healthy individual.

It will be understood that the steps and descriptions of the flowcharts of this disclosure are merely illustrative. Any of the steps and descriptions of the flowcharts may be modified, omitted, rearranged, and/or performed in alternate orders or in parallel, two or more of the steps may be combined, or any additional steps may be added, without departing from the scope of the present disclosure. For example, the ingestible device may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of FIG. 64 may be combined with any other system, device, or method described in this application, and any of the ingestible devices or systems discussed in this application could be used to perform one or more of the steps in FIG. 64.

Figure 65:
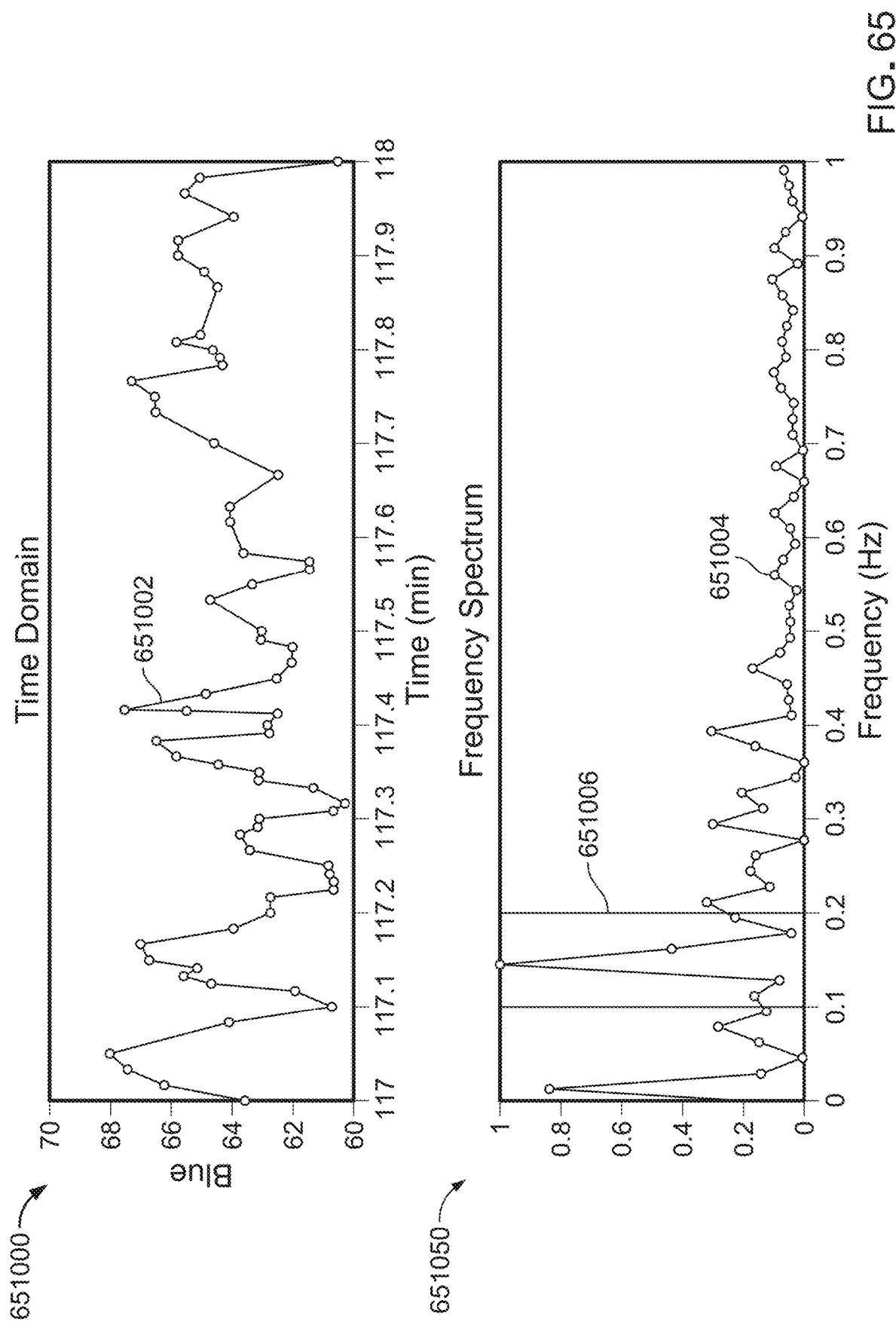
FIG. 65 is a plot illustrating data collected during an example operation of an ingestible device.

FIG. 65 is a plot illustrating data collected during an example operation of an ingestible device, which may be used when detecting a transition from a duodenum to a jejunum, in accordance with some embodiments of the disclosure. Diagram 651000 depicts a time domain plot 651002 of a data set of reflectance levels measured by an ingestible device (e.g., the second subset of data discussed in relation to 65908). In some embodiments, the ingestible device may be configured to gather data points at semi-regular intervals approximately 0.5 seconds apart. By comparison, diagram 651050 depicts a frequency domain plot 651004 of the same data set of reflectance levels measured by an ingestible device (e.g., as a result of the ingestible device calculating a frequency spectrum at 65910). In some embodiments, the ingestible device may be configured to calculate the frequency spectrum through any convenient means.

In diagram 651050, the range of frequencies 651006 between 0.05 Hz to 0.33 Hz may be the range of frequencies that the ingestible device searches in order to detect muscle contractions. As shown in diagram 651050, there is a strong peak in the frequency domain plot 651004 around 0.14 Hz, which is consistent with the frequency of peristaltic motion in a healthy human individual. In this case, the ingestible device analyzing frequency domain plot 651004 may be configured to determine that the data is consistent with a detected muscle contraction (e.g., using a process similar to 65912 of process 65900), and may store data (e.g., in memory circuitry of a PCB) indicating that a muscle contraction has been detected. Because the muscle contraction was detected from the one-minute window of data ending at 118 minutes, the ingestible device may also store data indicating that the muscle contraction was detected at the 118-minute mark (i.e., which may indicate that the ingestible device was turned on and ingested by the subject 118 minutes ago).

Figure 66:
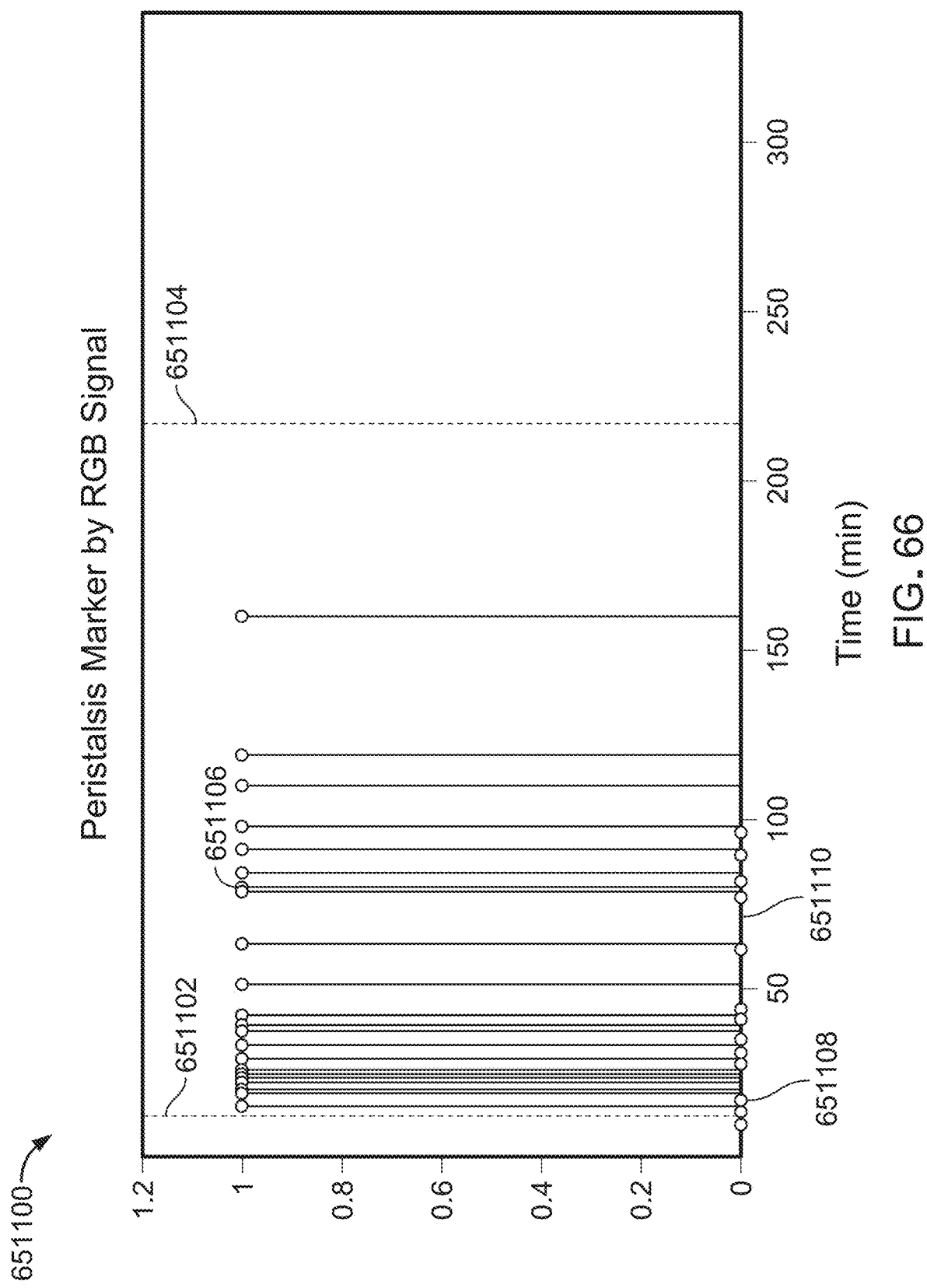
FIG. 66 is a plot illustrating muscle contractions detected by an ingestible device over time.
Figure 67:
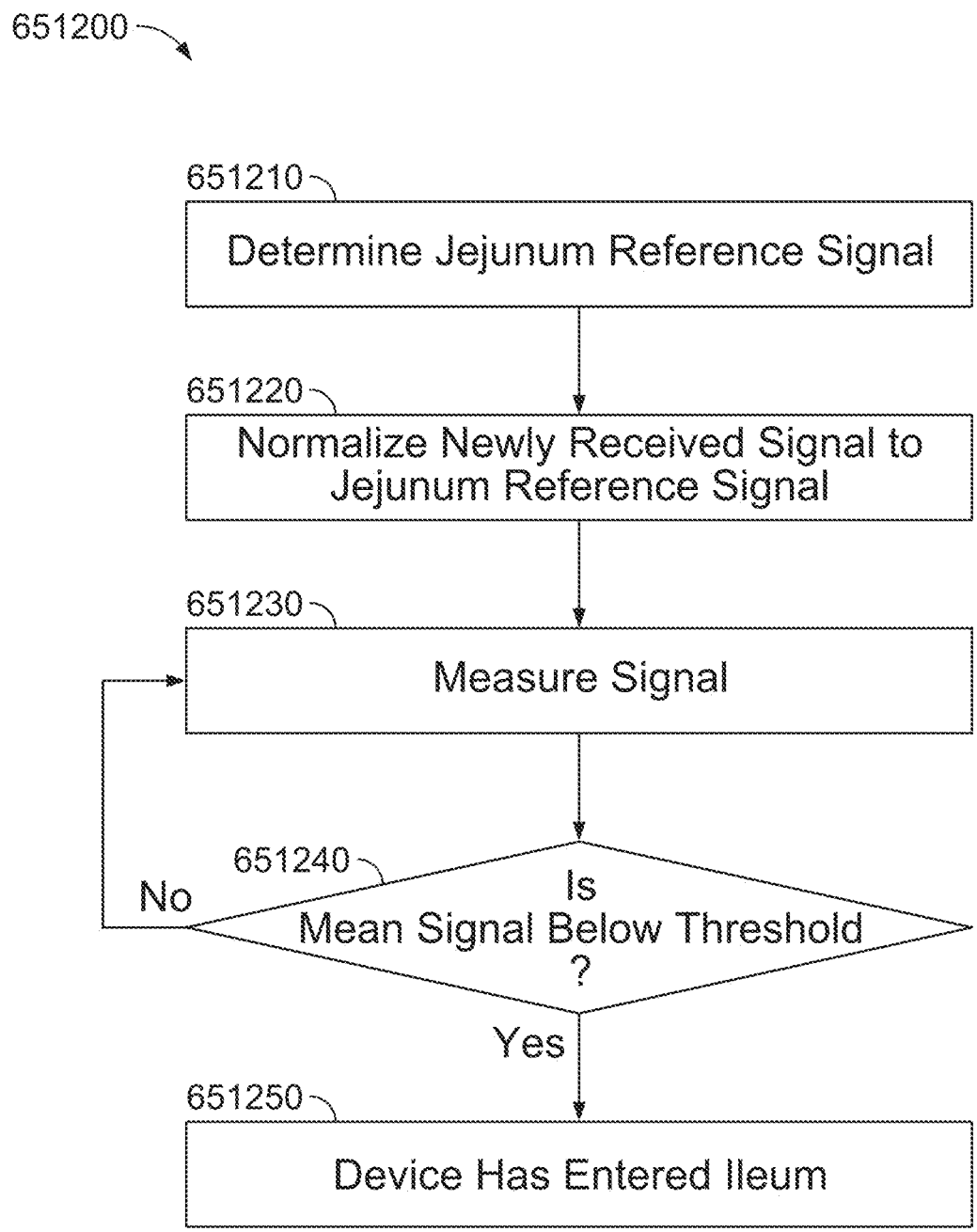
FIG. 67 is a flowchart of illustrative steps for detecting a transition from a jejunum to an ileum.

FIG. 66 is a plot illustrating muscle contractions detected by an ingestible device over time, which may be used when determining a location of an ingestible device as it transits through a gastrointestinal (GI) tract, in accordance with some embodiments of the disclosure. In some embodiments, the ingestible device may be configured to detect muscle contractions, and store data indicative of when each muscle contraction is detected (e.g., as part of 65914 of process 65900). Plot 651100 depicts the detected muscle contractions 651106 over time, with each muscle contraction being represented by a vertical line reaching from "0" to "1" on the y-axis.

At 651102, around the 10-minute mark, the ingestible device first enters the duodenum (e.g., as determined by the ingestible device performing process 65600). Shortly thereafter, at 651108, the ingestible device begins to detect several muscle contractions 651106 in quick succession, which may be indicative of the strong peristaltic waves that form in the jejunum. Later, around 651110, the ingestible device continues to detect intermittent muscle contractions, which may be consistent with the ingestible device within the ileum. Finally, at 651104, the ingestible device transitions out of the small intestine, and into the cecum. Notably, the ingestible device detects more frequent muscle contractions in the jejunum portion of the small intestine as compared to the ileum portion of the small intestine, and the ingestible device does not measure any muscle contractions after having exited the small intestine. In some embodiments, the ingestible device may incorporate this information into a localization process. For example, the ingestible device may be configured to detect a transition from a jejunum to an ileum in response to determining that a frequency of detected muscle contractions (e.g., the number of muscle contractions measured in a given 10-minute window) has fallen below a threshold number. As another example, the ingestible device may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

FIG. 66 is a flowchart 651200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more mesentery fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 651200 represents a single sliding window process. In step 651210, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 651220, the detected signal (e.g., reflected red light) just after the period of time used in step 651210 is normalized to the reference signal determined in step 651210. In step 651230, the signal (e.g., reflected red light) is detected. In step 651240, the mean signal detected based on the single sliding window is compared to a signal threshold. The signal threshold in step 651240 is generally a fraction of the reference signal of the jejunum reference signal determined in step 651210. For example, the signal threshold can be from 60% to 90% (e.g., from 70% to 80%) of the jejunum reference signal. If the mean signal exceeds the signal threshold, then the process determines that the device has entered the ileum at step 651250. If the mean signal does not exceed the signal threshold, then the process returns to step 651230.

Figure 68:
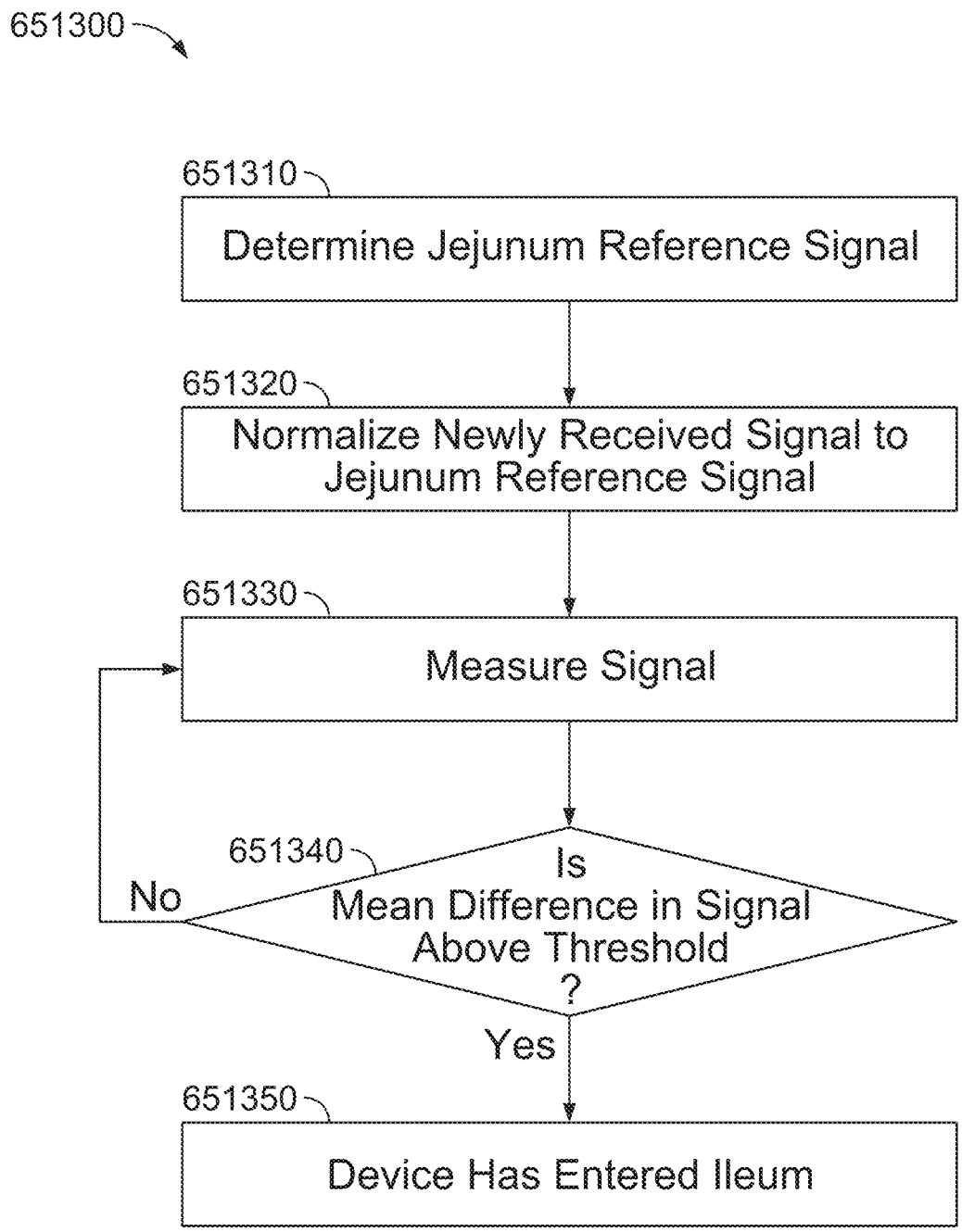
FIG. 68 is a flowchart of illustrative steps for detecting a transition from a jejunum to an ileum.

FIG. 68 is a flowchart 651200 for certain embodiments for determining a transition of the device from the jejunum to the ileum using a two sliding window process. In step 651310, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 651320, the detected signal (e.g., reflected red light) just after the period of time used in step 651310 is normalized to the reference signal determined in step 651310. In step 651330, the signal (e.g., reflected red light) is detected. In step 651340, the mean difference in the signal detected based on the two sliding windows is compared to a signal threshold. The signal threshold in step 651340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 651350. If the signal threshold is not exceeded, then the process returns to step 651330.

Figure 69:
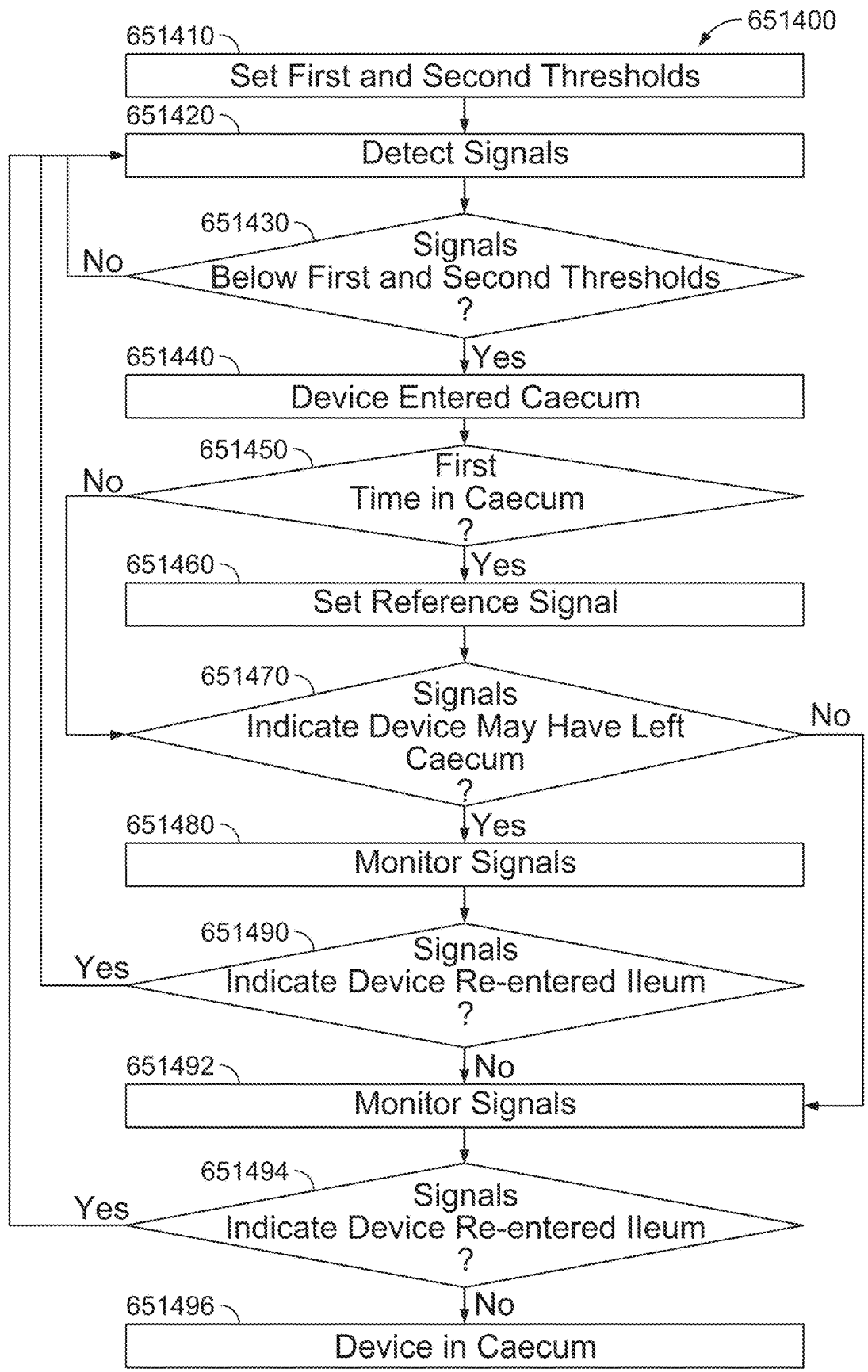
FIG. 69 is a flowchart of illustrative steps for detecting a transition from an ileum to a cecum.

FIG. 69 is a flowchart 651400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 651400, the sliding window analysis (first and second windows) discussed with respect to process 65600 is continued.

Step 651410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 651420 includes detecting the signals in the first and second windows that are to be used for comparing to the first and second thresholds.

Step 651430 includes comparing the detected signals to the first and second thresholds. If the corresponding value is not below the first threshold or the corresponding value is not below the second threshold, then it is determined that the device has not left the ileum and entered the cecum, and the process returns to step 651420. If the corresponding value is below the first threshold and the corresponding value is below the second threshold, then it is determined that the device has left the ileum and entered the cecum, and the proceeds to step 651440.

Step 651450 includes determining whether it is the first time that that the device was determined to leave the ileum and enter the cecum. If it is the first time that the device was determined to leave the ileum and enter the cecum, then the process proceeds to step 651460. If it is not the first time that the device has left the ileum and entered the cecum, then the process proceeds to step 651470.

Step 651460 includes setting a reference signal. In this step the optical signal (e.g., ratio of detected red light to detected green light) as a reference signal.

Step 651470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 651460) and the coefficient of variation for the corresponding detected signal (e.g., ratio of detected green light to detected blue light) exceeds the second threshold. If it is determined that the device may have left the cecum and returned to the ileum, the process proceeds to step 651480.

Step 651480 includes continuing to detect the relevant optical signals for a period of time (e.g., at least one minute, from five minutes to 15 minutes).

Step 651490 includes determining whether the signals determined in step 651480 indicate (using the methodology discussed in step 651470) that the device re-entered the ileum. If the signals indicate that the device re-entered the ileum, the process proceeds to step 651420. If the signals indicate that the device is in the cecum, the process proceeds to step 651492.

Step 651492 includes continuing to monitor the relevant optical signals for a period of time (e.g., at least 30 minutes, at least one hour, at least two hours).

Step 651494 includes determining whether the signals determined in step 651492 indicate (using the methodology discussed in step 651470) that the device re-entered the ileum. If the signals indicate that the device re-entered the ileum, the process proceeds to step 651420. If the signals indicate that the device is in the cecum, the process proceeds to step 651496.

At step 651496, the process determines that the device is in the cecum.

Figure 70:
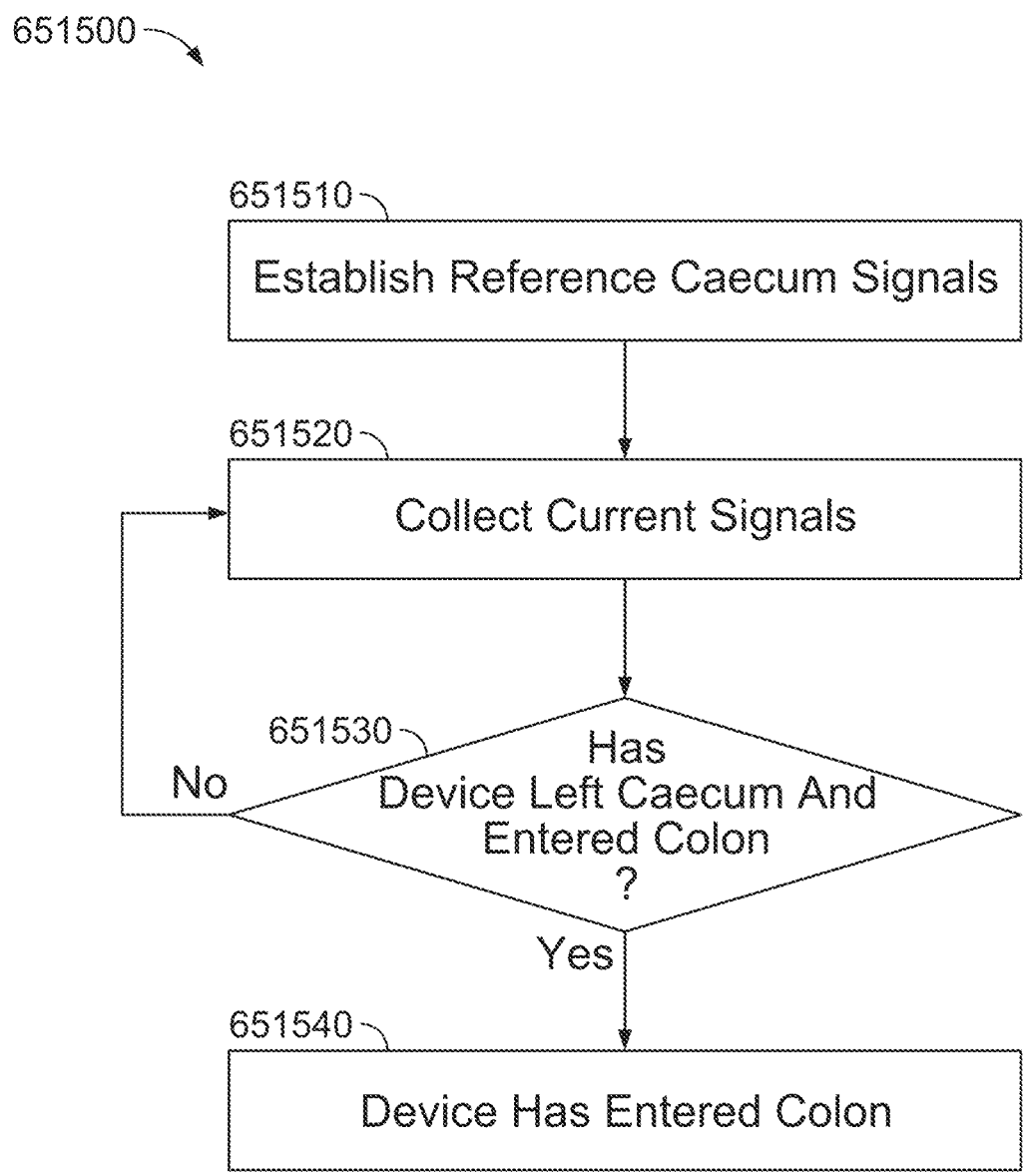
FIG. 70 is a flowchart of illustrative steps for detecting a transition from a cecum to a colon.

FIG. 70 is a flowchart 651500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 651500, the sliding window analysis (first and second windows) discussed with respect to process 651400 is continued.

In step 651510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 651480). The average values for the recorded optical signals (e.g., the ratio of reflected red signal to reflected green signal, and reflected blue signal) establish the cecum reference signals.

In step 651520, the optical signals are detected after it has been determined that the device entered the cecum (e.g., at step 651440). The optical signals are normalized to the cecum reference signals.

Step 651530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 651540. Otherwise, none of the three criteria are satisfied, the process returns to step 651520.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 65500, process 65600, process 65900, process 651200, process 651300, process 651400 and process 651500). Also, the applications of the ingestible devices described herein are not limited merely to gathering data, sampling and testing portions of the GI tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the GI tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within a PCB 65120) may be written in a high-level procedural language such as object oriented programming, a scripting language or both. Accordingly, the program code may be written in C, $C^{++}$ or any other suitable programming language and may include modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product including a computer readable medium that bears computer usable instructions for one or more processors. The medium may be provided in various forms, including non-transitory forms such as, but not limited to, one or more discettes, compact discs, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

For illustrative purposes the examples given herein focus primarily on a number of different example embodiments of an ingestible device. However, the possible ingestible devices that may be constructed are not limited to these embodiments, and variations in the general shape and design may be made without significantly changing the functions and operations of the device. For example, some embodiments of the ingestible device may feature a sampling chamber substantially towards the middle of the device, along with two sets of axial sensing sub-units, each located on substantially opposite ends of the device. In addition, the applications of the ingestible device are not limited merely to gathering data, sampling and testing portions of the GI tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain analytes, chemical compounds or impurities in the GI tract, or the combination of localization, sampling, and appropriate diagnostic and assay techniques incorporated into a sampling chamber may be particularly well suited to determine the presence of small intestinal bacterial overgrowth (SIBO). It is also noted that although embodiments described herein focus on an ingestible device in the GI tract, such ingestible device described in FIGS. 1-34 may be used for delivering substances including medicaments and therapeutics in other parts of the body, such as but not limited to the female reproductive tract, and/or the like.

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, which is limited only by the appended embodiments. The appended embodiments should be given the broadest interpretation consistent with the description as a whole.

Implementations of the subject matter and the operations described in this specification can be implemented by digital electronic circuitry, or via computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, discs, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical discs, or optical discs. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic discs, e.g., internal hard discs or removable discs; magneto optical discs; and CD ROM and DVD-ROM discs. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Implementations of the subject matter described in this specification can be implemented in a computing system that includes a back end component, e.g., as a data server, or that includes a middleware component, e.g., an application server, or that includes a front end component, e.g., a user computer having a graphical display or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some implementations, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

Figure 71:
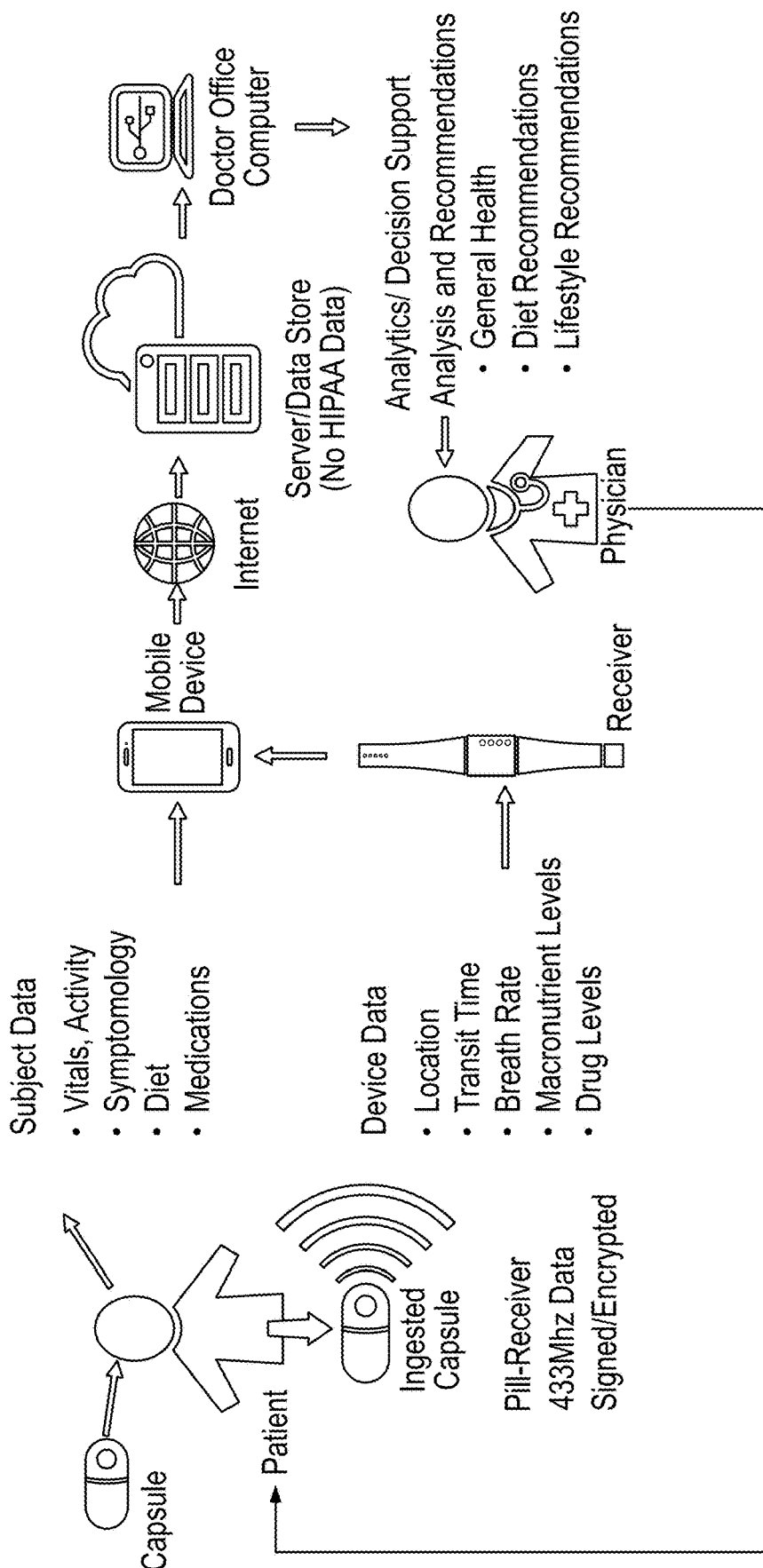
FIG. 71 illustrates an exemplary system for collecting, communicating and/or analyzing data about a subject

FIG. 71 illustrates a nonlimiting example of a system for collecting, communicating and/or analyzing data about a subject, using an ingestible device as disclosed herein. For example, an ingestible device may be configured to communicate with an external base station. As an example, an ingestible device can have a communications unit that communicates with an external base station which itself has a communications unit. FIG. 71 illustrates exemplary implementation of such an ingestible device. As shown in FIG. 71, a subject ingests an ingestible device as disclosed herein. Certain data about the subject (e.g., based on a collected sample) and/or the location of the ingestible device in the GI tract of the subject is collected or otherwise available and provided to a mobile device, which then forwards the data via the internet and a server/data store to a physician's office computer. The information collected by the ingestible device is communicated to a receiver, such as, for example, a watch or other object worn by the subject. The information is then communicated from the receiver to the mobile device which then forwards the data via the internet and a server/data store to a physician's office computer. The physician is then able to analyze some or all of the data about the subject to provide recommendations, such as, for example, general health recommendations, dietary health recommendations and/or lifestyle recommendations. While FIG. 71 shows a particular approach to collecting and transferring data about a subject, the disclosure is not limited. As an example, one or more of the receiver, mobile device, internet, and/or server/data store can be excluded from the data communication channel. For example, a mobile device can be used as the receiver of the device data, e.g., by using a dongle. In such embodiments, the item worn by the subject need not be part of the communication chain. As another example, one or more of the items in the data communication channel can be replaced with an alternative item. For example, rather than be provided to a physician's office computer, data may be provided to a service provider network, such as a hospital network, an HMO network, or the like. In some embodiments, subject data may be collected and/or stored in one location (e.g., a server/data store) while device data may be collected and/or stored in a different location (e.g., a different server/data store).

An ingestible device may include one or more environmental sensors. Environmental sensor may be used to generate environmental data for the environment external to device in the GI tract of the subject. Environmental data may be used to further characterize the GI tract of the subject either alone or in combination with the spectral data. In some embodiments, environmental data is generated at the same location within the GI tract of the subject where a sample is procured. Examples of environmental sensor include, but are not limited to a capacitance sensor, a temperature sensor, an impedance sensor, a pH level sensor, a heart rate sensor, acoustic sensor, image sensor, and/or a movement sensor. In some embodiments, the ingestible device includes a plurality of different environmental sensors for generating different kinds of environmental data. In some embodiments, the image sensor is a video camera suitable for obtaining images in vivo of the tissues forming the GI tract of the subject. In some embodiments, the environmental data is used to help determine one or more characteristics of the GI tract the subject such as for the diagnosis of a medical condition. In some embodiments, the ingestible device may include a camera for generating video imaging data of the GI tract which can be used to determine, among other things, the location of the device. Examples of video imaging capsules include Medtronic's PillCam™, Olympus' Endocapsule®, and IntroMedic's MicroCam™ (see Basar et al. "Ingestible Wireless Capsule Technology: A Review of Development and Future Indication" *International Journal of Antennas and Propagation* (2012); 1-14). Other imaging technologies include thermal imaging cameras, and those that employ ultrasound or Doppler principles to generate different images (see Chinese patent disclosure CN104473611: "Capsule endoscope system having ultrasonic positioning function"). In another embodiment, the ingestible device described herein may be localized using a gamma scintigraphy technique or other radio-tracker technology as employed by Phaeton Research's Enterion™ capsule (See Teng, Renli, and Juan Maya. "Absolute bioavailability and regional absorption of ticagrelor in healthy volunteers." *Journal of Drug Assessment* 3.1 (2014): 43-50), or monitoring the magnetic field strength of permanent magnet in the ingestible device (see T. D. Than, et al., "A review of localization systems for robotic endoscopic capsules," *IEEE Trans. Biomed. Eng.*, vol. 59, no. 9, pp. 2387-2399, September 2012). In some embodiments, the one or more environmental sensors measure pH, temperature, transit times, or combinations thereof. Examples of devices useful to detect pH changes include Medimetrics' IntelliCap® technology (see Becker, Dieter, et al. "Novel orally swallowable IntelliCap® device to quantify regional drug absorption in human GI tract using diltiazem as model drug." *AAPS PharmSciTech* 15.6 (2014): 1490-1497) and Rani Therapeutics' Auto-Pill™ technology (see U.S. Pat. No. 9,149,617), hereby incorporated by reference in its entirety.

Detection Methods and Systems

Live Cell Dye

Certain systems described herein employ methods, compositions and detection systems found to accurately and reliably correlate fluorescence to total bacteria count (TBC) in an autonomous, ingestible device, or other similarly-sized device. In some embodiments, the methods and devices described herein can be used for the detection of TBC in a sample from the gastrointestinal tract of the subject to determine whether the subject has or is at risk of developing a GI disorder (e.g., SIBO). The compositions include novel combinations of dyes, buffers and detergents that allow for the selective staining of viable bacterial cells in samples that include non-bacterial cells and other components that otherwise make detecting or quantifying live bacterial cells challenging. In some embodiments, the systems allow for bacteria to be quantified in near real-time and the results to be shared telemetrically outside of the device. Above, various types of cells (e.g., bacterial cells) are disclosed which can be detected using the methods described in this section.

In some embodiments, the disclosure provides a composition including a dye and optionally a reagent for selective lysis of eukaryotic cells. In some embodiments, the composition includes both a dye and a reagent for selective lysis of eukaryotic cells. In some embodiments, the composition further comprises one or more reagents independently selected from the group consisting of: a second reagent for selective lysis of eukaryotic cells, an electrolyte (e.g., $MgCl_2$), an anti-fungal reagent (e.g., amphotericin-B), and an antibiotic. In some embodiments, the composition comprises water and is in the form of an aqueous solution. In some embodiments, the composition is a solid or semi-solid. In some embodiments, the compositions described here are suitable for use in a kit or device for detecting or quantifying viable bacterial cells in a sample. In some embodiments, such a device is an ingestible device for detecting or quantifying viable bacterial cells in vivo (e.g., in the GI tract). In some embodiments, viable bacterial cells in a sample are detected or quantified in the presence of one or more antibiotics to determine antibiotic resistance of the bacteria in the sample. In some embodiments, anomalous bacterial populations in a sample may be detected or quantified, for example through the use of a composition comprising a dye as disclosed herein, to determine whether a subject has an infection, such as Small Intestinal Bacterial Overgrowth (SIBO), or to characterize bacterial populations within the GI tract for diagnostic or other purposes.

In some embodiments, the dye suitable for use in the composition of the present disclosure is a dye that is capable of being internalized by a viable cell, binding to or reacting with a target component of the viable cell, and having fluorescence properties that are measurably altered when the dye is bound to or reacted with the target component of the viable cell. In some embodiments, the dye of the present disclosure is actively internalized by penetrating viable cells through a process other than passible diffusion across cell membranes. Such internalization includes, but is not limited to, internalization through cell receptors on cell surfaces or through channels in cell membranes. In some embodiments, the target component of a viable cell to which the dye is bound to or reacted with is selected from the group consisting of: nucleic acids, actin, tubulin, enzymes, nucleotide-binding proteins, ion-transport proteins, mitochondria, cytoplasmic components, and membrane components. In some embodiments, the dye suitable for use herein is a fluorogenic dye that is capable of being internalized and metabolized by a viable cell, and wherein the dye fluoresces when metabolized by the viable cell. In some embodiments, the dye is a chemiluminescent dye that is capable of being internalized and metabolized by a viable cell, and wherein the dye becomes chemiluminescent when metabolized by the viable cell.

In some embodiments, the composition includes a dye that fluoresces when bound to nucleic acids. Examples of such dyes include, but are not limited to, acridine orange (U.S. Pat. No. 4,190,328); calcein-AM (U.S. Pat. No. 5,314,805); DAPI; Hoechst 33342; Hoechst 33258; PicoGreen™; SYTO® 16; SYBR® Green I; Texas Red®; Redmond Red™; Bodipy® Dyes; Oregon Green™; ethidium bromide; and propidium iodide.

In some embodiments, the composition includes a lipophilic dye that fluoresces when metabolized by a cell. In some embodiments, the dye fluoresces when reduced by a cell or a cell component. Examples of dyes that fluoresce when reduced include, but are not limited to, resazurin; $C^{12}$-resazurin; 7-hydroxy-9H-(1,3 dichloro-9,9-dimethyl-acridin-2-ol) N-oxide; 6-chloro-9-nitro-5-oxo-5H-benzo[a]phenoxazine; and tetrazolium salts. In some embodiment, the dye fluoresces when oxidized by a cell or a cell component. Examples of such dyes include, but are not limited to, dihydrocalcein AM; dihydrorhodamine 123; dihydroethidium; 2,3,4,5,6-pentafluorotetramethyldihydrorosamine; and 3'-(p-aminophenyl) fluorescein.

In some embodiments, the composition includes a dye that becomes chemiluminescent when oxidized by a cell or a cell component, such as luminol.

In some embodiments, the composition includes a dye that fluoresces when de-acetylated and/or oxidized by a cell or a cell component. Examples of such dyes include, but are not limited to, dihydrorhodamines; dihydrofluoresceins; 2', 7'-dichlorodihydrofluorescein diacetate; 5-(and 6-)carboxy-2', 7'-dichlorodihydrofluorescein diacetate; and chloromethyl-2', 7'-dichlorodihydrofluorescein diacetate acetyl ester.

In some embodiments, the composition includes a dye that fluoresces when reacted with a peptidase. Examples of such dyes include, but are not limited to, (CBZ-Ala-Ala-Ala-Ala)2-R110 elastase 2; (CBZ-Ala-Ala-Asp)2-R110 granzyme B; and 7-amino-4-methylcoumarin, N-CBZ-L-aspartyl-L-glutamyl-L-valyl-L-aspartic acid amide.

In some embodiments, the composition of this disclosure includes a dye selected from the group consisting of resazurin, fluorescein diacetate fluorescein diacetate (FDA), Calcein AM, and SYTO® 9. In some embodiments, the dye is FDA or SYTO® 9. In some embodiments, the methods described herein may make use of more than one dye (e.g., two, three, four, five, six, seven, eight, nine, ten, or more dyes). The use of multiple dyes allows for the detection of multiple analytes (e.g., multiplexing), for example, when each dye is detectable at a different wavelength. More generally, multiple dyes operating with different fluorescent wavelengths can be used as appropriate.

SYTO® 9, when used alone, labels nucleic acids of bacteria cells. The excitation/emission wavelengths for SYTO® 9 is 480/500 nm, with the background remaining non-fluorescent. See, e.g., J. Appl. Bacteriol. 72, 410 (1992); Lett. Appl. Microbiol. β, 58 (1991); Curr. Microbiol. 4, 321 (1980); J. Microbiol. Methods β, 87 (1991); and Microbiol. Rev. 51, 365 (1987); and J. Med. Microbiol. 39, 147 (1993).

FDA is a non-polar, non-fluorescent compound that can cross the membranes of mammalian and bacterial cells. The acetyl esterases (present only within viable cells) hydrolyze the FDA into the fluorescent compound fluorescein. Fluorescein is a fluorescent polar compound that is retained within these cells. Living cells can be visualized in a photospectrometer when assayed with an excitation wavelength of 494 nm and an emission wavelength of 518 nm. See, e.g., Brunius, G. (1980). *Technical aspects of the use of 3', 6'-Diacetyl fluorescein for vital fluorescent staining of bacteria*. Current Microbiol. 4: 321-323; Jones, K. H. and Senft, J. A. (1985). *An improved method to determine cellviability by simultaneous staining with fluorescein diacetate—propidium iodide*. J. Histochem. Cytochem. 33: 77-79; Ross, R. D., Joneckis, C. C., Ordonez, J. V., Sisk, A. M., Wu, R. K., Hamburger, A. W., and Nora, R. E. (1989). *Estimation of cell survival by flow cytometric quantification of fluorescein diacetate/propidium iodide viable cell number*. Cancer Research. 49: 3776-3782.

Calcein-AM, which is an acetoxylmethyl ester of calcein, is highly lipophilic and cell permeable. Calcein-AM in itself is not fluorescent, but the calcein generated by esterase in a viable cell emits a green fluorescence with an excitation wavelength of 490 nm and an emission of 515 nm. Therefore, Calcein-AM can only stain viable cells. See, e.g., Kimura, K., et al., *Neurosci. Lett.*, 208, 53 (1998); Shimokawa, I., et al., *J. Geronto.*, 51a, b49 (1998); Yoshida, S., et al., *Clin. Nephrol.*, 49, 273 (1998); and Tominaga, H., et al., *Anal. Commun.*, 36, 47 (1999).

Resazurin (also known as Alamar Blue) is a blue compound that can be reduced to pink resorufin which is fluorescent. This dye is mainly used in viability assays for mammalian cells. $C^{12}$-resazurin has better cell permeability than resazurin. When lipohilic $C^{12}$-resazurin crosses the cell membranes, it is subsequently reduced by living cells to make a red fluorescent resorufin. The adsorption/emission of $C^{12}$-resazurin is 563/587 nm. See, e.g., Appl Environ Microbiol 56, 3785 (1990); J Dairy Res 57, 239 (1990); J Neurosci Methods 70, 195 (1996); J Immunol Methods 210, 25 (1997); J Immunol Methods 213, 157 (1998); Antimicrob Agents Chemother 41, 1004 (1997).

In some embodiments, the composition of this disclosure optionally further includes a reagent for selective lysis of eukaryotic cells. In some embodiments, the composition includes a dye as described herein and a reagent for selective lysis of eukaryotic cells. In some embodiments, the reagent for selective lysis of eukaryotic cells is a detergent, such as a non-ionic or an ionic detergent. Examples of the reagent for selective lysis of eukaryotic cells include, but are not limited to, alkylglycosides, Brij 35 (C12E23 Polyoxyethyleneglycol dodecyl ether), Brij 58 (C16E20 Polyoxyethyleneglycol dodecyl ether), Genapol, glucanids such as MEGA-8, -9, -10, octylglucoside, Pluronic F127, Triton X-100™ ($C_{14}H_{22}O(C_2H_4O)_n$), Triton X-114 ($C_{24}H_{42}O_6$), Tween 20 (Polysorbate 20) and Tween 80 (Polysorbate 80), Nonidet P40, deoxycholate, reduced Triton X-100™ and/or Igepal Calif. 630. In some embodiments, the composition of this disclosure includes a dye as described herein and deoxycholate (e.g., sodium deoxycholate) as a reagent for selective lysis of eukaryotic cells. In some embodiments, the composition of this disclosure includes deoxycholate at a concentration selected from 0.0001% to 1 wt %. In some embodiments, the composition of this disclosure includes deoxycholate at a concentration of 0.005 wt %. In some embodiments, the composition may include more than one reagent for selective lysis of eukaryotic cells.

In some embodiments, the composition may include two different reagents for selective lysis of eukaryotic cells. In some instances, when more than one selective lysis reagents are used, more effective and/or complete selective lysis of eukaryotic cells in a sample may be achieved. For example, the composition may include deoxycholate (e.g., sodium deoxycholate) and Triton X-100™ as two different reagents for selective lysis of eukaryotic cells. In some embodiments, the composition includes deoxycholate (e.g., sodium deoxycholate) at a concentration selected from 0.0001% to 1 wt % (e.g., 0.005 wt %) and Triton X-100™ at a concentration selected from 0.1 to 0.05 wt %.

In some embodiments, after a sample (e.g., a biological sample) is treated or contacted with a composition including a dye and one or more reagents for selective lysis of eukaryotic cells as described herein, the eukaryotic cells (e.g., animal cells) in the sample are selectively lysed whereby a substantial percentage (e.g., more than 20%, 40%, 60%, 80%, 90% or even more that 95%) of the bacterial cells in the same sample remains intact or alive.

In some embodiments, the composition does not include a reagent for selective lysis of eukaryotic cells, and such a composition is useful for detecting or quantifying viable bacterial cells in a sample (e.g., an environmental sample such as a water sample) that does not contain any eukaryotic cells.

In some embodiments, the composition of this disclosure further includes an electrolyte, such as a divalent electrolyte (e.g., $MgCl_2$). In some embodiments, the composition includes $MgCl_2$ at a concentration selected from 0.1 mM to 100 mM (e.g., a concentration selected from 0.5 mM to 50 mM).

In some embodiments, the composition of this disclosure further includes water and is in a form of an aqueous solution. In some embodiments, the composition has a pH selected from 5-8 (e.g., a pH selected from 6-7.8, such as pH being 6.0). In some embodiments, the composition is a solid or a semi-solid.

In some embodiments, the composition further includes an anti-fungal agent. Suitable anti-fungal agents for use herein include, but are not limited to, fungicidal and fungistatic agents including terbinafine, itraconazole, micronazole nitrate, thiapendazole, tolnaftate, clotrimazole and griseofulvin. In some embodiments, the anti-fungal agent is a polyene anti-fungal agent, such as amphotericin-B, nystatin, and pimaricin.

In some embodiments, the composition does not contain any anti-fungal agent. In some embodiments, the composition contains broad spectrum antibiotics but not any anti-fungal agent. Such compositions that do not contain anti-fungal agents but contain broad spectrum antibiotics may be useful in detecting or quantifying fungi (e.g., yeast) in a sample.

In some embodiments, the composition does not contain any anti-fungal agent or any antibiotics. Such compositions that do not selectively lyse mammalian cells may be useful in detecting or quantifying mammalian cells (e.g., cells from the GI tract) in a sample since many dyes have a higher affinity for mammalian as compared to bacteria or fungi cells. In some embodiments, the composition contains broad spectrum antibiotics and one or more anti-fungal agents. Such compositions that contain anti-fungal agents and broad spectrum antibiotics may be useful in detecting or quantifying mammalian cells (e.g., cells from the GI tract) in a sample. The detection or quantification of mammalian cells may be useful for determining cell turnover in a subject. High cell turnover is sometimes associated with a GI injury (e.g., lesion), the presence of a tumor(s), or radiation-induced colitis or radiation enteropathy.

In some embodiments, the composition further includes an antibiotic agent as described herein. Such a composition may be useful in detecting or quantifying antibiotic-resistant strains of bacteria in a sample.

In some embodiments, the composition of this disclosure includes Triton X-100, deoxycholate, resazurin, and $MgCl_2$. In some embodiments, the composition includes Triton X-100™, deoxycholate, resazurin, amphotericin-B and $MgCl_2$. In some embodiments, the composition includes 0.1 wt % or 0.05 wt % Triton X-100™; 0.005 wt % deoxycholate; 10 mM resazurin; 2.5 mg/L amphotericin-B and 50 mM $MgCl_2$. In some embodiments, the composition has a pH of 6.0.

In some embodiments, the compositions of this disclosure are suitable for use in a kit or device, e.g., for detecting or quantifying viable bacterial cells in a sample. In some embodiments, such a device is an ingestible device for detecting or quantifying viable bacterial cells in vivo (e.g., in the GI tract).

In one aspect, this disclosure provides a method for detecting the presence of viable bacterial cells in a sample, including: (a) contacting the sample with a composition as described herein; and (b) measuring total fluorescence or rate of change of fluorescence as a function of time of the sample, thereby detecting viable bacterial cells in the sample.

In some embodiments, the total fluorescence or the rate of change of fluorescence as a function of time of the sample is measured over multiple time points for an extended period of time in step (b), thereby detecting viable bacterial cells in the sample. For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the method further includes correlating the total fluorescence or the rate of change of fluorescence as a function of time determined in step (b) to the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method includes communicating the results of the onboard assay(s) to an ex vivo receiver.

In some embodiments, a control may be employed in the method as described herein. Such a control may be a positive control, e.g., a composition as described herein further including a known number of viable bacterial cells. In some embodiments, the control may be a negative control, e.g., a composition as described herein that has not been contacted with any viable bacterial cells. In some embodiments, this disclosure provides a method for detecting the presence of viable bacterial cells in a sample, including: (a) contacting the sample with a composition as described herein; (b) measuring total fluorescence or rate of change of fluorescence as a function of time of the sample; and (c) comparing the total fluorescence measured in step (b) to the total fluorescence produced by a control as described herein, or comparing the rate of change of fluorescence as a function of time measured in step (b) to the rate of change of fluorescence as a function of time produced by a control as described herein, thereby detecting viable bacterial cells.

In some embodiments of the method, the control may be (1) a composition identical to the one used in step (a) but has not been contacted with any viable bacterial cells; or (2) a composition identical to the one used in step (a) further including a known number of viable bacterial cells (e.g., a composition identical to the one used in step (a) further including $10^2$, $10^3$, $10^4$, $10^5$, $10^6$, or $10^7$ CFU/mL of bacterial cells). In some embodiments, the total fluorescence or the rate of change of fluorescence as a function of time of the sample is measured over multiple time points for an extended period of time in step (b), thereby detecting viable bacterial cells in the sample. For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the method further includes correlating the comparative total fluorescence determined in step (c) to the number of viable bacterial cells in the sample. In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method includes communicating the results of the onboard assay(s) to an ex vivo receiver.

In some embodiments, methods as described herein are highly sensitive in detecting or quantifying viable bacterial cells in various samples. In some embodiments, the lowest detection or quantification limit of the present methods is $10^2$ CFU/mL. In some embodiments, the highest detection or quantification limit of the present methods is $10^7$ CFU/mL, $10^8$ CFU/mL, $10^9$ CFU/mL, $10^{10}$ CFU/mL or more. In some embodiments, the methods allow detection or quantification of $10^2$ to $10^7$ CFU/mL bacterial cells in various samples. In some embodiments, methods of this disclosure may be used to distinguish samples bases on the quantity of viable bacterial cells contained therein. For instance, the methods may be used to distinguish among samples including $10^2$, $10^3$, $10^4$, $10^5$, $10^6$, or $10^7$ CFU/mL of bacterial cells.

In one aspect, this disclosure provides a kit including a composition as described herein and instructions, e.g., for detecting or quantifying viable bacterial cells in a sample. In another aspect, this disclosure provides a device (e.g., an ingestible device) including a composition as described herein, e.g., for detecting or quantifying viable bacterial cells in a sample. The detection of live cells is the gold standard of viable plate counting and represents one of the advantages of exemplary compositions and methods described herein.

In one aspect, this disclosure provides a method of assessing or monitoring the need to treat a subject suffering from or at risk of overgrowth of bacterial cells in the GI tract, including: (a) obtaining a sample from the GI tract of the subject; (b) contacting the sample with a composition as described herein; (c) measuring total fluorescence or rate of change of fluorescence as a function of time of the sample; and (d) correlating the total fluorescence or the rate of change of fluorescence as a function of time measured in step (c) to the number of viable bacterial cells in the sample, wherein the number of the viable bacterial cells determined in step (d) greater than about $10^5$ CFU/mL indicates a need for treatment, e.g., with an antibiotic agent as described herein.

In some embodiments, the total fluorescence or the rate of change of fluorescence as a function of time of the sample is measured over multiple time points for an extended period of time in step (c). For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes In some embodiments, the total fluorescence or the rate of change of fluorescence as a function of time of the sample is measured continuously for a period of 0-330 minutes. In some embodiments, the method does not require ex vivo plating or culturing. In some embodiments, the method is performed in vivo (e.g., in an ingestible device in vivo). In some embodiments, the method includes communicating the results of the onboard assay(s) to an ex vivo receiver.

In some embodiments, a control may be used in the method of assessing the need to treat a subject suffering from or at risk of overgrowth of bacterial cells in the GI tract. Such a control may be a positive control, e.g., a composition as described herein further including a known number of viable bacterial cells. In some embodiments, the control may be a negative control, e.g., a composition as described herein that has not been contacted with any viable bacterial cells. In some embodiments, this disclosure provides a method of assessing or monitoring the need to treat a subject suffering from or at risk of overgrowth of bacterial cells in the GI tract, including: (a) obtaining a sample from the GI tract of the subject; (b) contacting the sample with a composition as described herein; (c) measuring total fluorescence of the sample; (d) comparing the total fluorescence measured in step (c) to the total fluorescence produced by a control as described herein; and (e) correlating the comparative fluorescence determined in step (d) to the number of viable bacterial cells in the sample, wherein the number of the viable bacterial cells determined in step (e) greater than about $10^5$ CFU/mL indicates a need for treatment, e.g., with an antibiotic agent as described herein.

In some embodiments, this disclosure provides a method of assessing or monitoring the need to treat a subject suffering from or at risk of overgrowth of bacterial cells in the GI tract, including: (a) obtaining a sample from the GI tract of the subject; (b) contacting the sample with a composition as described herein; (c) measuring rate of change of fluorescence as a function of time of the sample; (d) comparing the rate of change of fluorescence as a function of time measured in step (c) to the rate of change of fluorescence as a function of time produced by a control as described herein; and (e) correlating the comparative rate of change of fluorescence as a function of time determined in step (d) to the number of viable bacterial cells in the sample. The number of the viable bacterial cells determined in step (e) greater than about $10^5$ CFU/mL indicates a need for treatment, e.g., with an antibiotic agent as described herein.

In some embodiments of the method, the control may be (1) a composition identical to the one used in step (b) but has not been contacted with any viable bacterial cells; or (2) a composition identical to the one used in step (b) further including a known number of viable bacterial cells (e.g., a composition identical to the one used in step (b) further including $10^2$, $10^3$, $10^4$, $10^5$, $10^6$, or $10^7$ CFU/mL of bacterial cells). In some embodiments, the total fluorescence or the rate of change of fluorescence as a function of time of the sample is measured over multiple time points for an extended period of time in step (c), thereby detecting viable bacterial cells in the sample. For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method is performed in vivo (e.g., in an ingestible device in vivo). In some embodiments, the method includes communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In one aspect, the present disclosure provides a member made of an absorptive material (e.g., an absorptive sponge) having absorbed therein a composition (e.g., a composition as described herein) including a dye and a reagent for selective lysis of eukaryotic cells. In some embodiments, the absorptive sponge is a hydrophilic sponge. In some embodiments, the absorptive sponge is selected from the group consisting of: fibers of cotton, rayon, glass, polyester, polyethylene, polyurethane, nitrocellulose, and the like. In some embodiments, the absorptive sponge is polyester or polyethylene. In some embodiments, the absorptive sponge is selected from the group consisting of: Ahlstrom Grade 6613H, Porex 1/16" Fine Sheet 4897, Porex 1/8" Fine Sheet 4898, Porex 4588 0.024" Conjugate release pad, Porex PSU-567, and Filter Papers. In some embodiments, the absorptive sponge is Ahlstrom Grade 6613H (Lot 150191) or Porex PSU-567.

The present disclosure further provides a method for preparing an absorptive sponge as described herein, including the step of injecting into the absorptive sponge an aqueous solution including a composition of the present disclosure. In some embodiments, the method including a step of drying the absorptive sponge having absorbed therein the aqueous solution at a temperature in the range of 0-100° C., 0-50° C., 0-40° C., 0-30° C., 0-20° C., 0-10° C., or 0-4° C.), for a time period sufficient to reduce the total water content to below 50%, 40%, 30%, 20%, 15%, 10%, 7%, 5%, 3%, 1%, 0.7%, 0.5%, 0.3%, or 0.1% by weight.

In some embodiments, the absorptive sponge of this disclosure are suitable for use in a kit or device, e.g., for detecting or quantifying viable bacterial cells in a sample. In some embodiments, such a device is an ingestible device for detecting or quantifying viable bacterial cells in vivo (e.g., in the GI tract).

In one aspect, this disclosure provides a method for detecting the presence of viable bacterial cells in a sample, including: (a) fully or partially saturating (e.g., at 50% or half saturation) an absorptive sponge as described herein, or an absorptive sponge prepared according to a method as described herein, with the sample; and (b) measuring total fluorescence or rate of change of fluorescence as a function of time of the fully or partially saturated sponge (e.g., 50% or half-saturated) prepared in step (a), thereby detecting viable bacterial cells in the sample.

In some embodiments, the total fluorescence or the rate of change of fluorescence as a function of time of the sponge is measured over multiple time points for an extended period of time in step (b), thereby detecting viable bacterial cells in the sample. For instance, in some embodiments, the total fluorescence or the rate of change of fluorescence as a function of time of the sample is measured continuously for a period of 0-1000 minutes, 0-900 minutes, 0-800 minutes, 0-700 minutes, 0-600 minutes, 0-500 minutes, 0-400 minutes, 0-350 minutes, or 0-330 minutes. In some embodiments, the total fluorescence or the rate of change of fluorescence as a function of time of the sample is measured continuously for a period of 0-330 minutes. In some embodiments, the method further includes correlating the total fluorescence or the rate of change of fluorescence as a function of time determined in step (b) to the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method includes communicating the results of the onboard assay(s) to an ex vivo receiver.

In some embodiments, a control may be employed in the method as described herein. Such a control may be a positive control, e.g., an absorptive sponge as described herein further including a known number of viable bacterial cells. In some embodiments, the control may be a negative control, e.g., an absorptive sponge as described herein that has not been contacted with any viable bacterial cells.

In some embodiments, this disclosure provides a method for detecting the presence of viable bacterial cells in a sample, including: (a) fully or partially saturating (e.g., at 50% or half saturation) an absorptive sponge as described herein, or an absorptive sponge prepared according to a method as described herein, with the sample; (b) measuring total fluorescence or rate of change of fluorescence as a function of time of the fully or partially saturated sponge (e.g., at 50% or half saturation) prepared in step (a); and (c) comparing the total fluorescence measured in step (b) to the total fluorescence produced by a control as described herein, or comparing the rate of change of fluorescence as a function of time measured in step (b) to the rate of change of fluorescence as a function of time produced by a control as described herein, thereby detecting viable bacterial cells.

In some embodiments of the method, the control may be (1) an absorptive sponge identical to the one used in step (a) that has not been contacted with any viable bacterial cells, or (2) an absorptive sponge identical to the one used in step (a) and is fully or partially saturated with a solution including a known number of viable bacterial cells (e.g., an absorptive sponge identical to the one used in step (a) further including $10^2$, $10^3$, $10^4$, $10^5$, $10^6$, or $10^7$ CFU/mL of bacterial cells). In some embodiments, the total fluorescence or the rate of change of fluorescence as a function of time of the sponge is measured over multiple time points for an extended period of time in step (b), thereby detecting viable bacterial cells in the sample. For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the method further includes correlating the comparative total fluorescence determined in step (c) to the number of viable bacterial cells in the sample. In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method includes communicating the results of the onboard assay(s) to an ex vivo receiver.

In some embodiments, methods as described herein are highly sensitive in detecting and quantifying viable bacterial cells in various samples. In some embodiments, the lowest detection or quantification limit of the present methods is $10^2$ CFU/mL. In some embodiments, the highest detection or quantification limit of the present methods is $10^7$ CFU/mL, $10^8$ CFU/mL, $10^9$ CFU/mL, $10^{10}$ CFU/mL or more. In some embodiments, the methods allow detection or quantification of $10^2$ to $10^7$ CFU/mL bacterial cells in various samples. In some embodiments, methods of this disclosure may be used to distinguish samples bases on the quantity of viable bacterial cells contained therein. For instance, the methods may be used to distinguish among samples that contain $10^2$, $10^3$, $10^4$, $10^5$, $10^6$, or $10^7$ CFU/mL of bacterial cells.

In one aspect, this disclosure provides a kit including an absorptive sponge as described herein and instructions, e.g., for detecting or quantifying viable cells using the absorptive sponge. In another aspect, this disclosure provides a device (e.g., an ingestible device) including an absorptive sponge as described herein, e.g., for detecting or quantifying viable bacterial cells in a sample.

In one aspect, this disclosure provides a method of assessing or monitoring the need to treat a subject suffering from or at risk of overgrowth of bacterial cells in the GI tract, including: (a) obtaining a sample from the GI tract of the subject; (b) fully or partially saturating (e.g., at 50% or half saturation) an absorptive sponge as described herein, or an absorptive sponge prepared according to a method as described herein, with the sample; (c) measuring total fluorescence or rate of change of fluorescence as a function of time of the fully or partially saturated sponge (e.g., at 50% or half saturation) prepared in step (b); and (d) correlating the total fluorescence or the rate of change of fluorescence as a function of time measured in step (c) to the number of viable bacterial cells in the sample, wherein the number of the viable bacterial cells determined in step (d) greater than about $10^5$ CFU/mL indicates a need for treatment, e.g., with an antibiotic agent as described herein.

In some embodiments, the total fluorescence or the rate of change of fluorescence as a function of time of the fully or partially saturated sponge is measured over multiple time points for an extended period of time in step (c). For instance, in some embodiments, the total fluorescence or the rate of change of fluorescence as a function of time of the fully or partially saturated sponge is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the fully or partially saturated sponge is measured continuously for a period of 0-330 minutes. In some embodiments, the method does not require ex vivo plating or culturing. In some embodiments, the method does not require aspiration. In some embodiments, the method is performed in vivo (e.g., in an ingestible device in vivo).

In some embodiments, a control may be used in the method of assessing the need to treat a subject suffering from or at risk of overgrowth of bacterial cells in the GI tract. Such a control may be a positive control, e.g., an absorptive sponge as described herein further including a known number of viable bacterial cells. In some embodiments, the control may be a negative control, e.g., an absorptive sponge as described herein that has not been contacted with any viable bacterial cells.

In some embodiments, this disclosure provides a method of assessing or monitoring the need to treat a subject suffering from or at risk of overgrowth of bacterial cells in the GI tract, including: (a) obtaining a sample from the GI tract of the subject; (b) fully or partially saturating (e.g., at 50% or half saturation) an absorptive sponge as described herein, or an absorptive sponge prepared according to a method as described herein, with the sample; (c) measuring total fluorescence of the fully or partially saturated sponge (e.g., at 50% or half saturation) prepared in step (b); (d) comparing the total fluorescence measured in step (c) to the total fluorescence produced by a control as described herein; and (e) correlating the comparative fluorescence determined in step (d) to the number of viable bacterial cells in the sample, wherein the number of the viable bacterial cells determined in step (e) greater than about $10^5$ CFU/mL indicates a need for treatment, e.g., with an antibiotic agent as described herein.

In some embodiments, this disclosure provides a method of assessing or monitoring the need to treat a subject suffering from or at risk of overgrowth of bacterial cells in the GI tract, including: (a) obtaining a sample from the GI tract of the subject; (b) fully or partially saturating (e.g., at 50% or half saturation) an absorptive sponge as described herein, or an absorptive sponge prepared according to a method as described herein, with the sample; (c) measuring rate of change of fluorescence as a function of time of the fully or partially saturated sponge (e.g., at 50% or half saturation) prepared in step (b); (d) comparing the rate of change of fluorescence as a function of time measured in step (c) to the rate of change of fluorescence as a function of time produced by a control as described herein; and (e) correlating the comparative rate of change of fluorescence as a function of time determined in step (d) to the number of viable bacterial cells in the sample, wherein the number of the viable bacterial cells determined in step (e) greater than about $10^5$ CFU/mL indicates a need for treatment, e.g., with an antibiotic agent as described herein.

In some embodiments of the method, the control may be (1) an absorptive sponge identical to the one used in step (a) that has not been contacted with any viable bacterial cells, or (2) an absorptive sponge identical to the one used in step (a) and is fully or partially saturated with a solution including a known number of viable bacterial cells (e.g., a composition identical to the one used in step (b) further including $10^2$, $10^3$, $10^4$, $10^5$, $10^6$, or $10^7$ CFU/mL of bacterial cells). In some embodiments, the total fluorescence or the rate of change of fluorescence as a function of time of the sponge is measured over multiple time points for an extended period of time in step (c), thereby detecting viable bacterial cells in the sample. For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method includes communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In some embodiments, fluorescence intensity is measured with an optical reader. The actual configuration and structure of the optical reader may generally vary as is readily understood by those skilled in the art. Typically, the optical reader contains an illumination source that is capable of emitting light at a defined wavelength and a detector that is capable of registering a signal (e.g., transmitted, reflected, or fluorescence light). Optical readers may generally employ any known detection technique, including, for instance, luminescence (e.g., fluorescence, phosphorescence, etc.), absorbance (e.g., fluorescent or non-fluorescent), diffraction, etc. Exemplary optical readers, illumination sources and detectors are disclosed in U.S. Pat. No. 7,399,608, which is hereby incorporated by reference herein in its entirety.

Figure 72A:
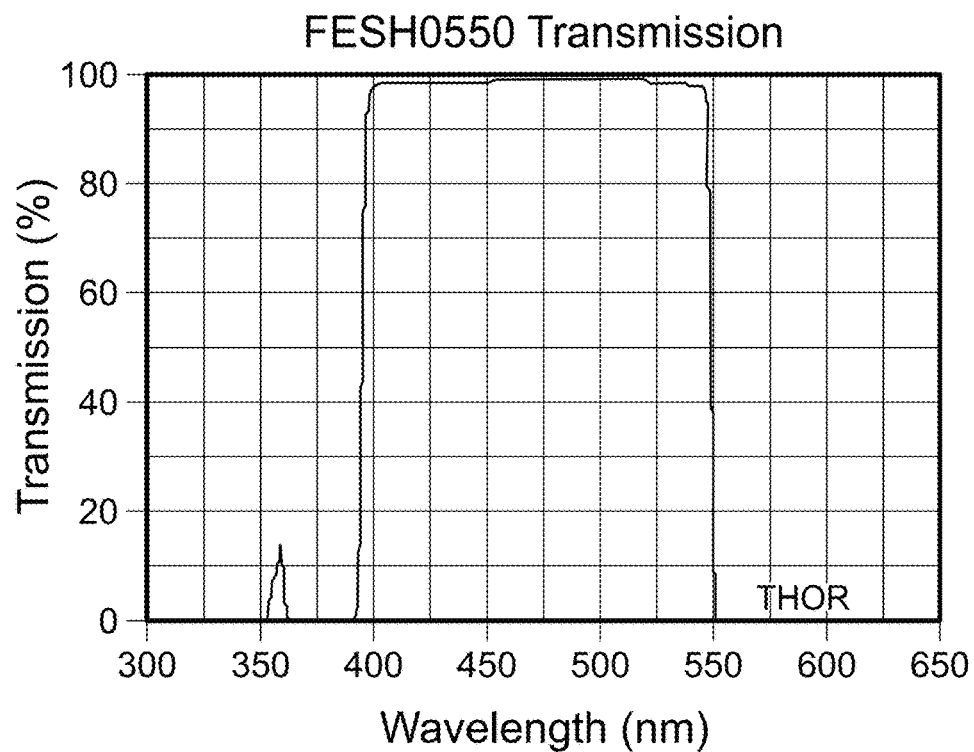
FIG. 72A shows the use of a Thorlabs FESH0550 shortpass filter for filtering excitation wavelength.
Figure 72B:
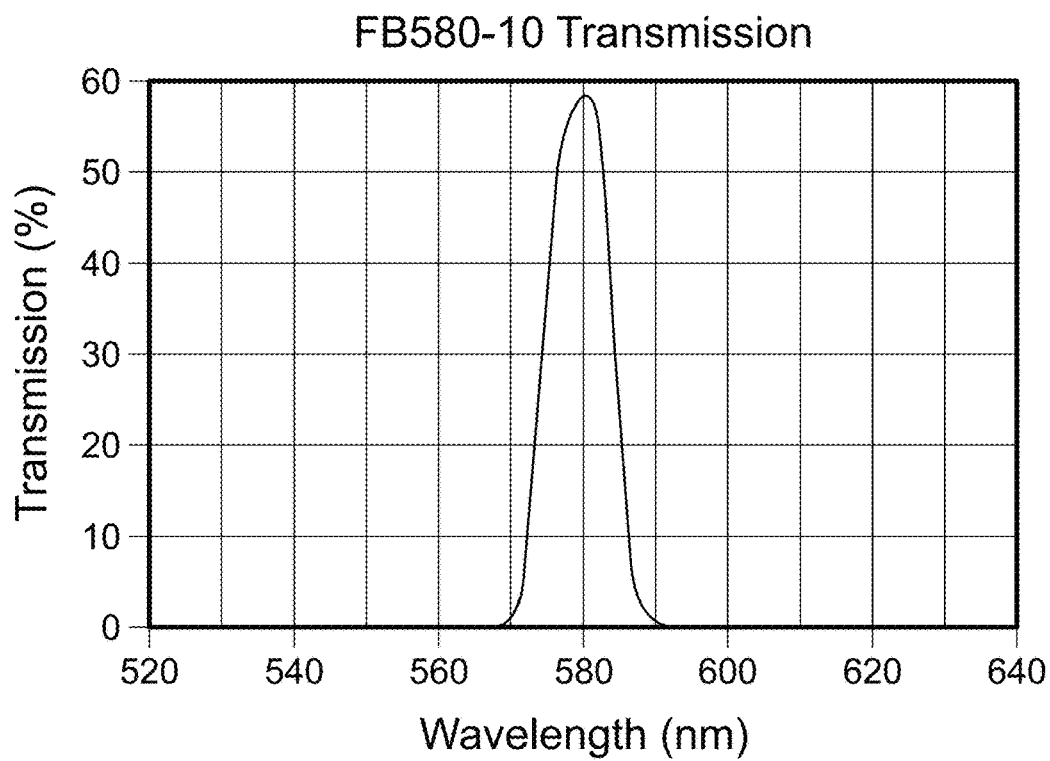
FIG. 72B shows the use of a Thorlabs FB580-10 bandpass filter for filtering emission wavelength.
Figure 72C:
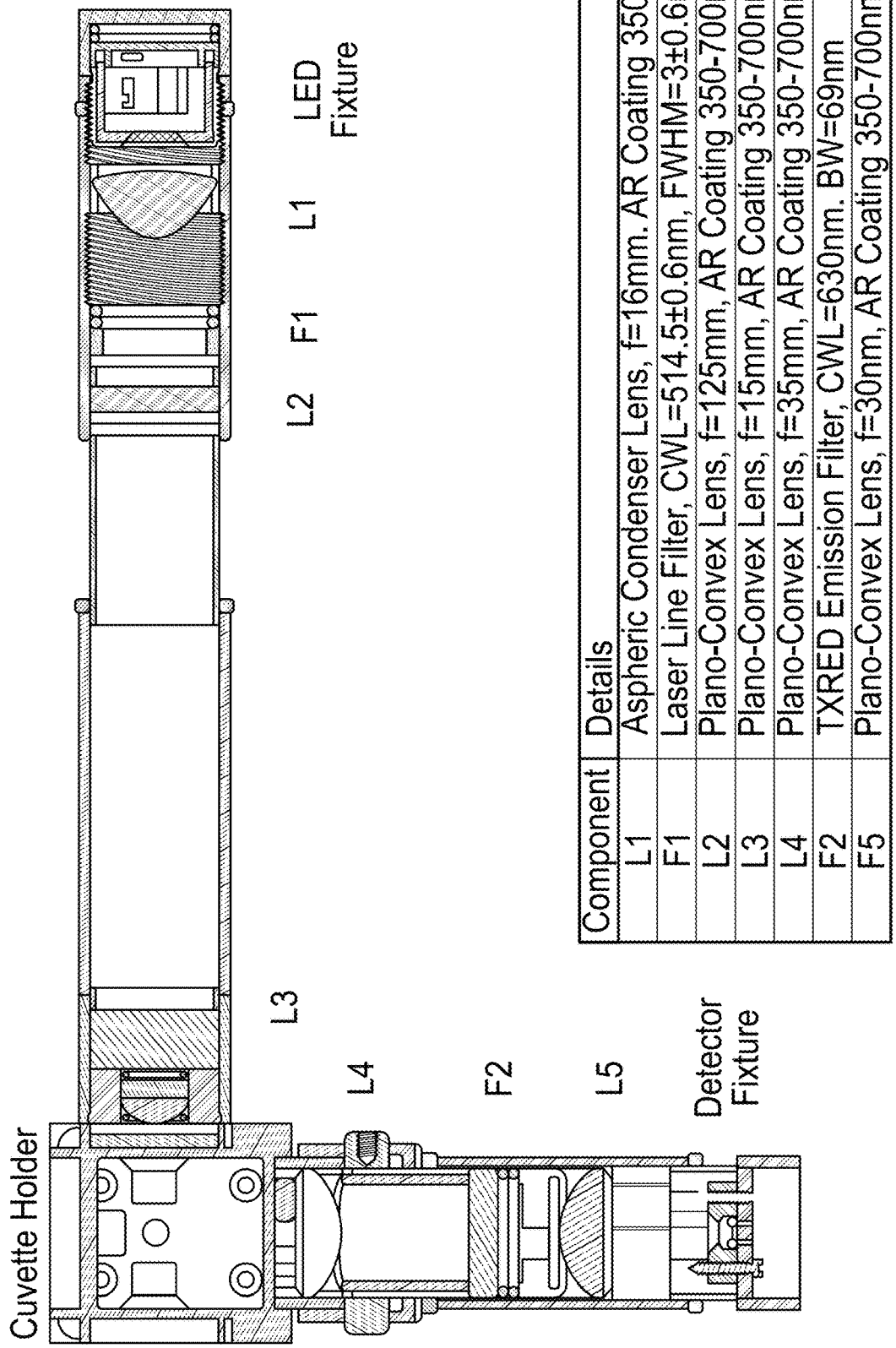
FIG. 72C shows a cross sectional view of an exemplary fluorescent assay test fixture depicting collimating, focusing, and filtering lenses.

In some embodiments, the illumination source may be any device known in the art that is capable of providing electromagnetic radiation, such as light in the visible or near-visible range (e.g., infrared or ultraviolet light). For example, suitable illumination sources that may be used in the present disclosure include, but are not limited to, light emitting diodes (LED), flashlamps, cold-cathode fluorescent lamps, electroluminescent lamps, and so forth. The illumination may be multiplexed and/or collimated. In some embodiments, the illumination may be pulsed to reduce any background interference. In some embodiments, filters may be used to improve optics. See, e.g., Reichman, Jay, Handbook of optical filters for fluorescence microscopy, Chroma Technology Corporation (2000). In some embodiments, excitation source may be a LED with a band-pass filter, e.g., a filter for 500 nm+/−10 nm wavelength to selectively excite a sample with 500 nm light. In some embodiments, to cut out any stray longer wavelengths from the green LED, a Thorlabs FESH0550 shortpass filter may be used for excitation (FIG. 72A). In some embodiments, the emission from a sample is captured at a 90° angle with an avalanche photo-diode detector with a bandpass filter, e.g., a filter for 590 nm+/−20 nm wavelength, placed in front of the detector, to selectively capture light emitted at 590 nm. In some embodiments, a Thorlabs FB580-10 bandpass filter may be used as an emission filter (FIG. 72B). A cross sectional view of an exemplary fluorescent assay test fixture depicting collimating, focusing, and filtering lenses is shown in FIG. 72C. In some embodiments, a 5-50 nanosecond delay may be used before emission is measured. Typical fluorophore used for time delayed fluorescence are lanthanide metal chelates (Europium, Samarium, Terbium, etc), ruthenium complexes and others known in the art. In some embodiments, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. In some embodiments, the illumination source may provide diffuse illumination to the dye. For example, an array of multiple point light sources (e.g., LEDs) may simply be employed to provide relatively diffuse illumination. In some embodiments, the illumination source is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Disclosure of a voltage across the electrodes generates a changing electric field within the luminescent material that causes it to emit light.

In some embodiments, the detector may be any device known in the art that is capable of sensing a signal. In some embodiments, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers. In some embodiments, a photomultiplier may be used to increase the intensity of the signal.

In another aspect, the present disclosure provides ingestible devices containing a microscopic evaluation system. In some embodiments, bacterial cells in a sample may be first labeled with fluorescent dyes (such as those described herein), and the fluorescently-labeled cells may be imaged and counted by the microscopic evaluation using an ingestible device as described herein. In other embodiments, the fluorescently-labeled cells are counted as they pass through an onboard flow system (e.g., microfluidic single cell channeling). Examples of flow cytometry systems include hydrodynamic focusing, small diameter capillary tube flow, and rectangular capillary tube flow. As described herein, live bacteria cells are labeled, and the principles of flow cytometry are used to quantify labeled cells. Generally speaking, the photons from an incident laser beam are absorbed by the fluorophore and raised to a higher, unstable energy level. Within less than a nanosecond, the fluorophore re-emits the light at a longer representative wavelength where it is passed through a series of dichroic filters. This reemitted light can be collected and interpreted as proportional to the number of labeled bacteria cells. In some embodiments, a sheath fluid is not used as part of the flow system to help accommodate the volume restrictions of the device. In some embodiments, a rectangular capillary tube is used to achieve a sufficiently large cross-sectional area and relatively thin inspection area. The flow cytometry optical system operates parallel to the fluidics system and serves to observe the redirection of light passing through the cell and delivers information about the bacterial cells. In some embodiments, rather than using a conventional laser and spherical lenses to focus the light to a point, an LED and cylindrical lenses are used to focus the light to a line across a rectangular capillary tube. In other embodiments, collimating lenses are used to make the light source parallel, while cylindrical lenses are used to refine the inspection area. An exemplary optical configuration for this arrangement can be seen in FIG. 30. In some embodiments, optical filters can be added to permit the use of fluorophores. The characteristic wavelength of reemitted light from the fluorophores can be isolated and detected with the use of dichroic, bandpass, and short or long wave pass filters. Generally, multiple dichroic lenses and photomultipliers are used, however, due to space limitations, only a single side-scatter detector and forward scatter detector may be used in certain embodiments.

One of the design challenges of integrating flow cytometry into the device is to provide a pumping mechanism. Without moving fluid, individual bacteria cells cannot be identified and accounted for by flow cytometry within a fixed volume of fluid. In some embodiments, a gear motor is to move fluid through the device. For example, a micro-motor including a planetary gearhead (e.g., with a 25:1 reduction) can provide the desired amount of torque to create fluid flow. In another embodiment, a series of piezo-electric resistors embedded in the surface of a microfabricated plate is used to create flow. In yet another embodiment, a micropump that includes a pair of one-way valves and uses a magnetic pump membrane actuated by an external magnetic field is used to create flow.

In some embodiments, the system architecture includes an opening and sealing mechanism combined with a rotary wiper which creates a pressure driven flow via a gear motor. The gear motor can be used for other functions in the device. As shown in FIG. 31, the components of the optics and flow chamber systems fit within the device. In some embodiments, the sample fluid is absorbed via a flexible membrane at the top of the capsule. In some embodiments, the gear motor has 270° of permissible travel which serves to open and fill the fluid chamber. During closure, the motor closes the ingress port while simultaneously pushing the fluid through the rectangular capillary tube where the optical system is located. The threaded component allows the flexible membrane to close and seal the ingress channel without changing the wiper height. In some embodiments, the volume of the sample chamber is 25 μL, 50 μL, 75 μL or more. In some embodiments, two or more samples are taken from the GI tract to procure a sufficient sample size. Referring to FIG. 31, an LED on the left side of the capillary tube and the two low-light detectors on the right for capturing forward and side scatter are shown. Once the fluid passes through the capillary tube, it exits the capsule via a one-way valve. In certain embodiments, the flow system allows for the detection of cell size and internal cell complexity, in addition to cell quantitation.

In some embodiment, the ingestible devices as described herein may be used to analyze samples (e.g., samples from the GI tract) to detect or quantify viable bacterial cells in a sample. In some embodiments, the devices of this disclosure may be used to measure the concentration of viable bacteria in specific regions of the GI tract. Such data may be used to determine whether a subject has a condition in need for treatment, such as an infection, Small Intestinal Bacterial Overgrowth (SIBO), or a SIBO-related condition, or to quantify bacterial populations within the GI tract (or within specific regions of the GI tract) for other diagnostic purposes.

An ingestible device used in a live cell dye method can be configured so that one or more than one samples may be analyzed.

As an example, in some embodiments, the ingestible device has only one sample chamber. In such embodiments, the chamber can be used to analyze one sample. In certain embodiments, an ingestible device having a single sample chamber can be used to analyze multiple different embodiments. The sample chamber may include a sponge that is used such that the different samples are analyzed at different points in time, such as, for example, taken at different locations within the GI tract (e.g., duodenum, jejunum, ileum) as the device passes through the GI tract. For example, a given sponge may be contacted multiple times and used for analyte detection. In some embodiments, the sponge may be contacted with non-saturating amounts of sample multiple times and used for analyte detection. Alternatively or additionally, the sample chamber may be used with multiple dyes (e.g., used in a single reaction) that are detectable at different wavelengths. Multiple analytes can be detected, for example, using different antibodies (e.g., detecting fluorescence at different wavelengths)

As another example, in certain embodiments, the ingestible device has multiple chambers for analyzing samples. In such embodiments, each chamber can be used to analyze different samples. Features noted in the preceding paragraph may be implemented with an ingestible device having multiple sample chambers.

In some embodiments, data may be generated after the ingestible device has exited the subject, or the data may be generated in vivo and stored on the device and recovered ex vivo. Alternatively, the data can be transmitted wirelessly from the ingestible device while the device is passing through the GI tract of the subject.

In one aspect, this disclosure provides a method for detecting the presence of viable bacterial cells in a sample, including: (a) providing an ingestible device as described herein; (b) transferring a fluid sample from the GI tract of a subject into a sampling chamber of the ingestible device in vivo; and (c) detecting the presence of viable bacterial cells in the fluid sample (e.g., in vivo).

In some embodiments, the method for detecting the presence of viable bacterial cells in a sample includes: (a) providing an ingestible device as described herein; (b) transferring a fluid sample from the GI tract of a subject into a sampling chamber of the ingestible device in vivo, wherein the sampling chamber of the device is configured to hold an absorptive sponge as described herein, or an absorptive sponge prepared according to the method for preparing an absorptive sponge as described herein; (c) fully or partially saturating (e.g., at 50% or half saturation) the absorptive sponge with the fluid sample; and (d) measuring total fluorescence or rate of change of fluorescence as a function of time of the fully or partially saturated sponge (e.g., 50% or half-saturated) prepared in step (c), thereby detecting viable bacterial cells in the sample (e.g., in vivo).

In some embodiments, the method described herein further includes a step of calibrating the ingestible device, wherein the fluorescent properties of the absorptive sponge contained in the sampling chamber of the device are determined prior to the introduction of the sample. In some embodiments, each ingestible device is calibrated by measuring the fluorescence of the absorptive sponge held in the sampling chamber of the device and comparing the measured florescence to a positive or negative control as described herein. In some embodiments, each ingestible device is calibrated by measuring the fluorescence of the absorptive sponge held in the sampling chamber of the device to provide a baseline fluorescence. In some embodiments, the baseline fluorescence should be within a set number (900+/−450 FU). In some embodiments, a subset of ingestible devices may be treated with 0, $10^4$, $10^5$, $10^6$ and $10^7$ CFU bacteria in duodenal or jejunal aspirates to generate a calibration curve. The calibration curve may be stored and used to quantify bacteria in all the devices in the batch. See, e.g., David Wild, *Standardization and Calibration*, The Immunoassay Handbook, Gulf Professional Publishing, 2005. In some embodiments, the total fluorescence or the rate of change of fluorescence as a function of time of the sponge is measured over multiple time points for an extended period of time in step (d), thereby detecting viable bacterial cells in the sample. For instance, in some embodiments, the total fluorescence or the rate of change of fluorescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the method further includes correlating the total fluorescence or the rate of change of fluorescence as a function of time determined in step (d) to the number of viable bacterial cells in the sample. In some embodiments, the method does not require ex vivo plating or culturing. In some embodiments, the method does not require aspiration. In some embodiments, the method is performed in the ingestible device in vivo.

In some embodiments, a control may be employed in the method as described herein. Such a control may be an internal control (e.g., the fluorescence coming from resorufin impurity in resazruin (900+/−450 FU) in the sponge may be used as an internal control for optics and amount of dye in the sponge). In some embodiments, each ingestible device as described herein is individually calibrated wherein the fluorescent properties of the absorptive sponge contained in the sampling chamber of the device are determined prior to the introduction of sample.

In some embodiments, methods as described herein are highly sensitive in detecting and quantifying viable bacterial cells in various samples. In some embodiments, the lowest detection or quantification limit of the present methods is $10^2$ CFU/mL. In some embodiments, the highest detection or quantification limit of the present methods is $10^7$ CFU/mL, $10^8$ CFU/mL, $10^9$ CFU/mL, $10^{10}$ CFU/mL or more. In some embodiments, the methods allow detection or quantification of $10^2$ to $10^7$ CFU/mL bacterial cells in various samples. In some embodiments, methods of this disclosure may be used to distinguish samples bases on the quantity of viable bacterial cells contained therein. For instance, the methods may be used to distinguish among samples that contain $10^2$, $10^3$, $10^4$, $10^5$, $10^6$, or $10^7$ CFU/mL of bacterial cells.

In one aspect, this disclosure provides a method of assessing or monitoring the need to treat a subject suffering from or at risk of overgrowth of bacterial cells in the GI tract, including: (a) providing an ingestible device as described herein; (b) transferring a fluid sample from the GI tract of a subject into a sampling chamber of the ingestible device in vivo; and (c) quantifying viable bacterial cells present in the fluid sample (e.g., in vivo), wherein the number of the viable bacterial cells determined in step (c) greater than about $10^5$ CFU/mL indicates a need for treatment, e.g., with an antibiotic agent as described herein.

In some embodiments, the method of assessing or monitoring the need to treat a subject suffering from or at risk of overgrowth of bacterial cells in the GI tract includes: (a) providing an ingestible device as described herein; (b) transferring a fluid sample from the GI tract of a subject into a sampling chamber of the device in vivo, wherein the sampling chamber of the device as described herein is configured to hold an absorptive sponge as described herein, or an absorptive sponge prepared according to the method for preparing an absorptive sponge as described herein; (c) fully or partially saturating (e.g., at 50% or half saturation) the absorptive sponge in the sampling chamber with the fluid sample; (d) measuring total fluorescence of the fully or partially saturated sponge (e.g., at 50% or half saturation) prepared in step (c); and (e) correlating the total fluorescence measured in step (d) to the number of viable bacterial cells in the sample, wherein the number of the viable bacterial cells determined in step (e) greater than about $10^5$ CFU/mL indicates a need for treatment, e.g., with an antibiotic agent as described herein.

In some embodiments, the method of assessing or monitoring the need to treat a subject suffering from or at risk of overgrowth of bacterial cells in the GI tract includes: (a) providing an ingestible device as described herein; (b) transferring a fluid sample from the GI tract of a subject into a sampling chamber of the device in vivo, wherein the sampling chamber of the device as described herein is configured to hold an absorptive sponge as described herein, or an absorptive sponge prepared according to the method for preparing an absorptive sponge as described herein; (c) fully or partially saturating (e.g., at 50% or half saturation) the absorptive sponge in the sampling chamber with the fluid sample; (d) measuring rate of change of fluorescence as a function of time of the fully or partially saturated sponge (e.g., at 50% or half saturation) prepared in step (c); and (e) correlating the rate of change of fluorescence as a function of time measured in step (d) to the number of viable bacterial cells in the sample, wherein the number of the viable bacterial cells determined in step (e) greater than about $10^5$ CFU/mL indicates a need for treatment, e.g., with an antibiotic agent as described herein.

In some embodiments, the total fluorescence or the rate of change of fluorescence as a function of time of the sponge is measured over multiple time points for an extended period of time in step (d). For instance, in some embodiments, the total fluorescence rate of change of fluorescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total fluorescence or the rate of change of fluorescence as a function of time of the sample is measured continuously for a period of 0-330 minutes. In some embodiments, the method does not require ex vivo plating or culturing. In some embodiments, the method does not require aspiration. In some embodiments, the method is performed in vivo (e.g., in an ingestible device in vivo). In some embodiments, the method includes communicating the results of the onboard assay(s) to an ex vivo receiver. In some embodiments, the ingestible device and the method may be further used to monitor the subject after the treatment (e.g., with an antibiotic). In some embodiments, the ingestible device and the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the ingestible device and the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In some embodiments, the compositions, methods and devices described herein may use a combination of (e.g., two or more) analyte-binding agents to detect, characterize and/or quantitate the type of analyte (e.g., a microorganism and a protein, a metabolite) present in a sample. For example, in some embodiments, the compositions, methods and devices described herein may be used to determine the types of microorganisms (e.g., bacteria, protozoans, or viruses) present in a sample. In some embodiments, a first analyte-binding agent that binds to an analyte and comprises a first fluorescent dye, may be used in combination with a second analyte-binding agent, wherein the second analyte-binding agent comprises a second fluorescent dye that exhibits increased fluorescence when spatially proximal to the first fluorescent dye. In some embodiments, spatial proximity between the first fluorescent dye and the second fluorescent dye results in energy transfer from the first fluorescent dye to the second fluorescent dye. The detection of the fluorescence emitted by the second fluorescent dye can be used, for example, to determine whether both analyte-binding agents are located in close proximity to each other in the sample. Alternatively, a first analyte-binding agent that binds to an analyte and comprises a first fluorogenic dye may be used in combination with a second analyte-binding agent, wherein the second analyte-binding agent comprises a second fluorescent dye that exhibits increased fluorescence when spatially proximal to the first fluorogenic dye. In some embodiments, the first fluorogenic dye exhibits no fluorescence or reduce fluorescence when the first-analyte binding agent is not bound to the analayte. In some embodiments, the first fluorogenic dye exhibits increased fluorescence upon binding of the first analyte-binding agent to the analyte. In some embodiments, spatial proximity between the first fluorogenic dye and the second fluorescent dye results in energy transfer from the first fluorogenic dye to the second fluorescent dye. The detection of the fluorescence emitted by the second fluorescent dye can be used, for example, to determine whether both analyte-binding agents are located in close proximity to each other in the sample. In some embodiments, the first and the second analyte-binding agents bind to the same region (e.g., epitope) of the analyte (e.g., a protein). For instance, in some embodiments, the first and the second analyte-binding agents comprise the same type of analyte-binding moiety or reagent (e.g., the same antibody). In some embodiments, the first and the second analyte-binding agents bind to separate regions (e.g., epitopes) of the analyte (e.g., a protein). In some embodiments, the first and the second analyte-binding agents bind to the separate regions of the analyte (e.g., a protein) that do not spatially overlap. In some embodiments, the first analyte-binding agent and the second analyte-binding agent are configured such that when both analyte-binding agents are bound to the analyte, their respective dyes are in close proximity (e.g., allowing for energy transfer to occur). In some embodiments, the first and/or second analyte binding agent(s) is an antigen-binding agent (e.g., an antibody). In some embodiments, the first and/or second analyte binding agent(s) is an affimer. In some embodiments, the first and/or second analyte binding agent(s) is an antigen-binding agent is an aptamer.

In some embodiments, the compositions, methods and devices described herein make use of fluorescent oxygen channeling immunoassay (FOCI) compositions and methods. FOCI is generally described in U.S. Pat. Nos. 5,807,675; 5,616,719; and 7,635,571, the entire contents of which are expressly incorporated herein by reference. In some embodiments, a first analyte-binding agent that is capable of binding to an analyte and comprises a photosensitizer is used in combination with a second analyte-binding agent comprising a fluorogenic dye. In some embodiments, the photosensitizer of the first analyte-binding agent generates singlet oxygen in an excited state thereby causing the fluorogenic dye of the second analyte-binding agent to emit fluorescence upon reacting with the singlet oxygen. In some embodiments, the emitted fluorescence can be detected to, e.g., determine the presence and/or absence of the analyte and/or to quantitate and/or analyze the analyte in a sample. In some embodiments, the first and the second analyte-binding agents bind to the same region (e.g., epitope) of the analyte (e.g., a protein). For example, in some embodiments, the first and the second analyte-binding agents comprise the same type of analyte-binding moiety or reagent (e.g., the same antibody). In some embodiments, the first and the second analyte-binding agents bind to separate regions (e.g., epitopes) of the analyte (e.g., a protein). In some embodiments, the first and the second analyte-binding agents bind to the separate regions of the analyte (e.g., a protein) that do not spatially overlap. In some embodiments, the first analyte-binding agent and the second analyte-binding agent are configured such that when both analyte-binding agents are bound to the analyte, the singlet oxygen generated by photosensitizer of the first analyte-binding agent is in close proximity to the fluorogenic dye of the second analyte-binding agent. In some embodiments, the first and/or second analyte binding agent(s) is an antigen-binding agent (e.g., an antibody). In some embodiments, the first and/or second analyte binding agent(s) is an affimer. In some embodiments, the first and/or second analyte binding agent(s) is an antigen-binding agent is an aptamer.

Figure 73A:
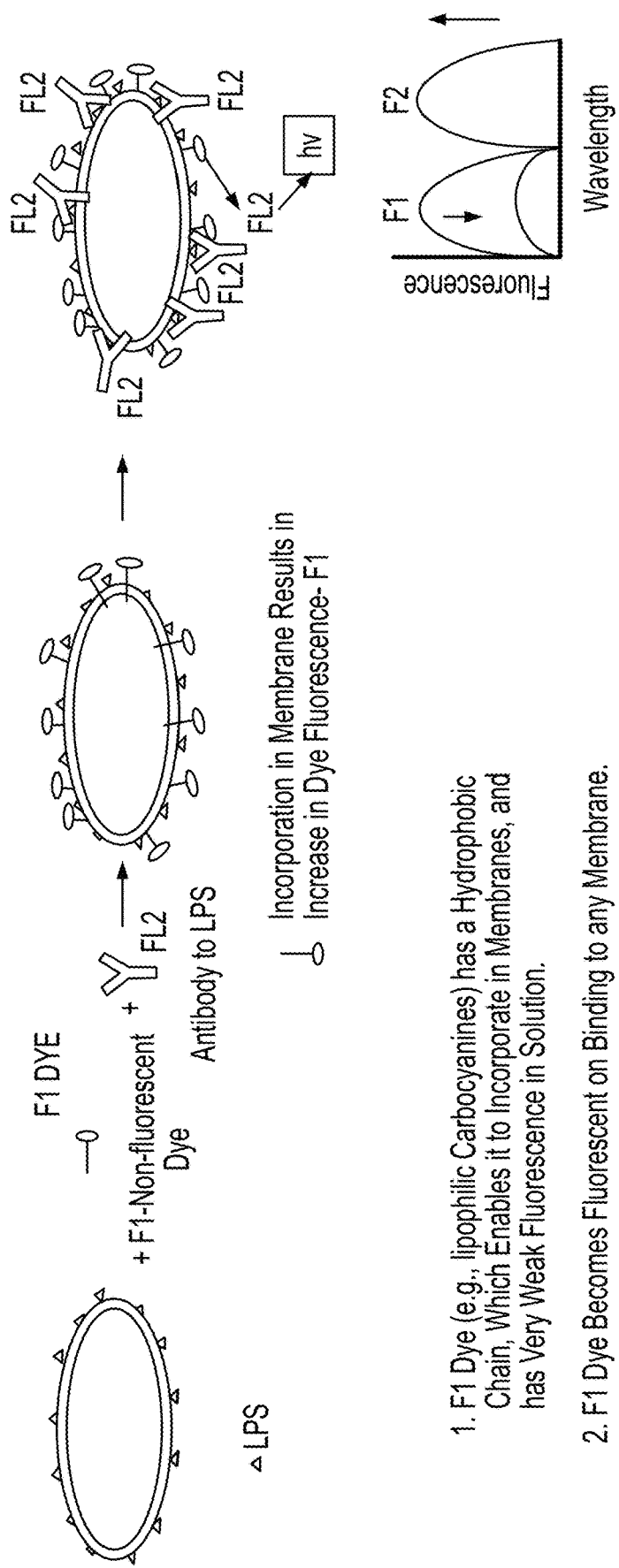
FIG. 73A shows a first proximity assay, where a bacteria-specific antibody to Linker of T cell activation (LTA) or lipopolysaccharide (LPS) is labeled with F2 dye. F1 dye has a hydrophobic chain, which enables it to incorporate in bacterial membranes. F1 dye becomes fluorescent upon binding to the bacterial membranes. Binding of the anti-LPS or anti-LTA antibody labeled with F2 to the bacterial surface would result in close proximity of F1 and F2 dyes, leading to an energy transfer from F1 to F2 (i.e., F1 fluorescence decreases and F2 fluorescence increases).
Figure 73B:
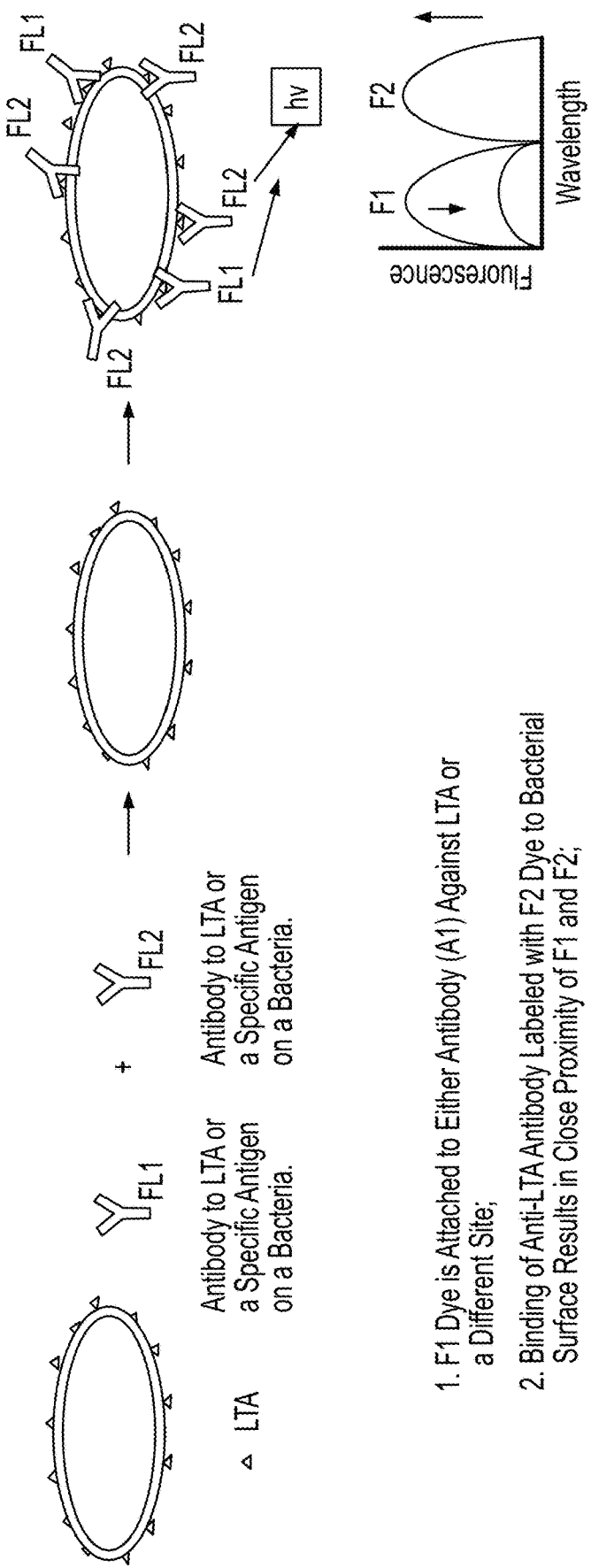
FIG. 73B shows a second proximity assay, where F1 dye is attached to a first antibody against LTA (or a specific antigen on a bacteria), and F2 dye is attached to a second antibody against LTA (or a specific antigen on a bacteria). Binding of both antibodies to the bacterial surface (e.g., to LTA or the specific antigen) would result in close proximity of F1 and F2dyes, leading to an energy transfer from F1 to F2 (i.e., F1 fluorescence decreases and F2 fluorescence increases).

In some embodiments, the use of a combination of analyte-binding agents allows for the detection, analysis and/or quantitation of a multitude of analytes. Multiple combinations of analyte-binding agents may be used for the detection, analysis and/or quantitation of a complex mixture of analytes. For example, multiple analyte-binding agents having different dyes, and/or analyte specificities may be used to analyze a sample. For instance, in order to detect different species of bacteria (or e.g., LTA vs. LPS) present in a sample, one can couple a live cell dye (F1) as described herein to an antibody or to an antibiotic that is microorganism-specific (e.g., bacteria specific or bacterial species-specific). Antibodies that specifically bind to a biomolecule (e.g., a surface antigen) present in a microorganism (e.g., a bacteria) of a genus, species or strain of interest and do not cross-react with other microorganism biomolecules and/or eukaryotic biomolecules may also be used, including the exemplary antibodies described herein. A second antibody or antibiotic having a fluorescent dye (F2) that binds to the same microorganism and that gets excited (via an energy transfer from F1 to F2) when in close proximity to F1 may be employed to detect, analyze and/or quantitate the microorganism to which the antibodies and/or antibiotics bind. Two exemplary proximity assays are depicted in FIGS. 73A and 73B.

Analyte Diluting and Culturing

In some embodiments, the disclosure provides methods of obtaining, culturing, and/or detecting cells and/or analytes in vivo within the gastrointestinal (GI) tract or reproductive tract of a subject. Associated devices are also disclosed. The methods and devices described provide a number of advantages for obtaining and/or analyzing fluid samples from a subject. In some embodiments, diluting the fluid sample increases the dynamic range of analyte detection and/or reduces background signals or interference within the sample. For example, interference may be caused by the presence of non-target analytes or non-specific binding of a dye or label within the sample. In some embodiments, culturing the sample increases the concentration of cells (e.g., a specific type of cells) and/or analytes (e.g., a specific analyte of interest) produced by the cells thereby facilitating their detection and/or characterization. Above, various types of analytes are disclosed which may be detected and/or characterized as described herein.

In certain embodiments, the methods and devices a described herein may be used to obtain information regarding bacterial populations in the GI tract of a subject. This has a number of advantages and is less invasive than surgical procedures such as intubation or endoscopy to obtain fluid samples from the GI tract. The use of an ingestible device as described herein also allows for fluid samples to be obtained and data to be generated on bacterial populations from specific regions of the GI tract.

In some embodiments, the methods and devices described herein may be used to generate data such as by analyzing the fluid sample, dilutions thereof or cultured samples for one or more cells and/or analytes. The data may include, but is not limited to, the types of bacteria present in the fluid sample or the concentration of bacteria in specific regions of the GI tract. Such data may be used to determine whether a subject has an infection, such as Small Intestinal Bacterial Overgrowth (SIBO), or to characterize bacterial populations within the GI tract for diagnostic or other purposes.

For example, in one aspect, the data may include, but is not limited to, the concentration of bacteria in a specific region of the GI tract that is one or more of the duodenum, jejunum, ileum, ascending colon, transverse colon or descending colon. In one aspect, the specific region of the GI tract is the duodenum. In one aspect, the specific region of the GI tract is the jejunum. In one aspect, the specific region of the GI tract is the ileum. In one aspect, the specific region of the GI tract is the ascending colon. In one aspect, the specific region of the GI tract is the transverse colon. In one aspect, the specific region of the GI tract is the descending colon. In a related embodiment, the data may be generated every one or more days to monitor disease flare-ups, or response to the therapeutic agents disclosed herein.

Data may be generated after the device has exited the subject, or the data may be generated in vivo and stored on the device and recovered ex vivo. Alternatively, the data can be transmitted wirelessly from the device while the device is passing through the GI tract of the subject or in place within the reproductive tract of the subject.

In some embodiments, a method comprises: providing a device comprising one or more dilution chambers and dilution fluid; transferring all or part of a fluid sample obtained from the GI tract or reproductive tract of the subject into the one or more dilution chambers in vivo; and combining the fluid sample and the dilution fluid to produce one or more diluted samples in the one or more dilution chambers.

In certain embodiments, a method comprises: providing an ingestible device comprising one or more dilution chambers; transferring all or part of a fluid sample obtained from the GI tract into the one or more dilution chambers comprising sterile media; culturing the sample in vivo within the one or more dilution chambers to produce one or more cultured samples; and detecting bacteria in the one or more cultured samples.

In some embodiments, a method comprises: providing a device comprising one or more dilution chambers; transferring all or part of a fluid sample obtained from the GI tract or reproductive tract into the one or more dilution chambers; combining all or part of the fluid sample with a dilution fluid in the one or more dilution chambers; and detecting the analyte in the one or more diluted samples.

In certain embodiments, a device comprises: one or more dilution chambers for diluting a fluid sample obtained from the GI tract or reproductive tract; and dilution fluid for diluting the sample within the one or more dilution chambers.

In some embodiments, the device comprises: one or more dilution chambers for culturing a fluid sample obtained from the GI tract; sterile media for culturing the sample within the one or more dilution chambers; and a detection system for detecting bacteria.

In certain embodiments, a device comprises: one or more dilution chambers for culturing a fluid sample obtained from the GI tract; sterile media for culturing the sample within the one or more dilution chambers; and a detection system for detecting bacteria.

Also provided is the use of a device as described herein for diluting one or more samples obtained from the GI tract or reproductive tract of a subject. In one embodiment, there is provided the use of an ingestible device as described herein for detecting cells and/or analytes in vivo within the gastrointestinal (GI) tract of a subject.

Further provided is a system comprising a device as described herein and a base station. In one embodiment, the device transmits data to the base station, such as data indicative of the concentration and/or types of bacteria in the GI tract of the subject. In one embodiment, the device receives operating parameters from the base station. Some embodiments described herein provide an ingestible device for obtaining one or more samples from the GI tract or reproductive tract of a subject and diluting and/or culturing all or part of the one or more samples. The ingestible device includes a cylindrical rotatable element having a port on the wall of the cylindrical rotatable element. The ingestible device further includes a shell element wrapping around the cylindrical rotatable element to form a first dilution chamber between the cylindrical rotatable element and the shell element. The shell element has an aperture that exposes a portion of the wall of the cylindrical rotatable element to an exterior of the ingestible device.

In some embodiments, the ingestible device includes one or more dilution chambers for receiving a fluid sample from the GI tract or reproductive tract of a subject or a dilution thereof. In some embodiments, one or more dilutions of the fluid sample are cultured in one or more dilution chambers. In some embodiments, the dilution chambers each define a known volume, optionally the same volume or different volumes. In some embodiments, the dilution chambers define a fluid volume ranging from about 10 µL to about 1 mL. The dilution chambers may define a fluid volume less than or equal to about 500 µL, less than or equal to about 250 µL, less than or equal to about 100 µL, or less than or equal to about 50 pt. In some embodiments, the dilution chambers define a fluid volume of greater than or equal to about 10 µL, greater than or equal to about 20 µL, greater than or equal to about 30 µL, or greater than or equal to about 50 µL. In some embodiments, the dilution chambers define a fluid volume between about 10 µL and 500 µL, between about 20 µL and 250 µL, between about 30 µL and 100 µL or about 50 pt.

In some embodiments, dilution fluid in the device is combined with all or part of the fluid sample, or dilution thereof, to produce one or more dilutions. In some embodiments, the dilution fluid is sterile media suitable for culturing one or more cells within the dilution chambers.

In some embodiments, the one or more dilution chambers may be filled with the dilution fluid prior to a patient ingesting the ingestible device. Alternatively, in another embodiment, the dilution fluid may be added into the one or more dilution chambers in vivo from a reservoir of the ingestible device. Sampling and dilution of the GI fluid sample may take place in vivo. For example, an actuator of the ingestible device may pump the dilution fluid from the reservoir into a dilution chamber when it is determined that the ingestible device is located at a predetermined location within the GI tract. In some embodiments, the dilution chambers each contain a volume of sterile media suitable for culturing a fluid sample from the GI tract or reproductive tract. In some embodiments, the dilution chambers are at least 95%, at least 97%, at least 98%, or at least 99% full of sterile media. In some embodiments, the dilution chambers each contain oxygen to facilitate aerobic bacteria growth. In another embodiment a non-dilution chamber includes oxygen and is added to one or more of the dilution chambers to facilitate aerobic bacteria growth.

In some embodiments, the culturing may take place in vivo immediately after the GI fluid sample has been diluted. Or alternatively, the culturing may take place ex vivo, e.g., when the ingestible device has been evacuated and recovered such that the dilution chamber containing the diluted GI fluid sample may be extracted and the culturing may be performed in a laboratory. The recovery of the ingestible device may be performed in a similar manner as embodiments described in U.S. Provisional Application No. 62/434,188, filed on Dec. 14, 2016, which is herein expressly incorporated by reference in its entirety.

In some embodiments, the dilution fluid includes one or more agents for inhibiting the growth of fungus. In some embodiments, the anti-fungal agent is amphotericin B. In some embodiments, the dilution fluid contains about 2.5 mg/L of Amphotericin B.

In some embodiments, the media includes one or more antimicrobial agents in order to determine antibiotic sensitivity/resistance of bacteria within the fluid sample. For example, if bacteria grow in a dilution chamber containing media without antibiotics but do not grow in a separate dilution chamber containing media including antimicrobial agents, the sample may be identified as containing bacteria sensitive to that antibiotic. Alternatively, if bacteria grow in both dilution chambers (with and without antibiotics), the sample can be identified as containing bacteria resistant to that antibiotic. In some embodiments, the bacteria remaining in the dilution chamber(s) are quantified using, e.g., any detection and/or quantification method described herein. In some embodiments, the presence and/or absence of a particular type of bacteria in the dilution chamber (e.g., a bacteria of a particular genus, species and/or strain) is detected and/or quantified using a method described herein.

In another embodiment, the dilution fluid includes a substrate or reagent for measuring bacterial activity or response. For example, in some embodiments, the dilution fluid includes one or more conjugated bile acids and deconjugated bile acids or a reduction in conjugated bile acids are detected in the diluted samples and/or cultured samples as a sign of bile salt hydrolase activity. In another embodiment, the substrate may be an enzyme, for example, glutamate dehydrogenase (GDH). In the case of GDH, it may be used to detect an antigen that is produced in high amounts by *C. difficile*, both toxin and non-toxin producing strains. This test indicates if *C. difficile* is present but not necessarily if the bacteria are producing toxins.

In another embodiment, products of the bacteria are detected or measured while the bacteria are being cultured in the media. For example, *Clostridium difficile* toxin A can be measured to detect if bacteria are producing toxins.

In some embodiments, the methods and devices described herein may be used to obtain, dilute, culture and/or detect eukaryotic cells from the subject. For example, epithelial cells or PBMC's from the GI tract can be diluted or cultured in the ingestible device. Optionally, the eukaryotic cells may be analyzed within the device and/or collected once the device has exited. In some embodiments, the dilution fluid further includes a substrate or reagent for measuring eukaryotic activity or response in vivo. For example, in some embodiments, a biomarker in the sample may be detected, analyzed and/or quantitated. The detection of the biomarker in the sample may be used to diagnose or monitor a disease or disorder or the treatment thereof. Exemplary biomarkers are described in detail above, including biomarkers associated with GI disorders, inflammation, and cancer. In some embodiments, the biomarker is present on a eukaryotic cell present in the sample. In some embodiments one or more biomarkers associated with inflammation and/or cancer are detected within the diluted samples and/or cultured samples. In some embodiments, measuring the amount of cell growth proteins or cell-cell adhesion proteins (e.g., beta-catenin, ErbB1, EbrB2, ErbB3, pAkt, c-Met, p53) produced may be correlated to the presence or absence of oncogenic cells, while measuring cytokines (e.g., IL-6 and TNF-alpha) may be correlated with inflammation.

In some embodiments, a fluid sample is transferred from the GI tract into one or more dilution chambers while the ingestible device is passing through the GI tract of a subject in vivo. By controlling when the fluid sample is transferred into the one or more dilution chambers, it is possible to obtain a fluid sample from a particular region of the GI tract. In operation, the exterior of the ingestible device will be in contact with biological fluids in the GI tract. As the ingestible device travels along the GI tract, it will typically be surrounded by fluid that is characteristic of that section of the GI tract. For example, when the ingestible device is in the stomach, the device will be in contact with stomach fluid which may include gastric acid, digestive enzymes, and partially digested food. When the ingestible device is in the jejunum, the device will be in contact with jejunal fluid.

In some embodiments, the device has one or more ports, valves and/or pumps that are used, either alone or in combination, for controlling the transfer of fluid from the GI tract or reproductive tract into the one or more dilution chambers. The device may also contain one or more ports, valves and/or pumps for controlling the transfer of fluid between dilution chambers within the device, optionally to produce a serial dilution of the original fluid sample from the GI tract or reproductive tract. In some embodiments, the device described herein may be used for obtaining, diluting, culturing, or detecting cells from other parts of the body, such as but not limited to the female reproductive tract, and/or the like. Compositions and methods for sampling the GI or reproductive tract are discussed in greater detail in U.S. Provisional Application No. 62/376,688 filed Aug. 18, 2016, which is hereby incorporated by reference herein in its entirety.

In some embodiments, the device includes a microcontroller for controlling the one or more ports, valves and/or pumps. In some embodiments, the microcontroller is programmed to control the ports, valves and/or pumps in response to data from the one or more environmental sensors. Alternatively or in addition, the microcontroller is programmed to control the ports, valves and/or pumps in response to wireless a signal from a base station or in response to a signal generated by the microcontroller, such as a timer.

In some embodiments the device includes a pump having an input conduit on the exterior of the device and an output conduit into a first dilution chamber. In some embodiments, the pump is operational to transfer fluid from the GI tract into the first dilution chamber. Preferably, the pump is controllable to transfer a predetermined volume of liquid from the GI tract into a dilution chamber. In some embodiments, the device includes a pump controllable to transfer a predetermined volume of liquid between dilution chambers, optionally the same pump or a different pump as used to transfer the fluid sample into the first dilution chamber. In some embodiments, the pump is a solenoid pump. In some embodiments, the pump is controllable to transfer a fluid volume from about 1 µL to about 50 µL, about 2 µL to about 20 µL, about 3 µL to about 15 µL, or about 5 µL.

In another embodiment, the device includes a port for receiving a fluid sample from the GI tract or reproductive tract. In some embodiments, the port is exposed to the exterior of the device. Optionally, the device includes a cover movable to expose the port to the exterior of the device. In operation, when the port is exposed fluid from the GI tract or reproductive tract enters into the port through surface tension, movement of the subject and/or peristaltic effects. Optionally, the port is coated with a hydrophilic coating to encourage fluid to flow into the port.

In some embodiments, the port is movable from an open position such that the port is exposed to the exterior of the device, to a first position such that the port is in fluid communication with a first dilution chamber. In some embodiments, moving the port from the open position to the first position transfers a predetermined volume of a fluid sample from the GI tract or reproductive tract into the first dilution chamber. For example, in some embodiments the port defines a fluid volume of about 1 µL to about 50 µL, about 2 µL to about 20 µL, about 3 µL to about 15 µL, or about 5 µL.

A skilled person will appreciate that when the port is in fluid communication with the first dilution chamber, the port and the first dilution chamber will define a combined volume such that any fluid in the port and dilution chamber will mix to form a dilution. In some embodiments, the mixing of fluid will be enhanced through the peristaltic action of the GI tract as well as movement of the subject. In some embodiments, the first incubation chamber contains dilution fluid such as sterile media and moving the port to the first position produces a first dilution including a predetermined volume of fluid sample from the GI tract and a predetermined volume of dilution fluid. For example, in some embodiments the port has a fluid volume of 5 µl and the first dilution chamber has 45 µL of dilution fluid, such that the first dilution is a 10 fold dilution of the fluid sample.

In some embodiments, the first dilution is cultured to produce a single cultured sample and cells and/or analytes are detected within the cultured sample. Alternatively, in some embodiments a portion of the first dilution is transferred to one or more additional dilution chambers to produce a serial dilution of the fluid sample from the GI tract. In some embodiments, the serial dilution is produced by controlling the transfer of fluid between the dilution chambers.

For example, in some embodiments the ingestible device includes a port movable to sequentially align with one or more additional i dilution chambers, thereby transferring a portion of first dilution of the fluid sample to each additional dilution chamber. Alternatively or in addition, one or more pumps and/or valves may be used to sequentially transfer a portion of the fluid sample or dilution thereof to each dilution chamber.

In some embodiments, the device includes a port movable from a first position in fluid communication with a first dilution chamber to a second position such that the port is in fluid communication with a second dilution chamber. In some embodiments, the port is movable from the second position to a third position such that the port is in fluid communication with a third dilution chamber. In some embodiments, the port is movable from the third position to a fourth position such that the port is in fluid communication with a fourth dilution chamber. In some embodiments, the port is movable from the fourth position to a fifth position such that the port is in fluid communication with a fifth dilution chamber. Optionally, the device may contain more than five dilution chambers for producing more than five dilutions of the original fluid sample. In some embodiments, the dilution chambers are suitable for culturing the dilutions in vivo within the device.

In some embodiments, the port is a depression on the surface of a movable element. In some embodiments, the movable element is coupled to an actuator for moving the port relative to the positions of the one of more dilution chambers. Optionally, the actuator is an electric motor.

In some embodiments the port is a depression on the surface of a rotatable element. In some embodiments, the device includes an actuator coupled to the rotatable element for rotating the port to align with one or more dilution chambers. In some embodiments, the dilution chambers are positioned circumferentially around the axis of rotation of the rotatable element. In some embodiments, rotating the rotatable element sequentially moves the port from the open position to the first position and optionally one or more of the second position, third position and fourth position.

FIG. 27 shows one embodiment of a portion of an ingestible device 4000 with a port 4154*b* in an open position to the exterior of the ingestible device 400. The ingestible device 400 may include a cylinder-shaped rotatable element 4150 that includes sampling ports 4154a-b on the wall of the rotatable element 4150. The sampling chamber 4150 is wrapped by a shell element 4140 with dividers to form a series of dilution chambers 4151a-n between the shell element 4140 and the rotatable element 4150. In operation, when the ingestible device 4000 determines the device itself arrives at a target location within the GI tract, the rotatable element 4150 may be rotated into an open position such that an aperture of the shell element 4140 is aligned with the port 4154b on the wall of the rotatable element 4150 and the port 4154b is exposed to the exterior of the ingestible device 4000 through the aperture. In this way, fluid from the GI tract can enter the port 4154b and occupy the volume defined by the port 4154b. In the embodiment shown in FIG. 27, the port 4154b may be a depression on the surface of a rotatable element 4150 and a number of dilution chambers 4151a-n are positioned circumferentially around the axis of rotation of the rotatable element 4150. As previously discussed, each of the dilution chambers 4151a-n may store a dilution fluid. In some embodiments, the depression is a cylindrical depression. Optionally, the depression may be a rectangular depression, or any concave depression forming a regular or irregular shape. In another embodiment, the port 4154b may be connected to a chamber (not shown) within the rotatable element 4150 to create an enlarged space to store the GI fluid sample from the external environment of the ingestible device.

In some embodiments, the ingestible device 4000 may further include a controller and an actuator. The controller may determine that the ingestible device 4000 is located at a target location of the GI tract, and then the actuator may trigger the rotation of the rotatable element 4150 to align the port 4154b at the open position to initiate the sampling. For example, the housing of ingestible device 4000 may have a pH-sensitive enteric coating to detect or otherwise be sensitive to a pH level of the environment external to the ingestible device 4000, based on which the controller may determine whether the ingestible device has arrived at a target location. For another example, the ingestible device 4000 may include an optical sensing unit that transmits an illumination to the environment and collects a reflectance, based on which, the regio-specific location of the ingestible device 4000 may be identified based on optical characteristics of the reflectance. Further embodiments of localization of the ingestible device 4000 may be found in PCT International Application No. PCT/US2015/052500, filed on Sep. 25, 2015, which is herein expressly incorporated by reference in its entirety.

FIG. 28 shows one embodiment of a portion of an ingestible device with a port 4154b at a first position aligned with a first dilution chamber 4151a. In operation, the rotatable element 4150 may be rotated to align the sampling port 4154b and the first dilution chamber 4151a such that the fluid sample from the GI tract stored within the volume of the sampling port 4154b can be combined with dilution fluid in the first dilution chamber to form a first dilution. The first dilution may then occupy the combined volume of the port 4154b and first dilution chamber 4151a. Optionally, the rotatable element 4150 may be subsequently rotated to a second position such that the port 4154b containing a portion of the first dilution is then moved to be aligned and in fluid communication with another dilution chamber, e.g., a second dilution chamber that is next to the first dilution chamber along the rotational direction. In this way, the first dilution stored within the port 154b may then again be diluted with the dilution fluid stored within the second dilution chamber. Similarly, if the rotatable element 4150 keeps rotating and allows the port 4154b to be serially aligned with each dilution chamber, then the original GI fluid sample may be diluted serially and each dilution chambers 4151a-n may be left with a diluted GI fluid sample at a different dilution ratio.

FIG. 29 shows one embodiment of an element 4140 forming part of a set of 5 dilution chambers (e.g., including 4151a-b) for surrounding a rotatable element (e.g., 4150 in FIGS. 28 and 29) in an ingestible device as described herein. In some embodiments, the device may contain a single dilution chamber. Alternatively, the device may contain 2, 3, 4, 5, 6, 7, 8 or greater than 8 dilution chambers.

In some embodiments, each dilution chamber 4151a-n may be filled with a dilution fluid prior to the ingestible device 4000 being administered. In another embodiment, the dilution fluid may be stored in a separate reservoir (not shown) within the ingestible device 4000. At the time when the ingestible device 4000 is determined to be at a target location within the GI tract, a pumping mechanism may pump the dilution fluid into one or more dilution chambers 4151a-b via one or more outlet (not shown) of the reservoir. The pumping mechanism and the reservoir that stores the dilution fluid, may take a form similar to the electromechanical delivery mechanism of an ingestible device as described in U.S. Provisional Application No. 62/385,553, filed on Sep. 9, 2016, which is herein expressly incorporated by reference in its entirety.

In some embodiments, the shell element 4140 may have valves or pumps (not shown) between the dilution chambers 4151a-n. For example, the diluted fluid from a first dilution chamber may be pumped into a second dilution chamber via a valve between the two chambers. The pump and valve mechanism may take a form similar to the electromechanical delivery mechanism of an ingestible device as described in U.S. Provisional Application No. 62/385,553, filed on Sep. 9, 2016, which is herein expressly incorporated by reference in its entirety.

In some embodiments, the method and devices described herein involve combining a fluid sample, or dilution thereof, with dilution fluid to produce one or more dilutions of the fluid sample. For example, in some embodiments the fluid sample is combined with dilution fluid in a first dilution chamber to produce a first dilution, a portion of the first dilution is combined with dilution fluid in a second dilution chamber to produce a second dilution, a portion of the second dilution is combined with dilution fluid in a third dilution chamber to produce a third dilution, and optionally a portion of the third dilution is combined with dilution fluid in a fourth dilution chamber to produce a fourth dilution, and optionally a portion of the fourth dilution is combined with dilution fluid in a fifth dilution chamber to produce a fifth dilution.

The relative dilution of the fluid sample will depend on the relative amount of fluid sample, or dilution thereof, and dilution fluid that is combined in each dilution chamber. In some embodiments, the fluid sample, or dilution thereof, is combined with dilution fluid at a ratio between about 1:1 and about 1:1000, between about 1:1 and 1:100, between about 1:1 and about 1:20, or between about 1:1 and about 1:10. Optionally, the relative amounts of fluid sample, or dilution thereof, and dilution fluid that are combined in each dilution chamber are varied such that different dilution chambers contain different dilutions. In some embodiments, the method and devices described herein produce a series of 10-fold dilutions of the fluid sample. In some embodiments, the methods and devices described herein produce a series of dilutions of a fluid sample such that for a given bacterial concentration in the fluid sample, some of the dilutions will not be expected to contain any bacteria, and some of the dilutions will be expected to contain bacteria and therefore exhibit bacterial growth when cultured.

As set out in examples below, determining the presence or absence of bacterial growth in one or more dilutions can be used to estimate the concentration of bacteria within the original fluid sample from the GI tract. The use of a dilution series and a binary detection system that detects the presence or absence of bacterial growth presents a number of advantages over more complicated detection systems that seek to directly quantify the concentration of bacteria within a sample. For example, binary detection systems are robust and amenable to miniaturization and therefore suitable for use in an ingestible device as described herein. Also, diluting the fluid sample increases the dynamic range while reducing interference. Accordingly, in some embodiments the methods and devices described herein include detecting the presence or absence of the growth of a cell, optionally bacterial growth. In some embodiments, the methods and devices described herein include detecting the presence or absence of bacterial growth in one or more dilutions of the fluid sample from the GI tract.

In some embodiments, the presence or absence of bacterial growth in one or more dilutions is used to estimate the concentration of bacteria in the fluid sample. For example, in some embodiments a fluid sample of about 5 μL is diluted about 10000 times in one of the dilution chambers and detecting the presence of bacterial growth in the dilution chamber is indicative of a bacterial concentration of $10^5$ or greater colony forming units/mL (CFU/mL) in the fluid sample. 10 μL of a fluid sample with a bacterial concentration of $10^4$ CFU/mL would contain about 100 CFU. A 10000-fold dilution of such a 10 μL fluid sample would be unlikely to contain any CFUs or bacteria (theoretically 0.01 bacteria) and therefore would not be expected to exhibit bacterial growth when cultured.

Alternatively, in some embodiments the methods and devices described herein include detecting a level of bacterial concentration within one or more cultured samples. For example, in some embodiments a quantifiable property of a cultured sample is measured in order to provide an estimate of the level of bacteria within the cultured samples in order to estimate the concentration of bacteria within the original fluid sample.

In some embodiments, the devices described herein include a detection system for detecting one or more cells and/or analytes. In some embodiments the cells are bacteria (e.g., bacteria of a particular genus, species and/or strain). Different detection systems known in the art for detecting bacteria may be used with the device as described herein. In some embodiments, the detection system detects the presence or absence of bacterial growth within a diluted sample. In some embodiments, the detection system detects the presence or absence of bacterial growth within a cultured sample. Alternatively or in addition, the detection system detects a level of bacteria within one or more cultured samples. For example, in some embodiments a Coulter counter is used to detect and/or quantify bacteria in the fluid samples, dilutions thereof or cultured samples. In another embodiment, an optical detection system is used to detect and/or quantify bacteria within the fluid samples, dilutions thereof or cultured samples.

In some embodiments, the detection system detects cells and/or analytes in a dilution or cultured sample within the one or more dilution chambers. Alternatively, the device includes one or more separate detection chambers and the detection system detects cells and/or analytes in the fluid sample or dilutions therefor within the detection chamber. In some embodiments, fluid communication between one or more dilution chambers and one or more detection chambers is controlled by one or more ports, valves and/or pumps.

In some embodiments, the detection system detects cells and/or analytes at a plurality of time points. For example, in some embodiments the detection system detects bacteria within the sterile media prior to combining the fluid sample from the GI tract and the sterile media in order to ensure that any bacterial growth is due to the bacteria introduced into the dilution chambers from the GI tract. In some embodiments, the detection system detects bacteria at a first time point and at a second time point. In some embodiments, the second time point is selected to allow for the growth of bacteria within the cultured fluid sample relative to the first time point. For example, in some embodiments the second time point is between about 1 hour and 6 hours, between about 1 hour and 4 hours, or between about 2 hours and 4 hours after the first time point. In some embodiments, detecting bacteria at the first time point serves as a control.

In some embodiments, the detection system detects the level of bacteria at three or more time points to determine a growth curve for bacteria in the one or more cultured samples. For example, the level of bacteria may be detected within one or more culture samples every 30 or 60 minutes after a sample is collected for a total of 2-12 hours; thereby producing a growth curve. The growth curve may then be compared to one or more standard growth curves. In some embodiments, the standard growth curves are representative of the growth of samples with a known concentration of bacteria. In some embodiments, the standard growth curves are representative of growth curves from subjects with Small Intestinal Bacterial Overgrowth (SIBO).

In some embodiments, the embodiments described herein use an optical detection system for detecting one or more cells and/or analytes. In some embodiments, the optical detection system includes a light source and a photodetector. In some embodiments, the light source and photodetector are operable to define a light path through a dilution chamber or detection chamber. In some embodiments, the optical detection system measures the absorbance of light or optical density along the light path at one or more wavelengths.

In some embodiments, the optical detection system measures the absorbance of light at one or more wavelengths between 400 nm and 1000 nm. In some embodiments, the optical detection system measures the absorbance of light at one or more wavelengths between about 500 and 700 nm. In some embodiments, the optical detection system measures the absorbance of light at about 600 nm.

In some embodiments, the device described herein includes one or more environmental sensors for measuring environmental data of the GI tract or reproductive tract external to the device in the subject. In some embodiments, the environmental data is used to help determine one or more characteristics of the GI tract or reproductive tract of the subject such as for the diagnosis of a medical condition. Alternatively or in addition, the environmental data is used to determine the location of the device within the GI tract of the subject. In some embodiments, the one or more environmental sensors include a capacitance sensor, a temperature sensor, an impedance sensor, a pH level sensor and/or a light sensor. In some embodiments, the one or more environmental sensors measure pH, temperature, transit times, or combinations thereof. Examples of devices that detect pH changes include Medimetrics' IntelliCap® technology (see Becker, Dieter, et al. "Novel orally swallowable IntelliCap® device to quantify regional drug absorption in human GI tract using diltiazem as model drug." *AAPS PharmSciTech* 15.6 (2014): 1490-1497) and Rani Therapeutics' Auto-Pill™ technology (see U.S. Pat. No. 9,149,617).

In some embodiments, data regarding the location of the device within the GI tract of the subject is used to determine when to obtain a fluid sample from the GI tract and transfer the fluid sample into the one or more dilution chambers. Accordingly, in some embodiments the device includes a microcontroller configured to transfer the fluid sample from the GI tract of the subject to the one or more dilution chambers based on the location of the device within the GI tract.

In some embodiments, the device includes a communication sub-unit that is configured to receive operating parameters from an external base station and/or transmit data to an external base station. Also provided is a system including a device as described herein and an external base station. In some embodiments, the operating parameters include timing instructions for obtaining a fluid sample from the GI tract and transferring the sample into one or more dilution chambers. In some embodiments, the data transmitted to the external base station includes data indicative of the presence of absence of bacterial growth in the cultured samples.

In general, it is possible for the ingestible device to obtain different samples from different predetermined regions of the GI tract, or for certain actions within the ingestible device to be triggered based on its location in the GI tract. For example, it may be possible for the ingestible device to use various combinations of light emitting diodes and sensors to determine whether the device is in the stomach, small intestine, or large intestine. This may be done by emitting light at different wavelengths, measuring the level of light reflected at each wavelength by the environment surrounding the ingestible device, and using this information to determine an approximate location of the ingestible device based on the different reflectance properties of the various different portions of the GI tract. Once the ingestible device determines that it is in a particular predetermined portion of the GI tract (e.g., the small intestine, or a specific part of the small intestine such as the jejunum), the ingestible device may be configured to obtain a sample from that portion of the GI tract, and store the sample in one or more sampling or incubation chambers within the ingestible device.

In another embodiment, an ingestible device may be localized using a gamma scintigraphy technique or other radio-tracker technology as employed by Phaeton Research's Enterion™ capsule (See Teng, Renli, and Juan Maya. "Absolute bioavailability and regional absorption of ticagrelor in healthy volunteers." *Journal of Drug Assessment* 3.1 (2014): 43-50), or monitoring the magnetic field strength of permanent magnet in the ingestible device (see T. D. Than, et al., "A review of localization systems for robotic endoscopic capsules," *IEEE Trans. Biomed. Eng.*, vol. 59, no. 9, pp. 2387-2399, September 2012).

In still other embodiments, an ingestible device may include a camera for generating video imaging data of the GI tract which can be used to determine, among other things, the location of the device. Examples of video imaging capsules include Medtronic's PillCam™, Olympus' Endocapsule®, and IntroMedic's MicroCam™ (see Basar et al. "Ingestible Wireless Capsule Technology: A Review of Development and Future Indication" *International Journal of Antennas and Propagation* (2012); 1-14). Other imaging technologies include thermal imaging cameras, and those that employ ultrasound or Doppler principles to generate different images (see Chinese patent application CN104473611: "Capsule endoscope system having ultrasonic positioning function").

LOCI

In some embodiments, the application provides an ingestible device for detecting an analyte in a sample, wherein the ingestible device includes a sampling chamber that is configured to hold a composition including: (1) a plurality of donor particles, each of the plurality of donor particles including a photosensitizer and having coupled thereto a first analyte-binding agent (e.g., an antigen-binding agent) that binds to the analyte, wherein the photosensitizer, in its excited state, is capable of generating singlet oxygen; and (2) a plurality of acceptor particles, each of the plurality of acceptor particles including a chemiluminescent compound and having coupled thereto a second analyte-binding agent (e.g., an antigen-binding agent) that binds to the analyte, wherein said chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap. In some embodiments, the first and/or second analyte binding agent(s) is an antibody. In some embodiments, the first and/or second analyte binding agent(s) is an affimer. In some embodiments, the first and/or second analyte binding agent(s) is an antigen-binding agent is an aptamer.

In some embodiments, this application provides an ingestible device for detecting an analyte in a sample, wherein the ingestible device includes a sampling chamber that is configured to hold a member made of an absorptive material (e.g., an absorptive pad or absorptive sponge) having absorbed therein a composition including: (1) a plurality of donor particles, each of the plurality of donor particles including a photosensitizer and having coupled thereto a first analyte-binding agent (e.g., an antigen-binding agent) that binds to the analyte, wherein the photosensitizer, in its excited state, is capable of generating singlet oxygen; and (2) a plurality of acceptor particles, each of the plurality of acceptor particles including a chemiluminescent compound and having coupled thereto a second analyte-binding agent (e.g., an antigen-binding agent) that binds to the analyte, wherein said chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In some embodiments, the absorptive material is an absorptive sponge. In some embodiments, the absorptive sponge is a hydrophilic sponge. In some embodiments, the absorptive sponge is selected from the group consisting of: fibers of cotton, rayon, glass, polyester, polyethylene, polyurethane, nitrocellulose, and the like. In some embodiments, the absorptive sponge is polyester or polyethylene. In some embodiments, the absorptive sponge is selected from the group consisting of: Ahlstrom Grade 6613H, Porex 1/16" Fine Sheet 4897, Porex 1/8" Fine Sheet 4898, Porex 4588 0.024" Conjugate release pad, Porex PSU-567, and Filter Papers. In some embodiments, the absorptive sponge is Ahlstrom Grade 6613H (Lot 150191) or Porex PSU-567. The present application further provides a method for preparing an absorptive material as described herein, including the step of injecting into the absorptive material an aqueous solution including a composition of the present application. In some embodiments, the method including a step of drying the absorptive material having absorbed therein the aqueous solution at a temperature in the range of 0-100° C., 0-50° C., 0-40° C., 0-30° C., 0-20° C., 0-10° C., or 0-4° C.), for a time period sufficient to reduce the total water content to below 50%, 40%, 30%, 20%, 15%, 10%, 7%, 5%, 3%, 1%, 0.7%, 0.5%, 0.3%, or 0.1% by weight.

In some embodiments, the disclosure provides a method of measuring the presence, absence or amount of one or more analytes from one or more samples in the gastrointestinal tract. In general, in embodiments involving LOCI, the analyte is capable of being bound by two analyte-binding agents at the same time to allow for detection of the analyte using the methods described herein. Exemplary analytes that can be be used in embodiments involving LOCI include, but are not limited to, proteins, peptides, and microorganisms (e.g., bacteria). Various examples of analytes suitable for use in embodiments involving LOCI are described above.

In some embodiments the one or more analytes are measured multiple times, for example, at different time points or at different locations. In one embodiment, a single device measures one or more analytes or more time points or locations; thereby creating a "molecular map" of a physiological region. Measurements can be taken at any location in the gastrointestinal tract. For example, in one aspect, analytes from samples from one or more of the duodenum, jejunum, ileum, ascending colon, transverse colon or descending colon can be measured to create a molecular map of the small and large intestine. In one aspect, the sample is from the duodenum. In one aspect, In one aspect, the sample is from the jejunum. In one aspect, the sample is from the ileum. In one aspect, the sample is from the ascending colon. In one aspect, the sample is from the transverse colon. In one aspect, the sample is from the descending colon.

In another aspect, a series of measurements can be taken over a shorter distance of the gastrointestinal tract (e.g., the ileum) to create a higher resolution molecular map. In some embodiments, previous endoscopic imaging may identify a diseased area for molecular mapping (e.g., biomarker mapping). For example, a gastroenterologist may use imaging (e.g., an endoscope equipped with a camera) to identify the presence of Crohn's disease in the ileum and cecum of a patient, and the methods and techniques of the present invention herein may be used to measure inflammation-associated analytes in this diseased area of the patient. In a related embodiment, the inflammation-associated analytes, or any analyte, may be measured every one or more days to monitor disease flare-ups, or response to therapeutics. Exemplary inflammation-associated analytes include anti-glycan antibodies; anti-*Saccharomyces cerevisiae* antibodies (ASCA); anti-laminaribioside antibodies (ALCA); anti-chitobioside antibodies (ACCA); anti-mannobioside antibodies (AMCA); anti-laminarin (anti-L) antibodies; anti-chitin (anti-C) antibodies; anti-outer membrane porin C (anti-OmpC) antibodies; anti-Cbir1 flagellin antibodies; anti-I2 antibodies (see, e.g., Mitsuyama et al. (2016) *World J. Gastroenterol.* 22(3): β04-10); autoantibodies targeting the exocrine pancreas (PAB); perinuclear anti-neutrophil antibody (pANCA); calprotectin; a cytokine such as vascular endothelial growth factor (VEGF), C-reactive protein (CRP), interleukin-6 (IL-6), or tumor necrosis factor alpha (TNF-α); an adhesion molecule such as intracellular adhesion molecule (ICAM) (e.g., ICAM-1) or vascular adhesion molecule (VCAM) (e.g., VCAM-1); or serum amyloid A (SAA).

Photosensitizers that are to be excited by light will be relatively photostable and will not react efficiently with singlet oxygen. Several structural features are present in most useful sensitizers. Most sensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures. Typical sensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment. Examples of other photosensitizers that may be utilized in the present invention are those that have the above properties and are enumerated in N. J. Turro, "Molecular Photochemistry," page 132, W. A. Benjamin Inc., N.Y. 1965.

In some embodiments, the photosensitizers are relatively non-polar to assure dissolution into a lipophilic member when the photosensitizer is incorporated in an oil droplet, liposome, latex particle, etc.

In some embodiments, the photosensitizers suitable for use herein include other substances and compositions that can produce singlet oxygen with or without activation by an external light source. Thus, for example, molybdate ($MoO_4^=$) salts and chloroperoxidase and myeloperoxidase plus bromide or chloride ion (Kanofsky, *J. Biol. Chem.* (1983) 259 5596) have been shown to catalyze the conversion of hydrogen peroxide to singlet oxygen and water. Either of these compositions can, for example, be included in particles and used in the assay method wherein hydrogen peroxide is included as an ancillary reagebly, chloroperoxidase is bound to a surface and molybdate is incorporated in the aqueous phase of a liposome. Also included within the scope of the invention as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A chemiluminescent compound is a substance that undergoes a chemical reaction with singlet oxygen to form a metastable intermediate that can decompose with the simultaneous or subsequent emission of light within the wavelength range of 250 to 1200 nm. Exemplary chemiluminescent compounds suitable for use in the present application include those described in U.S. Pat. Nos. 6,251,581 and 7,709,273, and Patent Cooperation Treaty (PCT) International Application Publication No. WO1999/042838. Exemplary chemiluminescent compound includes the following:

| Chemiluminescer | Half-Life | Emission Max |
|---|---|---|
| Thioxene + Diphenyl anthracene: | 0.6 seconds | 430 nm |
| Thioxene + Umbelliferone derivative | 0.6 seconds | 500 nm |
| Thioxene + Europium chelate | 0.6 seconds | 615 nm |
| Thioxene + Samarium Chelate | 0.6 seconds | 648 nm |
| Thioxene + terbium Chelate | 0.6 seconds | 540 nm |
| N-Phenyl Oxazine + Umbelliferone derivative | 30 seconds | 500 nm |
| N-Phenyl Oxazine + Europium chelate | 30 seconds | 613 nm |
| N-phenyl Oxazine + Samarium Chelate | 30 seconds | 648 nm |
| N-phenyl Oxazine + terbium Chelate | 30 seconds | 540 nm |
| Dioxene + Umbelliferone derivative | 300 seconds | 500 nm |
| Dioxene + Europium chelate | 300 seconds | 613 nm |
| Dioxene + Samarium Chelate | 300 seconds | 648 nm |
| N-phenyl Oxazine + terbium Chelate | 300 seconds | 540 nm |

All of the above mentioned applications are hereby expressly incorporated by reference herein in their entireties. Emission will usually occur without the presence of an energy acceptor or catalyst to cause decomposition and light emission. In some embodiments, the intermediate decomposes spontaneously without heating or addition of ancillary reagents following its formation. However, addition of a reagent after formation of the intermediate or the use of elevated temperature to accelerate decomposition can be desirable for some chemiluminescent compounds. The chemiluminescent compounds are usually electron rich compounds that react with singlet oxygen, frequently with formation of dioxetanes or dioxetanones. Exemplary of such compounds are enol ethers, enamines, 9-alkylidenexanthans, 9-alkylidene-N-alkylacridans, aryl vinyl ethers, dioxenes, arylimidazoles and lucigenin. Other chemiluminescent compounds give intermediates upon reaction with singlet oxygen, which subsequently react with another reagent with light emission. Exemplary compounds are hydrazides such as luminol and oxalate esters.

The chemiluminescent compounds of interest will generally emit at wavelengths above 300 nanometers and usually above 400 nm. Compounds that alone or together with a fluorescent molecule emit light at wavelengths beyond the region where serum components absorb light will be of particular use in the present invention. The fluorescence of serum drops off rapidly above 500 nm and becomes relatively unimportant above 550 nm. Therefore, when the analyte is in serum, chemiluminescent compounds that emit light above 550 nm, e.g., above 600 nm may be suitable for use. In order to avoid autosensitization of the chemiluminescent compound, in some embodiments, the chemiluminescent compounds do not absorb light used to excite the photosensitizer. In some embodiments, the sensitizer is excited with light wavelengths longer than 500 nm, it will therefore be desirable that light absorption by the chemiluminescent compound be very low above 500 nm.

Where long wavelength emission from the chemiluminescent compound is desired, a long wavelength emitter such as a pyrene, bound to the chemiluminescent compound can be used. Alternatively, a fluorescent molecule can be included in the medium containing the chemiluminescent compound. In some embodiments, fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, $Eu(fod)_3$, $Eu(TTA)_3$, $Ru(bpy)_3^{++}$ (wherein bpy=2,2'-dipyridyl, etc. In general these dyes act as acceptors in energy transfer processes and in some embodiments, have high fluorescent quantum yields and do not react rapidly with singlet oxygen. They can be incorporated into particles simultaneously with the incorporation of the chemiluminescent compound into the particles.

In general, the particles are at least about 20 nm and not more than about 20 microns, usually at least about 40 nm and less than about 10 microns, e.g., from about 0.10 to 2.0 microns diameter, normally having a volume of less than 1 picoliter. Exemplary particles (including both donor and acceptor particles) suitable for use in the present application include those described in U.S. Pat. Nos. 6,251,581, and 7,709,273, and PCT International Publication No. WO1999/042838, which are hereby expressly incorporated by reference herein in their entireties. In some embodiments, a particle as used herein may be a bead make of suitable material. The particle (e.g., a bead) may be organic or inorganic, swellable or non-swellable, porous or non-porous, having any density, but in some embodiments, of a density approximating water, generally from about 0.7 to about 1.5 g/ml, may be suspendible in water, and composed of material that can be transparent, partially transparent, or opaque. The particles may or may not have a charge, and when they are charged, in some embodiments, they are negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles included of organic or inorganic polymers; lipid bilayers, e.g., liposomes, phospholipid vesicles; oil droplets; silicon particles; metal sols; cells; and dye crystallites.

The organic particles will normally be polymers, either addition or condensation polymers, which are readily dispersible in the assay medium. The organic particles will also be adsorptive or functionalizable so as to bind at their surface, either directly or indirectly, an analyte-binding agent and to bind at their surface or incorporate within their volume a photosensitizer or a chemiluminescent compound.

The particles can be derived from naturally occurring materials, naturally occurring materials which are synthetically modified and synthetic materials. Natural or synthetic assemblies such as lipid bilayers, e.g., liposomes and non-phospholipid vesicles, are suitable for use herein. Among organic polymers of particular interest are polysaccharides, particularly cross-linked polysaccharides, such as agarose, which is available as SEPHAROSE® (Pharmacia Biotech), dextran, available as SEPHADEX® (Pharmacia Biotech) and SEPHACRYL® (Pharmacia Biotech), cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also be dispersed water insoluble dyes such as porphyrins, phthalocyanines, etc., which may also act as photosensitizers. Particles may also include diatoms, cells, viral particles, magnetosomes, cell nuclei and the like.

Where the particles are commercially available, the particle size may be varied by breaking larger particles into smaller particles by mechanical means, such as grinding, sonication, agitation, etc.

In some embodiments, the particles are polyfunctional or are capable of being polyfunctionalized or are capable of being bound or coupled to or associated with an analyte-binding agent, photosensitizer, or chemiluminescent compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of an analyte-binding agent, chemiluminescent compound or photosensitizer to the particle is employed, the manner of linking is well known and is amply illustrated in the literature. See for example Cautrecasas, *J. Biol, Chem.,* 245:3059 (1970). The length of a linking group may vary widely, depending upon the nature of the compound being linked, the nature of the particle, the effect of the distance between the compound being linked and the particle on the binding of analyte-binding agents and the analyte and the like.

The photosensitizer and/or chemiluminescent compound can be chosen to dissolve in or noncovalently bind to the surface of the particles. In some embodiments, these compounds may be hydrophobic to reduce their ability to dissociate from the particle and thereby cause both compounds to associate with the same particle. This possibly can be further reduced by utilizing particles of only one composition that are associated with either the photosensitizer or chemiluminescent compound or by using two types of particles that differ in composition so as to favor association of the photosensitizer with one type of particle and association of the chemiluminescent compound with the other type of particle.

The number of photosensitizer or chemiluminescent molecules associated with each particle will on the average usually be at least one and may be sufficiently high that the particle consists entirely of photosensitizer or chemiluminescer molecules. In some embodiments, the number of molecules will be selected empirically to provide the highest signal to background in the assay. In some cases this will be best achieved by associating a multiplicity of different photosensitizer molecules to particles. In some embodiments, the photosensitizer or chemiluminescent compound to analyte-binding agent ratio in the particles should be at least 1, such as at least 100 to 1 up to over 1,000 to 1.

Generally, oil droplets are fluid particles included of a lipophilic compound coated and stabilized with an emulsifier that is an amphiphilic molecule such as, for example, phospholipids, sphingomyelin, albumin and the like.

The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are of di or higher functionality, generally having hydroxyl or amino groups.

The oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

An analyte-binding agent will usually be adsorbed to the surface of the oil droplet or bonded directly or indirectly to a surface component of the oil droplet. The analyte-binding agent may be incorporated into the liquid particles either during or after the preparation of the liquid particles. The analyte-binding agent will normally be present in from about 0.5 to 100, about 1 to 90, about 5 to 80 and about 50 to 100 mole percent of the molecules present on the surface of the particle.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, diapalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecylphosphate)-propanol, stearoyloxyethylene phosphate, phospholipids, dialkylphosphates, sodium dodecyl sulfate, cationic detergents, anionic detergents, proteins such as albumin, non-ionic detergents, etc.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can include a fluorocarbon oil or a silicone oil (silicon particle). Such droplets are described by Giaever in U.S. Pat. Nos. 4,634,681 and 4,619,904, each of is incorporated by reference herein in its entirety. These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Analyte-binding agents can be bound to the droplets in a number of ways. As described by Giaever, the particular analyte-binding agents, particularly a proteinoceous analyte-binding agent, can be coated on the droplets by introducing an excess of the analyte-binding agent into the aqueous medium prior to or after the emulsification step. Washing steps are desirable to remove excess analyte-binding agent. Functionalization of the oil introduces functionalities described above for linking to analyte-binding agents. Such functionalities can also be employed to link the droplets to a photosensitizer or a chemiluminescent compound. On the other hand, the photosensitizer or chemiluminescent compound will frequently be chosen to be soluble in the oil phase of the oil droplet and will not be covalently bound. When the oil is a fluorocarbon, a fluorinated photosensitizer or chemiluminescent compound will often be more soluble than the corresponding unfluorinated derivation. Other oil droplets described by Giaever also find use in the present invention.

In general, liposomes are microvesicles of approximately spherical shape and are one of the materials for use in the present invention. The liposomes have a diameter that is at least about 20 nm and not more than about 20 microns, usually at least about 40 nm and less than about 10 microns. In some embodiments, the diameter of the liposomes will be less than about two microns so as to limit settling or floatation.

The outer shell of a liposome consists of an amphiphilic bilayer that encloses a volume of water or an aqueous solution. Liposomes with more than one bilayer are referred to as multilamellar vesicles. Liposomes with only one bilayer are called unilamellar vesicles. Multilamellar vesicles are suitable for use in the present invention when using a lipophilic photosensitizer or chemiluminescent compound because of their ability to incorporate larger quantities of these materials than unilamellar vesicles. The amphiphilic bilayer is frequently included of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Suitable phospholipids include, but are not limited to, L-α-palmitoyl oleoyl-phosphatidylcholine (POPC), palmitoyl oleoylphosphatidyl-glycerol (POPG), L-α-dioleoylphosphatidylglycerol, L-α (dioleoyl)-phosphatidyl ethanolamine (DOPE) and L-α (dioleoyl)-phosphatidyl β-(4-(N-maleimidomethyl)-cyclohexane-1-carboxyamido)ethanol (DOPE-MCC).

The phospholipids in the bilayer may be supplemented with cholesterol and may be replaced with other amphiphilic compounds that have a polar head group, usually charged, and a hydrophobic portion usually included of two linear hydrocarbon chains. Examples of such substituents include dialkylphosphate, dialkoxypropylphosphates wherein the alkyl groups have linear chains of 12-20 carbon atoms, N-(2,3-di(9-(Z)-octa-decenyloxy))-prop-1-yl-N,N,N,-trimethyl-ammonium chloride (DOTMA), as disclosed in U.S. patent application Ser. No. 811,146 filed on Dec. 19, 1985, which is hereby incorporated herein by reference, sphingomyelin, cardiolipin, and the like.

In some embodiments, liposomes utilized in the present invention have a high negative charge density to stabilize the suspension and to prevent spontaneous aggregation.

For use in the present invention the liposomes should be capable of binding to an analyte-binding agent and be capable of having a photosensitizer or chemiluminescent compound associated with either the aqueous or the non-aqueous phase. The liposomes utilized in the present invention will usually have analyte-binding agents bound to the outer surface of the lipid vesicle.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 (which is incorporated by reference herein in its entirety) discloses a method of extruding liposomes under pressure through a uniform pore-size membrane to improve size uniformity.

Preparation of liposomes containing a hydrophobic or amphiphilic photosensitizer or a chemiluminescent compound dissolved in the lipid bilayer can be carried out in a variety of methods, including a method described by Olsen, et al., *Biochemica et Biophysica Acta,* 557(9), 1979. Briefly, a mixture of lipids containing the appropriate compound in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes, for example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of SEPHACRYL® S-1000 (Pharmacia Biotech). The column can be eluted with buffer and the liposomes collected. Storage in the cold prolongs shelf-life of the liposomes produced by this method. Alternatively the photosensitizer or chemiluminescent compound can be added to the liquid suspension following preparation of the liposomes.

Labeling of droplets and liposomes will often involve, for example, inclusion of thiol or maleimide or biotin groups on the molecules including the lipid bilayer. Photosensitizers, chemiluminescent molecules or analyte-binding agents may then be bound to the surface by reaction of the particles with one of these materials that is bound to a sulfhydryl reactive reagent, a sulfhydryl group, or avidin, respectively. Sulfhydryl reactive groups include alkylating reagents such as bromoacetamide and maleimide.

Analyte-binding agents can be attracted to the surface of the liposome particles by weak hydrophobic interactions, however such interactions are not generally sufficient to withstand the shear force encountered during incubation and washing. It is possible to covalently bond analyte-binding agents to a liposome particle that has been functionalized, for example by use of DOPE-MCC, as shown above, by combining said liposome with the selected analyte-binding agent functionalized with a mercaptan group. For example, if the analyte-binding agent is an antibody, it may be reacted with S-acetyl-mercaptosuccinic anhydride (SAMSA) and hydrolyzed to provide a sulfhydryl modified antibody.

Generally, latex signifies a particulate water suspendible water insoluble polymeric material usually having particle dimensions of 20 nm to 20 μm, e.g., 100 to 1000 nm in diameter. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyrridine, vinyl-chloride acrylate copolymers, and the like. Non-crosslinked polymers of styrene and carboxylated styrene or styrene functionalized with other active groups such as amino, hydroxyl, halo and the like are suitable for use herein. In some embodiments, copolymers of substituted styrenes with dienes such as butadiene will be used.

The association of the photosensitizer or chemiluminescent compound with latex particles utilized in the present invention may involve incorporation during formation of the particles by polymerization but will usually involve incorporation into preformed particles, usually by noncovalent dissolution into the particles. Usually a solution of the chemiluminescent compound or sensitizer will be employed. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. In some embodiments, solvents for incorporating photosensitizer are those that will not quench the triplet excited state of the photosensitizer either because of their intrinsic properties or because they can subsequently be removed from the particles by virtue of their ability to be dissolved in a solvent such as water that is insoluble in the particles. Aromatic solvents are also suitable for use herein, such as solvents that are soluble in the particle. For incorporating chemiluminescent compounds in particles a solvent should be selected that does not interfere with the luminescence because of their intrinsic properties or ability to be removed from the particles. In some embodiments, aromatic solvents may be used. Typical aromatic solvents include dibutylphthalate, benzonitrile, naphthonitrile, dioctylterephthalate, dichlorobenzene, diphenylether, dimethoxybenzene, etc.

Except when the photosensitizer or chemiluminescent compound is to be covalently bound to the particles, it may be suitable to use electronically neutral photosensitizers or chemiluminescent compounds. In some embodiments, the liquid medium selected does not soften the polymer beads to the point of stickiness. One technique includes suspending the selected latex particles in a liquid medium in which the photosensitizer or chemiluminescent compound has at least limited solubility. In some embodiments, the concentrations of the photosensitizer and chemiluminescent compound in the liquid media will be selected to provide particles that have the highest efficiency of singlet oxygen formation and highest quantum yield of emission from the chemiluminescent compound in the media but less concentrated solutions will sometimes be used. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer labeled particles and the quantum yield of the chemiluminescent compound particles with the proviso that the particles should not melt or become aggregated at the selected temperature. Elevated temperatures are normally employed. The temperatures for the procedure will generally range from 20° C. to 200° C., more usually from 50° C. to 170° C. It has been observed that some compounds that are nearly insoluble at room temperature are soluble in, for example, low molecular weight alcohols, such as ethanol and ethylene glycol and the like, at elevated temperatures. Carboxylated modified latex particles have been shown to tolerate low molecular weight alcohols at such temperatures.

An analyte-binding agent may be physically adsorbed on the surface of the latex particle or may be covalently bonded to the particle. In cases wherein the analyte-binding agent is only weakly bound to the surface of the latex particle, the binding may in certain cases be unable to endure particle-to-particle shear forces encountered during incubation and washings. Therefore, it may be suitable to covalently bond analyte-binding agents to the latex particles under conditions that will minimize adsorption. This may be accomplished by chemically activating the surface of the latex. For example, the N-hydroxysuccinimide ester of surface carboxyl groups can be formed and the activated particles to reduce nonspecific binding of assay components to the particle surface are then contacted with a linker having amino groups that will react with the ester groups or directly with an analyte-binding agent that has an amino group. The linker will usually be selected to reduce nonspecific binding of assay components to the particle surface and will in some embodiments, provide suitable functionality for both attachment to the latex particle and attachment of the analyte-binding agent. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

In one method, MAD is first attached to carboxyl-containing latex particles using a water soluble carbodiimide, for example, 1-(3-dimethylaminopropyl)-3-ethyl carbodiimide. The coated particles are then equilibrated in reagents to prevent nonspecific binding. Such reagents include proteins such as bovine gamma globulin (BGG), and detergent, such as Tween® 20, (ICI Americas, Inc.) TRITON X-100® (Rohm and Haas Company) and the like. xAn analyte-binding agent having a sulfhydryl group, or suitably modified to introduce a sulfhydryl group, is then added to a suspension of the particles, whereupon a covalent bond is formed between the analyte-binding agent and the MAD on the particles. Any excess unreacted analyte-binding agent can then be removed by washing.

In general, metal sols are particles included of a heavy metal, i.e., a metal of atomic number greater than 20 such as a Group IB metal, e.g., gold or silver or chalcogens such as selenium or tellurium.

Metal sol particles are described, for example, by Leuvering in U.S. Pat. No. 4,313,734, the disclosure of which is incorporated herein by reference in its entirety. Such sols include colloidal aqueous dispersion of a metal, metal compound, or polymer nuclei coated with a metal or metal compound.

The metal sols may be of metals or metal compounds, such as metal oxides, metal hydroxides and metal salts or of polymer nuclei coated with metals or metal compounds. Examples of such metals are platinum, gold, silver mercury, lead, palladium, and copper, and of such metal compounds are silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide. In general, the metals or metal compounds useful may be readily demonstrated by means of known techniques.

In some embodiments, it may advantageous to use sols included of dispersed particles consisting of polymer nuclei coated with the above mentioned metals or metal compounds. These particles have similar properties as the dispersed phase of pure metals or metal compounds, but size, density and metal contact can be optimally combined.

The metal sol particles may be prepared in a large number of ways which are in themselves known. For example, for the preparation of a gold sol Leuvering refers to an article by G. Frens in *Nature Physical Science* 241, 20 (1973).

The metal sol particles can be modified to contain various functional groups as described above for linking to an analyte-binding agent or a photosensitizer or a chemiluminescent compound. For example, polymeric bonding agents can be used to coat the particles such as polymers containing thiol groups that bond strongly to many heavy metals or silylating agents that can bond and form polymeric coatings as, for example, by reaction of metal particles with thioalkoxy aminoalkylsilanes as described in EPO Patent Appl. 84400952.2 by Advanced Magnetics for coating magnetic particles.

Generally, dye crystallites are microcrystals of pure or mixed solid water insoluble dyes, such as those described herein. The dye crystallites useful in the present invention have a size range of 20 nm to 20 µm.

One method for preparing dye crystallites is described in U.S. Pat. No. 4,373,932 (Gribnau, et al.), the disclosure of which is incorporated herein by reference in its entirety. Gribnau describes colloidal dye particles and aqueous dispersions of a hydrophobic dye or pigment, which may have an immunochemically reactive component directly or indirectly attached. The dye particles are prepared in general by dispersing a dye in water and then centrifuging. A dye pellet is obtained and resuspended in water, to which glass beads are added. This suspension is rolled for several days at room temperature. The liquid is decanted and centrifuged, and the dye particles are obtained after aspiration of the liquid.

Another method for preparing dye crystallites is by slow addition of a solution of the dye in a water miscible solvent to water. Another method is by sonication of a suspension of the solid dye in water.

Binding of analyte-binding agents to the dye particles can be achieved by direct or indirect adsorption or covalent chemical attachment. The latter is governed by the presence of suitable functional groups in any coating material and in the dye. For example, functional groups can be introduced onto the surface of a dye crystallite by coupling a compound containing a diazotized aromatic amino group and the desired functional group to a phenolic or anilino group of the dye.

Where the dye has a carboxyl group, the dye crystallite can be activated by a carbodiimide and coupled to a primary amino component. Aliphatic primary amino groups and hydroxyl groups can be activated, for example, by cyanogen bromide or halogen-substituted di- or tri-azines, after which attachment with a primary amino component or with, for example, a component containing a —SH, or —OH or group can take place. Use can also be made of bifunctional reactive compounds. For example, glutaraldehyde can be used for the mutual coupling of primary amino components of the dye and an analyte-binding agent, and, for example, a heterobifunctional reagent such as N-succinimidyl 3-(2-pyridyldithio) propionate can be employed for the coupling of a primary amino component to a component containing a thiol group.

In some embodiments, the composition for use in the ingestible devices of the present application further includes a medium having suspended therein said plurality of donor particles and said plurality of acceptor particles. In some embodiments, the medium is an aqueous medium. In some embodiments, the aqueous medium has a pH selected from 5-8 (e.g., a pH selected from 6-7.8, such as pH being 6.0). The standard buffer was 50 mM sodium phosphate/0.15 M NaCl, pH 7.0. St.Av Donor beads are incubated in 1 um HABA ((2-(4-HYDROXYPHENYLAZO)BENZOIC ACID) before depositing them on the pad. The assay buffer was 0.1 M Tris'HCl/0.3 M NaCi/bovine serum albumin (1 mg/ml), pH 8.2 with 50 mM hydroxyl propyl cyclodextrin and tween-20-0.1%.

Suitable acceptor particles for use in the ingestible devices of this application may be any type of particles as described herein. In some embodiments, the acceptor particles are selected from the group consisting of latex particles, lipid bilayers, oil droplets, silica particles, and metal sols. In some embodiments, the acceptor particles are latex particles, such as, but not limited Polystyrene latex particles (175 nm) having about 8.3 carboxyl groups per $nm^2$ of surface, and/or the like.

Suitable chemiluminescent compounds for use in the ingestible devices of this application include those chemiluminescent compounds or substances as described in PCT International Publication No. WO1999042838 A1 (Table 1); and U.S. Pat. No. 7,709,273. In some embodiments, the chemiluminescent compounds are selected from the group consisting of example chemiluminescent compounds described in PCT International Publication No. WO1999042838 A1 (Table 1); and U.S. Pat. No. 7,709,273. The above mentioned applications are hereby expressly incorporated by reference in their entireties.

Suitable donor particles for use in the ingestible devices of this application may be any type of particles as described herein. In some embodiments, the donor particles are selected from the group consisting of latex particles, lipid bilayers, oil droplets, silica particles, and metal sols. In some embodiments, the donor particles are latex particles, such as, but not limited to Polystyrene latex particles (175 nm) having about 8.3 carboxyl groups per $nm^2$ of surface. Latex particles can vary between 175 nm to 800 nm. In some embodiments, the donor particles are latex particles (e.g., any type of latex particles described herein) that are coated with streptavidin.

Suitable photosensitizers for use in the ingestible devices of this application include any of the photosensitizers as described U.S. Pat. Nos. 6,251,581, 5,516,636, 8,907,081, 6,545,012, 6,331,530, 8,247,180, 5,763,602, 5,705,622, 5,516,636, 7,217,531, and U.S. Patent Publication No. 2007/0059316. In some embodiments, the photosensitizers are selected from the group consisting of t-Bultyl Silicon Pthalocynine, Chlorophyll, and Silicon Napthalo cyanine.

The photosensitizer and chemiluminescent compound can be incorporated into donor and acceptor particles, respectively, by virtue of being soluble in at least one phase of the particles, in which case the photosensitizer and chemiluminescent compound will be at much higher concentration within the particle than in the bulk assay medium. When the photosensitizer and chemiluminescent compound are covalently bound to donor and acceptor particles, respectively, the photosensitizer and chemiluminescent compound or the particles, or components thereof, are functionalized to provide a means of attaching the photosensitizer and chemiluminescent compounds and the particles. Example ways to incorporate photosensitier and chemiluminescent compounds in latex particles can be found in PCT International Publication No. WO1999/042838 and U.S. Pat. No. 7,709, 273. For particles that are oil droplets or liposomes the photosensitizer and chemiluminescent compound can be attached to one or more long hydrocarbon chains, each generally having at least 10 to 30 carbon atoms. If the particles are droplets of a fluorocarbon, the photosensitizer or chemiluminescent compound incorporated into these particles may be fluorinated to enhance solubility and reduce exchange into other particles bound with the other label, and the hydrocarbon chain used for linking will preferably be replaced with a fluorocarbon chain. For silicon fluid particles the photosensitizer and chemiluminescent compound can be bound to a polysiloxane. In order to maximize the number of photosensitizer or chemiluminescent compound molecules per particle, in some embodiments, it may be desirable to minimize the charge and polarity of the photosensitizer or chemiluminescent compound so that it resides within the non-aqueous portion of the particle. When the particle is a liposome and it is desired to retain the photosensitizer or chemiluminescent compound in the aqueous phase of the liposome, in some embodiments, photosensitizers or chemiluminescent compounds that are highly polar or charged may be used.

In some embodiments, the ratio of the number of donor particles to the number of the acceptor particles ranges from 10:1 to 1:10. In some embodiments, the ratio of the number of donor particles to the number of the acceptor particles ranges from 5:1 to 1:10. In some embodiments, the ratio of the number of donor particles to the number of the acceptor particles ranges from 5:1 to 10:1.

Suitable analytes to be detected, quantified, or measured by the ingestible devices of this application include any of the analytes as described herein. In some embodiments, the analyte is selected from the group consisting of proteins, peptides, cell surface receptors, receptor ligands, nucleic acids, carbohydrates, cells, microorganisms, and fragments thereof. In some embodiments, the analyte is selected from the group consisting of TNFα, lipoteichoic acid (LTA), lipopolysaccharide (LPS), lipopolysaccharide binding protein (LBP), calprotectin, cytokines and chemokines, IL12/23, IL-6, IL-10, MADCAM, α4β7 integrin, HGF, EGF, HB-EGF, TGFb, Adalimumab, Infliximab, Cimzia, Vedolizumab, Tysabri, Simponi, Remsima, bevacizumab (Avastin), and cetuximab (Erbitux).

The first analyte-binding agent coupled to or associated with the donor particles and the second analyte-binding agent coupled to or associated with the acceptor particles are capable of binding to the same analyte. The analyte, when present, therefore affects the amount of the photosensitizer of the donor particles and the chemiluminescent compound of the acceptor particles that can come into close proximity, wherein the short-lived singlet oxygen generated by the photosensitizer can react with the chemiluminescent compound prior to its spontaneous decay and upon reaction, the chemiluminescent compound produces luminescence. The intensity of luminescence produced is related to the amount of analyte in the sample. The chemiluminescent compound is capable of activation by singlet oxygen, and the photosensitizer catalyzes the formation of singlet oxygen usually in response to photoexcitation followed by energy transfer to molecular oxygen.

In some embodiments, an analyte causes molecules of the photosensitizer and the chemiluminescent compound to be closer to each other than their average distance in the bulk solution of the assay medium. This partitioning will depend upon the amount of analyte present in the sample to be analyzed. The photosensitizer molecules that do not become associated with the chemiluminescent compound produce singlet oxygen that is unable to reach the chemiluminescent compound before undergoing decay in the aqueous medium. However, when the photosensitizer and the chemiluminescent compound come in close proximity with each other in response to the amount of the analyte, the singlet oxygen produced upon irradiation of the photosensitizer can activate the chemiluminescent compound before undergoing decay.

In some embodiments, the first analyte-binding agent coupled to or associated with the donor particles and the second analyte-binding agent coupled to or associated with the acceptor particles are independently selected from the group consisting of antibodies, aptamers, cell surface receptors, receptor ligands, biotin, streptavidin, avidin, protein A, G, and L, and derivatives thereof. In some embodiments, the first analyte-binding agent is the same as the second analyte-binding agent. In some embodiments, the first analyte-binding agent is different from the second analyte-binding agent. In some embodiments, the first analyte-binding agent is an antibody or a derivative thereof (e.g., a biotinylated antibody). In some embodiments, the second analyte-binding agent is an antibody or a derivative thereof (e.g., a biotinylated antibody). In some embodiments, the second analyte-binding agent is an antibody covalently conjugated to the acceptor particles. In some embodiments, the first analyte-binding agent is a biotinylated antibody and the donor particles are coated with streptavidin. In some embodiments, the first analyte-binding agent is a biotinylated antibody and the donor particles are coated with streptavidin, and the second analyte-binding agent is an antibody covalently conjugated to the acceptor particles.

In some embodiments, the first analyte-binding agent coupled to or associated with the donor particles is an antibody selected from the group consisting of anti-bacterial antibodies. In some embodiments, the antibody is selected from the group consisting of anti-Gram positive bacteria antibodies, anti-Gram positive bacteria LTA antibodies, anti-Gram negative bacteria antibodies, anti-lipoteichoic acid antibodies, anti-E. coli antibodies, anti-lipid A antibodies, anti-TNFα antibodies, and derivatives thereof. In some embodiments, the antibody is selected from the group consisting of MA1-7401 antibody, MA1-40134 antibody, ab127996 antibody, ab35654 antibody, ab35654 antibody, ab137967 antibody, ab8467 antibody, and derivatives or fragments thereof.

In some embodiments, the second analyte-binding agent coupled to or associated with the acceptor particles is an antibody selected from the group consisting of anti-bacterial antibodies. In some embodiments, the antibody is selected from the group consisting of anti-Gram positive bacteria antibodies, anti-Gram positive bacteria LTA antibodies, anti-Gram negative bacteria antibodies, anti-lipoteichoic acid antibodies, anti-E. coli antibodies, anti-lipid A antibodies, anti-TNFα antibodies, and derivatives thereof. In some embodiments, the antibody is selected from the group consisting of MA1-7401 antibody, MA1-40134 antibody, ab127996 antibody, ab35654 antibody, ab35654 antibody, ab137967 antibody, ab8467 antibody, and derivatives or fragments thereof.

In some embodiments, the donor particles include more than one type of analyte-binding agent. In some embodiments, the acceptor particles include more than one type of analyte-binding agent. For example, analyte-specific reagents can be used on donor and acceptor beads. For Analyte 1, parameters are set as excitation at 680 nm, emission at 615 nm (half-life 0.6 seconds). For Analyte 2, parameters are set as excitation at 680 nm, emission at 615 nm (half-life 30 seconds). For Anaylte 3, parameters are set as excitation at 680 nm, emission at 615 nm (half-life 300 seconds). After the first excitation, emission for analyte 1 is measure from: 0-6 seconds; emission for analyte 2 is measured from 6-300 seconds; and emission for analyte 3 is measured from 300-600 seconds. Signals are deconvoluted as described in further detail in PCT International Publication No. WO1999/042838. In some embodiments, emission wavelengths may be used to evaluate multiple analytes as discussed herein.

In some embodiments, the composition for use in the ingestible devices of the present application further includes cyclodextrin with a concentration range of 25-50 mM, or 1-500 mM.

In one aspect, this application provides a kit including an ingestible device as described herein. In some embodiments, the kit further includes instructions, e.g., for detecting or quantifying an analyte in a sample. In some embodiments, such a device is an ingestible device for detecting or quantifying viable bacterial cells in vivo (e.g., in the GI tract).

Certain illustrative embodiments will now be described, including various systems and methods for obtaining samples using ingestible devices. In particular, techniques are described that allow an ingestible device to obtain a sample from within a gastrointestinal (GI) tract. These samples may include any of the fluids, solids, particulates, or other substances found within the GI tract. However, it will be understood by one of ordinary skill in the art that the systems and methods described herein may be adapted and modified as is appropriate for the applications being addressed, and that the systems and methods described herein may be employed in other suitable applications, and that such other additions and modifications will not depart from the scope of the present disclosure. Generally, the ingestible devices described herein may include actuators, sensors, valves, chambers, logic devices, telemetry systems, microcontrollers or other devices and processors that may be configured using a combination of hardware, firmware, and software to carry out one or more of the methods described herein.

In some embodiments, the ingestible device further includes an illuminating source. The illuminating source is capable of irradiating the composition held in the sampling chamber of the ingestible devices with light having a wavelength with energy sufficient to convert the photosensitizer to an excited state and thereby render it capable of activating molecular oxygen to singlet oxygen. The excited state for the photosensitizer capable of exciting molecular oxygen is generally a triplet state which is more than about 20, e.g., at least 23, Kcal/mol more energetic than the photosensitizer ground state. In some embodiments, the composition is irradiated with light having a wavelength of about 450 to 950 nm although shorter wavelengths can be used, for example, 230-950 nm. The luminescence produced may be measured in any convenient manner such as photographically, visually or photometrically to determine the amount thereof, which is related to the amount of analyte in the medium.

In some embodiments, the 632.6 nm emission line of a helium-neon laser is an inexpensive light source for excitation. Photosensitizers with absorption maxima in the region of about 620 to about 650 nm are compatible with the emission line of a helium-neon laser and are, therefore, useful illuminating sources for use in the present application. Example irradiating wavelengths for diode lasers include 680 nm, 780 nm, and/or the like. In some embodiments, the illuminating source is capable of irradiating the composition with light having a wavelength selected from the group consisting of 678 nm, 633 nm, and 780 nm.

Other means of excitation of the photosensitizer are also contemplated herein. In some embodiments, excitation of the photosensitizer may be achieved by energy transfer from an excited state of an energy donor such as a second photosensitizer. When a second photosensitizer is used, wavelengths of light can be used which are inefficiently absorbed by the photosensitizer but efficiently absorbed by the second photosensitizer. The second photosensitizer may be bound to an assay component that is associated/coupled, or becomes associated/coupled, with the first photosensitizer, for example, bound to a surface or incorporated in the particle having the first photosensitizer. When a second photosensitizer is employed it will usually have a lowest energy triplet state at higher energy than the lowest energy triplet state of the first photosensitizer.

In some embodiments, the ingestible device includes a detector for detecting the luminescence emitted by the chemiluminescent compound. In some embodiments, the detector is a photodiode that is capable of detecting the luminescence emitted by the chemiluminescent compound at a wavelength selected from 613 nm and 660 nm. Additional suitable detection wavelengths include but not limited to 430 nm, 500 nm, 540 nm, 615 nm, 680 nm, and/or the like.

In some embodiments, chemiluminecence intensity is measured with an optical reader. The actual configuration and structure of the optical reader may generally vary as is readily understood by those skilled in the art. Typically, the optical reader contains an illumination source that is capable of emitting light at a defined wavelength and a detector that is capable of registering a signal (e.g., transmitted, reflected, or fluorescence light). Optical readers may generally employ any known detection technique, including, for instance, luminescence (e.g., fluorescence, phosphorescence, etc.), absorbance (e.g., fluorescent or non-fluorescent), diffraction, etc. Exemplary optical readers, illumination sources and detectors are disclosed in U.S. Pat. No. 7,399,608, which is hereby incorporated by reference herein in its entirety.

In some embodiments, the illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some embodiments, multiplexed analysis is enabled. For a single sample, multiple different analytes can be measured by detecting different wavelengths of emitted lights. The multiplexing can be further increased by using both emitted light and the half-life of emitted light (e.g., 0.6 seconds to 300 seconds). For example, the chemiluminescent compound as used herein can emit light within the wavelength range of 250 to 1200 nm and with emission life time of 0.6-300 seconds; and thus emitted lights of different wavelengths within the wavelength range can be multiplexed (e.g., up to 11, etc.). In some embodiments, the illumination may be pulsed to reduce any background interference. In some embodiments, filters may be used to improve optics. See, e.g., Reichman, Jay, Handbook of optical filters for fluorescence microscopy, Chroma Technology Corporation (2000). In some embodiments, excitation source may be a LED with a band-pass filter, e.g., a filter for 680 or 780 nm+/−20 nm wavelength to selectively excite a sample with 680 or 780 nm light. In some embodiments, to cut out any stray longer wavelengths from the green LED, a Thorlabs FESH0550 shortpass filter may be used for excitation (FIG. 72A). In some embodiments, the emission from a sample is captured at a 90° angle with an avalanche photodiode detector with a bandpass filter, e.g., a filter for 430 nm+/−20, 450 nm+/−20, 510 nm+/−20, 6130 nm+/−10, 648 nm+/−10 nm wavelength, placed in front of the detector, to selectively capture light emitted at at specific nm. In some embodiments, a Thorlabs FB580-10 bandpass filter may be used as an emission filter (FIG. 72B). A cross sectional view of an exemplary Chemiluminescent assay test fixture depicting collimating, focusing, and filtering lenses is shown in FIG. 72C. In some embodiments, a 5-50 microsecond delay may be used before emission is measured. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. In some embodiments, the illumination source may provide diffuse illumination to the dye. For example, an array of multiple point light sources (e.g., LEDs) may simply be employed to provide relatively diffuse illumination. In some embodiments, the illumination source is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

In some embodiments, the detector may be any device known in the art that is capable of sensing a signal. In some embodiments, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers. In some embodiments, a photomultiplier may be used to increase the intensity of the signal.

In another aspect, the present application provides ingestible devices containing a microscopic evaluation system. In some embodiments, bacterial cells in a sample may be first labeled with fluorescent dyes (such as those described herein), and the fluorescently-labeled cells may be imaged and counted by the microscopic evaluation using an ingestible device as described herein. In other embodiments, the fluorescently-labeled cells are counted as they pass through an onboard flow system (e.g., microfluidic single cell channeling). Examples of flow cytometry systems include hydrodynamic focusing, small diameter capillary tube flow, and rectangular capillary tube flow. As described herein, live bacteria cells are labeled, and the principles of flow cytometry are used to quantify labeled cells. Generally speaking, the photons from an incident laser beam are absorbed by the fluorophore and raised to a higher, unstable energy level. Within less than a nanosecond, the fluorophore re-emits the light at a longer representative wavelength where it is passed through a series of dichroic filters. This reemitted light can be collected and interpreted as proportional to the number of labeled bacteria cells. In some embodiments, a sheath fluid is not used as part of the flow system to help accommodate the volume restrictions of the device. In some embodiments, a rectangular capillary tube is used to achieve a sufficiently large cross-sectional area and relatively thin inspection area. The flow cytometry optical system operates parallel to the fluidics system and serves to observe the redirection of light passing through the cell and delivers information about the bacterial cells. In some embodiments, rather than using a conventional laser and spherical lenses to focus the light to a point, an LED and cylindrical lenses are used to focus the light to a line across a rectangular capillary tube. In other embodiments, collimating lenses are used to make the light source parallel, while cylindrical lenses are used to refine the inspection area. An exemplary optical configuration for this arrangement can be seen in FIG. 30. In some embodiments, optical filters can be added to permit the use of fluorophores. The characteristic wavelength of reemitted light from the fluorophores can be isolated and detected with the use of dichroic, bandpass, and short or long wave pass filters. Generally, multiple dichroic lenses and photomultipliers are used, however, due to space limitations, only a single side-scatter detector and forward scatter detector may be used in certain embodiments.

Where the analyte is bacteria cells, one of the design challenges of integrating flow cytometry into the device is to provide a pumping mechanism. Without moving fluid, individual bacteria cells cannot be identified and accounted for by flow cytometry within a fixed volume of fluid. In some embodiments, a gear motor is to move fluid through the device. For example, a micromotor including a planetary gearhead (e.g., with a 25:1 reduction) can provide the desired amount of torque to create fluid flow. In another embodiment, a series of piezoelectric resistors embedded in the surface of a microfabricated plate is used to create flow. In yet another embodiment, a micropump that includes a pair of one-way valves and uses a magnetic pump membrane actuated by an external magnetic field is used to create flow.

In some embodiments, the system architecture includes an opening and sealing mechanism combined with a rotary wiper which creates a pressure driven flow via a gear motor. The gear motor can be used for other functions in the device. As shown in FIG. 31, the components of the optics and flow chamber systems fit within the device. In some embodiments, the sample fluid is absorbed via a flexible membrane at the top of the capsule. In some embodiments, the gear motor has 270° of permissible travel which serves to open and fill the fluid chamber. During closure, the motor closes the ingress port while simultaneously pushing the fluid through the rectangular capillary tube where the optical system is located. The threaded component allows the flexible membrane to close and seal the ingress channel without changing the wiper height. In some embodiments, the volume of the sample chamber is 25 µL, 50 µL, 75 µL or more (e.g., within the range of 10-500 µls). In some embodiments, two or more samples are taken from the GI tract to procure a sufficient sample size. Referring to FIG. 31, an LED on the left side of the capillary tube and the two low-light detectors on the right for capturing forward and side scatter are shown. Once the fluid passes through the capillary tube, it exits the capsule via a one-way valve. In certain embodiments, the flow system allows for the detection of cell size and internal cell complexity, in addition to cell quantitation. The sampling chamber may have a capacity of 100 uls (total volume). The sampling chamber may also have multiple compartments, each storing a different assay mix for a different location within the GI tract. The compartments of the sampling chamber may each have a capacity of 10-20 uls.

In some embodiments, the ingestible device further includes an internal calibrator. The miniaturized device may include 5 ugs of OMNI Beads (Silicon Napthalocyanine+ Thioxene+Europium Chelate), having parameters set as: excitation: 780 nm; 50 millisecond delay; record emission at 615 nm for 6 seconds. The OMNI beads may be embedded on the pad and signals may be used to characterize signal uniformity and reliability of the miniturized device. The ingestible device can be calibrated during manufacturing in the factory and before the patients ingests the device.

Internal standards may be used to calibrate the signal from the analyte of interest. The signal from internal standard will be measured at the same time as the analyte of interest. Donor beads with SA and HABA (10 ugs)+Biotin-PEG-2,4 DNP (5 nmoles)+Anti-2,4 DNP labeled acceptor beads (10 ugs) with thioxene and Samarium Chelate or N-phenyl oxazine and Samarium Chelate may be used. Sample addition to the pad results in acceptor and donar beads binding to Biotin-Peg-2,4 DNP and forming a dimer which when excited with 680 nm light generates a chemiluminescent signal at 648 nm, e.g., with either 0.6 or 30 seconds halflife depending on the analyte(s) of interest. The internal control may correct sample effects and instrument (the ingestible device) drift.

In one aspect, the present application provide methods for detecting, quantifying, or measuring an analyte in a sample using the ingestible devices as described herein. In some embodiment, the ingestible devices as described herein may be used to analyze samples (e.g., samples from the GI tract) to detect or quantify analytes, such as viable bacterial cells, in a sample in vivo. In some embodiments, the devices of this application may be used to measure the concentration of analytes (e.g., viable bacteria cells) in various specific regions of the GI tract. Such data may be used to determine whether a subject has a condition in need for treatment (such as an infection, e.g., Small Intestinal Bacterial Overgrowth (SIBO), or a SIBO-related condition), the site of disease for treatment, or to quantify bacterial populations within the GI tract (or within specific regions of the GI tract) for other diagnostic purposes. In some embodiments, the ingestible devices described herein may be used to detect and/or quantify specific genera, species, or strains of microorganisms present in a sample in vivo.

In some embodiments, data may be generated after the ingestible device has exited the subject, or the data may be generated in vivo and stored on the device and recovered ex vivo. Alternatively, the data can be transmitted wirelessly from the ingestible device while the device is passing through the subject (e.g. passing through the GI tract of the subject).

In some embodiments, this disclosure provides methods for detecting an analyte in a sample, such as a fluid sample, of a subject. The methods can include: (1) providing an ingestible device; (2) transferring the fluid sample of the subject into the sampling chamber of said ingestible device in vivo; (3) irradiating the composition held in the sampling chamber of the ingestible device with light to excite the photosensitizer; and (4) measuring total luminescence or rate of change of luminescence emitted from the composition held in the sampling chamber of the ingestible device as a function of time, thereby detecting the analyte in the fluid sample. In some embodiments, the presence of an analyte in the sample is used to diagnose and/or monitor a disease or disorder in the subject. In some embodiments, the absence of an analyte in the sample is used to diagnose and/or monitor a disease or disorder in the subject.

In some embodiments, this disclosure provides methods of determining the level of an analyte in a sample, such as a fluid sample, of a subject. The methods can include: (1) providing an ingestible device; (2) transferring the fluid sample of the subject into the sampling chamber of said ingestible device in vivo; (3) irradiating the composition held in the sampling chamber of the ingestible device with light to excite the photosensitizer; and (4) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject or the treatment thereof.

In some embodiments, the total luminescence or the rate of change of luminescence as a function of time of the sponge is measured over multiple time points for an extended period of time in step (4). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver.

In certain embodiments, the disclosure provides methods of determining the level of an analyte in a sample of a subject, such as a human subject. The methods can include: (1) providing an ingestible device, said device including a sampling chamber that is configured to hold a member made of an absorptive material (e.g., an absorptive pad or absorptive sponge) having absorbed therein a composition, as described herein; (2) transferring the fluid sample of the subject into the sampling chamber of said ingestible device in vivo; (3) fully or partially saturating the absorptive material held in the sampling chamber of the ingestible device with the fluid sample; (4) irradiating the absorptive material held in the sampling chamber of the ingestible device with light to excite the photosensitizer; and (5) measuring total luminescence or rate of change of luminescence emitted from the composition held in the sampling chamber of the ingestible device as a function of time, thereby detecting the analyte in the fluid sample. In some embodiments, the presence of an analyte in the sample is used to diagnose and/or monitor a disease or disorder in the subject. In some embodiments, the absence of an analyte in the sample is used to diagnose and/or monitor a disease or disorder in the subject.

In certain embodiments, the disclosure provides methods of determining the level of an analyte in a sample, such as a fluid sample, of a subject. The methods can include: (1) providing a ingestible device, said device including a sampling chamber that is configured to hold an a member made of absorptive material (e.g., an absorptive pad and/or an absorptive sponge) having absorbed therein a composition, as described herein; (2) transferring the fluid sample of the subject into the sampling chamber of said ingestible device in vivo; (3) fully or partially saturating the absorptive material held in the sampling chamber of the ingestible device with the fluid sample; (4) irradiating the absorptive material held in the sampling chamber of the ingestible device with light to excite the photosensitizer; and (5) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the total luminescence or the rate of change of luminescence as a function of time of the sponge is measured over multiple time points for an extended period of time in step (5). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver.

In some embodiments, the disclosure provides a method of assessing or monitoring the need to treat a subject suffering from or at risk of overgrowth of bacterial cells in the gastrointestinal (GI) tract, including: (1) providing a ingestible device of the present application for detecting an analyte; (2) transferring a fluid sample from the GI tract of the subject into the sampling chamber of said ingestible device in vivo; (3) irradiating the composition held in the sampling chamber of the ingestible device with light to excite the photosensitizer; (4) measuring total luminescence or rate of change of luminescence emitted from the composition held in the sampling chamber of the ingestible device as a function of time; (5) correlating the total luminescence or the rate of change of luminescence as a function of time measured in step (4) to the amount of the analyte in the fluid sample; and (6) correlating the amount of the analyte in the fluid sample to the number of viable bacterial cells in the fluid sample. In some embodiments, a number of viable bacterial cells determined in step (6) greater than a control number of viable bacterial cells, indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (6) greater that about $10^3$ CFU/mL indicates a need for treatment. In some embodiments, a number of viable bacterial cells determined in step (6) greater that about $10^4$ CFU/mL indicates a need for treatment. In some embodiments, a number of the viable bacterial cells determined in step (6) greater than about $10^5$ CFU/mL indicates a need for treatment, e.g., with an antibiotic agent as described herein. In some embodiments, a number of viable bacterial cells determined in step (6) greater that about $10^6$ or more CFU/mL indicates a need for treatment.

In some embodiments, the disclosure provides a method of assessing or monitoring the need to treat a subject suffering from or at risk of a gastrointestinal (GI) tract microbial infection (e.g., with a pathogenic microorganism), including: (1) providing an ingestible device of the present application for detecting analyte; (2) transferring a fluid sample from the GI tract of the subject into the sampling chamber of said ingestible device in vivo; (3) irradiating the composition held in the sampling chamber of the ingestible device with light to excite the photosensitizer; (4) measuring total luminescence or rate of change of luminescence emitted from the composition held in the sampling chamber of the ingestible device as a function of time; (5) correlating the total luminescence or the rate of change of luminescence as a function of time measured in step (4) to the amount of the analyte in the fluid sample; and (6) correlating the amount of the analyte in the fluid sample to the number of microorganisms (e.g., pathogenic microorganisms) in the fluid sample. In some embodiments, the analyte is specific for a particular genus, species, or strain of microorganism. In some embodiments, a number of microorganisms determined in step (6) greater than a control number of microorganisms indicates a need for treatment (e.g., with an antibiotic agent described herein). In some embodiments, the control number of microorganisms is 0, 1, $10^2$, $10^3$, $10^4$, $10^5$, $10^6$, $10^7$, $10^8$, $10^9$, or more. For example, in some embodiments, a number of microorganisms determined in step (6) greater that about 0 indicates a need for treatment. In some embodiments, a number of microorganisms determined in step (6) greater that about 1 indicates a need for treatment. In some embodiments, a number of microorganisms determined in step (6) greater that about $10^2$ indicates a need for treatment. In some embodiments, a number of microorganisms determined in step (6) greater that about $10^3$ indicates a need for treatment. In some embodiments, a number of microorganisms determined in step (6) greater that about $10^4$ indicates a need for treatment. In some embodiments, a number of the microorganisms determined in step (6) greater than about $10^5$ indicates a need for treatment, e.g., with an antibiotic agent as described herein. In some embodiments, a number of microorganisms determined in step (6) greater that about $10^6$ indicates a need for treatment. In some embodiments, the control number of microorganisms is 0, 1, $10^2$, $10^3$, $10^4$, $10^5$, $10^6$, $10^7$, $10^8$, $10^9$, or more CFU/mL. For example, in some embodiments, a number of microorganisms cells determined in step (6) greater that about 0 CFU/mL indicates a need for treatment. In some embodiments, a number of microorganisms determined in step (6) greater that about 1 CFU/mL indicates a need for treatment. In some embodiments, a number of microorganisms determined in step (6) greater that about $10^2$ CFU/mL indicates a need for treatment. In some embodiments, a number of microorganisms determined in step (6) greater that about $10^3$ CFU/mL indicates a need for treatment. In some embodiments, a number of microorganisms determined in step (6) greater that about $10^4$ CFU/mL indicates a need for treatment. In some embodiments, a number of the microorganisms determined in step (6) greater than about $10^5$ CFU/mL indicates a need for treatment, e.g., with an antibiotic agent as described herein. In some embodiments, a number of microorganisms determined in step (6) greater that about $10^6$ or more CFU/mL indicates a need for treatment.

In some embodiments, the total luminescence or the rate of change of luminescence as a function of time of the sponge is measured over multiple time points for an extended period of time in step (4). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-β20 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver. In some embodiments, the ingestible device and the method may be further used to monitor the subject after the treatment (e.g., with an antibiotic). In some embodiments, the ingestible device and the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the ingestible device and the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In some embodiments, the presence of bacteria of a specific genera, species, and/or strains may be detected using an ingestible device described herein in order to ascertain which bacteria are resistant and/or sensitive to an antibiotic administered to the subject. For example, in some embodiments, the ingestible device and the methods described herein may be used to monitor a subject before and after treatment with an antibiotic to determine the presence and/or absence of a bacteria of a specific genera, species, and/or strain. A comparison of the type of bacteria that are present in the GI tract of the subject before and after the treatment with the antibiotic can be used to assess which types of bacteria were susceptible and/or resistant to the treatment with the antibiotic.

In some embodiments, the ingestible device and the methods described herein may be used to detect the presence of bacteria of a specific genera, species, and/or strains in a sample from the GI tract from a subject in order to select an antibiotic treatment that will render the detected bacteria either susceptible or resistant to the antibiotic treatment.

In certain embodiments, the disclosure provides methods of assessing or monitoring the need to treat a subject suffering from or at risk of overgrowth of bacterial cells in the GI tract. The methods can include: (1) providing an ingestible device for detecting an analyte, said device including a sampling chamber that is configured to hold an absorptive material (e.g., an absorptive pad and/or and absorptive sponge) having absorbed therein a composition; (2) transferring a fluid sample from the GI tract of the subject into the sampling chamber of said ingestible device in vivo; (3) fully or partially saturating the absorptive material held in the sampling chamber of the ingestible device with the fluid sample; (4) irradiating the absorptive material held in the sampling chamber of the ingestible device with light to excite the photosensitizer; (5) measuring total luminescence or rate of change of luminescence emitted from the composition held in the sampling chamber of the ingestible device as a function of time; (6) correlating the total luminescence or the rate of change of luminescence as a function of time measured in step (5) to the amount of the analyte in the fluid sample; and (7) correlating the amount of the analyte in the fluid sample to the number of viable bacterial cells in the fluid sample. In some embodiments, a number of viable bacterial cells determined in step (7) greater than a control number of viable bacterial cells indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (7) greater that about $10^3$ CFU/mL indicates a need for treatment. In some embodiments, a number of viable bacterial cells determined in step (7) greater that about $10^4$ CFU/mL indicates a need for treatment. In some embodiments, a number of the viable bacterial cells determined in step (7) greater than about $10^5$ CFU/mL indicates a need for treatment, e.g., with an antibiotic agent as described herein. In some embodiments, a number of viable bacterial cells determined in step (7) greater that about $10^6$ or more CFU/mL indicates a need for treatment.

In some embodiments, the disclosure provides a method of assessing or monitoring the need to treat a subject suffering from or at risk of a gastrointestinal (GI) tract microbial infection (e.g., with a pathogenic microorganism), including: (1) providing an ingestible device for detecting an analyte, said device including a sampling chamber that is configured to hold a member made of an absorptive material (e.g., an absorptive pad and/or and absorptive sponge) having absorbed therein a composition; (2) transferring a fluid sample from the GI tract of the subject into the sampling chamber of said ingestible device in vivo; (3) fully or partially saturating the absorptive material held in the sampling chamber of the ingestible device with the fluid sample; (4) irradiating the absorptive material held in the sampling chamber of the ingestible device with light to excite the photosensitizer; (5) measuring total luminescence or rate of change of luminescence emitted from the composition held in the sampling chamber of the ingestible device as a function of time; (6) correlating the total luminescence or the rate of change of luminescence as a function of time measured in step (5) to the amount of the analyte in the fluid sample; and (7) correlating the amount of the analyte in the fluid sample to the number of microorganisms (e.g., pathogenic microorganisms) in the fluid sample. In some embodiments, the analyte is specific for a particular genus, species, or strain of microorganism. In some embodiments, a number of microorganisms determined in step (7) greater than a control number of microorganisms indicates a need for treatment (e.g., with an antibiotic agent described herein). In some embodiments, the control number of microorganisms is 0, 1, $10^2$, $10^3$, $10^4$, $10^5$, $10^6$, $10^7$, $10^8$, $10^9$, or more. For example, in some embodiments, a number of microorganisms determined in step (7) greater that about 0 indicates a need for treatment. In some embodiments, a number of microorganisms determined in step (7) greater that about 1 indicates a need for treatment. In some embodiments, a number of microorganisms determined in step (7) greater that about $10^2$ indicates a need for treatment. In some embodiments, a number of microorganisms determined in step (7) greater that about $10^3$ indicates a need for treatment. In some embodiments, a number of microorganisms determined in step (7) greater that about $10^4$ indicates a need for treatment. In some embodiments, a number of the microorganisms determined in step (7) greater than about $10^5$ indicates a need for treatment, e.g., with an antibiotic agent as described herein. In some embodiments, a number of microorganisms determined in step (7) greater that about $10^6$ indicates a need for treatment. In some embodiments, the control number of microorganisms is 0, 1, $10^2$, $10^3$, $10^4$, $10^5$, $10^6$, $10^7$, $10^8$, $10^9$, or more CFU/mL. For example, in some embodiments, a number of microorganisms cells determined in step (7) greater that about 0 CFU/mL indicates a need for treatment. In some embodiments, a number of microorganisms determined in step (7) greater that about 1 CFU/mL indicates a need for treatment. In some embodiments, a number of microorganisms determined in step (7) greater that about $10^2$ CFU/mL indicates a need for treatment. In some embodiments, a number of microorganisms determined in step (7) greater that about $10^3$ CFU/mL indicates a need for treatment. In some embodiments, a number of microorganisms determined in step (7) greater that about $10^4$ CFU/mL indicates a need for treatment. In some embodiments, a number of the microorganisms determined in step (7) greater than about $10^5$ CFU/mL indicates a need for treatment, e.g., with an antibiotic agent as described herein. In some embodiments, a number of microorganisms determined in step (7) greater that about $10^6$ or more CFU/mL indicates a need for treatment.

In some embodiments, the total luminescence or the rate of change of luminescence as a function of time of the sponge is measured over multiple time points for an extended period of time in step (4). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver. In some embodiments, the ingestible device and the method may be further used to monitor the subject after the treatment (e.g., with an antibiotic). In some embodiments, the ingestible device and the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the ingestible device and the method may be used to detect infection with antibiotic-resistant strains of bacteria in a subject. For instance, such infection may be indicated where the number of viable bacterial cells or pathogens in a sample from the GI tract of the subject does not substantially decrease after antibiotic treatment or other treatments.

In some embodiments, the disclosure provides a method of measuring the presence, absence or amount of one or more analytes from one or more samples in the gastrointestinal tract. In some embodiments, the one or more analytes are measured multiple times, for example, at different time points or at different locations. In one embodiment, a single device measures one or more analytes or more time points or locations; thereby creating a "molecular map" of a physiological region. Measurements can be taken at any location in the gastrointestinal tract. For example, in one aspect, analytes from samples from one or more of the duodenum, jejunum, ileum, ascending colon, transverse colon or descending colon can be measured to create a molecular map of the small and large intestine. In one aspect, the sample is from the duodenum. In one aspect, the sample is from the jejunum. In one aspect, the sample is from the ileum. In one aspect, the sample is from the ascending colon. In one aspect, the sample is from the transverse colon. In one aspect, the sample is from the descending colon.

In another aspect, a series of measurements can be taken over a shorter distance of the gastrointestinal tract (e.g., the ileum) to create a higher resolution molecular map. In some embodiments, previous endoscopic imaging may identify a diseased area for molecular mapping. For example, a gastroenterologist may use imaging (e.g., an endoscope equipped with a camera) to identify the presence of Crohn's Disease in the ileum and cecum of a patient, and the methods and techniques of the present invention herein may be used to measure inflammation-associated analytes in this diseased area of the patient. In a related embodiment, the inflammation-associated analytes, or any analyte, may be measured every one or more days to monitor disease flare-ups, or response to therapeutics.

In certain embodiments, the disclosure provides methods of generating a molecular map of the gastrointestinal (GI) tract. The methods can include: (1) providing an ingestible device of the present application for detecting an analyte; (2) transferring a fluid sample from the GI tract of the subject into the sampling chamber of said ingestible device in vivo; (3) irradiating the composition held in the sampling chamber of the ingestible device with light to excite the photosensitizer; (4) measuring total luminescence or rate of change of luminescence emitted from the composition held in the sampling chamber of the ingestible device as a function of time; (5) correlating the total luminescence or the rate of change of luminescence as a function of time measured in step (4) to the amount of the analyte in the fluid sample; and (6) correlating the amount of the analyte in the fluid sample to a marker of disease in the fluid sample.

The presence or amount of one or more markers of disease indicates a need for treatment, e.g., with an anti-inflammatory agent as described herein. Markers of disease are described herein and include, but are not limited, inflammatory markers like cytokines and chemokines. In one example, TNFα, calprotectin and C-reactive protein (CRP) are measured at multiple locations of the colon (ascending, transverse, descending) to identify "hot spots" in a subject suspected of suffering from ulcerative colitis. In some embodiments, the same ingestible device, or one administered subsequently, is also able to deliver a therapeutic agent at the site of disease as described in the above embodiment. Means for delivering a therapeutic agent are described in US Provisional applications 62/385,553 and 62/478,955, filed Sep. 9, 2016 and Mar. 30, 2017, respectively, which are hereby expressly incorporated by reference in their entireties.

In some embodiments, the method described herein further includes a step of calibrating the ingestible device, e.g., by using OMNI beads as discussed herein.

In some embodiments, methods as described herein are highly sensitive in detecting and quantifying an analyte (e.g., viable bacterial cells) in various samples. Where the analyte is viable bacterial cells, in some embodiments, the lowest detection or quantification limit of the present methods is $10^2$ CFU/mL. In some embodiments, the highest detection or quantification limit of the present methods is $10^7$ CFU/mL, $10^8$ CFU/mL, $10^9$ CFU/mL, $10^{10}$ CFU/mL or more. In some embodiments, the methods allow detection or quantification of $10^2$ to $10^7$ CFU/mL bacterial cells in various samples. In some embodiments, methods of this application may be used to distinguish samples bases on the quantity of viable bacterial cells contained therein. For instance, the methods may be used to distinguish among samples that contain $10^2$, $10^3$, $10^4$, $10^5$, $10^6$, or $10^7$ CFU/mL of bacterial cells. The sensitivity of the assay is similar to that of the live cell assay.

In some embodiments, the compositions, methods and devices described herein may be used to determine the types of microorganisms (e.g., bacteria) present in a sample (e.g., for diagnostic purposes). Microoganisms (e.g., pathogenic microorganisms or commensal microorganisms) that may be detected using the compositions, methods, and devices described herein include bacteria, protozoans, viruses, and fungi.

In some aspects, this disclosure provides methods for detecting the presence of an analyte in a sample, wherein the analyte is a microorganism of interest (e.g., a microorganism of a particular genus, species and/or strain). In some embodiments, the microorganism of interest is a pathogenic microorganism. In some embodiments, the microorganism of interest is a commensal microorganism. Microorganisms of interest may be specifically detected using an analyte-binding agent described herein that specifically binds to the microorganism of interest (or to a molecule thereof (e.g., a protein or nucleic acid)). One of ordinary skill will understand that more than one genus, species, and/or strain of microorganism may be detected using the methods described herein by, for example, by utilizing analyte-binding agents (e.g., antibodies) that specifically bind to antigens (e.g., surface antigens) of the microorganisms that will be detected. Exemplary antibodies are described above.

In some embodiments, the methods may include: (a) providing a first composition to a subject comprising an analyte-binding agent that binds to a microorganism of interest (e.g., an antibody), wherein the analyte binding agent comprises a photosensitizer; (b) providing an ingestible device to the subject for detecting the analyte-binding agent in a sample; (c) transferring a sample of the subject into a sampling chamber of said ingestible device in vivo; (d) irradiating the composition held in the sampling chamber of the ingestible device with light to excite the photosensitizer of the analyte-binding agent; and (e) measuring total luminescence or rate of change of luminescence emitted from the composition held in the sampling chamber of the ingestible device as a function of time, thereby detecting the microorganism of interest in the sample. The first composition may be provided to the subject before, after, or concurrently with the ingestible device.

In some embodiments, the methods may include: (a) providing an ingestible device for detecting a microorganism of interest in a sample to a subject; (b) transferring the sample of the subject into a sampling chamber of said ingestible device in vivo, wherein the sampling chamber comprises an analyte-binding agent that binds to the microorganism of interest (e.g., an antibody), wherein the analyte binding agent comprises a photosensitizer; (c) irradiating the composition held in the sampling chamber of the ingestible device with light to excite the photosensitizer of the analyte-binding agent; and (d) measuring total luminescence or rate of change of luminescence emitted from the composition held in the sampling chamber of the ingestible device as a function of time, thereby detecting the microorganism of interest in the sample. The first composition may be provided to the subject before, after, or concurrently with the ingestible device.

In some embodiments, the methods may include providing an ingestible device for detecting a microorganism of interest in a sample to a subject, wherein the ingestible device includes a sampling chamber that is configured to hold a composition including: (1) a plurality of donor particles, each of the plurality of donor particles including a photosensitizer and having coupled thereto a first analyte-binding agent (e.g., antibody) that binds to the microorganism of interest, wherein the photosensitizer, in its excited state, is capable of generating singlet oxygen; and (2) a plurality of acceptor particles, each of the plurality of acceptor particles including a chemiluminescent compound and having coupled thereto a second analyte-binding agent (e.g., an antigen-binding agent) that binds to the microorganism of interest, wherein said chemiluminescent compound is capable of reacting with singlet oxygen to emit luminescence.

In some embodiments, this methods may include providing an ingestible device for detecting a microorganism of interest in a sample to a subject, wherein the ingestible device includes a sampling chamber that is configured to hold a member made of an absorptive material (e.g., an absorptive pad and/or and absorptive sponge) having absorbed therein a composition including: (1) a plurality of donor particles, each of the plurality of donor particles including a photosensitizer and having coupled thereto a first analyte-binding agent (e.g., an antibody) that binds to the microorganism of interest, wherein the photosensitizer, in its excited state, is capable of generating singlet oxygen; and (2) a plurality of acceptor particles, each of the plurality of acceptor particles including a chemiluminescent compound and having coupled thereto a second analyte-binding agent (e.g., an antigen-binding agent) that binds to the microorganism of interest, wherein said chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In some embodiments, the methods further comprise quantitating the amount of microorganism (e.g., by using a flow cytometry system present in the ingestible device). In some embodiments, the compositions, methods and devices described herein are used to detect and/or quantitate a microorganism of interest in a first region of the GI tract of the subject.

In some embodiments, the methods described herein are used to detect and/or quantitate a microorganism of interest in the GI tract of a subject before, after, or during a course of treatment with an antibiotic, thereby allowing for a determination as to whether a particular microorganism of interest is susceptible or resistant to the antibiotic. For example, when a subject is treated with an antibiotic in order to reduce the population of bacteria of a particular genus, species and/or strain, the methods can be used to evaluate and/or monitor the effectiveness of the antibiotic treatment in vivo. In some embodiemts, it may be desireable to administer a microorganism of interest (e.g., a commensal bacterial species (e.g., a probiotic or a live biotherapeutic described herein) to a subject in order to increase to abundance of said microorganism of interest in the GI tract of the subject (e.g., for therapeutic purposes). In some embodiments, the methods described herein are used to detect and/or quantitate a microorganism of interest in the GI tract of the subject before, after, or during the administration of the microorganism of interest to the subject, e.g., to determine whether the microorganism of interest has effectively colonized a region of the GI tract of the subject.

Diffractive Optics

In some embodiments, the disclosure provides diffractive optics detection technology that can be used with, for example, ingestible device technology. In some embodiments, an ingestible device includes the diffractive optics technology (e.g., diffractive optics detection system). In certain embodiments, the disclosure provides diffractive optics technology (e.g., diffractive optics detection systems) that are used outside the body of subject. As an example, an ingestible device can be used to obtain one more samples in the body (e.g., in the GI tract) of a subject, and the diffractive optics technology can be used to analyze the sample(s). Such analysis can be performed in vivo (e.g., when the ingestible device contains the diffractive optics) and/or ex vivo (e.g., when diffractive optics are external to the ingestible device).

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. Diffraction gratings, like focusing optics, can be operated in both transmission and reflection modes.

Figure 110:
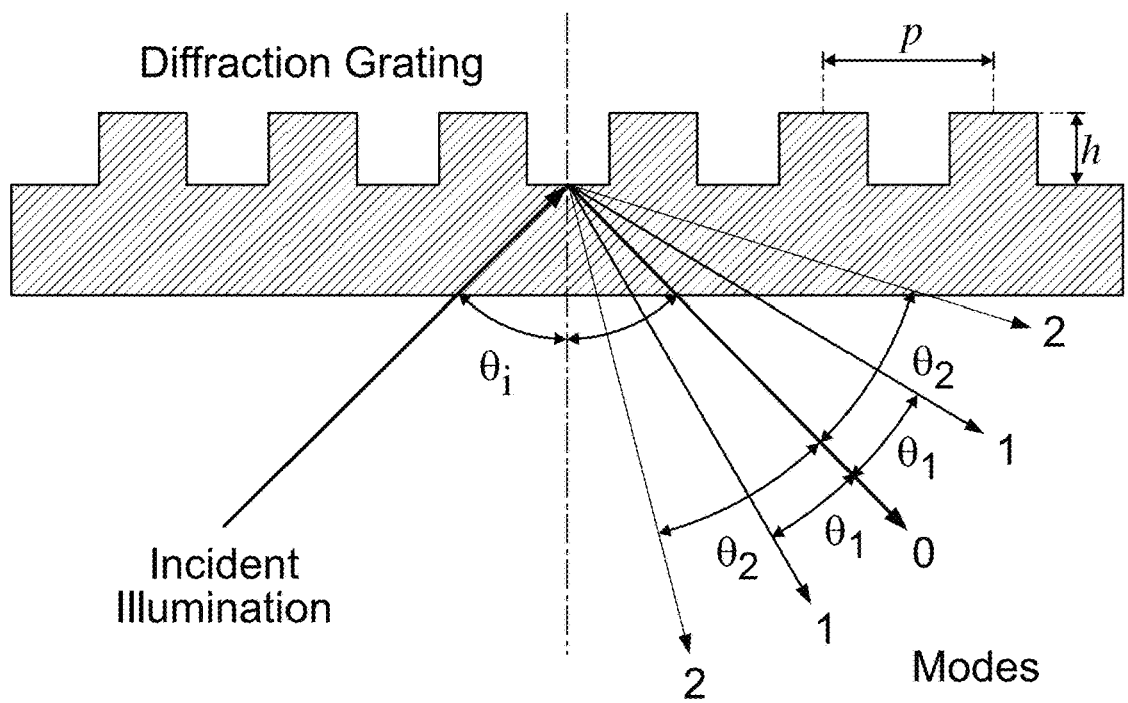
FIG. 110 is a cross-sectional view of an exemplary diffraction grating.

FIG. 110 illustrates diffraction of light by an exemplary diffraction grating operating in reflection mode in which incident illumination is diffracted into light having different diffraction orders m, where m is an integer (e.g., 0, 1, 2). The grating has a substrate with a regularly repeating series of grooves and recessions. The midpoint of adjacent grooves are a distance P from each other, where P is the period of diffraction grating. Likewise, the midpoint of adjacent recessions are a distance P from each other.

The period P of diffraction grating determines the diffraction angle for each diffraction orders, as given by the ideal grating equation:

$$m\lambda = P(\sin \theta_m - \sin \theta_i)$$

where $\lambda$ is the wavelength of the incident light, $\theta_i$ is the angle of the incident light, $\theta_m$ is the diffraction angle of the $m^{th}$ diffraction order. Both $\theta_i$ and $\theta_m$ are measured from the normal to the grating plane.

As shown in FIG. 110, a height h corresponds to the distance between the top of recessions and the bottom of grooves. For the diffraction grating shown in FIG. 110, changing the height $\varphi$ results in a change of the relative intensity of light that is diffracted into the different diffraction orders m. Thus, for example, binding a material to the upper surface of the grooves (thereby changing the height h), can change the intensity of light diffracted into a given diffraction order (e.g., fifth diffraction order).

Thus, from the foregoing, it is apparent that the diffractive properties of a given diffraction grating are dependent on a number of different variables.

In some embodiments, the disclosure implements the dependence of the diffractive properties of a diffraction grating on the height h to determine the presence and/or amount of one or more analytes of interest in a sample.

Figure 111:
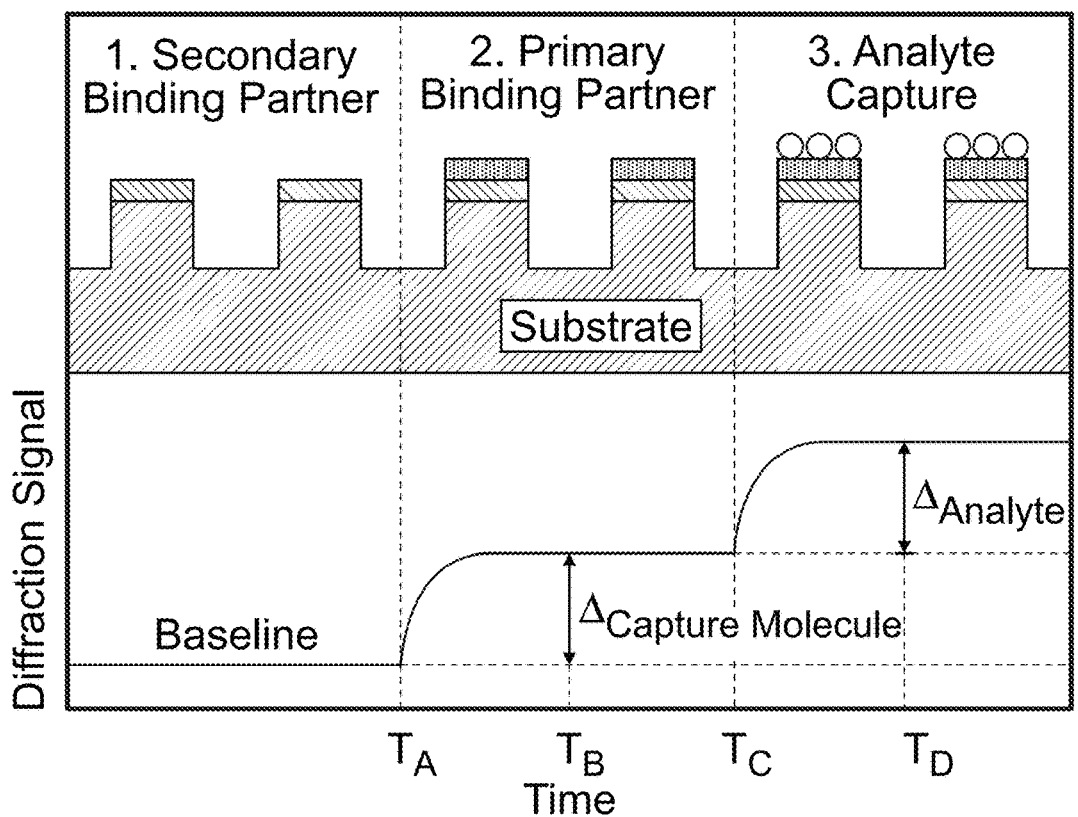
FIG. 111 depicts exemplary diffraction signals at different steps in a process.

For example, FIG. 111 depicts an embodiment of this approach. The approach depicted in FIG. 111 includes two steps for preparing the system prior to being exposed to a sample which may contain an analyte. In step 1, the upper surfaces of the grooves of are patterned with secondary binding partners. The pattern is chosen so that the substrate and secondary binding partners act together as a diffraction grating producing a diffracted signal intensity, labelled as "Baseline" at desirable locations. Next, in step 2, the system is exposed to a medium containing primary binding partners for a period of time to allow for binding between the secondary and primary binding partners to take place. The binding event between the binding partners is accompanied by a change in the local thickness of the layer on the substrate (a first change in $\varphi$), resulting in a change in the optical properties of the diffraction grating and a corresponding first change in the diffracted signal intensity, referred to as $\Delta_{Capture\ Molecule}$. The primary binding partners are then capable of recognizing and binding to an analyte.

In step 3, the system is exposed to a sample. If the sample contains the analyte, binding occurs between the primary binding partner and the analyte. As shown in FIG. 111, such binding results in another change in the local thickness of the layer (a second change in $\varphi$). This causes a corresponding second change in the diffracted signal intensity, referred to as $\Delta_{Analyte}$. The ratio between the two signals $\Delta_{Analyte}$ and $\Delta_{Capture\ Molecule}$ is used as a measure of analyte binding, e.g., to determine whether the analyte is present in the sample and/or to determine how much of the analyte is present in the sample.

Although a reflection diffraction grating is discussed above, more generally, any diffraction grating of appropriate design may be used. In some embodiments, a transmission diffraction grating is used.

In the foregoing discussion, the binding partners and analyte are depicted as binding to the upper surface of grooves 1002. However, the disclosure is not restricted to such embodiments. For example, in certain embodiments, the binding partners and analyte bind to the upper surface of recessions 1004.

In general, the light used in the diffractive optics can be of any appropriate wavelength. Exemplary wavelengths include visible light, infrared red (IR) and ultraviolet (UV). Optionally, the light can be monochromatic or polychromatic. The light can be coherent or incoherent. The light can be collimated or non-collimated. In some embodiments, the light is coherent and collimated. Generally, any appropriate light source may be used, such as, for example, a laser (e.g., a laser diode) or a light emitting diode. In some embodiments, the light source is a laser diode operating at 670 nm wavelength, e.g., at 3 mWatts power. Optionally, an operating wavelength of a laser diode can be 780 nm, e.g., when larger grating periods are used. In certain embodiments, the light source is a laser, such as, for example, a He—Ne laser, a Nd:YVO4 laser, or an argon-ion laser. In some embodiments, the light source is a low power, continuous waver laser. In some embodiments, different wavelengths may be used, and, in such embodiments, a different source of electromagnetic radiation may be used.

The diffracted light can be detected using any appropriate light detector(s). Examples of light detectors include photodetectors, such as, for example, position sensitive photodiodes, photomultiplier tubes (PMTs), photodiodes (PDs), avalanche photodiodes (APDs), charged-coupled device (CCD) arrays, and CMOS detectors. In some embodiments, the diffracted light is detected via one or more individual photodiodes.

In general, the diffraction grating is made of a material that is transparent in the wavelength of the radiation used to illuminate the sensor. Any appropriate material may be used for the diffraction grating substrate, such as glass or a polymer. Exemplary polymers include polystyrene polymers (PSEs), cyclo-olefin polymers (COPs), polycarbonate polymers, polymethyl methacrylates, and methyl methacrylate styrene copolymers. Exemplary COPs include Zeonex (e.g., Zeonex E48R, Zeonex F52R).

The light may be incident on the diffraction grating any appropriate angle. In some embodiments, the light is incident on the diffraction grating with an angle of incidence of from 30° to 80° (e.g., from 40° to 80°, from 50° to 70°, from 55° to 65°, 60°). Optionally, the system is configured so that that diffractive grating and light source can move relative to each other In general, the light detector can be positioned with respect to the diffractive grating so that the diffraction grating can be illuminated at a desired angle of incidence and/or so that diffracted light can be detected at a desired angle and/or so that diffracted light of a desired order can be detected.

The period P of the diffraction grating can be selected as desired. In some embodiments, the period P is from 0.5 microns to 50 microns (e.g., from one micron to 15 microns, from one micron to five microns). In some embodiments, the grating is a repeating patter of 1.5 micron and 4.5 micron lines with a period of 15 microns.

The height h of the diffraction grating can be selected as desired. In certain embodiments, the height h is from one nanometer to about 1000 nanometers (e.g., from about five nanometers to about 250 nanometers, from five nanometers to 100 nanometers).

In general, the diffractive optics can be prepared using any appropriate method, such as, for example, surface ablation, photolithograph (e.g., UV photolithography), laser etching, electron beam etching, nano-imprint molding, or microcontact printing.

Optionally, the diffractive optics system can include one or more additional optical elements, such as, for example, one or more mirrors, filters and/or lenses. Such optical elements can, for example, be arranged between the light source and the diffractive grating and/or between the diffractive grating and the detector.

In general, the diffractive optics disclosure relates to systems designed to determine the presence and/or amount of an analyte (e.g., bacterial cells) in a sample (e.g., a sample taken from the GI tract) using diffractive optics. The sample can be taken using an ingestible device, such as described herein. Typically, in the analytical techniques disclosed herein, the primary binding partner is a molecular compound capable of recognizing and binding to the analyte (i.e., an analyte-binding agent), such as an antibody, and the secondary binding partner is a molecular compound capable of binding to both the primary binding partner and to the substrate of the diffractive optical system, allowing immobilization of the primary binding partner onto the diffractive optical system.

In some of the embodiments of the devices described herein, a primary binding partner specifically binds to a secondary binding partner through non-covalent interactions (e.g., electrostatic, van der Waals, hydrophobic effect). In some embodiments, a primary binding partner specifically binds to a secondary binding partner via a covalent bond (e.g., a polar covalent bond or a non-polar covalent bond). In some embodiments of any of the devices described herein, the primary and the secondary binding partner can be interchanged. For example, the primary binding partner can be biotin, or a derivative thereof, and the secondary binding partner is avidin, or a derivative thereof. In other examples, the primary binding partner can be avidin, or a derivative thereof, and the secondary binding partner is biotin.

In some embodiments, the binding of the primary and the secondary binding partner is essentially irreversible. In some embodiments, the binding of the primary and the secondary binding partner is reversible. In some embodiments, the primary binding partner is CaptAvidin™ biotin-binding protein and the secondary binding partner is biotin, or vice versa. In some embodiments, the primary binding partner is DSB-X™ biotin and the secondary binding partner is avidin, or vice versa. In some embodiments, the primary binding partner is desthiobiotin and the secondary binding partner is avidin, or vice versa (Hirsch et al., *Anal Biochem.* 308(2): 343-357, 2002). In some embodiments, the primary binding partner is glutathione (GSH) or a derivative thereof, and the secondary binding partner is glutathione-S-transferase (GST).

The primary and secondary binding partners provided herein can bind with a dissociation equilibrium constant ($K_D$) of less than $1\times10^{-7}$M, less than $1\times10^{-8}$M, less than $1\times10^{-9}$M, less than $1\times10^{-10}$ M, less than $1\times10^{-11}$ M, less than $1\times10^{-12}$ M, less than $1\times10^{-13}$ M, less than $1\times10^{-14}$ M, less than $1\times10^{-15}$ M, less than $1\times10^{-16}$ M, or less than $1\times10^{-17}$ M. In some embodiments, the primary and secondary binding partners provided herein can bind with a $K_D$ of about 1.1 nM to about 500 nM, such as from about 2.0 nM to about 6.7 nM (inclusive).

In some embodiments of any of the devices described herein, a surface of the device includes a plurality of covalently attached secondary binding partners that can specifically bind to the primary binding partner.

In some embodiments of any of the devices and methods described herein, the primary binding partner can bind to the secondary binding partner and the analyte. In some embodiments, the primary binding partner comprises an antibody (e.g., a bispecific antibody or a single chain antibody), an affimer, an aptamer, an antibody fragment, or an antigen-binding molecule (e.g., a variable light chain domain, a variable heavy chain domain).

In some embodiments, the primary binding partner can bind to any analyte disclosed herein. Exemplary analytes are described in detail above and can be targeted for detection using the methods described herein. In some embodiments, the primary binding partner comprises an analyte-binding agent described herein (e.g., an antibody, an aptamer, an affimer, or a nucleic acid). For example, in some embodiments, the primary binding partner is a nucleic acid (e.g., a DNA molecule, a RNA molecule). In some embodiments, the primary binding partner comprises a portion of a nucleic acid that is complementary to the nucleic acid sequence of the analyte.

In some embodiments of any of the devices described herein, the device can include a label that binds to the analyte and does not prevent binding of the analyte to the primary binding partner. In some embodiments, the label can amplify the diffraction signal of the analyte. In some embodiments, the label is an aptamer, a nanoparticle (e.g, a gold nanoparticle (AuNP), a magnetic nanoparticle (MNP)), a quantum dot (QD), or a carbon nanomaterial (e.g., a graphene and carbon nanotube). See, e.g., Zhu et al. (2014) Toxins 6(4): β25-β48. In some embodiments, the label is a metal nanoparticle or a semi-conductor nanoparticle. General methods of using metal nanoparticles for signal amplification are known in the art, e.g., Ju et al. (2011) Nano-Biosensing: Principles, Development and Application, Biological and Medical Physics, Biomedical Engineering, Chapter 2: pages 39-84, Dykman and Khlebtsov (2011) Acta Naturae 3(3): 34-55, and are incorporated by reference herein. Nanoparticles can be used, e.g., as a fluorescent biological label, a drug delivery system, or a gene delivery system. In some embodiments, a nanoparticle is used for protein detection, or protein isolation and/or purification. As used herein, the term "nanoparticle" refers to an object that has a maximum linear dimension of between 1 nm to about 200 nm (e.g., between 10 to about 100 nm, between 50 to about 100 nm). As an alternative to nanoparticles, or in addition to nanoparticles, microparticles (e.g., maximum linear dimension of from 0.2 microns to 100 microns) may be used.

In some embodiments, the label is from about 1 nm to 200 nm (e.g., about 50 nm to about 200 nm).

In some embodiments, the label (e.g., any of the labels described herein) includes one or more antibodies (e.g., any of the antibodies and/or antibody fragments described herein). For example, in some embodiments wherein the label is a gold nanoparticle, the gold nanoparticle is coupled to one or more antibodies or antibody fragments that bind to a portion of the analyte. In some embodiments, the one or more antibodies or antibody fragments bind to the analyte at a different site on the analyte than the primary binding partner, such that the analyte is bound to the primary binding partner and to one or more antibodies or antibody fragments of the label at the same time. In some embodiments, the label increases the size of the captured analyte. In some embodiments, the label increases the refractive index difference between the grating and the detected material.

In some embodiments, the label is a nanoparticle (e.g., a gold nanoparticle) that includes the primary binding partner that has a nucleic acid sequence that is complementary to the analyte, and is covalently linked to the nanoparticle.

As used herein, an "aptamer" is a RNA/DNA hybrid molecule that has a secondary and/or tertiary structure and can bind to an analyte. An aptamer can include any nucleic acid sequence that does not interfere with the binding of the antigen to the primary binding partner.

In some embodiments, the determining step (during which the primary binding partner binds to the analyte) can detect at least $10^2$ CFU/mL (e.g., at least $10^2$ CFU/mL, at least $10^3$ CFU/mL, at least $10^4$ CFU/mL, at least $10^5$ CFU/mL, at least $10^6$ CFU/mL, at least $10^7$ CFU/mL, at least $10^8$ CFU/mL, at least $10^9$ CFU/mL, at least $10^{10}$ CFU/mL, at least $10^{11}$ CFU/mL, at least $10^{12}$ CFU/mL, at least $10^{13}$ CFU/mL, at least $10^{14}$ CFU/mL, at least $10^{15}$ CFU/mL, at least $10^{16}$ CFU/mL, at least $10^{18}$ CFU/mL, such as between $10^2$ CFU/mL and $10^{20}$ CFU/mL) of an analyte (e.g., any of the bacterium described herein). In some embodiments, the determining step can determine between $10^4$ CFU/mL and $10^6$ CFU/mL.

One or more additional steps can be performed in any of the diffractive optics methods described herein. In some embodiments, the one or more additional steps are performed: prior to the binding of the primary binding partner to the secondary binding partner, after the binding of the primary binding partner to the secondary binding partner, prior to the binding of the primary binding partner to the analyte, or after the binding of the primary binding partner to the analyte.

In some embodiments, the one or more additional steps can include: a blocking of the sensors step, at least one (e.g., 1, 2, 3 or 4) wash step, a capturing step, and/or a filtering step. In some embodiments, the blocking step can include blocking a sensor within the ingestible device with a solution comprising at least 1% (e.g., at least 2%, at least 3%, at least 4%, at least 5%, at least 6%, at least 7%, at least 8%, at least 9%; 1%, 2%, 3%, 4%, 5%, 6%, 7%, 8%, 9% or 10%) bovine serum albumin (BSA) in a buffered solution (e.g., phosphate buffered saline (PBS), Tris buffered saline (TBS)). In some embodiments, the at least one wash step can include washing with a buffered solution (e.g., phosphate buffered saline (PBS), Tris buffered saline (TBS)). In general, blocking is performed during capsule manufacture, rather than in vivo.

In some embodiments, the capturing step includes enriching the analyte. In some embodiments, the capturing step includes physically separating the analyte from the remaining sample using a filter, a pore, or a magnetic bead. In some embodiments, the analyte is captured by size exclusion.

In some embodiments of any of the methods described herein, the determining step (during which the primary binding partner binds to the analyte is detected) can occur in 15 seconds (e.g., at least 30 seconds, at least one minute, at least 2 minutes, at least 5 minutes, at least 15 minutes, at least 30 minutes, at least 1 hour, at least 5 hours, at least 10 hours). In some embodiments, the binding of the primary binding partner to the analyte can occur during a period of time of, for example, in at least 5 seconds.

In some embodiments, the binding of the primary binding partner to the analyte can occur during a period of time of, for example, five seconds, 10 seconds, 30 seconds, 60 seconds, 5 minutes, 15 minutes, 60 minutes, 5 hours, or 24 hours).

EXAMPLES

Live Cell Dye Detection Examples

Bacterial organisms used include the ones listed in the table below.

| Code | Organism | Source | Dilution* |
|---|---|---|---|
| EC | *Escherichia coli* | ATCC 25922 | 1:1,000 |
| SA | *Staphylococcus aureus* | ATCC 29213 | 1:100 |
| KP | *Klebsiella pneumoniae* | ATCC 4352 | 1:1,000 |
| PA | *Pseudomonas aeruginosa* | ATCC 15442 | 1:1,000 |
| SM | *Streptococcus mutans* | ATCC 25175 | 1:100 |
| EF | *Enterococcus faecalis* | ATCC 49533 | 1:100 |
| GP | SA + SM + EF | Various | 1:1:1 |
| GN | EC + PA + KP | Various | 1:1:1 |
| MIX | SA + SM + EF + EC + PA + KP | Various | 1:1:1:1:1:1 |

* Previously determined optimal dilution in 0.9% saline to achieve inoculum density of $10^5$ CFU/mL

Example 1: Meta-Analysis of Hydrogen Breath Testing

SIBO was reported in 4-78% patients with irritable bowel syndrome (IBS). Quantitative culture of upper gut aspirate, although has been considered the gold standard for the diagnosis of SIBO, was invasive. The glucose and lactulose hydrogen breath tests (GHBT, LHBT) were not invasive, but there have been contradictory data on their performance in the diagnosis of SIBO. In fact, in a recent study of the utility of early (breath hydrogen increase 20 ppm above basal within 90 min) and double peaks on lactulose and glucose hydrogen breath tests (LHBT and GHBT, respectively) to diagnose SIBO, it was demonstrated that the sensitivity of the GHBT test and the diagnostic performances of the LHBT and breath methane were all very poor. See Ghoshal, U. C. et al., *Breath tests in the diagnosis of small intestinal bacterial overgrowth in patients with irritable bowel syndrome in comparison with quantitative upper gut aspirate culture*. European Journal of Gastroenterology & Hepatology 2014, 26:753-760.

Figure 74:
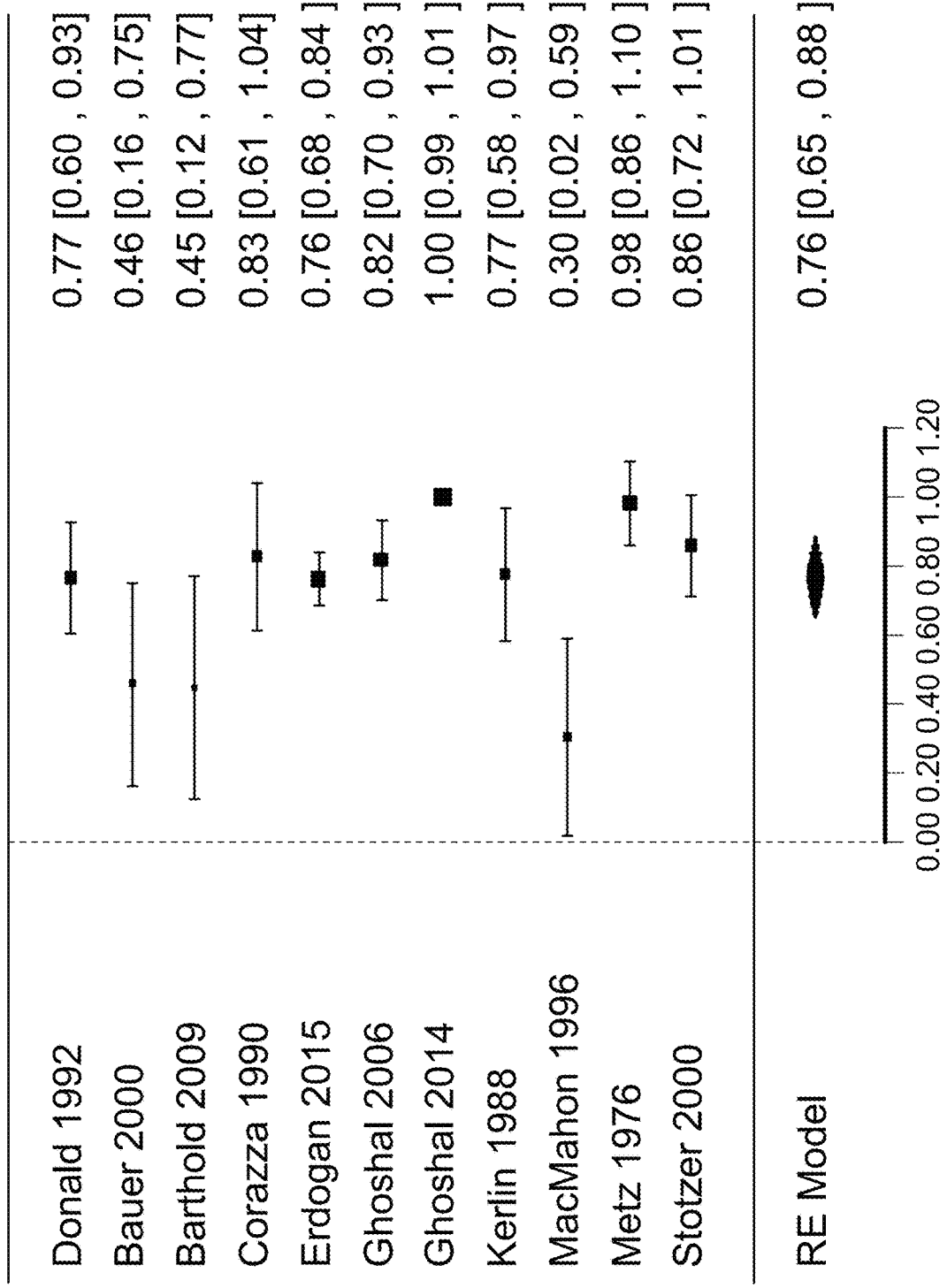
FIG. 74 shows a forest plot showing the results of 11 studies that compared the results of glucose breath test and endoscopy aspirate culture.

For example, FIG. 74 shows a forest plot showing the results of 11 studies that compared the results of glucose breath test and endoscopy aspirate culture. The table below shows the fixed-effects and random-effects model estimates of the mean positive and negative percent agreement combining the 11 studies. The homogeneity of effects across studies was tested with a Chi-square test and homogeneity of effects was rejected for both positive percent agreement ($c^2$=91.5, df=10, p-value<0.0001) and negative percent agreement ($c^2$=107.5, df=10, p-value<0.0001). When significant heterogeneity across studies exists, a random-effect model more accurately models the heterogeneity.

Fixed-effects and random-effects model estimates of the mean positive and negative percent agreement combining eleven studies.

|  | Mean positive percent agreement | Mean negative percent agreement |
|---|---|---|
| Model | (95% CI) | (95% CI) |
| Random-effects model | 54% (40%, 68%) | 76% (65%, 88%) |

Example 2: Kinetic Analysis of Dyes 2.1 Culture/Inoculum Preparation:

Using a cryogenic stock (at −70° C.), a first sub-culture of the bacterial organisms was streaked out on TSA (or other appropriate media). The plate was then incubated at 35±2° C. for 16 to 24 hours and stored wrapped in parafilm (or similar material) at 4° C. The resulting plate may be used for up to 120 hours. From the first sub-culture, a second sub-culture was streaked out on TSA (or other appropriate media). The resulting plate was then incubated at 35±2° C. for 16 to 24 hours. The second sub-culture should be used within 24 hours starting from the time it was first removed from incubation. Using the second sub-culture, an isolated colony was aseptically removed from the Agar plate and inoculated with 100 mL of TSB (or other appropriate liquid media). The culture was then placed on an orbital shaker in a humidified incubator and incubated at 200 rpm at 35±2° C. for 16 to 24 hours. Three (3) samples (200 μL each) of the diluted organism were used for an inoculum check by serially diluting and spot plating on TSA. The culture conditions and incubation times were calibrated such that the initial inoculum density was about $1.0 \times 10^8$ CFU/mL. A dilution range was prepared by aseptically performing appropriate serial dilutions (i.e. 1 mL of $10^8$ CFU/mL into 9 mL of sterile PBS to give a dilution of $10^7$ CFU/mL). The final concentrations were confirmed by serial dilution and spot plate counts. See, e.g., Gaudy, A. F., Abu-Niaaj, F., Gaudy, E. T., *Statistical study of the spot plate technique for viable cell counts*. Applied Microbiology, Vol 11, 1962 pp. 305-309.

2.2 Sample Capture and Inoculum Adjustment:

A plate was prepared in triplicate using a Sterilin 96 well round bottom microctitre plate (P/N H511A), where the plate was loaded with 100 μL of a diluted dynamic range of bacteria. An exemplary plate set-up is presented in FIG. 75C.

2.3 Live Stain Preparations:

Live stain was prepared fresh on the day of the experiment. The live stain dilutions were protected from light. The live stain treatments were aseptically prepared as described below using 15 mL sterile conical tubes.

Treatment 1 (Resazurin, or "REZ"):

Working stain was prepared according to manufacturer instructions. Resazurin salt was used to prepare a 10 mM stock solution in PBS, pH 6.0, with 50 mM $MgCl_2$, 0.003% Deoxycholate. The stock solution was mixed via vortexing until a homogenous suspension was produced. The stock solution was stored in dark until used.

2.4 Test Fixture Preparation:

The spectrophotometer was set and calibrated according to manufacturer's SOPs. The data program was set up to excite and read the emission intensity of the culture. Appropriate volume of working stain (20 μL for REZ) was aseptically added and the resulting mixture was mixed thoroughly via pipette mixing in each well. The plate was protected from light.

Figure 75A:
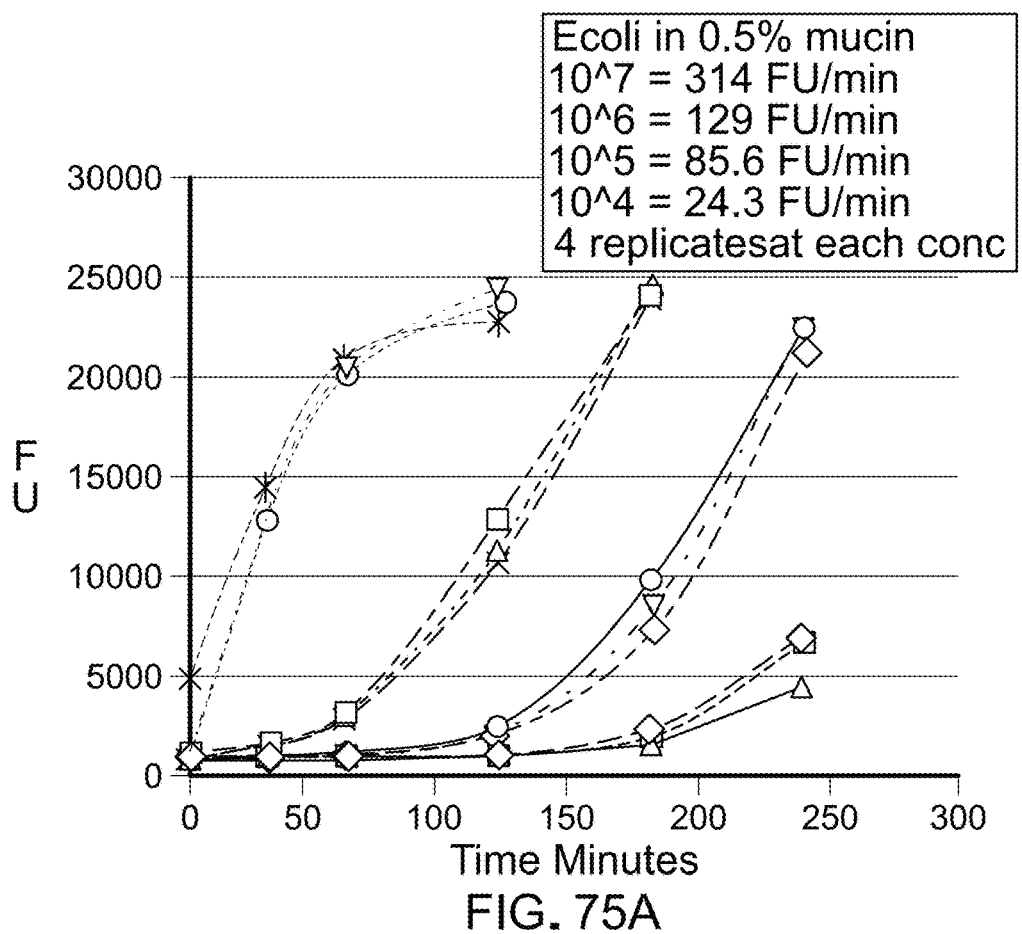
FIG. 75A shows kinetic analysis of Resazurin when added to varying concentrations of *E. coli* ATCC 25922. Four replicates were run in 4 different plates on the same day, where FU=relative fluorescence units.
Figure 75B:
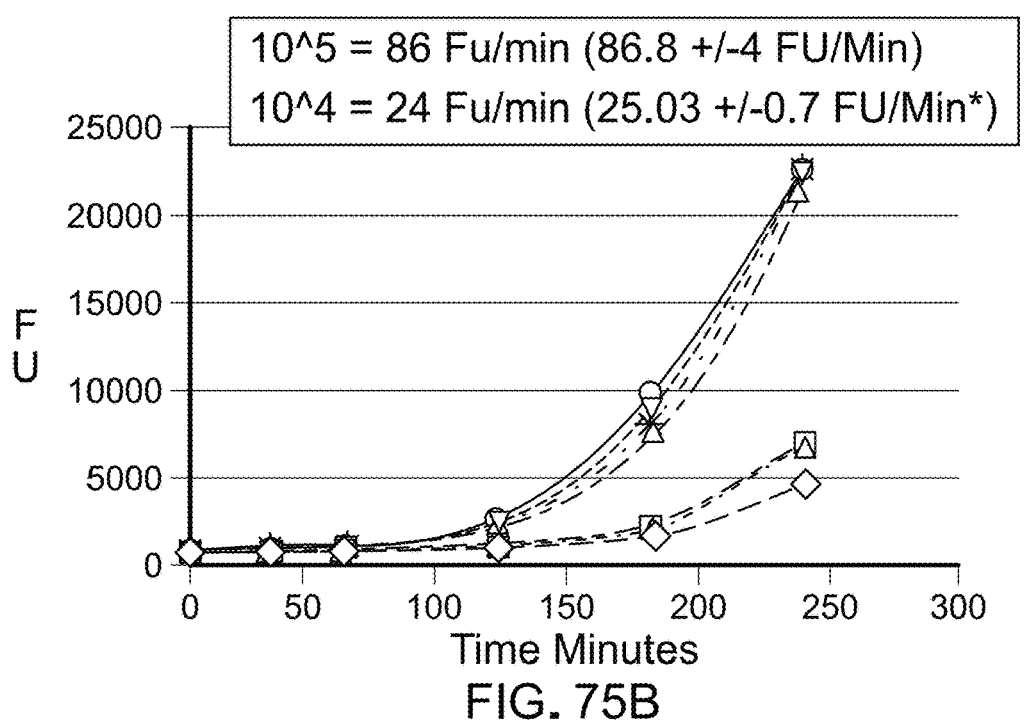
FIG. 75B shows an expanded view of the kinetic analysis of Resazurin when added to $10^4$ and $10^5$ CFU/mL of *E. coli* ATCC 25922.

2.5 Sample Acquisition, Incubation and Detection:

Exact inoculation time was recorded in the log book and on the device. The plate was incubated at 37° C. degrees, at 200 rpm and was protected from light. Plate was read and recorded at 530 nm Excitation, detecting 600 nm Emission. The plate was covered and returned to the 37° C. incubator @ 200 rpm between readings. This procedure was performed every 30 minutes for the test cycle. The test cycle spanned 6 hours. The kinetic analysis results of resazurin in various concentrations of bacteria are depicted in FIGS. 75A and 75B.

Figure 76A:
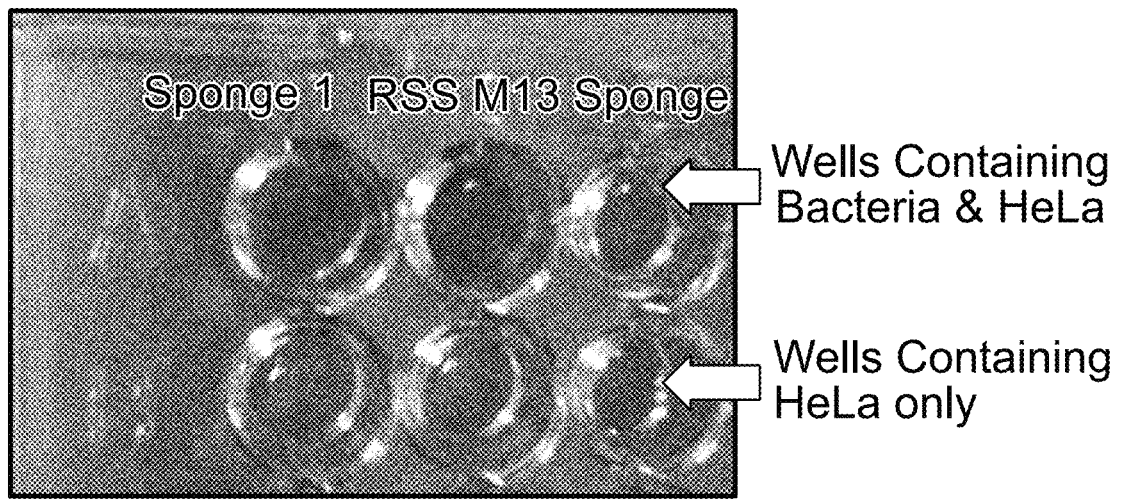
FIG. 76A shows the wells in the presence or absence of an absorptive sponge.
Figure 76B:
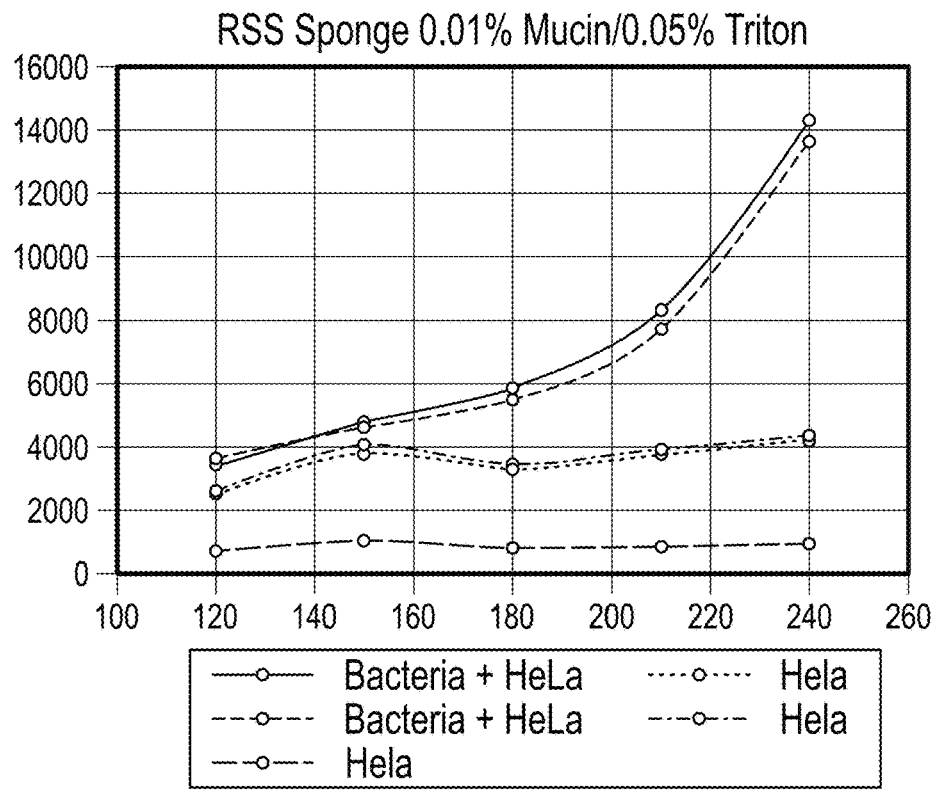
FIG. 76B shows fluorescence detection plotted over time (120 min to 240 min) in the presence of RSS Sponge, which is saturated with a solution containing a dye, and 0.01% Mucin/0.05% Triton.
Figure 76C:
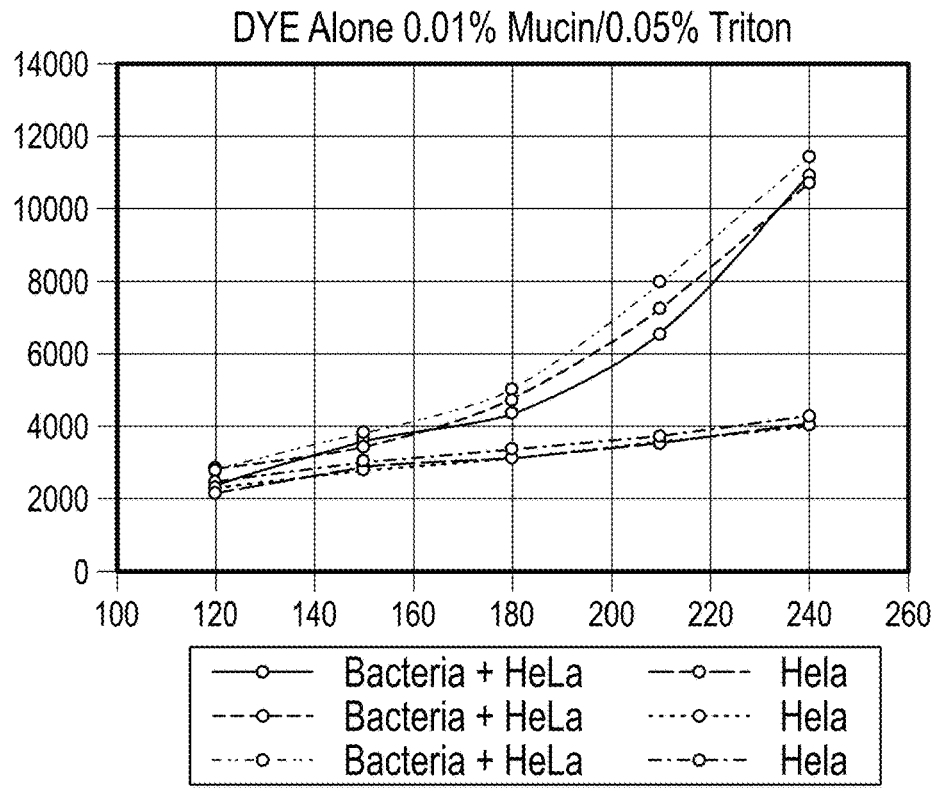
FIG. 76C shows fluorescence detection plotted over time (120 min to 240 min) in the presence of a solution containing a dye and 0.01% Mucin/0.05% Triton (no sponge was present).
Figure 76D:
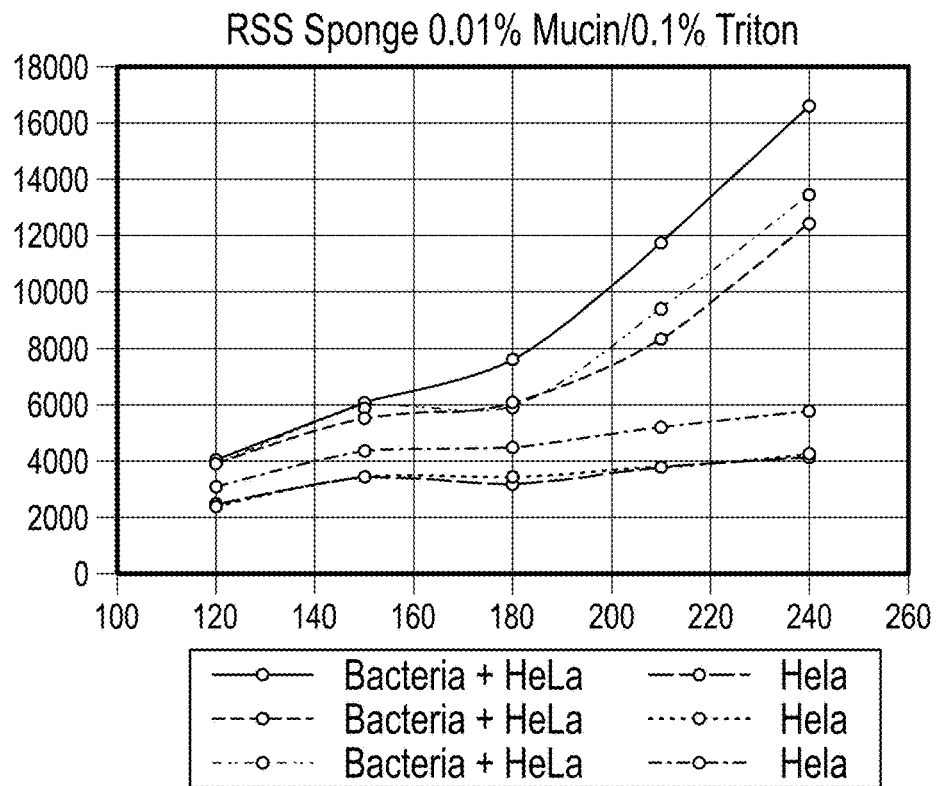
FIG. 76D shows fluorescence detection plotted over time (120 min to 240 min) in the presence of RSS sponge, which is saturated with a solution containing a dye and 0.01% Mucin/0.1% Triton.
Figure 76E:
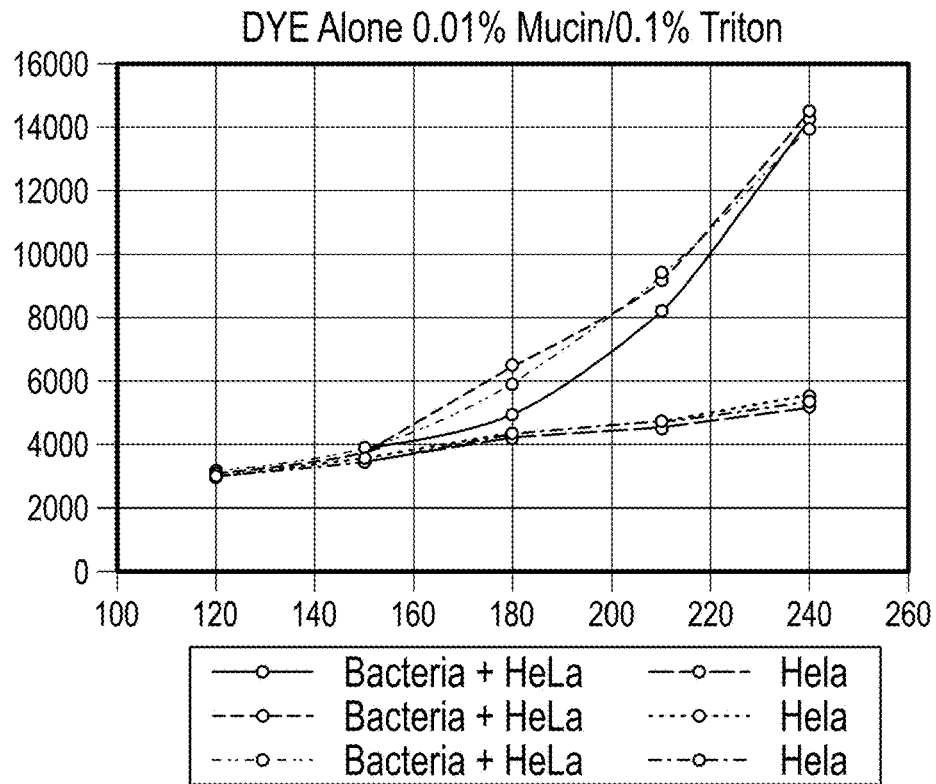
FIG. 76E shows fluorescence detection plotted over time (120 min to 240 min) in the presence of a solution containing a dye and 0.01% Mucin/0.1% Triton (no sponge was present).
Figure 76F:
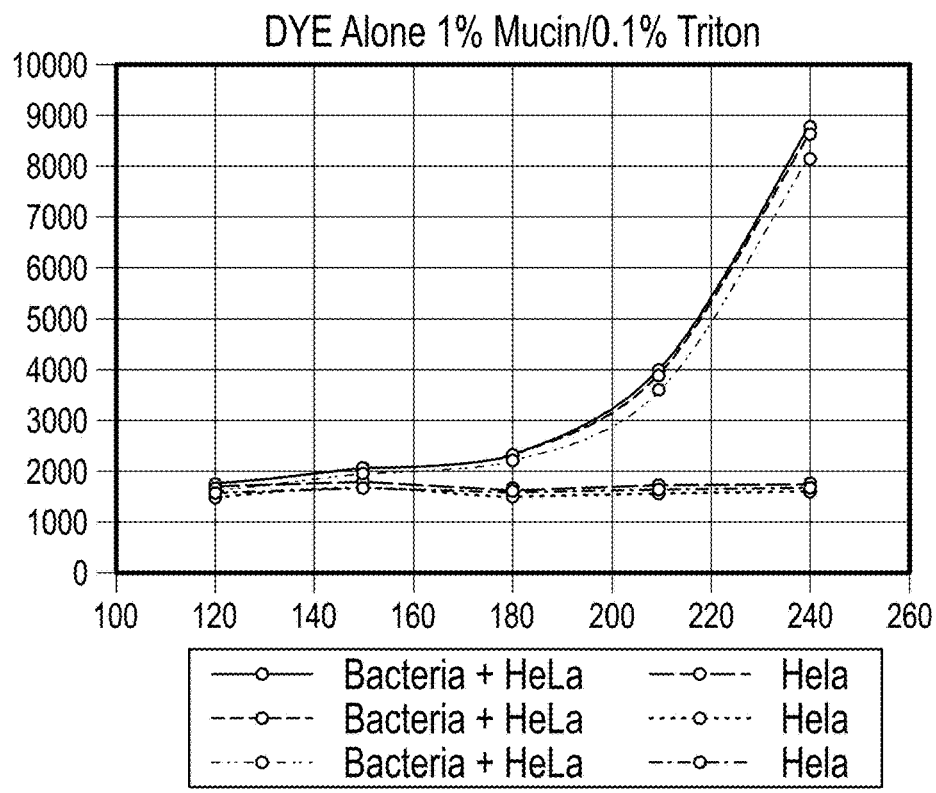
FIG. 76F shows fluorescence detection plotted over time (120 min to 240 min) in the presence of a solution containing a dye and 1% Mucin/0.1% Triton (no sponge was present).
Figure 76G:
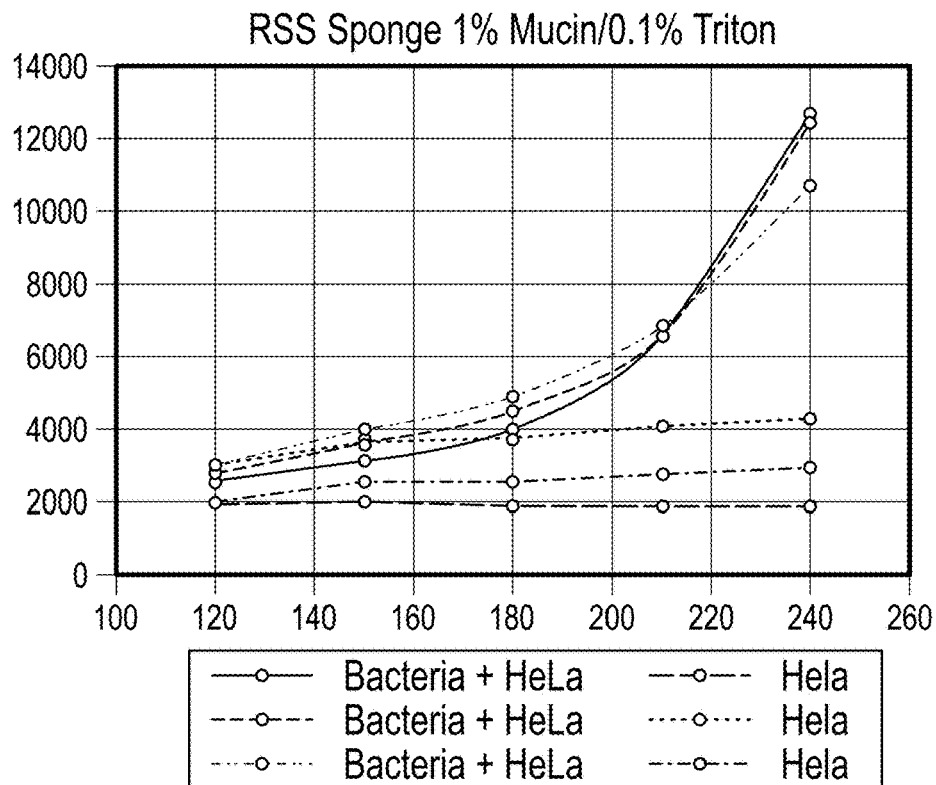
FIG. 76G shows fluorescence detection plotted over time (120 min to 240 min) in the presence of RSS sponge, which is saturated with a solution containing a dye and 0.01% Mucin/0.1% Triton.
Figure 76H:
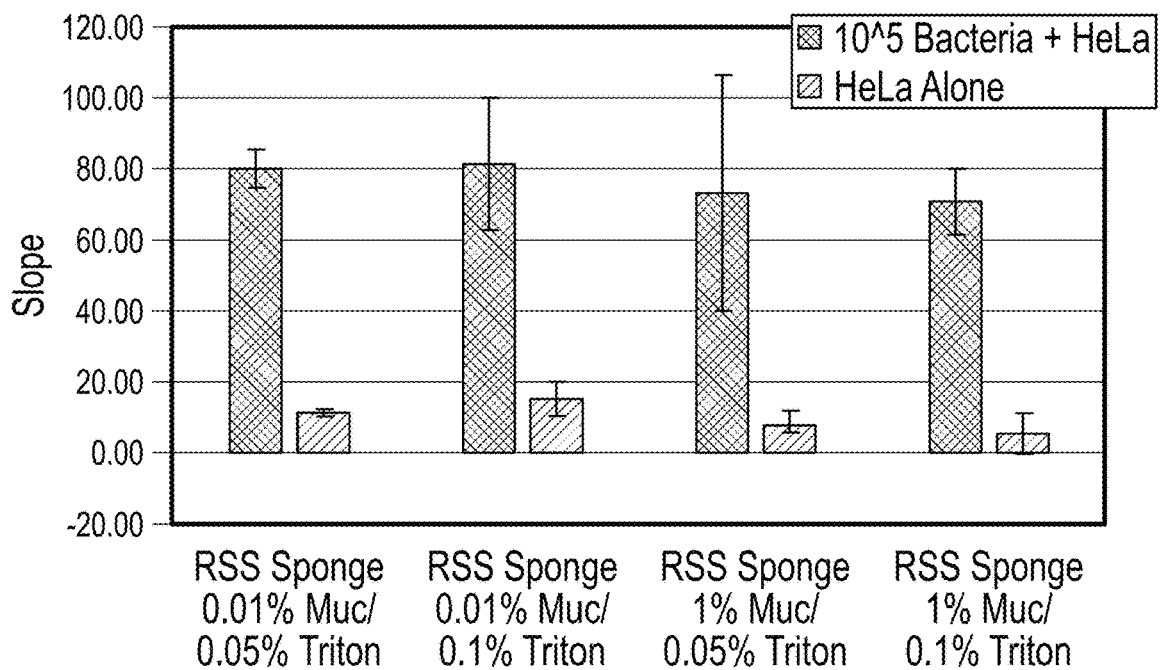
FIG. 76H summarizes the mean slopes presented in the fluorescence detection over time in the presence of sponge.
Figure 76I:
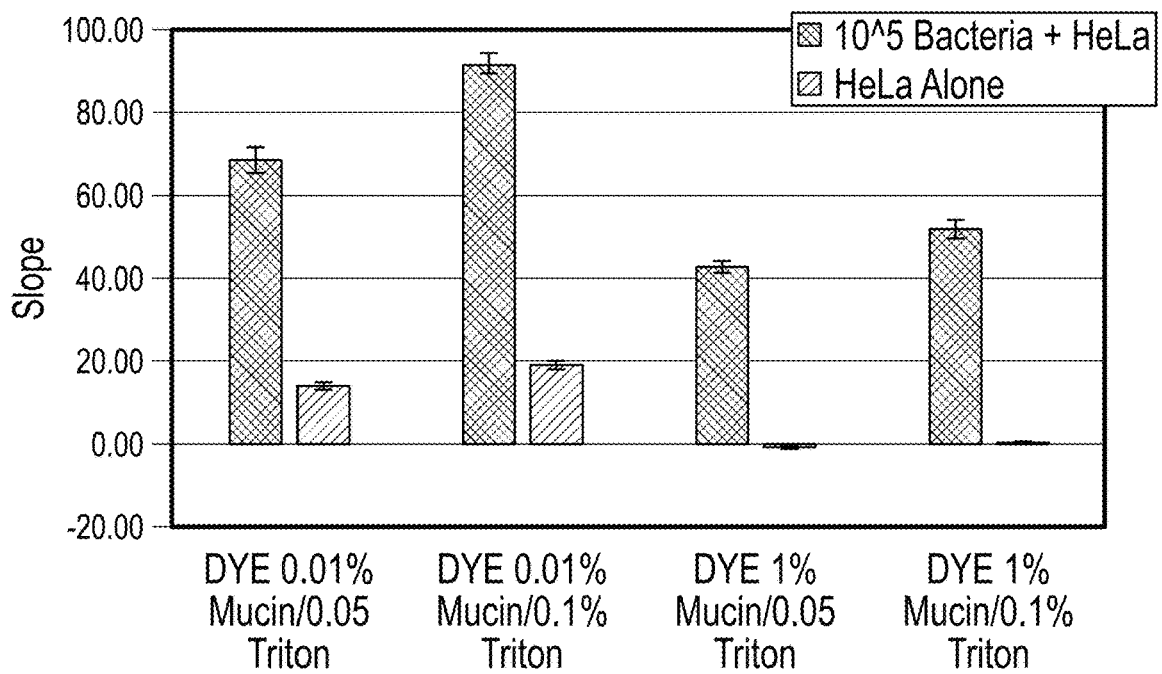
FIG. 76I summarizes the mean slopes presented in the fluorescence detection over time in the absence of sponge.
Figure 77A:
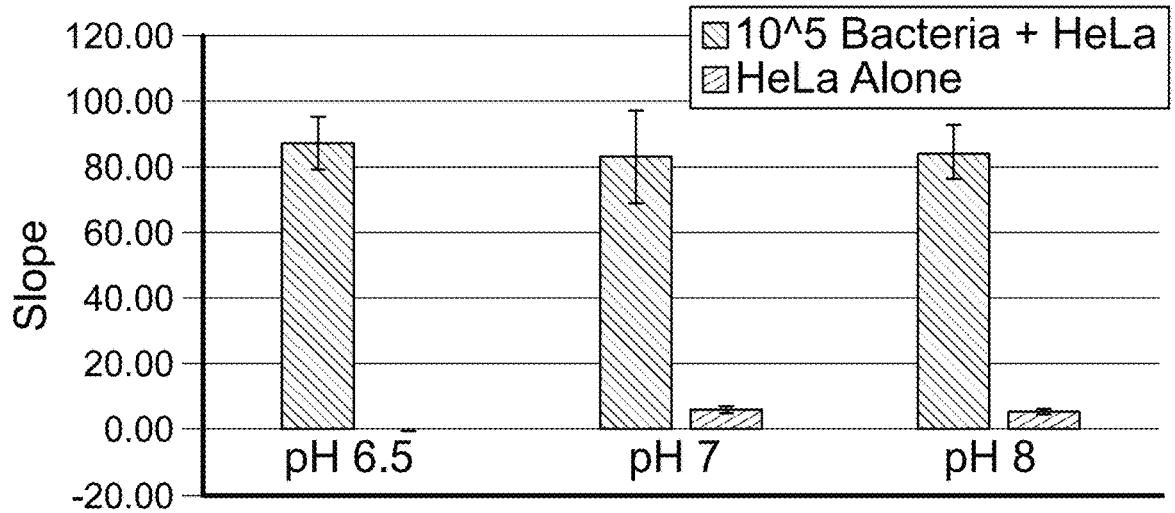
FIG. 77A shows the effect of pH on detection of live bacterial cells in a sample. The data demonstrates that the pH variation within the pH range of 6.5-8 does not impact the ability to accurately discern positive and negative calls.
Figure 77B:
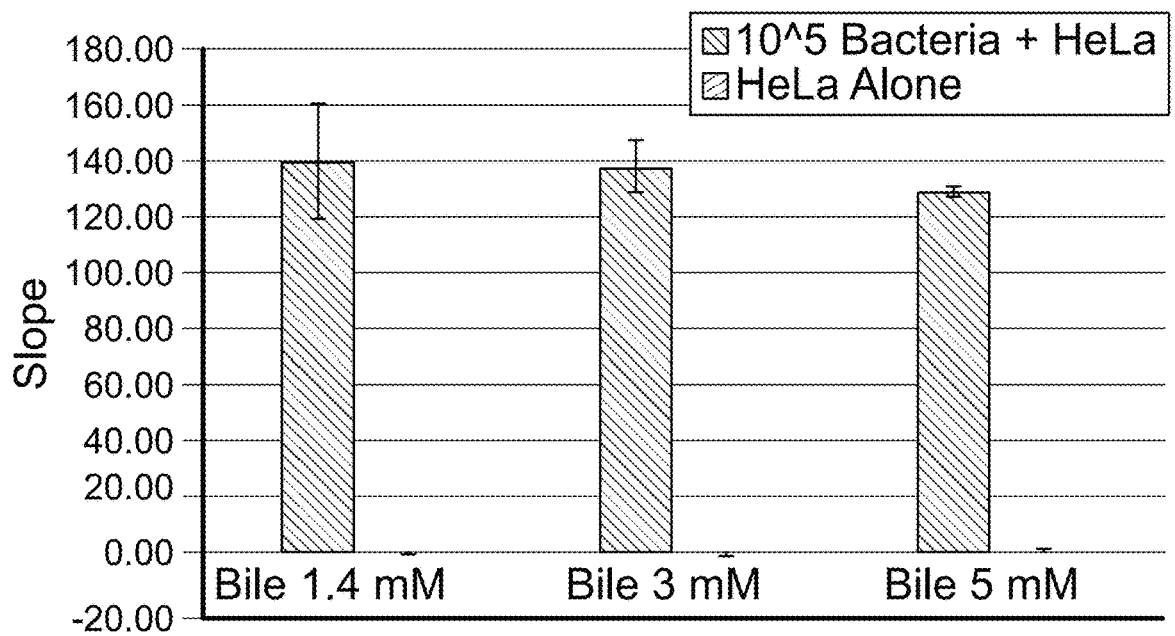
FIG. 77B shows the effect of bile on detection of live bacterial cells in a sample. The use of deoxycholate buffers the effects of bile concentration. The presence of bile in the tested concentration ranges showed no impact on the ability to accurately discern positive and negative calls.
Figure 77C:
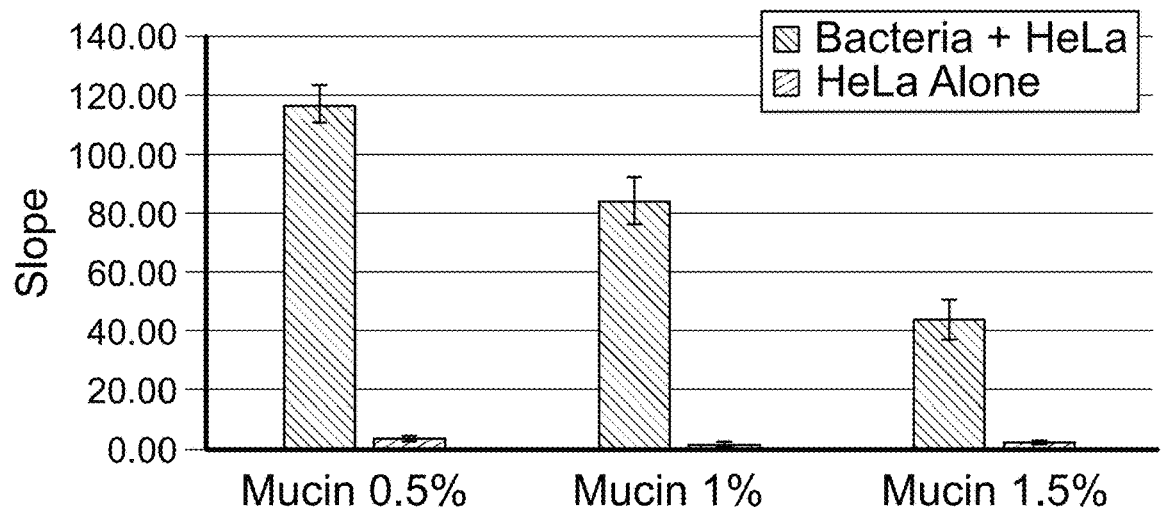
FIG. 77C shows the effect of mucin on detection of live bacterial cells in a sample. With both *E. coli* and *S. aureus*, there was a decrease in mean slope which correlated to an increase in mucin concentration. This, however, did not impact the ability to accurately discern positive and negative calls. The effect of mucin can be further mitigated using higher mucin concentrations in the dye formulation.
Figure 77D:
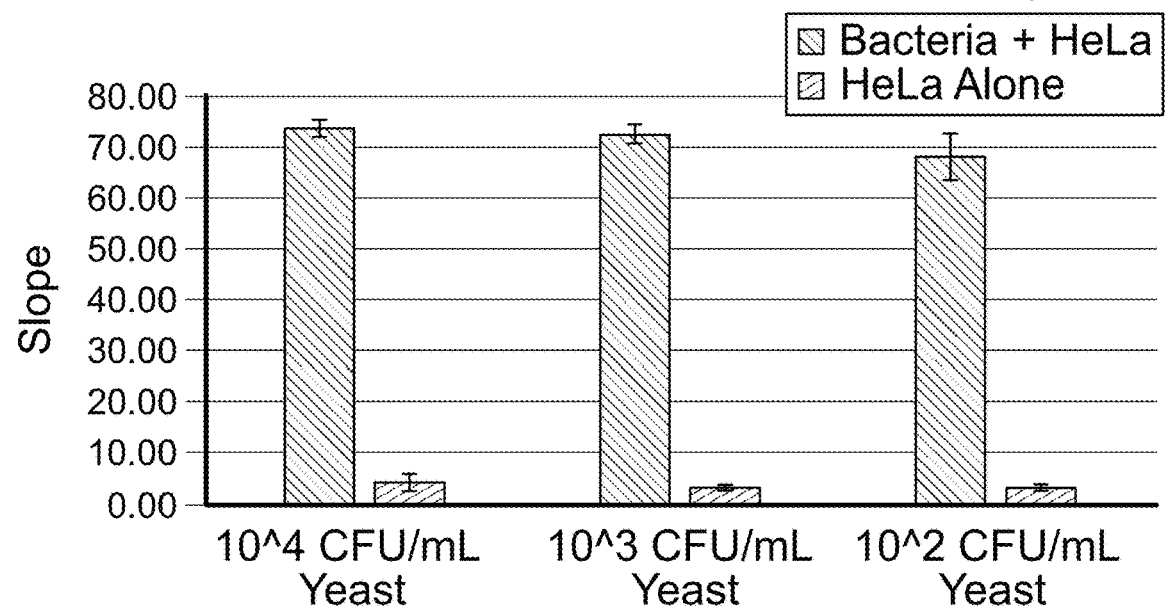
FIG. 77D shows the effect of yeast on detection of live bacterial cells in a sample. Use of amphotericin B buffered the effects of increased yeast concentration. Yeast at tested concentrations showed no impact on the ability to accurately discern positive and negative calls.
Figure 78A:
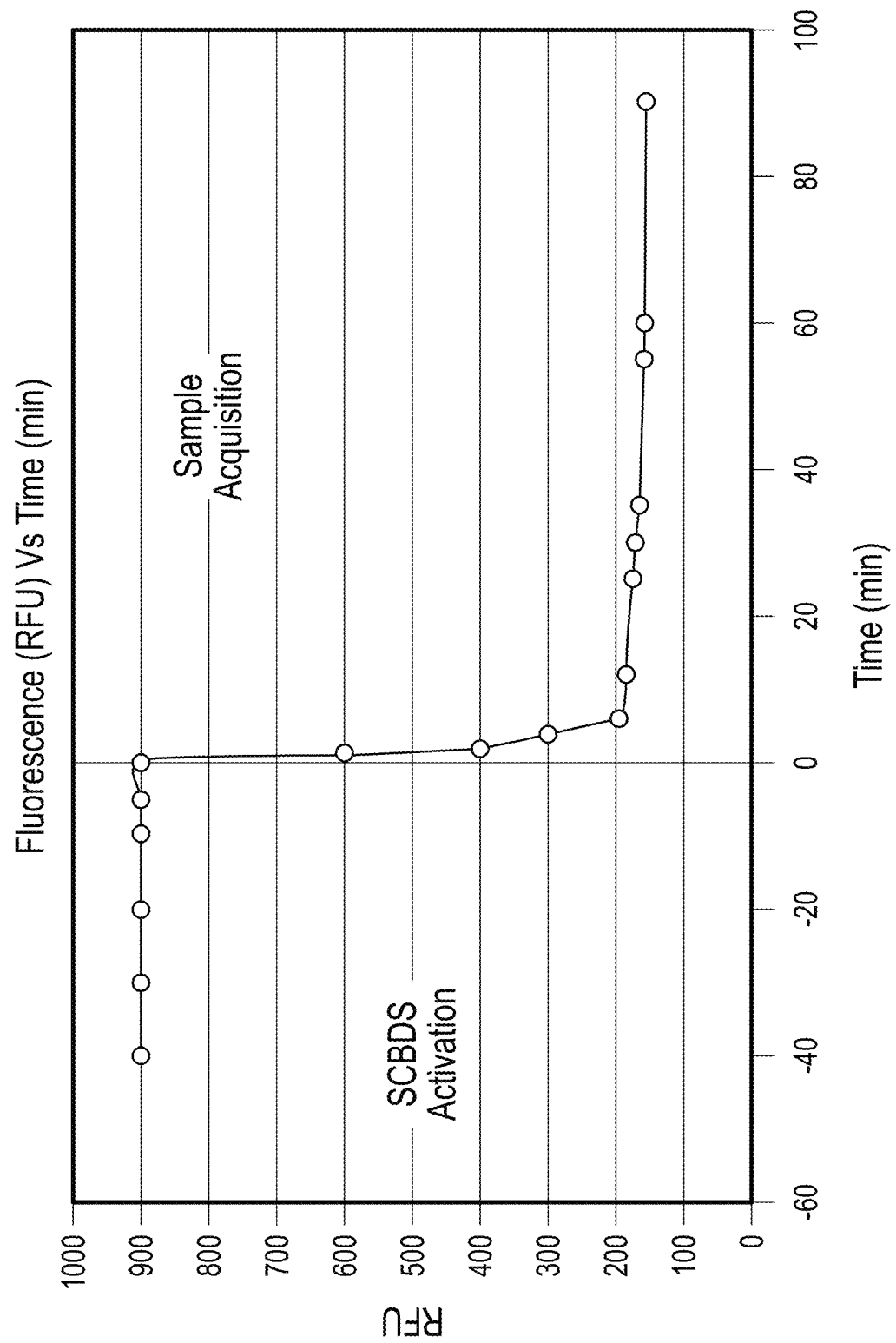
FIG. 78A shows simulated data demonstrating Failure Mode #1 where an ingestible device of this disclosure (e.g., a capsule) samples early in the stomach. The low pH of the stomach acid (pH 1-4) reduces the baseline fluorescence (sampled at activation) rapidly (within 5 minutes after sample acquisition). Capsule reports: ERROR, DX data not valid.
Figure 78B:
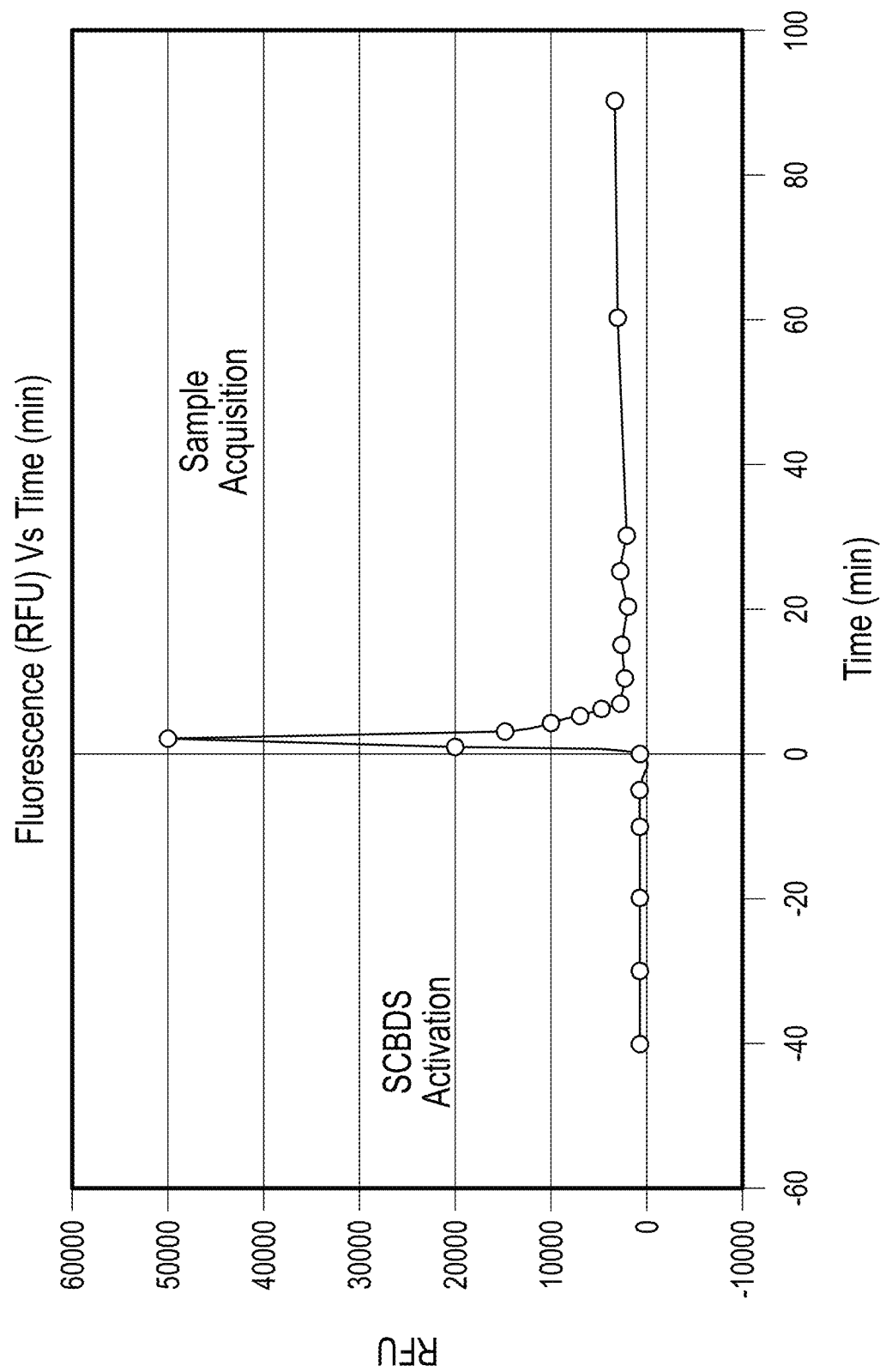
FIG. 78B shows simulated data demonstrating Failure Mode #2 where a capsule samples late in the colon. The high levels of bacteria (>$10^{12}$ CFU/mL rapidly convert Resazurin to Resorufin (within 1 minute during sample acquisition). Rapid auto quenching reduces the signal quickly below 3,000 RFU within 5 minutes. Capsule reports: ERROR, DX data not valid.
Figure 78C:
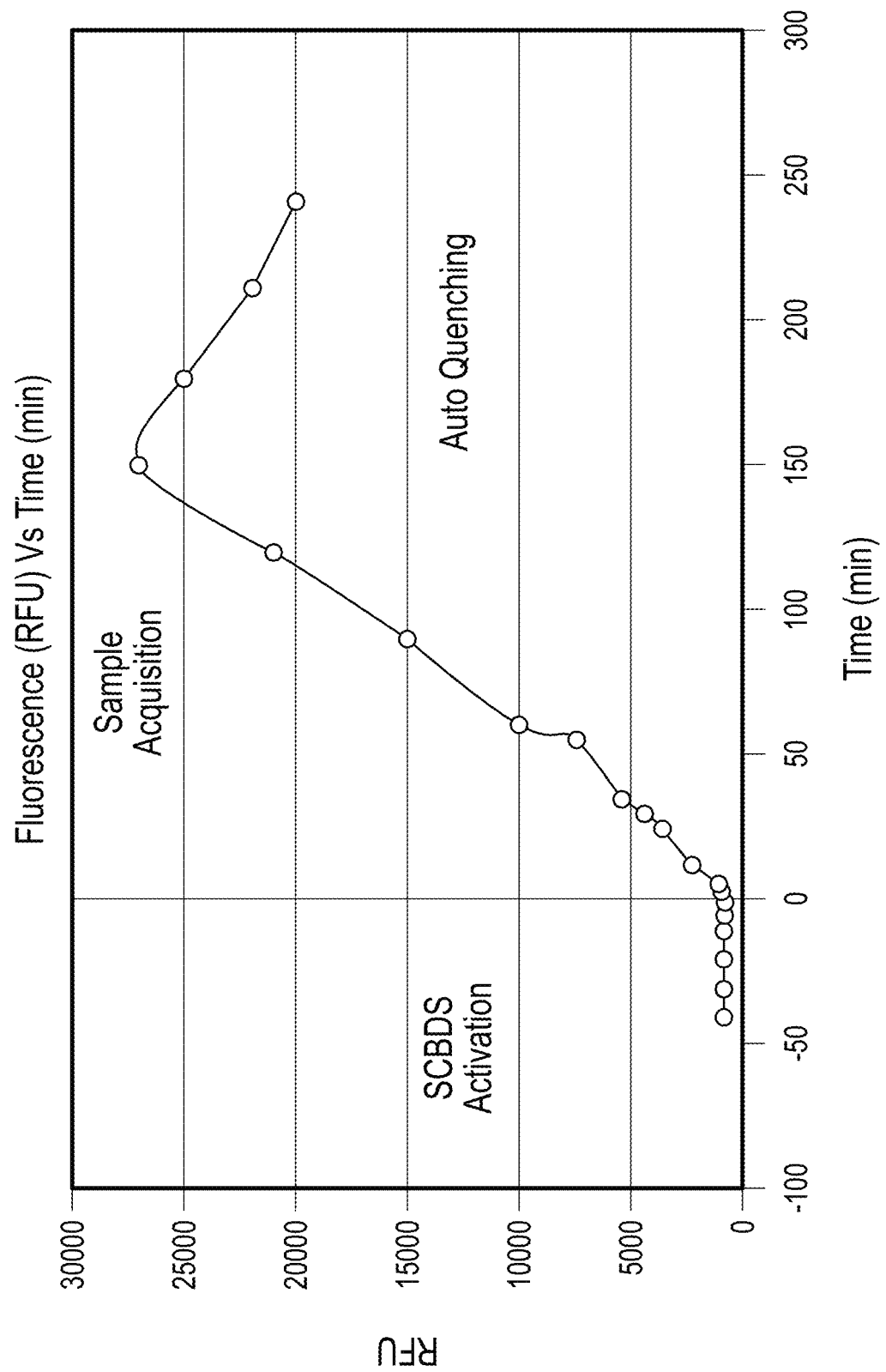
FIG. 78C shows simulated data demonstrating early detection of a SIBO+Ve case presenting with >$10^7$ CFU/mL. The high levels of bacteria rapidly convert Resazurin to Resorufin (within 60 minutes after Sample acquisition). Rapid auto quenching reduces the signal quickly below 20,000 RFU within 240 minutes. Capsule reports: Positive SIBO call within 60 minutes.
Figure 78D:
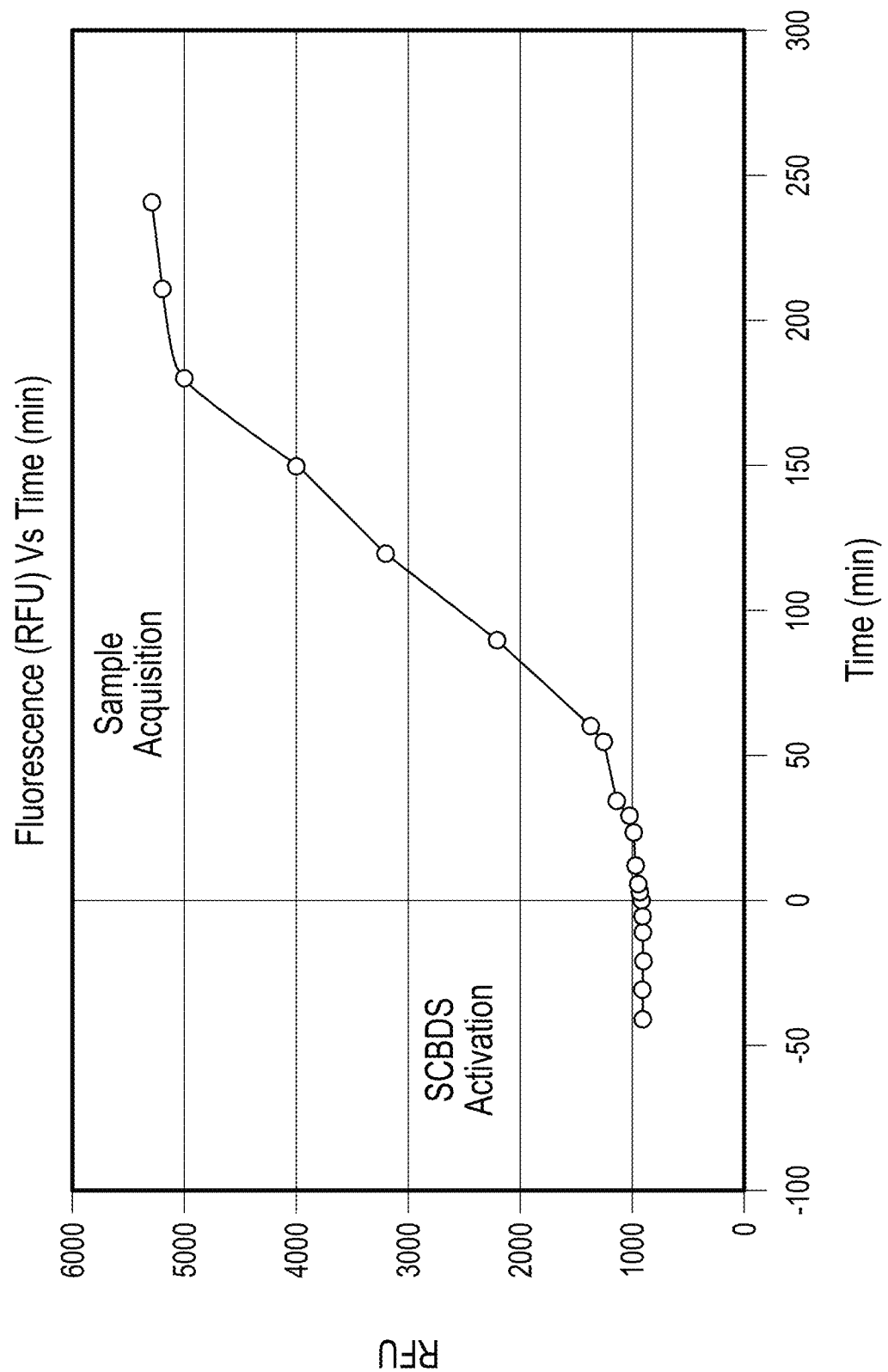
FIG. 78D shows simulated data demonstrating early detection of a SIBO+Ve case presenting with >10$^5$ CFU/mL. The low levels of bacteria slowly convert Resazurin to Resorufin (within 240 minutes after Sample acquisition). Capsule reports: Positive SIBO call with 240 minutes.
Figure 78E:
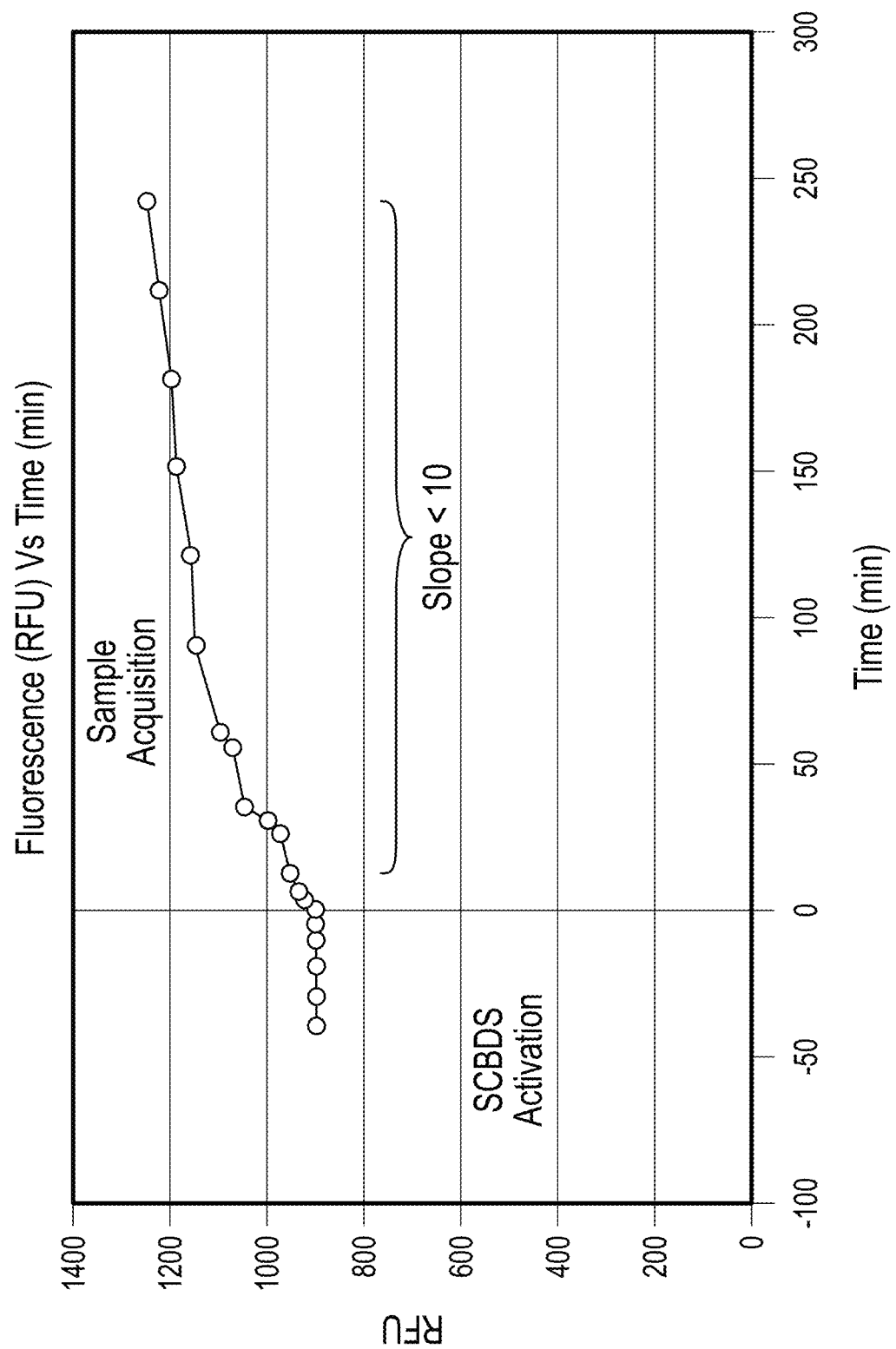
FIG. 78E shows simulated data demonstrating early detection of a SIBO+Ve case presenting with <10$^4$ CFU/mL. The low levels of bacteria slowly convert Resazurin to Resorufin (within 240 minutes after Sample acquisition). Slope<10. Capsule reports: Negative SIBO call with 240 minutes.

Example 3: Selective Lysis of HeLa Cells and Selective Detection of Bacterial Cells in the Presence of Mammalian Cells 3.1 Simulated Jejunal Sample Preparation:
   HeLa grown up to $10^4$ Cells/100 μLin RPMI
   Bacteria (*E. coli* ATCC 25922) was added to "Positive Test Samples" to a final concentration of $10^5$ CFU/mL in HeLa+RPMI fluid.
3.2 Sample Acquisition (Liquid):
   20 μL various dye formulations including resazruin were added to wells containing "Positive Test Samples" or HeLa alone in triplicate.
3.3 Sample Acquisition (Sponge):
   20 μL various dye formulations were added to sponge samples and allowed to saturate. Sponges were exposed to wells containing "Positive Test Samples" or HeLa alone in triplicate by placing with sterile forceps and submerging with a sterile pipette tip. See FIG. 76A.
3.4 Sample Reading (Liquid and Sponge):
   Plates were placed in the plate reader at 37° C. and read at 550 nm Excitation, detecting 590 nm Emission
   Reading every 30 minutes.
   Plates kept at 37° C. in 5% $CO_2$ between reads.
3.5 Data Acquisition and +/− Calls:
   Kinetic Read Out: increase in fluorescence over time represents a positive signal
   Slopes presented from 120 min to 240 min
   Difference in Slope was the basis for positive/negative calls
Replicates and Control:
   Testing performed in triplicate
   Each test compared to positive ($10^5$ CFU/mL bacteria) and control ($10^4$ HeLa cells alone)
   Master Control:
      Negative: PBS alone, no HeLa or bacteria plus baseline dye (10 mM resazurin, 50 mM $MgCl_2$, 0.005% Deoxycholate)
      Positive: PBS alone, plus $10^5$ bacteria plus baseline dye
The kinetic fluorescence measurements with various dye formulations in the presence or absence of the sponge are depicted in FIGS. 76B-G. The mean slopes of the kinetic measurements in the presence or absence of the sponge are summarized in FIGS. 76H and 76I.

Example 4: Interference Assay 4.1 Culture/Inoculum Preparation:
   Using a cryogenic stock (at −70° C.), a first sub-culture of the bacterial organisms was streaked out on TSA (or other appropriate media). The plate was then incubated at 35±2° C. for 16 to 24 hours and stored wrapped in parafilm (or similar material) at 4° C. The resulting plate may be used for up to 120 hours. From the first sub-culture, a second sub-culture was streaked out on TSA (or other appropriate media). The resulting plate was then incubated at 35±2° C. for 16 to 24 hours. The second sub-culture should be used within 24 hours starting from the time it was first removed from incubation. Using the second sub-culture, an isolated colony was aseptically removed from the Agar plate and inoculated with 100 mL of TSB (or other appropriate liquid media). The culture was then placed on an orbital shaker in a humidified incubator and incubated at 200 rpm at 35±2° C. for 16 to 24 hours. Three (3) samples (200 μL each) of the diluted organism were used for an inoculum check by serially diluting and spot plating on TSA. The culture conditions and incubation times were calibrated such that the initial inoculum density was about $1.0 \times 10^8$ CFU/mL. A dilution range was prepared by aseptically performing appropriate serial dilutions (i.e. 1 mL of $10^8$ CFU/mL into 9 mL of sterile PBS to give a dilution of $10^7$ CFU/mL). The final concentrations were confirmed by serial dilution and spot plate counts. See, e.g., Gaudy, A. F., Abu-Niaaj, F., Gaudy, E. T., *Statistical study of the spot plate technique for viable cell counts*. Applied Microbiology, Vol 11, 1962 pp. 305-309.

Summary of various samples used in the interference assay:

| CODE | SAMPLE | LOT/PART NUMBER | DESCRIPTION | HAZARD |
|---|---|---|---|---|
| C | PBS | GibcoRef 10010-023; Lot 1764980 | Baseline Control | See MSDS |
| SJ | Simulated Jejunal Fluid | FaSSIF-V2 | Simulated Jejunal fluid | See MSDS |
| pH | FaSSIF-V2 at modified Ph | Batch #3, STF | pH 6.5, pH 7.0, pH 8.0 | See MSDS |
| B | Bile Acids added to FaSSIF-V2 | Oxgall (Sigma Aldrich, SKU B3883) | 1.4, 3, 5.5 mM | See MSDS |
| M | Mucin added to FaSSIF-V2 | Porcine Mucin (Sigma Aldrich, SKU M2378) | 0.5%, 1%, and 1.5% | See MSDS |
| F | Fungal cells added to FaSSIF-V2 | *C. albicans* ATCC 18804 | $1.0 \times 10^2$, $1.0 \times 10^3$, $1.0 \times 10^4$ CFU/mL | |
| Hi-Lo | High concentration/ Sub-LOD concentration | Challenge Strain | $1.0 \times 10^7$, $1.0 \times 10^4$, $1.0 \times 10^3$ CFU/mL | |

4.2 Sample Capture and Inoculum Adjustment:
   A plate was prepared in triplicate using a Sterilin 96 well round bottom microtitre plate (P/N H511A), where the plate was loaded with 100 μL of a diluted dynamic range of bacteria. An exemplary plate set-up is presented in FIG. 75C.
4.3 Live Stain Preparations:
   Live stain was prepared fresh on the day of the experiment. The live stain dilutions were protected from light. The live stain treatments were aseptically prepared as described below using 15 mL sterile conical tubes.
Treatment 1 (Resazurin or "REZ"):
   Working stain was prepared according to manufacturer instructions. Resazruin salt was used to prepare a 10 mM Resazurin solution in PBS, containing 0.005% Deoxycholate, 0.1% v/v Triton X-100, 2.5 mg/L Amphotericin B, 50 mM $MgCl_2$ with a pH of 6.0. The solution was mixed via vortexing until a homogenous suspension was produced and was then stored in dark until used.
4.4 Test Fixture Preparation:
   The spectrophotometer was set and calibrated according to manufacturer's SOPs. The data program was set up to excite and read the emission intensity of the culture. Appropriate volume of working stain (20 μL for REZ) was aseptically added and the resulting mixture was mixed thoroughly via pipette mixing in each well. The plate was protected from light.

4.5 Sample Acquisition, Incubation and Detection:

Exact inoculation time was recorded in the log book and on the device. The plate was incubated at 37° C. degrees, at 200 rpm and was protected from light. Plate was read and recorded at 530 nm Excitation, detecting 600 nm Emission. The plate was covered and returned to the 37° C. incubator @ 200 rpm between readings. This procedure was performed every 30 minutes for the test cycle. The test cycle spanned 6 hours.

The effects of various interfering factors are depicted in FIGS. 77A-D.

Example 5: Failure Modes of the Live Stain Assay 5.1 Culture/Inoculum Preparation:

Using a cryogenic stock (at −70° C.), a first sub-culture of the bacterial organisms was streaked out on TSA (or other appropriate media). The plate was then incubated at 35±2° C. for 16 to 24 hours and stored wrapped in parafilm (or similar material) at 4° C. The resulting plate may be used for up to 120 hours. From the first sub-culture, a second sub-culture was streaked out on TSA (or other appropriate media). The resulting plate was then incubated at 35±2° C. for 16 to 24 hours. The second sub-culture should be used within 24 hours starting from the time it was first removed from incubation. Using the second sub-culture, an isolated colony was aseptically removed from the Agar plate and inoculated with 100 mL of TSB (or other appropriate liquid media). The culture was then placed on an orbital shaker in a humidified incubator and incubated at 200 rpm at 35±2° C. for 16 to 24 hours. Three (3) samples (200 µL each) of the diluted organism were used for an inoculum check by serially diluting and spot plating on TSA. The culture conditions and incubation times were calibrated such that the initial inoculum density was about $1.0 \times 10^8$ CFU/mL. A dilution range was prepared by aseptically performing appropriate serial dilutions (i.e. 1 mL of $10^8$ CFU/mL into 9 mL of sterile PBS or Fasted State Simulated Intestinal Fluid (FaSSIF) to give a dilution of $10^7$ CFU/mL). Note final concentrations were confirmed by serial dilution and spot plate counts. See, e.g., Gaudy, A. F., Abu-Niaaj, F., Gaudy, E. T., *Statistical study of the spot plate technique for viable cell counts*. Applied Microbiology, Vol 11, 1962 pp. 305-309.

Simulation of Failure Modes:
1: Opens in Stomach: Dilution in FaSSIF pH 2
2: Opens in Colon. $10^{12}$ CFU/mL *E. coli* prepared in FaSSIF to simulate feces.

5.2 Sample Capture and Inoculum Adjustment:

A plate was prepared in triplicate using a Sterilin 96 well round bottom microtitre plate (P/N H511A), where the plate was loaded with 100 µL of a diluted dynamic range of bacteria. An exemplary plate set-up is presented in FIG. 75C.

5.3 Live Stain Preparations:

Live stain was prepared fresh on the day of the experiment. The live stain dilutions were protected from light. The live stain treatments were aseptically prepared as described below using 15 mL sterile conical tubes.

Treatment 1 (Resazurin or "REZ"):

Working stain was prepared according to manufacturer instructions. Resazruin salt was used to prepare a 10 mM Resazurin solution in PBS, containing 0.005% Deoxycholate, 0.1% v/v Triton X-100, 2.5 mg/L Amphotericin B, 50 mM $MgCl_2$ with a pH of 6.0. The solution was mixed via vortexing until a homogenous suspension was produced and was then stored in dark until used.

5.4 Test Fixture Preparation:

Set and calibrated the spectrophotometer according to manufacturer's SOPs. Set up the data program to excite and read the emission intensity of the culture. Aseptically added the appropriate volume of working stain (20 µL for REZ). Mixed thoroughly via pipette mixing in each well. Used fresh tips for each well. Protected the plate from light.

5.5 Sample Acquisition, Incubation and Detection:

Exact inoculation time was recorded in the log book and on the device. The plate was incubated at 37° C. degrees, at 200 rpm and was protected from light. Plate was read and recorded at 530 nm Excitation, detecting 600 nm Emission. The plate was covered and returned to the 37° C. incubator @ 200 rpm between readings. This procedure was performed every 30 minutes for the test cycle. The test cycle spanned 6 hours.

Simulated failure modes and early detection of SIBO are depicted in FIGS. 78A-E.

Example 6: Jejunal Duodenal Aspriate (MDB) Assay 6.1 Experimental Design:

Subject "MDB" from clinical duodenal aspirates was selected based on number of aliquots and sterility testing.

6.2 Culture/Inoculum Preparation:

Using a cryogenic stock (at −70° C.), a first sub-culture of the bacterial organisms was streaked out on TSA (or other appropriate media). The plate was then incubated at 35±2° C. for 16 to 24 hours and stored wrapped in parafilm (or similar material) at 4° C. The resulting plate may be used for up to 120 hours. From the first sub-culture, a second sub-culture was streaked out on TSA (or other appropriate media). The resulting plate was then incubated at 35±2° C. for 16 to 24 hours. The second sub-culture should be used within 24 hours starting from the time it was first removed from incubation. Using the second sub-culture, an isolated colony was aseptically removed from the Agar plate and inoculated with 100 mL of TSB (or other appropriate liquid media). The culture was then placed on an orbital shaker in a humidified incubator and incubated at 200 rpm at 35±2° C. for 16 to 24 hours. Three (3) samples (200 µL each) of the diluted organism were used for an inoculum check by serially diluting and spot plating on TSA. The culture conditions and incubation times were calibrated such that the initial inoculum density was about $1.0 \times 10^8$ CFU/mL. A dilution range was prepared by aseptically performing appropriate serial dilutions (i.e. 1 mL of $10^8$ CFU/mL into 9 mL of sterile PBS or FaSSIF to give a dilution of $10^7$ CFU/mL). Note final concentrations were confirmed by serial dilution and spot plate counts. See, e.g., Gaudy, A. F., Abu-Niaaj, F., Gaudy, E. T., *Statistical study of the spot plate technique for viable cell counts*. Applied Microbiology, Vol 11, 1962 pp. 305-309. pH measurements were taken.

6.3 Sample Capture and Inoculum Adjustment:

A plate was prepared in triplicate using a Sterilin 96 well round bottom microtitre plate (P/N H511A), where the plate was loaded with 100 µL of a diluted dynamic range of bacteria. An exemplary plate set-up is presented in FIG. 79A.

6.4 Live Stain Preparations:

Live stain was prepared fresh on the day of the experiment. The live stain dilutions were protected from light. The live stain treatments were aseptically prepared as described below using 15 mL sterile conical tubes.

Treatment 1 (Resazurin or "REZ"):

Working stain was prepared according to manufacturer instructions. Resazruin salt was used to prepare a 10 mM Resazurin solution in PBS, containing 0.005% Deoxycholate, 0.1% v/v Triton X-100, 2.5 mg/L Amphotericin B, 50 mM $MgCl_2$ with a pH of 6.0. The solution was mixed via vortexing until a homogenous suspension was produced and was then stored in dark until used.

6.5 Test Fixture Preparation:

Set and calibrated the spectrophotometer according to manufacturer's SOPs. Set up the data program to excite and read the emission intensity of the culture. Aseptically added the appropriate volume of working stain (20 µL for REZ). Mixed thoroughly via pipette mixing in each well. Used fresh tips for each well. Protected the plate from light.

6.6 Sample Acquisition, Incubation and Detection:

Exact inoculation time was recorded in the log book and on the device. The plate was incubated at 37° C. degrees, at 200 rpm and was protected from light. Plate was read and recorded at 530 nm Excitation, detecting 600 nm Emission. The plate was covered and returned to the 37° C. incubator @ 200 rpm between readings. This procedure was performed every 30 minutes for the test cycle. The test cycle spanned 6 hours.

Figure 79B:
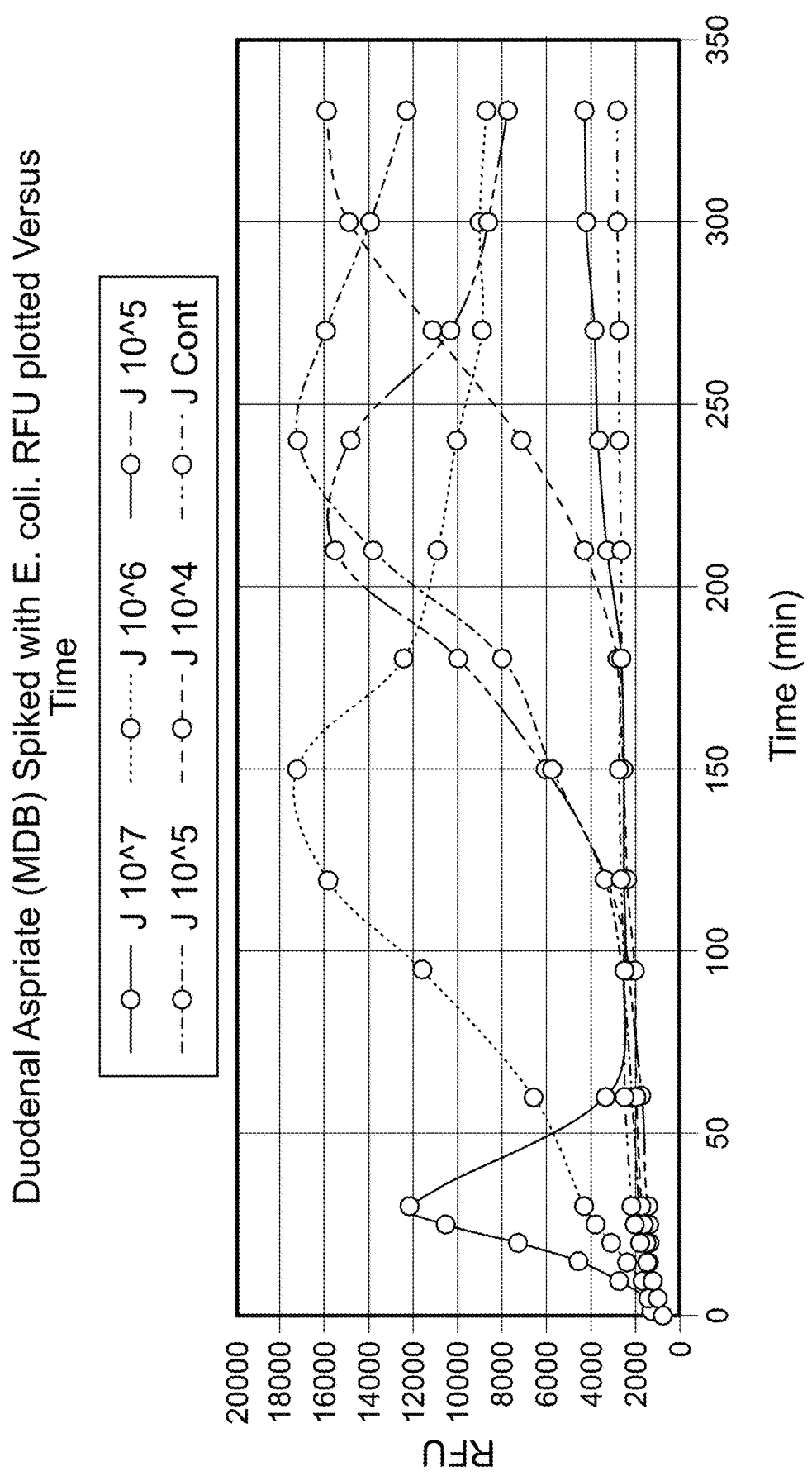
FIG. 79B shows fluorescence detection plotted over time in duodenal aspirate spiked with various concentrations of *E. coli*. The data demonstrated that there is a strong, discernable signal response from spiked duodenal samples in good agreement with the simulated data.

FIG. 79B shows fluorescence detection plotted over time in duodenal aspirate spiked with various concentrations of *E. coli*. The data demonstrated that there is a strong signal response from spiked duodenal samples which is in good agreement with simulated data.

Example 7: Simulated Performance of Live Cell Stain Assay with Jejunal Samples 7.1 Simulated Methodology:
  Matrix of all simulated conditions was generated and assigned to locations on a 96 well plate
  Simulated conditions include:
    pH 6, pH 6.5, pH 7
    Bile 1.3, 3, 5.5 mM
    Mucin 0.5%, 1%, 1.5%
    Yeast $10^2$, $10^3$, $10^4$ CFU/mL
    75% Horse Serum in FaSSIF
  Simulated organism spike was generated and overlaid across the 96 well plate matrix
    Gram Negative Mix (*E. coli, P. aeruginosa, K. pneumoniae*)
    Gram Positive Mix (*S. aureus, S. mutans, E. faecalis*)
    Total Mix: All 6 strains
    Dynamic range of each: $10^7$, $10^6$, $10^5$, $10^4$, 0 CFU/mL
  All Testing done in the presence of HeLa ($10^4$ CFU/mL in 50 µL)
  Testing with liquid DYE (20 µL into 100 µL sample)
  Read Slope over 330 minutes
    Algorithm using Early Calls (first 30 minutes) and Late (slope over full 330 minutes)
7.2 Spiked Human Sample Methodology:
  Pooled Mix of Human Duodenal "DiBaise" samples
  Pooled samples include:

| Initial | Sample ID No. | MC Micro | Pull |
|---|---|---|---|
| ERB | 115-01-006.1 | No growth | 1 |
| DKG | 115-01-032.1 | No growth | 1 |
| G-S | 115-01-037.1 | No growth | 4 |
| CRM | 115-01-038.1 | No growth | 4 |

-continued

| Initial | Sample ID No. | MC Micro | Pull |
|---|---|---|---|
| M-T | 115-01-045.1 | No growth | 2 |
| MDB | 115-01-050.1 | No growth | 7 |

Simulated organism spike was generated and overlaid across the 96 well plate matrix
    Gram Negative Mix (*E. coli, P. aeruginosa, K. pneumoniae*)
    Gram Positive Mix (*S. aureus, S. mutans, E. faecalis*)
    Total Mix: All 6 strains
    Dynamic range of each: $10^7$, $10^6$, $10^5$, $10^4$, 0 CFU/mL
  Testing with liquid DYE (20 µL into 100 µL sample)
  Read Slope over 330 minutes
    Algorithm using Early Calls (first 30 minutes) and Late (slope over full 330 minutes)
  Failure modes tested:

| Code | Failure Mode | Simulation |
|---|---|---|
| FM1 | Open in Stomach | pH 2 |
| FM2 | Open in Colon | $10^{\wedge}12$ CFU/mL |
| FM3 | Fail to Open | Dry Well |
| FM4 | Partial Fill $10^{\wedge}5$ Sample | 25 µL of $10^{\wedge}5$ mix |
| FM5 | Partial Fill $10^{\wedge}6$ Sample | 25 µL of $10^{\wedge}6$ mix |
| FM6 | PBS control "Master Control" | PBS |

Figure 80A:
FIG. 80A shows a simulated performance with jejunal samples, where Pe=(PP+PN)×(PP+NP)/N^2+(PN+NN)×(NP+NN)/N^2. A kappa statistic equal to zero indicates that agreement is no better than chance, a kappa of 1.0 indicates perfect agreement, 0-0.4 indicates poor agreement, 0.4-0.75 indicates fair to good agreement and greater than 0.75 indicates excellent agreement (Fleiss 1981).
Figure 80B:
FIG. 80B shows a simulated performance with Human Duodenal Samples, where Pe=(PP+PN)×(PP+NP)/N^2+(PN+NN)×(NP+NN)/N^2. A kappa statistic equal to zero indicates that agreement is no better than chance, a kappa of 1.0 indicates perfect agreement, 0-0.4 indicates poor agreement, 0.4-0.75 indicates fair to good agreement and greater than 0.75 indicates excellent agreement (Fleiss 1981).

FIG. 80A shows a simulated performance with jejunal samples and FIG. 80B shows a simulated performance with human duodenal Samples, where Pe=(PP+PN)×(PP+NP)/N^2+(PN+NN)×(NP+NN)/N^2. A kappa statistic equal to zero indicates that agreement is no better than chance, a kappa of 1.0 indicates perfect agreement, 0-0.4 indicates poor agreement, 0.4-0.75 indicates fair to good agreement and greater than 0.75 indicates excellent agreement (Fleiss 1981).

Example 8. Simulated Performance of the Resazurin-Based Viable Bacterial Cell Quantitation Assay Using Anaerobic Bacteria-Enriched Fecal and Duodenal Samples To evaluate the lower limit of detection of a resazurin-based viable bacterial cell quantitation under conditions that similar to those found in the human intestinal tract, the following experiment was performed using pooled fecal and duodenal clinical samples enriched with anaerobic bacteria.

Clinical samples consisting of pooled isolates of fecal slurries or pooled isolates of duodenal aspirates were used to inoculate anaerobic enrichment media (Reinforced Clostridial Media (RCM)) under strict anaerobic conditions. The samples were enriched for 24 hours at 37° C. and a dynamic dilution range targeting $10^7$ to $10^2$ CFU/mL was prepared in either liquid format (fecal slurries were diluted to form simulated fecal fluid analogue (SFFA; 1:7.5 fecal matter:PBS); and duodenal aspirates were diluted in simulated jejunal fluid analogue (SJFA; 1:1:1 cRPMI:tryptic soy broth; FASSIF-V2 (Fasted State Simulated Intestinal Fluid Version 2; BIORELVANT), pH 6.5) or assay pad (sponge) format ($1\times10^5$ CFU/mL targeted for pad testing). As control, the same dilution range was prepared in phosphate-buffered saline (PBS). Total bacterial count (TBC) was determined using the resazurin assay described above in Examples 2-6 using a 96-well flat plate format. Fluorescence was detected using a Plate Reader photospectrometer with kinetic readings made at 550 nm excitation and 590 nm emission. Due to the unknown growth characteristics of the clinical samples, the target CFU ranges were missed by an order of 1 Log as confirmed by subsequent viable plate counts, resulting in a $10^8$ to $10^4$ CFU/mL dynamic range). The assay was performed kinetically up to 330 minutes and data was collected. The assay was also run for 22 hours (1,320 minutes) and the data sets were compared. As an endpoint control, assay plates were left overnight under anaerobic conditions in order to confirm endpoints.

Figure 130:
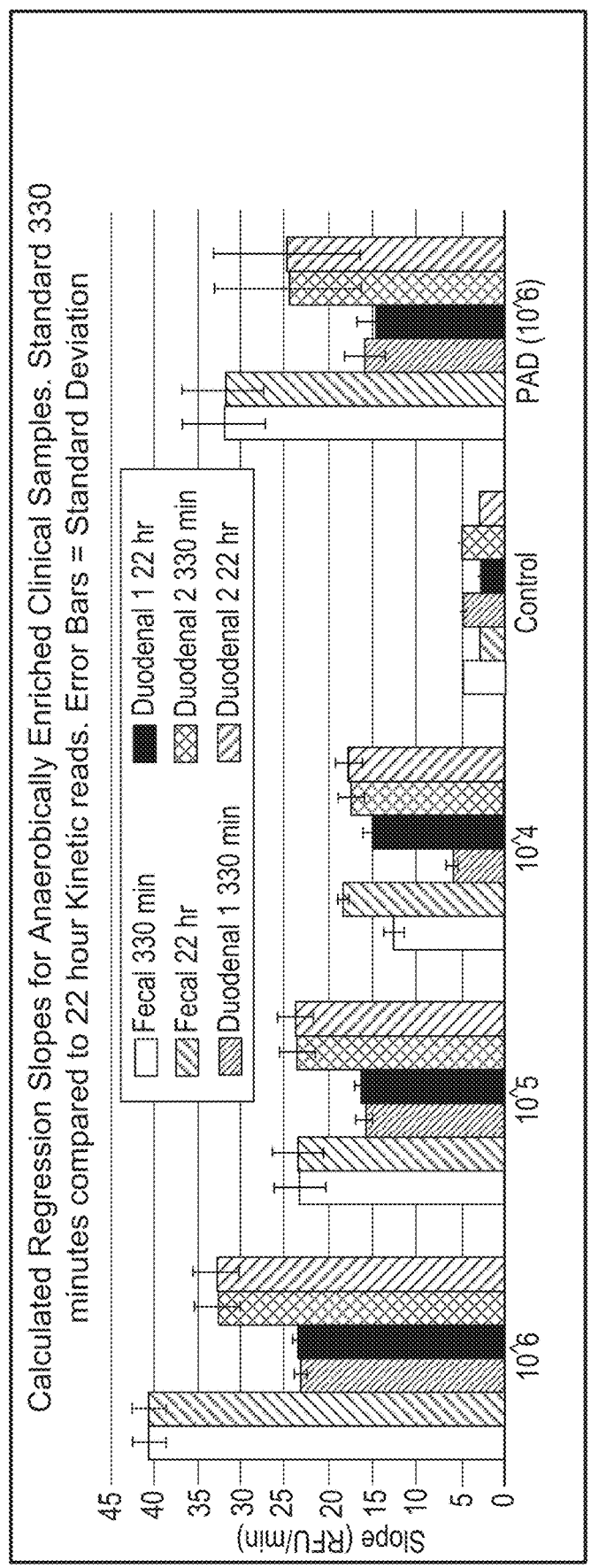
FIG. 130 is a bar graph showing the calculated regression slopes for total bacterial count determinations using a resazurin-based assay with samples comprising either anaerobically enriched fecal or duodenal aspirate clinical samples plated at a dynamic dilution range using a liquid format ($10^4$-$10^6$ CFU/mL dynamic range) or in pad format ($1\times10^6$ CFU/mL.) The assay was read after 330 minutes or 22 hours. RFU: relative fluorescence units; Control: samples diluted in PBS.
Figure 133A:
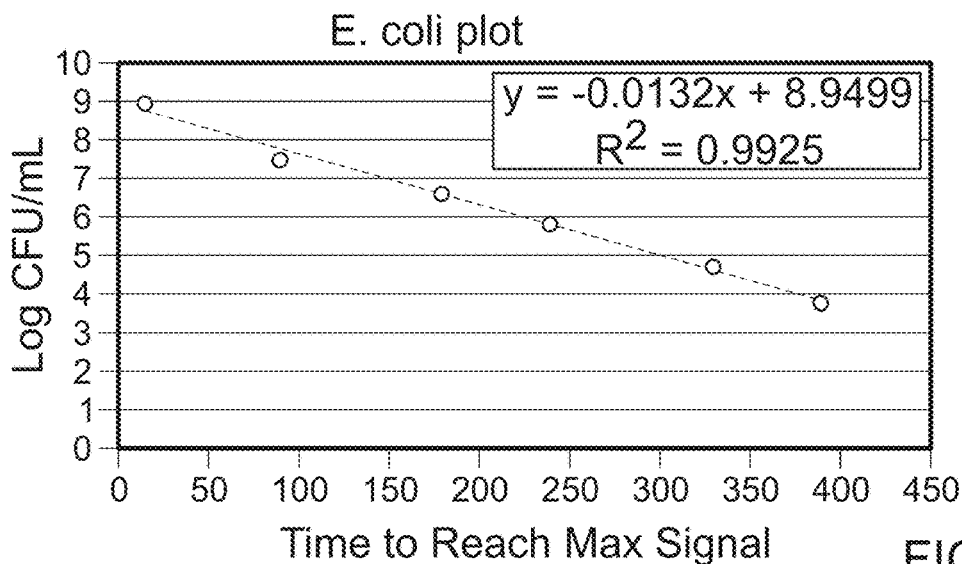
FIGS. 133A-133H are regression plots showing the relation between the number of bacterial colony forming units (CFU)/mL and the time to reach maximum signal detection in resazurin-based assays using samples comprising the aerobic bacteria Escherichia coli (FIG. 133A), Staphylococcus aureus (FIG. 133B), Klebsiella pneumoniae (FIG. 133C), Pseudomonas aeruginosa (FIG. 133D), Enterobacter aerogenes (FIG. 133E), Streptococcus mutans (FIG. 133F), Enterococcus faecalis (FIG. 133G), and Proteus mirabilis (FIG. 133H). Charted data are mean (n=3) regression slopes to maximum signal detection.
Figure 133B:
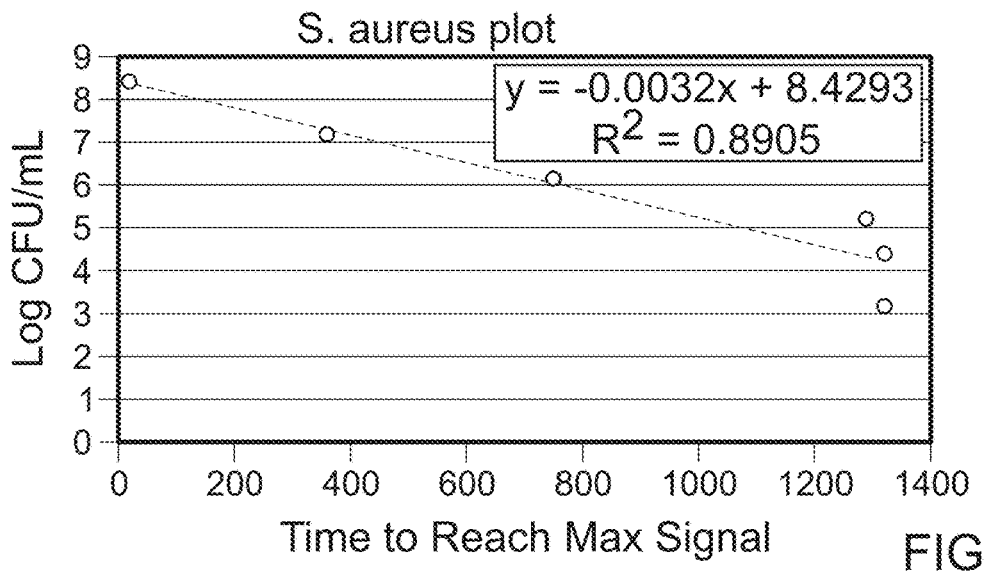
Figure 133C:
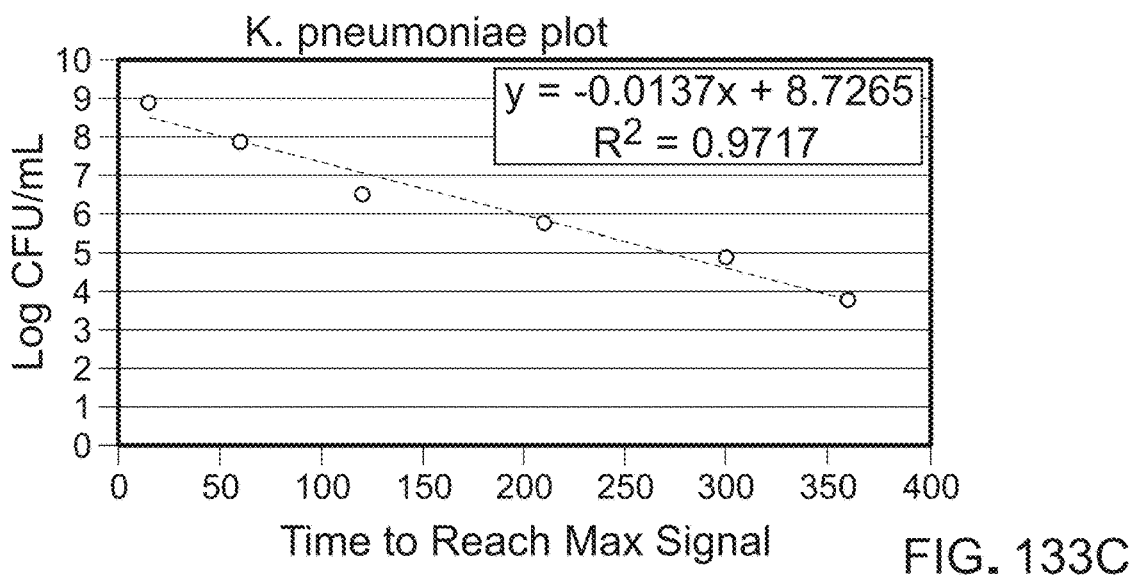
Figure 133D:
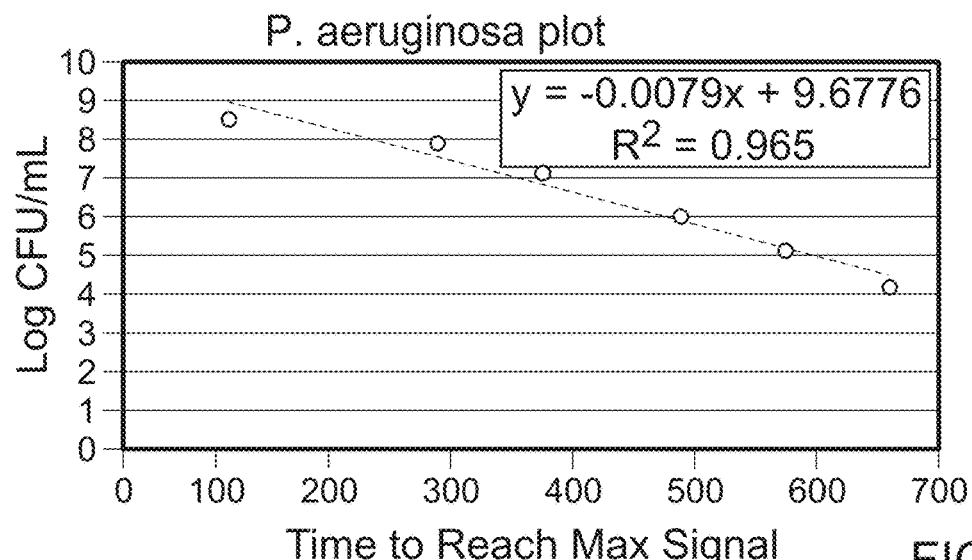
Figure 133E:
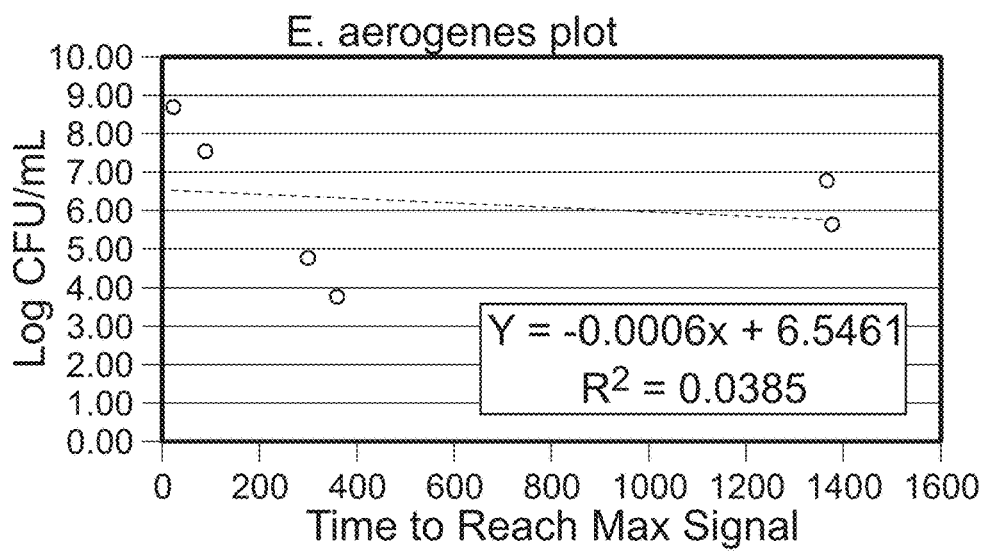
Figure 133F:
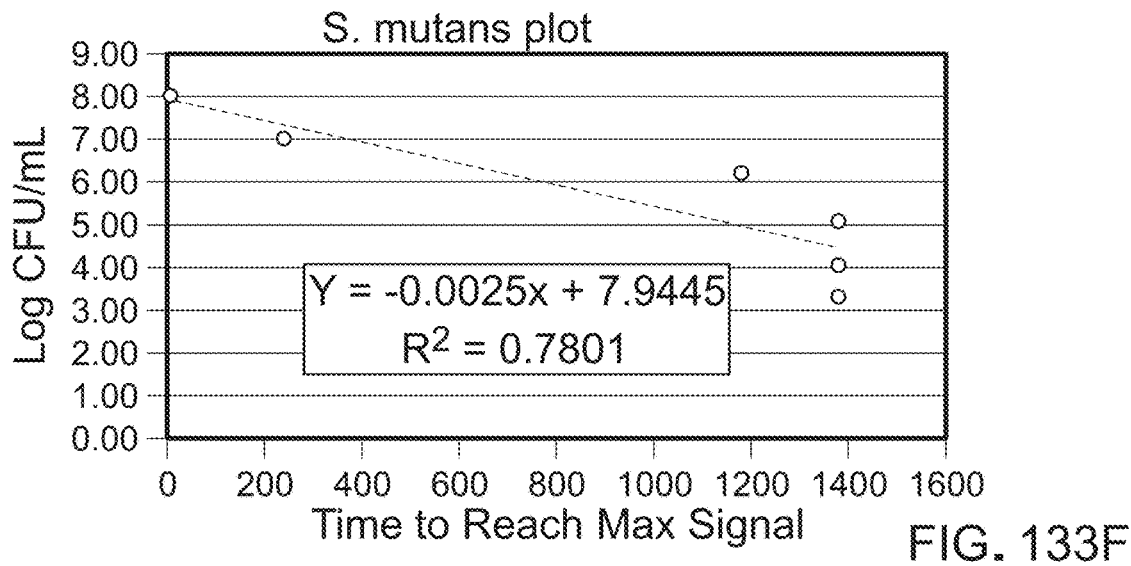
Figure 133G:
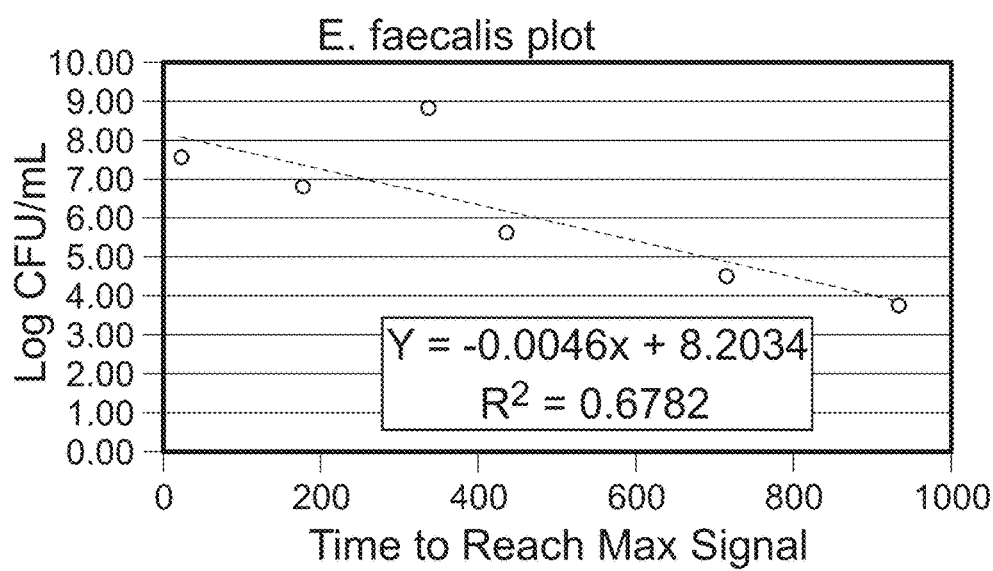
Figure 133H:
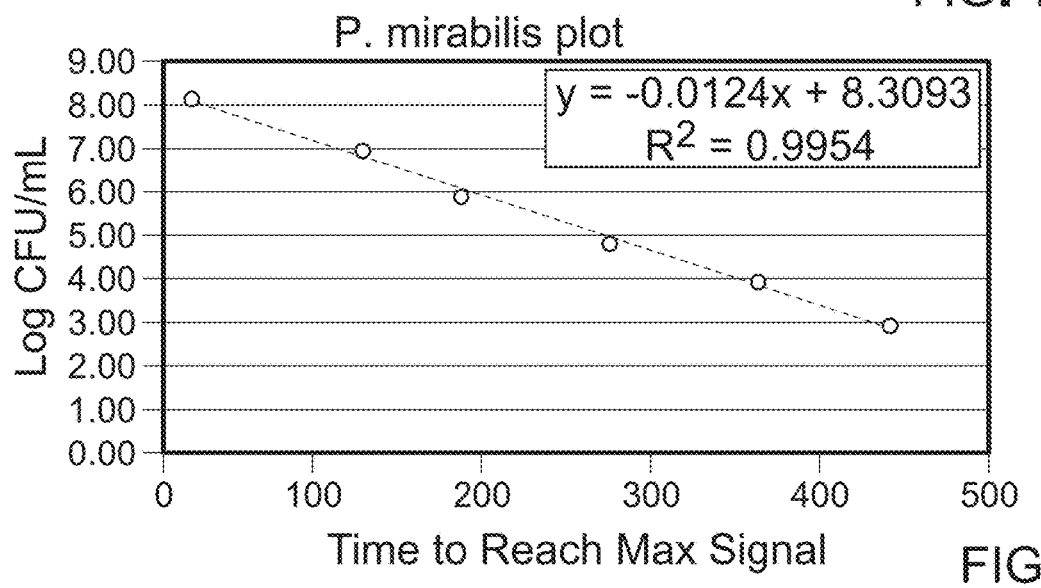
Figure 134A:
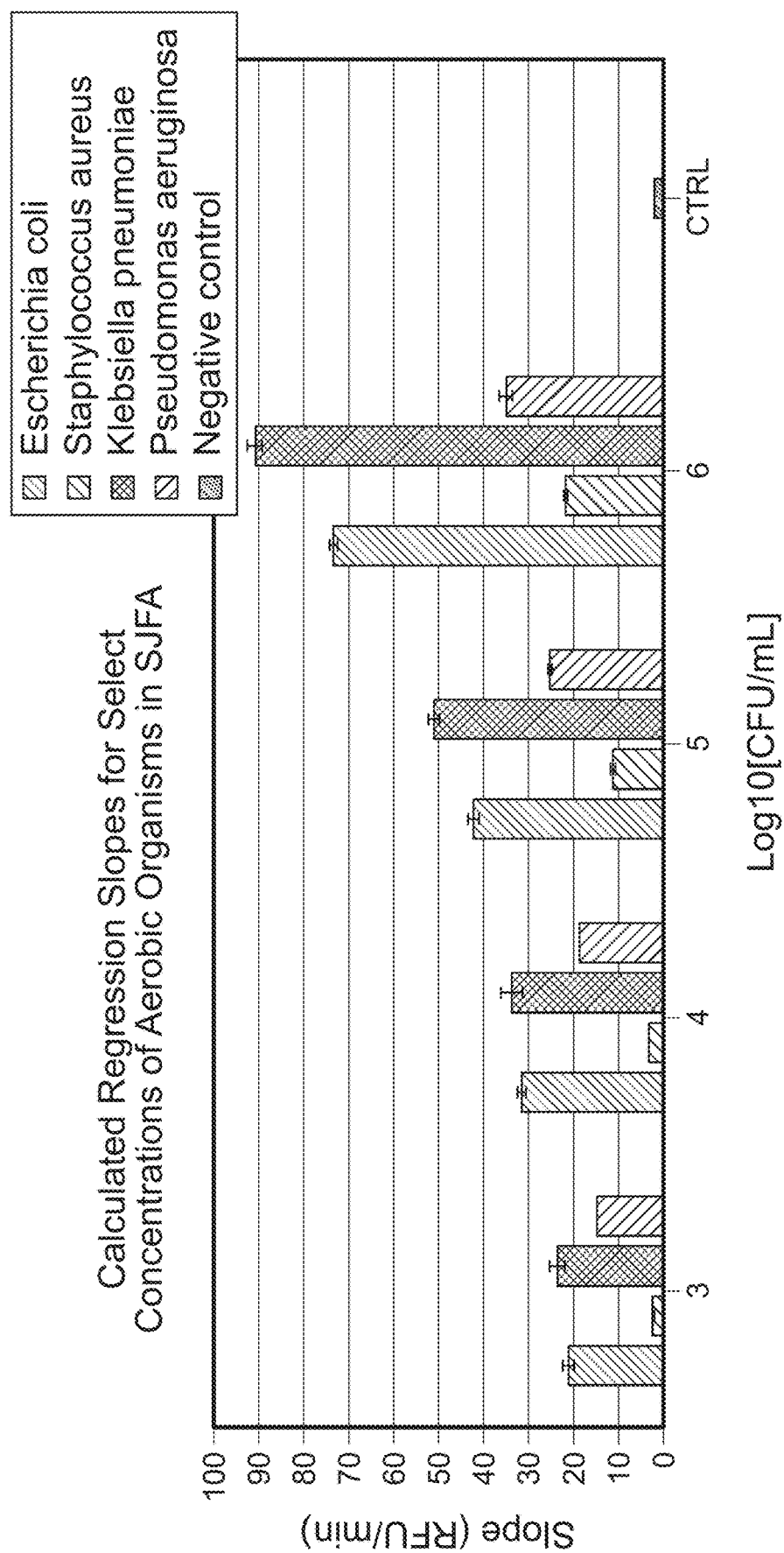
FIG. 134A is a bar graph showing the calculated regression slopes for total bacterial count determinations using a resazurin-based assay with samples comprising a dynamic dilution range of Escherichia coli, Staphylococcus aureus, Klebsiella pneumoniae, Pseudomonas aeruginosa, or negative control ("CTRL"). Charted data are mean (n=3) regression slopes to maximum signal detection.
Figure 134B:
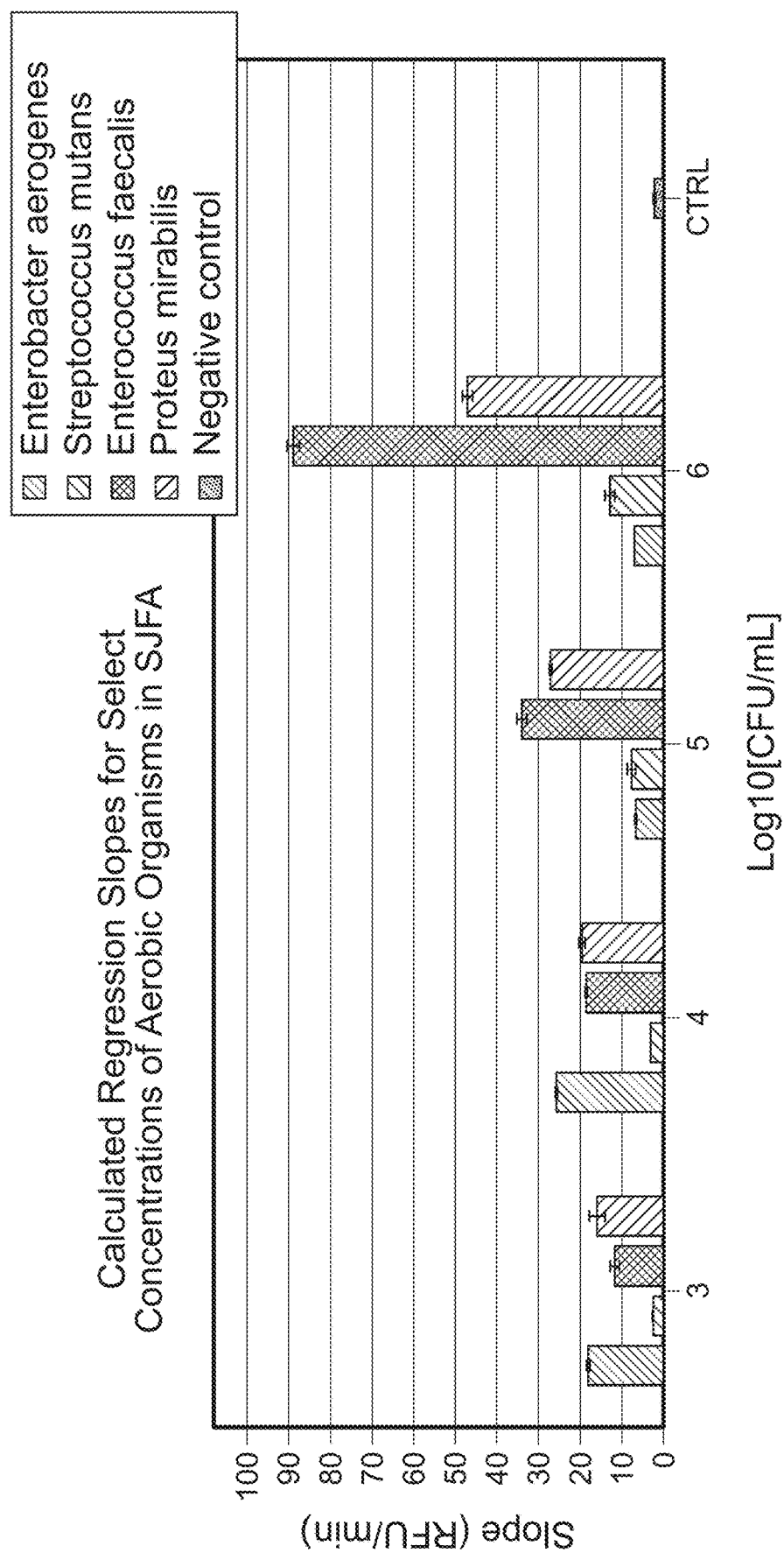
FIG. 134B is a bar graph showing the calculated regression slopes for total bacterial count determinations using a resazurin-based assay with samples comprising a dynamic dilution range of Enterobacter aerogenes, Streptococcus mutans, Enterococcus faecalis, Proteus mirabilis or negative control ("CTRL").
Figure 135A:
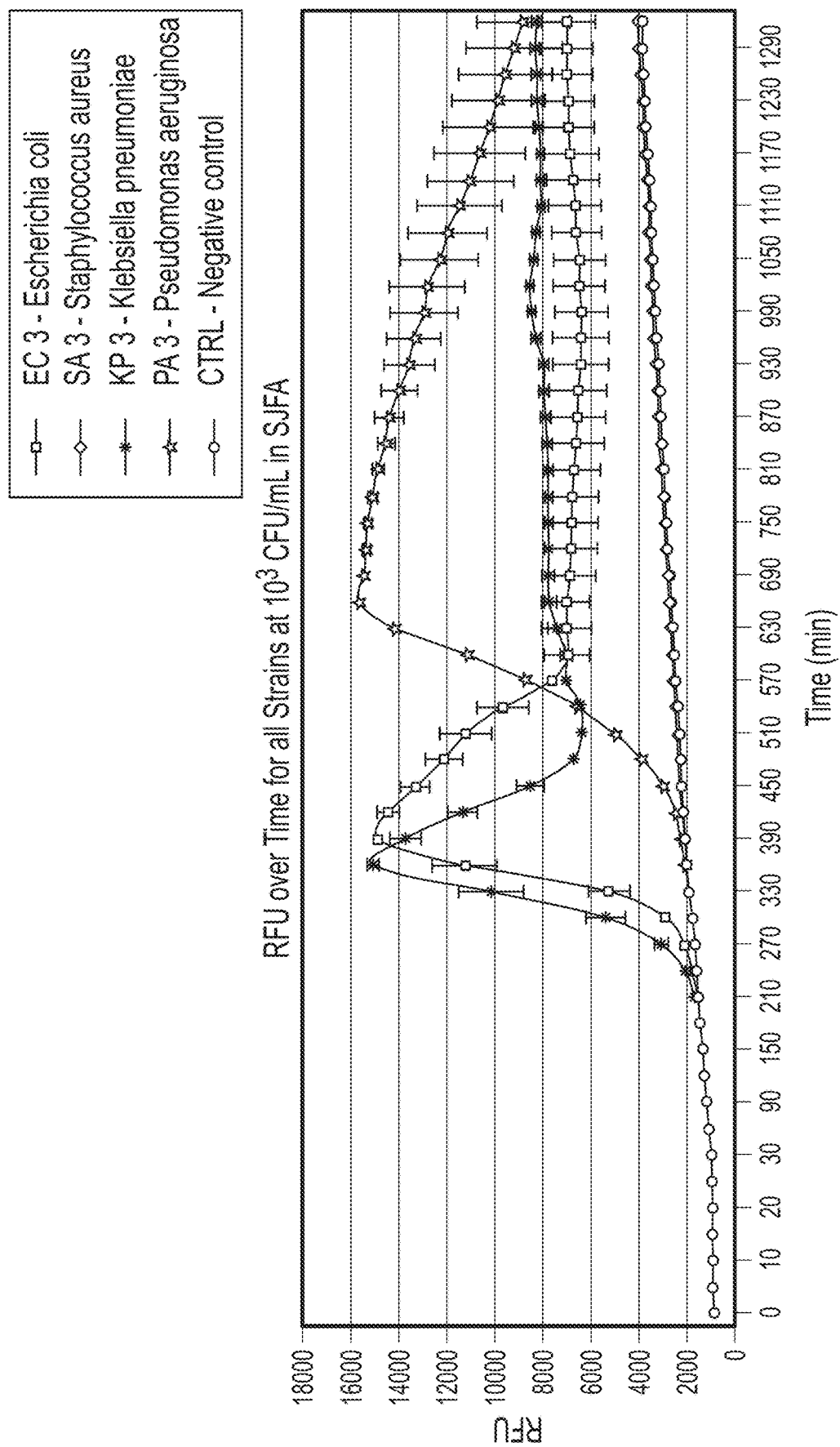
FIGS. 135A-135D are line graphs showing the relative fluorescent units (RFU) as a function of time for resazurin-based assay with samples comprising a dynamic dilution range of Escherichia coli, Staphylococcus aureus, Klebsiella pneumoniae, Pseudomonas aeruginosa, or negative control ("CTRL").
Figure 135B:
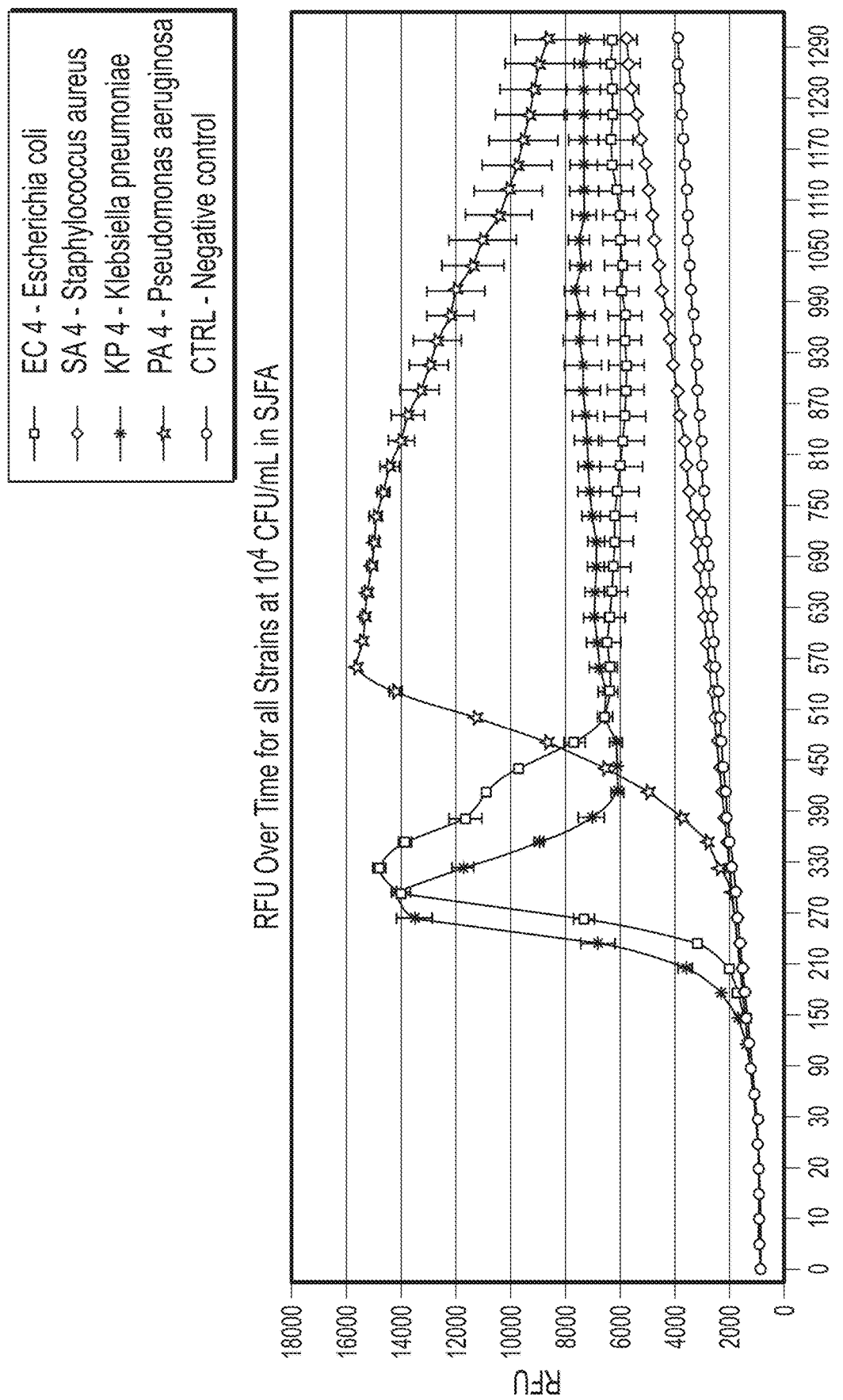
Figure 135C:
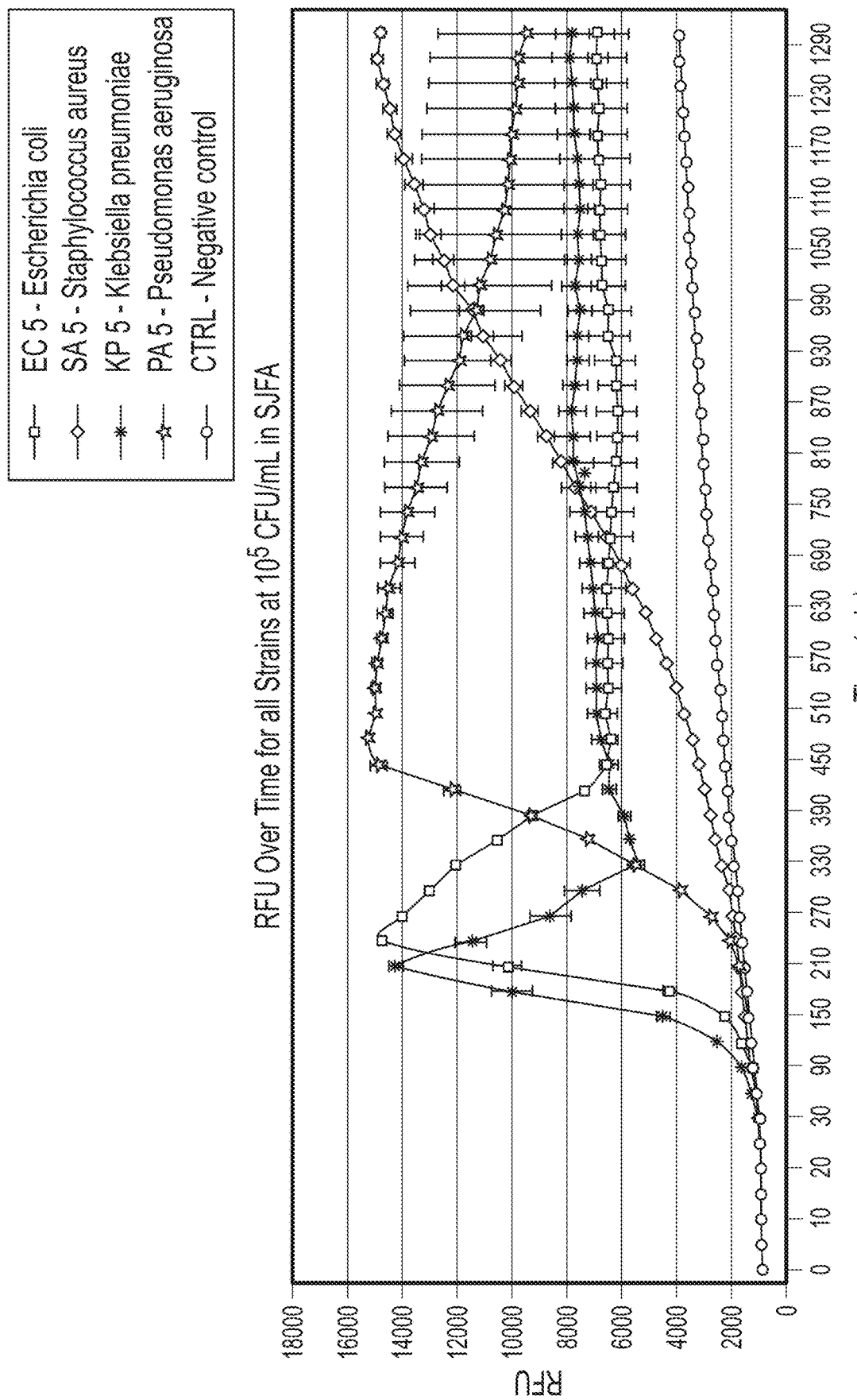
Figure 135D:
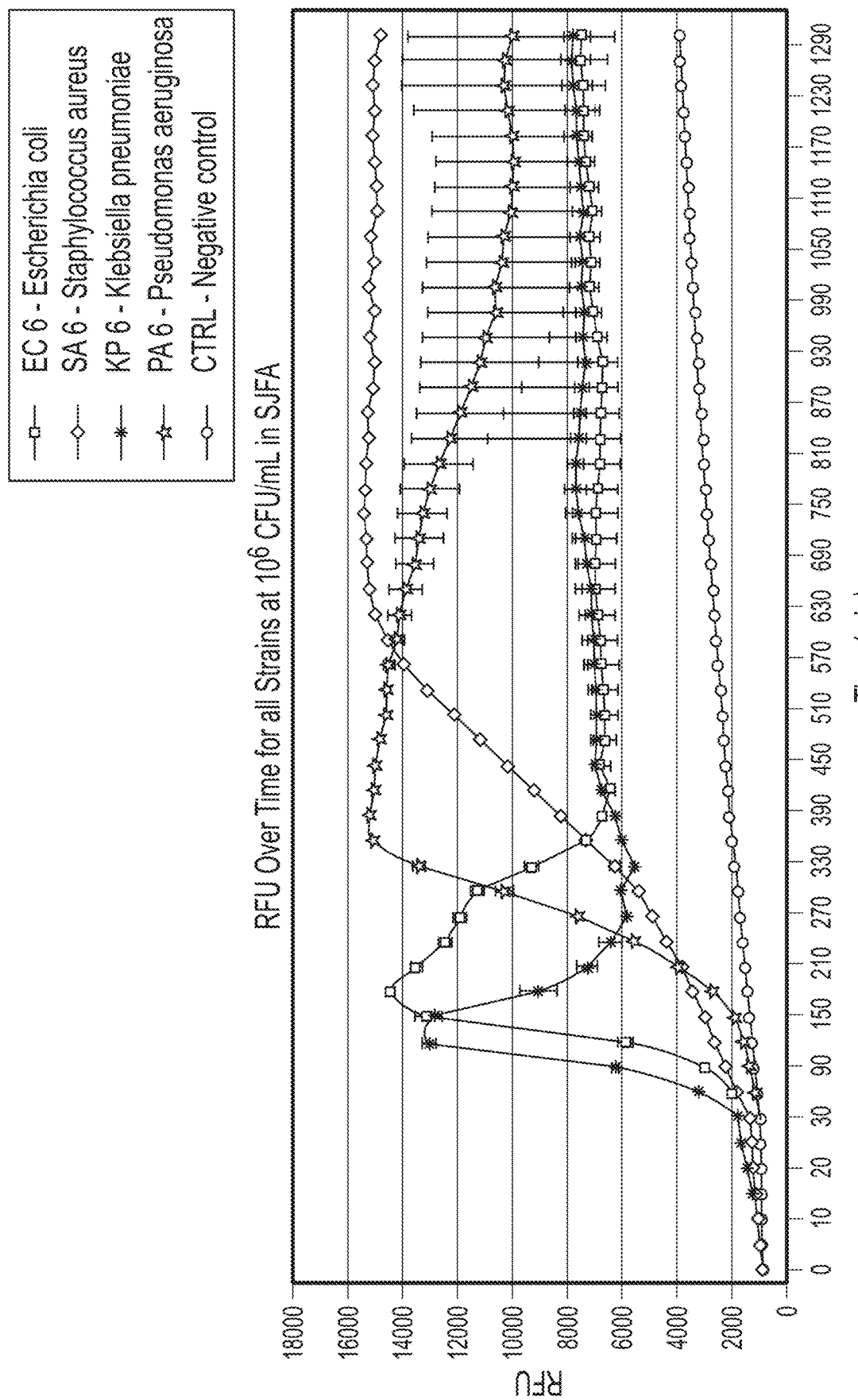
Figure 136A:
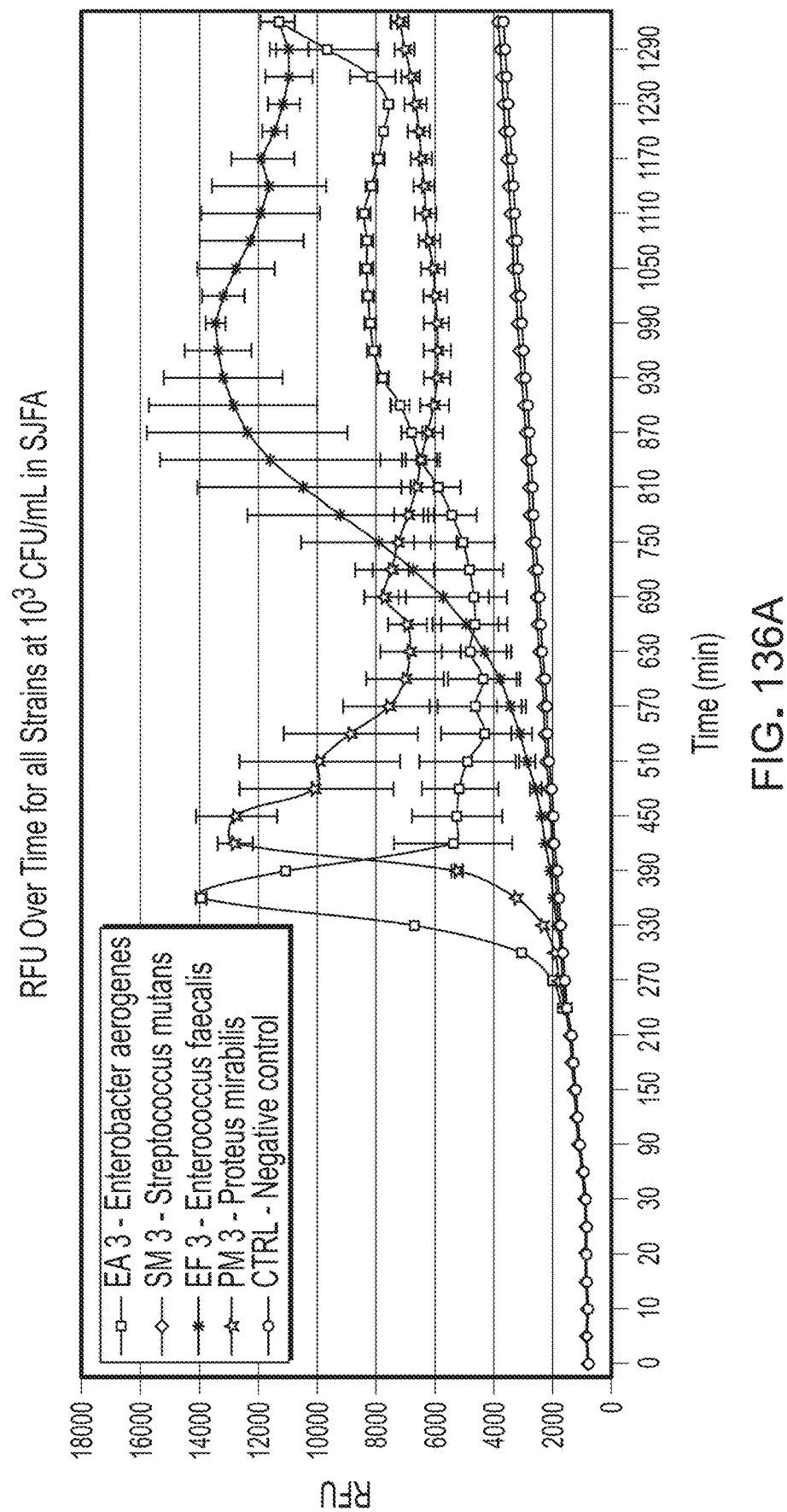
FIGS. 136A-136D are line graphs showing the relative fluorescent units (RFU) as a function of time for resazurin-based assay with samples comprising a dynamic dilution range of Enterobacter aerogenes, Streptococcus mutans, Enterococcus faecalis, Proteus mirabilis, or negative control ("CTRL").
Figure 136B:
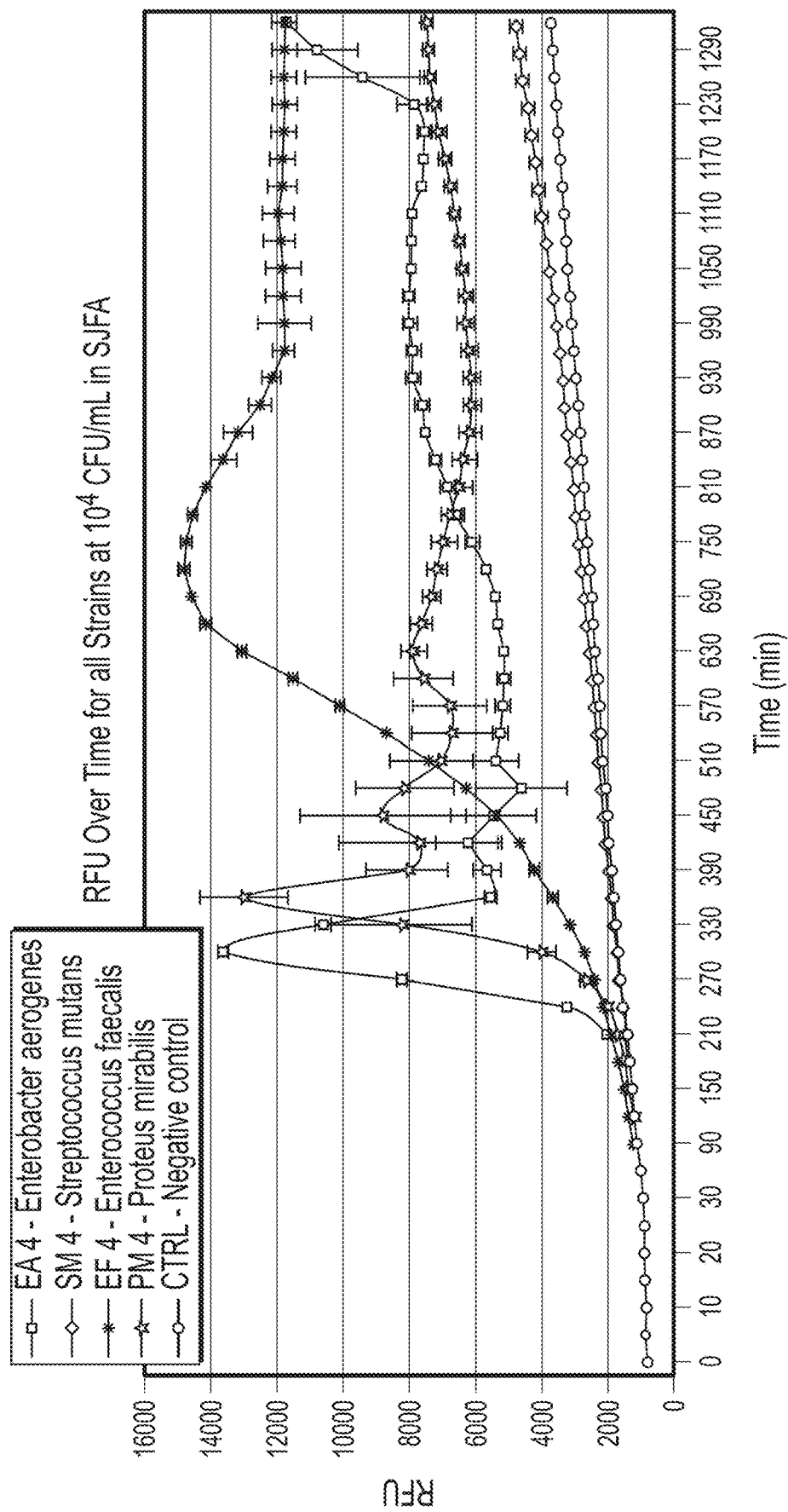
Figure 136C:
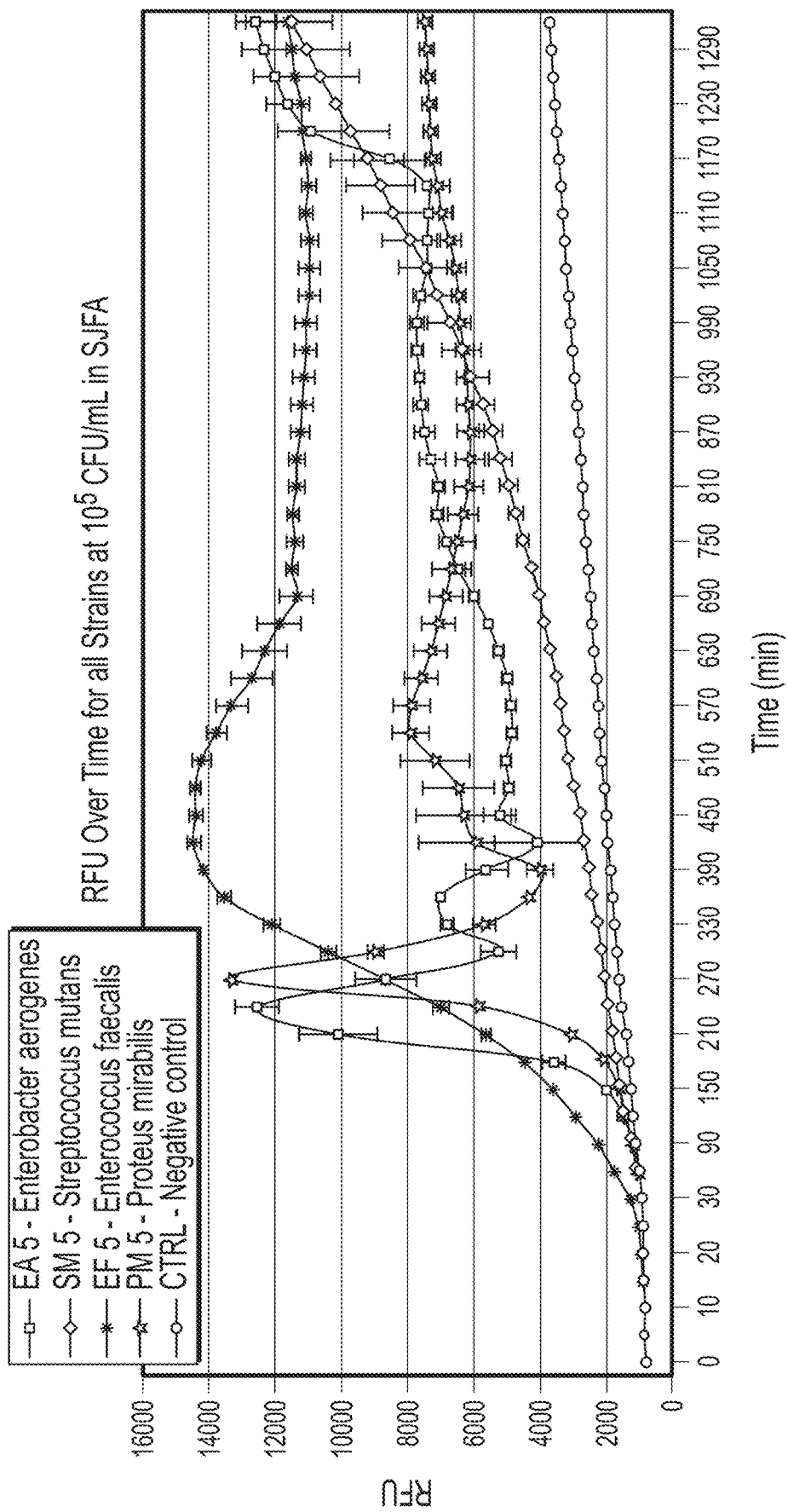
Figure 136D:
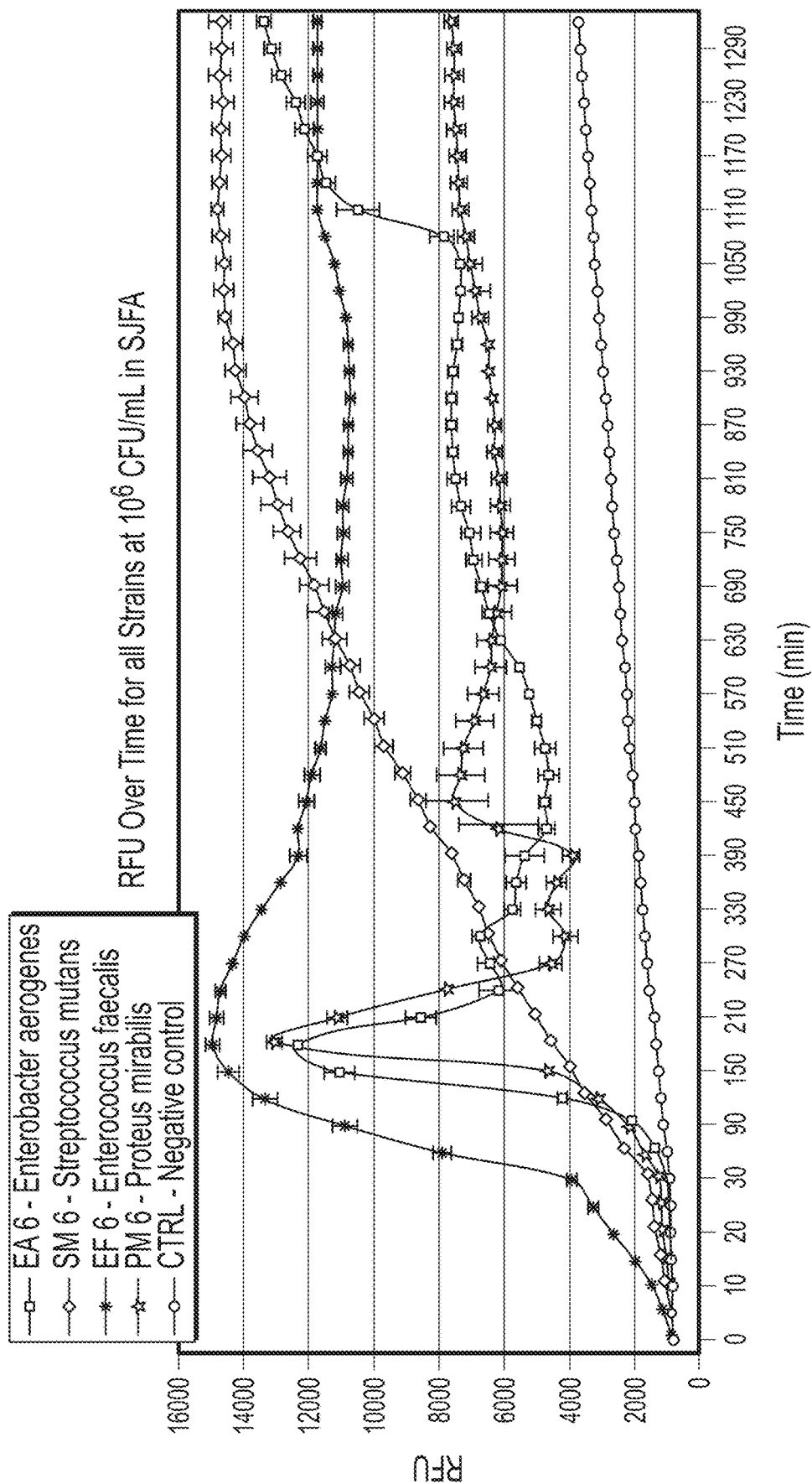

As shown in FIG. 130, the assay was able to detect all mixed clinical isolates in the liquid format over the entire dynamic range tested (i.e., $1 \times 10^9$ to $1 \times 10^4$). Moreover, as also shown in FIG. 130, the assay successfully detected the pooled clinical isolates in the assay pad format. All bacteria-containing samples scored higher that the slope of 3 standard deviations above the highest mean baseline control (4.86+ (3×0.16))=5.34. This experiment demonstrates that an resazurin-based assay can be used to effectively quantify total bacterial count in complex bacterial compositions over a dynamic range of CFU.

Example 9. Simulated Performance of a Resazurin-Based Viable Bacterial Cell Quantitation Assay Using Anaerobic Bacterial Samples To evaluate the ability of the resazurin-based viable bacterial cell quantitation assay to detect and quantify populations of anaerobic bacterial strains grown to mid-exponential phase, the following experiment was performed using clinically-derived fecal sample consisting of strict anaerobes (not typed), as well as deposited analytical strains (ATCC).

Samples consisted of bacterial strains grown to mid-exponential phase (where they are most metabolically active). Without wishing to be bound by any particular theory, bacteria grown at mid-exponential phase should comprise greater NADH activity resulting in a lower limit of detection (e.g., $1 \times 10^3$ CFU/mL) because of the production of stronger fluorescence signal when resazurin in reduced. Bacterial strains *Bacteroides vulgatus* (ATCC 29327), *Bacteroides vulgatus* (ATCC 8482), *Clostridium butyricum* (ATCC 19398), *Clostridium perfringens* (ATCC β124), *Clostridium sporogenes* (ATCC 7955), and a clinical isolate were used to inoculate RCM media under strict anaerobic conditions over a 24 hour period at 37° C. Growth samples were obtained at 2, 4, 6, and 24 hours, diluted in SJFA, and total bacterial count (TBC) was determined using the resazurin assay described above in Examples 2-6 using a 96-well flat plate format using a liquid format. Fluorescence was detected using a Plate Reader photospectrometer with kinetic readings made at 550 nm excitation and 590 nm emission. PBS controls were used to evaluate the media reduction effects and to serve as signal control. The assay was performed kinetically up to 330 minutes and data was collected.

As shown in FIGS. 131A and 131B, bacteria grown and collected at mid-exponential growth phase exhibited increased signal detection when used in the assay. For example, increased signal was detected with the strains *Clostridium butyricum* (ATCC 19398), which was detectable at $1 \times 10^3$ CFU/mL, *Clostridium perfringens* (ATCC β124), and the clinical isolate.

Example 10. Simulated Performance of a Resazurin-Based Viable Bacterial Cell Quantitation Assay Using Anaerobic Bacterial Samples Under Microaerophilic and Anaerobic Conditions To evaluate the lower limit of detection of a resazurin-based viable bacterial cell quantitation assay performed under either microaerophilic or strict anaerobic conditions, the following experiment was performed.

Six test panels were prepared using the bacterial strains *Bacteroides vulgatus* (ATCC 8482), *Clostridium butyricum* (ATCC 19398), *Clostridium sporogenes* (ATCC 7955), and two non-typed clinical isolates comprising strict anaerobic bacteria were used to inoculate RCM media under strict anaerobic conditions over a 24 hour period at 37° C. Each panel was prepared by diluting the bacteria in SJFA at a dynamic range of $10^7$ to $10^2$ CFU/mL in liquid format and total bacterial count (TBC) was determined using the resazurin assay described above. PBS controls were used to evaluate the media reduction effects and to serve as signal control. Panels were prepared under strict anaerobic conditions, and 5 panels were incubated at 37° C. and assayed at the following timepoints: 90 minutes, 150 minutes, 270 minutes, 330 minutes, and 24 hours. Duplicate plates run kinetically under oil using plate sealers to ensure microaerophilic conditions were also assayed. Plate counts were confirmed by subsequence viable plate counts. Aerobic screening plates were also run to rule out false positives caused by facultative anaerobic conditions. Total bacterial count (TBC) was determined using the resazurin assay described above in Examples 2-6. Fluorescence was detected using a Plate Reader photospectrometer with kinetic readings made at 550 nm excitation and 590 nm emission. The assay was performed kinetically up to 330 minutes and data was collected. The assay was also run for 22 hours (1,320 minutes) and data sets were compared. As an endpoint control, assay plates were left overnight under anaerobic conditions in order to confirm endpoints.

As shown in FIGS. 132A, 132B, and 132C, *Clostridium butyricum* (ATCC 19398), as well as one of the clinical samples (RNA 6) was detected below $1 \times 10^5$ CFU/mL using both the strict anaerobic and microaerophilic conditions. Further, strict anaerobic conditions improved the detection of *C. butyricum*. The assay was also able to detect the mixed clinical isolates up to a concentration of $1 \times 10^2$ CFU/mL during the extended kinetic read (i.e., 24 hours). Control assays performed under aerobic conditions confirmed the presence of anaerobic conditions, however, low levels of facultative anaerobes were detected in the assays using clinical isolates.

Example 11. Simulated Performance of a Resazurin-Based Viable Bacterial Cell Quantitation Assay Using Anaerobic Bacterial Strains Using Extended Kinetic Read Periods To evaluate whether extending the period of time in which the kinetic assay was read could improve the lower limit of detection of a resazurin-based viable bacterial cell quantitation assay (see, e.g., Van den Driessche et al. (2014) 98: 31-4, incorporated herein by reference), the following experiment was performed.

Samples consisting of the aerobic bacterial strains *Escherichia coli* (ATCC 25922), *Staphylococcus aureus* (ATCC 29213), *Klebsiella pneumoniae* (ATCC 4352), *Pseudomonas aeruginosa* (ATCC 15442), *Enterobacter aerogenes* (ATCC β048), *Streptococcus mutans* (ATCC 700610), *Enterococcus faecalis* (ATCC 49533), and *Proteus* mirabilis (ATCC 7002) were used to inoculate RCM media under aerobic conditions over a 24 hour period at 37° C. Each panel was prepared by diluting the bacteria in SJFA at a dynamic range of $10^8$ to $10^2$ CFU/mL in liquid format, and total bacterial count (TBC) was determined using the resazurin assay described above in Examples 2-6 using a 96-well flat plate format using a liquid format. Fluorescence was detected using a Plate Reader photospectrometer with kinetic readings made at 550 nm excitation and 590 nm emission. PBS controls were used to evaluate the media reduction effects and to serve as signal control. The assays were run on three separate plates on three separate days to accommodate the different growth profiled and conditions of the bacterial strains. The assay was performed kinetically up to 330 minutes and data was collected. The assay was also run for 20 hours (1,200 minutes) and the data sets were compared.

As shown in FIGS. 133A-133H, 134A, 134B, 135A-135D, and 136A-136D, the assay was able to detect all of the bacterial strains over the entire dynamic range, with the exception of S. aureus (ATCC 29213) which had a lowest level of detection (LLOD) of $1\times10^4$ CFU/mL, and S. mutans (ATCC 700610), which had an LLOD of 1×104 CFU/mL. Moreover, E. aerogenes (ATCC 13048) exhibited a double peak (FIGS. 136A-136D) which appears to be a false negative result attributable to in vitro growth conditions of the bacterial strain. Thus, this experiment demonstrates that extending the period of time in which the kinetic assay is read improves the lower limit of detection of the assay.

Typical optical detection systems include a container for holding the sample, as well as a light source and photodetector. $OD_{600}$ (the absorbance, or optical density, of a sample measured at a wavelength of 600 nm) is preferable to UV spectroscopy when measuring the growth over time of a cell population because at this wavelength, the cells will not be killed as may occur under UV light. UV light has also been shown to cause small to medium-sized mutations in bacteria, potentially altering or destroying genes of interest or altering the growth behavior of a bacterial population.

Experiments were conducted to evaluate the ability of a standard laboratory bench top photospectrometer to accurately predict total bacterial counts over a dynamic range of $10^2$ CFU/mL to $10^8$ CFU/mL. Another objective was to evaluate the differences (if any) between quantifying Gram-Negative and Gram-Positive organism using OD.

Methods and Materials

Two bench top photospectrometers (Photospectrometer 1: SPECTRAMAX® M5, S/N MV 02773 using software (SOFTMAX® Pro5 s/n SMP500-14128-ATVW), operating at Absorbance 600 nm. Photospectrometer 2: Fisher Scientific, Cell Density Meter Model 40, Serial Number 247, operating at standard setting (A=600 nm)) were used to determine the CFU/mL of Gram-negative (*Escherichia coli* ATCC 25922 and DH5-Alpha) and Gram-positive (*Staphylococcus epidermidis* ATCC 12228) bacteria diluted phosphate buffered saline over a dynamic range of $10^8$ CFU/mL to $10^2$ CFU/mL. Experiments were conducted in triplicate.

Results

Figure 81A:
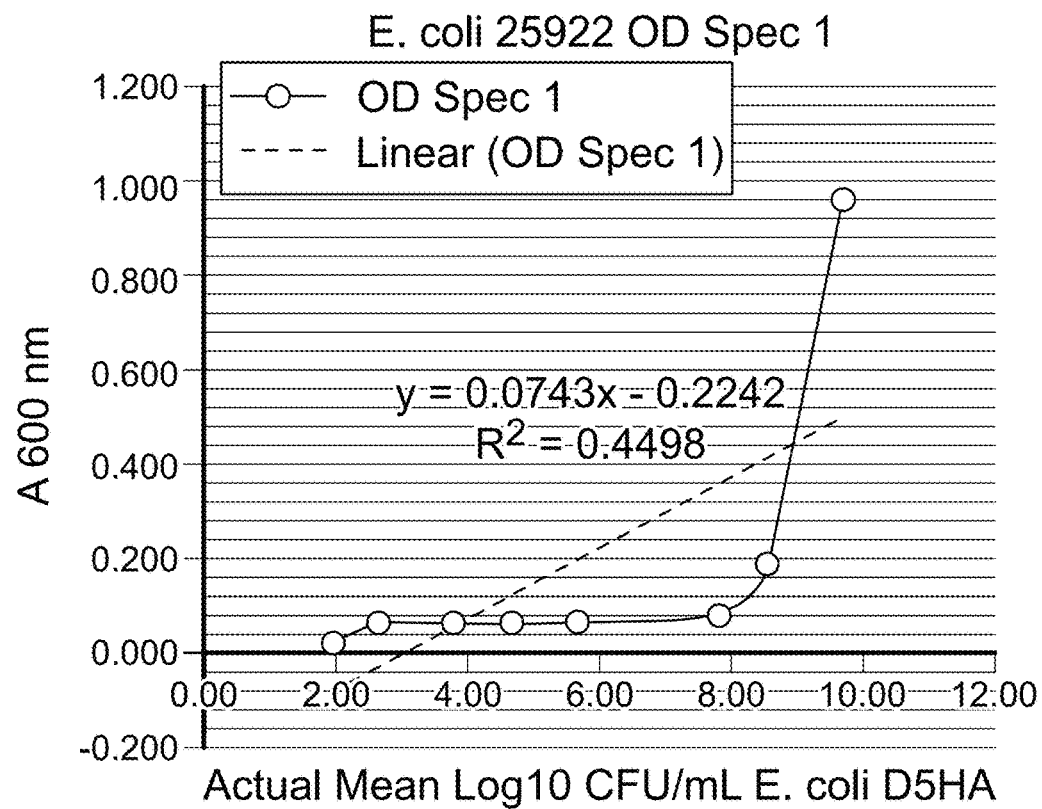
FIG. 81A shows results from testing *E. coli* DH5-Alpha, using Spectrophotometer 1, Absorbance (600 nm) Y-axis, plotted over actual mean log 10 CFU/mL.
Figure 81B:
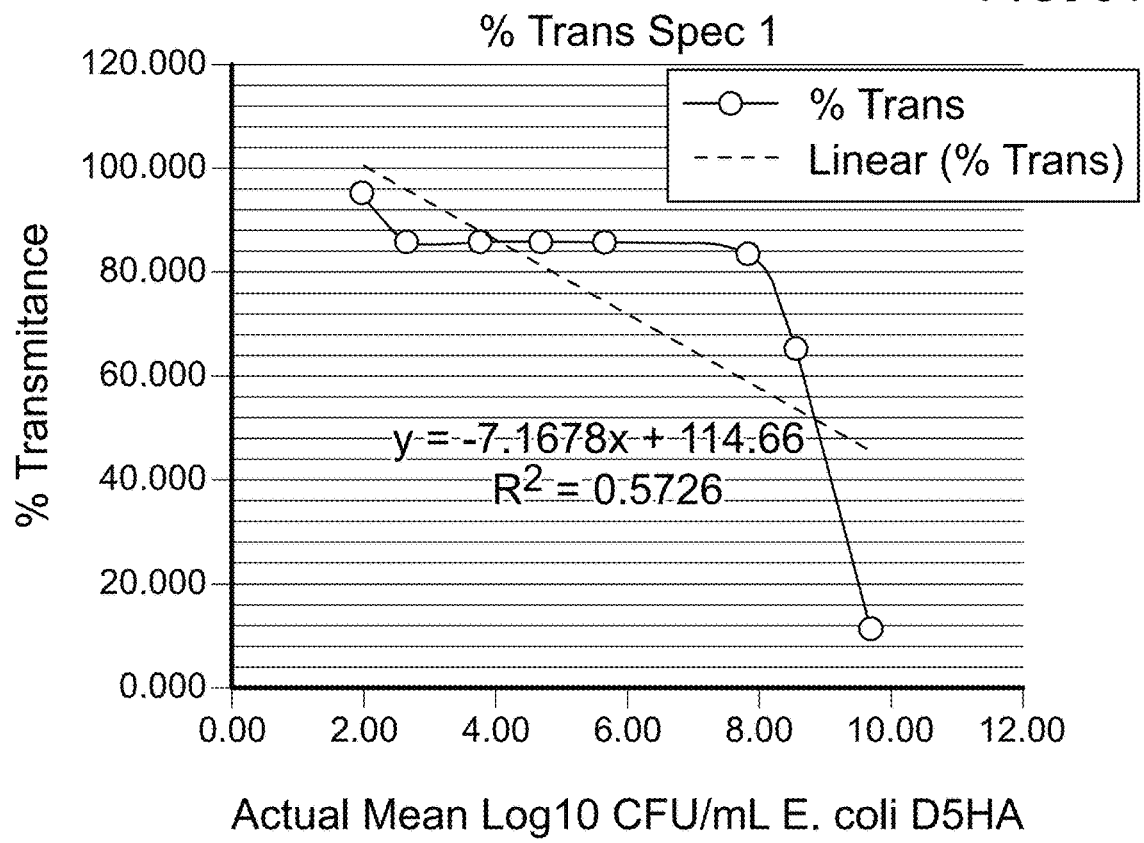
FIG. 81B shows the % transmittance over actual mean log 10 CFU/mL.
Figure 82A:
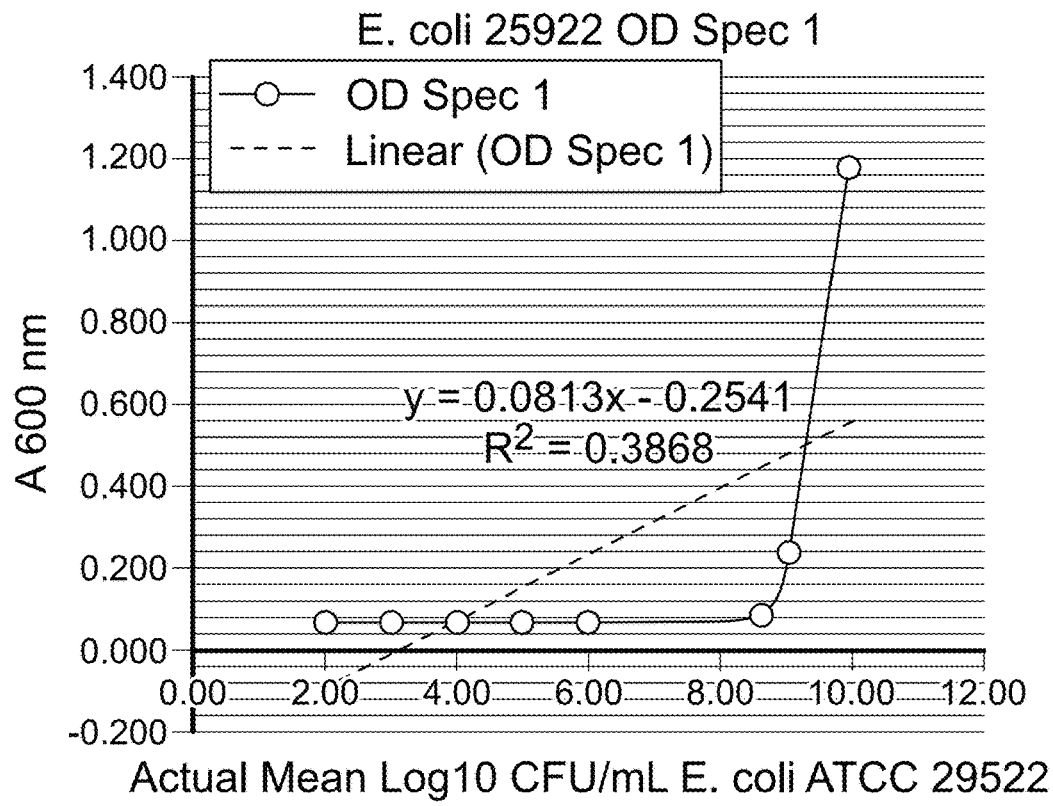
FIG. 82A shows results from testing *E. coli* ATCC 25922, using Spectrophotometer 1, Absorbance (600 nm) Y-axis, plotted over actual mean log 10 CFU/mL.
Figure 82B:
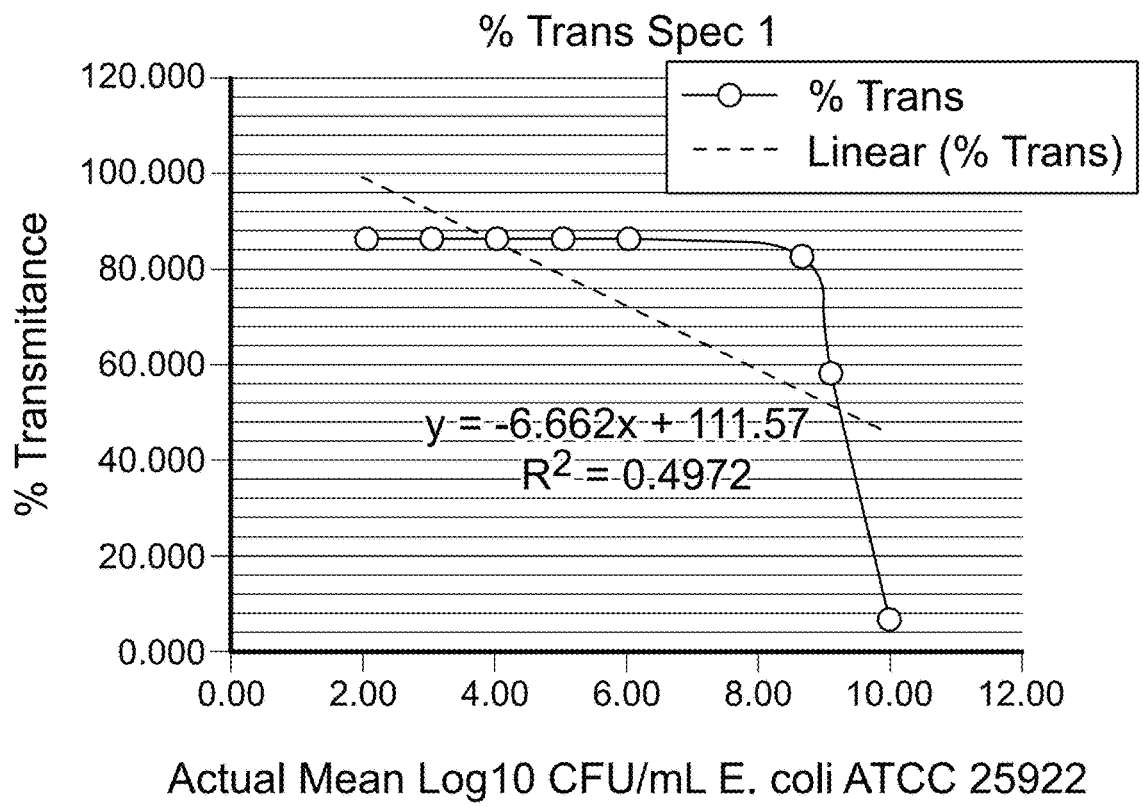
FIG. 82B shows the % transmittance over actual mean log 10 CFU/mL.
Figure 83A:
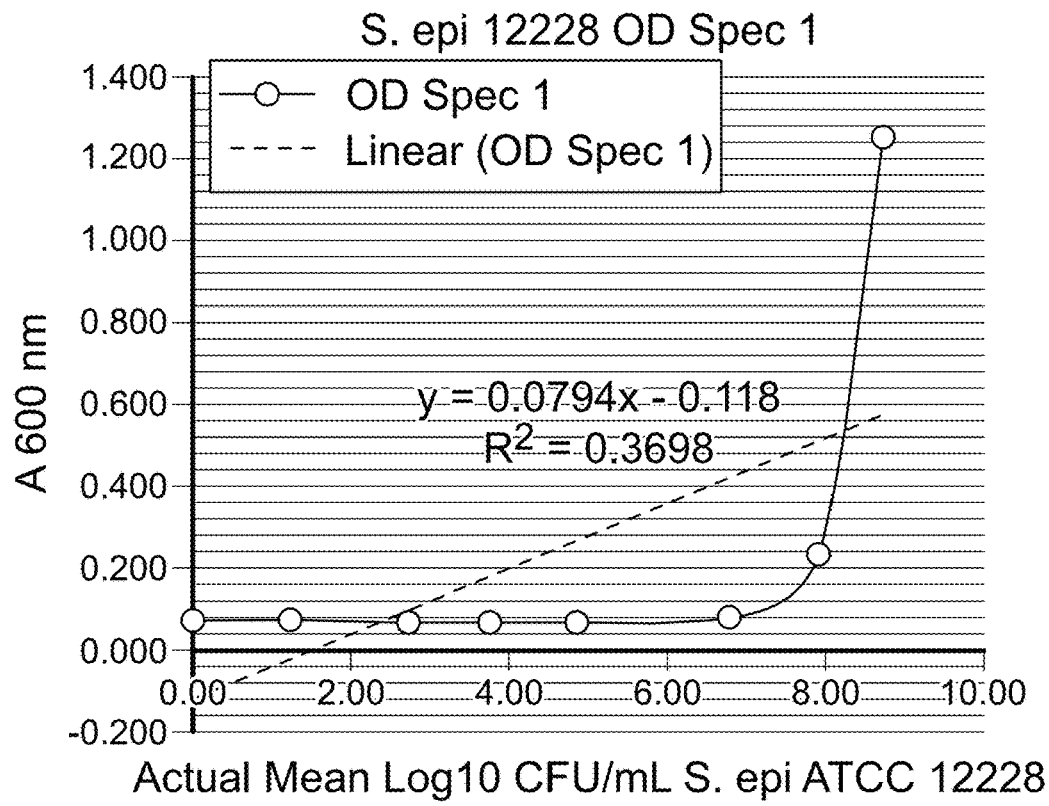
FIG. 83A shows results from testing *S. epidermidis* ATCC 12228, using Spectrophotometer 1, Absorbance (600 nm) Y-axis, plotted over actual mean log 10 CFU/mL.
Figure 83B:
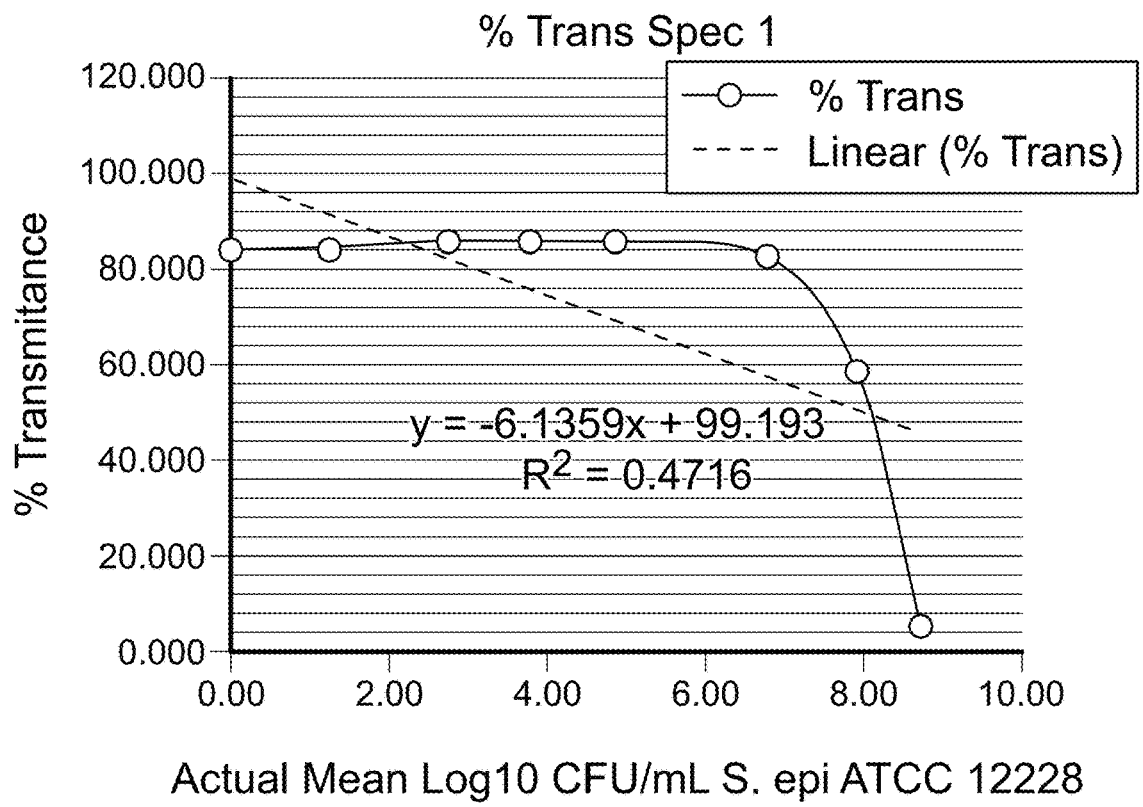
FIG. 83B shows the % transmittance over actual mean log 10 CFU/mL.

Results from testing dilution series of two strains of *E. coli* (DH5-Alpha and ATCC 25922) and a strain of *S. epidermidis* (ATCC 12228) using two different spectrophotometers (OD Spec 1 and OD Spec 2) are shown in the following six tables and FIGS. 81-83.

| Code | CFU/mL | Log10 | ±SD | OD Spec 1 | ±SD | OD Spec 2 | ±SD | % Trans | ±SD |
|---|---|---|---|---|---|---|---|---|---|
| EC 0 | 4.67E+09 | 9.67 | 0.03 | 0.961 | 0.020 | 1.00 | 0.092 | 11.33 | 0.162 |
| EC 1 | 3.33E+08 | 8.52 | 0.13 | 0.186 | 0.008 | 0.13 | 0.012 | 65.15 | 1.166 |
| EC 2 | 6.33E+07 | 7.80 | 0.30 | 0.080 | 0.001 | −0.01 | 0.006 | 83.25 | 0.126 |
| EC 3 | 4.33E+05 | 5.64 | 0.63 | 0.068 | 0.001 | −0.01 | 0.017 | 85.44 | 0.048 |
| EC 4 | 4.47E+04 | 4.65 | 0.70 | 0.067 | 0.001 | −0.01 | 0.006 | 85.78 | 0.063 |
| EC 5 | 5.50E+03 | 3.74 | 0.04 | 0.066 | 0.000 | −0.01 | 0.006 | 85.84 | 0.024 |
| EC 6 | 4.17E+02 | 2.62 | 0.08 | 0.066 | 0.001 | −0.02 | 0.006 | 85.81 | 0.052 |
| EC 7 | 8.33E+01 | 1.92 | 1.79 | 0.022 | 0.038 | −0.02 | 0.015 | 95.26 | 8.194 |

*E. coli* DH5-Alpha mean results (n=3).

Analyte Diluting and Culturing Examples

Example 1: Direct Optical Detection of Bacterial Counts in Samples Having a Dynamic Range of $10^2$ CFU/mL to $10^8$ CFU/mL

| Test | P | S/NS |
|---|---|---|
| $10^{\wedge}8$ Vs $10^{\wedge}7$ | 0.0000 | S |
| $10^{\wedge}7$ Vs $10^{\wedge}6$ | 0.0000 | S |
| $10^{\wedge}6$ Vs $10^{\wedge}5$ | 0.0000 | S |
| $10^{\wedge}5$ Vs $10^{\wedge}4$ | 0.0241 | S |
| $10^{\wedge}4$ Vs $10^{\wedge}3$ | 0.1161 | NS |
| $10^{\wedge}3$ Vs $10^{\wedge}2$ | 0.1142 | NS |

Significance of distinguishing between dilutions tested using non-pairwise two-tailed Student's T-test (for statistical significance, p≤0.05) utilizing data from OD Spec 1.

The concentration of bacteria in a sample can be detected by measuring the absorbance of light through the sample. Transmission (T) and Optical Density (OD) are two common ways to express the absorbance of light. Transmission (T) is normally expressed as a percentage or fraction of unity (i.e. no absorbance and full transmission of light). OD is expressed as the negative logarithm of transmission.

| Code | CFU/mL | Log10 | ±SD | OD Spec 1 | ±SD | OD Spec 2 | ±SD | % Trans | ±SD |
|---|---|---|---|---|---|---|---|---|---|
| EC 0 | 8.83E+09 | 9.95 | 0.06 | 1.179 | 0.006 | 1.31 | 0.010 | 6.65 | 0.122 |
| EC 1 | 1.13E+09 | 9.05 | 0.12 | 0.237 | 0.003 | 0.21 | 0.030 | 57.98 | 0.376 |
| EC 2 | 4.17E+08 | 8.62 | 0.48 | 0.085 | 0.001 | 0.03 | 0.012 | 82.32 | 0.103 |
| EC 3 | 9.83E+05 | 5.99 | 0.10 | 0.069 | 0.000 | 0.01 | 0.012 | 85.39 | 0.022 |

-continued

| Code | CFU/mL | Log10 | ±SD | OD Spec 1 | ±SD | OD Spec 2 | ±SD | % Trans | ±SD |
|---|---|---|---|---|---|---|---|---|---|
| EC 4 | 9.83E+04 | 4.99 | 0.08 | 0.067 | 0.000 | 0.01 | 0.012 | 85.76 | 0.003 |
| EC 5 | 1.03E+04 | 4.01 | 0.68 | 0.067 | 0.000 | 0.01 | 0.012 | 85.72 | 0.064 |
| EC 6 | 1.00E+03 | 3.00 | 0.24 | 0.067 | 0.001 | 0.02 | 0.000 | 85.75 | 0.061 |
| EC 7 | 1.00E+02 | 2.00 | 1.83 | 0.067 | 0.000 | 0.01 | 0.012 | 85.73 | 0.049 |

*E. coli* ATCC 25922 mean results (n=3).

| Test | P | S/NS |
|---|---|---|
| $10^{\wedge}8$ Vs $10^{\wedge}7$ | 0.0000 | S |
| $10^{\wedge}7$ Vs $10^{\wedge}6$ | 0.0000 | S |
| $10^{\wedge}6$ Vs $10^{\wedge}5$ | 0.0000 | S |
| $10^{\wedge}5$ Vs $10^{\wedge}4$ | 0.0132 | S |
| $10^{\wedge}4$ Vs $10^{\wedge}3$ | 0.3739 | NS |
| $10^{\wedge}3$ Vs $10^{\wedge}2$ | 0.3739 | NS |

Significance of distinguishing between dilutions tested using non-pairwise two-tailed Student's T-test (for statistical significance, $p \leq 0.05$) utilizing data from OD Spec 1.

| Code | CFU/mL | Log10 | ±SD | OD Spec 1 | ±SD | OD Spec 2 | ±SD | % Trans | ±SD |
|---|---|---|---|---|---|---|---|---|---|
| EC 0 | 5.33E+08 | 8.73 | 0.08 | 1.250 | 0.015 | 1.40 | 0.023 | 5.63 | 0.199 |
| EC 1 | 8.33E+07 | 7.92 | 0.02 | 0.231 | 0.003 | 0.22 | 0.017 | 58.68 | 0.399 |
| EC 2 | 6.17E+06 | 6.79 | 0.23 | 0.083 | 0.001 | 0.02 | 0.000 | 82.65 | 0.081 |
| EC 3 | 7.17E+04 | 4.86 | 0.12 | 0.068 | 0.000 | 0.01 | 0.010 | 85.46 | 0.039 |
| EC 4 | 5.83E+03 | 3.77 | 0.02 | 0.067 | 0.000 | 0.01 | 0.012 | 85.73 | 0.052 |
| EC 5 | 5.33E+02 | 2.73 | 0.12 | 0.067 | 0.001 | 0.00 | 0.000 | 85.79 | 0.019 |
| EC 6 | 1.67E+01 | 1.22 | 1.56 | 0.076 | 0.001 | 0.02 | 0.000 | 84.50 | 1.118 |
| EC 7 | 0.00E+00 | 0.00 | 0.00 | 0.075 | 0.001 | 0.00 | 0.000 | 84.17 | 0.165 |

*S. epidermidis* ATCC 12228 mean results (n=3).

| Test | P | S/NS |
|---|---|---|
| $10^{\wedge}8$ Vs $10^{\wedge}7$ | 0.0000 | S |
| $10^{\wedge}7$ Vs $10^{\wedge}6$ | 0.0000 | S |
| $10^{\wedge}6$ Vs $10^{\wedge}5$ | 0.0000 | S |
| $10^{\wedge}5$ Vs $10^{\wedge}4$ | 0.0550 | NS |
| $10^{\wedge}4$ Vs $10^{\wedge}3$ | 0.6779 | NS |
| $10^{\wedge}3$ Vs $10^{\wedge}2$ | 0.1161 | NS |

Significance of distinguishing between dilutions use tested using non-pairwise two-tailed Student's T-test (for statistical significance, $p \leq 0.05$) utilizing data from OD Spec 1.

The lower limit of detection for *E. coli* in a dilute carrier using OD was determined to be about $10^5$ CFU/mL. The lower limit of detection for *S. epidermidis* in a dilute carrier using OD was determined to be about $10^6$ CFU/mL. Of the two photospectrometers evaluated, only one (OD Spec 1) was able to determine CFU/mL levels below $10^6$ CFU/mL due to design operational sensitivity. As shown in FIGS. 81-83, the detection of bacteria in a dilute carrier is non-linear. Furthermore, standard laboratory bench top photo-spectrometers do not appear to accurately predict total bacterial counts below $10^6$ CFU/mL in a dilute carrier. Accordingly, optical detection assays for the direct evaluation of samples from the GI tract appear to be limited to detecting bacterial counts of $10^6$ CFU/mL and above and may not be useful for detecting levels of bacteria associated with GI disorders such as SIBO.

Example 2: Optical Detection of Bacterial Counts in Incubated Samples

Experiments were performed to investigate the optical detection of bacteria in samples that are incubated prior to a detection step. The experiments simulated an ingestible device that contains sterile media which is inoculated by a sample from the GI tract and incubated in transit. Growth of the bacteria over time was tracked back to the initial inoculum in order to provide an estimate of the initial inoculum density.

The experiments also evaluated the ability of OD methods to accurately predict total bacterial counts over a dynamic range that reflects the levels of bacterial counts in the GI tract as well as evaluate the differences (if any) between the detection of Gram-Negative and Gram-Positive bacteria.

Materials and Methods

A standard bench top photo spectrometer (Photospectrometer 1: SPECTRAMAX® M5, S/N MV 02773 using software (SOFTMAX® Pro5 s/n SMP500-14128-ATVW), operating at Absorbance 600 nm) was used to determine the CFU/mL of Gram-negative (*Escherichia coli* ATCC 25922) and Gram-positive (*Staphylococcus epidermidis* ATCC 12228) bacteria diluted in a standard growth media (Tryptic Soy Broth; TSB) over a dynamic range of $10^4$ CFU/mL to $10^6$ CFU/mL over a re-growth and incubation period. Samples were tested after incubating at 37° C. for t=0, t=1.5 hour, t=2.25 hours, t=3 hours, and t=4 hours. Experiments were conducted in triplicate.

Results

Figure 84A:
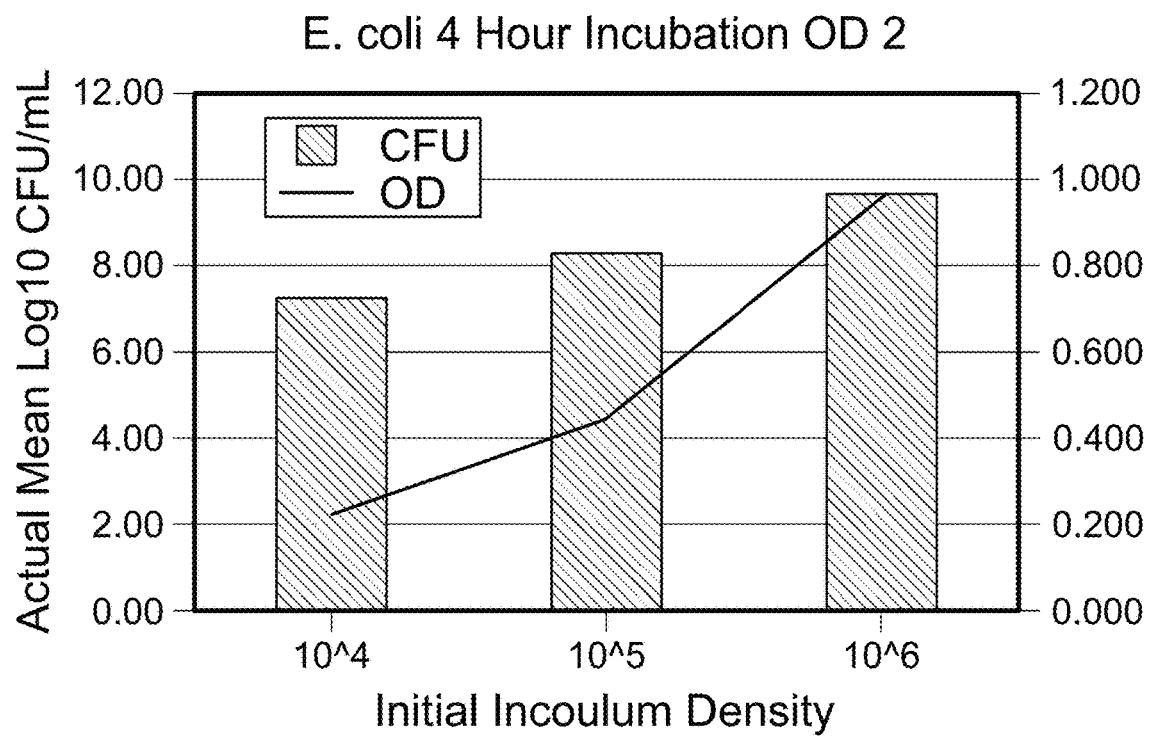
FIGS. 84A and 84B show a graphical representation of OD prediction of CFU/mL at time=4 hours for *E. coli* ATCC 25922 (84A) and *S. epidermidis* ATCC 12228 (84B). Bars represent actual mean $Log_{10}$ CFU/mL recovered after a 4 hour incubation at 37° C. The line represents the Mean OD 600 measurement for each initial inoculum density. Initial inoculum densities sampled cover a dynamic range of 10$^4$, 10$^5$ and 10$^6$ CFU/mL.

As shown in the following table and FIG. 84 the inoculation and incubation of sterile media with a bacterial sample and testing the sample for optical density allowed for the accurate prediction ($p \leq 0.005$) of the initial inoculum density.

Figure 84B:
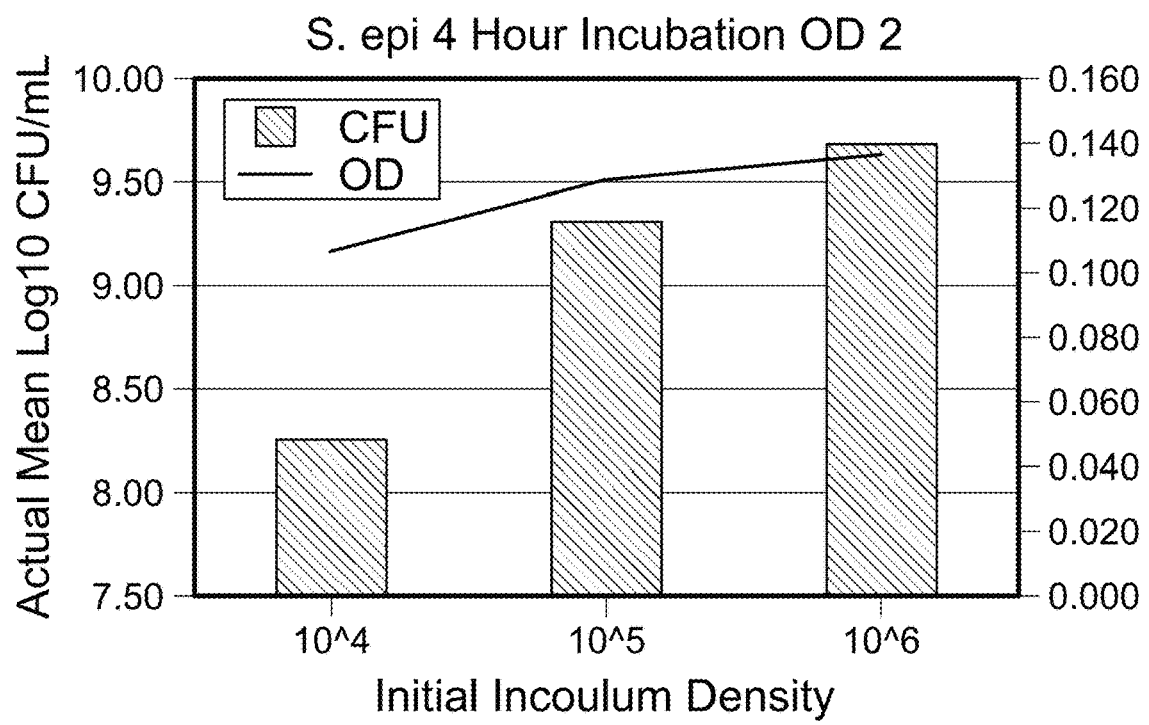
Figure 85A:
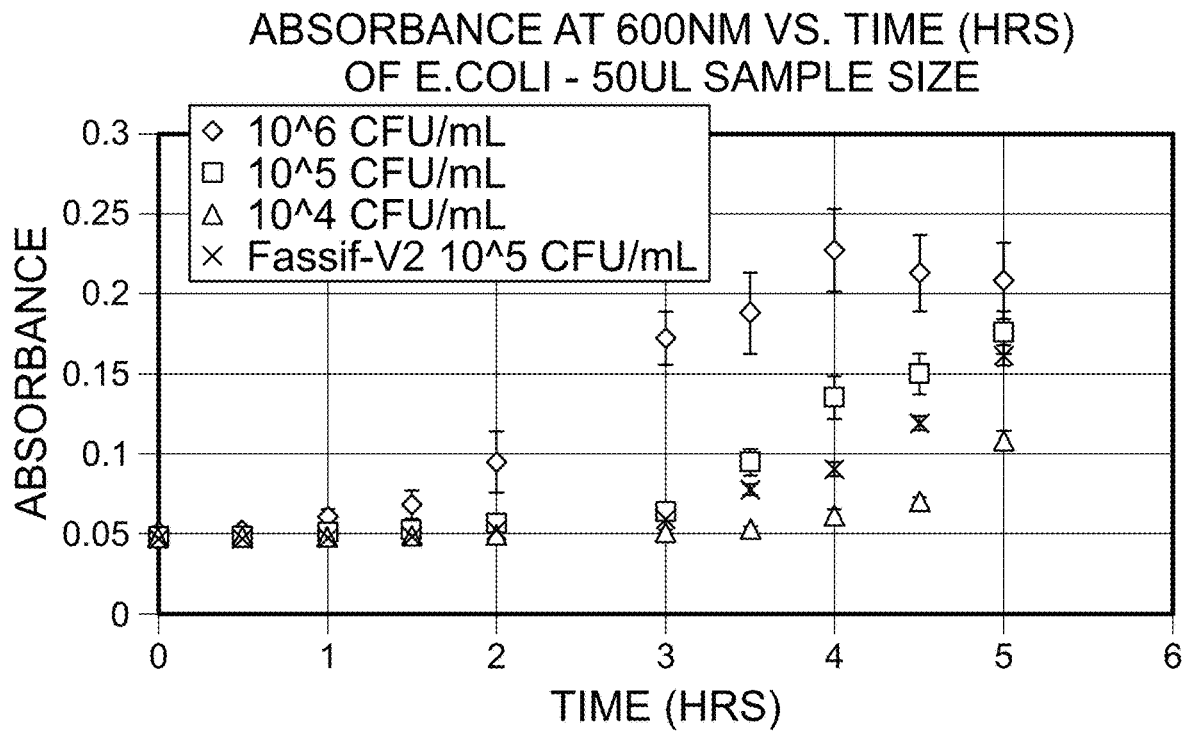
FIGS. 85A and 85B show a graphical representation of OD (A 600 nm) (85A) and % Transmittance (85B) data over a 5 hour time course assay for *E. coli* ATCC 25922 using a 50 μL sample volume.
Figure 85B:
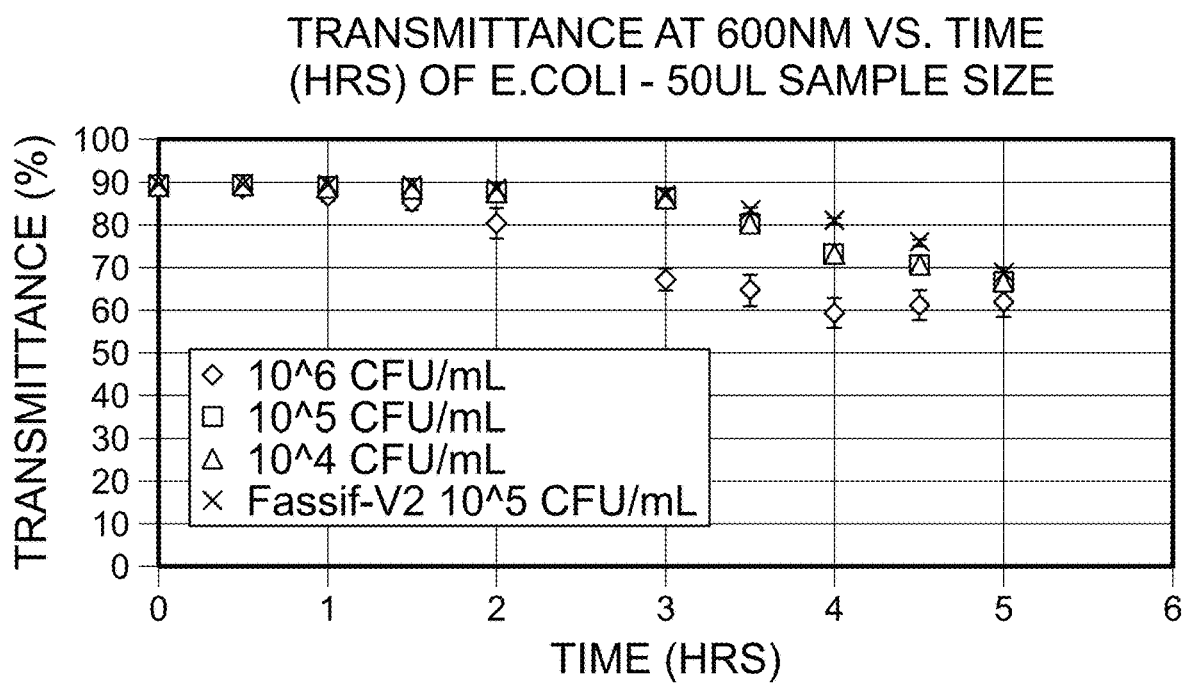
Figure 86A:
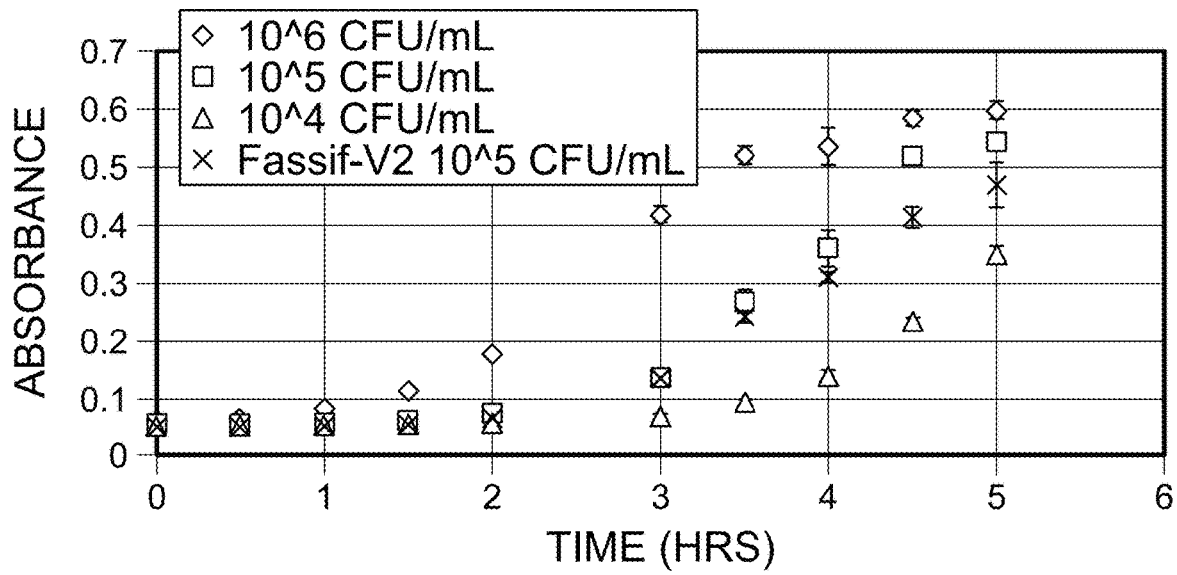
FIGS. 86A and 86B show a graphical representation of OD (A 600 nm) (86A) and % Transmittance (86B) data over a 5 hour time course assay for *E. coli* ATCC 25922 using a 200 μL sample volume.
Figure 86B:
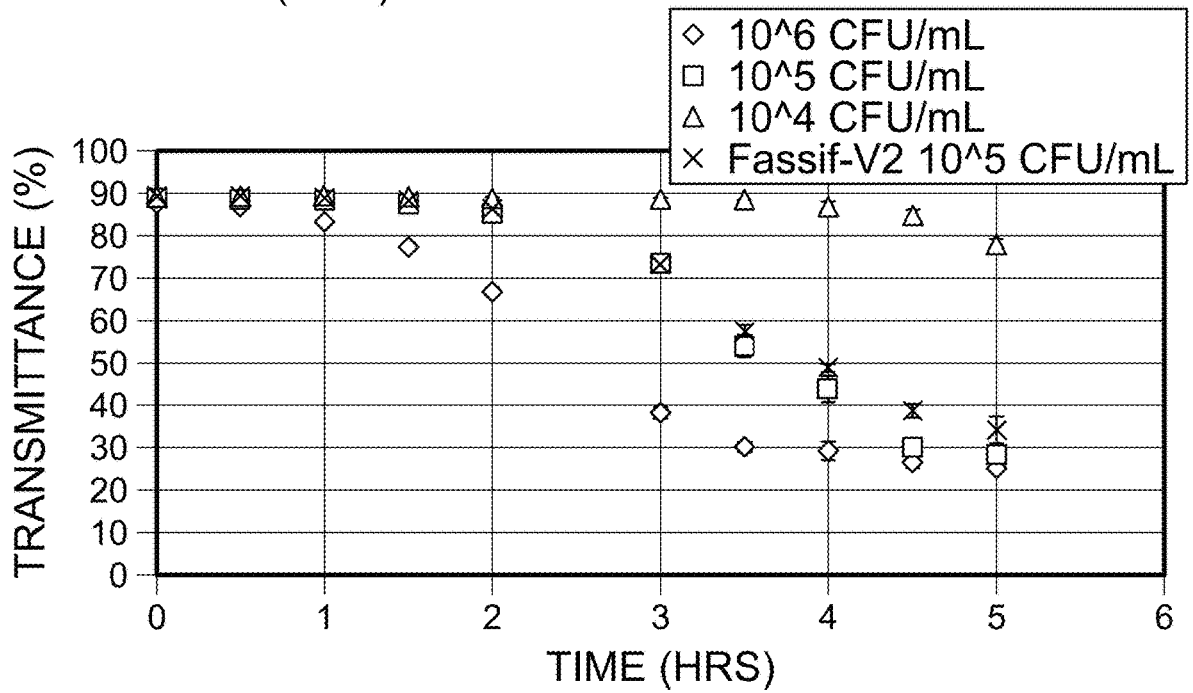
Figure 87A:
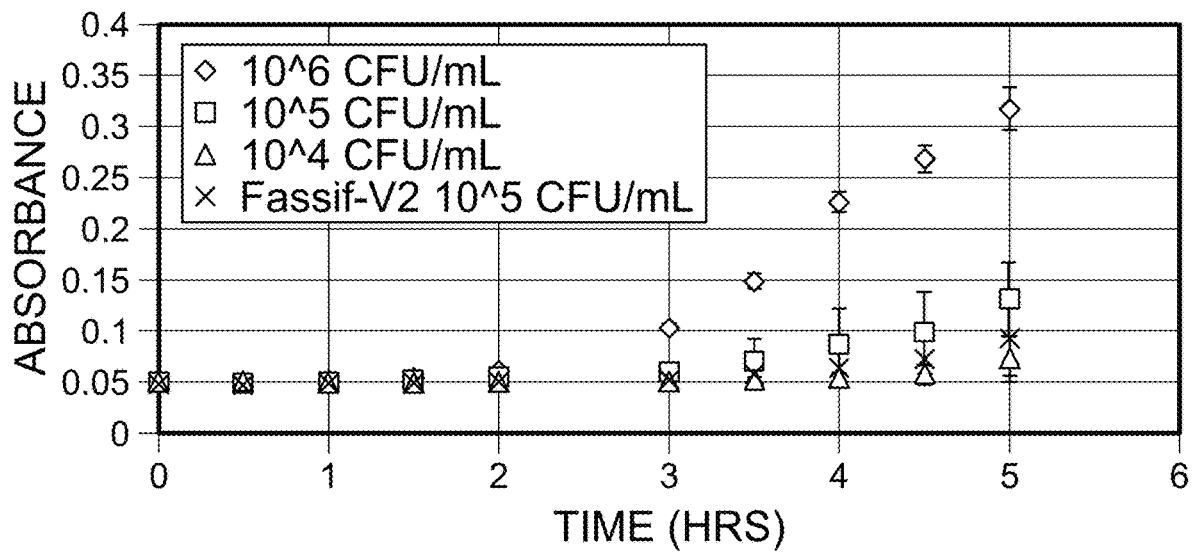
FIGS. 87A and 87B show a graphical representation of OD (A 600 nm) (87A) and % Transmittance (87B) data over a 5 hour time course assay for *S. epidermidis* ATCC 12228 using a 50 μL sample volume.
Figure 87B:
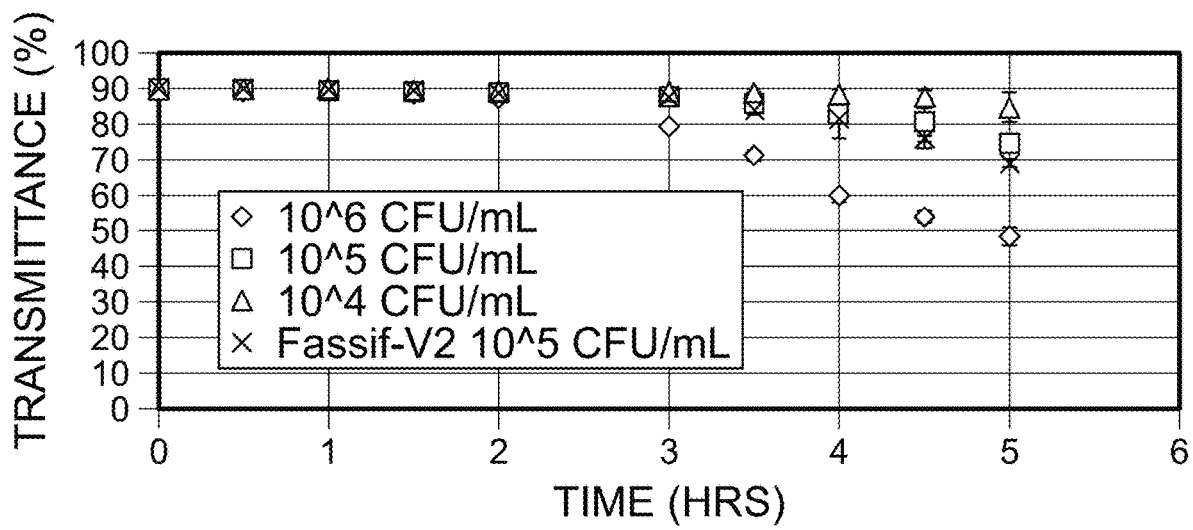
Figure 88A:
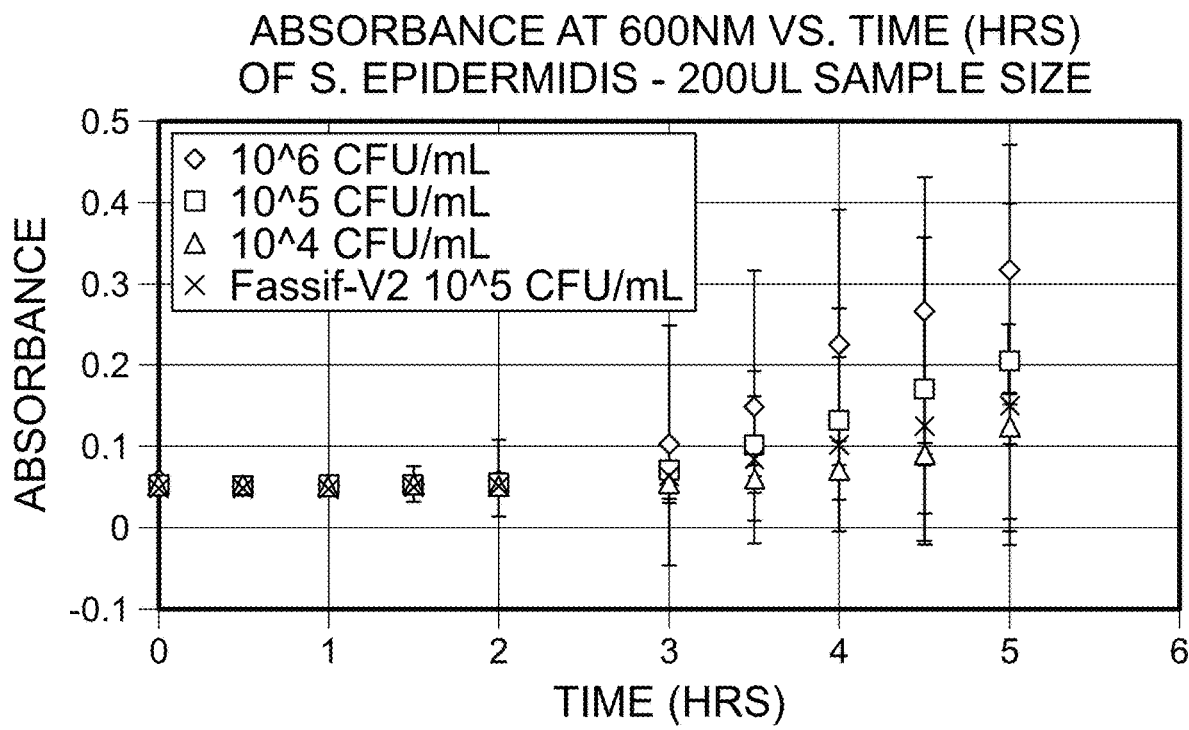
FIGS. 88A and 88B show a graphical representation of OD (A 600 nm) (88A) and % Transmittance (88B) data over a 5 hour time course assay for *S. epidermidis* ATCC 12228 using a 200 μL sample volume.
Figure 88B:
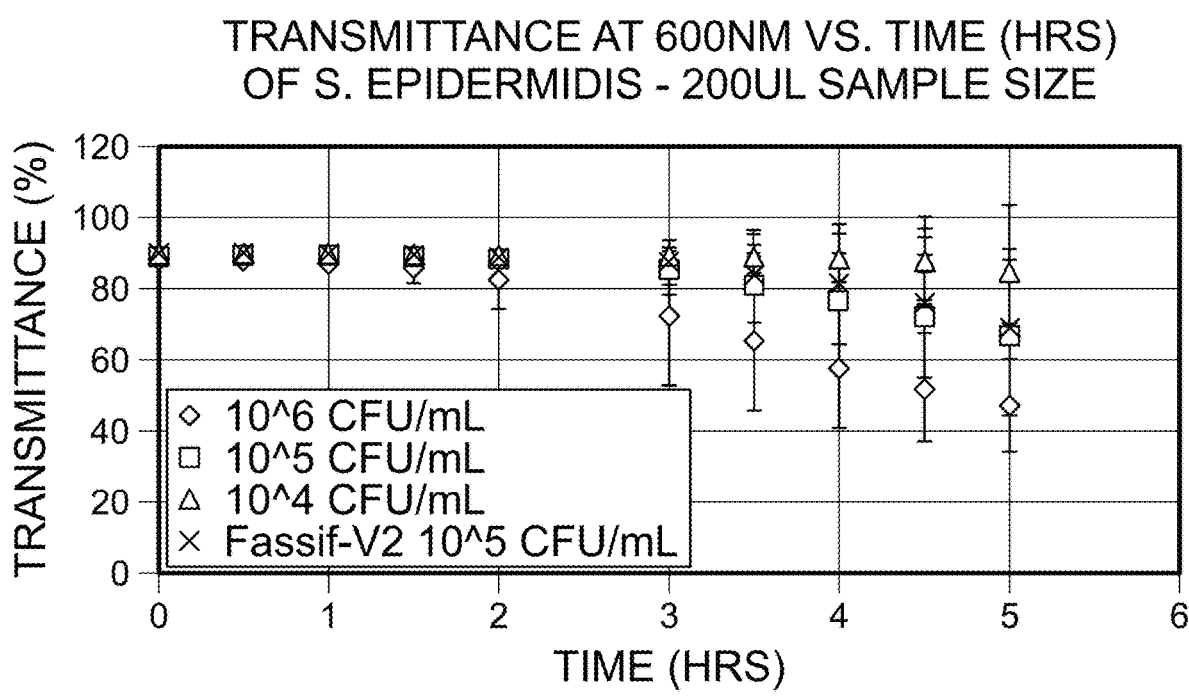

The use of an incubation period followed by OD was able to predict the initial inoculum density of *E. coli* ATCC 25922 (FIG. 84A) and *S. epidermidis* ATCC 12228 (FIG. 84B). An incubation time of about 4 hours was used to reasonably predict the inoculum density of *S. epidermidis* ATCC 12228. Resolution of the initial inoculum density could be obtained at 2.25 and 3 hrs for *E. coli* ATCC 25922.

Under this test system, a standard laboratory bench top photo-spectrometer accurately differentiated between initial inoculum densities of $10^4$, $10^5$ and $10^6$ CFU/mL for both Gram-Negative and Gram-Positive organisms after 4 hours incubation.

The use of a contained media/incubation system has several advantages over preforming a direct OD analysis of a GI fluid sample such as jejunal fluid in order to determine bacterial counts. These include using a base line reading at time=0 as an internal control and to account for possible interference from GI fluids. The use of an anti-fungal agent (i.e. amphotericin B) in the inoculated media may also be used to prevent the growth of fungal counts from the system.

Time=0

| SE | T = 0 | S. epidermidis ATCC 12228 | | | | | |
|---|---|---|---|---|---|---|---|
| Mean | Code | CFU/mL | Log10 | ±SD | OD Spec 1 | ±SD | % Trans | ±SD |
| | O/N | 1.07E+09 | 9.03 | 0.23 | 0.911 | 0.001 | 12.49 | 0.021 |
| | SE 4 | 6.67E+04 | 4.82 | 0.29 | 0.081 | 0.001 | 59.52* | 40.650 |
| | SE 5 | 5.67E+05 | 5.75 | 0.17 | 0.080 | 0.000 | 83.08 | 0.023 |
| | SE 6 | 9.67E+06 | 6.99 | 0.01 | 0.089 | 0.000 | 81.98 | 0.982 |

*Off scale data point

| EC | T = 0 | E. coli ATCC 25922 | | | | | |
|---|---|---|---|---|---|---|---|
| Mean | Code | CFU/mL | Log10 | ±SD | OD Spec 1 | ±SD | % Trans | ±SD |
| | O/N | 1.15E+08 | 8.06 | 0.11 | 0.902 | 0.003 | 11.19 | 1.223 |
| | EC 4 | 8.67E+05 | 5.94 | 0.08 | 0.086 | 0.000 | 82.06 | 0.007 |
| | EC 5 | 7.00E+06 | 6.85 | 0.25 | 0.083 | 0.000 | 82.67 | 0.011 |
| | EC 6 | 4.50E+07 | 7.65 | 0.53 | 0.094 | 0.001 | 80.60 | 0.014 |

Time=1.5 hours

| | | S. epidermidis ATCC 12228 | | | | | | |
|---|---|---|---|---|---|---|---|---|
| SE | T = 1.5 HRS | | | | OD | | % | |
| Mean | Code | CFU/mL | Log10 | ±SD | Spec 1 | ±SD | Trans | ±SD |
| | SE 4 | 1.25E+05 | 5.10 | 0.13 | 0.093 | 0.000 | 80.80 | 0.008 |
| | SE 5 | 1.45E+06 | 6.16 | 0.25 | 0.080 | 0.000 | 83.10 | 0.010 |
| | SE 6 | 1.40E+07 | 7.15 | 0.14 | 0.094 | 0.000 | 80.52 | 0.018 |

| | | E. coli ATCC 25922 | | | | | | |
|---|---|---|---|---|---|---|---|---|
| EC | T = 1.5 HRS | | | | OD | | % | |
| Mean | Code | CFU/mL | Log10 | ±SD | Spec 1 | ±SD | Trans | ±SD |
| | EC 4 | 1.43E+06 | 6.16 | 0.12 | 0.086 | 0.000 | 82.00 | 0.011 |
| | EC 5 | 9.33E+06 | 6.97 | 0.24 | 0.083 | 0.001 | 82.53 | 0.014 |
| | EC 6 | 1.70E+08 | 8.23 | 0.15 | 0.109 | 0.001 | 77.84 | 0.092 |

Time=2.25 hours

| | | S. epidermidis ATCC 12228 | | | | | | |
|---|---|---|---|---|---|---|---|---|
| SE | T = 2.25 HRS | | | | OD | | % | |
| Mean | Code | CFU/mL | Log10 | ±SD | Spec 1 | ±SD | Trans | ±SD |
| | SE 4 | 1.05E+05 | 5.02 | 0.15 | 0.127 | 0.001 | 74.92 | 0.142 |
| | SE 5 | 1.07E+06 | 6.03 | 0.05 | 0.100 | 0.001 | 95.68 | 0.048 |
| | SE 6 | 1.22E+07 | 7.09 | 0.02 | 0.012 | 0.000 | 97.38 | 0.012 |

-continued

| | | E. coli ATCC 25922 | | | | | | |
|---|---|---|---|---|---|---|---|---|
| EC | T = 2.25 HRS | | | | OD | | % | |
| Mean | Code | CFU/mL | Log10 | ±SD | Spec 1 | ±SD | Trans | ±SD |
| | EC 4 | 2.35E+06 | 6.37 | 0.03 | 0.101 | 0.000 | 79.27 | 0.017 |
| | EC 5 | 3.98E+07 | 7.60 | 0.28 | 0.113 | 0.000 | 77.05 | 0.032 |
| | EC 6 | 9.25E+08 | 8.97 | 0.31 | 0.217 | 0.002 | 59.93 | 0.541 |

Time=3 hours

| | | S. epidermidis ATCC 12228 | | | | | | |
|---|---|---|---|---|---|---|---|---|
| SE | T = 3 HRS | | | | OD | | % | |
| Mean | Code | CFU/mL | Log10 | ±SD | Spec 1 | ±SD | Trans | ±SD |
| | SE 4 | 9.33E+04 | 4.97 | 0.12 | 0.118 | 0.001 | 76.08 | 0.125 |
| | SE 5 | 6.25E+06 | 6.80 | 0.68 | 0.125 | 0.001 | 74.98 | 0.013 |
| | SE 6 | 1.05E+07 | 7.02 | 0.08 | 0.102 | 0.000 | 79.11 | 0.031 |

| | | E. coli ATCC 25922 | | | | | | |
|---|---|---|---|---|---|---|---|---|
| EC | T = 3 HRS | | | | OD | | % | |
| Mean | Code | CFU/mL | Log10 | ±SD | Spec 1 | ±SD | Trans | ±SD |
| | EC 4 | 9.67E+04 | 4.99 | 0.14 | 0.163 | 0.001 | 68.65 | 0.076 |
| | EC 5 | 1.05E+06 | 6.02 | 0.08 | 0.218 | 0.003 | 60.27 | 0.145 |
| | EC 6 | 1.95E+07 | 7.29 | 0.02 | 0.668 | 0.001 | 21.78 | 0.303 |

Time=4 hours

| | | S. epidermidis ATCC 12228 | | | | | | |
|---|---|---|---|---|---|---|---|---|
| SE | T = 4 HRS | | | | OD | | % | |
| Mean | Code | CFU/mL | Log10 | ±SD | Spec 1 | ±SD | Trans | ±SD |
| | SE 4 | 1.80E+08 | 8.26 | 0.04 | 0.108 | 0.001 | 78.10 | 0.176 |
| | SE 5 | 2.10E+09 | 9.32 | 0.23 | 0.129 | 0.001 | 74.29 | 0.006 |
| | SE 6 | 4.83E+09 | 9.68 | 0.16 | 0.551 | 0.718 | 73.06 | 0.087 |

-continued

| EC Mean Code | T = 4 HRS CFU/mL | Log10 | ±SD | OD Spec 1 | ±SD | % Trans | ±SD |
|---|---|---|---|---|---|---|---|
| | *E. coli* ATCC 25922 | | | | | | |
| EC 4 | 1.70E+07 | 7.23 | 0.20 | 0.223 | 0.001 | 60.10 | 0.214 |
| EC 5 | 2.03E+08 | 8.31 | 0.12 | 0.445 | 0.003 | 35.90 | 0.177 |
| EC 6 | 5.22E+09 | 9.72 | 0.20 | 0.955 | 0.008 | 11.17 | 0.065 |

Results from testing incubated samples of *E. coli* and *S. epidermidis* using OD 600 having an initial bacterial density of $10^4$, $10^5$ or $10^6$ CFU/mL.

Example 3: OD Testing of Bacterial Samples in Small Sample Volumes and Simulated Jejunal Fluid Additional experiments were performed similar to those described in Example 2 to assess the robustness of the method using two different sample volumes (200 μL and 50 μL). For these experiments a plate reader was used in place of a benchtop photospectrometer. Experiments were also performed to evaluate possible interference effects due to jejunal fluids by testing an inoculum diluted in Fasted State Simulated Intestinal Fluid Version Two (FaSSIF-V2) available from BioRelevant, London UK (Cat: V2FA501 Lot: 02-1408-07, pH 6.5)

Materials and Methods

Experiments were performed using a plate reader photospectrometer in order to estimate the CFU/mL of Gram-negative (*Escherichia coli* ATCC 25922) and Gram-positive (*Staphylococcus epidermidis* ATCC 12228) bacterial samples inoculated into a standard growth media (TSB) having an initial bacterial concentration of $10^6$ CFU/mL to $10^4$ CFU/mL following an incubation period or between 0 hours and 5 hours. The FaSSF-V2 interference tests utilized an initial bacteria concentration made up to $10^5$ CFU/mL in FaSSF-V2 and added to a well containing nutrient buffer (FLUKA Tryptic Soy Broth; L/N BCBL6035V). Bacterial samples were combined in a 1:1 ratio (vol/vol) with nutrient buffer (e.g. 25 μL of sample was added to 25 μL TSB, or 100 μL sample was added to 100 μL TSB). Two separate sets of experiments were performed and the experiments in each set were conducted in quintuplicate (n=5).

Results

The following table shows representative data and FIGS. 85-88 show raw data presented as optical density (A 600 nm) and % transmittance for each strain tested over a dynamic range of $10^4$ CFU/mL, $10^5$ CFU/mL and $10^6$ CFU/mL using test volumes of 50 or 200 μL. Initial readings at time=0, shortly after (less than 1 minute) the sample was combined with the media were recorded and may be used to set a baseline.

2 hours is approximately 6 bacterial generations and is about the minimum incubation time to detect discrete differences between the initial sample concentrations. After an incubation time of 3 hours, there is good discrete resolution between initial sample concentrations. After an incubation time of 4.5 hours, the OD measurements still provide discrete resolution between the different initial sample concentrations. However, as the incubation time is extended, it is expected that a decrease in resolution may occur as the concentration of bacteria and OD measurements increase beyond the dynamic range of the assay.

Measuring the OD of incubated samples was able to accurately differentiate between initial inoculum densities of $10^4$, $10^5$ and $10^6$ CFU/mL for both Gram-Negative and Gram-Positive organisms after between about 2 and 4 hours incubation. The use of a 50 μL sample size had no negative impacts on resolution or assay function. Accordingly, smaller sample volumes such as those used within an ingestible device are expected to accurately differentiate between inoculum densities at least between $10^4$ and $10^6$. Furthermore, the presence of simulated jejunal fluid constituents had no significant impacts on resolution or assay function.

Time=0 Optical Density (A600 nm)

| Volume | Sample | Mean | SD | CV | Sample | Mean | SD | CV |
|---|---|---|---|---|---|---|---|---|
| 50 | EC 10^6 | 0.05076 | 0.000378 | 0.74% | SE 10^6 | 0.05026 | 0.00023 | 0.46% |
| | EC 10^5 | 0.0486 | 0.000122 | 0.25% | SE 10^5 | 0.0486 | 0.000566 | 1.16% |
| | EC 10^4 | 0.04826 | 0.000195 | 0.40% | SE 10^4 | 0.0486 | 0.000524 | 1.08% |
| 200 | EC 10^6 | 0.0586 | 0.0003 | 0.51% | SE 10^6 | 0.05668 | 0.001114 | 1.97% |
| | EC 10^5 | 0.05228 | 0.000449 | 0.86% | SE 10^5 | 0.05204 | 0.000513 | 0.99% |
| | EC 10^4 | 0.05162 | 0.000228 | 0.44% | SE 10^4 | 0.05124 | 0.000365 | 0.71% |
| 50 | FEC | 0.04692 | 0.000342 | 0.73% | FSE | 0.04686 | 0.000385 | 0.82% |
| 200 | FEC | 0.04858 | 0.00013 | 0.27% | FSE | 0.04848 | 0.000683 | 1.41% |

Time=0% Transmittance

| Volume | Sample | Mean | SD | CV | Sample | Mean | SD | CV |
|---|---|---|---|---|---|---|---|---|
| 50 | EC 10^6 | 88.96929 | 0.077465 | 0.09% | SE 10^6 | 89.07176 | 0.047212 | 0.05% |
| | EC 10^5 | 89.41287 | 0.025212 | 0.03% | SE 10^5 | 89.41292 | 0.116413 | 0.13% |
| | EC 10^4 | 89.4829 | 0.040165 | 0.04% | SE 10^4 | 89.41291 | 0.107928 | 0.12% |
| 200 | EC 10^6 | 87.37759 | 0.060358 | 0.07% | SE 10^6 | 87.76496 | 0.225133 | 0.26% |
| | EC 10^5 | 88.65846 | 0.091745 | 0.10% | SE 10^5 | 88.70748 | 0.10469 | 0.12% |
| | EC 10^4 | 88.79327 | 0.046621 | 0.05% | SE 10^4 | 88.87101 | 0.074608 | 0.08% |
| 50 | FEC | 89.75943 | 0.070709 | 0.08% | FSE | 89.77184 | 0.079515 | 0.09% |
| 200 | FEC | 89.41698 | 0.026846 | 0.03% | FSE | 89.43766 | 0.140643 | 0.16% |

Time=2 hours Optical Density (A600 nm)

| Volume | Sample | Mean | SD | CV | Sample | Mean | SD | CV |
|---|---|---|---|---|---|---|---|---|
| 50 | EC 10^6 | 0.09496 | 0.019572 | 20.61% | SE 10^6 | 0.05978 | 0.000811 | 1.36% |
|  | EC 10^5 | 0.05656 | 0.005479 | 9.69% | SE 10^5 | 0.05296 | 0.007494 | 14.15% |
|  | EC 10^4 | 0.04966 | 0.000313 | 0.63% | SE 10^4 | 0.04868 | 0.000901 | 1.85% |
| 200 | EC 10^6 | 0.17412 | 0.00476 | 2.73% | SE 10^6 | 0.0858 | 0.04698 | 54.76% |
|  | EC 10^5 | 0.07048 | 0.001542 | 2.19% | SE 10^5 | 0.05574 | 0.008028 | 14.40% |
|  | EC 10^4 | 0.05366 | 0.000416 | 0.78% | SE 10^4 | 0.05154 | 0.001343 | 2.61% |
| 50 | FEC | 0.05248 | 0.004659 | 8.88% | FSE | 0.04892 | 0.002437 | 4.98% |
| 200 | FEC | 0.06332 | 0.001865 | 2.94% | FSE | 0.05088 | 0.005232 | 10.28% |

Time=2 hours % Transmittance

| Volume | Sample | Mean | SD | CV | Sample | Mean | SD | CV |
|---|---|---|---|---|---|---|---|---|
| 50 | EC 10^6 | 80.42426 | 3.536326 | 4.40% | SE 10^6 | 87.14061 | 0.162647 | 0.19% |
|  | EC 10^5 | 87.79454 | 1.098591 | 1.25% | SE 10^5 | 88.53018 | 1.510366 | 1.71% |
|  | EC 10^4 | 89.19491 | 0.064304 | 0.07% | SE 10^4 | 89.39655 | 0.185424 | 0.21% |
| 200 | EC 10^6 | 66.97317 | 0.731932 | 1.09% | SE 10^6 | 82.4395 | 8.278532 | 10.04% |
|  | EC 10^5 | 85.02021 | 0.301153 | 0.35% | SE 10^5 | 87.96682 | 1.605999 | 1.83% |
|  | EC 10^4 | 88.37718 | 0.084642 | 0.10% | SE 10^4 | 88.80996 | 0.274631 | 0.31% |
| 50 | FEC | 88.62167 | 0.947562 | 1.07% | FSE | 89.34813 | 0.499954 | 0.56% |
| 200 | FEC | 86.43372 | 0.371856 | 0.43% | FSE | 88.94982 | 1.063177 | 1.20% |

Time=3 hours Optical Density (A600 nm)

| Volume | Sample | Mean | SD | CV | Sample | Mean | SD | CV |
|---|---|---|---|---|---|---|---|---|
| 50 | EC 10^6 | 0.17258 | 0.016967 | 9.83% | SE 10^6 | 0.1019 | 0.004229 | 4.15% |
|  | EC 10^5 | 0.06378 | 0.002404 | 3.77% | SE 10^5 | 0.0569 | 0.005458 | 9.59% |
|  | EC 10^4 | 0.05122 | 0.000904 | 1.76% | SE 10^4 | 0.0495 | 0.001382 | 2.79% |
| 200 | EC 10^6 | 0.41688 | 0.014442 | 3.46% | SE 10^6 | 0.15826 | 0.148057 | 93.55% |
|  | EC 10^5 | 0.13256 | 0.003445 | 2.60% | SE 10^5 | 0.07074 | 0.036146 | 51.10% |
|  | EC 10^4 | 0.06532 | 0.000928 | 1.42% | SE 10^4 | 0.05412 | 0.006027 | 11.14% |
| 50 | FEC | 0.05918 | 0.001763 | 2.98% | FSE | 0.05126 | 0.005307 | 10.35% |
| 200 | FEC | 0.1338 | 0.006236 | 4.66% | FSE | 0.06366 | 0.033788 | 53.08% |

Time=3 hours % Transmittance

| Volume | Sample | Mean | SD | CV | Sample | Mean | SD | CV |
|---|---|---|---|---|---|---|---|---|
| 50 | EC 10^6 | 67.24879 | 2.617102 | 3.89% | SE 10^6 | 79.08907 | 0.769339 | 0.97% |
|  | EC 10^5 | 86.34264 | 0.478239 | 0.55% | SE 10^5 | 87.7258 | 1.094922 | 1.25% |
|  | EC 10^4 | 88.87523 | 0.185061 | 0.21% | SE 10^4 | 89.22812 | 0.283507 | 0.32% |
| 200 | EC 10^6 | 38.3101 | 1.285504 | 3.36% | SE 10^6 | 72.27026 | 19.29999 | 26.71% |
|  | EC 10^5 | 73.69719 | 0.584028 | 0.79% | SE 10^5 | 85.19592 | 6.697644 | 7.86% |
|  | EC 10^4 | 86.03612 | 0.183721 | 0.21% | SE 10^4 | 88.29036 | 1.214937 | 1.38% |
| 50 | FEC | 87.26154 | 0.354801 | 0.41% | FSE | 88.87217 | 1.077773 | 1.21% |
| 200 | FEC | 73.4913 | 1.059753 | 1.44% | FSE | 86.56754 | 6.385675 | 7.38% |

Time=4.5 hours Optical Density (A600 nm)

| Volume | Sample | Mean | SD | CV | Sample | Mean | SD | CV |
|---|---|---|---|---|---|---|---|---|
| 50 | EC 10^6 | 0.22736 | 0.026112 | 11.49% | SE 10^6 | 0.2259 | 0.009883 | 4.37% |
|  | EC 10^5 | 0.13502 | 0.009231 | 6.84% | SE 10^5 | 0.08518 | 0.035907 | 42.15% |
|  | EC 10^4 | 0.06162 | 0.003552 | 5.76% | SE 10^4 | 0.0526 | 0.004575 | 8.70% |
| 200 | EC 10^6 | 0.53434 | 0.032055 | 6.00% | SE 10^6 | 0.2615 | 0.165496 | 63.29% |
|  | EC 10^5 | 0.35818 | 0.03018 | 8.43% | SE 10^5 | 0.13256 | 0.138883 | 104.77% |
|  | EC 10^4 | 0.13744 | 0.006781 | 4.93% | SE 10^4 | 0.07006 | 0.036316 | 51.84% |
| 50 | FEC | 0.09056 | 0.004601 | 5.08% | FSE | 0.06224 | 0.016994 | 27.30% |
| 200 | FEC | 0.30832 | 0.009083 | 2.95% | FSE | 0.1017 | 0.107891 | 106.09% |

Time=4.5 hours % Transmittance

| Volume | Sample | Mean | SD | CV | Sample | Mean | SD | CV |
|---|---|---|---|---|---|---|---|---|
| 50 | EC 10^6 | 59.32856 | 3.530779 | 5.95% | SE 10^6 | 59.4552 | 1.34997 | 2.27% |
|  | EC 10^5 | 73.29227 | 1.549138 | 2.11% | SE 10^5 | 82.40721 | 6.450136 | 7.83% |
|  | EC 10^4 | 86.7744 | 0.709678 | 0.82% | SE 10^4 | 88.59704 | 0.927041 | 1.05% |
| 200 | EC 10^6 | 29.28356 | 2.22116 | 7.59% | SE 10^6 | 57.49285 | 16.66898 | 28.99% |
|  | EC 10^5 | 43.92071 | 3.108927 | 7.08% | SE 10^5 | 76.33877 | 19.42472 | 25.45% |
|  | EC 10^4 | 72.87896 | 1.130378 | 1.55% | SE 10^4 | 85.33154 | 6.738642 | 7.90% |
| 50 | FEC | 81.18195 | 0.857394 | 1.06% | FSE | 86.70049 | 3.30725 | 3.81% |
| 200 | FEC | 49.17635 | 1.034605 | 2.10% | FSE | 80.88278 | 16.85387 | 20.84% |

Results from testing different initial concentrations of *E. coli* (EC) and *S. epidermidis* (SE) using 50 µL, and 200 µL, samples.

Example 4: Testing of Bacterial Samples Under Conditions that Simulate an Ingestible Device in the GI Tract Experiments were performed in order to simulate an ingestible device that contains sterile media that is inoculated with a sample of fluid from the GI tract and incubated in transit. The experiments were designed to evaluate whether the assay could predict total bacterial counts over a dynamic range of $10^3$ CFU/mL to $10^7$ CFU/mL under a series of different conditions of pH, bile acids, fungal strains, mucin concentrations. The samples were also incubated under conditions of shear forces and temperature that simulate conditions of an ingestible device in transit within the GI tract.

Materials and Methods

Gram-negative (*Escherichia coli* ATCC 25922) and Gram-positive (*Staphylococcus epidermidis* ATCC 12228) bacterial cultures were diluted in a standard growth media (TSB) over a dynamic range of $10^7$ CFU/mL to $10^3$ CFU/mL. The assay utilized 50 µL, sample volumes, under shear (110 rpm) and at body temperature (37° C.) over a 4 hour incubation period to simulate transit of an ingestible device within the GI tract. Experiments were performed under various conditions as indicated including: different pH levels (6.5, 7.0 and 7.8); different concentrations of bile acids (1.4, 3 and 5.5 mM; Oxgall Sigma Aldrich, SKU B3883); the presence of fungal cells (*C. albicans* at 0, 1×10$^3$ CFU/mL) with or without modified anti-fungal recovery media (TSB containing 2.5 mg/L Amphotericin B (Sigma-Aldrich, P/N A9528); and different concentrations of mucin (0.5%, 1% and 1.5%). Experiments were conducted in quintuplicate. All testing was completed in simulated jejunal fluid (FaSSIF-V2; available from BioRelevant (London, UK) Cat: V2FA501 Lot: 02-1408-07, pH 6.5) using a 50 µL sample volume and a 4 hour incubation period.

Results

Results from testing the bacterial samples under different conditions are shown in the following two tables (*E. coli, S. epidermidis*) as well as FIGS. 89-96.

Bile

Figure 89:
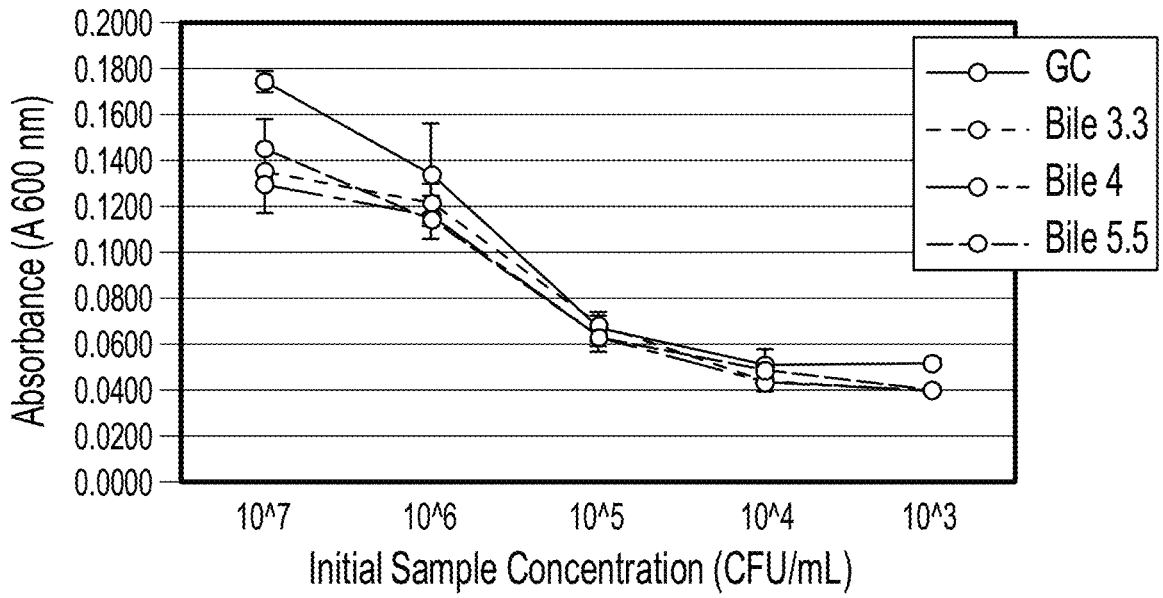
FIG. 89 shows results from a bile acid concentration test with *E. coli* ATCC 25922 Optical Density (A 600 nm) plotted at t=4 hours over a dynamic range of initial inoculum densities in a 50 μL sample volume. Growth control (GC) data is also plotted for reference.
Figure 90:
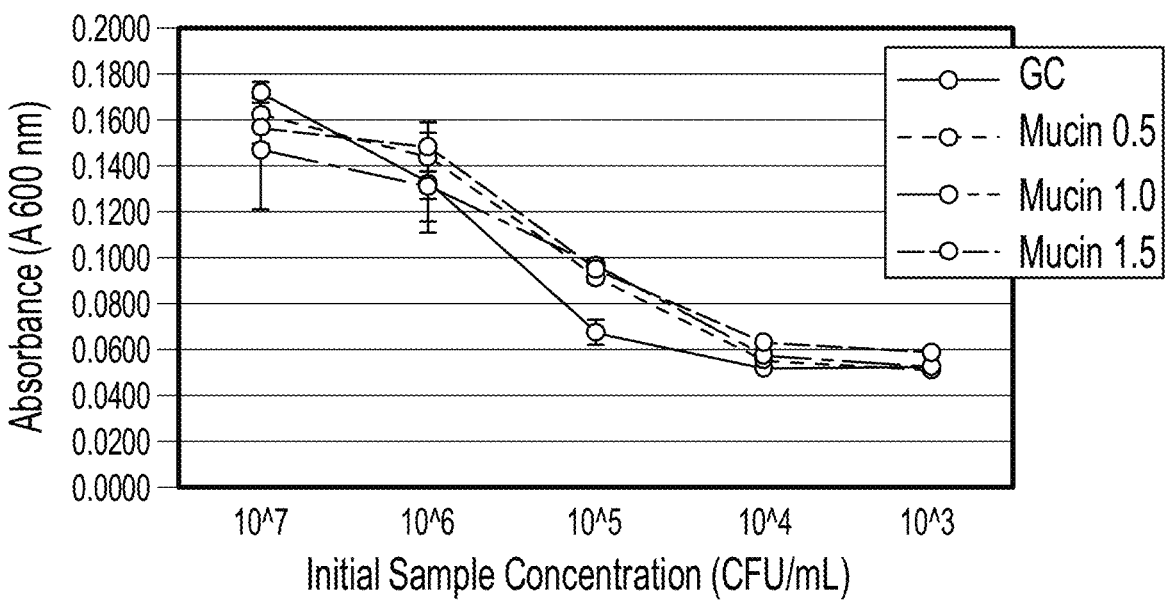
FIG. 90 shows results from a mucin concentration test with *E. coli* ATCC 25922 Optical Density (A 600 nm) plotted at t=4 hours over a dynamic range of initial inoculum densities in a 50 μL sample volume. Growth control (GC) data is also plotted for reference.
Figure 93:
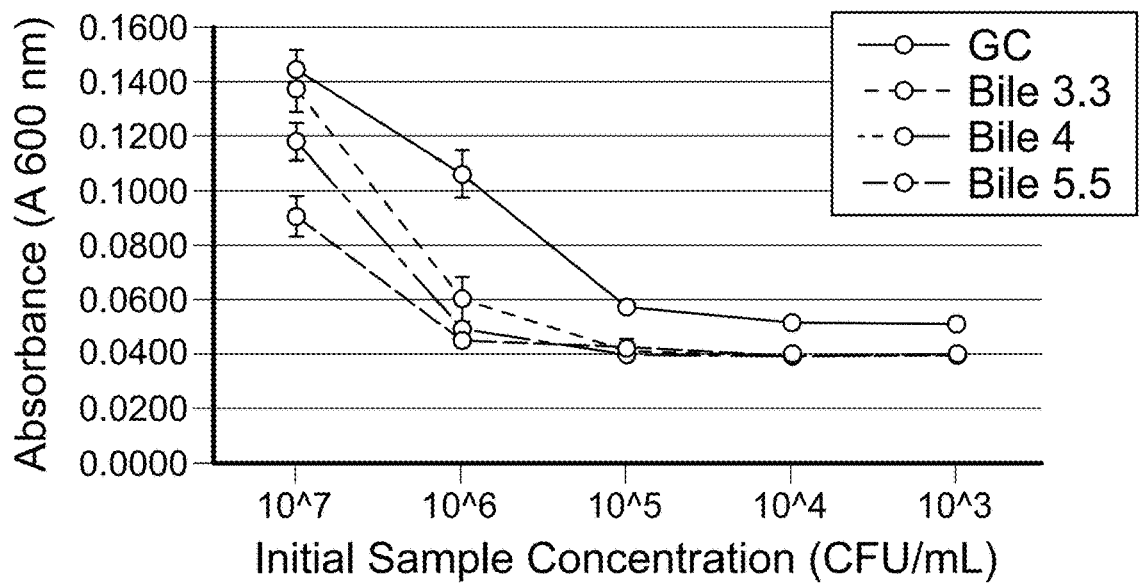
FIG. 93 shows results from a bile acid concentration test with *S. epidermidis* ATCC 12228 Optical Density (A 600 nm) plotted at t=4 hours over a dynamic range of initial inoculum densities in a 50 μL sample volume. Growth Control (GC) data is also plotted for reference.

As shown in FIG. 89 (*E. coli*) and FIG. 93 (*S. epidermidis*) the presence of bile reduced the optical density of the samples relative to the growth control. The observed reduction in OD increased with increased bile concentration. This did not limit the ability of the assay to resolve discrete differences in initial inoculum density. The lower limit of detection was $10^4$ CFU/mL.

Mucin

Figure 94:
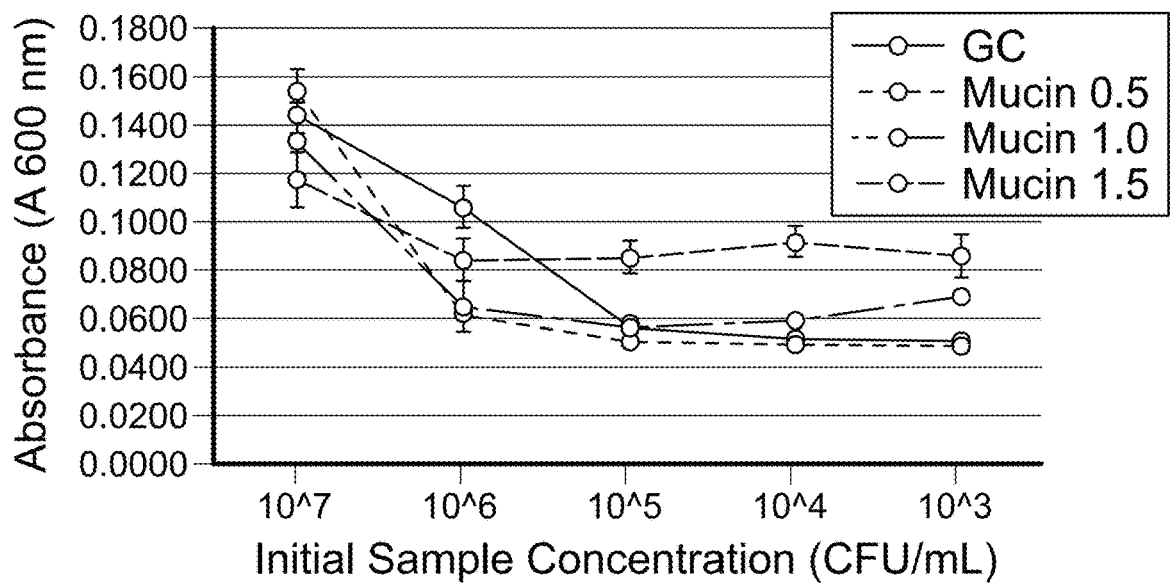
FIG. 94 shows results from a mucin concentration test with *S. epidermidis* ATCC 12228 Optical Density (A 600 nm) plotted at t=4 hours over a dynamic range of initial inoculum densities in a 50 μL sample volume. Growth Control (GC) data is also plotted for reference.

Mucin at 1.5% limited the ability of the assay to predict initial inoculum concentration of *S. epidermidis* to $10^6$ CFU/mL, however the assay was able to accurately resolve differences in the initial inoculum density when greater than $10^5$ CFU/mL at 1% and 0.5% mucin concentrations (FIG. 94).

Under the conditions tested, mucin did not have any significant impact on the optical density of samples of *E. coli* relative to the growth control. The addition of mucin up to a concentration of 1.5% did not limit the ability of the assay to resolve discrete differences in the initial inoculum density. The lower limit of detection was $10^4$ CFU/mL.

Figure 91:
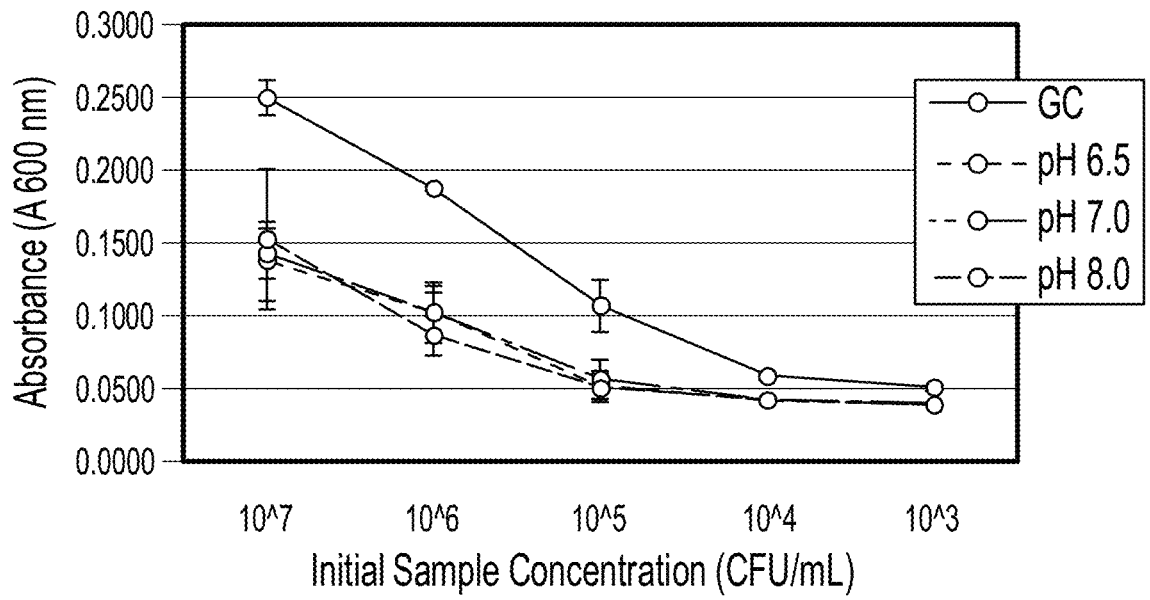
FIG. 91 shows results from a pH range test with *E. coli* ATCC 25922 Optical Density (A 600 nm) plotted at t=4 hours over a dynamic range of initial inoculum densities in a 50 μL sample volume. Growth control (GC) data is also plotted for reference.
Figure 95:
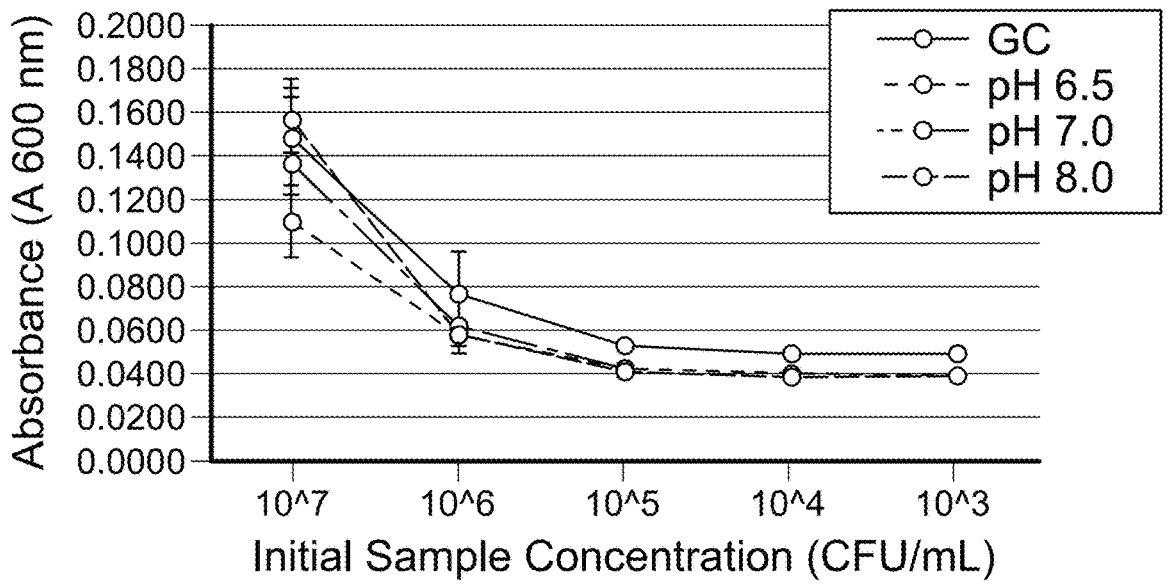
FIG. 95 shows results from a pH range test with *S. epidermidis* ATCC 12228 Optical Density (A 600 nm) plotted at t=4 hours over a dynamic range of initial inoculum densities in a 50 μL sample volume. Growth Control (GC) data is also plotted for reference.

As shown in FIGS. 91 and 95, increasing the pH reduced the optical density of the tested samples compared to the growth control. This did not limit the ability of the assay to resolve discrete differences in initial inoculum density. The lower limit of detection was $10^4$ CFU/mL.

Fungal Contamination

Figure 92:
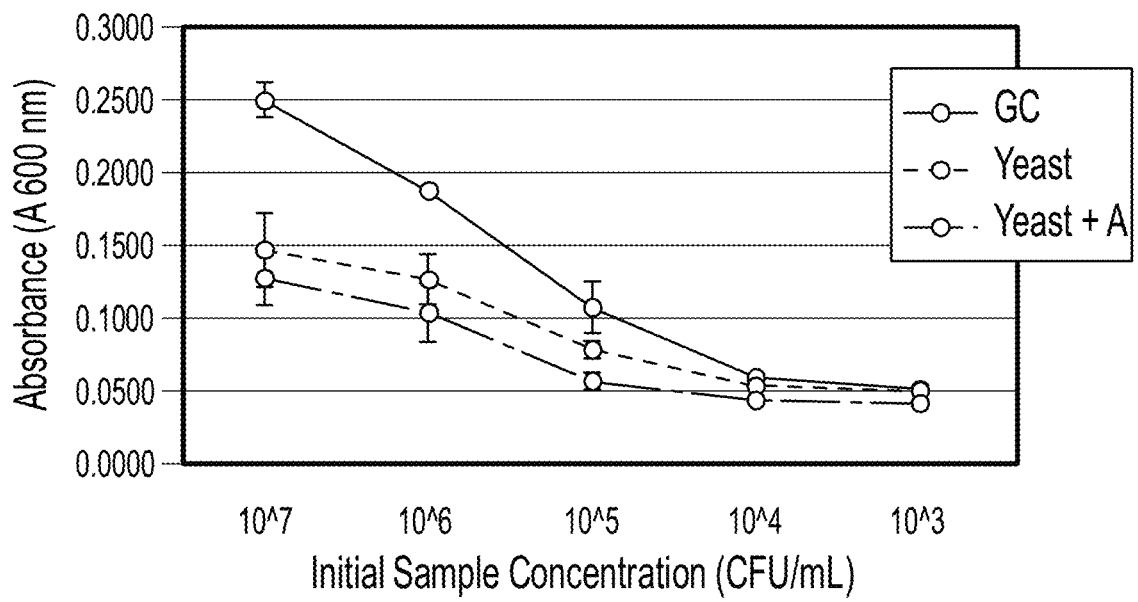
FIG. 92 shows results from a fungal interference test with *E. coli* ATCC 25922 Optical Density (A 600 nm) plotted at t=4 hours over a dynamic range of initial inoculum densities in a 50 μL Sample volume. Growth control (GC) data is also plotted for reference. A=amphotericin B.
Figure 96:
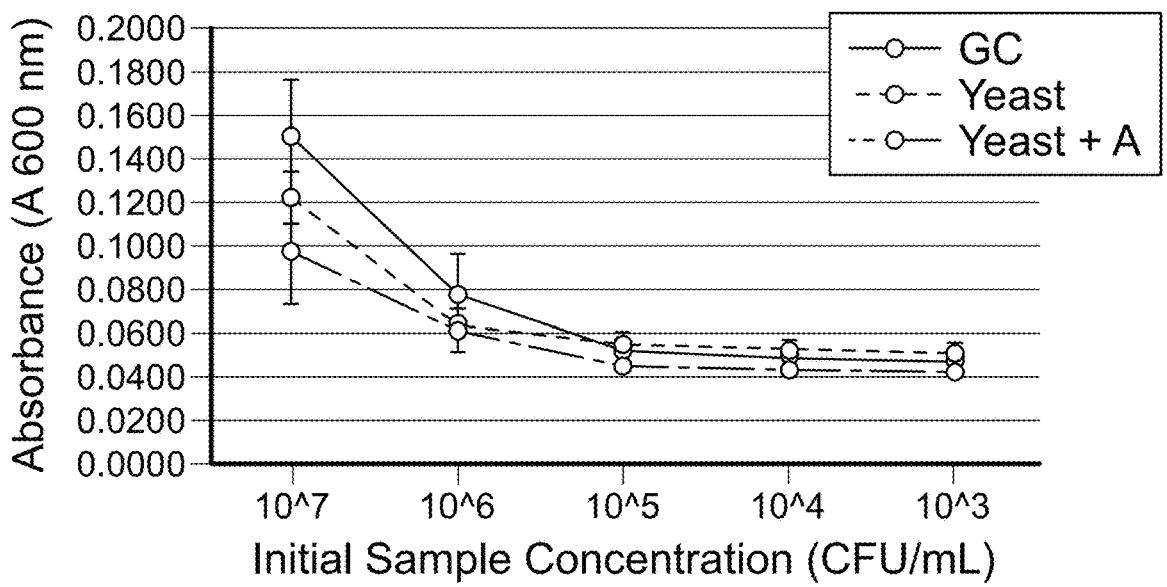
FIG. 96 shows results from a fungal interference test with *S. epidermidis* ATCC 12228 Optical Density (A 600 nm) plotted at t=4 hours over a dynamic range of initial inoculum densities in a 50 μL sample volume. Growth Control (GC) data is also plotted for reference. A=amphotericin B.

As shown in FIGS. 92 and 96, fungal contamination did not limit the ability of the assay to resolve discrete differences in initial inoculum density. The lower limit of detection was $10^4$ CFU/mL. The addition of amphotericin B reduced the background fungal growth (as determined by plate counts and reduced optical density) and did not impact the ability of the assay to resolve discrete differences in initial inoculum density.

*E. coli* ATCC 25922 Growth Control

| Sample | EC 10^7 | EC 10^6 | EC 10^5 | EC 10^4 | EC 10^3 |
|---|---|---|---|---|---|
| Mean | 0.1739 | 0.1333 | 0.0665 | 0.0504 | 0.0511 |
| SD | 0.0048 | 0.0222 | 0.0056 | 0.0010 | 0.0020 |
| CV | 2.73% | 16.68% | 8.36% | 1.95% | 3.84% |

*E. coli* ATCC 25922 Bile 3.3 mM

| Sample | EC 10^7 | EC 10^6 | EC 10^5 | EC 10^4 | EC 10^3 |
|---|---|---|---|---|---|
| Mean | 0.1348 | 0.1210 | 0.0679 | 0.0432 | 0.0393 |
| SD | 0.0104 | 0.0086 | 0.0056 | 0.0004 | 0.0004 |
| CV | 7.68% | 7.11% | 8.26% | 0.99% | 1.06% |

*E. coli* ATCC 25922 Bile 4 mM

| Sample | EC 10^7 | EC 10^6 | EC 10^5 | EC 10^4 | EC 10^3 |
|---|---|---|---|---|---|
| Mean | 0.1292 | 0.1152 | 0.0627 | 0.0427 | 0.0392 |
| SD | 0.0124 | 0.0093 | 0.0043 | 0.0005 | 0.0003 |
| CV | 9.58% | 8.11% | 6.87% | 1.23% | 0.67% |

E. coli ATCC 25922 Bile 5.5 mM

| Sample | EC 10^7 | EC 10^6 | EC 10^5 | EC 10^4 | EC 10^3 |
|---|---|---|---|---|---|
| Mean | 0.1447 | 0.1138 | 0.0625 | 0.0481 | 0.0395 |
| SD | 0.0130 | 0.0029 | 0.0058 | 0.0093 | 0.0002 |
| CV | 9.00% | 2.57% | 9.25% | 19.37% | 0.49% |

E. coli ATCC 25922 Mucin 0.5%

| Sample | EC 10^7 | EC 10^6 | EC 10^5 | EC 10^4 | EC 10^3 |
|---|---|---|---|---|---|
| Mean | 0.1643 | 0.1451 | 0.0909 | 0.0540 | 0.0496 |
| SD | 0.0073 | 0.0109 | 0.0020 | 0.0003 | 0.0008 |
| CV | 4.43% | 7.52% | 2.25% | 0.60% | 1.57% |

E. coli ATCC 25922 Mucin 1.0%

| Sample | EC 10^7 | EC 10^6 | EC 10^5 | EC 10^4 | EC 10^3 |
|---|---|---|---|---|---|
| Mean | 0.1484 | 0.1319 | 0.0965 | 0.0562 | 0.0511 |
| SD | 0.0268 | 0.0158 | 0.0027 | 0.0038 | 0.0030 |
| CV | 18.06% | 12.02% | 2.76% | 6.70% | 5.79% |

E. coli ATCC 25922 Bile 1.5%

| Sample | EC 10^7 | EC 10^6 | EC 10^5 | EC 10^4 | EC 10^3 |
|---|---|---|---|---|---|
| Mean | 0.1583 | 0.1496 | 0.0948 | 0.0620 | 0.0575 |
| SD | 0.0182 | 0.0038 | 0.0032 | 0.0012 | 0.0004 |
| CV | 11.53% | 2.54% | 3.33% | 1.97% | 0.68% |

E. coli ATCC 25922 pH 6.5

| Sample | EC 10^7 | EC 10^6 | EC 10^5 | EC 10^4 | EC 10^3 |
|---|---|---|---|---|---|
| Mean | 0.1383 | 0.1036 | 0.0525 | 0.0416 | 0.0402 |
| SD | 0.0271 | 0.0174 | 0.0095 | 0.0026 | 0.0006 |
| CV | 19.62% | 16.79% | 18.04% | 6.28% | 1.48% |

E. coli ATCC 25922 pH 7.0

| Sample | EC 10^7 | EC 10^6 | EC 10^5 | EC 10^4 | EC 10^3 |
|---|---|---|---|---|---|
| Mean | 0.1432 | 0.1026 | 0.0566 | 0.0422 | 0.0399 |
| SD | 0.0175 | 0.0207 | 0.0139 | 0.0020 | 0.0016 |
| CV | 12.24% | 20.22% | 24.55% | 4.76% | 3.98% |

E. coli ATCC 25922 pH 8.0

| Sample | EC 10^7 | EC 10^6 | EC 10^5 | EC 10^4 | EC 10^3 |
|---|---|---|---|---|---|
| Mean | 0.1530 | 0.0868 | 0.0507 | 0.0424 | 0.0389 |
| SD | 0.0481 | 0.0135 | 0.0098 | 0.0043 | 0.0004 |
| CV | 31.43% | 15.55% | 19.34% | 10.09% | 0.95% |

E. coli ATCC 25922 Yeast

| Sample | EC 10^7 | EC 10^6 | EC 10^5 | EC 10^4 | EC 10^3 |
|---|---|---|---|---|---|
| Mean | 0.1468 | 0.1267 | 0.0782 | 0.0531 | 0.0495 |
| SD | 0.0256 | 0.0175 | 0.0059 | 0.0032 | 0.0049 |
| CV | 17.47% | 13.85% | 7.52% | 6.06% | 9.81% |

E. coli ATCC 25922 Yeast+Amphotericin B

| Sample | EC 10^7 | EC 10^6 | EC 10^5 | EC 10^4 | EC 10^3 |
|---|---|---|---|---|---|
| Mean | 0.1274 | 0.1038 | 0.0562 | 0.0432 | 0.0410 |
| SD | 0.0181 | 0.0203 | 0.0056 | 0.0020 | 0.0011 |
| CV | 14.21% | 19.53% | 10.03% | 4.73% | 2.71% |

Results from testing the OD (600 nm) of different initial concentrations of E. coli ATCC 25922 under various conditions of mucin, bile pH and yeast after a 4 hour incubation.

Growth Control—S. epiderimidis ATCC 12228

| Sample | SE 10^7 | SE 10^6 | SE 10^5 | SE10^4 | SE 10^3 |
|---|---|---|---|---|---|
| Mean | 0.1443 | 0.1061 | 0.0576 | 0.0516 | 0.0510 |
| SD | 0.0074 | 0.0087 | 0.0015 | 0.0009 | 0.0013 |
| CV | 5.10% | 8.18% | 2.58% | 1.81% | 2.59% |

S. epiderimidis ATCC 12228 Bile 3.3 mM

| Sample | SE 10^7 | SE 10^6 | SE 10^5 | SE10^4 | SE10^3 |
|---|---|---|---|---|---|
| Mean | 0.1373 | 0.0602 | 0.0413 | 0.0396 | 0.0398 |
| SD | 0.0086 | 0.0080 | 0.0003 | 0.0002 | 0.0005 |
| CV | 6.23% | 13.22% | 0.63% | 0.55% | 1.14% |

S. epiderimidis ATCC 12228 Bile 4 mM

| | Sample | | | | |
|---|---|---|---|---|---|
| | SE 10^7 | SE 10^6 | SE 10^5 | SE10^4 | SE10^3 |
| Mean | 0.1179 | 0.0493 | 0.0400 | 0.0392 | 0.0400 |
| SD | 0.0068 | 0.0026 | 0.0003 | 0.0003 | 0.0004 |
| CV | 5.76% | 5.29% | 0.85% | 0.83% | 1.08% |

S. epiderimidis ATCC 12228 Bile 5.5 mM

| | Sample | | | | |
|---|---|---|---|---|---|
| | SE 10^7 | SE 10^6 | SE 10^5 | SE10^4 | SE10^3 |
| Mean | 0.0907 | 0.0449 | 0.0422 | 0.0400 | 0.0397 |
| SD | 0.0073 | 0.0010 | 0.0032 | 0.0004 | 0.0003 |
| CV | 8.07% | 2.26% | 7.49% | 0.98% | 0.70% |

*S. epiderimidis* ATCC 12228 Mucin 0.5%

|      | Sample   |          |          |          |          |
|------|----------|----------|----------|----------|----------|
|      | SE 10^7  | SE 10^6  | SE 10^5  | SE10^4   | SE10^3   |
| Mean | 0.1550   | 0.0616   | 0.0503   | 0.0495   | 0.0489   |
| SD   | 0.0090   | 0.0007   | 0.0016   | 0.0005   | 0.0008   |
| CV   | 5.78%    | 1.06%    | 3.26%    | 1.05%    | 1.65%    |

*S. epiderimidis* ATCC 12228 Mucin 1.0%

|      | Sample   |          |          |          |          |
|------|----------|----------|----------|----------|----------|
|      | SE 10^7  | SE 10^6  | SE 10^5  | SE10^4   | SE10^3   |
| Mean | 0.1340   | 0.0650   | 0.0562   | 0.0587   | 0.0689   |
| SD   | 0.0162   | 0.0105   | 0.0025   | 0.0008   | 0.0007   |
| CV   | 12.11%   | 16.14%   | 4.44%    | 1.32%    | 1.00%    |

*S. epiderimidis* ATCC 12228 Mucin 1.5%

|      | Sample   |          |          |          |          |
|------|----------|----------|----------|----------|----------|
|      | SE 10^7  | SE 10^6  | SE 10^5  | SE10^4   | SE10^3   |
| Mean | 0.1177   | 0.0841   | 0.0851   | 0.0916   | 0.0857   |
| SD   | 0.0112   | 0.0094   | 0.0067   | 0.0063   | 0.0094   |
| CV   | 9.50%    | 11.20%   | 7.93%    | 6.83%    | 10.98%   |

*S. epiderimidis* ATCC 12228 pH 6.5

|      | Sample   |          |          |          |          |
|------|----------|----------|----------|----------|----------|
|      | SE 10^7  | SE 10^6  | SE 10^5  | SE10^4   | SE10^3   |
| Mean | 0.1104   | 0.0587   | 0.0420   | 0.0401   | 0.0398   |
| SD   | 0.0167   | 0.0047   | 0.0008   | 0.0004   | 0.0005   |
| CV   | 15.12%   | 7.98%    | 2.01%    | 1.08%    | 1.18%    |

*S. epiderimidis* ATCC 12228 pH 7.0

|      | Sample   |          |          |          |          |
|------|----------|----------|----------|----------|----------|
|      | SE 10^7  | SE 10^6  | SE 10^5  | SE10^4   | SE10^3   |
| Mean | 0.1373   | 0.0624   | 0.0411   | 0.0394   | 0.0394   |
| SD   | 0.0304   | 0.0128   | 0.0006   | 0.0004   | 0.0006   |
| CV   | 22.17%   | 20.56%   | 1.38%    | 1.10%    | 1.41%    |

*S. epiderimidis* ATCC 12228 pH 8.0

|      | Sample   |          |          |          |          |
|------|----------|----------|----------|----------|----------|
|      | SE 10^7  | SE 10^6  | SE 10^5  | SE10^4   | SE10^3   |
| Mean | 0.1570   | 0.0591   | 0.0410   | 0.0389   | 0.0390   |
| SD   | 0.0149   | 0.0062   | 0.0011   | 0.0009   | 0.0006   |
| CV   | 9.49%    | 10.52%   | 2.69%    | 2.32%    | 1.47%    |

*S. epiderimidis* ATCC 12228 Yeast

|      | Sample   |          |          |          |          |
|------|----------|----------|----------|----------|----------|
|      | SE 10^7  | SE 10^6  | SE 10^5  | SE10^4   | SE10^3   |
| Mean | 0.1216   | 0.0640   | 0.0544   | 0.0518   | 0.0501   |
| SD   | 0.0117   | 0.0078   | 0.0065   | 0.0051   | 0.0044   |
| CV   | 9.59%    | 12.11%   | 12.02%   | 9.83%    | 8.70%    |

*S. epiderimidis* ATCC Yeast Amphotericin B

|      | Sample   |          |          |          |          |
|------|----------|----------|----------|----------|----------|
|      | SE 10^7  | SE 10^6  | SE 10^5  | SE10^4   | SE10^3   |
| Mean | 0.0971   | 0.0611   | 0.0454   | 0.0437   | 0.0425   |
| SD   | 0.0237   | 0.0097   | 0.0026   | 0.0015   | 0.0015   |
| CV   | 24.37%   | 15.91%   | 5.75%    | 3.53%    | 3.48%    |

Results from testing OD (600 nm) for samples of different initial concentrations of *S. epiderimidis* ATCC 12228 under various conditions of mucin, bile pH and yeast after a 4 hour incubation.

Example 5: Development of a Miniature OD Reader for Use in an Ingestible Device

Experiments were performed to assess a low-cost miniature optical detection system suitable for use in an ingestible device.

Materials and Methods

An exemplary miniature optical detection system was assembled using a Kingbright 1608SURCK LED centered around 640 nanometers with a maximum luminous intensity of approximately 80 millicandela. The LED was driven by a bipolar junction transistor constant current source. An operational amplifier provided a servo arrangement to set the current through the transistor proportional to the input voltage to the operational amplifier. This precisely linearly modulates the light output of the LED proportional to the applied voltage. The detector was an OSRAM SFH 2430 photodiode. This photodiode features a large active area (7 mm$^2$) and has a spectral response fairly well-matched to the LED. The photodiode was used in the low-speed photovoltaic mode as it provides better linearity and lower dark current than the higher-speed photoconductive mode. A MAX9617 zero-drift chopper operational amplifier used as a transconductance amplifier to convert the small photocurrents to a readable voltage.

The LED and photodiode were mounted on separate tabs and inserted into header sockets so that the LED and photodiode were approximately aligned vertically with a gap between them. A 3D printed shroud isolated the LED and photodiode from ambient light and provided a slot to hold the 50 μL cuvette. Data acquisition was accommodated through a standard BNC Jack. Current data acquisition in the BSL-2 lab was acquired through the use of voltage detection through a standard QMS multimeter.

Test measurements were performed by passing a DC-offset signal generator source through the system. Square, sine, and ramp waveforms were all reproduced faithfully. (Data not Shown).

Prior to testing with live bacterial cultures, the miniature OD reader was tested utilizing a dilution range of optically appropriate dye (0.25% w/v CoomassR-250). A dilution range was prepared from 100% to 1.562% in sterile 0.9% saline. Serial dilutions were prepared X2 in quintuplicate. 50 μL Samples were read in parallel using the miniature device and compared to a standard high performance bench top photospectrometer S/N 01164 (Photospectrometer 1: SPECTRAMAX® M5, S/N MV 02773 using software (SOFTMAX® Pro5 s/n SMP500-14128-ATVW), operating at Absorbance 600 nm).

For testing the miniature OD reader with live bacterial cultures, an overnight culture of E. coli ATCC 25922 was prepared in Tryptic Soy Broth. Samples having a calibrated dynamic concentration range of $10^7$ CFU/mL, $10^6$ CFU/mL and $10^5$ CFU/mL were then prepared in sterile 0.9% saline. Plate counts were performed to confirm cell density. 50 µL samples were read in parallel using the miniature OD reader and compared to a standard high performance bench top spectrophotometer (Spec 2: Fisher Scientific, Cell Density Meter Model 40, Serial Number 247, operating at standard setting (A=600 nm)). Testing was performed in triplicate.

Results

Figure 97:
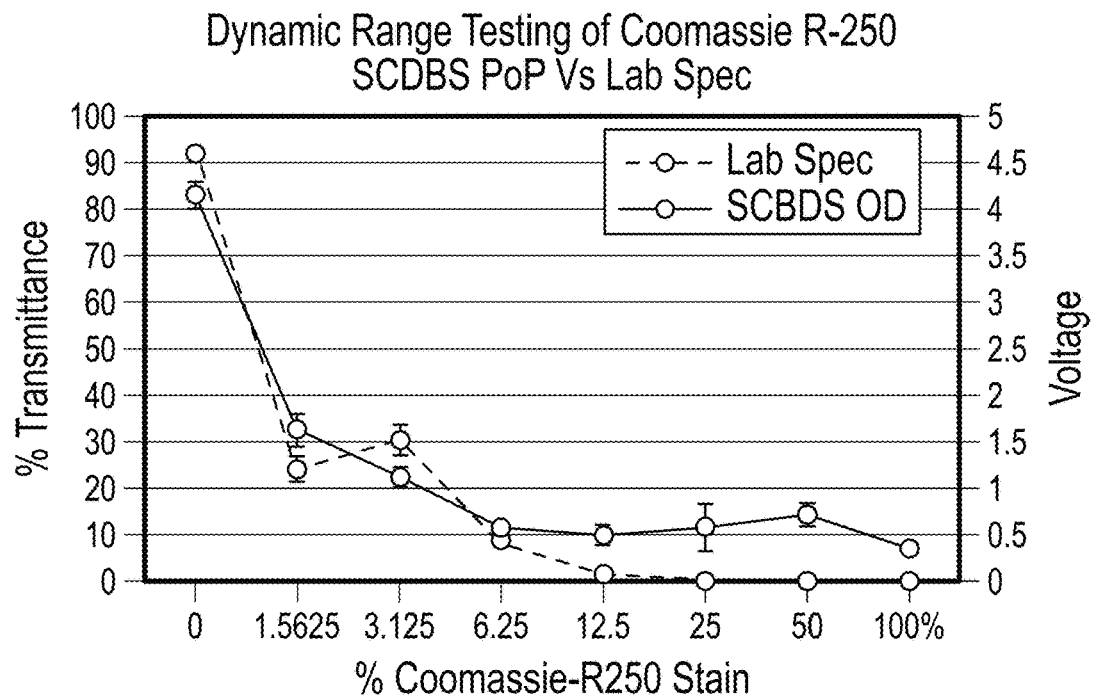
FIG. 97 shows the results from dynamic range testing of a miniature OD reader (SCDBS OD) compared to a lab spectrometer (Lab Spec) using Coomassie R-250. Primary vertical axis is % Transmittance (Lab Spec); Secondary vertical axis is voltage (SCDBS OD output). Comparative data outputs plotted against the dye concentration range (% dye in 0.9% Saline).

Results of pre-qualification dye testing (repeated in quintuplicate) using Coomassie R-250 are shown in FIG. 97. Within the context of the test matrix and test conditions, the miniature OD reader performed within similar specifications to the standard bench top spectrophotometer. Both the miniature OD reader and laboratory grade spectrophotometer had lower resolutions (and increased CV) as the concentration of the dye approached 100%. 0% dye (baseline data) for the miniature OD reader had an increased CV (3.48% vs. 0.25%) compared to the laboratory grade spectrophotometer. This is likely due to reduced light path and alignment issues as a result of the higher tolerances built into the 3D printed shroud to allow for large sample cuvettes.

Figure 98:
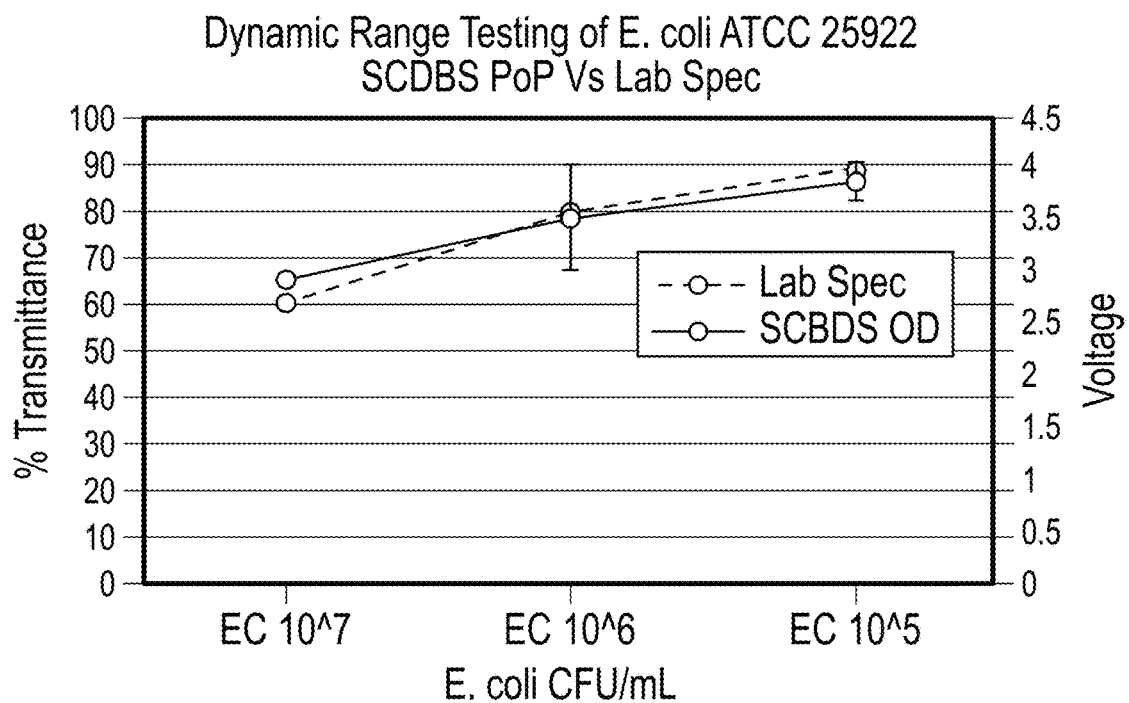
FIG. 98 shows the results from dynamic range testing of a miniature OD reader (SCDBS OD) compared to a lab spectrometer (Lab Spec) using bacterial samples of *E. coli* ATCC 25922. Primary vertical axis is % Transmittance (Lab Spec); Secondary vertical axis is voltage (SCDBS OD output). Comparative data outputs plotted against the bacterial concentration range (CFU/mL in 0.9% Saline).

Results of biological testing of the miniature OD reader with E. coli (repeated in triplicate) are shown in FIG. 98. Within the context of the test matrix and test conditions, the miniature OD reader performed within similar specifications to the standard bench top spectrophotometer it was compared against. Both the miniature OD reader and laboratory grade spectrophotometer had good resolutions within the dynamic range tested.

At a concentration of 0 CFU/mL (baseline data) the miniature OD reader had an increased CV (0.39% vs. 0.01%) compared to the laboratory grade spectrophotometer. This was also seen at $10^6$ CFU/mL. Again, this is likely due to reduced light path and alignment issues as a result of the higher tolerances built into the 3D printed shroud to allow for large sample cuvettes. Addition modifications and alignment of the miniature OD reader should further improve resolution of the device for use in an ingestible device.

While the miniature OD reader exhibited increased CV relative to the laboratory grade spectrophotometer, it was still capable of quantifying the concentration of bacteria in cell culture samples. Furthermore, the miniature OD reader can readily be used to detect the presence or absence of bacterial growth in a sample as a relative increase in the OD of the sample over time Example 6: Detection of Bacterial Counts in a Serial Dilution Using Small Sample Volumes Additional experiments were conducted to investigate the detection of bacterial counts in serial dilutions using small sample volumes. Use of a serial dilution may allow for the detection of a broader range of initial bacterial densities within the dynamic range of the OD assay. The use of a serial dilution may also allow for the prediction of initial bacterial density based on the binary detection of the presence or absence of bacterial growth within each serial dilution. This simplifies the desired property that the response of the miniature OD reader accurately reflect the concentration of bacteria within the sample chamber and merely involves the OD reader detect whether or not bacterial growth has occurred. Experiments were conducted to simulate serial dilutions made from a small initial sample volume (~5 µL) in a series of dilution chambers in an ingestible device each containing a pre-determined amount of growth media (~45 µL).

Materials and Methods Cultures of Gram-negative (Escherichia coli ATCC 25922) and Gram-positive (Staphylococcus aureus ATCC 29213) bacteria were generated in Tryptic Soy Broth (TSB) prepared according to manufacturer's directions. Bacterial cultures were diluted in Phosphate Buffered Saline (Gibco Ref 10010-023; Lot 1764980, pH 6.8) over a dynamic range of $10^8$ CFU/mL to 0 CFU/mL. The concentration of the bacterial cultures was confirmed by plating on Tryptic Soy Agar (TSA).

10×, 100×, 1,000× and 10,000× serial dilutions of 5 µL samples of E. coli and S. epidermidis at initial concentrations from 0 (negative control) to $10^8$ CFU/mL were then generated in 96 well microtiter plates in a 50 µL total volume of TSB. The plates were incubated for 16 hours at 35°±2° C. at 200 RPM before measuring the OD of each sample at 600 nm using a plate reader. The experiment was run in triplicate (3 Repeats).

Results

The following table provides the theoretical number of individual bacterial organisms within different sample volumes for initial samples having a bacterial concentration between $10^3$ CFU/ml and $10^8$ CFU/ml. For a sample having an initial bacterial concentration of $10^4$ CFU/ml, a 5 µl sample contains about 50 CFUs or bacteria. A 10× dilution of the initial 5 µl sample contains about 5 CFUs or bacteria. A 100× dilution of the initial 5 µl sample is unlikely to contain more than one bacteria (theoretically 0.5 CFUs). A 1,000× dilution is unlikely to contain any bacteria (theoretically 0.05 CFUs or bacteria). Diluted samples that are statistically unlikely to contain more than one bacteria are unlikely to shown bacterial growth and an associated increase in OD when incubated in growth media. By generating a dilution series such that at least one sample in the series contains one or more CFUs and at least one sample in the series does not contain any CFUs, it is possible to estimate the approximate concentration of bacteria in the initial sample by detecting the presence of absence of growth in the samples.

| Volume (ml) | (µl) | 1.00E+03 | 1.00E+04 | 1.00E+05 | 1.00E+06 | 1.00E+07 | 1.00E+08 |
|---|---|---|---|---|---|---|---|
| 0.001 | 1 | 1 | 10 | 100 | 1000 | 10000 | 100000 |
| 0.005 | 5 | 5* | 50* | 500* | 5000* | 50000* | 500000* |
| 0.01 | 10 | 10 | 100 | 1000 | 10000 | 100000 | 1000000 |
| 0.02 | 20 | 20 | 200 | 2000 | 20000 | 200000 | 2000000 |
| 0.03 | 30 | 30 | 300 | 3000 | 30000 | 300000 | 3000000 |

-continued

| Volume (ml) | (µl) | 1.00E+03 | 1.00E+04 | 1.00E+05 | 1.00E+06 | 1.00E+07 | 1.00E+08 |
|---|---|---|---|---|---|---|---|
| 0.05 | 50 | 50 | 500 | 5000 | 50000 | 500000 | 5000000 |
| 0.075 | 75 | 75 | 750 | 7500 | 75000 | 750000 | 7500000 |
| 0.1 | 100 | 100 | 1000 | 10000 | 100000 | 1000000 | 10000000 |

Theoretical numbers of bacteria within different sample volumes across a range of $10^3$ to $10^8$ CFU/ml. *=theoretical number of bacteria for a sample volume of 5 µl at various initial concentrations.

The following table shows the expected results of growth (cells with "X") or no growth (empty cells) for a dilution series based on an initial 5 µl sample with bacterial concentrations ranging from $10^8$ to 0 CFU/ml.

| Chamber | Media | Input | Dilution | $10^8$ | $10^7$ | $10^6$ | $10^5$ | $10^4$ | $10^3$ | $10^2$ | $10^1$ | 0 |
|---|---|---|---|---|---|---|---|---|---|---|---|---|
| 1 | 45 uL | 5 uL | 10X | X | X | X | X | X | X | X | | |
| 2 | 45 uL | 5 uL | 100x | X | X | X | X | X | X | | | |
| 3 | 45 uL | 5 uL | 1,000x | X | X | X | X | X | | | | |
| 4 | 45 uL | 5 uL | 10,000x | X | X | X | X | | | | | |

Expected pattern of growth/no growth for a dilution series of bacteria at initial sample concentrations of 0 to $10^8$ CFU/ml.

Empty cells represent no expected bacteria or growth; cells with "X" represent expected growth.

Figure 99:
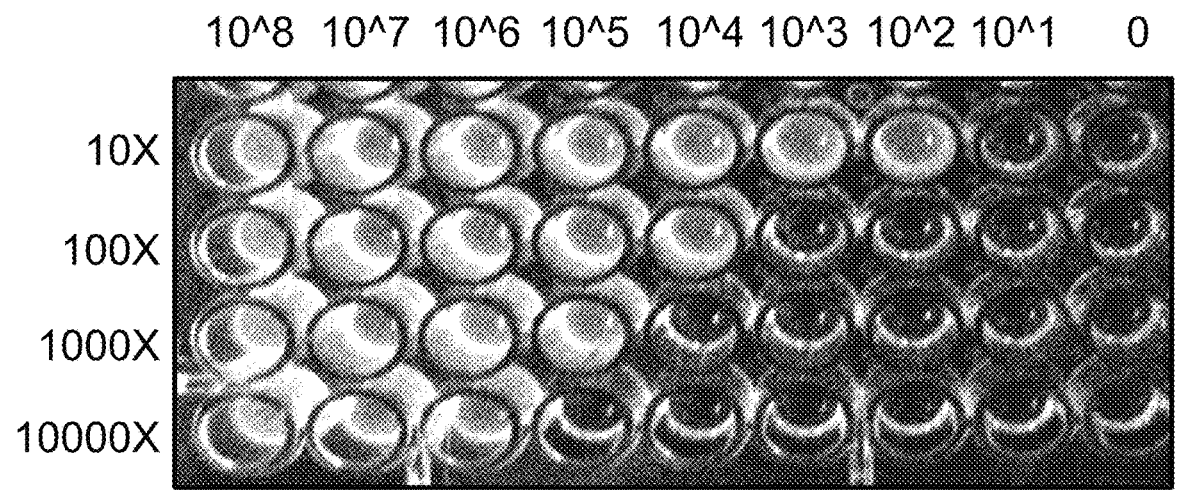
FIG. 99 shows the visual appearance of a plate incubated for 16 hours with serial dilutions of a 5 μl sample of bacterial culture of *S. aureus* ATCC 29213 having initial bacterial concentrations from 0 (control) to 10$^8$ CFU/ml. Wells without bacterial growth have a clear appearance and are clearly distinguished from wells with bacterial growth that have a cloudy appearance.

The following table shows the experimental results from incubating a dilutions series of *E. coli* or *S. aureus* cultures in a 96 well plate for 16 hours followed by measuring the OD of each well. The assay showed a binary response and clearly distinguished between wells that exhibited growth and a corresponding increase in OD and wells that did not exhibit any bacterial growth. The visual appearance of part of a 96 well plate containing serial dilutions of *S. aureus* after incubation for 16 hours is shown in FIG. 99. Wells that exhibited bacterial growth are readily distinguished by a cloudy appearance compared to wells that did not contain any CFU and did not exhibit any bacterial growth.

The OD for cells expected to contain more than 1 CFU did not necessarily increase in samples that contained a higher initial concentration of bacteria. Accordingly, shorter incubation times may also provide binary results with respect to determining the presence or absence of bacterial growth within dilution samples.

| | | Dil. | $10^8$ | $10^7$ | $10^6$ | $10^5$ | $10^4$ | $10^5$ | $10^2$ | $10^1$ | 0 |
|---|---|---|---|---|---|---|---|---|---|---|---|
| Rep 1 | | | | | | | | | | | |
| *E. coli* | | 10X | 0.16676* | 0.21836* | 0.19176* | 0.19726* | 0.08216* | 0.22276* | 0.21336* | 0.21126* | 0.00376 |
| | | 100x | 0.18846* | 0.24286* | 0.21806* | 0.23596* | 0.24406* | 0.24706* | 0.00256 | 0.00326 | 0.00216 |
| | | 1,000x | 0.24026* | 0.29146* | 0.23136* | 0.24576* | 0.26736* | 0.00296 | 0.00196 | 0.00306 | 0.00056 |
| | | 10,000x | 0.29436* | 0.28946* | 0.27426* | 0.28086* | 0.00136 | 0.00246 | 0.00106 | 0.00196 | 0.00046 |
| *S. aureus* | | 10X | 0.29706* | 0.27506* | 0.25366* | 0.16046* | 0.19186* | 0.20196* | 0.22216* | 0.00116 | 0.00086 |
| | | 100x | 0.16876* | 0.09296* | 0.15956* | 0.09466* | 0.14066* | 0.12216* | 0.00066 | 0.00136 | −0.00064 |
| | | 1,000x | 0.09536* | 0.07506* | 0.09106* | 0.09046* | 0.07576* | 6E−05 | 0.00026 | −0.00044 | −0.00034 |
| | | 10,000x | 0.09106* | 0.08776* | 0.09746* | 0.08326* | 0.01946 | 0.00066 | 0.00056 | 0.00046 | −0.00034 |
| Rep 2 | | | | | | | | | | | |
| *E. coli* | | 10X | 0.21968* | 0.19858* | 0.21688* | 0.22928* | 0.24658* | 0.22718* | 0.26508* | 0.00248 | 0.00388 |
| | | 100x | 0.22248* | 0.23578* | 0.24018* | 0.25708* | 0.26868* | 0.26378* | 0.00288 | 0.00428 | 0.00208 |
| | | 1,000x | 0.25848* | 0.28168* | 0.26978* | 0.26718* | 0.26718* | 0.00218 | 0.00118 | 0.00248 | 0.00068 |
| | | 10,000x | 0.32398* | 0.31988* | 0.27258* | 0.27938* | −0.00012 | 0.00258 | 0.00038 | 0.00198 | 0.00028 |
| *S. aureus* | | 10X | 0.32518* | 0.31738* | 0.26428* | 0.31508* | 0.20918* | 0.24698* | 0.29648* | 0.00028 | −2E−05 |
| | | 100x | 0.36178* | 0.32758* | 0.30898* | 0.26408* | 0.25748* | 0.00078 | 0.00038 | 0.00078 | −0.00062 |
| | | 1,000x | 0.33968* | 0.31208* | 0.26818* | 0.31538* | 0.28798* | 0.00018 | 0.00068 | 0.00068 | 0.00118 |
| | | 10,000x | 0.31388* | 0.27688* | 0.27578* | 0.28988* | 0.00058 | −2E−05 | −0.00022 | −0.00022 | −0.00082 |
| Rep 3 | | | | | | | | | | | |
| *E. coli* | | 10X | 0.27164* | 0.23844* | 0.22834* | 0.23974* | 0.25164* | 0.26804* | 0.25984* | 0.00224 | 0.00894 |
| | | 100x | 0.30464* | 0.29534* | 0.26794* | 0.27094* | 0.26474* | 0.29604* | 0.00214 | 0.00424 | 0.00294 |
| | | 1,000x | 0.27224* | 0.32274* | 0.29104* | 0.26684* | 0.00104 | 0.00164 | 0.00064 | 0.00344 | 0.00534 |
| | | 10,000x | 0.36004* | 0.34164* | 0.32164* | 0.34874* | 0.00114 | 0.00124 | 0.00594 | 0.00244 | 0.00094 |
| *S. aureus* | | 10X | 0.36064* | 0.34184* | 0.29064* | 0.31634* | 0.25164* | 0.26924* | −0.00016 | 0.00384 | −6E−05 |
| | | 100x | 0.38244* | 0.34314* | 0.34474* | 0.30034* | 0.17124* | 0.00324 | 0.00204 | 0.00504 | −0.00086 |
| | | 1,000x | 0.39924* | 0.35684* | 0.28994* | 0.28854* | 0.10174* | 0.00544 | 0.00154 | 0.00434 | 0.00034 |
| | | 10,000x | 0.33174* | 0.29154* | 0.34714* | 0.28974* | 4E−05 | 0.00054 | 0.00074 | 0.00324 | −0.00036 |

OD results following a 16 hour incubation for serial dilutions of different initial concentrations of *E. coli* and *S. aureus*.

Values with asterisks (*) are representative of bacterial growth, and values without asterisks are not.

Dil. = Dilutioin.

LOCI Examples

Example 1. TNFα Detection and Quantification in Samples Using Various Concentrations of the Biotinylated Antibody, Acceptor Beads, and Donor Beads Assay components, including Biotinylated Antibody, Donor Beads and Acceptor Beads, were combined in a test matrix to optimize utilization in a homogenous test environment (i.e. on a sample pad within an ingestible device, such as an ingestible smart capsule). Concentrations of the Biotinylated Antibody, Donor Beads and Acceptor Beads were varied in a test matrix and assay sensitivity was compared across the test matrix.

Test I: Varying Concentrations of the Acceptor Beads and Donor Beads.

Experimental Materials:

AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidign (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% $NaN_3$, pH 7.4, AlphaLISA Immunoassay Buffer (10×) (Cat #AL000C). Standard analyte used for standard curves and analyte detection was lyophilized pTNFα (Cat #AL548S) (0.3 μg) was reconstituted in 100 milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 384-well microplates (white OptiPlate-384 (Cat #6007290) were supplied by PerkinElmer (Boston, Mass., USA). All data were analyzed using GEN 5 Software version 3.02.1, BioTek U.S. (Winooski, Vt.).

Apparatus:

The AlphaLISA signal was read by a Cytation 5 spectrophotometer (S/N 1609299) from BioTek U.S. (Winooski, Vt.). GEN 5 Software version 3.02.1 utilizing an AphaCube 384 (p/n β25001). Apha Endpoint reads with a gain of 200, Excitation time 80 msec, delay after excitation of 120 msec, integration time of 160 msec and read height of 11.5 mm.

Preparation of Standards and Samples:

A standard curve of pTNFα was prepared according to the kit instructions with a range of 300,000 pg/mL in 5 μL to 1 pg/mL in 5 μL. Four buffer only samples were loaded and treated as blanks for zero analyte control reads. The standard curve and samples were loaded in white 384 well microtitre plates.

Step 1: Acceptor Beads
Once the standard dilutions and samples (10, 3, 1 pg/mL in 5 μL) were added to the plate, the acceptor beads were added to the appropriate wells. Either 2 or 1 μL of Acceptor beads was used.
An adhesive seal was placed on top of the plate to prevent cross contamination during incubation.
This was wrapped in tin foil, and placed in a 37° C. incubator for 2 hours.

Step 2: Biotinylated Antibody
The plate was removed from the incubator, and the plate seal was removed and discarded.
Using a multichannel pipette add 2.5 μL of Biotinylated antibody to each well containing solution.
An adhesive seal was placed on top of the plate.
This was wrapped in tin foil, and placed in a 37° C. incubator for 1 hour.

Figure 100:
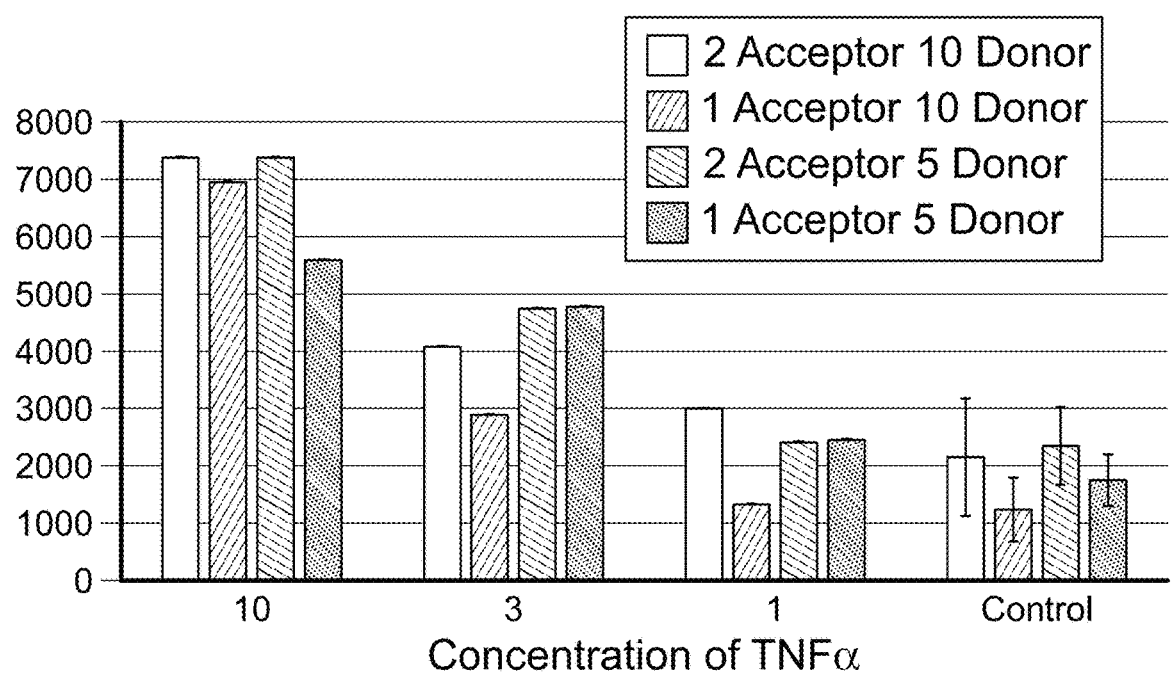
FIG. 100 shows results for detection of TNFα with varying concentrations of Acceptor and Donor Beads. This test matrix was composed of varying concentrations of both Donor and Acceptor Beads with a constant concentration of Biotinylated Antibody. Each varying bead concentration was tested against three different TNFα concentrations and compared against a control. Retest of this matrix narrowed down which combination of Donor/Acceptor Beads resulted in the best assay data.

Step 3: Donor Beads (Performed in the Dark)
The plate was removed from the incubator, and the plate seal was removed and discarded.
Using a multichannel pipette add either 10 or 5 uL of SA-Donor Beads to each well containing solution.
An adhesive seal was placed on top of the plate.
This was wrapped in tin foil, and placed in a 37° C. incubator for 30 minutes
Immediately after 30 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve. The results of this test are summarized in FIG. 100.

Test II: Varying Concentrations of the Acceptor Beads and Donor Beads.

Experimental Materials:

AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidign (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% $NaN_3$, pH 7.4, AlphaLISA Immunoassay Buffer (10×) (Cat #AL000C). Standard analyte used for standard curves and analyte detection was lyophilized pTNFα (Cat #AL548S) (0.3 μg) was reconstituted in 100 milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 384-well microplates (white OptiPlate-384 (Cat #6007290) were supplied by PerkinElmer (Boston, Mass., USA). All data were analyzed using GEN 5 Software version 3.02.1, BioTek U.S. (Winooski, Vt.).

Apparatus:

The AlphaLISA signal was read by a Cytation 5 spectrophotometer (S/N 1609299) from BioTek U.S. (Winooski, Vt.) using GEN 5 Software version 3.02.1 utilizing an AphaCube 384 (p/n β25001). Apha Endpoint reads with a gain of 200, Excitation time 80 msec, delay after excitation of 120 msec, integration time of 160 msec and read height of 11.5 mm.

Preparation of Standards and Samples:

A standard curve of pTNFα was prepared according to the kit instructions with a range of 300,000 pg/mL in 5 μL to 1 pg/mL in 5 μL. Four buffer only samples were loaded and treated as blanks for zero analyte control reads. The standard curve and samples were loaded in white 384 well microtitre plates.

Step 1: Acceptor Beads
Once the standard dilutions and samples (10, 3, 1 pg/mL in 5 μL) were added to the plate, the acceptor beads were added to the appropriate wells. Either 2 or 1 μL of Acceptor beads was used.
An adhesive seal was placed on top of the plate to prevent cross contamination during incubation.
This was wrapped in tin foil, and placed in a 37° C. incubator for 2 hours.

Figure 101:
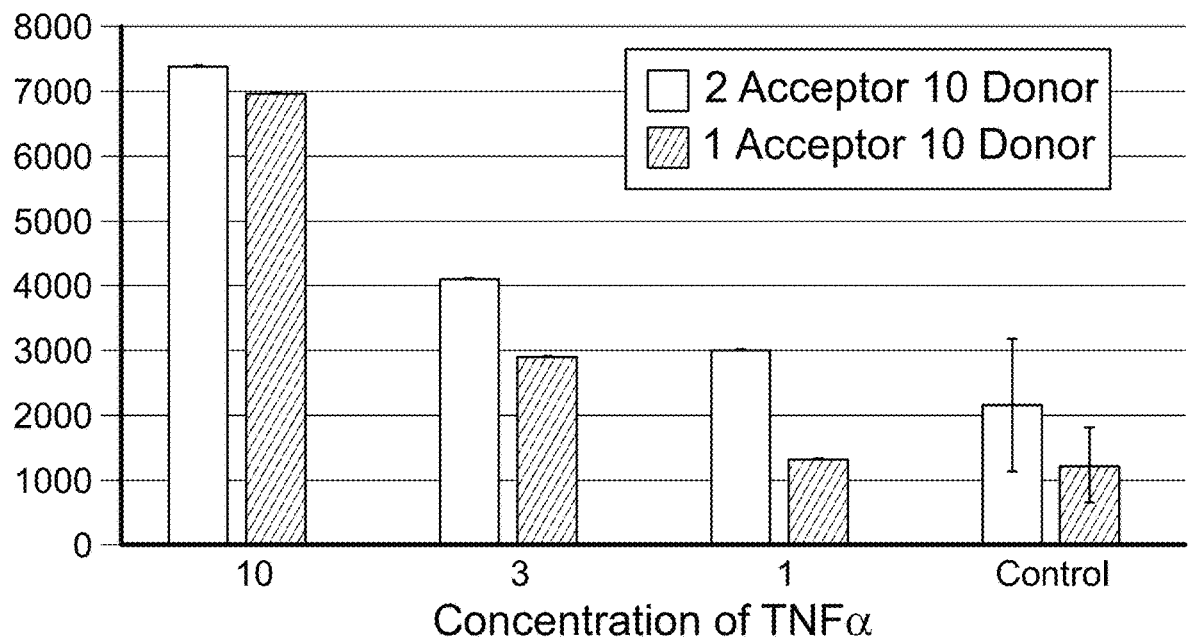
FIG. 101 shows results for detection of TNFα with varying concentrations of Acceptor and Donor Beads. This test matrix was composed of varying concentrations of both Donor and Acceptor Beads being tested in a 5:1 and 10:1 ratio, with a constant concentration of Biotinylated Antibody. Each varying concentration was tested against three different TNFα concentrations and compared against a control. Retest of this matrix narrowed down which ratio of Donor: Acceptor beads resulted in the best assay data.
Figure 102:
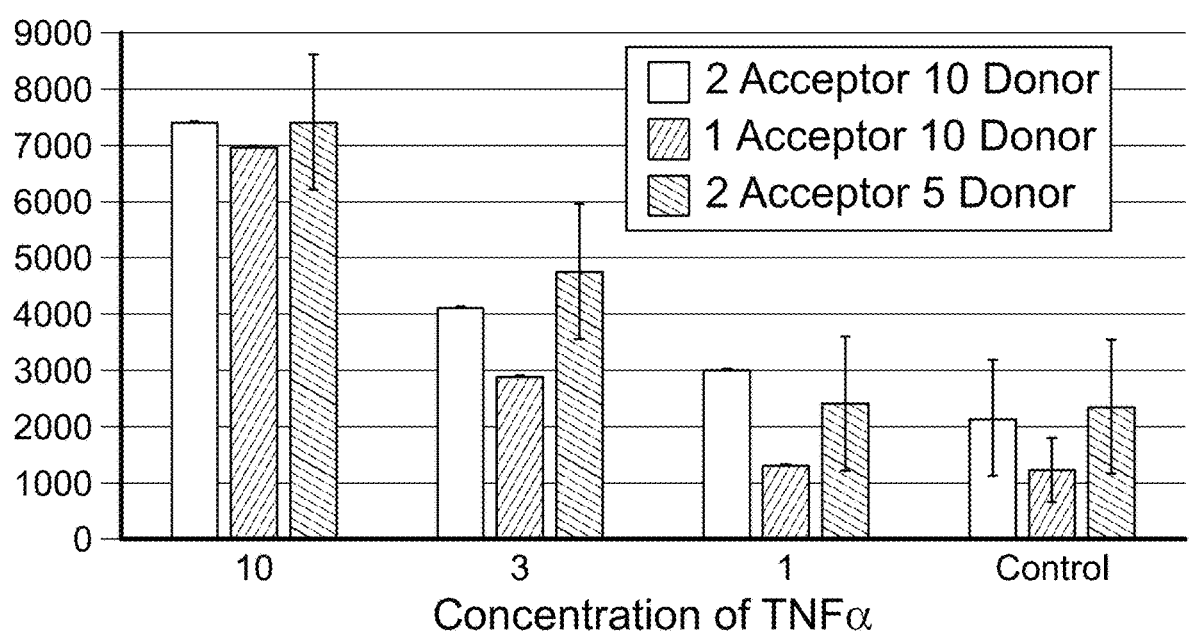
FIG. 102 shows results for detection of TNFα with varying concentrations of biotinylated antibody. This matrix tested an integrated test method (no intermediate incubations) against various concentrations of Donor: Acceptor Beads. Each varying concentration was tested against three different concentrations of TNFα and compared against a control. The donor and acceptor beads concentration may be varied, e.g., the donor bead concentration is 10 and 5 ugs/ml and the acceptor bead concentration is 1 and 2 ugs/ml, respectively.

Step 2: Biotinylated Antibody
  The plate was removed from the incubator, and the plate seal was removed and discarded.
  Using a multichannel pipette add 2.5 µL of Biotinylated antibody to each well containing solution.
  An adhesive seal was placed on top of the plate.
  This was wrapped in tin foil, and placed in a 37° C. incubator for 1 hour.
Step 3: Donor Beads (Performed in the Dark)
  The plate was removed from the incubator, and the plate seal was removed and discarded.
  Using a multichannel pipette add 10 µL of SA-Donor Beads to each well containing solution.
  An adhesive seal was placed on top of the plate.
  This was wrapped in tin foil, and placed in a 37° C. incubator for 30 minutes.
  Immediately after 30 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve. The results of this test are summarized in FIG. 101.
Test III: Varying Concentrations of the Biotinylated Antibody
Experimental Materials:
  AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidign (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% $NaN_3$, pH 7.4, AlphaLISA Immunoassay Buffer (10×) (Cat #AL000C). Standard analyte used for standard curves and analyte detection was lyophilized pTNFα (Cat #AL548S) (0.3 µg) was reconstituted in 100 µL milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 384-well microplates (white OptiPlate-384 (Cat #6007290) were supplied by PerkinElmer (Boston, Mass., USA). All data were analyzed using GEN 5 Software version 3.02.1, BioTek U.S. (Winooski, Vt.).
Apparatus:
  The AlphaLISA signal was read by a Cytation 5 spectrophotometer (S/N 1609299) from BioTek U.S. (Winooski, Vt.) using GEN 5 Software version 3.02.1 utilizing an AphaCube 384 (p/n β25001). Apha Endpoint reads with a gain of 200, Excitation time 80 msec, delay after excitation of 120 msec, integration time of 160 msec and read height of 11.5 mm.
Preparation of Standards and Samples:
  A standard curve of pTNFα was prepared according to the kit instructions with a range of 300,000 pg/mL in 5 µL to 1 pg/mL in 5 µL. Four buffer only samples were loaded and treated as blanks for zero analyte control reads. The standard curve and samples were loaded in white 384 well microtitre plates.
Step 1: Acceptor Beads
  Once the standard dilutions and samples (10, 3, 1 pg/mL in 5 µL) were added to the plate, the acceptor beads were added to the appropriate wells. Either 2 or 1 µL of Acceptor beads was used.
Step 2: Biotinylated Antibody
  Using a multichannel pipette add 2.5 µL of Biotinylated antibody and hydroxyl propyl cyclodextrin to each well containing solution.
Step 3: Donor Beads (Performed in the Dark)
  Using a multichannel pipette add either 5 or 10µL of SA-Donor Beads coated with HABA to each well containing solution.
  An adhesive seal was placed on top of the plate.
  This was wrapped in tin foil, and placed in a 37° C. incubator for 30 minutes.
  Immediately after 30 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve. The results of this test are summarized in FIG. 102.

Example 2. TNFα Detection and Quantification in Samples Using Various Concentrations of Cyclodextrin The assay components (used in a homogenous assay fashion in determined concentrations from the homogenous assay development tests) were combined with varying concentrations of cyclodextrin to mitigate the effects of bile acids that may be present in patient samples. The assay was conducted over a dynamic range of cyclodextirn and the sensitivity was compared across the test matrix.
Experimental Materials:
  AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidign (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% $NaN_3$, pH 7.4, AlphaLISA Immunoassay Buffer (10×) (Cat #AL000C). Standard analyte used for standard curves and analyte detection was lyophilized pTNFα (Cat #AL548S) (0.3 µg) was reconstituted in 100 milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 384-well microplates (white OptiPlate-384 (Cat #6007290) were supplied by PerkinElmer (Boston, Mass., USA). All data were analyzed using GEN 5 Software version 3.02.1, BioTek U.S. (Winooski, Vt.).
Apparatus:
  The AlphaLISA signal was read by a Cytation 5 spectrophotometer (S/N 1609299) rom BioTek U.S. (Winooski, Vt.) using GEN 5 Software version 3.02.1 utilizing an AphaCube 384 (p/n β25001). Apha Endpoint reads with a gain of 200, Excitation time 80 msec, delay after excitation of 120 msec, integration time of 160 msec and read height of 11.5 mm.
Preparation of Standards and Samples:
  2 Hydroxypropyl β-Cyclodextrin (P/N C0926-5G) from Sigma Aldrich (St. Louis, Mo.) was mixed over a dynamic range of 1000 mg/mL to 60 mg/mL in AlphaLISA Immunoassay Buffer (10×) (Cat #AL000C) for all integration experiments.
  A standard curve of pTNFα was prepared according to the kit instructions with a range of 300,000 pg/mL in 5 µL to 1 pg/mL in 5 μL. Four buffer only samples were loaded and treated as blanks for zero analyte control reads. The standard curve and samples were loaded in white 384 well microtitre plates.

Figure 103A:
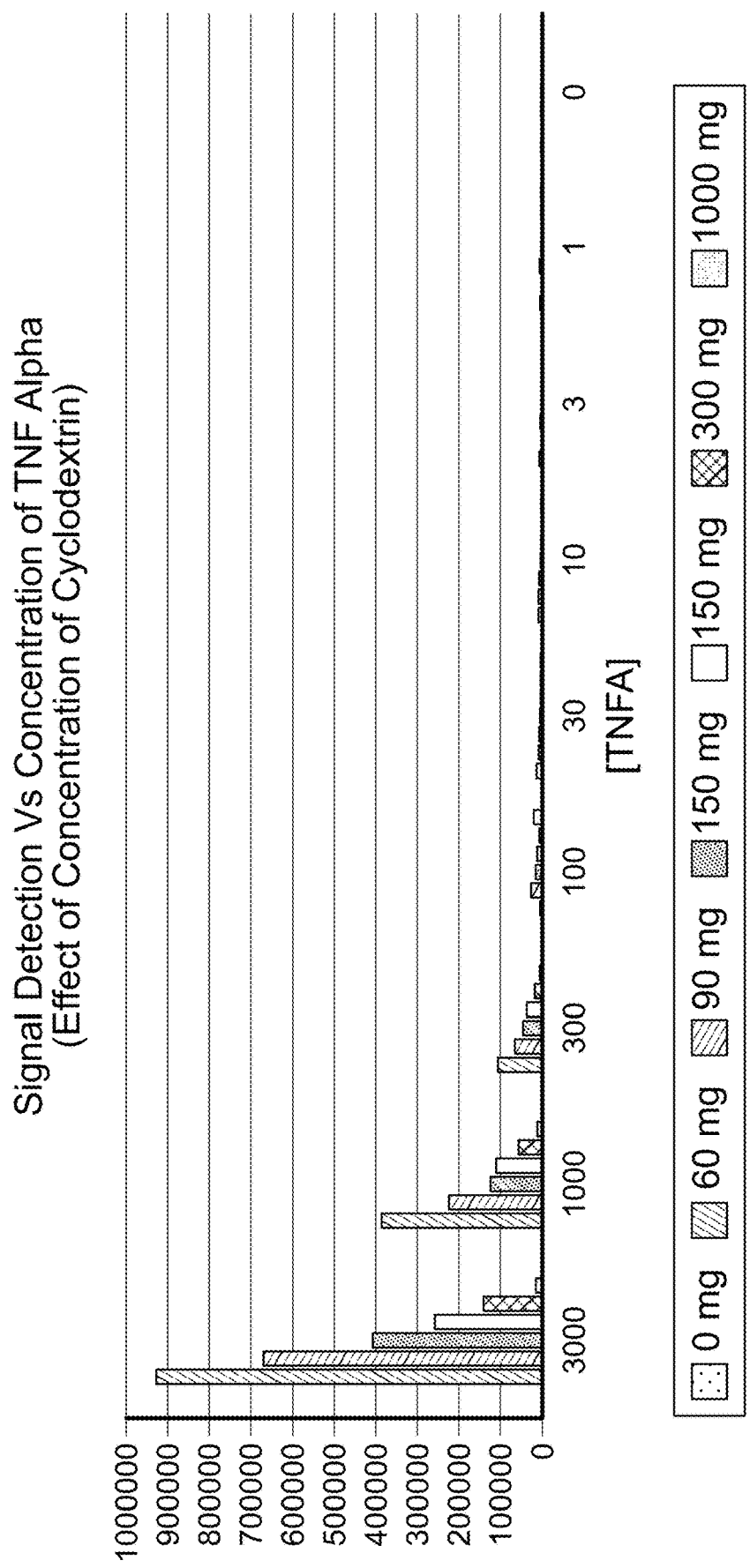
FIG. 103A shows the upper range of TNFα concentrations with varying cyclodextrin addition. Hydroxy propyl cyclodextrin is used to overcome sample interference, especially bile acid interferences; bile acids bind to hydroxy propyl cyclodextrin.
Figure 103B:
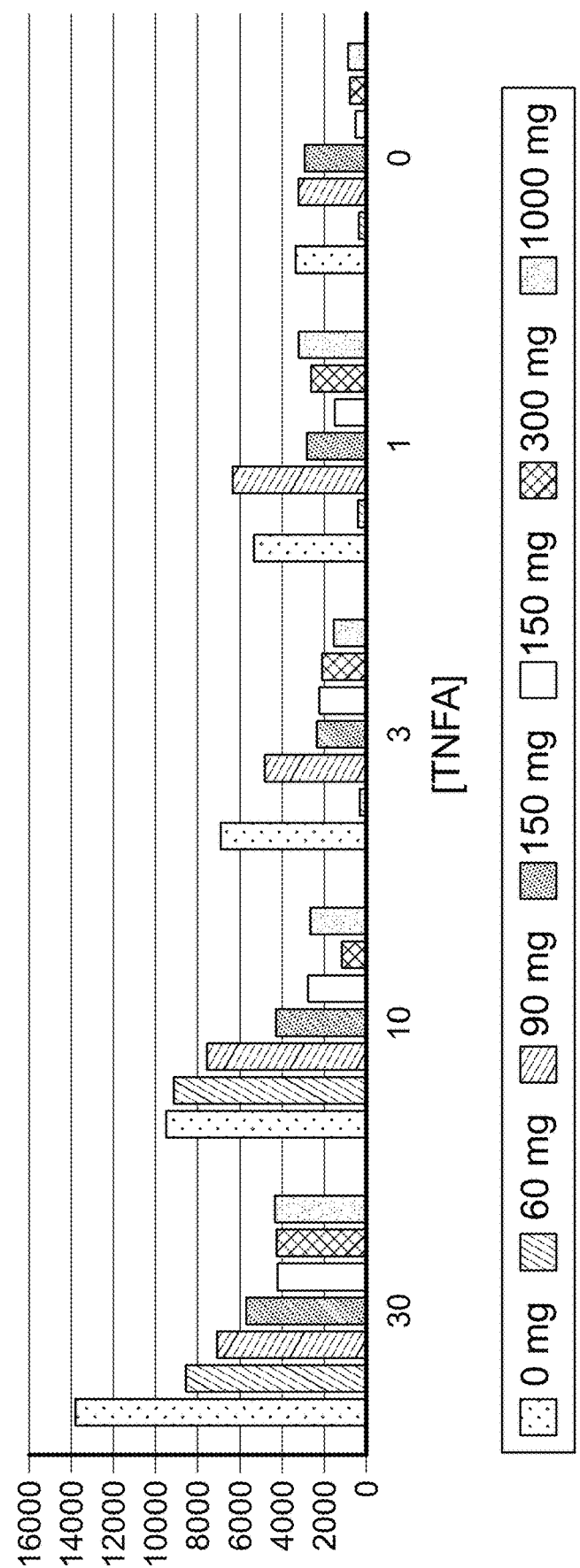
FIG. 103B shows the lower range of TNFα concentrations with varying cyclodextrin concentrations.

Step 1: Acceptor Beads
  Once the standard dilutions in various concentrations of cyclodextrin were added to the plate, the acceptor beads were added to the appropriate wells. 2 μL of Acceptor beads was used.
Step 2: Biotinylated Antibody
  Using a multichannel pipette add 2.5 μL of Biotinylated antibody to each well containing solution.
Step 3: Donor Beads (Performed in the Dark)
  Using a multichannel pipette add 10 μL of SA-Donor Beads to each well containing solution.
  An adhesive seal was placed on top of the plate.
  This was wrapped in tin foil, and placed in a 37° C. incubator for 30 minutes.
  Immediately after 30 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve. The results of this test are summarized in FIGS. 103A and 103B.

Example 3. TNFα Detection and Quantification in Samples on a Sample Pad

In order to integrate the assay into an ingestible device such as an ingestible smart capsule, in some embodiments, the assay may be integrated onto an absorptive sample pad (e.g., to allow wicking of the sample into the capsule). The assay components were homogenously combined onto various sponge samples. The assay was conducted over a dynamic range of TNFα and the sensitivity was compared across the test matrix.

Experimental Materials:
  AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidign (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% NaN$_3$, pH 7.4, AlphaLISA Immunoassay Buffer (10×) (Cat #AL000C). Standard analyte used for standard curves and analyte detection was lyophilized pTNFα (Cat #AL548S) (0.3 μg) was reconstituted in 100 milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 96-well microplates (white OptiPlate-96 were supplied by PerkinElmer (Boston, Mass., USA). All data were analyzed using GEN 5 Software version 3.02.1, BioTek U.S. (Winooski, Vt.).

Apparatus:
  The AlphaLISA signal was read by a Cytation 5 spectrophotometer (SN 1609299) from BioTek U.S. (Winooski, Vt.). GEN 5 Software version 3.02.1 utilizing an AphaCube 384 (p/n β25001). Apha Endpoint reads with a gain of 200, Excitation time 80 msec, delay after excitation of 120 msec, integration time of 160 msec and read height of 11.5 mm.

Figure 104:
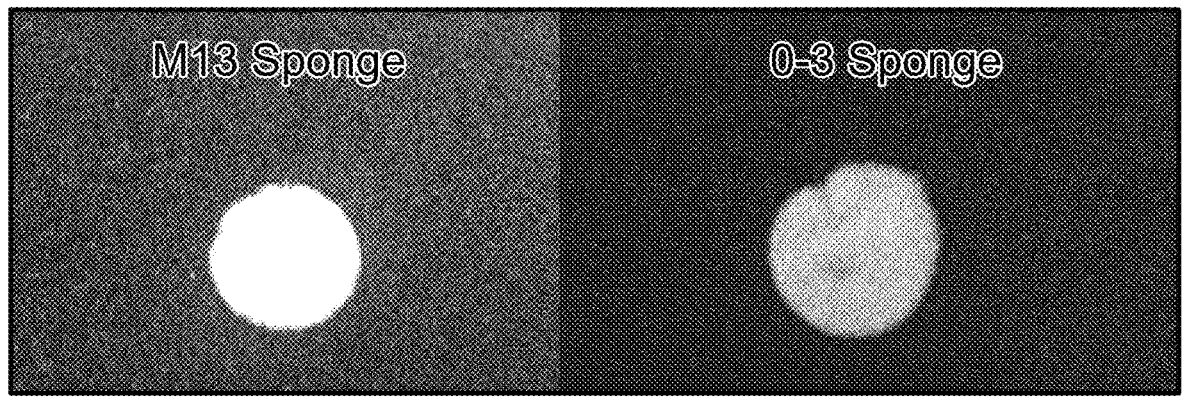
FIG. 104 shows samples of absorptive sponge material (M13: Ahlstrom (6613H)) and (O3: Whatman (Grade F/F) (29009411) cut to fit the 96 well microtitre plate configuration using a whole punch and trimmed with sterile scissors.

Preparation of Standards and Samples:
  Samples of sponge material (M13: Ahlstrom (6613H)) and (03: Whatman (Grade F/F) (29009411) were cut to fit the 96 well microtitire plate configuration using a whole punch and trimmed with sterile scissors. See FIG. 104.
  A standard curve of pTNFα was prepared according to the kit instructions with a range of 100,000 pg/mL in 5 μL to 1 pg/mL in 5 μL. Four buffer only samples were loaded and treated as blanks for zero analyte control reads. The standard curve and samples were loaded in white 96 well microtitire plates and kept protected from light until ready for use.

Figure 105:
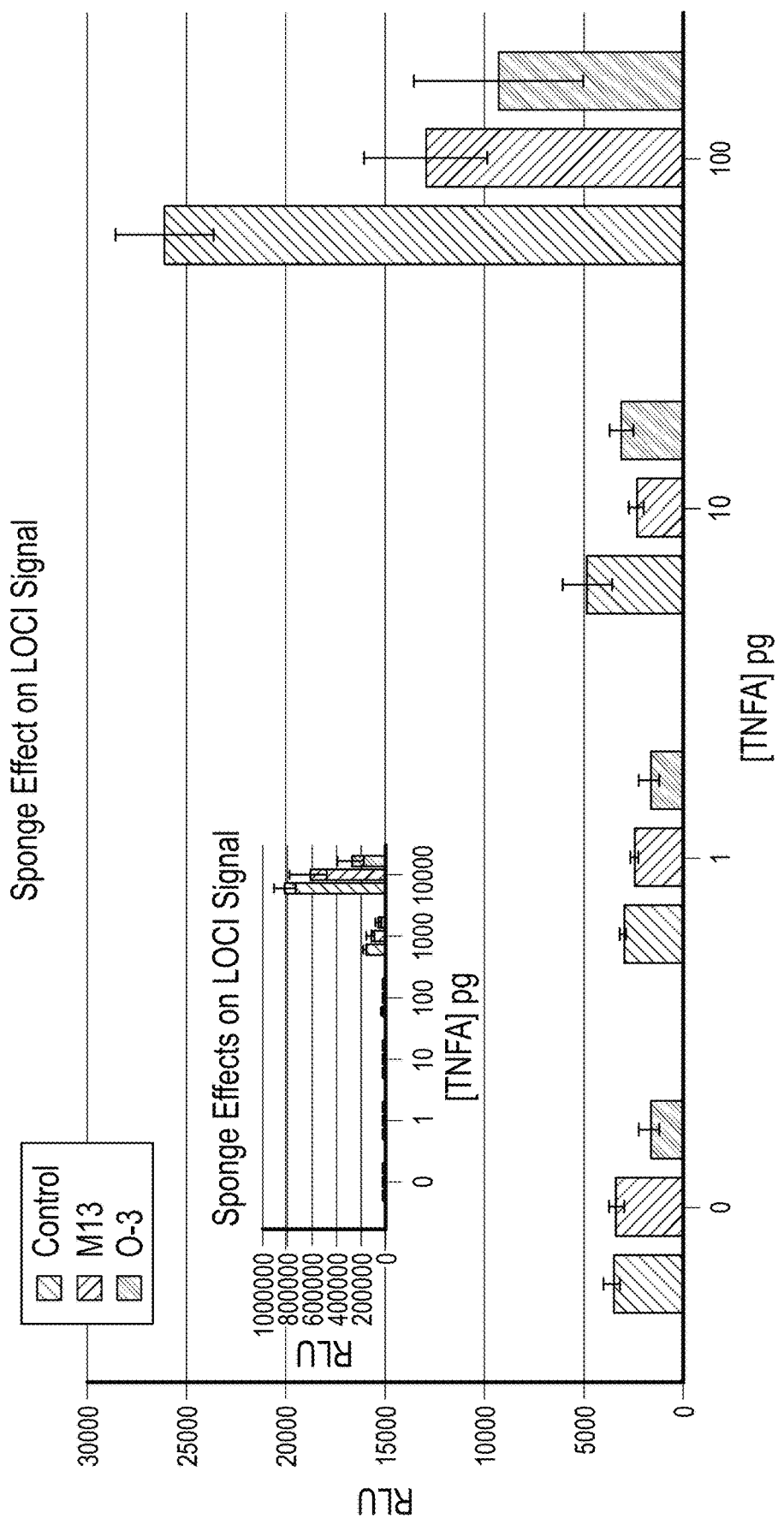
FIG. 105 shows results for detection of TNFα in samples on an absorptive sample pad. This test matrix consisted of running the optimized bead concentration on a sponge, with an n=3. The limit of detection for this assay is shown to be around 10 pg/ml for 03 and 100 pgs/ml for M3. Inset graph showing higher ranges of TNFα concentrations.

Sponge Preparation: Step 1: Acceptor Beads
  Sponges or no sponge samples were identified in the test plate.
  Sponge types were added to the identified wells or left blank.
  the acceptor beads were added to the appropriate wells. 2 μL of Acceptor beads was used.
Step 2: Biotinylated Antibody
  Using a multichannel pipette add 2.5 μL of Biotinylated antibody to each well containing solution.
Step 3: Donor Beads (Performed in the Dark)
  Using a multichannel pipette add 10 μL of SA-Donor Beads to each well containing solutions.
  NOTE: at this point wells either contain sponges or blank wells with the homogeneous AlphaLISA reagents.
  5 μL of pTNFα standard was added to the sponge or control wells.
  An adhesive seal was placed on top of the plate.
  This was wrapped in tin foil, and placed in a 37° C. incubator for 30 minutes.
  Immediately after 30 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve. The results of this test are summarized in FIG. 105.

Example 4. Continuous TNFα Detection and Quantification

In some embodiments, the assay may be exposed to multiple samples of analyte (i.e. adiluminab, TNFα etc.) during the transit of the ingestible device (e.g., an ingestible smart capsule) in vivo to investigate localization of analytes of interest and targeted drug deployment. The assay components were homogenously combined. The assay was conducted over a dynamic range of TNFα with repeat addition of analyte into the same sample well over time. The sensitivity was compared over time to evaluate this mode of sampling.

Experimental Materials:
  AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidign (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% NaN$_3$, pH 7.4, AlphaLISA Immunoassay Buffer (10×) (Cat #AL000C). Standard analyte used for standard curves and analyte detection was lyophilized pTNFα (Cat #AL548S) (0.3 μg) was reconstituted in 100 milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 384-well microplates (white OptiPlate-384 (Cat #6007290) were supplied by PerkinElmer (Boston, Mass., USA). All data were analyzed using GEN 5 Software version 3.02.1, BioTek U.S. (Winooski, Vt.).

Apparatus:

The AlphaLISA signal was read by a Cytation 5 spectrophotometer (S/N 1609299) from BioTek U.S. (Winooski, Vt.). GEN 5 Software version 3.02.1 utilizing an AphaCube 384 (p/n β25001). Apha Endpoint reads with a gain of 200, Excitation time 80 msec, delay after excitation of 120 msec, integration time of 160 msec and read height of 11.5 mm.

Preparation of Standards and Samples:

A standard preparation of pTNFα was prepared according to the kit instructions with a range of 5000 pg/mL in 5 μL.

Step 1: Acceptor Beads

The plate was set up to with 5 μL of control 5000 pg/mL in 5 μL of pTNFα or TEST: uL of 5000 pg/mL in 5 μL of pTNFα that would have an additional 5000 pg/mL in 5 μL of pTNFα continually added over time.

Once the standard dilutions were added to the plate, the acceptor beads were added to the appropriate wells. 2 μL of Acceptor beads was used.

Step 2: Biotinylated Antibody

Using a multichannel pipette add 2.5 μL of Biotinylated antibody to each well containing solution.

Step 3: Donor Beads (Performed in the Dark)

Using a multichannel pipette add 10 μL of SA-Donor Beads to each well containing solution.

An adhesive seal was placed on top of the plate.

This was wrapped in tin foil, and placed in a 37° C. incubator for 15 minutes.

Immediately after 15 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve.

Step 4: Repeat Testing

Using a multichannel pipette add 5 μL of buffer was added to the control or 5 μL of control 5000 pg/mL in 5 μL of pTNFα was added to the test.

An adhesive seal was placed on top of the plate.

This was wrapped in tin foil, and placed in a 37° C. incubator for 15 minutes.

The plate was re-read.

This was repeated over the course of 6 hours.

Figure 106A:
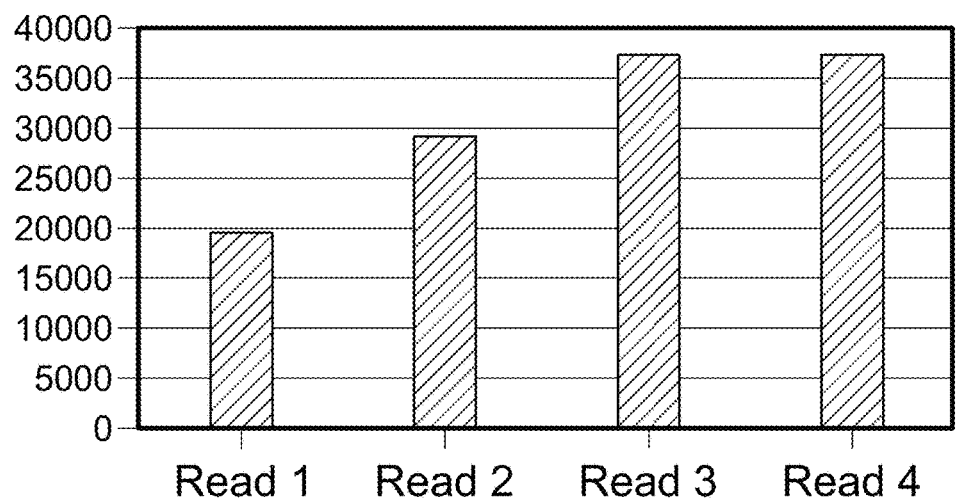
FIG. 106A shows the results of repeat TNFα detection in the same assay mixture over time. TNFα was added to the well containing the assay mixture after 15 minute incubations.
Figure 106B:
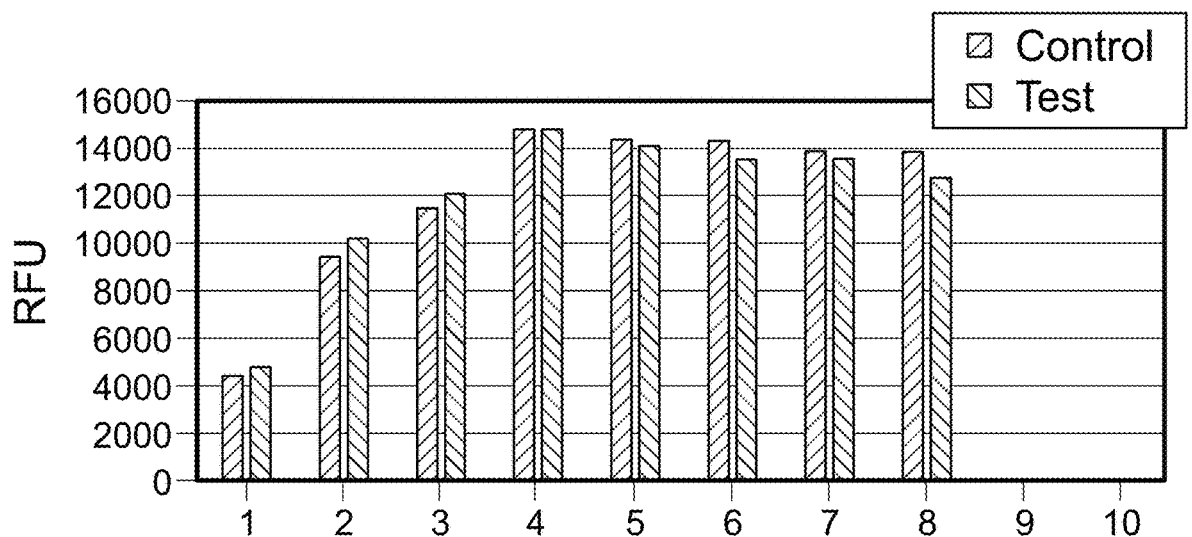
FIG. 106B shows the results of repeat TNFα detection in the same assay mixture over time. The test matrices consisted of exemplary bead concentrations (2 μL Acceptor Beads, 2.5 μL Biotinylated Antibody and 10 μL Donor Beads) tested in wells, with continuous reads on a lower instrument setting. Every 15 minutes, 5 μL of TNFα was added to the well, and the test well was re-read.

The test results are summarized in FIGS. 106A and 106B.

Example 5. TNFα Detection and Quantification on Various Sample Pads

In some embodiments, the assay may be formulated with cyclodextrin (to mitigate bile acid effects in the samples) and to be integrated onto an absorptive assay sampling pad. The following sets of experiments evaluate this combination. The assay was prepared with various concentrations of cyclodextrin on a selection of assay sample pads. Testing was conducted over a dynamic range of TNFα. The sensitivity was compared over time.

Experimental Materials:

AlphaLISA TNFα (porcine) detection kit product number AL548 Hv/C/F obtained from PerkinElmer (Boston, Mass., USA) was used for experimental work. Specifically the following reagent used consisted of the following: AlphaLISA Anti-p TNFα acceptor beads (5 mg/mL) stored in PBS, 0.05% Proclin-300, pH 7.2; Streptavidin (SA)-coated donor beads (5 mg/mL) stored in 25 mM HEPES, 100 mM NaCl, 0.05% Proclin-300, pH 7.4; Biotinylated Antibody Anti-p TNFα (500 nM) stored in PBS, 0.1% Tween-20, 0.05% NaN$_3$, pH 7.4, AlphaLISA Immunoassay Buffer (10×) (Cat #AL000C). Standard analyte used for standard curves and analyte detection was lyophilized pTNFα (Cat #AL548S) (0.3 μg) was reconstituted in 100 milli-Q grade water and was used with 60 minutes or aliquoted into screw-capped polypropylene vials and stored at −20° C. until desired. Other chemicals and reagents used were of analytical grade and from Sigma Aldrich (St. Louis, Mo.). White 96-well microplates (white OptiPlate-96 were supplied by PerkinElmer (Boston, Mass., USA). All data were analyzed using GEN 5 Software version 3.02.1, BioTek U.S. (Winooski, Vt.).

Apparatus:

The AlphaLISA signal was read by a Cytation 5 spectrophotometer (S/N 1609299) from BioTek U.S. (Winooski, Vt.). GEN 5 Software version 3.02.1 utilizing an AphaCube 384 (p/n 1325001). Apha Endpoint reads with a gain of 200, Excitation time 80 msec, delay after excitation of 120 msec, integration time of 160 msec and read height of 11.5 mm.

Preparation of Standards and Samples:

2 Hydroxypropyl β-Cyclodextrin (P/N C0926-5G) from Sigma Aldrich (St. Louis, Mo.) was mixed at either 50, 25 or 0 mg/mL in AlphaLISA Immunoassay Buffer (10×) (Cat #AL000C) for all integration experiments.

Samples of sponge material (M13: Ahlstrom (6613H)) and (O3: Whatman (Grade F/F) (29009411) were cut to fit the 96 well microtitre plate configuration using a whole punch and trimmed with sterile scissors. See, e.g., FIG. 104.

A standard curve of pTNFα was prepared according to the kit instructions with a range of 100,000 pg/mL in 5 μL to 1 pg/mL in 5 μL. Four buffer only samples were loaded and treated as blanks for zero analyte control reads. The standard curve and samples were loaded in white 96 well microtitre plates and kept protected from light until ready for use.

Sponge Preparation: Step 1: Acceptor Beads

Sponges or no sponge samples were identified in the test plate.

Sponge types were added to the identified wells or left blank.

The acceptor beads were added to the appropriate wells. 2 μL of Acceptor beads was used.

Step 2: Biotinylated Antibody

Using a multichannel pipette add 2.5 μL of Biotinylated antibody to each well containing solution.

Step 3: Donor Beads (Performed in the Dark)

Using a multichannel pipette add 10 μL of SA-Donor Beads to each well containing solutions.

NOTE: at this point wells either contain sponges or blank wells with the homogeneous AlphaLISA reagents.

5 μL of pTNFα standard was added to the sponge or control wells.

An adhesive seal was placed on top of the plate.

This was wrapped in tin foil, and placed in a 37° C. incubator for 30 minutes

Figure 107A:
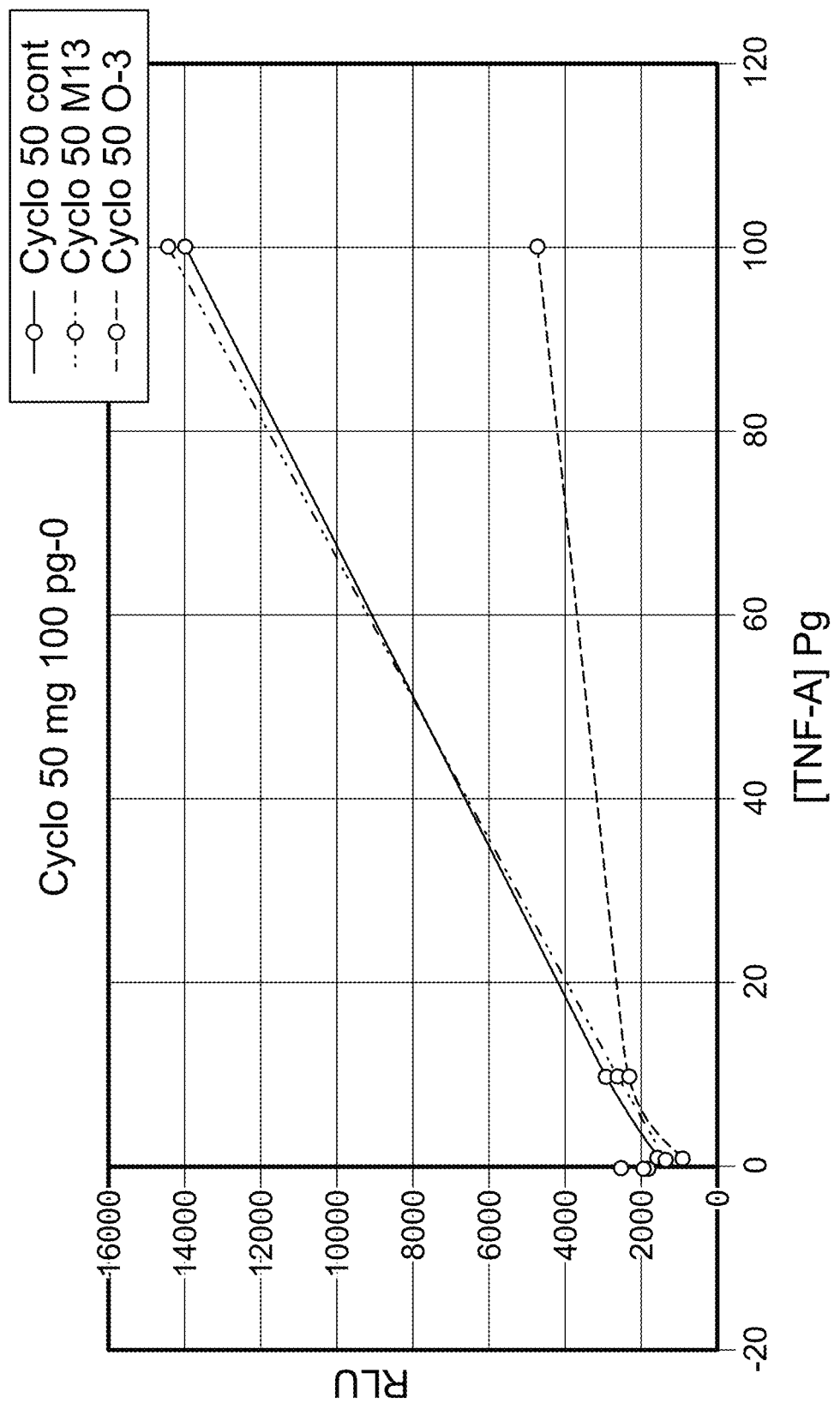
FIG. 107A shows results for TNFα detection and quantification on absorptive sample pads, where the assay was prepared with 50 mg of cyclodextrin.
Figure 107B:
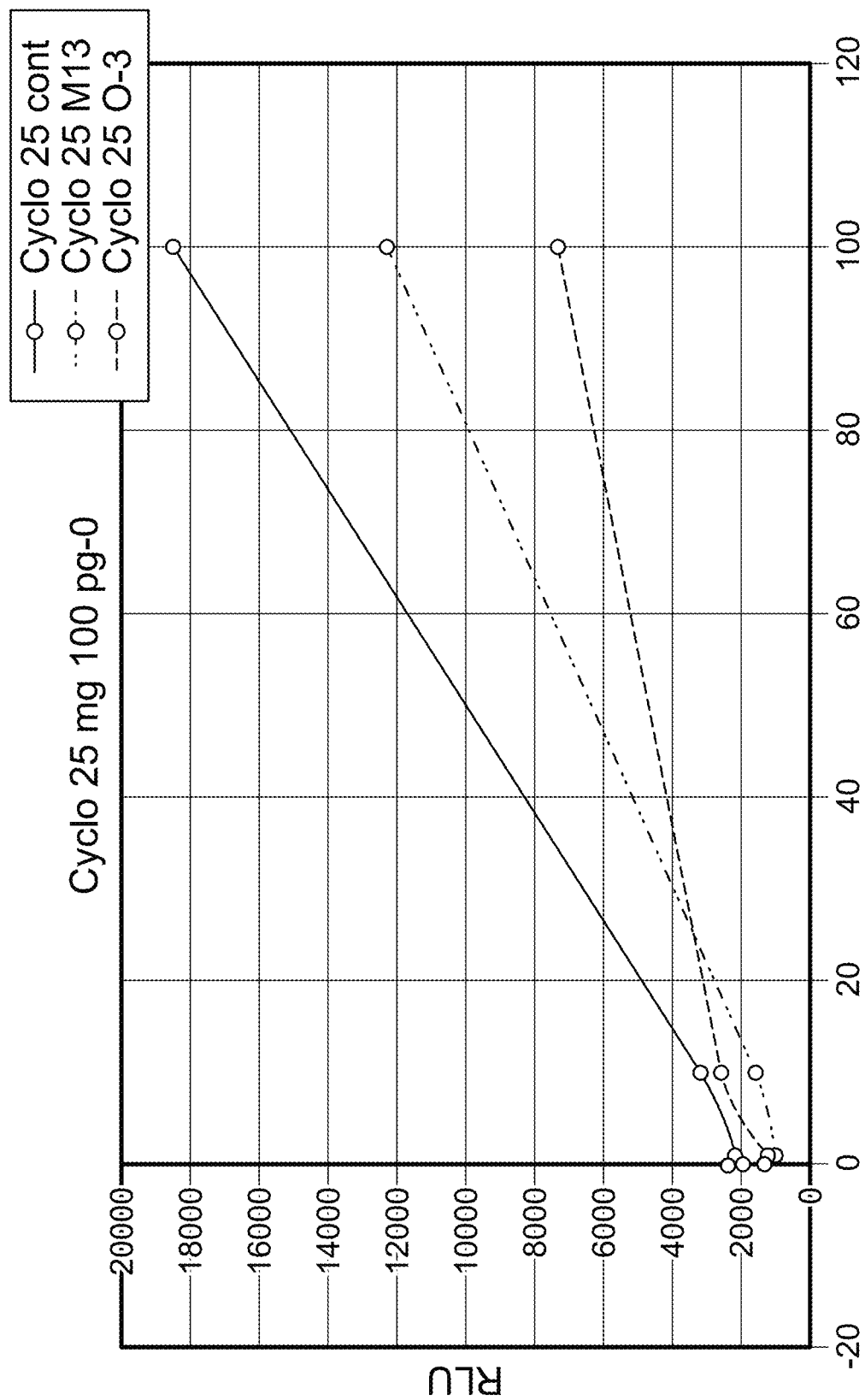
FIG. 107B shows results for TNFα detection and quantification on absorptive sample pads, where the assay was prepared with 25 mg of cyclodextrin.

Immediately after 30 minutes, the plate was spun down in a centrifuge at a pulse for 30 seconds at 9×g. The plate was immediately read the plate on the Cytation 5 Imager using the Alpha Cube to ensure proper wavelengths. The concentrations of pTNFα in the samples were calculated from the calibration curve. The results of this test are summarized in FIGS. 107A and 107B, where the results demonstrated that cyclodextrin at 25 mg yielded greater sensitivity under the test conditions.

Example 6. Dynamic Range Testing of Omnibeads in Solution

In some embodiments, the ingestible devices as described herein utilize OMNI Beads, which have been designed as a tool to identify instrument-related variability in AlphaScreen assays. These beads contain all of the chemical components for the generation of a strong signal without requiring the presence of AlphaScreen Acceptor and Donor beads. Omnibeads are therefore suitable for the regular verification of the performance of instruments used for AlphaScreen assays. Initial OMNI Bead utility testing was conducted using commercially sourced Omni beads to evaluate the utility of the present assay system.
Experimental Materials:
AlphaScreen® OminBeads™ (P/N 6760626D) (5 mg/mL in 100 μL) from PerkinElmer (Boston, Mass., USA) was used for experimental work. Other chemicals and reagents used were of analytical grade and from Sigma Aldrich (St. Louis, Mo.). White 384-well microplates (white OptiPlate-384 (Cat #6007290) were supplied by PerkinElmer (Boston, Mass., USA). All data were analyzed using GEN 5 Software version 3.02.1, BioTek U.S. (Winooski, Vt.).
Apparatus:
The AlphaLISA signal was read by a Cytation 5 spectrophotometer (S/N 1609299) from BioTek U.S. (Winooski, Vt.). GEN 5 Software version 3.02.1 utilizing an AphaCube 384 (p/n 1325001). Apha Endpoint reads with a gain of 200, Excitation time 80 msec, delay after excitation of 120 msec, integration time of 160 msec and read height of 11.5 mm.
Preparation of Standards and Samples:
A standard curve of omni beads was prepared according to the kit instructions with a 5 μg/mL stock into PBS Buffer to make a 0.5 μg/mL solution was serially diluted down 1:10 from Row A to Row G, and read on the plate reader at 680/615 nm. The standard curve and samples were loaded in white 384 well microtitre plates.

This was wrapped in tin foil, and placed in a 25° C. incubator for 5 and 2 hours respectively.

Figure 108:
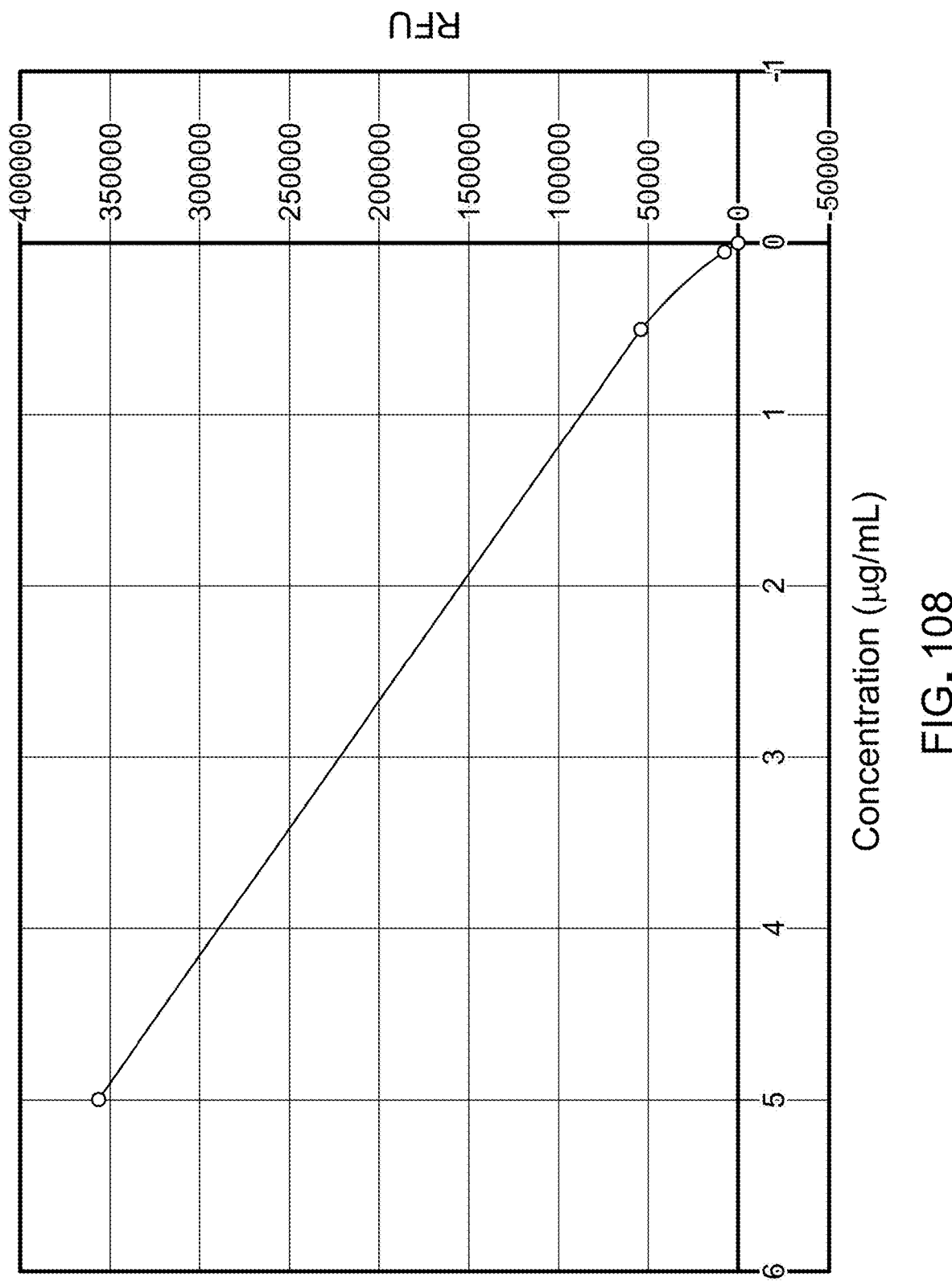
FIG. 108 shows assay signal readouts over the tested dilution range of OMNI beads. The OMNI beads 5 μg/mL stock solution was added into PE Buffer to make a 0.5 μg/mL solution, which was subsequently serially diluted down 1:10 from Row A to Row G, and read on the plate reader at 680/615 nm. The OMNI beads are used to calibrate the capsule and to characterize signal uniformity and reliability of the capsule. The OMNI beads may be loaded with Napthalo-silicon pthalocyanine (Excitation: 780 nm and emission 615 nm).
Figure 109A:
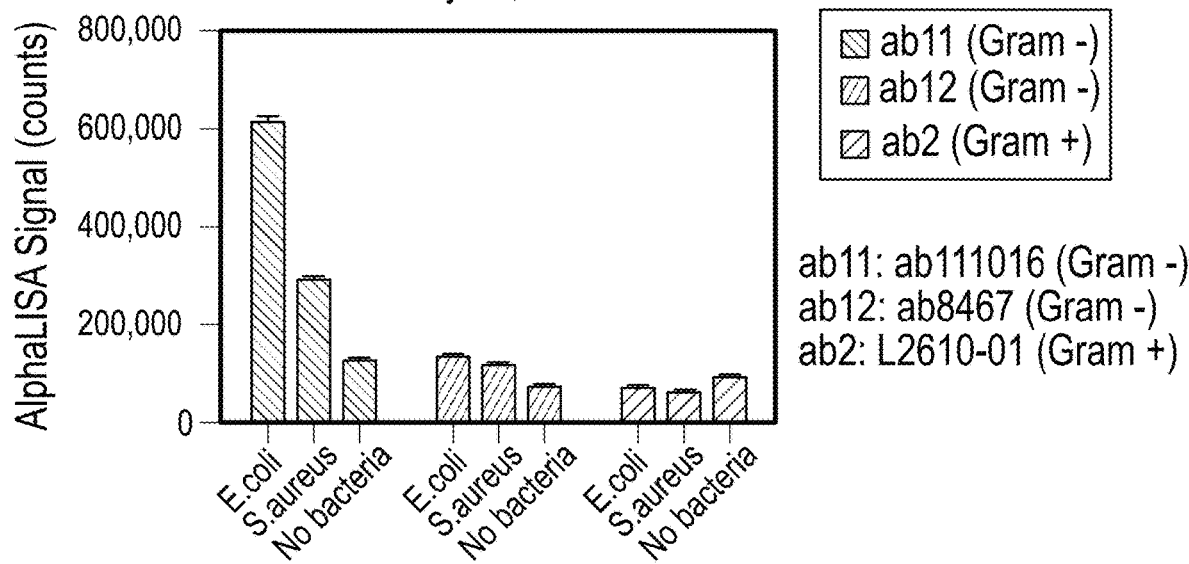
FIG. 109A shows results of preliminary antibody specificity investigation. Specificity of antibodies Ab11, Ab12 and Ab2 were tested using the antibody screening protocol. The assay was performed in 50 μL volume. Graph bars represent mean and standard deviation (SD) from triplicates determination.
Figure 109B:
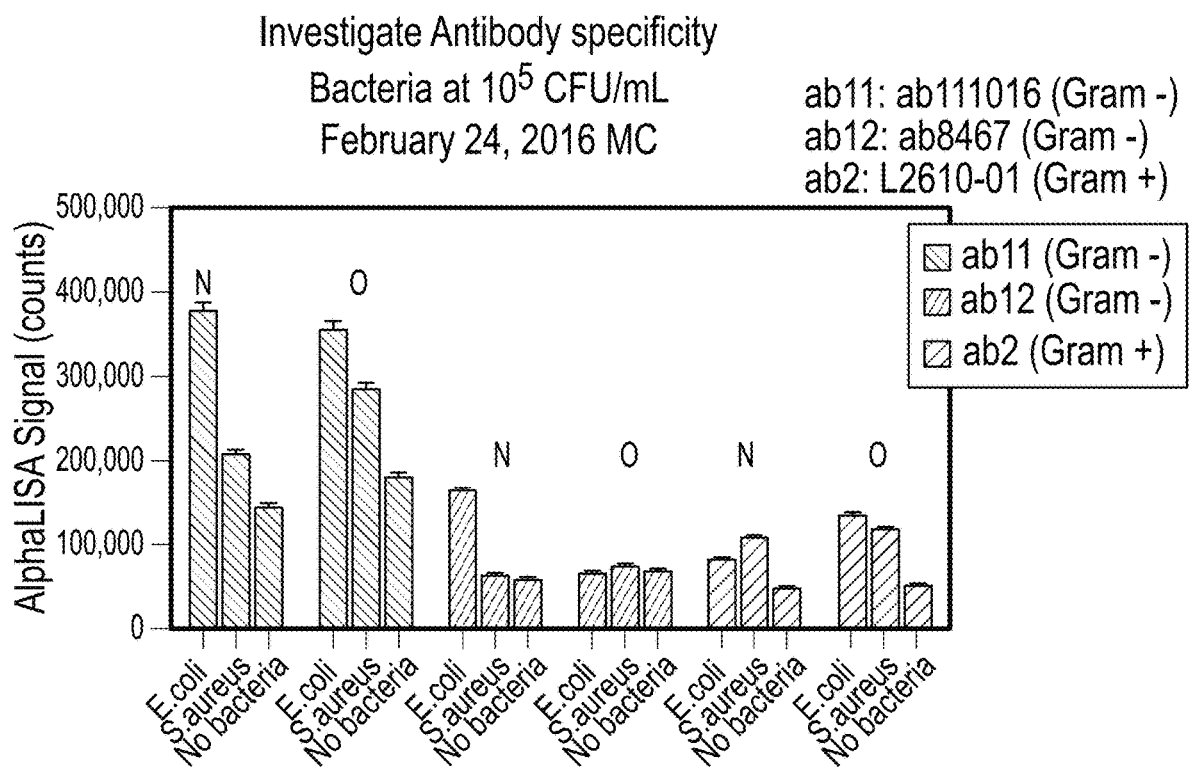
FIG. 109B shows results for antibody screening of Gram negative bacteria. Specificity of the anti-Gram-negative antibodies Ab11 and Ab12, and of the anti-Gram-positive antibody Ab2 using the antibody screening protocol. Two separate batches of bacteria were used for each condition, as indicated (N=new batch; O=old batch). The assay was performed in 50 μL. Graph bars represent mean and SD from triplicates determination.
Figure 109C:
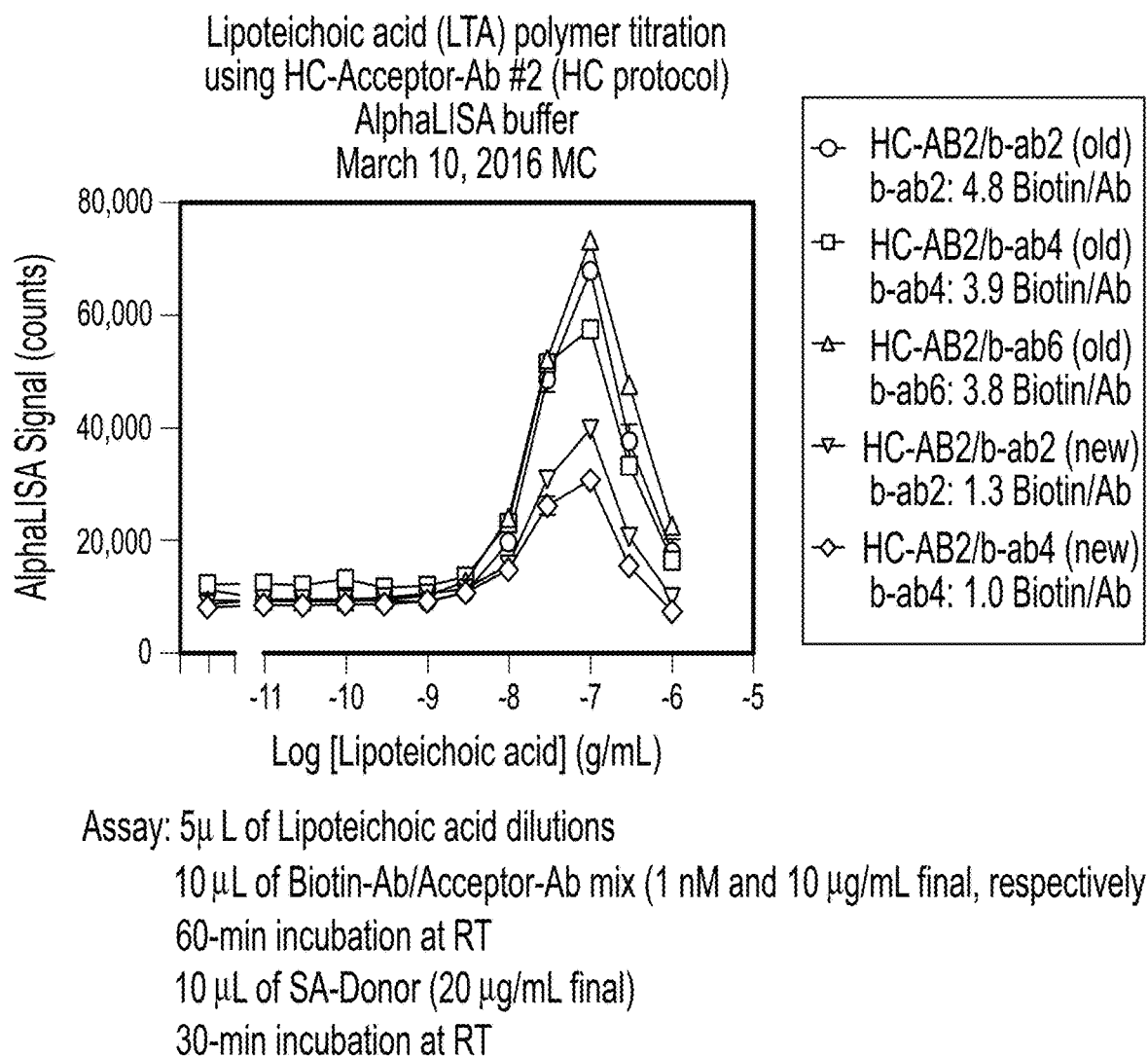
FIG. 109C shows results for antibody screening of Gram positive bacteria. The assay was performed in 25 μL volume using the AlphaLISA buffer. Two lots of biotin-Ab were tested for ab #2 and 4 and only one lot for ab #6. Biotin-Ab and high concentration acceptor-Ab beads were tested at 1 nM and 10 μg/mL, respectively. The Streptavidin-Donor (SA-Donor) beads were used at 20 μg/mL.
Figure 109D:
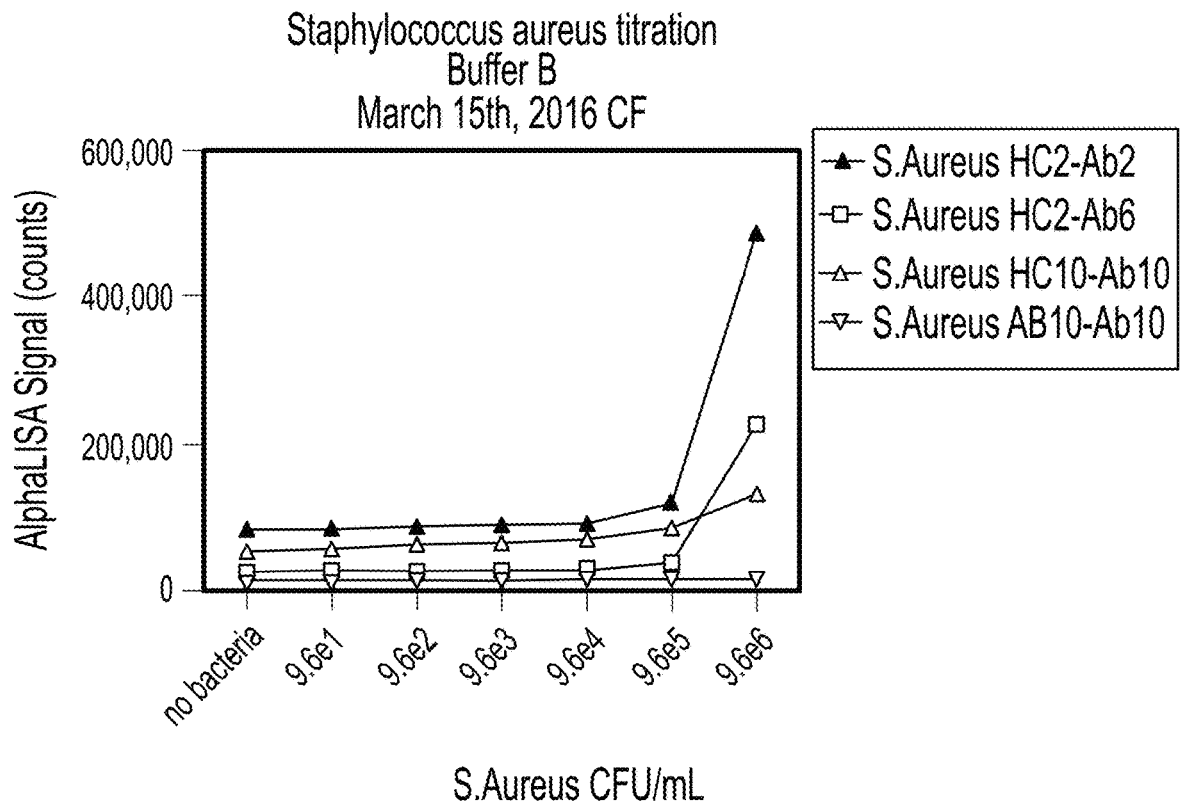
FIG. 109D shows results for the detection of a dynamic range of S. aureus. High conjugation (HC) acceptor beads or normal acceptor beads (AB10) were used at 40 μg/mL final and the Biotin-Ab at 0.3 nM final for S. aureus (Ab2, Ab6) using different dilutions of bacteria. The SA-Donor beads were used at 10 μg/mL. Bacteria were washed twice in PBS before final resuspension in Buffer B. Assay protocol is given below each graph along with signal-to-background ratio (S/B) obtained for each dilution of bacteria tested (no bacteria condition as background). Graph bars represent mean and SD from triplicate determination.
Figure 109E:
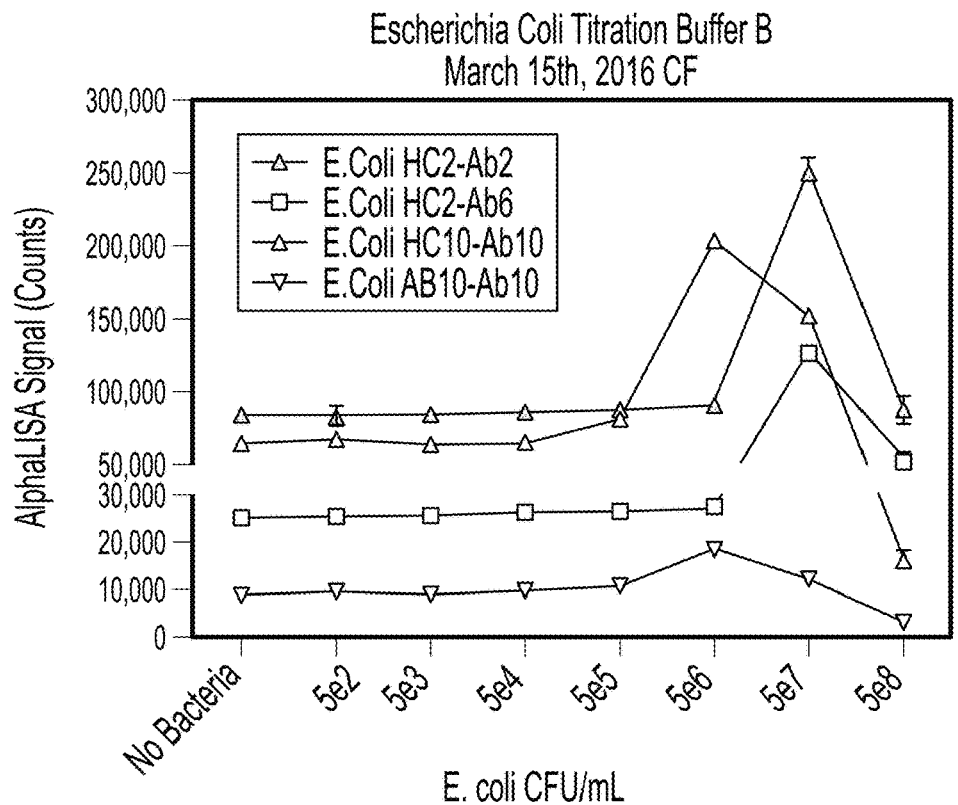
FIG. 109E shows detection of a dynamic range of E. coli. High conjugation (HC) acceptor beads or normal acceptor beads (AB10) were used at 40 μg/mL final and the Biotin-Ab at 3 nM final for E. coli (Ab10) using different dilutions of bacteria. The SA-Donor beads were used at 10 μg/mL. Bacteria were washed twice in PBS before final resuspension in Buffer B. Assay protocol is given below each graph along with S/B obtained for each dilution of bacteria tested (no bacteria condition as background). Graph bars represent mean and SD from triplicate determination.
Figure 109F:
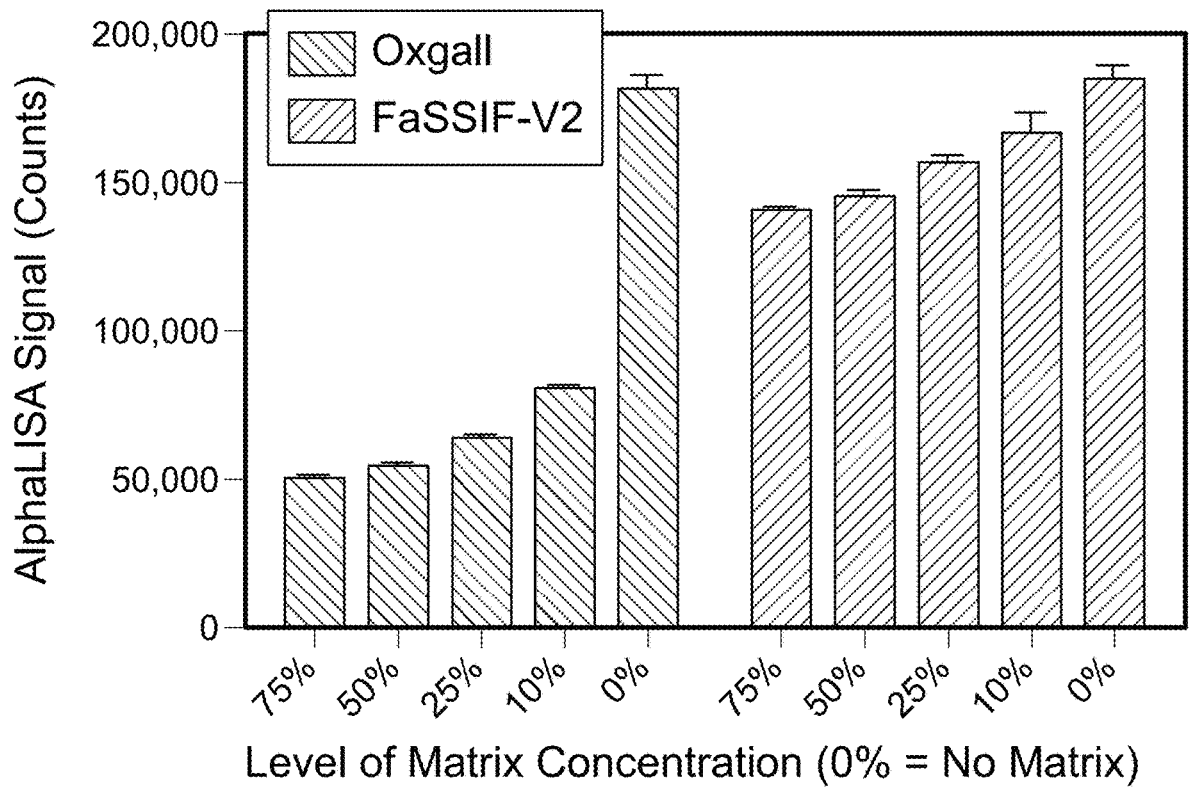
FIG. 109F shows interference of simulated intestinal fluid and bile. FASSIF-V2, a complex of taurocholate and lecithin, which is used as an example substitute for gas trointestinal fluids, and Oxgall, which can be usually obtained from cows, and is mixed with alcohol, were tested using TruHits, where TruHits assay principle and protocols were used. The Oxgall is a greenish-brown liquid mixture containing cholesterol, lecithin, taurocholic acid, and glycocholic acid, which is used as an example substitute for GI fluids.
Figure 109G:
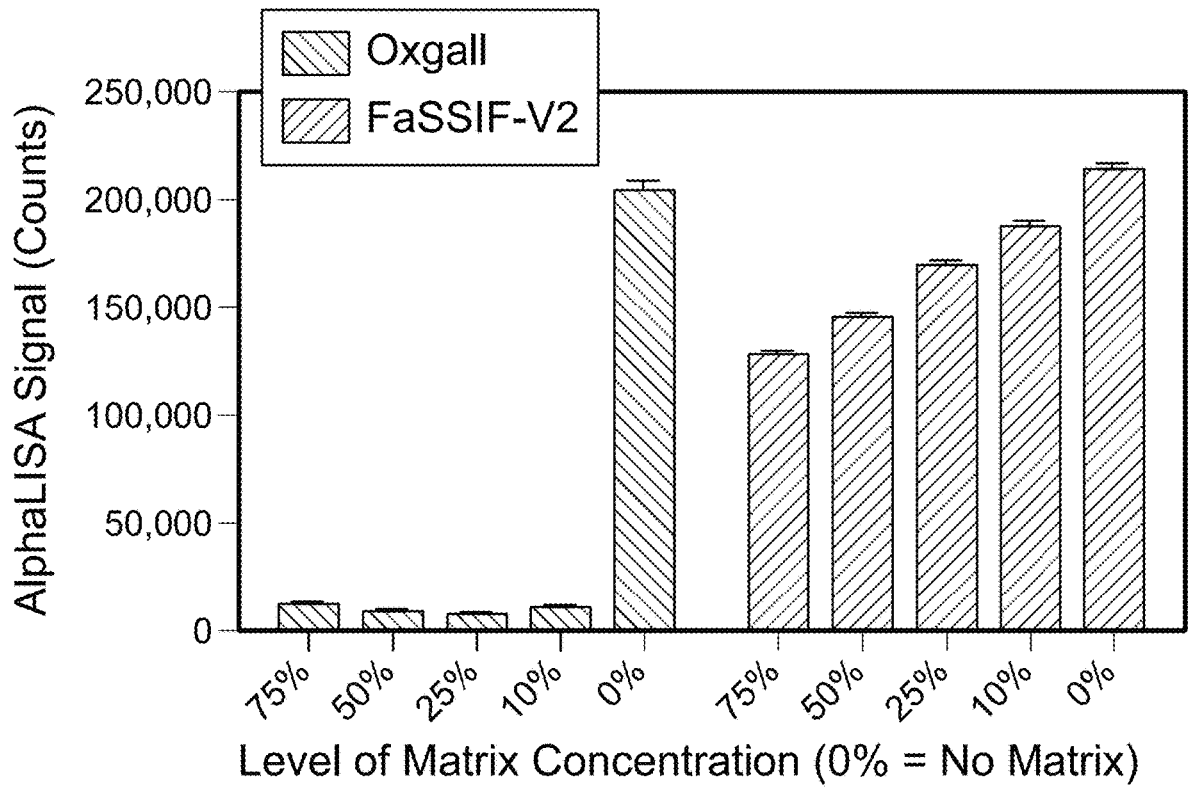
FIG. 109G shows interference of simulated intestinal fluid and bile. FASSIF-V2 and Oxgall were tested using TruHits, where increasing concentrations (percentages) of FASSIF- V2 and Oxgall were tested using the standard protocol shown in Panel A, e.g., St-Av Donor beads and biotin labeled acceptor beads.
Figure 109H:
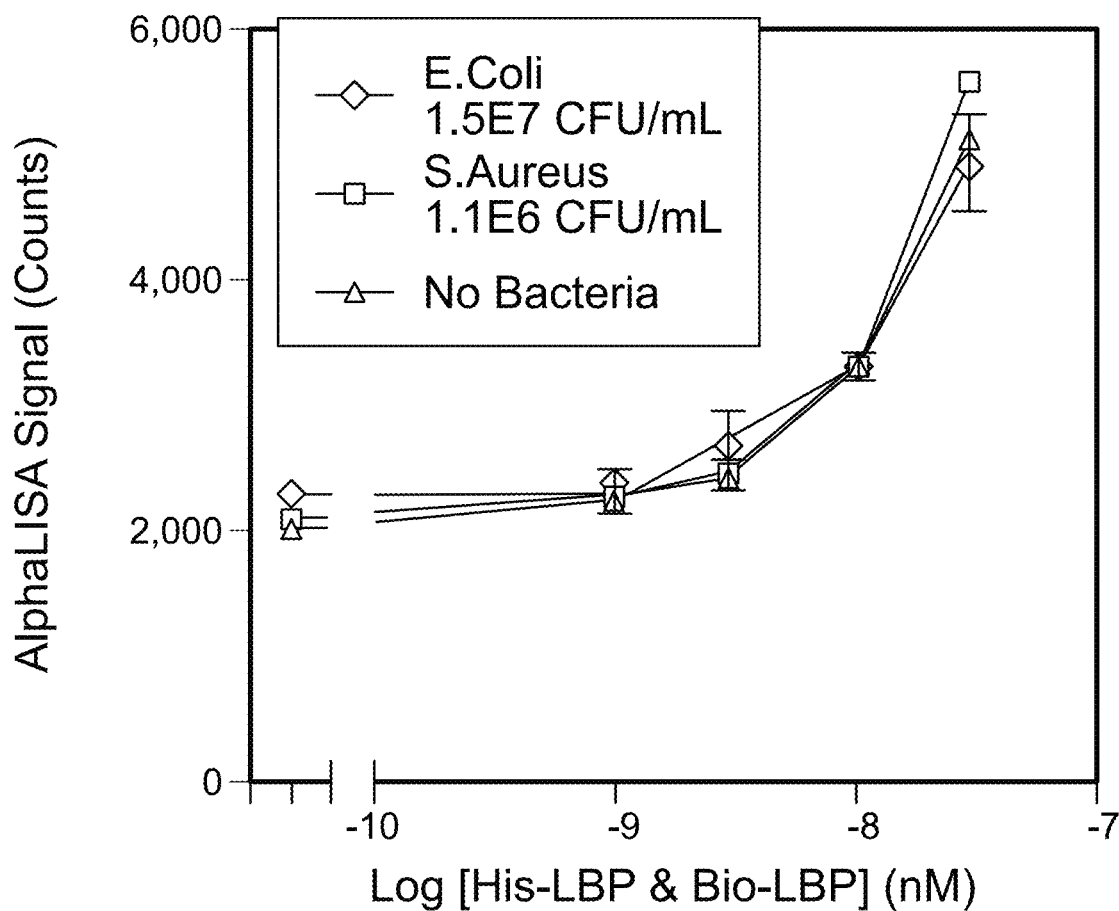
FIG. 109H shows results of LBP-based assays using fresh bacteria. A fixed dilution of S. aureus and E. coli (washed twice in PBS before final resuspension in Buffer B) was tested in with increasing concentrations of tagged LBP. The detection involved an equimolar mix of His-LBP and Bio-LBP.
Figure 109I:
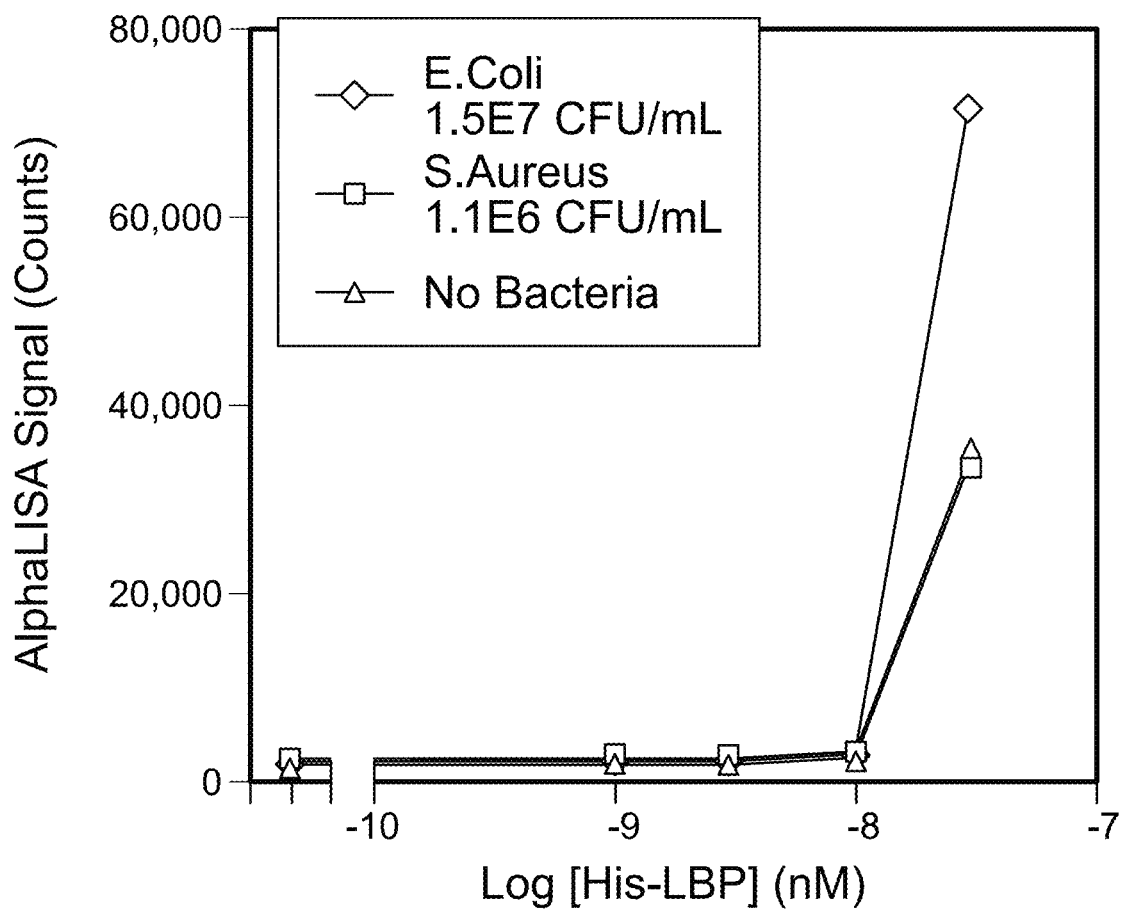
FIG. 109I shows results of LBP-based assays using fresh bacteria. A fixed dilution of S. aureus and E. coli (washed twice in PBS before final resuspension in Buffer B) was tested with increasing concentrations of tagged LBP. The assay involved His-LBP only.

Immediately after the incubation periods, the plate was spun down in a centrifuge at a pulse for 30 seconds at 9×g. The plate was immediately read the plate on the Cytation 5 Imager using the Alpha Cube to ensure proper wavelengths. The test results are summarized in FIG. 108.

Example 7. Bacterial Detection (SIBO)

In some embodiments, the ingestible devices of the present application may be used for total bacterial quantification. To that end, the chemiluminescent particles may be coated with specific antibodies that are capable of binding to the conserved antigens lipoteichoic acid (LTA) or lipopolysaccharide (LPS) found on aerobic and anaerobic Gram-positive (GP) and Gram-negative (GN) bacteria, respectively. LTA and LPS targets are located on the surface of their respective bacteria and are primary constituents of the cell walls. LTA and LPS antigens can be found on rapidly growing as well as stationary phase bacteria. Alternatively Lipopolysaccharide Binding Protein (LBP) (which binds with high affinity (Kd=1 nM) to lipid A), the common moiety of LPS, is a good alternative to LPS alone. This immuno-based analytical approach is similar to the one used by the Platelet PGD® Test (Verax Biomedical). Chemiluminescent particles labeled with antibodies targeting proteoglycans (PG) present in both GP and GN bacteria will also be tested. While LOCI has not been previously used for detection of viable bacteria, Mechaly et al. (2013) describe its application for detection of anthrax spores using a sandwich assay format. See, e.g., Mechaly, A., Cohen, N., Weiss, S. et al. Anal Bioanal Chem (2013) 405: 3965. This provides proof-of-principle for detection and quantification of bacterial cells using LOCI.
a. LOCI Detection of Gram-Negative and Gram-Positive Bacteria:
1. Experimental design: Various antibodies to LBP, LPS or LTA were biotinylated and tested for detection limits across a dynamic range of Gram-Negative and Gram-Positive organism concentrations. Assay sensitivity was compared across a test matrix of various rations of SA-donor beads, acceptor beads, antibody type and concentrations to facilitate a down selection process:
Materials
LOCI beads:
AlphaLISA unconjugated Europium Acceptor beads from PerkinElmer #6772002
AlphaPlex unconjugated Samarium acceptor beads from PerkinElmer #6792002
AlphaScreen SA-Donor beads from PerkinElmer #6760002
Antibodies (a number was assigned to each Ab to facilitate experiments and results viewing) used in this test include those listed in Table 1.

TABLE 1

Antibodies tested in the current study

| Ab ID | Antigen | Clone# | Provider | Cat# | Ab lot# |
|---|---|---|---|---|---|
| 1 | Anti-Gram Positive (3801) | 3801 | abm | Y070061 | AP4902 |
| 2 | Anti-Lipoteichoic acid | 5E367 | US Biological | L2610-01 | L15120226 |
| 3 | Anti-Lipoteichoic acid | 5E368 | US Biological | L2610-02 | L15120225/L10121063 |
| 4 | Gram Positive Bacteria LTA | G35C | Thermo Fisher | MA1-7401 | Q12081161/QL2120881 |
| 5 | Gram Positive Bacteria | BDI813 | GeneTex | GTX42624 | 821504924 |
| 6 | Gram Positive Bacteria | 3811 | ProSci | 35-578 | 17646-1504 |
| 7 | Gram Positive Bacteria | BDI380 | Abcam | ab20344 | GR215075-5/GR2511764-1 |
| 8 | Anti-E. coli LPS | 2D7/1 | Abcam | ab35654 | GR236327-1/GR236327-2 |

TABLE 1-continued

Antibodies tested in the current study

| Ab ID | Antigen | Clone# | Provider | Cat# | Ab lot# |
|---|---|---|---|---|---|
| 9 | Anti-Gram negative | 13-337.5 | Abcam | ab41199 | GR183947-1 |
| 10 | Anti-Gram negative | 11-445.2 | Abcam | ab41202 | GR211477-1 |
| 11 | Anti-Gram negative | GNE11-270.3.1 | Abcam | ab111016 | GR251899-1 |
| 12 | Anti-Lipid A | 26-5 | Abcam | ab8467 | GR205999-1 |
|  | Anti-DNP | SPE-7 | Sigma | D8406 | 123M4894 |
|  | Anti-DNP | 2-9(4) | Abcam | Ab24319 | GR163969-5 |
|  | Anti-DNP | LO-DNP-30 | Fisher | MA5-16776 | QL2131322 |

Bacteria Strains:
*Escherichia coli* from ATCC #25922
*Staphylococcus aureus* from ATCC #29213
*Staphylococcus epidermis* from ATCC #14990 lot #63229747
*Klebsiella pneumonia* from ATCC #4352 lot #61698735
*Pseudomonas aeruginosa* from ATCC #15442 lot #63229753
*Clostridium sporogenes* from ATCC #7955 lot #61203517
*Bacteroides vulgatus* from ATCC #8482 lot #62382072
*Enterobacter aerogenes* from ATCC #β048 lot #61741619
*Streptococcus pneumonia* from ATCC #27336 lot #58049252
*Streptococcus mutans* from ATCC #25175 lot #62284317
*Enterococcus faecalis* from ATCC #49533 lot #62175902
*Proteus mirabilis* from ATCC #25933 lot #61757217
Reagents for bead conjugation and biotinylation:
Chromalink Biotin from Solulink #B1001-105
Sodium phosphate from Fisher #BP331-500
Na cyanoborohydride from Sigma #156159
PBS from Corning #21-040-CV lot #21040337
Proclin-300 from Supelco #48912-U lot #LC00240
Carboxymethoxylamine from Sigma #Cβ408 lot #MKBV4120V
10% Tween-20 from Thermo, #28320 lot #OC183327
Reagents for Antibody purification:
Zeba desalting column 0.5 mL from Thermo Scientific #89882
Zeba desalting column 2 mL from Thermo Scientific #89880
Amicon Ultra 0.5 mL Ultracell (30,000 MWCO) from Millipore, cat #UFC503024
BSA removal kit from Abcam #ab173231
Reagents for buffer preparation:
HEPES acid free from BioBasic #7365-45-9
HEPES sodium salt from MP Biochemicals #105593
5% Alkali-soluble Casein from EMD Millipore #70955-225 mL
Dextran from Spectrum #D1004
Human IgG from Jackson #009-000-002
Dinitrophenyl (DNP)-Biotin-BSA protein conjugate from Alpha Diagnostic Intl #DNP35-BTN-10
384-well white opaque OptiPlate from PerkinElmer #6007290
Top Seal-A from PerkinElmer #6050185
EnVision Multimode Plate Reader Model 2104 from PerkinElmer
Lambda Bio+ spectrophotometer from PerkinElmer
Incubator set at 37° C.

Methods
Antibody Purification (Pre-Treatment)
Antibodies 1 to 7 listed in Table 1 were provided at a low concentration (0.1 mg/mL) and in a solution containing sodium azide, which is not compatible with the biotinylation reaction. Therefore, the antibody solution was first concentrated using an AMICON centrifugal filter and then passed through a ZEBA desalting column using PBS as the solvent to remove the sodium azide. Antibody 12 contained BSA in its formulation. BSA removal was performed using the ABCAM BSA removal kit and the antibody pellet resuspended in PBS. Following this pre-treatment procedures, the antibody concentrations were determined spectrophotometrically and are listed in Table 2.

TABLE 2

Final antibody concentrations after treatment

| Antibody ID | Cat# | [Ab] (mg/mL) |
|---|---|---|
| 1 | Y070061 | 0.94 |
| 2 | L2610-01 | 0.94 |
| 3 | L2610-02 | 0.76 |
| 4 | MA1-7401 | 0.62 |
| 5 | GTX42624 | 0.64 |
| 6 | 35-578 | 1.04 |
| 7 | ab20344 | 0.65 |
| 12 | ab8467 | 0.63 |

Biotinylation of Ab
For biotinylation of Abs, 0.04 mg of Ab and 3.05 µL of Chromalink biotin (2 mg/mL) were mixed together for a 30:1 ratio biotin/Ab. The 0.08 mL reaction volume was completed with PBS pH 7.4 and the reaction was incubated for 2 hours at 23° C. Purification of biotinylated antibody was performed using ZEBA 0.5 mL desalting columns. Ratio of biotinylation was measured at 354 nm along with reading at 280 nM for protein recovery. Final biotin/Ab labeling ratios are summarized in Table 3.

TABLE 3

Biotin per antibody ratio

| Antibody ID | Cat# | Biotin/Ab |
|---|---|---|
| ab1 | Y070061 | 2.4 |
| ab2 | L2610-01 | 4.8 |
| ab3 | L2610-02 | 1.9 |
| ab4 | MA1-7401 | 3.9 |

TABLE 3-continued

Biotin per antibody ratio

| Antibody ID | Cat# | Biotin/Ab |
|---|---|---|
| ab5 | GTX42624 | 2.5 |
| ab6 | 35-578 | 3.8 |
| ab7 | ab20344 | 1.3 |
| ab8 | ab35654 | 0.8 |
| ab9 | ab41199 | 6.1 |
| ab10 | ab41202 | 7.6 |
| ab11 | ab111016 | 6.4 |
| ab12 | ab8467 | 7.7 |

AlphaLISA Europium and Samarium Acceptor Beads Conjugation

For Acceptor bead conjugation, 0.02 mg of antibody, 0.0625% of Tween-20, 1.0 mg of AlphaLISA beads and 1.25 mg/mL of NaBH$_3$CN were mixed together. The 0.045 mL reaction volume was completed with a solution of β0 mM of Na Phosphate buffer pH 8.0 and the reaction was incubated for 18 hours at 37° C. The reaction was stopped by the addition of 2 of a 65 mg/mL of a CMO solution and the reaction was allowed to proceed for one hour at 37° C. Beads were then washed by centrifugation 2 times for 15 minutes (14,000 rpm/4° C.) and bead pellets were resuspended in 0.2 mL of 100 mM Tris pH 8.0. Afterward, a third centrifuge step was done and beads were resuspended in PBS pH 7.2 containing 0.05% Proclin-300 for a 5 mg/mL concentration.

AlphaLISA Detection Assay: Antibody Screening

The assay buffer (Buffer B) consisted of 25 mM HEPES pH 7.4, 0.1% Casein, 1 mg/mL Dextran-500.

The protocol was as follows. In a 1.5 mL assay tube, 40 μL of bacteria at 5E10$^5$ CFU/mL (1E10$^5$ CFU/mL final) was mixed with 80 μL of Biotin-Ab (10 nM final). The reaction was incubated for 60 minutes at 37° C. After the incubation, bacteria were centrifuged for 15 minutes at 6,000 g. Supernatant was carefully removed and 200 μL of SA-coated Donor and SA-coated Acceptor bead mix (10 μg/mL and 40 μg/mL final, respectively, in assay Buffer B) were added under subdued light conditions and the pellet was gently resuspended. The reaction was incubated for another 60 minutes at 37° C. and finally 50 μL were distributed in triplicate in an OptiPlate-384 prior to reading the plate using an EnVision reader.

AlphaLISA Detection Assay: Matrix and Titration Experiment

Unless otherwise stated in the text and/or figures, the general protocol was as follows. In an OptiPlate-384, 10 μL of bacteria at 5E10$^5$ CFU/mL (1E10$^5$ CFU/mL final) was mixed with 20 of Biotin-Ab and AlphaLISA Ab beads (10 nM and 40 μg/mL final, respectively). The reaction was incubated for 60 minutes at 37° C. Finally, 20 μL of SA-coated Donor beads (10 μg/mL final) were added under subdued light conditions and plate was then incubated for 30 minutes in the dark (37° C.) prior to reading the plate using an EnVision reader. All LOCI reagents were diluted in assay Buffer B.

DNP Internal Control Assay

Unless otherwise stated in the text and/or figures, the general protocol was as follows. In an OptiPlate-384, 5 μL of the diluted DNP probe was mixed with 10 μL of Anti-DNP Sm Acceptor beads (10 or 20 μg/mL final). The reaction was incubated for 60 minutes at 37° C. Finally, 10 μL of SA-coated Donor beads (20 μg/mL final) were added under subdued light conditions and plate was then incubated for 30 minutes in the dark (37° C.) prior to reading the plate using an EnVision reader equipped with AlphaPlex Samarium detection features (optical module #2102-5910 and a Sm emission filter at 644 nm). All LOCI reagents were diluted in assay Buffer B.

Bacterial Culture Conditions

Bacteria cultures were prepared pursuant to SOPs MP-0001 and MP-0004 with appropriate modifications.

Streaking and Isolating Bacteria

Day 1. Using a sterile loop, bacterial glycerol stock (from ATCC) were gently spread over a section of an agar plate to create streak #1. Using a freshly sterilized loop, the bacteria from streak #1 were spread over a second section of the agar plate to generate streak #2. Finally, using a third sterile loop, the bacteria from streak #2 were spread over the last section of the agar plate, to create streak #3. Plates were incubated for 24-48 hours at 37° C. For anaerobic cultures, inoculation was done in liquid medium, since the bacteria would not grow on agar plates.

Day 2. A single colony from the agar plate was re-streaked onto a new agar plate (as above), and incubated for 24-48 hours at 37° C. Anaerobic strains were cultured for 4 days. For anaerobic bacteria, 100 μL of liquid culture was used to inoculate 30 mL liquid medium.

Liquid Bacterial Culture and Glycerol Stock (Note: Overnight Culture was Used for the Glycerol Stock)

Day 3. A single colony (or 125 μL liquid culture) was used to inoculate 30 mL of liquid broth, which was grown overnight at 37° C. (24 to 48 hours) at 300 rpm or no shaking for anaerobic bacteria.

Day 4. The next day, bacterial glycerol stocks were generated by adding 50% glycerol stock to a final concentration of 10% glycerol to the bacterial culture. Aliquots (of at least 200 μL) the bacterial glycerol stocks were stored at −80° C. In some cases the cultures were centrifuged at 5100 rpm for 5 min, and resuspended to adequate densities. Aliquots varied from 200 μL to 1 mL depending on growth and suspended volumes.

Day 5. The next day, bacterial glycerol stocks were thawed and serially diluted: $10^{-2}$, $10^{-4}$, $10^{-6}$, $10^{-7}$, $10^{-8}$ and $10^{-9}$. 0.1 and 0.4 mL of the serial dilutions were plated in duplicate and incubated overnight.

Day 6. Bacterial counts were determined.

Selected test results are summarized in FIGS. 109A-109I.

Diffractive Optics Examples

A. Materials and Methods

The following materials and methods were used in the examples set forth herein.

Polystyrene Beads

Commercially available biotinylated yellow-green fluorescent polystyrene beads (FluoSpheres®, Invitrogen, Carlsbad, Calif.) were used in particle-size sensitivity experiments. The beads had nominal diameters of 0.2 μm and 1.0 μm and were supplied as suspensions (2% solids) in water containing 2 mM sodium azide at $2.5 \times 10^{12}$ particles/mL, $1.4 \times 10^{10}$ particles/mL, respectively.

Commercially available biotin coated polystyrene beads (Spherotech, Lake Forest, Ill.) were used in flow characterization experiments. The beads had a nominal diameter of 0.7-0.9 μm and were suspended in PBS buffer at $3.1 \times 10^{10}$ particles/mL.

Bacterial Cultures

Live bacteria preparations of *Staphylococcus aureus* (Sporometrics, Toronto, Canada), $1.1 \times 10^8$ CFU/mL, and *Escherichia coli* (Sporometrics, Toronto, Canada), $9.5 \times 10^7$ CFU/mL were stored at 4° C. until use. Before use, bacteria suspensions were vortexed vigorously, and an aliquot was aseptically removed from the stock vial and diluted in PBS to achieve the desired concentration. Bacteria dilutions were stored on ice and vortexed vigorously before loading into the dotLab mX System.

Gold Nanoparticles

Dressed Gold® goat anti-mouse (H+L) antibody conjugated gold nanoparticles with a nominal diameter of 40 nm were used in protein detection experiments. The gold nanoparticles were obtained from Bioassay Works (Ijamsville, Md.).

Antibodies

Commercially available monoclonal antibodies for anti-lipoteichoic acid, (US Biologicals) and anti-Gram negative endotoxin (Abcam, Cambridge, Mass.) were used. Antibodies were obtained unlabeled from the vendor and subsequently biotinylated and purified by BioAuxilium Research (Saint-Laurent, Canada).

Conjugated, antibody activities were tested by Progenity (Ann Arbor, Mich.).

Polyclonal BacTrace antibodies for *Escherichia coli* O145:H2 and *Staphylococcus aureus* were obtained from KPL (Milford, Mass.) to perform performance comparisons between monoclonal and polyclonal antibodies. The BacTrace® antibodies were biotinylated using the Lightning-Link® Biotin kit (Innova Biosciences, Cambridge, UK).

Biotinylated rabbit anti-mouse Fc antibodies, biotinylated goat anti-mouse IgG antibodies and purified mouse IgG were obtained from Axela, Inc. (Toronto, Canada).

Blocking and Wash Buffers

TheBlockingSolution block buffer was purchased from Candor Bioscience (Germany). Phosphate-buffered saline (PBS), PBS containing 0.1% Tween-20 (PBST) and Tris buffered saline (TB S) were from Axela, Inc. (Toronto, Canada).

Avidin Diffraction Grating Sensors

Avidin diffraction grating sensors included a flow channel containing a contiguous array of assay spots. Each assay spot consisted of avidin arranged in a distinct pattern of parallel lines forming a diffraction grating. Once mated with a fluidic adaptor which connected the sensor to the instrument microfluidic pump system, the flow channel above the spots had a capacity of 10 µL. An integrated prism below the flow channel allowed an incoming laser beam to enter the system and diffracted light to exit the system without disruption. Reflection rather than transmission through the flow channel was used to avoid potential interference from the sample. The diffraction grating sensors were imaged using the Axela dotLab mX System. The diffraction grating sensors were illuminated at a 60° incidence angle and the diffraction intensities from the 5th order mode were measured.

Fluidic Protocol

Avidin-coated diffraction grating sensors were mated to the dotLab mX System, which provided fluidic pump controls. The sensors were first washed with phosphate buffered saline with 0.1% Tween-20 (PBST) for one minute, blocked with TheBlockingSolution for two minutes, then washed again with PBST for one minute. The chips were then incubated with a biotinylated capture antibody solution (further described in the examples below) suspended in phosphate buffer saline (PBS) for 10-15 minutes. The chips were washed again with PBST for one minute and incubated with the bacterial suspension (further described in the examples below) for between 10-25 minutes. Unless otherwise specified, the mixing flow rate was set to 500 µL/min.

No-Flow Protocol

To achieve incubations without flow while still utilizing the dotLab mX System for diffraction analysis, a sensor scanning software was used. This software provided a general surface scan of the spots in a sensor and outputted a trace in which the x-axis represented the lateral position on a sensor, and the y-axis represented the diffraction intensity at each position. From sensor scans performed before and after "off-line" sample incubations, the relative changes in diffraction signal were estimated.

Washes were performed by gently pipetting fluid into the sensor cavity, incubating briefly on a rotary mixer, then aspirating the fluid off of the sensor. First, the sensors were washed with PBS, incubated with blocking solution for 1 hour at 150 RPM on a rotary mixer, then washed again with PBS. After blocking, a surface scan of the sensor was performed. Next, the sensor was incubated with a biotinylated capture antibody solution (further described in the examples below) suspended in PBS for 1 hour at 150 RPM on a rotary mixer. The sensor was rewashed with PBS to remove unbound capture antibody before a second sensor scan. After scanning, the sensor was incubated with the bacterial suspension (further described in the examples below) for 1 hour at 150 RPM. The sensor was washed with PBS to remove unbound bacteria before a final sensor scan occurs.

Figure 112:
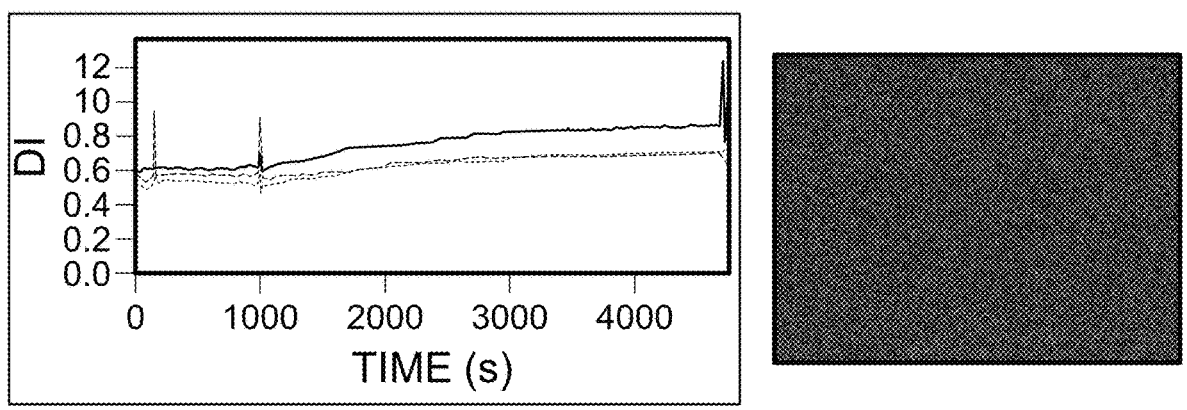
FIG. 112 shows diffraction intensity data and bead distribution data.
Figure 113:
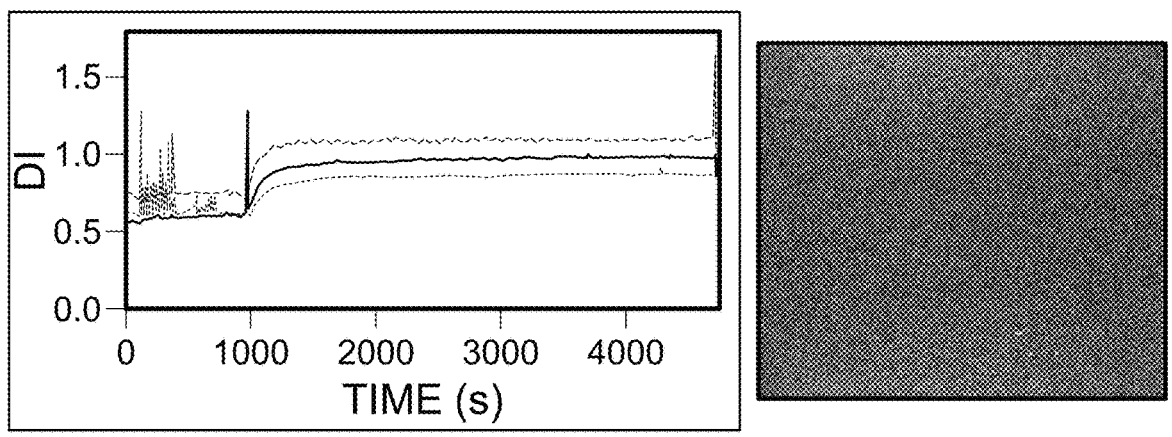
FIG. 113 shows diffraction intensity data and bead distribution data.

B. Sensitivity of Avidin Diffraction Grating Sensors to Particle Size and Flow Rate Previous embodiments of diffraction grating sensors were optimized to detect molecules such as antibodies, approximately 10 nm in size. In contrast, live bacteria typically range from 0.5 to 5.0 µm in size. To test the ability of the system to capture large particles, incubation experiments were performed using fluorescent polystyrene beads with nominal diameters of 0.2 µm and 1.0 µm. The flow rate was set at 100 µL/min. Upon microscopic examination, sensors incubated with 1.0 µm beads were found to have an uneven coating of beads (FIG. 112), suggesting that most beads failed to bind or were sheared off during incubation, while sensors incubated with 0.2 µm beads were observed have an even coating of beads (FIG. 113).

Figure 114:
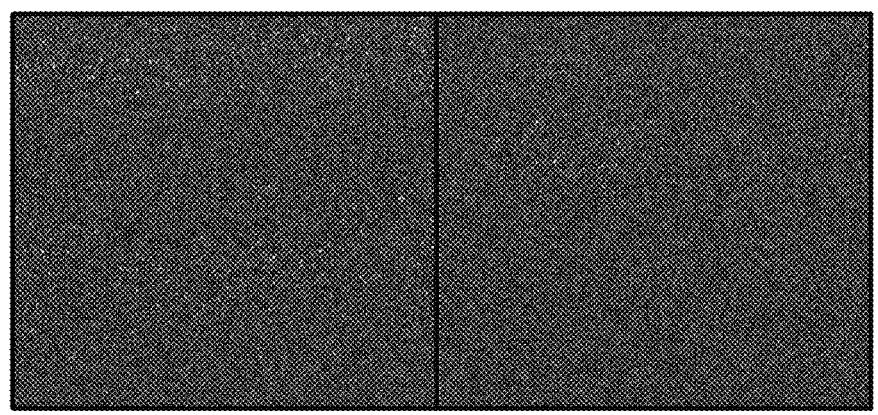
FIG. 114 shows bead distribution data.

To investigate whether shear force was the sole contributor of decreased binding performance in larger particles, the experiments were repeated under no-flow incubation conditions. Under microscopic examination, sensors incubated with 1.0 µm beads were again found to have more uneven coating than sensors incubated with 0.2 µm beads (FIG. 114), suggesting that steric hindrance may also have contributed to decreased binding at larger particle sizes.

Figure 115:
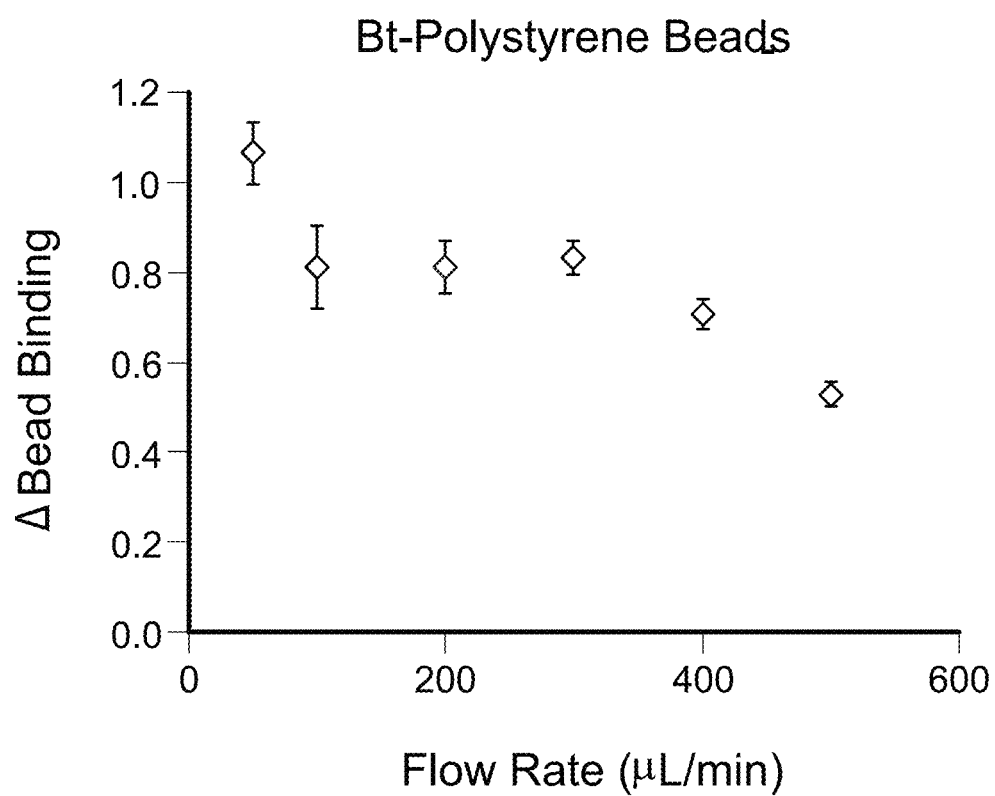
FIG. 115 shows data relating to incubation flow rate and binding signal.
Figure 116:
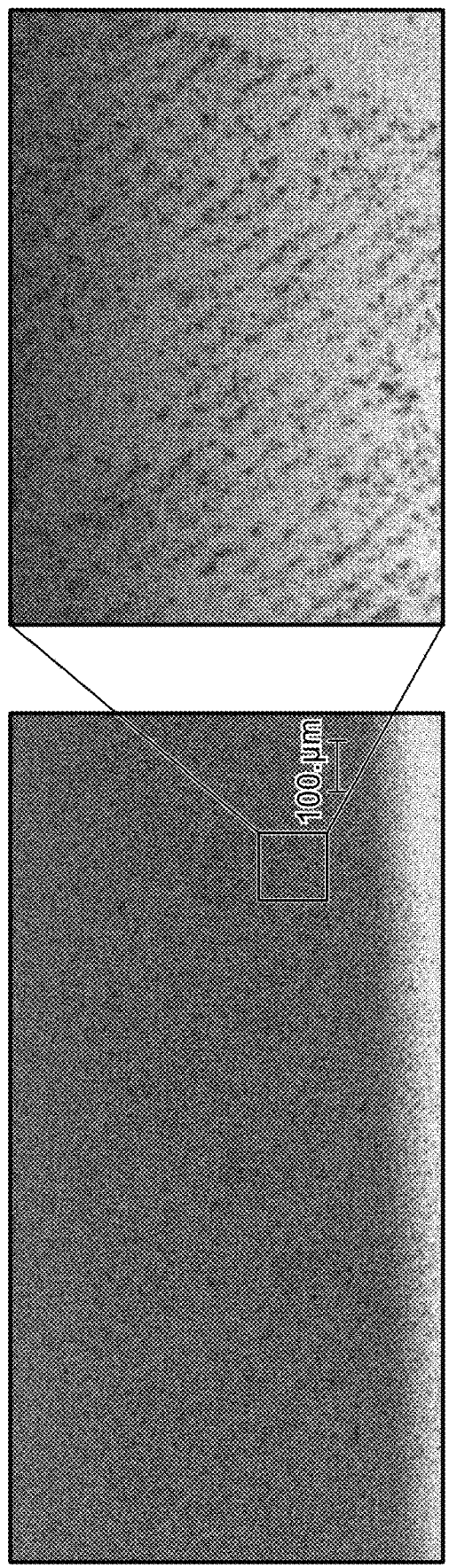
FIG. 116 shows data relating to binding.
Figure 117:
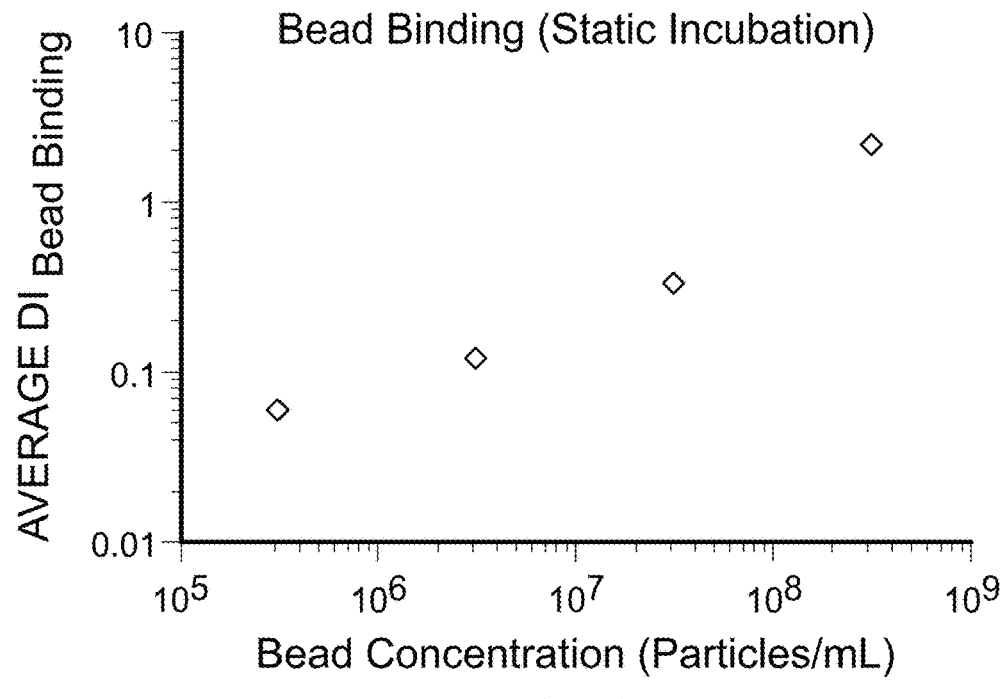
FIG. 117 shows data relating to binding signal for incubation without flow.

To determine the effect of flow rate on immobilization, 0.83 µm biotinylated polystyrene beads were used for direct immobilization on avidin sensors. Immobilization experiments were performed at varying flow between 0-500 µL/min. The flow rate was found to significantly impact the binding signal, with lower flow rates producing higher binding signal (FIG. 115). While significant bead binding was observed, the binding was not uniform at very high flow rates, as shear forces prevented the beads from binding to the avidin sensors (FIG. 116). The binding signal was maximized when immobilization was performed with no flow through the sensor (FIG. 117). These results suggested that for the detection of bacterial cells, flow rates should be significantly reduced compared to previous embodiments of diffraction grating sensors.

Figure 118:
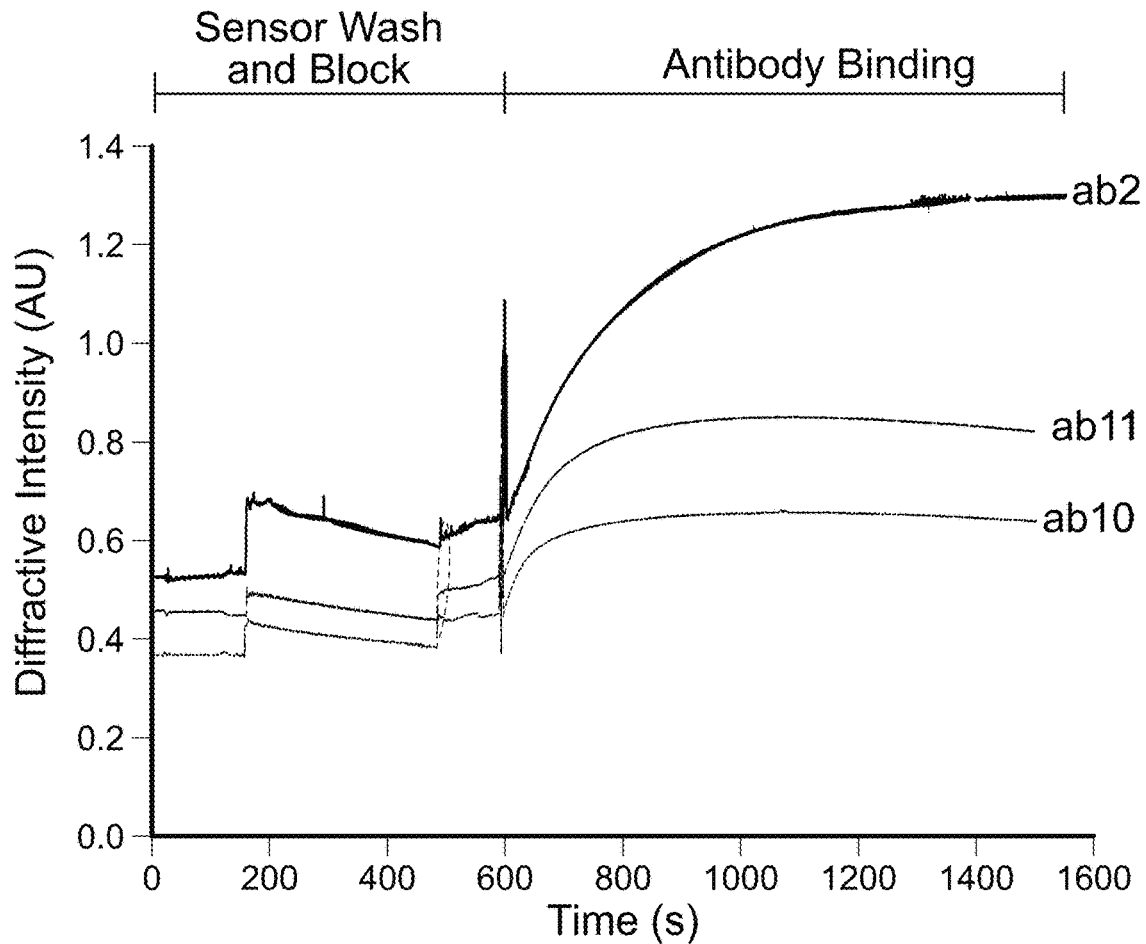
FIG. 118 shows binding signal data.

C. Biotinylated Anti-Lipoteichoic Acid, Anti-Gram Negative Endotoxin, Polyclonal Anti-*S. aureus*, and Anti-*E. coli* Antibodies Bound to Avidin Sensors Capture antibodies biotin-anti-lipoteichoic acid and biotin-anti-Gram negative endotoxin were characterized. Antibodies were immobilized to avidin diffraction grating sensors and monitored using the dotLab mX System. Each biotinylated capture antibody tested demonstrated detectable binding to avidin sensors, with biotinylated anti-lipoteichoic acid showing the highest binding signal (FIG. 118). Next, commercially available polyclonal S. aureus and E. coli capture antibodies were evaluated for suitability in an avidin sensor. Both antibodies were biotinylated and immobilized on avidin sensors and showed excellent binding signals. These results showed that the avidin sensor platform was capable of binding a variety of biotin-tagged antibodies.

Figure 119:
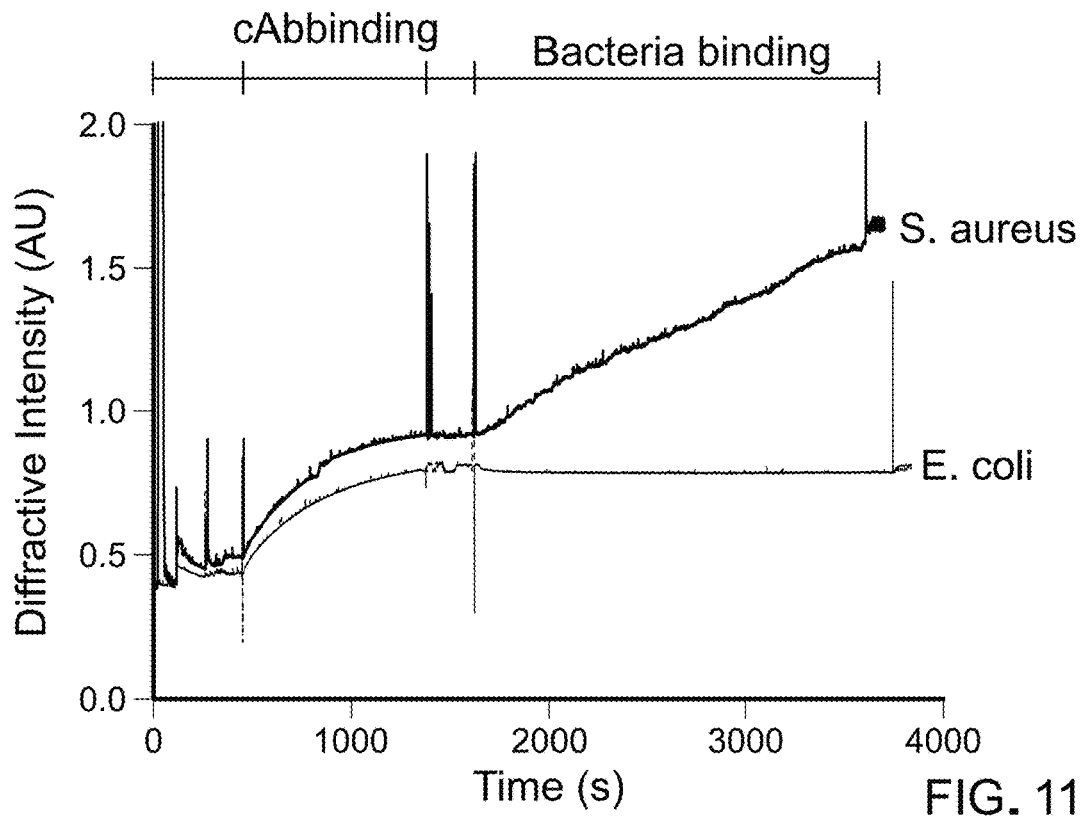
FIG. 119 shows diffraction intensity data.
Figure 120:
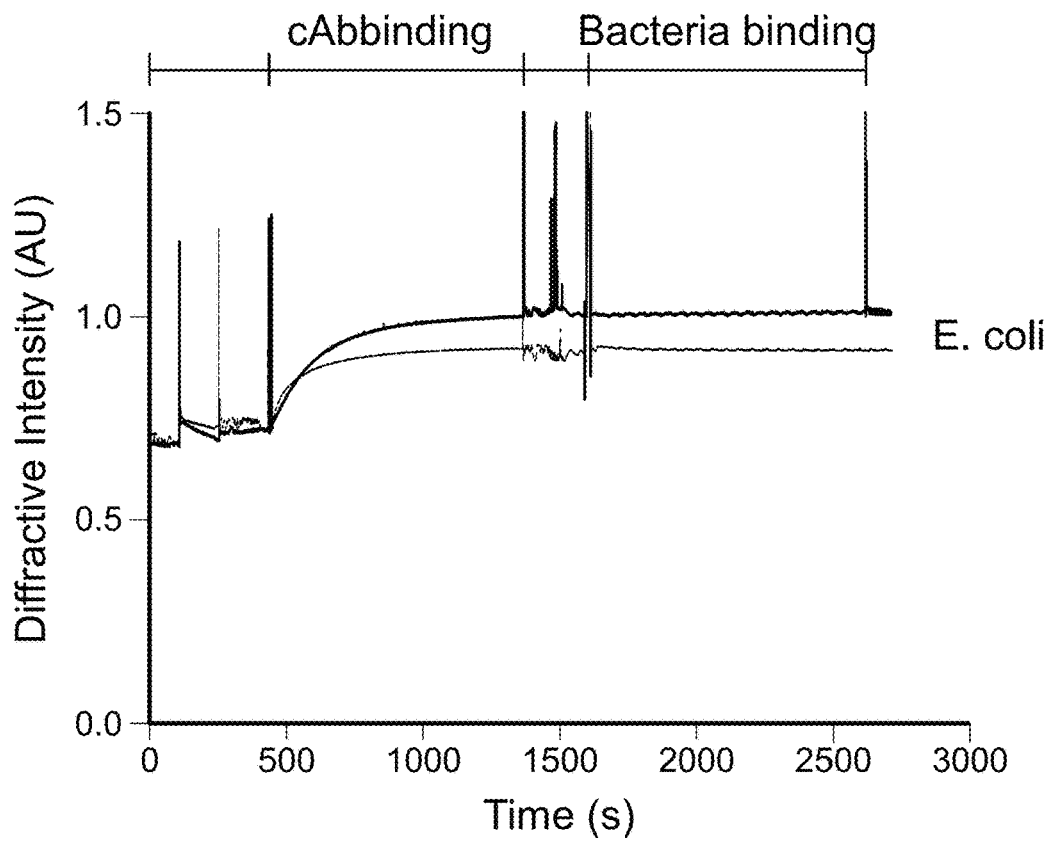
FIG. 120 shows diffraction intensity data.

D. Immobilized Biotinylated Anti-Lipoteichoic Acid Binds Specifically to S. aureus, To characterize the sensitivity and specificity of bacteria capture by the monoclonal antibody-coated diffraction grating sensors, the sensors were incubated with bacterial suspensions of S. aureus and E. coli. Anti-lipoteichoic acid antibodies were expected to bind to S. aureus, while anti-Gram negative endotoxin antibodies were expected to bind to E. coli. Biotinylated anti-lipoteichoic acid coated sensors showed readily detectible S. aureus binding at $1.1 \times 10^8$ CFU/mL, but no signal change in response to E. coli (FIG. 119). These findings demonstrated that the anti-lipoteichoic acid sensors were effectively capturing target bacteria in a highly specific manner. In contrast, biotinylated anti-Gram negative endotoxin coated sensors did not show a corresponding sensitivity to E. coli (FIG. 120). These results showed effective binding of S. aureus but not E. coli to their respective antibodies. The results demonstrated that diffraction grating sensors functionalized with monoclonal antibodies were capable of detecting bacteria-specific binding.

Figure 121:
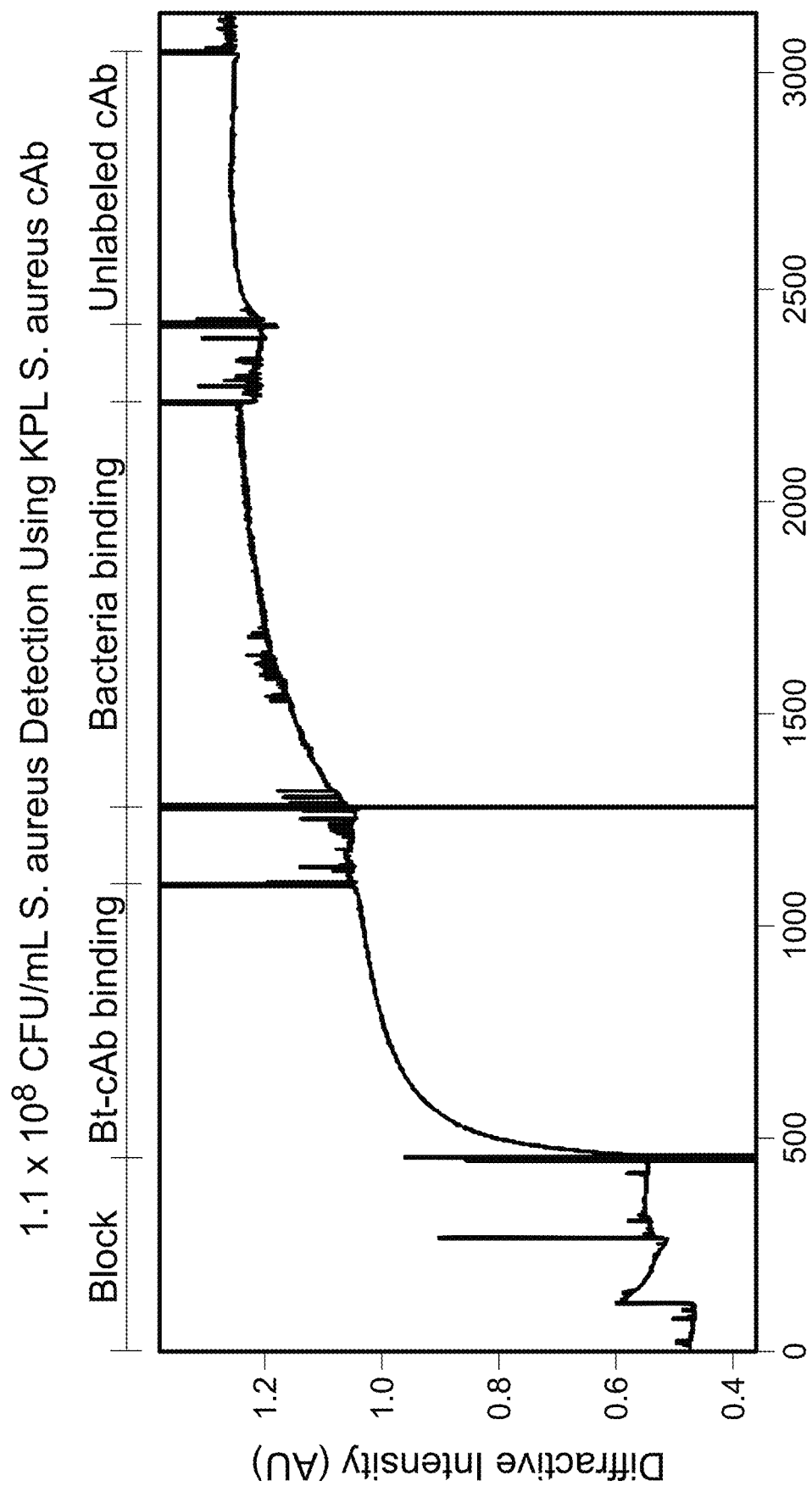
FIG. 121 shows diffraction intensity data.
Figure 122:
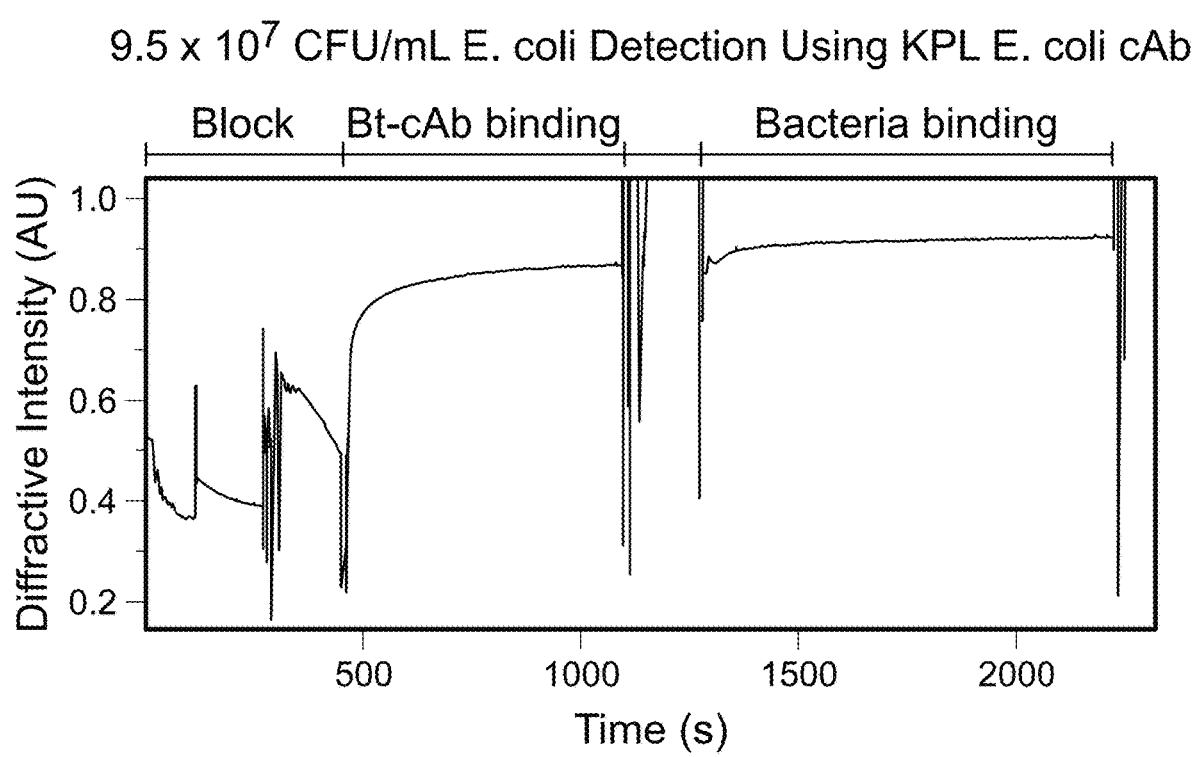
FIG. 122 shows diffraction intensity data.

E. Polyclonal Anti-S. aureus Binds Specifically to S. aureus, and Immobilized Biotinylated Polyclonal Anti-E. coli Binds Specifically to E. coli To characterize the sensitivity and specificity of polyclonal antibody-coated diffraction grating sensors, experiments were performed were performed using polyclonal antibodies (BacTrace® Goat anti-*Staphylococcus aureus*, BacTrace® Goat anti-Escherichia coli). Biotinylated anti-S. aureus coated sensors yielded similar results to anti-lipoteichoic acid coated sensors, showing specific binding signal to S. aureus. A small amplification of the bacteria binding signal was observed by subsequent incubation with unlabeled anti-S. aureus antibody demonstrating specificity of the S. aureus binding signal (FIG. 121). Use of a polyclonal anti-E. coli antibody produced a small but detectable binding signal (FIG. 122). These results showed that diffraction grating sensors functionalized with polyclonal antibodies are capable of detecting bacteria-specific binding.

F. Covalently Linkage Improves the Detection Characteristics of Avidin Sensors

Figure 123:
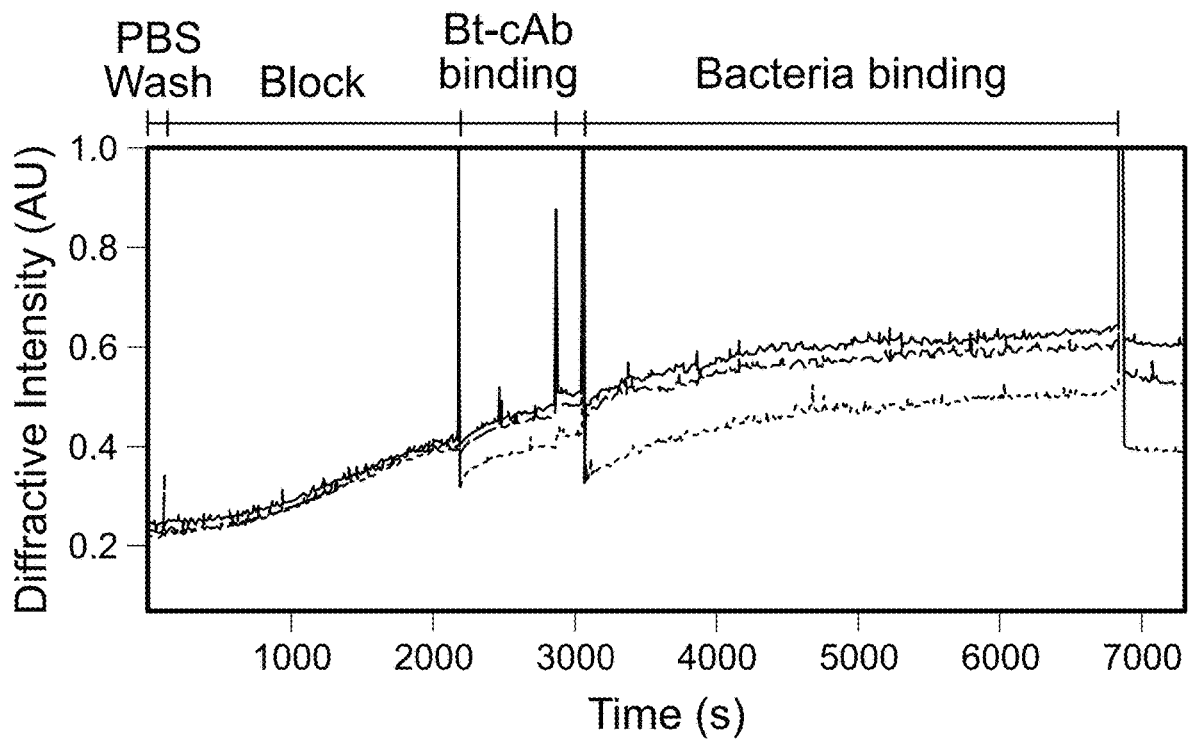
FIG. 123 shows diffraction intensity data.
Figure 124:
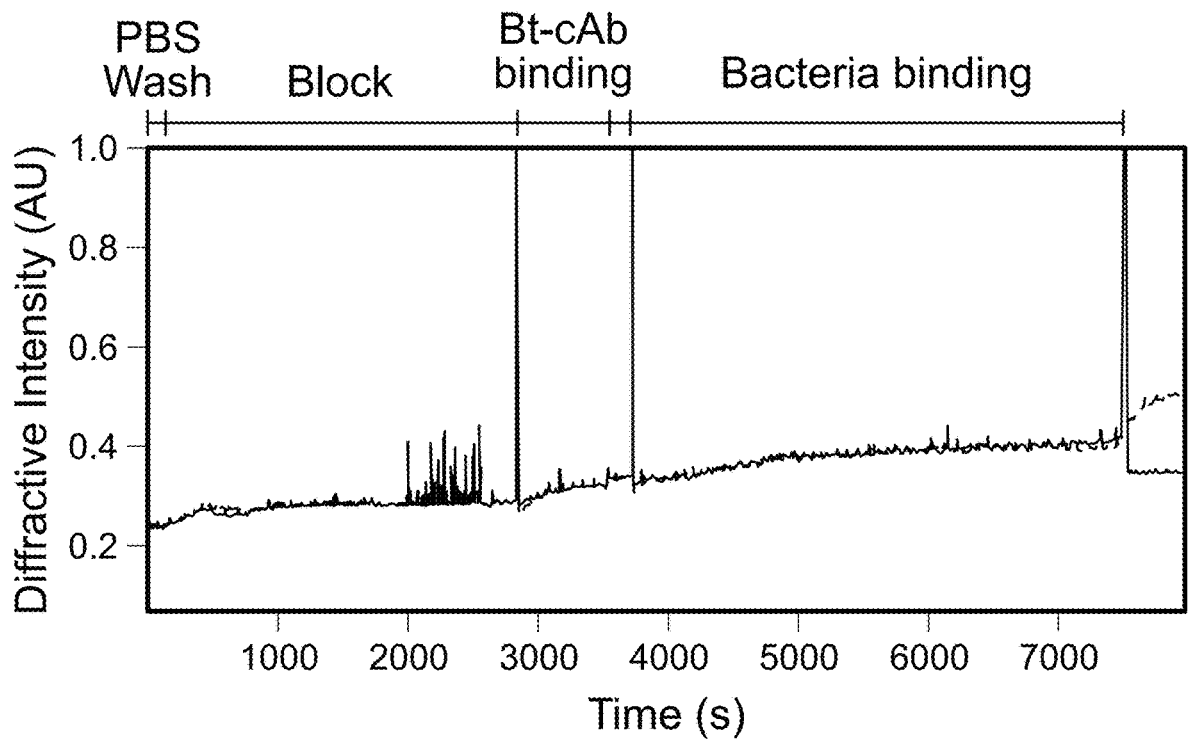
FIG. 124 shows diffraction intensity data.

Because the binding of large particles can be hindered by shear forces, experiments were performed to functionalize the polystyrene surface of the avidin sensors with epoxysilane ((3-Glycidyloxypropyl)trimethoxysilane) to establish covalent linkages between the sensor substrate and the avidin capture molecules. Initial experiments showed that silanized sensors had similar diffraction intensities to control sensors, but exhibited a gradual increase in diffraction intensity during the blocking step (FIG. 123). The elimination of this signal by pre-washing the sensor in Tris buffer to inactivate available epoxy groups suggested that it was caused by the covalent binding of blocking buffer components to the sensor (FIG. 124).

Figure 125:
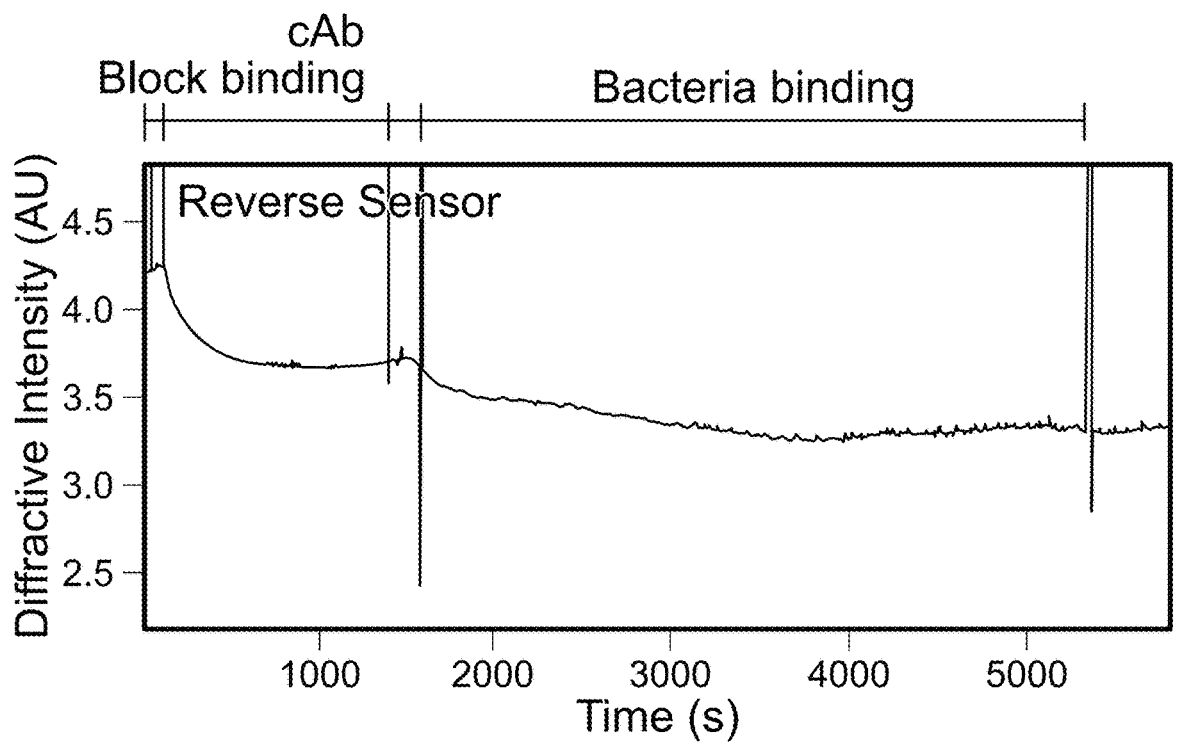
FIG. 125 shows diffraction intensity data.

Bacterial assays conducted with avidin-coated epoxysilane sensors (Tris washed) yielded a lower intensity difference between the binding signal and immobilized antibody signal but resulted in an overall better ratio between binding signal and immobilized antibody signal (FIG. 125). The improved ratio was crucial to the sensitivity performance of the device, and these results showed that silanization is a desirable modification for designing a bacterial assay.

Figure 126:
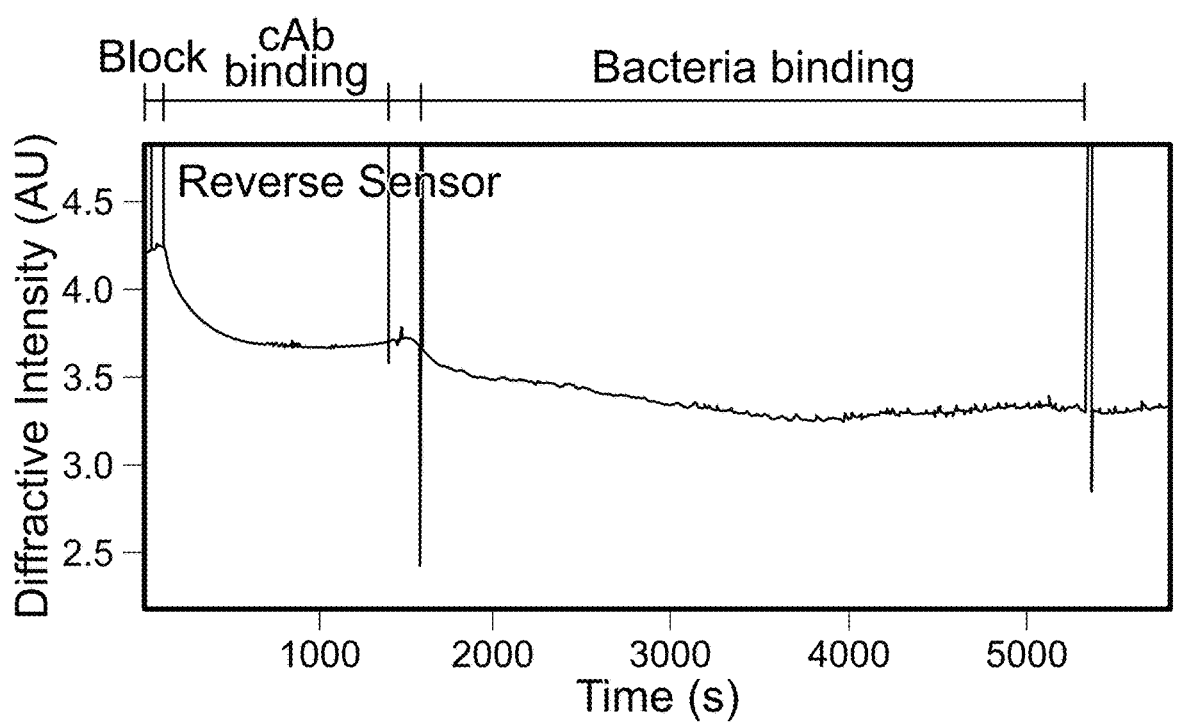
FIG. 126 shows diffraction intensity data.

G. Signal Generation in Avidin Diffraction Grating Sensors is Due to Changes Diffraction Grating To verify that the signal observed in avidin diffraction grating sensors arises from changes in the diffraction grating as opposed to some other phenomenon, a set of diffraction grating sensors were manufactured with a reverse detection geometry; instead of standard functionalization of the lines corresponding to the diffraction grating, avidin was deposited into the troughs of the diffraction grating. On these reverse diffraction gratings, a binding signal would be expected to be observed as a decrease as opposed to an increase in the diffraction intensity. Bead experiments showed that the reverse geometry sensors performed identically to standard sensors, but with an inverted signal (FIG. 126). These results showed that the signal observed in the sensors arises entirely from changes in the diffraction grating.

H. Signal Amplification Using Gold Nanoparticles

Figure 127:
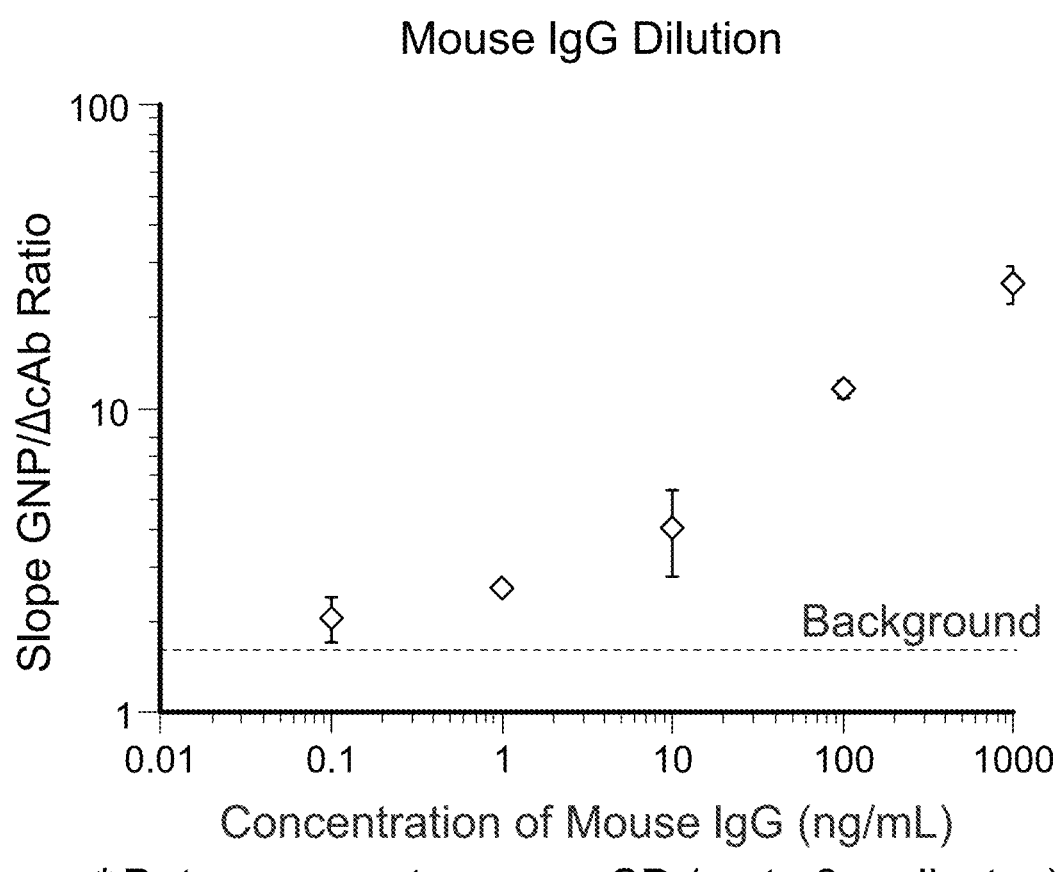
FIG. 127 shows gold nanoparticle amplification-related data.

Experiments were performed using mouse IgG to demonstrate the system's sensitivity to antibody binding when using gold nanoparticles. Unlike previous embodiments of diffraction grating sensors, a signal amplification step was added to the protocol, where the sensor was incubated with anti-mouse IgG gold-nanoparticle conjugates. The gold nanoparticles enhanced the signal from the associated analyte in two ways: (1) they increased the apparent size of the captured antibody and thus the measurable change in the diffraction grating, and (2) they had a significantly different refractive index which resulted in stronger diffraction signals from the same geometric variation in the diffraction grating. Experiments showed that the nanoparticle assay had a mouse IgG detection limit of roughly 100 pg/mL, equivalent to a sensitivity of 667 amol/L (FIG. 127). These results illustrated the ability to achieve high analytical sensitivity using gold nanoparticle-based amplification strategies.

Figure 128:
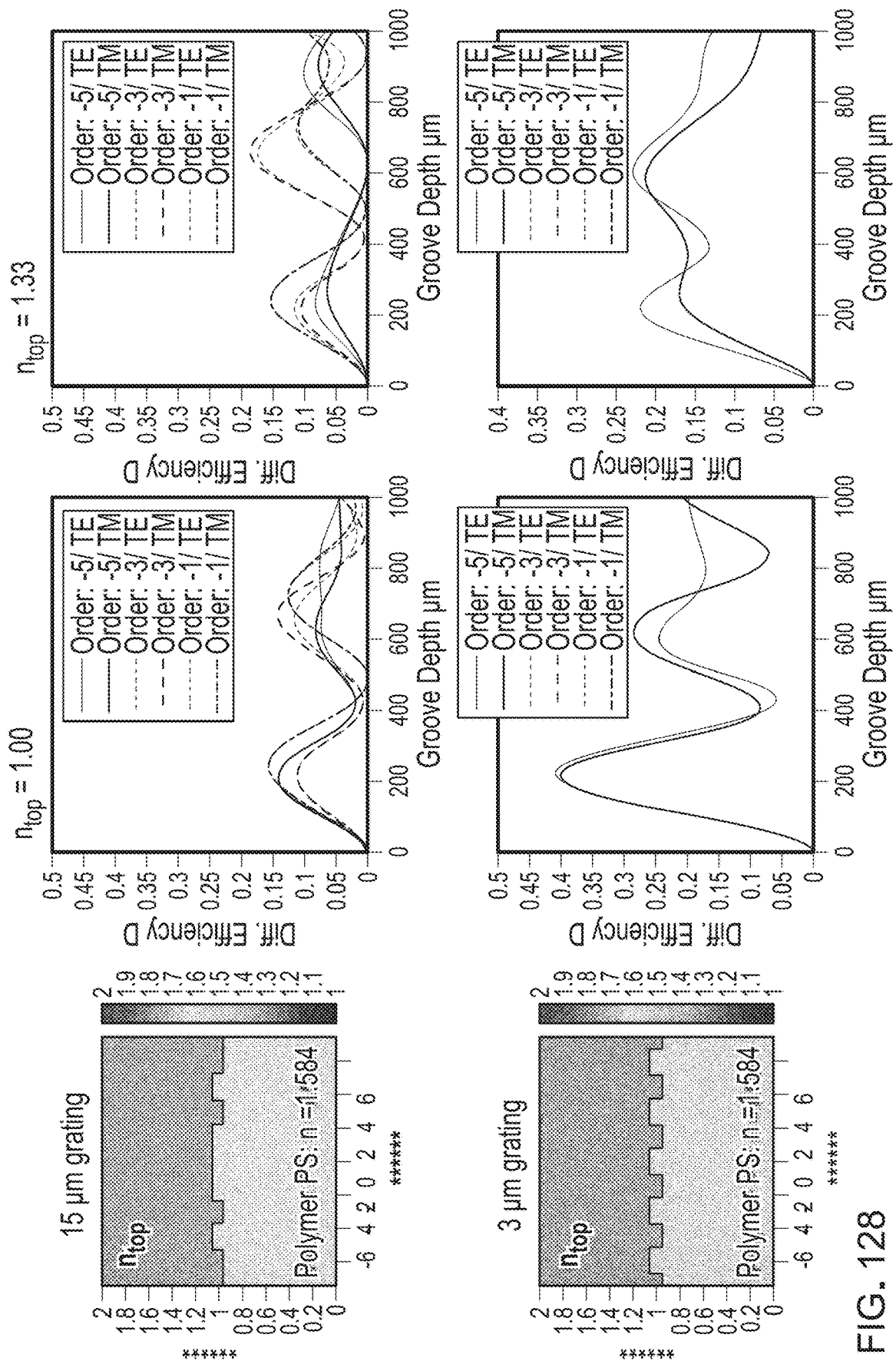
FIG. 128 shows exemplary data for the impact of grating design on diffraction efficiency.
Figure 129:
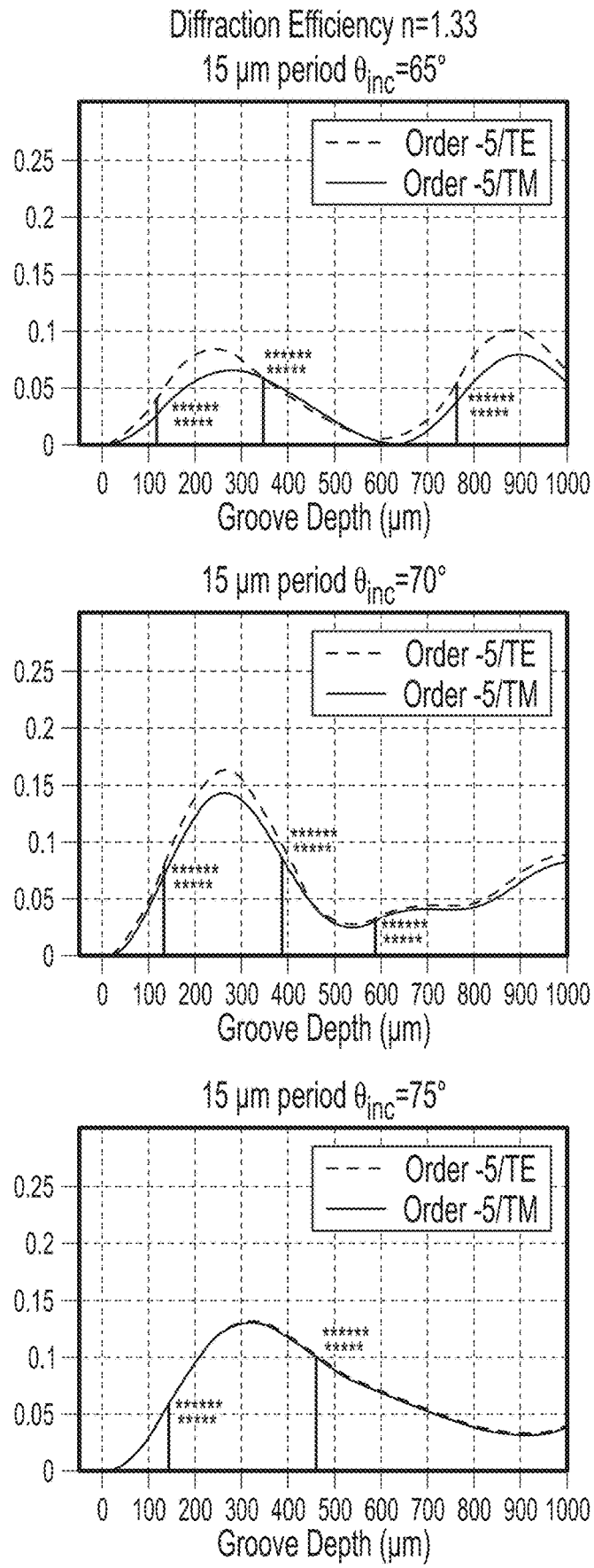
FIG. 129 shows exemplary data for the impact of angle of incidence on diffraction efficiency.

I. Grating Period, Illumination Wavelength, and Angle of Incidence can be Tuned to Optimize Detection of Large Particle Sizes In simulation studies, a significant increase in the detection efficiency of large particles was achieved by optimizing optical parameters, namely grating period, illumination wavelength, and angle of incidence. Performance of diffraction grating sensors was enhanced to detect particles sized at 120 and 350 nm. By modifying the illumination wavelength and/or grating period, sensitivity to larger particles around 1.0 µm in size could be enhanced (e.g., by a factor of 2.5 time) (FIG. 128). By changing the incidence angle of illumination (e.g., to 70° from)45°, the sensitivity is increased (e.g., five-fold increase in sensitivity) (FIG. 129). These results showed that the optical design of the system can significantly affect the sensitivity of the diffraction grating sensor to different analyte sizes.

Localization Examples

Experiment 1

An ingestible medical device according to the disclosure ("TLC1") was tested on 20 subjects to investigate its localization ability. TLC1 was a biocompatible polycarbonate capsule that contained a power supply, electronics and software. An onboard software algorithm used time, temperature and reflected light spectral data to determine the location of the capsule as it traveled the GI tract. The capsule is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the capsule was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For Pill-Cam, the algorithm was as follows:
1. Start mouth-esophagus transition detection after capsule is activated/administrated
2. Check whether Green<102.3 and Blue<94.6
   a. If yes, mark as mouth-esophagus transition
   b. If no, continue to scan the data
3. After detecting mouth-esophagus transition, continue to monitor Green and Blue signals for another 30 seconds, in case of location reversal
   a. If either Green>110.1 or Blue>105.5, mark it as mouth-esophagus location reversal
   b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two-minute gap between the front (first) and back (second) windows. The two-minute gap was designed, at least in part, to skip the rapid transition from stomach to small intestine and capture the small intestine signal after capsule settles down in small intestine. The algorithm was as follows:
1. Start to check for stomach-duodenum transition after capsule enters stomach
2. Setup the two windows (front and back)
   a. Time length of each window: 3 minutes for TLC1; 30 seconds for PillCam
   b. Time gap between two windows: 2 minutes for both devices
   c. Window sliding step size: 0.5 minute for both devices
3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the time-stamp when reversal happened and then repeat steps a-c to look for the next pyloric transition
      ii. If the capsule has not gone back to stomach 2 hours after previously confirmed pyloric transition, stops location reversal monitoring and assume the capsule would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the capsule went back to stomach after first the first stomach-duodenum transition. The total agreement between the TLC1 algorithm detection and CT scans was 17/17=100%.

For one of the PillCam subjects, the capsule stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:
1. Good cases (48 subjects):
   a. For 25 subjects, our detection matches exactly with the physician's notes b. For 19 subjects, the difference between the two detections is less than five minutes
  c. For four subjects, the difference between the two detections is less than 10 minutes (The full transition could take up to 10 minutes before the GB signal settled)
2. Failed cases (6 subjects):
  a. Four subjects had high standard deviation of Green/Blue signal in the stomach
  b. One subject had bile in the stomach, which greatly affected Green/Blue in stomach
  c. One subject had no Green/Blue change at pyloric transition The total agreement for the PillCam stomach-duodenum transition localization algorithm detection and physician's notes was 48/54=89%.

Duodenum-Jejunum Transition

For TLC1, it was assumed that the device left the duodenum and entered the jejunum three minutes after it was determined that the device entered the duodenum. Of the 17 subjects noted above with respect to the TLC1 investigation of the stomach-duodenum transition, 16 of the subjects mentioned had CT images that confirmed that the duodenum-jejunum transition was located somewhere between stomach and jejunum. One of the 17 subjects had a prolonged transit time in duodenum. The total agreement between algorithm detection and CT scans was 16/17=94%.

For PillCam, the duodenum-jejunum transition was not determined.

Jejunum-Ileum Transition

It is to be noted that the jejunum is redder and more vascular than ileum, and that the jejunum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:
1. Obtain 20 minutes of Red signal after the duodenum-jejunum transition, average the data and record it as the jejunum reference signal
2. Start to check the jejunum-ileum transition 20 minutes after the device enters the jejunum
  a. Normalize the newly received data by the jejunum reference signal
  b. Two approaches:
    i. Single-sliding-window analysis
      Set the transition flag if the mean of reflected red signal is less than 0.8
    ii. Two-sliding-window analysis:
      Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:
1. Single-sliding-window analysis:
  a. 11 cases having jejunum-ileum transition detected somewhere between jejunum and cecum
  b. 24 cases having jejunum-ileum transition detected after cecum
  c. 19 cases having no jejunum-ileum transition detected
  d. Total agreement: 11/54=20%
2. Two-sliding-window analysis:
  a. 30 cases having jejunum-ileum transition detected somewhere between jejunum and cecum
  b. 24 cases having jejunum-ileum transition detected after cecum
  c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:
1. Start to monitor ileum-cecum transition after the capsule enters the stomach
2. Setup the two windows (front (first) and back (second))
  a. Use a five-minute time length for each window
  b. Use a 10-minute gap between the two windows
  c. Use a one-minute window sliding step size
3. Compare signals in the two sliding windows
  a. Set ileum-cecum transition flag if
    i. Reflected red/green has a significant change or is lower than a threshold
    ii. Coefficient of variation of reflected green/blue is lower than a threshold
  b. If this is the first ileum-cecum transition detected, record average reflected red/green signal in small intestine as small intestine reference signal
  c. Mark location reversal (i.e. capsule returns to terminal ileum) if
    i. Reflected red/green is statistically comparable with small intestine reference signal
    ii. Coefficient of variation of reflected green/blue is higher than a threshold
  d. If a possible ileum-cecum transition is detected, continue to scan for another 10 minutes for TLC1 (15 minutes for PillCam) in case of false positive flag
    i. If within this time frame (10 minutes for TLC1, 15 minutes for PillCam), location reversal is detected, the previous ileum-cecum transition flag is a false positive flag. Clear the flag and continue to check
    ii. If no location reversal has been identified within this time frame (10 minutes for TLC1, 15 minutes for PillCam) following the possible ileum-cecum transition flag, mark it as a confirmed ileum-cecum transition
  e. Continue monitoring data for another 2 hours after the confirmed ileum-cecum transition, in case of location reversal i. If a location reversal is identified, flag the timestamp when reversal happened and then repeat steps a-d to look for the next ileum-cecum transition
ii. If the capsule has not gone back to small intestine 2 hours after previously confirmed ileum-cecum transition, stop location reversal monitoring and assume the capsule would stay in large intestinal area The flag setting and location reversal criteria particularly designed for TLC1 device were as follows:
1. Set ileum-cecum transition flag if
   a. The average reflected red/Green in the front window is less than 0.7 or mean difference between the two windows is higher than 0.6
   b. And the coefficient of variation of reflected green/blue is less than 0.02
2. Define as location reversal if
   a. The average reflected red/green in the front window is higher than small intestine reference signal
   b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:
1. Good cases (39 subjects):
   a. For 31 subjects, the difference between the PillCam detection and the physician's notes was less than five minutes
   b. For 3 subjects, the difference between the PillCam detection and the physician's notes was less than 10 minutes
   c. For 5 subjects, the difference between the PillCam detection and the physician's notes was less than 20 minutes (the full transition can take up to 20 minutes before the signal settles)
2. Marginal/bad cases (13 subjects):
   a. Marginal cases (9 subjects)
      i. The PillCam ileum-cecum transition detection appeared in the terminal ileum or colon, but the difference between the two detections was within one hour
   b. Failed cases (4 subjects)
      i. Reasons of failure:
         1. The signal already stabilized in the terminal ileum
         2. The signal was highly variable from the entrance to exit
         3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition

Data demonstrated that, for TLC1, mean signal of reflected red/green provided the most statistical difference before and after the cecum-colon transition. Data also demonstrated that, for TLC1, the coefficient of variation of reflected bluee provided the most statistical contrast at cecum-colon transition. The same signals were used for PillCam. The cecum-colon transition localization algorithm was as follows:
1. Obtain 10 minutes of reflected red/green and reflected blue signals after ileum-cecum transition, average the data and record it as the cecum reference signals
2. Start to check cecum-colon transition after capsule enters cecum (The cecum-colon transition algorithm is dependent on the ileum-cecum transition flag)
   a. Normalize the newly received data by the cecum reference signals
   b. Two-sliding-window analysis:
      i. Use two adjacent 10 minute windows
      ii. Set the transition flag if any of the following criteria were met
         The mean difference in reflected red/green was more than 4× the standard deviation of reflected red/green in the back (second) window
         The mean of reflected red/green in the front (first) window was higher than 1.03
         The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:
1. 27 cases had the cecum-colon transition detected somewhere between the cecum and the colon
2. one case had the cecum-colon transition detected in the ileum
3. 24 cases had no cecum-colon transition localized The total agreement: 27/52=52%.

The following table summarizes the localization accuracy results.

| Transition | TLC1 | PillCam |
| --- | --- | --- |
| Stomach-Duodenum | 100% (17/17) | 89% (48/54) |
| Duodenum-Jejunum | 94% (16/17) | N/A |
| Ileum-Cecum | 89% (16/18) | 75% (39/52) |
| Ileum-terminal ileum/cecum/colon | 100% (18/18) | 92% (48/52) |

Other Embodiments

While certain embodiments have been described, the disclosure is not limited to such embodiments.

As an example, while embodiments have been described in which a secondary binding partner is used, the disclosure is not limited to such embodiments. In such embodiments, the baseline can be generated from the primary binding partner bound to the substrate.

As another example, while the use of a secondary binding partner, such as, for example, avidin, can enhance versatility and allow immobilization of a primary binding partner (e.g., a capture antibody) as desired, other embodiments are also contemplated. For example, a different method can be used to immobilize a primary binding partner which may yield enhanced performance and/or simplified sensor manufacture. An example is the use of an epoxysilane coated surface to directly immobilize the primary binding partner.

As a further example, embodiments have been described in which the primary binding partner is immobilized during the assay and in which its binding signal ($\Delta_{Capture\ Molecule}$) is used to normalize the analyte binding signal ($\Delta_{Analyte}$). However, the disclosure is not limited to such embodiments. For example, in some embodiments, the primary binding partner can be pre-immobilized on a diffraction grating. In such embodiments, an in situ assay can be a one step process involving binding of analyte to the primary binding partner (e.g., without ratio/normalization).

As another example, although embodiments are disclosed in which blocking steps were used, the disclosure is not limited in this regard. For example, in some embodiments, a sensor can be pre-blocked, e.g., during sensor manufacturing.

As a further example, while detection methods have been disclosed that are based on electrical current, the disclosure is not limited in this manner. For example, in certain embodiments, other detection methods can be used. Examples of such detection methods include fluorescent detection (e.g., using one or more dyes, using quantum dots), photoactivatable enzymes, and photocleavable substrates.

As an additional example, in some embodiments, a diffraction grating material can include one or more patterned proteins and/or one or more other patterned biomolecules. Patterning can be implemented using any appropriate technique, such as a stamp (e.g., a polydimethylsiloxane stamp) or photolithography.

Ingestible Device Localization

An ingestible device according to the disclosure ("TLC1") was tested on 20 subjects to investigate its localization ability. TLC1 was a biocompatible polycarbonate capsule that contained a power supply, electronics and software. An onboard software algorithm used time, temperature and reflected light spectral data to determine the location of the capsule as it traveled the GI tract. The capsule is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the capsule was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For PillCam, the algorithm was as follows:

5. Start mouth-esophagus transition detection after capsule is activated/administrated
6. Check whether Green<102.3 and Blue<94.6
    a. If yes, mark as mouth-esophagus transition
    b. If no, continue to scan the data
7. After detecting mouth-esophagus transition, continue to monitor Green and Blue signals for another 30 seconds, in case of location reversal
    a. If either Green>110.1 or Blue>105.5, mark it as mouth-esophagus location reversal
    b. Reset the mouth-esophagus flag and loop through step 2 and 3 until the confirmed mouth-esophagus transition detected
8. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two minute gap between the front (first) and back (second) windows. The two minute gap was designed, at least in part, to skip the rapid transition from stomach to small intestine and capture the small intestine signal after capsule settles down in small intestine. The algorithm was as follows:

4. Start to check for stomach-duodenum transition after capsule enters stomach
5. Setup the two windows (front and back)
    a. Time length of each window: 3 minutes for TLC1; 30 seconds for PillCam
    b. Time gap between two windows: 2 minutes for both devices
    c. Window sliding step size: 0.5 minute for both devices
6. Compare signals in the two sliding windows
    a. If difference in mean is higher than 3 times the standard deviation of Green/Blue signal in the back window
        i. If this is the first time ever, record the mean and standard deviation of signals in the back window as stomach reference
        ii. If mean signal in the front window is higher than stomach reference signal by a certain threshold (0.3 for TLC1 and 0.18 for PillCam), mark this as a possible stomach-duodenum transition
b. If a possible pyloric transition is detected, continue to scan for another 10 minutes in case of false positive flag
  i. If within this 10 minutes, location reversal is detected, the previous pyloric transition flag is a false positive flag. Clear the flag and continue to check
  ii. If no location reversal has been identified within 10 minutes following the possible pyloric transition flag, mark it as a confirmed pyloric transition
c. Continue monitoring Green/Blue data for another 2 hours after the confirmed pyloric transition, in case of location reversal
  i. If a location reversal is identified, flag the timestamp when reversal happened and then repeat steps a-c to look for the next pyloric transition
  ii. If the capsule has not gone back to stomach 2 hours after previously confirmed pyloric transition, stops location reversal monitoring and assume the capsule would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the capsule went back to stomach after first the first stomach-duodenum transition. The total agreement between the TLC1 algorithm detection and CT scans was 17/17=100%.

For one of the PillCam subjects, the capsule stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:
3. Good cases (48 subjects):
  a. For 25 subjects, our detection matches exactly with the physician's notes
  b. For 19 subjects, the difference between the two detections is less than five minutes
  c. For four subjects, the difference between the two detections is less than 10 minutes (The full transition could take up to 10 minutes before the GB signal settled)
4. Failed cases (6 subjects):
  a. Four subjects had high standard deviation of Green/Blue signal in the stomach
  b. One subject had bile in the stomach, which greatly affected Green/Blue in stomach
  c. One subject had no Green/Blue change at pyloric transition The total agreement for the PillCam stomach-duodenum transition localization algorithm detection and physician's notes was 48/54=89%.

Duodenum-Jejunum Transition

For TLC1, it was assumed that the device left the duodenum and entered the jejunum three minutes after it was determined that the device entered the duodenum. Of the 17 subjects noted above with respect to the TLC1 investigation of the stomach-duodenum transition, 16 of the subjects mentioned had CT images that confirmed that the duodenum-jejunum transition was located somewhere between stomach and jejunum. One of the 17 subjects had a prolonged transit time in duodenum. The total agreement between algorithm detection and CT scans was 16/17=94%.

For PillCam, the duodenum-jejunum transition was not determined.

Jejenum-Ileum Transition

It is to be noted that the jejunum is redder and more vascular than ileum, and that the jejunum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:
3. Obtain 20 minutes of Red signal after the duodenum-jejunum transition, average the data and record it as the jejunum reference signal
4. Start to check the jejunum-ileum transition 20 minutes after the device enters the jejunum
  a. Normalize the newly received data by the jejunum reference signal
  b. Two approaches:
    i. Single-sliding-window analysis
      Set the transition flag if the mean of reflected red signal is less than 0.8
    ii. Two-sliding-window analysis:
      Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:
3. Single-sliding-window analysis:
  a. 11 cases having jejunum-ileum transition detected somewhere between jejunum and cecum
  b. 24 cases having jejunum-ileum transition detected after cecum
  c. 19 cases having no jejunum-ileum transition detected
  d. Total agreement: 11/54=20%
4. Two-sliding-window analysis:
  a. 30 cases having jejunum-ileum transition detected somewhere between jejunum and cecum
  b. 24 cases having jejunum-ileum transition detected after cecum
  c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:
4. Start to monitor ileum-cecum transition after the capsule enters the stomach
5. Setup the two windows (front (first) and back (second))
   a. Use a five minute time length for each window
   b. Use a 10 minute gap between the two windows
   c. Use a one minute window sliding step size
6. Compare signals in the two sliding windows
   a. Set ileum-cecum transition flag if
      i. Reflected red/green has a significant change or is lower than a threshold
      ii. Coefficient of variation of reflected green/blue is lower than a threshold
   b. If this is the first ileum-cecum transition detected, record average reflected red/green signal in small intestine as small intestine reference signal
   c. Mark location reversal (i.e. capsule returns to terminal ileum) if
      i. Reflected red/green is statistically comparable with small intestine reference signal
      ii. Coefficient of variation of reflected green/blue is higher than a threshold
   d. If a possible ileum-cecum transition is detected, continue to scan for another 10 minutes for TLC1 (15 minutes for PillCam) in case of false positive flag
      i. If within this time frame (10 minutes for TLC1, 15 minutes for PillCam), location reversal is detected, the previous ileum-cecum transition flag is a false positive flag. Clear the flag and continue to check
      ii. If no location reversal has been identified within this time frame (10 minutes for TLC1, 15 minutes for PillCam) following the possible ileum-cecum transition flag, mark it as a confirmed ileum-cecum transition
   e. Continue monitoring data for another 2 hours after the confirmed ileum-cecum transition, in case of location reversal
      i. If a location reversal is identified, flag the timestamp when reversal happened and then repeat steps a-d to look for the next ileum-cecum transition
      ii. If the capsule has not gone back to small intestine 2 hours after previously confirmed ileum-cecum transition, stop location reversal monitoring and assume the capsule would stay in large intestinal area The flag setting and location reversal criteria particularly designed for TLC1 device were as follows:
3. Set ileum-cecum transition flag if
   a. The average reflected red/Green in the front window is less than 0.7 or mean difference between the two windows is higher than 0.6
   b. And the coefficient of variation of reflected green/blue is less than 0.02
4. Define as location reversal if
   a. The average reflected red/green in the front window is higher than small intestine reference signal
   b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:
3. Good cases (39 subjects):
   a. For 31 subjects, the difference between the PillCam detection and the physician's notes was less than five minutes
   b. For 3 subjects, the difference between the PillCam detection and the physician's notes was less than 10 minutes
   c. For 5 subjects, the difference between the PillCam detection and the physician's notes was less than 20 minutes (the full transition can take up to 20 minutes before the signal settles)
4. Marginal/bad cases (13 subjects):
   a. Marginal cases (9 subjects)
      i. The PillCam ileum-cecum transition detection appeared in the terminal ileum or colon, but the difference between the two detections was within one hour
   b. Failed cases (4 subjects)
      i. Reasons of failure:
         1. The signal already stabilized in the terminal ileum
         2. The signal was highly variable from the entrance to exit
         3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition

Data demonstrated that, for TLC1, mean signal of reflected red/green provided the most statistical difference before and after the cecum-colon transition. Data also demonstrated that, for TLC1, the coefficient of variation of reflected bluee provided the most statistical contrast at cecum-colon transition. The same signals were used for PillCam. The cecum-colon transition localization algorithm was as follows:
3. Obtain 10 minutes of reflected red/green and reflected blue signals after ileum-cecum transition, average the data and record it as the cecum reference signals
4. Start to check cecum-colon transition after capsule enters cecum (The cecum-colon transition algorithm is dependent on the ileum-cecum transition flag)
   a. Normalize the newly received data by the cecum reference signals
   b. Two-sliding-window analysis:
      i. Use two adjacent 10 minute windows
      ii. Set the transition flag if any of the following criteria were met The mean difference in reflected red/green was more than 4× the standard deviation of reflected red/green in the back (second) window The mean of reflected red/green in the front (first) window was higher than 1.03

The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:

4. 27 cases had the cecum-colon transition detected somewhere between the cecum and the colon
5. one case had the cecum-colon transition detected in the ileum
6. 24 cases had no cecum-colon transition localized The total agreement: 27/52=52%.

The following table summarizes the localization accuracy results.

| Transition | TLC1 | PillCam |
| --- | --- | --- |
| Stomach-Duodenum | 100% (17/17) | 89% (48/54) |
| Duodenum-Jejunum | 94% (16/17) | N/A |
| Ileum-Cecum | 89% (16/18) | 75% (39/52) |
| Ileum-terminal ileum/cecum/colon | 100% (18/18) | 92% (48/52) |

What is claimed is:

1. A method, comprising:
   1) disposing an ingestible device in the GI tract of a subject, the ingestible device comprising:
   a housing;
   a sample chamber in an interior of the housing, the sample chamber comprising dye capable of binding to or reacting with a target component of a viable cell, wherein the dye exhibits fluorescence that is measurably altered when the dye is bound to or reacted with the target component of the viable cell and a reagent capable of selectively lysing eukaryotic cells;
   a light source in the interior of the housing; and
   a light detector in the interior of the housing; and
   2) while the ingestible device is in the GI tract of the subject:
   a) collecting a bacteria-containing sample from a region of the GI tract with the ingestible device, selectively lysing eukaryotic cells in the bacteria containing sample by combining the bacteria-containing sample with the reagent to rehydrate the reagent within the sample chamber and exposing the bacteria-containing sample to the dye in the sample chamber;
   b) emitting light from the light source of the ingestible device and filtering the emitted light through an optical filter to control for scatter onto the solution so that the light interacts with the dye to produce fluorescence within the GI tract of the subject; and
   c) measuring with the light detector a parameter selected from: i) total fluorescence from the dye; or ii) rate of change of fluorescence from the dye as a function of time within the GI tract of the subject; and
   3) correlating the measured parameter to a number of viable bacterial cells in the bacteria-containing sample to generate an indication of a disease or condition present in the subject;
   4) transmitting, from the ingestible device towards an environment external to the housing of the ingestible device, a first illumination at a first wavelength and a second illumination at a second wavelength:
   detecting a first reflectance from the environment resulting from the first illumination:
   detecting a second reflectance from the environment resulting from the second illumination, wherein the first reflectance value is indicative of an amount of light in the first reflectance, and the second reflectance value is indicative of an amount of light in the second reflectance;
   storing a ratio of the first reflectance value and the second reflectance value in a data set, the data set including a plurality of values, each of the plurality of values corresponding to a respective ratio of a respective first reflectance and a respective second reflectance detected at a respective time:
   obtaining, from the data set, a first subset of values, the first subset of values corresponding to a first predetermined number of recent measurements;
   obtaining, from the data set, a second subset of values, the second subset of values corresponding to a second predetermined number of past measurements, the recent measurements being taken at a recent time range that is separated from a past time range when the past measurements were taken by at least a predetermined period of time: and
   identifying a change in the location of the ingestible device within the GI tract of the body when a difference between a first mean value of the first subset of values and a second mean value of the second subset of values exceeds a threshold value.

2. The method of claim 1, further comprising using the correlation to determine whether the subject is suffering from or at risk of overgrowth of bacterial cells in the GI tract.

3. The method of claim 1, further comprising using the correlation to determine that the subject needs treatment for overgrowth of bacterial cells in the GI tract when the number of the viable bacterial cells in the bacteria-containing sample is greater than about $10^5$ colony forming units (CFU)/mL.

4. The method of claim 1, wherein:
   the measuring comprises measuring the total fluorescence from the resorufin at different points in time; and
   the correlating comprises comparing the measured total fluorescence from the resorufin at the different points in time to a total fluorescence produced by a control, and correlating the comparative fluorescence at the different points in time to the number of viable bacterial cells present in the bacteria-containing sample.

5. The method of claim 4, wherein the control comprises a composition identical to the bacteria-containing sample that does not comprise viable bacterial cells.

6. The method of claim 4, wherein the control comprises a composition identical to the bacteria-containing sample but that comprises a known number of viable bacterial cells.

7. The method of claim 1, wherein:
the measuring comprises measuring the rate of change of fluorescence from the resorufin as a function of time; and
the correlating comprises comparing the rate of change of fluorescence from the resorufin as a function of time to a rate of change of fluorescence produced by a control as a function of time, and correlating the comparative rate of change of fluorescence as a function of time to the number of viable bacterial cells in the bacteria-containing sample.

8. The method of claim 7, wherein the control comprises a composition identical to the bacteria-containing sample that does not comprise viable bacterial cells.

9. The method of claim 7, wherein the control comprises a composition identical to the bacteria-containing sample but that comprises a known number of viable bacterial cells.

10. The method of claim 1, wherein the bacteria-containing sample has a pH of at least 6.5 and at most 8.

11. The method of claim 1, wherein the bacteria-containing sample comprises at least 1.4 mM bile and at most 5 mM bile.

12. The method of claim 1, wherein the bacteria-containing sample comprises at least $10^2$ CFU/mL yeast and at most $10^4$ CFU/mL yeast.

13. The method of claim 1, the region of the GI tract comprises the duodenum.

14. The method of claim 1, the region of the GI tract comprises the jejunum.

15. The method of claim 1, wherein the bacteria-containing sample comprises anaerobic bacteria.

16. The method of claim 1, wherein the bacteria-containing sample comprises at least one member selected from the group consisting of a *bacteroides* bacterium and a *clostridium* bacterium.

17. The method of claim 1, wherein the bacteria-containing sample comprises aerobic bacteria.

18. The method of claim 1, wherein the bacteria-containing sample comprises at least one member selected from the group consisting of *Escherichia coli, Staphylococcus aureus, Klebsiella pneumoniae, Pseudomonas aeruginosa, Enterobacter aerogenes, Streptococcus mutans, Enterococcusfaecalis* and *Proteus mirabilis*.

19. The method of claim 1, wherein the dye is resazurin, and the reagent is a dried reagent;
wherein the collecting produces resorufin in a solution of the bacteria-containing sample and the rehydrated reagent; and
wherein emitting light includes emitting light having a first wavelength greater than 550 nm from the light source.

20. The method of claim 19, wherein:
the first wavelength is in the green spectrum of light between 495-600 nm; and a second wavelength is in the blue spectrum of light between 400-495 nm; and the first wavelength and the second wavelength are separated by at least 50 nm.

21. The method of claim 1, further comprising:
the measuring comprises measuring with the light detector a total fluorescence from the dye at different points in time within the GI tract of the subject;
comparing the measured total fluorescence from the dye at the different points in time to a total fluorescence produced by a control within the GI tract of the subject;
correlating the comparative fluorescence at the different points in time to a number of viable bacterial cells present in the sample; and
5) determining, based on the correlation, whether the subject is suffering from or at risk of overgrowth of bacterial cells in the GI tract,
wherein the region of the GI tract comprises a member selected from the group consisting of the duodenum and the jejunum.

22. The method of claim 21, wherein the control comprises a composition identical to the sample that does not comprise viable bacterial cells.

23. The method of claim 21, wherein the control comprises a composition identical to the sample but that comprises a known number of viable bacterial cells.

24. The method of claim 21, further comprising using the correlation to determine that the subject needs treatment for overgrowth of bacterial cells in the GI tract when the number of the viable bacterial cells in the bacteria-containing sample is greater than about $10^5$ colony forming units (CFU)/mL.

25. The method of claim 1, further comprising:
the measuring comprises measuring with the light detector a total fluorescence from the dye as a function of time within the GI tract of the subject;
comparing the measured rate of change of the fluorescence from the dye as a function of time to a rate of change of fluorescence produced by a control within the GI tract of the subject;
correlating the comparative rate of change of the fluorescence as a function of time to a number of viable bacterial cells present in the sample; and
5) determining, based on the correlation, whether the subject is suffering from or at risk of overgrowth of bacterial cells in the GI tract,
wherein the region of the GI tract comprises a member selected from the group consisting of the duodenum and the jejunum.

26. The method of claim 21, further comprising treating the bacteria-containing sample by combining the bacteria-containing sample with a dried antifungal agent to inhibit fungal growth in the bacteria-containing sample prior to exposing the bacteria-containing sample to the resazurin.

27. The method of claim 21, wherein the bacteria-containing sample is collected and disposed on an absorbent sponge within the sample chamber, the absorbent sponge being pre-treated with the dried reagent.

28. The method of claim 21, wherein the bacteria-containing sample is combined with a dried buffering agent when combined with the reagent to control a pH of the solution of the bacteria-containing sample and the rehydrated reagent.

29. The method of claim 1, further comprising:
c) measuring comprises measuring with the light detector a rate of change of fluorescence from the resorufin as a function of time within the GI tract of the subject;
3) comparing the measured rate of change of the fluorescence from the resorufin as a function of time to a rate of change of fluorescence produced by a control as a function of time within the GI tract of the subject;
4) correlating the comparative rate of change of the fluorescence as a function of time to a number of viable bacterial cells present in the sample; and
5) determining, based on the correlation, whether the subject is suffering from or at risk of overgrowth of bacterial cells in the GI tract,
wherein the region of the GI tract comprises a member selected from the group consisting of the duodenum and the jejunum.

30. The method of claim 29, wherein the control comprises a composition identical to the sample that does not comprise viable bacterial cells.

31. The method of claim 29, wherein the control comprises a composition identical to the sample but that comprises a known number of viable bacterial cells.

32. The method of claim 29, further comprising using the correlation to determine that the subject needs treatment for overgrowth of bacterial cells in the GI tract when the number of the viable bacterial cells in the bacteria-containing sample is greater than about $10^5$ colony forming units (CFU)/mL.

33. The method of claim 29, wherein at least one of the following holds:
the bacteria-containing sample has a pH of at least 6.5 and at most 8;
the bacteria-containing sample comprises at least 1.4 mM bile and at most 5 mM bile; and
the bacteria-containing sample comprises at least $10^2$ CFU/mL yeast and at most $10^4$ CFU/mL yeast.

34. The method of claim 29, further comprising treating the bacteria-containing sample by combining the bacteria-containing sample with a dried antifungal agent to inhibit fungal growth in the bacteria-containing sample prior to exposing the bacteria-containing sample to the resazurin.

35. The method of claim 29, wherein the bacteria-containing sample is collected and disposed on an absorbent sponge within the sample chamber, the absorbent sponge being pre-treated with the dried reagent.

36. The method of claim 29, wherein the bacteria-containing sample is combined with a dried buffering agent when combined with the reagent to control a pH of the solution of the bacteria-containing sample and the rehydrated reagent.

37. The method of claim 1, further comprising treating the bacteria-containing sample by combining the bacteria-containing sample with a dried antifungal agent to inhibit fungal growth in the bacteria-containing sample prior to exposing the bacteria-containing sample to the resazurin.

38. The method of claim 1, wherein the bacteria-containing sample is collected and disposed on an absorbent sponge within the sample chamber, the absorbent sponge being pre-treated with the dried reagent.

39. The method of claim 1, wherein the bacteria-containing sample is combined with a dried buffering agent when combined with the reagent to control a pH of the solution of the bacteria-containing sample and the rehydrated reagent.

* * * * *